United States Patent
Short

(10) Patent No.: US 6,713,279 B1
(45) Date of Patent: Mar. 30, 2004

(54) NON-STOCHASTIC GENERATION OF GENETIC VACCINES AND ENZYMES

(75) Inventor: Jay M. Short, Rancho Santa Fe, CA (US)

(73) Assignee: Diversa Corporation, San Diego, CA (US)

(*) Notice: Subject to any disclaimer, the term of this patent is extended or adjusted under 35 U.S.C. 154(b) by 0 days.

(21) Appl. No.: 09/498,557

(22) Filed: Feb. 4, 2000

Related U.S. Application Data

(63) Continuation-in-part of application No. 09/495,052, filed on Jan. 31, 2000, now Pat. No. 6,479,253, which is a continuation-in-part of application No. 09/332,835, filed on Jun. 14, 1999, now Pat. No. 6,537,776, which is a continuation-in-part of application No. 09/276,860, filed on Mar. 26, 1999, now Pat. No. 6,352,842, which is a continuation-in-part of application No. 09/267,118, filed on Mar. 9, 1999, now Pat. No. 6,238,884, which is a continuation-in-part of application No. 09/246,178, filed on Feb. 4, 1999, now Pat. No. 6,171,820, which is a continuation-in-part of application No. 09/185,373, filed on Nov. 3, 1998, now Pat. No. 6,335,179, which is a continuation of application No. 08/760,489, filed on Dec. 5, 1996, now Pat. No. 5,830,696, said application No. 09/246,178, is a continuation-in-part of application No. 08/962,504, filed on Oct. 31, 1997, which is a continuation-in-part of application No. 08/677,112, filed on Jul. 9, 1996, now Pat. No. 5,965,408, said application No. 09/246,178, is a continuation-in-part of application No. 08/651,568, filed on May 22, 1996, now Pat. No. 5,939,250

(60) Provisional application No. 60/008,311, filed on Dec. 7, 1995, now abandoned, and provisional application No. 60/008,316, filed on Dec. 7, 1995.

(51) Int. Cl.[7] ............................. C12P 21/06; C12Q 1/68; C12N 5/06; C12N 15/00

(52) U.S. Cl. ....................... 435/69.1; 435/6; 435/334; 435/320.1

(58) Field of Search ....................... 435/6, 69.1, 334, 435/320.1

(56) References Cited

U.S. PATENT DOCUMENTS

| 4,683,202 A | 7/1987 | Mullis |
| 4,800,159 A | 1/1989 | Mullis et al. |

(List continued on next page.)

FOREIGN PATENT DOCUMENTS

| EP | 0 285 123 | 10/1988 |
| EP | 0 316 018 A2 | 5/1989 |

(List continued on next page.)

OTHER PUBLICATIONS

Arkin and Youvan, "Optimizing nucleotide mixtures to encode specific subsets of amino acids for semi–radom mutagenesis," *Bio–technology* (*NY*) 10(3): 297–300 (Mar. 1992).

(List continued on next page.)

*Primary Examiner*—Hankyel T. Park
(74) *Attorney, Agent, or Firm*—Jane M. Love; James E. Butler

(57) ABSTRACT

This invention provides methods of obtaining novel polynucleotides and encoded polypeptides by use of non-stochastic methods of directed evolution (DirectEvolution™). These methods include non-stochastic polynucleotide site-saturation mutagenesis (Gene Site Saturation Mutagenesis™) and non-stochastic polynucleotide reassembly (GeneReassembly™). Through use of the claimed methods, genetic vaccines, enzymes, and other desirable molecules can be evolved towards desirable properties. For example, vaccine vectors can be obtained that exhibit increased efficacy for use as genetic vaccines. Vectors obtained by using the methods can have, for example, enhanced antigen expression, increased uptake into a cell, increased stability in a cell, ability to tailor an immune response, and the like. This invention provides methods of obtaining novel enzymes that have optimized physical &/or biological properties. Furthermore, this invention provides methods of obtaining a variety of novel biologically active molecules, in the fields of antibiotics, pharmacotherapeutics, and transgenic traits.

105 Claims, 64 Drawing Sheets

U.S. PATENT DOCUMENTS

Figure 1:
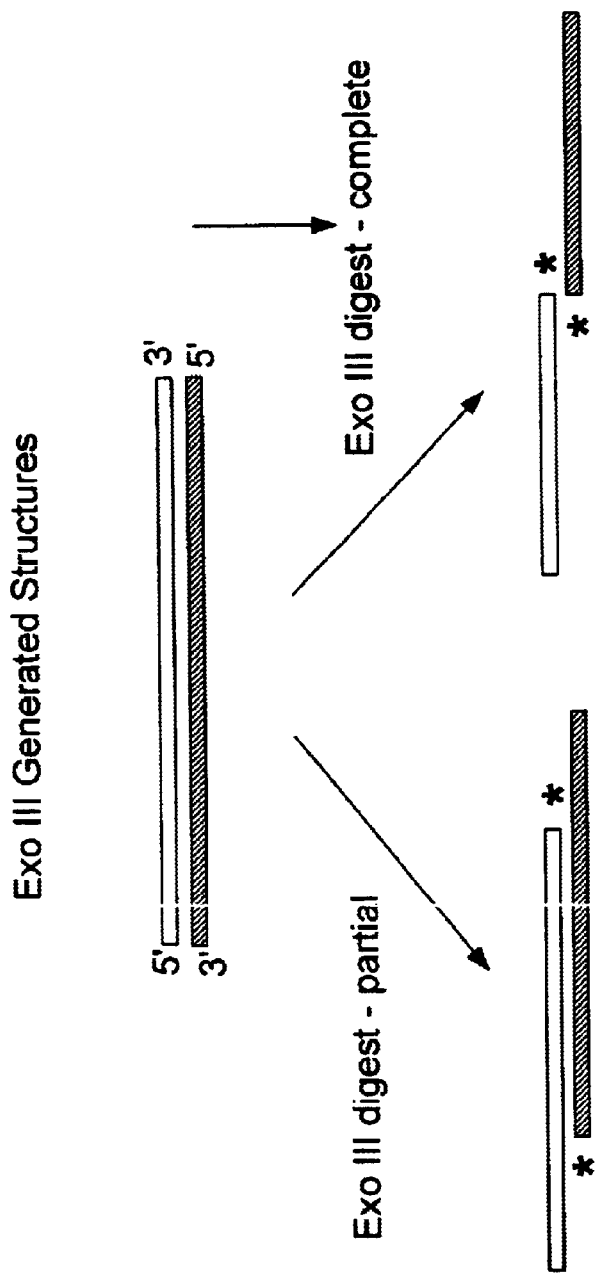

| | | |
|---|---|---|
| 4,959,312 A | 9/1990 | Sirotkin |
| 4,965,188 A | 10/1990 | Mullis et al. |
| 5,096,815 A | 3/1992 | Ladner et al. |
| 5,176,995 A | 1/1993 | Sninsky et al. |
| 5,187,083 A | 2/1993 | Mullis |
| 5,198,346 A | 3/1993 | Ladner et al. |
| 5,223,408 A | 6/1993 | Goeddel et al. |
| 5,223,409 A | 6/1993 | Ladner et al. |
| 5,234,824 A | 8/1993 | Mullis |
| 5,333,675 A | 8/1994 | Mullis et al. |
| 5,354,656 A | 10/1994 | Sorge et al. |
| 5,389,537 A | 2/1995 | Raines et al. |
| 5,512,463 A | 4/1996 | Stemmer |
| 5,605,793 A | 2/1997 | Stemmer |
| 5,645,988 A | 7/1997 | Vande Woude et al. |
| 5,658,727 A | 8/1997 | Barbas et al. |
| 5,723,323 A | 3/1998 | Kauffman et al. |
| 5,759,817 A | 6/1998 | Barbas |
| 5,763,192 A | 6/1998 | Kauffman et al. |
| 5,789,166 A | 8/1998 | Bauer et al. |
| 5,798,208 A | 8/1998 | Crea |
| 5,811,238 A | 9/1998 | Stemmer et al. |
| 5,814,476 A | 9/1998 | Kaufmann et al. |
| 5,817,483 A | 10/1998 | Kaufmann et al. |
| 5,824,469 A | 10/1998 | Horwitz et al. |
| 5,824,485 A | 10/1998 | Thompson et al. |
| 5,824,514 A | 10/1998 | Kauffman et al. |
| 5,830,696 A | 11/1998 | Short |
| 5,830,721 A | 11/1998 | Stemmer et al. |
| 5,837,458 A | 11/1998 | Minshull et al. |
| 5,866,363 A | 2/1999 | Pieczenik |
| 5,885,577 A | 3/1999 | Alvarez |
| 5,885,827 A | 3/1999 | Wabl et al. |
| 5,932,419 A | 8/1999 | Bauer et al. |
| 5,945,329 A | 8/1999 | Breddam et al. |
| 5,965,408 A | 10/1999 | Short |
| 5,976,862 A | 11/1999 | Kauffman et al. |
| 6,004,788 A | 12/1999 | Short |
| 6,054,267 A | 4/2000 | Short |
| 6,057,103 A | 5/2000 | Short |
| 6,171,820 B1 | 1/2001 | Short |
| 6,238,884 B1 | 5/2001 | Short et al. |
| 6,335,179 B1 | 1/2002 | Short |
| 6,352,842 B1 | 3/2002 | Short et al. |
| 6,358,709 B1 | 3/2002 | Short et al. |
| 6,361,974 B1 | 3/2002 | Short et al. |

FOREIGN PATENT DOCUMENTS

| | | |
|---|---|---|
| WO | WO 90/02809 | 3/1990 |
| WO | WO 91/12341 | 8/1991 |
| WO | WO 91/16427 | 10/1991 |
| WO | WO 95/20039 | 7/1995 |
| WO | WO 95/22625 | 8/1995 |
| WO | WO 96/06188 | 2/1996 |
| WO | WO 96/09411 | 3/1996 |
| WO | WO 96/41865 | 12/1996 |
| WO | WO 97/20078 | 6/1997 |
| WO | WO 97/20950 | 6/1997 |
| WO | WO 97/35957 | 10/1997 |
| WO | WO 98/01581 | 1/1998 |
| WO | WO 98/13487 | 4/1998 |
| WO | WO 98/27230 | 6/1998 |
| WO | WO 98/38297 | 9/1998 |
| WO | WO 98/42832 | 10/1998 |
| WO | WO 98/45331 | 10/1998 |
| WO | WO 98/48024 | 10/1998 |
| WO | WO 98/49286 | 11/1998 |
| WO | WO 98/58080 | 12/1998 |
| WO | WO 99/36553 | 7/1999 |
| WO | WO 00/52146 | 9/2000 |
| WO | WO 00/52153 | 9/2000 |
| WO | WO 00/52155 | 9/2000 |
| WO | WO 00/52180 | 9/2000 |
| WO | WO 01/30998 A1 | 5/2001 |
| WO | WO 01/31035 A2 | 5/2001 |
| WO | WO 01/31049 A2 | 5/2001 |
| WO | WO 01/42455 A1 | 6/2001 |

OTHER PUBLICATIONS

Burks et al., "In vitro scanning saturation mutagenesis of an antibody binding pocket," *Proc Natl Acad Sci USA* 94(2): 412–417 (Jan. 21, 1997).

Chen and Struhl, Saturation mutagenesis of a yeast his3 "TATA element": genetic evidence for a specific TATA.

Chiang et al., "Mutagenic oligonucleotide–directed PCR amplification (Mod–PCR): an efficient method for generation random base substitution mutations in a DNS sequence element," *PCR Methods Appl* 2(3): 210–217 (Feb. 1993).

Christian et al, "Simplified methods for construction, assessment and rapid screening of peptide libraries in bacteriophage," *J Mol Biol* 227(3): 711–718 (Oct. 5, 1992).

Cunniff and Mrogan, "Analysis of heat shock element recognition by saturation mutagenesis of the human HSP70.1 gene promoter," *J Biol Chem* 268(11): 8317–8324 (Apr. 15, 1993).

Cwirla et al., "Peptide on a phage: a vast library of peptides for identifying ligands," *Proc Natl Acad Sci USA* 87(16): 6378–6382 (Aug. 1990).

Delagrave and Youvan, "Searching Sequence Space to Engineer Proteins: Exponential Ensemble Mitagenesis," *Bio/Technology*, 11: 1548–1552 (Dec. 1993).

Dennis and Lazarus, "Kunitz domain inhibitors of tissue factor–factor Vlla. I. Potent inhibitors selected from libraries by phage display," *J Biol Chem* 269(35): 22129–22136 (Sep. 2, 1994).

Derbyshire et al., "A simple and efficient procedure for saturation mutagenesis using mixed oligodeoxynucleotides," *Gene* 46(2–3): 145–152 (1986).

Gogg et al., "Efficient saturation mutagenesis of a pentapeptide coding sequence using mixed oligonucleotides," *DNA* 6(4): 381–388 (Aug. 1987).

Hill and Struhl, "Mutagenesis with degenerate oligonucleotides: and efficient method for saturating a defined DNA region with base pair substitutions," *Methods Enzymol* 155: 558–568 (1987).

Horwitz and DiMaio, "Saturation mutagenesis using mixed oligonucleotides and M13 templates containing uracil," *Methods Enzymol* 185: 599–611 (1990).

Ihara et al., Requirement of the Pro–Cys–His–Arg sequence for $O^6$–methylguanine DNA methylransferase activity revealed by saturation mutagenesis with negative and positive screening, *Mol Gen Genet* 243(4): 379–389 (May 25, 1994).

J.W. Little, "Saturation mutagenesis of specific codons: elimination of molecule with stop codons from mixed pools of DNA," *Gene* 88(1): 113–115 (Mar. 30, 1990).

Morris and McIvor, "Saturation mutagenesis at dihydrofolate reductase codons 22 and 31. A variety of amino acid substitutions conferring methotrexate resistance," *Biochem Pharmacol* 47(7): 1207–1220 (Mar. 29, 1994).

Olesen and Kielland–Brandt, "Altering substrate preference of carboxypeptidase Y by a novel strategy of mutagenesis eliminating wild type backgroun," *Protein Eng* 6(4): 409–415 (Jun. 1993).

Olins et al., "Saturation mutagenesis of human interleukin–3," *J Biol Chem* 270(40): pp 23754–123760 (Oct. 6, 1995).

Oliphant and Struhl, "An efficient method for generation proteins with altered enzymatic properties: application to beta–lactamase," *Proc Natl Acad Sci USA* 86(23): 9094–9098 (Dec. 1989).

Oliphant et al., "Cloning of random–sequence oligodeoxynucleotides," *Gene* 44(2–3): 177–183 (1986).

Osuna et al., "combinatorial mutagenesis of three major groove–contacting residues of EcoRI: single and double amino acid replacements retaining methyltransferase–sensative activities," 016(1): 7–12 (Sep. 30, 1991).

Reidhaar–Olson et al., "Random mutagenesis of protein sequences using oligonucleotide cassettes," *Methods Enzymol* 208: 564–586 (1991).

Roberts et al., "Directed evolution of a protein: selection of potent neutrophil elastase inhibitors displayed on M13 fusion phage," *Proc Natl Acad Sci USA* 89(6): 2429–2433 (Mar. 15, 1992).

Sherman et al., "Saturation mutagenesis of the plasminogen acitibator inhibitor–1 reactive center," *J Biol Chem* 267(11): 7588–7595 (Apr. 15, 1992).

Singh et al., "Saturation mutagenesis of the octopine synthase enhancer: correlation of mutant pgenotypes with binding of a nuclear protein factor," *Proc Natl Acad Sci USA* 86(10): 3733–3737 (May 1989).

K. Sirotkin, "A computer program to display codon changes caused by a mutagenesis," *Comput Appl Biosci* 4(2): 243–247 (Apr. 1988).

K. Sirotkin, "Advantages to mutagenesis techniques generated populations containing the complete spectrum, of single codon changes," *J Theor Biol* 123(3): 261–279 (Dec. 7, 1986).

Soteropoulos and Perlin, "Genetic probing of the stalk segments associated with M2 and M3 of the plasma membrane H+ –ATPase from *Saccharomyces cerevisiae*," *J Biol Chem* 273(41): 26426–26431 (Oct. 9, 1998).

Soteropoulos et al., "Molecular genetic probing of energy coupling by the yeast plasma membrane proton pump," *Acta Physiol Scand* 643: 115–122 (Aug. 19998).

Tsiang et al., "Proteing engineering tyhrombin for optimal specificity and potency of anticoagulant activity in vivo," *Biochemistry* 35(51): 16449–16457 (Dec. 24, 1996).

Warren et al., "A rapid screen of active site mutants in glycinamide ribonucleotide transformylase," *Biochemistry* 35(27): 8855–8862 (Jul. 9, 1996).

Weiner et al., "A method for the site–directed mono– and multi–mutagenesis of double stranded DNA," *Gene* 126(1): 35–41 (Apr. 15, 1993).

Wells et al., "Cassette mutagenesis: an efficient method for generation of multiple mutations at defined sites," *Gene* 34(2–3): 315–323 (1985).

White et al., "Improved thermostability of the North American firefly luciferase: saturation mutagenesis at position 354," *Biochem.*

Yelton et al., "Affinity maturation of the BR96 anti–carcinoma antibody by codon–based mutaganesis,," *J Immunol* 155(4): 1994–2004 (Aug. 15, 1995).

Zilliacus et al., "Evolution of distinct DNA–binding specificities within the nuclear receptor family of transcription factors," *Proc Natl Acad Sci USA* 91(10): 4175–4179 (May 10, 1994).

Cadwell and Joyce, Randomization of Genes by PCR Mutagenesis, *Research*, 2:28–33 (1992).

Crameri et al., "Construction and evolution of antibody–phage libraries by DNA shuffling," *Nature Medicine*, 2(1): 100–102 (Jan. 1996).

Hermes et al., "Searching sequence space by definably random mutagenesis: Improving the catalytic potency of an enzyme," *Proc. Natl. Acad. Sci. USA*, 87: 696–700 (Jan. 1990).

Krishnan et al., "Direct and crossover PCR amplification to facilitate Tn5supF–based sequencing of a λ phage clones," *Nucleic Acids Research* 19(22): 6177–6182 (1991).

Marks et al., "By–Passing Immunization: Building High Affinity Human Antibodies by Chain Shuffling," *Bio/Technology* 10: 779–783 (Jul. 1992).

Meyerhans et al., "DNA recombination during PCR," *Nucleic Acids Research* 18(7): 1687–1691.

Moore et al., "Strategies for the in vitro evolution of protein function: enzyme evolution by random recombination of improved sequences," *Journal of Molecular Biology*, 272: 336–347 (19971).

Patten et al., Applications of DNA shuffling to pharmaceuticals and vaccines, *Current Opinion in Biotechnology*, 8(6): 724–733 (1997).

Reidhaar–Olson and Sauer, "Combinatorial Cassette Mutagenesis as a Probe of the Informational Content of Protein Sequences," *Science* 241: 53–57.

George P. Smith, " The progeny of sexual PCR," *Nature*, 370: 324–325.

Stemmer, "DNA shuffling by random fragmentation and reassembly: In vitro recombination for molecular evolution," *Proceedings of the National Academy of Sciences, USA*, 91: 10747–10752 (Oct. 1994).

Stemmer, "Rapid evolution of a protein in vitro by DNA shuffling," *Nature*, 370: 389–391 (Aug. 4, 1994).

Stemmer et al., Selection of an Active Single Chain Fv Antibody from a Protein Linker Library Prepared by Enzymatic Inverse PCR, *BioTechniques* 14(2): 256–265 (1993).

Zhao et al., "Functional and nonfunctional mutations distinguished by random recombination of homologous genes," *Proceedings of the National Academy of Sciences, USA*, 94: 7997–8000 (Jul. 1997).

Zhao et al., "Optimization of DNA shuffling for high fidelity recombination," *Nucleic Acids Research*, 25(6): 1307–1308 (Mar. 15, 1997).

Ge and Rudolph, "Simultaneous Introduction of Multiple Mutations Using Overlap Extensions PCR," *Biotechniques* 22: 28–30 (1997).

Schultz and Richards, "Site saturation studies of β–lactamase: Production and characterization of mutant β–lactamase with all possible amino acid substitutions at residue 71," *Proc. Natl. Acad. Sci. USA.* 83: 1588–1592.

Riechmann and Weill, " Phage Display and Selection of Site–Directed Randomized Single–Chain Antibody Fv Frahment for Its Affinity Improvement," *Biochemistry* 32: 8848–8855.

Zhao et al., "Molecular evolution by staggered extension process (StEP) in vitro recombination," *Nature Biotechnology* 16: 258–261 (1998).

Cwirla, Steven E. et al., "Peptides on Phage: A Vast Library of Peptides for Identifying Ligands," *Proc. Natl. Acad. Sci. USA*, vol. 87, Aug. 1990, pp. 6378–6382.

Hill, David E. et al., "[34] Mutagenesis with Degenerate Oligonucleotides: An Efficient Method for Saturating a Defined DNA Region with Base Pair Substitutions," *Methods in Enzymology*, vol. 155, 1987, pp. 558–569.

Murray, Richard et al., "Saturation Mutagenesis of a Major Histocompatibility Complex Protein Domain: Identification of a Single Conserved Amino Acid Important for Allorecognition," *Proc. Natl. Sci. USA*, vol. 85., May 1988, pp. 3535–3539.

UNIQUE OVERHANGS AND UNIQUE COUPLINGS
PANEL A
PANEL B
PANEL C
PANEL D
FIGURE 3

Figure 4B:
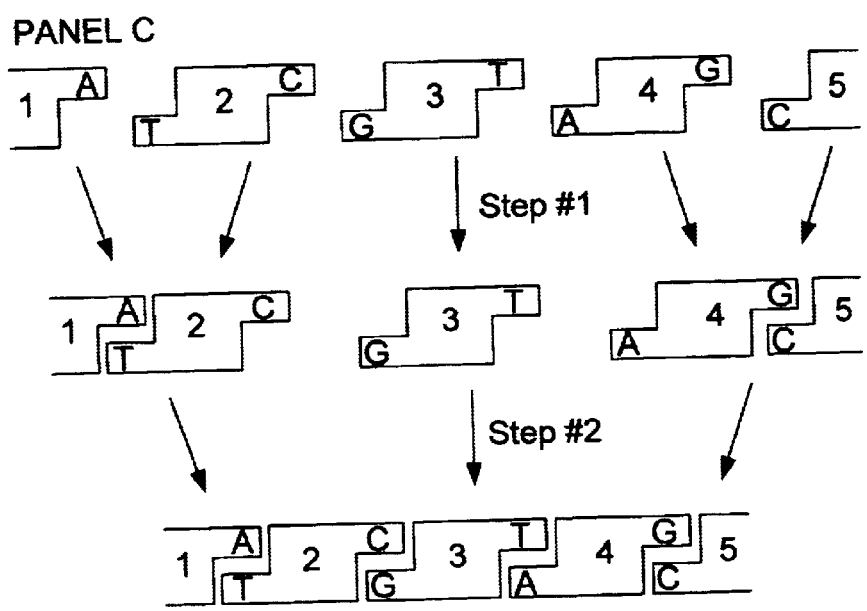

UNIQUE OVERALL ASSEMBLY ORDER ACHIEVED BY
SEQUENTIALLY COUPLING THE BUILDING BLOCKS.
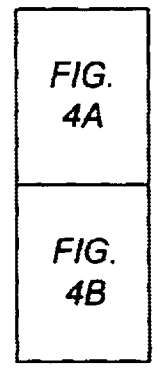
FIGURE 4
PANEL A
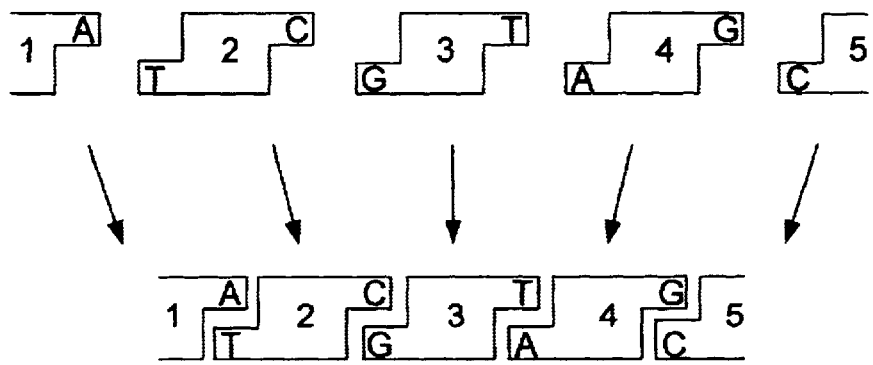
PANEL B
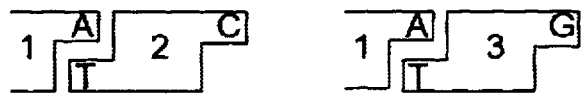
FIGURE 4A

```
                                                                    100
ACACGG CCA  GGGTGATTCC  GTTCTGTTTC  TTCACGGCAA  CCCGACGTCG
ACGTGGGAGA  GGGCGACCCG  ATCGTGTTCC  TCCACGGAAA  TCCCACGTCG
AGATGGGCGA  GGGTGATCCC  ATCATTTTCC  AACACGGCAA  TCCGACCTCA
ACGAAGGCAA  GGGTGACGCC  ATCGTCTTTC  AGCACGGCAA  CCCCACGTCG
AAGTGGGACG  GGGCGACCCC  ATCGTACTCT  TGCACGGCAA  CCCCACCTCG
ATACCGGCGA  GGGAGCGCCG  ATCGTGTTCC  TTCACGGCAA  CCCGACTTCC
GCGTCGGCGA  T...CTTCCC  GTCGTGTTCC  TGCACGGCAA  CCCCACGTCG
GACCGCGGGA  TGGCACGCCT  GTGCTGTTCC  TGCACGGTAA  CCCGACCTCG
------G---  ----------  -T--T--T--  --CACGG-AA  -CC-AC-TC-
```

*FIGURE 6B*

REPRESENTS 15% OF GENE

```
                                                            150
TCGTATCTGT GGAGGGGCGT AATGCCTTTT GTGACGGACG TCGCCCGATG
TCGTACCTGT GGCGGAAACGT GATTCCCCAC GTTGCCGGCT TGGGACGCTG
TCGTACCTGT GGCGCAAACAT CATGCCCCAT GTGCAACAGC TCGGTCGCTG
TCTTACTTGT GGCGCAAACAT CATGCCGCAC TTGGAAGGGC TGGGCCGGCT
TCGTACCTCT GGCGCAAACGT GTTGCCGCAC CTGGCGCCGT TAGGCCGCTG
TCCTATCTTT GGCGCAAACAT CATCCCCTAT CTCGCGGGATC ACGGCAGATG
TCTCACGTCT GGCGCAAACGT GATCCCGCAC GTCGCTGGCC AGCACCGGTG
TCCTACCTGT GGCGCAAACAT CATCCCGCAT GTAGCACCGA GTCATCGGTG
TC––––A–––T––T GG–G–––C–T ––T–CC––– ––T––––––– ––––G––––
```

FIGURE 6C

FIGURE 7

| Fig.7A |
|--------|
| Fig.7B |

```
              NcoI
                                                                                          CCGT
150am13_00  c ATG ATGCACG  GCGATATTTC  ATCGAGCAAT  GACACGGTCG  GCGTTG CCGT
150AM7_001  c ATG CATCACG  GCGACATTTC  ATCGAGCAAT  GACACGGTCG  GCGTTG CCGT
431am7_002  c ATG AGACACG  GAGATATCTC  CAGCAGCAAC  GATTGCGTGG  GCGTGG CCGT

GAG     GT
150am13_00    CGTGAAC TAC   AAGATG CCTC   GCCTTCATAC  CAAGGCG GAG   GT TTTA GCGA
150AM7_001    CGTGAACTAC    AAGATGCCGC    GGCTTCACAC  CAAGGCT GAG   GT GCTG GCCA
431am7_002    CGTGAACTAC    AAGATGCCGC    GGCTGCATAC  CCGCGCG GAG   GT GATG GAGA

CGG
150am13_00    ACGCCAGAAA   GATCGGC GAG   ATGATCGTCG  GCATGAAGAC  CGG CCT G CCC
150AM7_001    ACTGCCGCAA   GATCGCCGAC    ATGCTGGTCG  GCATGAAGAG  CGG CCT GCCG
431am7_002    ACGCCGCAA    GATCGCCGAC    ATGGTCGTGG  GCATGAAGCG  CGG CCT GCCC

CCACG
150am13_00    GGAATGGATC   TGGTGATCTT   CCCGGAA TAT   TCGAC CCACG   GCATCA TGTA
150AM7_001    GGAATGGATC   TGGTGATCTT   CCCGGAATAT    TCCAC CCACG   GCATCA TGTA
431am7_002    GGCATGGACC   TGGTCATCTT   CCCCGAGTAC    TCCAC CCACG   GCATCA TGTA

CCC    GG
150am13_00    CGACTCC AAG   GAAATGTACG  ATACCGCGTC  CGTCGTG CCC   GG CGAG GAGA
150AM7_001    CGACTCCAAG    GAGATGTACG  ACACGGCGTC  GACGGTG CCG   GG TGAA GAGA
431am7_002    CGACGCCAAG    GAAATGTACG  AAACCGCTTC  GGCCATT CCG   GG CGAA GAGA

G     GGG
150am13_00    CCGAGATTTT   TGCCGAA GCC   TGCCGCAAGG  CGAAAGTCT G   GGG CGT GTTC
150AM7_001    CCGAGATTTT   CGCCGAGGCC   TGCCGCAAGG  CCAAGGTCT G   GGG CGT GTTC
431am7_002    CTGCTGTGTT   CGCCGACGCC   TGCCGCAAGG  CCAACGTAT G   GGG CGT GTTT

AAAG    C
150am13_00    TCGCTCACCG   GCGAACGTCA   CGAGGAA CAT   CCGAAG AAGG   C GCCCT ACAA
150AM7_001    TCGCTGACCG   GCGAGCGCCA   CGAGGAGCAT  CCCAAT AAAG    C GCCGT ACAA
431am7_002    TCGCTGACGG   GCGAGCGCCA   CGAAGAGCAC  CCGAAC AAGG    C GCCGT ACAA

CAG    AA
150am13_00    CACGCTG ATC   CTGATGAACG  ACAAGGGCGA  GGTGGTC CAG   AA ATAC CGCA
150AM7_001    CACCCTGATC    CTGATGAACG  ACAAGGGTGA  AGTCGTT CAG   AA ATAT CGCA
431am7_002    CACGCTCATC    CTGATGAACA  ACAAGGGCGA  GATCGTG CAG   AA GTAC CGCA

GGTA
150am13_00    AGATCATGCC   GTGGGTT CCG   ATCGAGGGCT  GGTA CCCGG   CAACTG C ACC
150AM7_001    AGATCATGCC   GTGGGTGCCG   ATCGAAGGCT  GGTA TCCCGG   CAACTG CACG
431am7_002    AGATCATGCC   CTGGGTGCCG   ATCGAAGGCT  GGTA TCCGGG   CGATTG CACC

TGAAG
150am13_00    TACGTCTCCG   ACGGGCCGAA  GGGCA TGAAG   GTTTCGCTGA  TCATCT GCGA
150AM7_001    TACGTCTCCG   AAGGCCCGAA  GGGCA TGAAG   ATGTCGCTGA  TCATCT GCGA
431am7_002    TATGTGTCGG   AAGGCCCCAA  GGGAC TGAAG   ATCAGCCTCA  TCATCT GCGA

TCTGGCG
150am13_00    TGACGGC AAC   TATCCGGAAA   TCTGGCG CGA   CTGCGCC ATG   AAGGGC GCCG
150AM7_001    CGACGGCAAC    TACCCGGAAA   TCTGGCG TGA   CTGCGCGATG   AAGGGC GCCG
431am7_002    CGACGGCAAT    TACCCCGAGA   TCTGGCG CGA   TTGCGCCATG   CGGCGC GCCG
```

FIGURE 7A

| | | | | | |
|---|---|---|---|---|---|
| | | CCAG | | | |
| 150am13_00 | AGCTGATCGT | GCGCTGCCAG | GGCTACATGT | ATCCGGCCAA | GGACCAGCAG |
| 150AM7_001 | AACTGATCAT | CCGCTGCCAG | GGCTACATGT | ATCCGGCCAA | GGATCAGCAG |
| 431am7_002 | AGCTGATCGT | GCGTTGCCAG | GGATACATGT | ACCGGGCCAA | GGACCAGCAG |
| | | GC | | | |
| 150am13_00 | GTCATCATGG | CGAAGCGAT | GGCGTGGGCG | AATAATTGTT | ACGTCGCGGT |
| 150AM7_001 | GTGCTGATGG | CGAAGCAAT | GGCCTGGGCC | AACAACGTTT | ATGTCGCGGT |
| 431am7_002 | GTCATGGTGT | CCAAGCCAT | GGCGTGGATG | AACAACGTCT | ACGTGGCGGT |
| | | GGCTTCG | | | |
| 150am13_00 | TTCCAATGCC | GCGGGCTTCG | ATGGCGTCTA | TTCGTATTTC | GGCCACTCGG |
| 150AM7_001 | CGCCAATGCC | TCGGGCTTCG | ACGGCGTCTA | CTCGTATTTC | GGCCATTCGG |
| 431am7_002 | GGCCAATGCC | GCGGGCTTCG | ACGGCGTGTA | TTCCTACTTC | GGCCATTCGG |
| | | TTCGA | | | |
| 150am13_00 | CGATCATCGG | CTTCGATGGC | CGCACGCTCG | GCGAATGCGG | CGAGGAAGAA |
| 150AM7_001 | CGATCATCGG | CTTCGACGGC | CGTACCCTCG | GCGAATGCGG | CGAGGAGGAT |
| 431am7_002 | CCATCATCGG | CTTCGACGGC | CGCACGCTGG | GCGAATGCGG | TGAAGAAGAC |
| | | C    AGTA | | | |
| 150am13_00 | TACGGCATCC | AGTATGCCCA | GCTTTCGAAG | ATGCTGATCC | GCGACGCCCG |
| 150AM7_001 | TATGGCATCC | AGTATGCCGC | CATCTCCAAG | TCGCTGATCC | GCGACGCGCG |
| 431am7_002 | ATGGGCGTCC | AGTACGCCGA | GCTCTCCACC | AGCCTGATCC | GCGACGCGCG |
| | | CAATC | | | |
| 150am13_00 | CCGCACCGGA | CAATCGGAAA | ACCATCTCTT | CAAGCTGGTG | CATCGTGGCT |
| 150AM7_001 | CCGCACCGGC | CAATCGGAAA | ACCATCTCTT | CAAGCTGGTG | CACCGTGGCT |
| 431am7_002 | CAAGACCATG | CAGTCGCAGA | ACCACTTGTT | CAAGCTGGTG | CACCGCGGCT |
| | | GATCAA | | | |
| 150am13_00 | ACACCGGGTT | GATCAACTCC | GGCGAGGGCG | ACCGCGGTCT | CGCGGCCTGT |
| 150AM7_001 | ACACCGGCAT | GATCAATTCC | GGCGAGGGCG | ACCGCGGTGT | CGCGGCTTGC |
| 431am7_002 | ACACCGGCAA | GATCAATTCC | GGCGAAGAGG | CCACCGGCGT | CGCGGCATGC |
| | TTA | | | | |
| 150am13_00 | CCTTATGAGT | TCTACAACAA | ATGGATCGCC | GATCCGGAAG | GCACCCGCGA |
| 150AM7_001 | CCGTATGATT | TCTATTCGAA | ATGGATCGCC | GATCCGAGG | GTACACGCGA |
| 431am7_002 | CCGTACAACT | TCTACGCCAA | CTGGATCAAC | GATCCGGAGG | GCACGCGCAA |
| | ATGGT | | | | |
| 150am13_00 | AATGGTCGAG | TCCTTTACCC | GGCCGACGGT | GGGAACCGAT | GAAGCGCCCA |
| 150AM7_001 | GATGGTGGAA | TCCTTCACGC | GTCCGACGGT | GGGTGTGGAG | GAATGCCCGA |
| 431am7_002 | GATGGTCGAA | TCCTTCACCC | GGTCCACCGT | GGGCACGCCG | GAGTGCCCCA |
| | TCGAG | | | | |
| 150am13_00 | TCGAAGGCAT | CCCGAACAAG | GTCGCGGTGC | ACCGCTGA | aagct |
| 150AM7_001 | TCGAGGCAT | TCCGAACAAG | GCCACCACGC | ACCGCTGA | aagct |
| 431am7_002 | TGGACGGCAT | CCCCAACGAG | GACGCCAAGC | ACCGCTAG | aagct |
| | | | | | HindIII |

FIGURE 7B

Ncol
FIGURE 9

GAP LIGATION

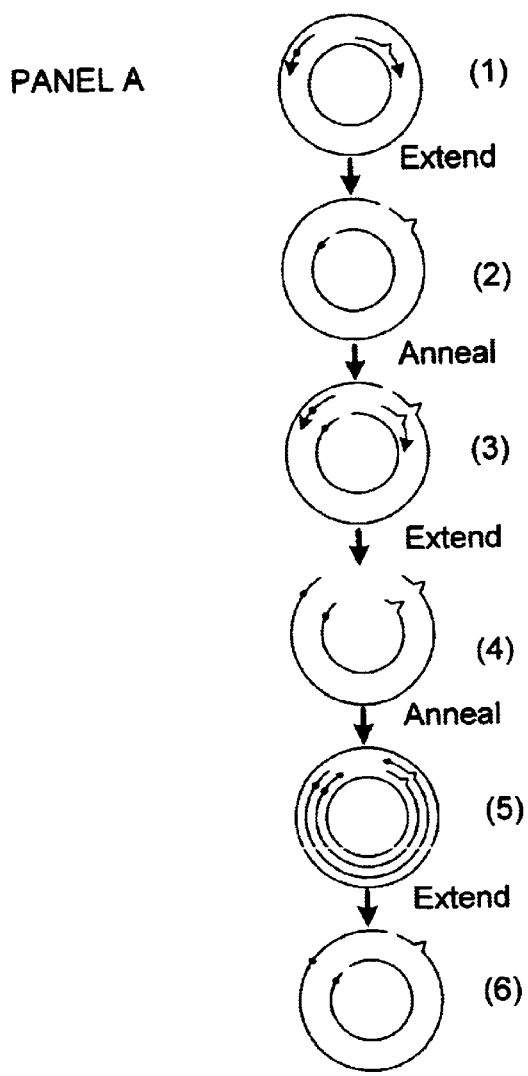
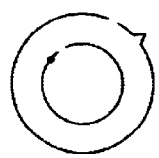
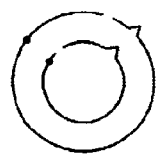
Molecule (A)   Molecule (B)
FIGURE 12

PANEL A
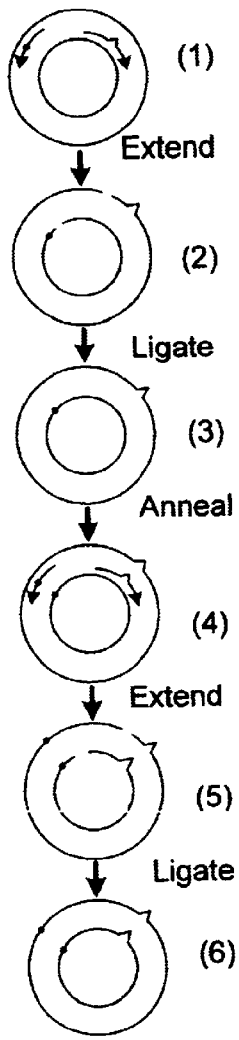
(1) Extend
(2) Ligate
(3) Anneal
(4) Extend
(5) Ligate
(6)
PANEL B
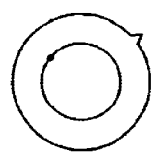 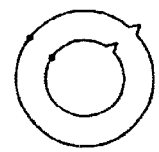
Molecule (A)  Molecule (B)
*FIGURE 13*

The figure below shows an example of the directed evolution of a genetic vaccine, comprised of an M13 phage-based vaccine, to achieve optimization for oral delivery.

FIGURE 30

An alignment of the nucleotide sequences of two human CMV strains and one monkey strain.

```
                          1                                                        50
AF026939CMV       (1)  ------------------GTGGAAACCTC----------TTCAGCATTT-GCTTGGAATCAGTAAG
AF047524humUL104  (1)  ------------------CTAGTGAAATCCGTATGACCTTCCAGCAGGCCGCGGATCATCAGGCC
AF078102Rhesus    (1)  ATCGATTTAAA-CTGCCCGA----TTGGAGGTTGTCGCTGAACACTTTGTGA 51                                                       100
AF026939CMV      (38)  CTAAAAACAAAATCAACCGGAGACCCCAGCTTTTCAGAACTGAAGGAAA---
AF047524humUL104 (49)  TCCATTTCGAAATGGGC--CGACAC--GGC--GCTCTGG-GCCGCGCTCCTC
AF078102Rhesus   (47)  GTCTTTTCGAAGTAGATATGACACT-GCTTTCAGAAGTGCCGCTGAA-----

101                                                       150
AF026939CMV      (87)  --CAGCCATCATGAGTGAGGTCACAAGAATTCCTTGGAAATCCT--------
AF047524humUL104 (94)  GTCTGCCGTGATCAGGCCGGGGCGCG----------GACCTTCAAGCTTCTGG
AF078102Rhesus   (95)  GGCTGGGGTACATATCTGAAGCAGCAGATGAGCTCC--GAGGACGTGA 151                                                       200
AF026939CMV     (133)  CCCACAGCTGAAATGCCATTTCAC----CTGGAACTTATTCAAGGAAGACA
AF047524humUL104(142)  GCCGGCGCT--CGAGCAGTTCCCCTTCTGGCGTCTACTCGGCCGTTCG
AF078102Rhesus  (144)  TACGCTGGACTGGAGATATCTGAAGCAGCAGATGAGCTCGTAATCT-GTGTTCCAACG 201                                                       250
AF026939CMV     (180)  GTGTCTTCA----AGGGATGTAGAAGATAGAGTGTG----AACCAGATTGA
AF047524humUL104(191)  CGG-CTCATTGACTGGCCGGGCCTTCTCGGCGTTTCTCGGCGCAAATCAGTCCA
AF078102Rhesus  (193)  TTGTCTCTGACTATGTTACAGGGTGTTTATCTGCGACAATAGATCAA
```

| FIG. 30A | FIG. 30B | FIG. 30C | FIG. 30D | FIG. 30E | FIG. 30F | FIG. 30G | FIG. 30H | FIG. 30i |
|---|---|---|---|---|---|---|---|---|

```
                           1001                                                         1050
AF026939CMV   (934) GATTGGTGCTGCTAGAAGGCAAAAGTAAGACAAAATGCAGAATACAGGAG
AF047524humUL104(942) GACGGTTTTGGTGTCCACACAGGAAGGGTCAAGTCTGCAGG---AAG
AF078102Rhesus (961) GCTGAGAATCGAGGAA-AGCGACGTGTTTC-GTCTAGCGAT---AAC
                           1051                                                        1100
AF026939CMV   (984) AATCTGAAGCTAGTGGAAATAAAGAGATG---ATTGAAGCACTAAAGCAAT
AF047524humUL104(986) GACTCGACGCTGTCCTCGATGCGCGATTTGCTGTCCGAGAGTT
AF078102Rhesus(1004) ATCCAAATGTTGTTCA-GATGCGGGTTTC----TTAAGCTCCGTGGCATT
                           1101                                                        1150
AF026939CMV  (1032) ATGCTATGGACTATTCGAATAAAGCTCTTGAGAAGGACTGAATCCTCTG
AF047524humUL104(1036) AAGAAAAACTTCATAATGGACTTTT-TGGCCGTCGCT-GCCCGGTCGTG
AF078102Rhesus(1049) ACGCGAT---TTGACCGGGATTGCG-TGGCGAGCTGGTCGTGGAGAGTA
                           1151                                                        1200
AF026939CMV  (1082) AATGCATACTCCGATCTCCGTGAG-TTCTGGAGGAGGAAATGTTATCAGA
AF047524humUL104(1084) C-TGC)--ATCTCCACCAGCTTCTTGAGCTTGAGCTGGTGGTGGCGGC
AF078102Rhesus(1095) AGTGC---TACTGCTATCAGTCCCGTAAGCAAGATCT-CTCTTGGTGCT
                           1201                                                        1250
AF026939CMV  (1131) CACCATTCAATAAGGAAGTCCCTGAT---GCTGAAAAGCAACAATC----C
AF047524humUL104(1131) TGGCCGGTCACCAC---TTTCACAGGAAAGTATTGAGCAACTGGCGGC
AF078102Rhesus(1143) CTATGTCAACAG----AGTTACCGCC-----GAGCAGCTC-----
```

```
                                                        2050
AF026939CMV   (1893) AGGCTGAGGCAGGA----GAATGGCGTGAACCTGAAGAAGAGTTGCAG
AF047524humUL104 (1882) CAGCAACGGCAGGAAGCTCATGGTCTTGGCCCGTGG-GGAAATGTGATG
AF078102Rhesus (1853) --GAAACACATTA--CATATTTAGACACACGT-ATCACTTGT------G
                                                        2100
AF026939CMV   (1940) TGAGCGAGATT----GGGCCGGTGC---ACTCCAGCCGGG-CAACAGAGC
AF047524humUL104 (1931) ACGGCTGGTCATCCACACGGAGGCCCAAGTACGACGACGCTT
AF078102Rhesus (1892) AAAGCTGAGTCA---ACATG---------ATGAATTGTCGGACGAGGCG
                                                        2150
AF026939CMV   (1984) AAGACTGGAATTCCTGCAGCCGGGGGATCCACT---ATTCTAGAGCGCC
AF047524humUL104 (1981) GATCCTGAACCCTCTGTCGGCCGCCACAGATGAAGGATCGCTGACAAGG
AF078102Rhesus (1932) GGTGTCGT-TCTGTGTTTCTGTGTAGAGTTTAC--ATTTATTATGGT---
                                                        2200
AF026939CMV   (2032) GCAAACGGCCGCCCTCTCGCGCGGAGCGCTTGCGCCCGAGGATTTTCGTTCCAG
AF047524humUL104 (2031) TCAAAGTCCCTCTCGCGGAGTCCGAGCGCTT----------
AF078102Rhesus (1979) TCAAAGTTCATTTCTAA--------------------------------
                     2201       2214
AF026939CMV   (2057) -------------TGGTTTCGCTCCAT-----------
AF047524humUL104 (2081) ---------------
AF078102Rhesus (1999) ---------------
```

*FIGURE 30I*

An alignment of IL-4 nucleotide sequences from 3 species (human, primate and canine).

```
                              1                                                  50
AF187322 Canis    IL-4   (1)  TGCATCGTTAGGTCTCCTAGTAAACTGATTGTCTGCTATTGTCACTGC
NM_000589 Homo sapien IL-4 (1) TGCATCGTTAGGTTCTCCTGATAAACTGATTAATT-GCCTCACATTGTCACTGC
          U19838 Cercocebus IL-4 (1)

51                                                 100
AF187322 Canis    IL-4   (51) AAATAGAATCTATTAATGGGTCTCACCTCCAACTGATTCAACTCTGG
NM_000589 Homo sapien IL-4 (50) AAATGAACACTATTAATGGGTCTCACCTCCCAACTGCTTCCCCCTCTGT
          U19838 Cercocebus IL-4 (1)                  ATGGGTCTCACCTCCAACTGCTTCCCCTCTGT 101                                                150
AF187322 Canis    IL-4  (101) TCTGCTTACTAGCACTCACCAGCACTTTGTCCACAGGACACTAACTTCAAT
NM_000589 Homo sapien IL-4 (100) TCTTCCTGCTAGCATGTGCCGGCAACTTTGTCCACAGGACACAAGTGCGAT
          U19838 Cercocebus IL-4 (35) TCTTCCTGCTAGCATGTGCCGGCAACTTTGCCCATGGACACAACTGCAT 151                                                200
AF187322 Canis    IL-4  (151) ATTACTATTAAAGAGACATCATCAAAATGTTGAACATCCTCACAGAGAGTAAA
NM_000589 Homo sapien IL-4 (150) ATCACCTTACAGGAGATCATCAAAACTTTGAACAGCCTCACAGAGCAGA
          U19838 Cercocebus IL-4 (85) ATGGCCTTACAGGAGATCATCAAAACTCGAACAGCCTCACAGAGCAGA 201                                                250
AF187322 Canis    IL-4  (201) CGACTCGTGCATGGAGTTGACTGTAGGAGGTTCTTCACTGTCCTCAAG
NM_000589 Homo sapien IL-4 (199) AGACTCTGTGCACCGAGTTGACCGTAACAGACATCTTTGCTGCCTCCAAG
          U19838 Cercocebus IL-4 (134) AGACTCTGTGCACCGAGTTGACCGTAACGGACATCCTTGCTGCCTCCAAG 251                                                300
AF187322 Canis    IL-4  (250) AACACAAGCGATAAGGAAGAATCTTCTGCAGAGCTGTACTGTACTGCGGCA
NM_000589 Homo sapien IL-4 (249) AACACAACTGAGAAGGAAAAACCTTCTGCAGGGCTGCACTGTGCTCCGCA
          U19838 Cercocebus IL-4 (184) AACACAACTGAGAAGGAAAACCTTCTGCAGGGCTGCACTGTGCTCCGCA
```

| FIG. 31A | FIG. 31B | FIG. 31C |
|---|---|---|

```
AF187322 Canis IL-4        (493) ACATAGCTTATTTAAATATATTTATA----ATTTATA-----CATAATA  600
NM_000589 Homo sapien IL-4 (549) G-ATAGCTTTATTTTTAAGTATTATATATTATTATNACTCATCATAAAA
U19838 Cercocebus IL-4     (464) ------------------------------------------------

AF187322 Canis IL-4        (536) TAA---TATATATAGACTCTAATATAAAAAAAAAAAA  637
NM_000589 Homo sapien IL-4 (598) TAAAGTATATATAGAATCTAA----------------
U19838 Cercocebus IL-4     (464) -------------------------------------
```

*FIGURE 31C*

Working Progenitor templates
Library of IL-12 genes
(p35/p40 fusions)
1) Directed Evolution  2) Express in bacterial host
Bacterial colonies 
3) Robotic colony picking
8) Optionally repeat steps 1-7
7) Identification and selection of clones
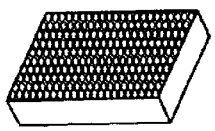  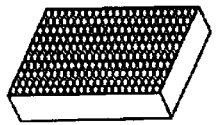
96 wells X 50
6) Transfer of supernatants to human T cell cultures
4) High throughput plasmid purification
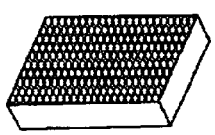  5) Transfection to CHO cells  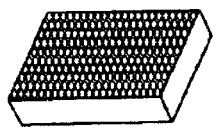
FIGURE 38

1) Directed Evolution
Library of Working
Progenitor templates of
CD80 &/or CD86 genes
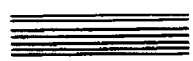
2) Express in
bacterial host
Bacterial colonies
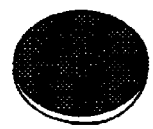
8) Optionally repeat steps 1-7
7) Identification and selection
of clones
3) Robotic colony picking
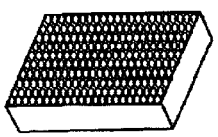
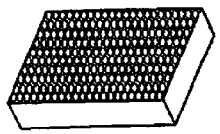
96 wells X 50
6) Co-culture with
T cell cultures
4) High throughput vector
purification
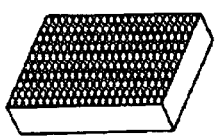
5) Transfection to dendritic
cells/ U937 cells
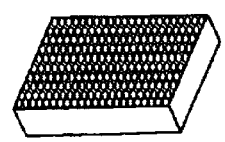
FIGURE 40

An alignment of two CMV-derived nucleotide sequences from human and primate species.

```
                         1                                                50
AF078102 Rhesus    (1)   ATCGATTTAAACTGCCCGATTGAGGTTGTCGCTGAACACTTTGTGAGTC-
  M67443 Towne     (1)   ----------------------------GCCATGGCATCCGTACTGGTCC
                         51                                              100
AF078102 Rhesus   (50)   -TTTTCGAAGGTAGATATGACACTGCTTTCCAGAAGTGCCGCTGAAGCCT
  M67443 Towne    (24)   CATTTCGGGGCACGTGCTGAAAGCCGTGTTTAGTCGCGGCGAC-ACGCCG
                         101                                             150
AF078102 Rhesus   (99)   GGGGTACATATCTGAAGCAGCGAGATGAGCGTCCCGAGGACGTG-ATACG
  M67443 Towne    (73)   GTG--------CTGCCGCA-CGAGACGCGACTCCTGCAGACGGGTATCCA
                         151                                             200
AF078102 Rhesus  (148)   C-TGCGACTACGGC-GTCTTCAGTTTGCGTAATCTCGTGTTCCAACGTTG
  M67443 Towne   (114)   CGTGCGCGTGAGCCAGCCCTCGCTGATCCTGGTGTCGCAGTACACGCCCG
                         201                                             250
AF078102 Rhesus  (196)   TCT-GAC--TATGTTACAG-GGTGTTTATCTGCGACAATACGATCAACCG
  M67443 Towne   (164)   ACTCGACGCCATGCCACCGCGGCGACAATCAGCTGCAGGTGCAGCACACG
                         251                                             300
AF078102 Rhesus  (242)   TG-TTTACGAGAATATATTAAAAAGAATTCTGGTACTATCATTCCGTTGC
  M67443 Towne   (214)   TACTTTACGGGCAGCGAGGTGGAGAACGTGTCGGTCAA------CGT-GC
                         301                                             350
AF078102 Rhesus  (291)   GCAACCCCTGTAGCTGGTTTCTCGTCCTTCGCTCTGGTATAGATATTCCC
  M67443 Towne   (257)   ACAACCCCACGGGCCGGA------------GC----------ATCTGCCC
                         351                                             400
AF078102 Rhesus  (341)   CAGGTAGAAACCCGT-TCGTTCGACGAGTAT-CTTTGCTGCAAAGAGAAA
  M67443 Towne   (285)   CAGCCAAGAGCCCATGTCGATCTATGTGTACGCGCTGCCGCTCA-AGATG
```

FIGURE 41A

| FIG. 41A | FIG. 41B | FIG. 41C | FIG. 41D | FIG. 41E | FIG. 41F |
|---|---|---|---|---|---|

```
                        2001                                                              2050
AF078102 Rhesus  (1926) GGTCCGGGTCGTTCGTGTTTCT-GTTACGAGTTTACATTTATTA
M67443 Towne     (1860) CGTCC----TCGCCCGGTGAGGACCCTCGTCGGAAGCGGCGCGATCAGC 2051                           2077
AF078102 Rhesus  (1975) TGGTTAAAGTCTTCTATTCTAA---
M67443 Towne     (1907) GAGGCCGAAGCGGC-AGCGGAAGCTT
```

*FIGURE 41F*

An alignment of the IFN-gamma nucleotide sequences from human, cat, rodent species

FIGURE 42A

| FIG. 42A |
|----------|
| FIG. 42B |

FIGURE 42

FIGURE 42B

SEQUENCE LISTING

```
<160> NUMBER OF SEQ ID NOS: 29

<210> SEQ ID NO 1
<211> LENGTH: 30
<212> TYPE: DNA
<213> ORGANISM: Artificial sequence
<220> FEATURE:
<223> OTHER INFORMATION: Defined sequence kernel
<221> NAME/KEY: misc_feature
<222> LOCATION: (1)..(30)
<223> OTHER INFORMATION: n is A, T, G, or C

<400> SEQUENCE: 1
nnknnknnkn nknnknnknn knnknnknnk                              30

<210> SEQ ID NO 2
<211> LENGTH: 30
<212> TYPE: DNA
<213> ORGANISM: Artificial sequence
<220> FEATURE:
<223> OTHER INFORMATION: Defined sequence kernel
<221> NAME/KEY: misc_feature
<222> LOCATION: (1)..(30)
<223> OTHER INFORMATION: n is A, T, G, or C

<400> SEQUENCE: 2
nnmnnmnnmn nmnnmnnmnn mnnmnnmnnm                              30

<210> SEQ ID NO 3
<211> LENGTH: 5
<212> TYPE: PRT
<213> ORGANISM: Artificial sequence
<220> FEATURE:
<223> OTHER INFORMATION: Antibody spacer peptide.  The entire peptide
      sequence can be repeated more than one time

<400> SEQUENCE: 3

Gly Gly Gly Gly Ser
1               5

<210> SEQ ID NO 4
<211> LENGTH: 16
<212> TYPE: PRT
<213> ORGANISM: Plasmodium berghei

<400> SEQUENCE: 4

Pro Pro Pro Pro Asn Pro Asn Asp Pro Pro Pro Asn Pro Asn Asp
1               5                   10                  15

<210> SEQ ID NO 5
<211> LENGTH: 20
<212> TYPE: PRT
<213> ORGANISM: Plasmodium yoelii

<400> SEQUENCE: 5

Gln Gly Pro Gly Ala Pro Gln Gly Pro Gly Ala Pro Gln Gly Pro Gly
1               5                   10                  15
```

```
Ala Pro Gln Gly
        20

<210> SEQ ID NO 6
<211> LENGTH: 12
<212> TYPE: PRT
<213> ORGANISM: Plasmodium berghei

<400> SEQUENCE: 6

Lys Gln Ile Arg Asp Ser Ile Thr Glu Glu Trp Ser
1               5                   10

<210> SEQ ID NO 7
<211> LENGTH: 10
<212> TYPE: PRT
<213> ORGANISM: Artificial sequence
<220> FEATURE:
<223> OTHER INFORMATION: Amino acid sequence encoded by primer sequences
<221> NAME/KEY: VARIANT
<222> LOCATION: (6)..(6)
<223> OTHER INFORMATION: Xaa is selected from leucine or isoleucine
<221> NAME/KEY: VARIANT
<222> LOCATION: (8)..(8)
<223> OTHER INFORMATION: Xaa is selected from glutamine and asparagine

<400> SEQUENCE: 7

Thr Thr Ile Asp Lys Xaa Leu Xaa His Glu
1               5                   10

<210> SEQ ID NO 8
<211> LENGTH: 10
<212> TYPE: PRT
<213> ORGANISM: Artificial sequence
<220> FEATURE:
<223> OTHER INFORMATION: Amino acid sequence encoded by primer sequences
<221> NAME/KEY: VARIANT
<222> LOCATION: (4)..(4)
<223> OTHER INFORMATION: Xaa is selected from methionine, lysine and
      aspartic acid
<221> NAME/KEY: VARIANT
<222> LOCATION: (7)..(7)
<223> OTHER INFORMATION: Xaa is selected from histidine, threanine and
      tyrosine
<221> NAME/KEY: VARIANT
<222> LOCATION: (8)..(8)
<223> OTHER INFORMATION: Xaa is selected from aspartic acid, glutamic
      acid and histidine

<400> SEQUENCE: 8

Phe Phe Trp Xaa Trp Val Xaa Xaa Met Leu
1               5                   10

<210> SEQ ID NO 9
<211> LENGTH: 10
<212> TYPE: DNA
<213> ORGANISM: Artificial sequence
<220> FEATURE:
<223> OTHER INFORMATION: BstNB I cleaves btw. nucleotide 9 & 10 of
      target sequence
<221> NAME/KEY: misc_feature
<222> LOCATION: (6)..(10)
<223> OTHER INFORMATION: n is any nucleotide

<400> SEQUENCE: 9 gagtcnnnnn                                                           10

<210> SEQ ID NO 10
<211> LENGTH: 10
<212> TYPE: DNA
```

```
<213> ORGANISM: Artificial sequence
<220> FEATURE:
<223> OTHER INFORMATION: BspG I restriction site

<400> SEQUENCE: 10
cgcgctggac                                                                10

<210> SEQ ID NO 11
<211> LENGTH: 223
<212> TYPE: DNA
<213> ORGANISM: Artificial sequence
<220> FEATURE:
<223> OTHER INFORMATION: Forward primer
<221> NAME/KEY: misc_feature
<222> LOCATION: (1)..(223)
<223> OTHER INFORMATION: n is any nucleotide
<221> NAME/KEY: misc_feature
<222> LOCATION: (1)..(10)
<223> OTHER INFORMATION: at least one nt. of nt. 1-10 is present
<221> NAME/KEY: misc_feature
<222> LOCATION: (21)..(120)
<223> OTHER INFORMATION: at least one nt. of nt. 21-120 is present
<221> NAME/KEY: misc_feature
<222> LOCATION: (124)..(223)
<223> OTHER INFORMATION: nt. 124-223 are optionally present

<400> SEQUENCE: 11
nnnnnnnnnn aagggaggag nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
atgnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnn                       223

<210> SEQ ID NO 12
<211> LENGTH: 215
<212> TYPE: DNA
<213> ORGANISM: Artificial sequence
<220> FEATURE:
<223> OTHER INFORMATION: Revers primer
<221> NAME/KEY: misc_feature
<222> LOCATION: (1)..(215)
<223> OTHER INFORMATION: n is any nucleotide
<221> NAME/KEY: misc_feature
<222> LOCATION: (1)..(10)
<223> OTHER INFORMATION: at least one nt. of nt. 1-10 is present
<221> NAME/KEY: misc_feature
<222> LOCATION: (16)..(115)
<223> OTHER INFORMATION: at least one nt. of 16-115 is present
<221> NAME/KEY: misc_feature
<222> LOCATION: (116)..(215)
<223> OTHER INFORMATION: nt. 116-215 are optionally present

<400> SEQUENCE: 12
nnnnnnnnnn aagggnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnn                                215

<210> SEQ ID NO 13
<211> LENGTH: 123
<212> TYPE: DNA
<213> ORGANISM: Artificial sequence
<220> FEATURE:
<223> OTHER INFORMATION: Forward primer with 10-100 template specific
      sequence
<221> NAME/KEY: misc_feature
<222> LOCATION: (24)..(123)
<223> OTHER INFORMATION: n is any nucleotide
```

```
<221> NAME/KEY: misc_feature
<222> LOCATION: (34)..(123)
<223> OTHER INFORMATION: nt. 34-123 are each optionally present

<400> SEQUENCE: 13
ctagaagaga ggagaaaacc atgnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120 nnn                                                                     123

<210> SEQ ID NO 14
<211> LENGTH: 121
<212> TYPE: DNA
<213> ORGANISM: Artificial sequence
<220> FEATURE:
<223> OTHER INFORMATION: Reverse primer with 10-100 nt long template
      specific sequence
<221> NAME/KEY: misc_feature
<222> LOCATION: (22)..(121)
<223> OTHER INFORMATION: n is any nucleotide
<221> NAME/KEY: misc_feature
<222> LOCATION: (32)..(121)
<223> OTHER INFORMATION: nt. 32-121 are each optionally present

<400> SEQUENCE: 14
gatcaaaggc gcgcctgcag gnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120 n                                                                       121

<210> SEQ ID NO 15
<211> LENGTH: 23
<212> TYPE: DNA
<213> ORGANISM: Artificial sequence
<220> FEATURE:
<223> OTHER INFORMATION: Forward primer

<400> SEQUENCE: 15
ctagaaggga ggagaaaacc atg                                                23

<210> SEQ ID NO 16
<211> LENGTH: 21
<212> TYPE: DNA
<213> ORGANISM: Artificial sequence
<220> FEATURE:
<223> OTHER INFORMATION: Reverse primer

<400> SEQUENCE: 16
gatcaaaggc gcgcctgcag g                                                  21

<210> SEQ ID NO 17
<211> LENGTH: 15
<212> TYPE: PRT
<213> ORGANISM: Artificial sequence
<220> FEATURE:
<223> OTHER INFORMATION: Linker peptide

<400> SEQUENCE: 17

Gly Gly Gly Gly Ser Gly Gly Gly Ser Gly Gly Gly Gly Ser
1               5                  10                  15

<210> SEQ ID NO 18
<211> LENGTH: 39
<212> TYPE: DNA
<213> ORGANISM: Artificial sequence
<220> FEATURE:
<223> OTHER INFORMATION: Forward primer 9511TopF
```

<400> SEQUENCE: 18
ctagaaggga ggagaattac atgaagcggc ttttagccc          39

<210> SEQ ID NO 19
<211> LENGTH: 27
<212> TYPE: DNA
<213> ORGANISM: Artificial sequence
<220> FEATURE:
<223> OTHER INFORMATION: Reverse primer 9511TopR

<400> SEQUENCE: 19
agctaagggt caaggccgca cccgagg          27

<210> SEQ ID NO 20
<211> LENGTH: 2056
<212> TYPE: DNA
<213> ORGANISM: Homo sapiens

<400> SEQUENCE: 20

| gtggaaacct cttcagcatt tgcttggaat cagtaagcta aaaacaaaat caaccgggac | 60 |
| cccagctttt cagaactgca gggaaacagc catcatgagt gaggtcacca agaattccct | 120 |
| ggagaaaatc ctcccacagc tgaaatgcca tttcacctgg aacttattca aggaagacag | 180 |
| tgtctcaagg gatctagaag atagagtgtg taaccagatt gaattttttaa acactgagtt | 240 |
| caaagctaca atgtacaact tgttggccta cataaaacac ctagatggta caacgaggc | 300 |
| agccctggaa tgcttacggc aagctgaaga gttaatccag caagaacatg ctgaccaagc | 360 |
| agaaatcaga agtctagtca cttggggaaa ctacgcctgg gtctactatc acttgggcag | 420 |
| actctcagat gctcagattt atgtagataa ggtgaaacaa acctgcaaga aattttcaaa | 480 |
| tccatacagt attgagtatt ctgaacttga ctgtgaggaa gggtggacac aactgaagtg | 540 |
| tggaagaaat gaaagggcga aggtgtgttt tgagaaggct ctggaagaaa agcccaacaa | 600 |
| cccagaattc tcctctggac tggcaattgc gatgtaccat ctggataatc acccagagaa | 660 |
| acagttctct actgatgttt tgaagcaggc cattgagctg agtcctgata accaatacgt | 720 |
| caaggttctc ttgggcctga aactgcagaa gatgaataaa gaagctgaag gagagcagtt | 780 |
| tgttgaagaa gccttggaaa agtctccttg ccaaacagat gtcctccgca gtgcagccaa | 840 |
| attttacaga agaaaaggtg acctagacaa agctattgaa ctgtttcaac gggtgttgga | 900 |
| atccacacca acaatggct acctctatca ccagattggg tgctgctaca aggcaaaagt | 960 |
| aagacaaatg cagaatacag gagaatctga agctagtgga aataaagaga tgattgaagc | 1020 |
| actaaagcaa tatgctatgg actattcgaa taaagctctt gagaagggac tgaatcctct | 1080 |
| gaatgcatac tccgatctcg ctgagttcct ggagacggaa tgttatcaga caccattcaa | 1140 |
| taaggaagtc cctgatgctg aaaagcaaca atcccatcag cgctactgca accttcgaaa | 1200 |
| atataatggg aagtctgaag acactgctgt gcaacatggt ttagagggtt tgtccataag | 1260 |
| caaaaaatca actgacaagg aagagatcaa agaccaacca cagaatgtat ccgaaaatct | 1320 |
| gcttccacaa aatgcaccaa attattggta tcttcaagga ttaattcata agcagaatgg | 1380 |
| agatctgctg caagcagcca atgttatga aaggaactg ggccgcctgc taagggatgc | 1440 |
| cccttcaggc ataggcagta ttttcctgtc agcatctgag cttgaggatg gtagtgagga | 1500 |
| aatgggccag ggcgcagtca gctccagtcc cagagagctc ctctctaact cagagcaact | 1560 |
| gaactgagac agaggaggaa aacagagcat cagaagcctg cagtggtggt tgtgacgggt | 1620 |

-continued

| aggaggatag gaagacaggg ggccccaacc tgggattgct gagcagggaa gctttgcatg | 1680 |
| --- | --- |
| ttgctctaag gtacattttt aaagagttgt tttttggccg ggcgcagtgg ctcatgcctg | 1740 |
| taatcccagc actttgggag gccgaggtgg gcggatcacg aggtctggag tttgagacca | 1800 |
| tcctggctaa cacagtgaaa tcccgtctct actaaaaata caaaaaatta gccaggcgtg | 1860 |
| gtggctggca cctgtagtcc cagctacttg ggaggctgag gcaggagaat ggcgtgaacc | 1920 |
| tggaaggaag aggttgcagt gagccaagat tgcgcccctg cactccagcc tgggcaacag | 1980 |
| agcaagactc ggaattcctg cagcccgggg gatccactat tctagagcgc cgcaacggcc | 2040 |
| gtggagtcca gagatg | 2056 |

<210> SEQ ID NO 21
<211> LENGTH: 2094
<212> TYPE: DNA
<213> ORGANISM: Homo sapiens

<400> SEQUENCE: 21

| ctagtgaaat ccgtatggac ctccagcacg ccgcggatca tcagggcctc catttcgaaa | 60 |
| --- | --- |
| tcggccgaca cgctctgggc cgcgccgctc ctcgtctgcc gtgatcaggc ggcgcggcgc | 120 |
| ggaccttca agcgttcctg ggccgccgct cgaggcagtt ccccttctg gcactccgcc | 180 |
| cgccgcttcg cggctcattt ggcgtcggcg cgccttctcg cggctgcaaa tcagctccac | 240 |
| gtatcggcaa aacttgctgt cgtcgtaggc ggcggccacg atctcgccga aggagagctg | 300 |
| caggtaggcc tcgggtacgg ggtccagcgt gcccagcgcc aggatgtgac acagataggg | 360 |
| cagggtcacg cgctctaccg tgtaattgga gtagacgatg gcctcttcgg ccccctgatg | 420 |
| cgtgaccaga cgccgcaggc gaaaggtgcg gaaatactcg ttttcccaca gctgcgtgag | 480 |
| gaagcgttcc agcgactcgg tgccgggcac gaactgcgag aagaagctgt tggccaccag | 540 |
| gcggttgtcc tccaccgcca acggacggaa aggcgccgcg tcgcgcgcct gcgcacggc | 600 |
| ctccaacacg ggcaggtggt agagttcggc gtcgcgcgcg cccaggctca tggagtcctc | 660 |
| gcggcgcgag gcgtagcgcg tgagcaggtc gcgcagttcg cgcacgcgat tctcccaggt | 720 |
| ctggttgagc gtgcgcaggt cctggatctc gtctacctgc gactggatct gctcctccag | 780 |
| gcacttgatg acctgcttct taaacaggtc gcggatgtcc cgctcgggcg ccgccgggcc | 840 |
| gggtggcggc ggcagcagcc cgacgtggcc cgcgggtcct cccaccacgg caccgccggg | 900 |
| ccccaccacg ccgggtccac ccggaccacg cgcgggtagc agacggtttt ggtccaccag | 960 |
| cgaagggctc aagtcctgca ggaaggactc gacgctgtcc tcgatgccga tgcgcgattt | 1020 |
| gctgtccgag acgttaagca aaacttcat aatggacttt ttggcgtcgc tgccccggtc | 1080 |
| gtgctgctcc atcatctcca ccagcttctt gcagttgagc tcgtggcggc tggcggtcac | 1140 |
| cactttcaca ggaaaggtat tgagcaactg gcagatcttt tggtggcggc agagcccgtc | 1200 |
| gtagcgcaga atctcctcgt gcaggtgtgc caccggcgtg gtgaacagca gcttgtcgcg | 1260 |
| ctcataagcc agcggttcgg tcgccacgta caagcggatg tgcttgccgc gcagctgcgc | 1320 |
| ctccagccgc tccgagcgca ccttcttgaa gacgcgtacc tcgggcgcgt tggctacgcg | 1380 |
| cacagctccc aggcgctcgg cctcctgcag cagcagcgcc aggttagcct gcagcaggtc | 1440 |
| ctgcgccagc gggtgtgtct cggtggctcg ctgcacggcc gcgcgtacaa attgcgcccg | 1500 |
| ctcggccgcc tcgctcggct tggtcttcac gtccagcagc ggtaccagtc ccaccgttac | 1560 |
| gcaccaatcc acgtagagac catagtcgtc gttatcggca tactgatata aaatgtcgcg | 1620 |
| gagcgcgccc agcacgcccg tttgcacgct ctggcgcaac gaggcgctcc acaccaacag | 1680 |

-continued

```
atactgctcc aggtcctctt cgtccagcgc gcggtaggga acagcgccg cgtgcaactt      1740 ccactcttcg gccacgcgcc gcaccgtgat ggtgtcaaag agcgttttgc acactccgta      1800
gagcagctgc ttgcgcagca cgcacgggtc gcgcagcact tggtgcatgc tttggccgcg      1860
acacgtcccc agaaagccgt gcagcaaccg caggaagctc atcgtctggc ccgtggggaa      1920
aatgtcgatg acggcctcgt catccacacc gcggcccacg cccaagtacg acgacgcctt      1980
gatcctcaac ctctcgtcgg ccgccaagat cgaacggatc gtcgacaagg tcaagtccct      2040
ctcgcgcgag cgctttgcgc ccgaggattt ttcgttccag tggtttcgct ccat            2094
```

<210> SEQ ID NO 22
<211> LENGTH: 1998
<212> TYPE: DNA
<213> ORGANISM: Rhesus monkey

<400> SEQUENCE: 22

```
atcgatttaa actgcccgat tgaggttgtc gctgaacact ttgtgagtct tttcgaaggt        60
agatatgaca ctgcttttcca gaagtgccgc tgaagcctgg ggtacatatc tgaagcagcg      120
agatgagcgt cccgaggacg tgatacgctg cgactacggc gtcttcagtt tgcgtaatct       180
cgtgttccaa cgttgtctga ctatgttaca gggtgtttat ctgcgacaat acgatcaacc      240
gtgtttacga gaatatatta aaaagaattc tggtactatc attccgttgc gcaacccctg      300
tagctggttt ctcgtccttc gctctggtat agatattccc caggtagaaa cccgttcgtt      360
cgacgagtat ctttgctgca aagagaaatt ggaagcactg gaatattggg ggtgcagtt       420 gcgtgatggc agtgatcgca aaaaaatcca ggagactacg tgtgtggttc tgctgggaag      480
ctatggattt gtgtacgtgt atgactggga cagtgacgga ctctttcaga taggtacctc      540
actcaaagaa ctcgcgcacc acggtttact gacatgtgaa tcggtatatc gccatccgca      600
aacgcccttc tccaccaccg agcctcgttt tcaagtcgag aaattgttgt gtctcgatcc      660
gacagacgca cgtggtctag ctaagaccgc agaaagagtt catggcgtta acgtagtagt      720 gaaaaccccct gggcgatcgg aggccgatcc cttgctcctt ctgggtactg tggagaagct      780
acgtcaaatg tatccctttg ctaaaatgag agctgataac tttagtaatc tcataaagta      840
tattaatcaa cgcatgtgtt gccgatggta cgtacttggt gttactggcc gttacgctaa      900
ttttggaatt tgctgacct gtggaataat tctgttggac gagtgcggcg tgtgttatgt      960
gctgagaatc gacgaaagcg acgtgtttcg tctagccgat aacatccaaa tgttgttcag    1020
atgcggcttt cttaagctcc gtggcattac gcgatttgac cgcggattgc gtggcgaggc    1080
tcgtctggag agtgagtgct actgctatca cggtgcccgt aagcaagatc tctcttggtg    1140
ctctatggtc aacacagtta ccgccgagca gctctgtggt gcgtacgact ggctcacgcg    1200
cagtaatcgc gctcatgata aaatacctac cagttgttgt tggggacgta gtgatttgat    1260
gcctaccgga gtattgcaag agaatcagaa ttggtgcttt ccgtggagca gtgtcacggt    1320
tctacaaggg cccaaagcg gtgcgtggca agaaaatgat gagttaacgg agaaaacgtc    1380
tgatggtact gtgatgtttc gtgtagacag aggttttct cccagaaccg taaagttcga    1440
gggtgaaagc gatgactaca cagaagagga ggaagatgat gataaccagt cagaagaaac    1500
ccctcagcat cagcctgttg tcattgttct acatgaaaca aacggcagtg ttgattctta    1560
tgatgatgag agtgagtcat ctctgtcctc agatacccat gatccaccac ccccagacat    1620
tatggccata atccaaaagg aatggcaaaa cgaagagccg gttaccaatg aaagagaatt    1680
```

| | |
|---|---|
| gttactgcgg cgtgcacgac gagctaaaca tatgaaaaag tggcattgtt ccctggaaag | 1740 |
| ggttagcatt tatgacccct tgaatgctaa tattcactgc tttgattaaa caatgcattt | 1800 |
| gtattcaatt atctaattcc ggtgtaccgt gtcatttctc catgcagtgg tgggaaacac | 1860 |
| attacatatt tagacacacg tatcacttgt gaaagctgag tcaacatcat gcaattgtcg | 1920 |
| gacgaggtcc gggtcgttcg ttctgtgttt ctgttacgag tttacatttt attatggttc | 1980 |
| aaagtcttct atttctaa | 1998 |

<210> SEQ ID NO 23
<211> LENGTH: 570
<212> TYPE: DNA
<213> ORGANISM: Canis

<400> SEQUENCE: 23

| | |
|---|---|
| tgcatcgtta gcgtctccta gtaaactgat ttgtctgcta ttgtcactgc aaatagagat | 60 |
| ctattaatgg gtctcacctc ccaactgatt ccaactctgg tctgcttact agcactcacc | 120 |
| agcacctttg tccacggaca taacttcaat attactatta aagagatcat caaaatgttg | 180 |
| aacatcctca cagcgagaaa cgactcgtgc atggagctga ctgtcaagga cgtcttcact | 240 |
| gctccaaaga acacaagcga taaggaaatc ttctgcagag ctgctactgt actgcggcag | 300 |
| atctatacac acaactgctc caacagatat ctcagaggac tctacaggaa cctcagcagc | 360 |
| atggcaaaca agacctgttc tatgaatgaa atcaagaaga gtacactgaa agacttcttg | 420 |
| gaaaggctaa aagtgatcat gcagaagaaa tactacaggc attgaagctg aatatttaa | 480 |
| tttatgagtt tttacatagc tttatttaa aatatttat aatttataca taatataata | 540 |
| tatatagact ctaatataaa aaaaaaaaa | 570 |

<210> SEQ ID NO 24
<211> LENGTH: 618
<212> TYPE: DNA
<213> ORGANISM: Homo sapiens

<400> SEQUENCE: 24

| | |
|---|---|
| tgcatcgtta gcttctcctg ataaactaat tgcctcacat tgtcactgca aatcgacacc | 60 |
| tattaatggg tctcacctcc caactgcttc ccctctgtt cttcctgcta gcatgtgccg | 120 |
| gcaactttgt ccacggacac aagtgcgata tcaccttaca ggagatcatc aaaactttga | 180 |
| acagcctcac agagcagaag actctgtgca ccgagttgac cgtaacagac atctttgctg | 240 |
| cctccaagaa cacaactgag aaggaaacct tctgcagggc tgcgactgtg ctccggcagt | 300 |
| tctacagcca ccatgagaag gacactcgct gcctgggtgc gactgcacag cagttccaca | 360 |
| ggcacaagca gctgatccga ttcctgaaac ggctcgacag gaacctctgg ggcctggcgg | 420 |
| gcttgaattc ctgtcctgtg aaggaagcca accagagtac gttggaaaac ttcttggaaa | 480 |
| ggctaaagac gatcatgaga gagaaatatt caaagtgttc gagctgaata ttttaattta | 540 |
| tgagttttg atagctttat tttttaagta tttatatatt tataactcat cataaaataa | 600 |
| agtatatata gaatctaa | 618 |

<210> SEQ ID NO 25
<211> LENGTH: 463
<212> TYPE: DNA
<213> ORGANISM: Cercocebus

<400> SEQUENCE: 25

| | |
|---|---|
| atgggtctca cctcccaact gcttcccct ctgttcttcc tgctagcatg tgccggcaac | 60 |

```
tttgcccatg acacaactg ccatatcgcc ttacgggaga tcatcgaaac tctgaacagc     120
ctcacagagc agaagactct gtgcaccaag ttgaccataa cggacatcct tgctgcctcc    180
aagaacacaa ctgagaagga aaccttctgc agggctgcga ctgtgctccg gcagttctac    240
agccaccatg agaaggacac tcgctgcctg ggtgcgagtg cacagcagtt ccacaggcac    300
aagcagctga tccgattcct gaaacggctc gacaggaacc tctggggcct ggcgggcttg    360
aactcctgtc ctgtgaagga agccagccag agtacgttgg aagacttctt ggaaaggcta    420
aagacgatca tgagagagaa atattcaaag tgttcgagct gaa                      463
```

<210> SEQ ID NO 26
<211> LENGTH: 1932
<212> TYPE: DNA
<213> ORGANISM: Homo sapiens

<400> SEQUENCE: 26

```
gccatggcat ccgtactggg tcccatttcg ggcacgtgc tgaaagccgt gtttagtcgc      60
ggcgacacgc cggtgctgcc gcacgagacg cgactcctgc agacgggtat ccacgtgcgc    120
gtgagccagc cctcgctgat cctggtgtcg cagtacacgc ccgactcgac gccatgccac    180
cgcggcgaca tcagctgca ggtgcagcac acgtacttta cgggcagcga ggtggagaac     240
gtgtcggtca acgtgcacaa ccccacgggc cggagcatct gccccagcca agagcccatg    300
tcgatctatg tgtacgcgct gccgctcaag atgctgaaca tccccagcat caacgtgcac    360
cactacccgt cggcggccga gcgcaaacac cgacacctgc ccgtagctga cgctgtgatt    420
cacgcgtcgg gcaagcagat gtggcaggcg cgtctcacgg tctcgggact ggcctggacg    480
cgtcagcaga accagtggaa agagcccgac gtctactaca cgtcagcgtt cgtgtttccc    540
accaaggacg tggcactgcg gcacgtggtg tgcgcgcacg agctggtttg ctccatggag    600
aacacgcgcg caaccaagat gcaggtgata ggtgaccagt acgtcaaggt gtacctggag    660
tccttctgcg aggacgtgcc ctccggcaag ctctttatgc acgtcacgct gggctctgac    720
gtggaagagg acctgacgat gacccgcaac ccgcaaccct tcatgcgccc ccacgagcgc    780
aacggcttta cggtgttgtg tcccaaaaat atgataatca aaccgggcaa gatctcgcac    840
atcatgctgg atgtggcttt tacctcacac gagcattttg ggctgctgtg tcccaagagc    900
atcccgggcc tgagcatctc aggtaaccta ttgatgaacg ggcagcagat cttcctggag    960
gtgcaagcga tacgcgagac cgtggaactg cgtcagtacg atcccgtggc tgcgctcttc   1020
tttttcgata tcgacttgct gctgcagcgc gggcctcagt acagcgaaca ccccaccttc   1080
accagccagt atcgcatcca gggcaagctt gagtaccgac acacctggga ccggcacgac   1140
gagggtgccg cccagggcga cgacgacgtc tggaccagcg gatcggactc gacgaggaa    1200 ctcgtaacca ccgagcgcaa gacgcccgc gttaccggcg cggcgccat ggcgggcgcc     1260 tccacttccg cgggccgcaa acgcaaatca gcatcctcgg cgacggcgtg cacggcgggc   1320
gttatgacac gcgccgcct taaggccgag tccaccgtcg cgcccgaaga ggacaccgac   1380
gaggattccg acaacgaaat ccacaatccg gccgtgttca cctggccgcc ctggcaggcc   1440
ggcatcctgg cccgcaacct ggtgcccatg gttgctacgt tcagggtca gaatctgaag    1500 taccaggagt tcttctggga cgccaacgac atctaccgca tcttcgccga attggaaggc   1560
gtatggcagc ccgctgcgca acccaaacgt cgccgccacc ggcaagacgc cttgcccggg   1620
ccatgcatcg cctcgacgcc caaaaagcac cgaggttgag ccacccgccg cgcacgctta   1680
```

-continued

```
ggacgactct ataaaaaccc acgtccactc agacacgcga cttttggccg ccacacctgt    1740
cgccgctgct atatttgcga cagttgccgg aacccttccc gacctcccac gaagacccgt    1800
tcacctttgc gcatcccctg accccccccc tcatcccgcc ttcgcgatgt ctcaggcatc    1860
gtcctcgccc ggtgagggac cctcgtcgga agcggccgcg atcagcgagg ccgaagccgc    1920
cagcggaagc tt                                                        1932

<210> SEQ ID NO 27
<211> LENGTH: 538
<212> TYPE: DNA
<213> ORGANISM: Marmota monax

<400> SEQUENCE: 27
ggcctaactc tctctgaaac gatgaaatac acaagttatt tcttggcttt tcagctctgc     60
atcattttgg gttcttctag ctgttactcc caggacacag ttaataaaga aatagaagat    120
ttaaaaggat attttaatgc aagtaattca aatgtatcag atggcgggtc tctcttcttg    180
gatattttgg ataaatggaa agaggagagt gacaaaaaag taatccagag ccaaattgtc    240
tctttctact tcaaactctt tgaacactta aaagacaaca agatcatcca aggagcatg    300 gacaccatca ggggggatct ttttgctaag ttcttcaaca gcagtaccaa taagctgcag    360
gacttcctaa aggtgtctca agttcaggta aatgacctga agatccagcg taaagcagtg    420
agtgaactca gaaagtgat gaatgatctg ttaccacact ctaccctaag gaagcgaaaa    480
aggagtcagt cttcgattcg gggtcggaga gcatccaaat aacagtcctc atgcctgc     538

<210> SEQ ID NO 28
<211> LENGTH: 567
<212> TYPE: DNA
<213> ORGANISM: Felis catus

<400> SEQUENCE: 28
ctactgattt caacttcttt ggcctaactc tccgaaacga tgaattacac aagttttatt     60
ttcgctttcc agctttgcat aattttgtgt tcttctggtt attactgtca ggccatgttt    120
tttaaagaaa tagaagagct aaagggatat tttaatgcaa gtaatccaga tgtagcagat    180
ggtgggtcgc tttcgtaga cattttgaag aactggaaag aggagagtga taaacaata     240 attcaaagcc aaattgtctc cttctacctg aaaatgtttg aaaacctgaa agatgatgac    300
cagcgcattc aaaggagcat ggacaccatc aaggaagaca tgcttgataa gttgttaaat    360
accagctcca gtaaacggga tgacttcctc aagctgattc aaatccctgt gaatgatctg    420
caggtccagc gcaaagcaat aaatgaactc ttcaaagtga tgaatgatct ctcaccaaga    480
tctaacctga ggaagcggaa aaggagccag aatctgtttc gaggccgtag agcatcgaaa    540
taatggttgt cctgcctgca atatttg                                       567

<210> SEQ ID NO 29
<211> LENGTH: 438
<212> TYPE: DNA
<213> ORGANISM: Homo sapiens

<400> SEQUENCE: 29
tgttactgcc aggacccata tgtaaaagaa gcagaaaacc ttaagaaata ttttaatgca     60
ggtcattcag atgtagcgga taatggaact cttttcttag cattttgaa gaattggaaa    120 gaggagagtg acagaaaaat aatgcagagc caaattgtct cctttactt caaactttt     180 agaaacttta agatgacca gagcatccaa aagagtgtgg agaccatcaa ggaagacatg    240
```

-continued

```
aatgtcaagt ttttcaatag caacaaaaag aaacgagatg acttcgaaaa gctgactaat    300
tattcggtaa ctgacttgaa tgtccaacgc aaagcaatac atgaactcat ccaagtgatg    360
gctgaactgt cgccagcagc taaaacaggg aagcggaaaa ggagtcagat gctgtttcga    420
ggtcgaagag catcccag                                                  438
```

NON-STOCHASTIC GENERATION OF GENETIC VACCINES AND ENZYMES

The present applications is a continuation-in-part and claims the benefit of U.S. application Ser. No. 09/495,052, filed on Jan. 31, 2000, now U.S. Pat. No. 6,479,253, which is a continuation-in-part of U.S. application Ser. No. 09/332, 835, filed Jun. 14, 1999, now U.S. Pat. No. 6,537,776, which is a continuation-in-part of U.S. application Ser. No. 09/276, 860, filed on Mar. 26, 1999, now U.S. Pat. No. 6,352,842, which is a continuation-in-part of U.S. application Ser. No. 09/267,118, filed Mar. 9, 1999, now U.S. Pat. No. 6,238,884, which is a continuation-in-part of U.S. application Ser. No. 09/246,178, filed Feb. 4, 1999, now U.S. Pat. No. 6,171,820, which is a continuation-in-part of U.S. application Ser. No. 09/185,373, filed on Nov. 3, 1998, now U.S. Pat. No. 6,335,179, which is a continuation of U.S. application Ser. No. 08/760,489, filed on Dec. 5, 1996, now U.S. Pat. No. 5,830,696, which is a continuation-in-part of U.S. Provisional Application 60/008,311, filed on Dec. 7, 1995, now abandoned, all of which are hereby incorporated by reference.

U.S. application Ser. No. 09/246,178, filed Feb. 4, 1999, now U.S. Pat. No. 6,171,820 is also a continuation-in-part of U.S. application Ser. No. 08/962,504, filed on Oct. 31, 1997, which is a continuation-in-part of U.S. application Ser. No. 08/677,112, filed on Jul. 9, 1996, now U.S. Pat. No. 5,965, 408, all of which are hereby incorporated by reference.

U.S. application Ser. No. 09/246,178, filed Feb. 4, 1999, now U.S. Pat. No. 6,171,820 is also a continuation-in-part of U.S. application Ser. No. 08/651,568, filed May 22, 1996, now U.S. Pat. No. 5,939,250, which is a continuation-in-part of U.S. Provisional Application No. 60/008,316, filed Dec. 7, 1995, all of which are hereby incorporated by reference.

CONTENTS

1. GENERAL
   1.1. FIELD OF THE INVENTION
   1.2. BACKGROUND
   1.3. SUMMARY OF THE INVENTION
   1.4. BRIEF DESCRIPTION OF THE DRAWINGS
2. DETAILED DESCRIPTION OF THE INVENTION
   2.1. DEFINITIONS
   2.2. GENERAL CONSIDERATIONS & FORMATS FOR RECOMBINATION
   2.3. VECTORS USED IN GENETIC VACCINATION
      2.3.1. VIRAL VECTORS
         2.3.1.1. ADENOVIRUSES
         2.3.1.2. ADENO-ASSOCIATED VIRUS (AAV)
         2.3.1.3. PAPILLOMA VIRUS
         2.3.1.4. RETROVIRUSES
      2.3.2. NON-VIRAL GENETIC VACCINE VECTORS
   2.4. MULTICOMPONENT GENETIC VACCINES
      2.4.1. VECTOR "AR ", DESIGNED TO PROVIDE OPTIMAL ANTIGEN RELEASE
      2.4.2. VECTOR COMPONENTS "CTL-DC", "CTL-LC" AND "CTL-MM"I DESIGNED FOR OPTIMAL PRODUCTION OF CTLs
      2.4.3. VECTORS "M" DESIGNED FOR OPTIMAL RELEASE OF IMMUNE MODULATORS
      2.4.4. VECTORS "CK", DESIGNED TO DIRECT RELEASE OF CHEMOKINES
      2.4.5. OTHER VECTORS
   2.5. SCREENING METHODS
      2.5.1. SCREENING FOR VECTOR LONGEVITY OR TRANSLOCATION TO DESIRED TISSUE
         2.5.1.1. SELECTION FOR EXPRESSION OF CELL SURFACE-LOCALIZED ANTIGEN
         2.5.1.2. SELECTION FOR EXPRESSION OF SECRETED ANTIGEN/CYTOKINE/CHEMOKINE
      2.5.2. FLOW CYTOMETRY
      2.5.3. ADDITIONAL IN VITRO SCREENING METHODS
      2.5.4. ANTIGEN LIBRARY IMMUNIZATION
      2.5.5. SCREENING FOR OPTIMAL INDUCTION OF PROTECTIVE IMMUNITY
      2.5.6. SCREENING OF GENETIC VACCINE VECTORS THAT ACTIVATE HUMAN ANTIGEN-SPECIFIC LYMPHOCYTE RESPONSES
      2.5.7. SCID-HUMAN SKIN MODEL FOR VACCINATION STUDIES
      2.5.8. MOUSE MODEL FOR STUDYING THE EFFICIENCY OF GENETIC VACCINES IN TRANSFECTING HUMAN MUSCLE CELLS AND INDUCING HUMAN IMMUNE RESPONSES IN VIVO
      2.5.9. SCREENINGFOR IMPROVED DELIVERY OF VACCINES
      2.5.10. ENHANCED ENTRY OF GENETIC VACCINE VECTORS INTO CELLS
   2.6. OPTIMIZATION OF GENETIC VACCINE COMPONENTS
      2.6.1. EPISOMAL VECTOR MAINTENANCE
      2.6.2. EVOLUTION OF OPTIMIZED PROMOTERS FOR EXPRESSION OF AN ANTIGEN
         2.6.2.1. CONSTITUTIVE PROMOTERS
         2.6.2.2. CELL-SPECIFIC PROMOTERS
         2.6.2.3. INDUCIBLE PROMOTERS
      2.6.3. EVOLUTION OF BINDING POLYPEPTIDES THAT ENHANCE SPECIFICITY AND EFFICIENCY OF GENETIC VACCINES
      2.6.4. EVOLUTION OF BACTERIOPHAGE VECTORS
         2.6.4.1. EVOLUTION OF EFFICIENT DELIVERY OF BACTERIGPLIAGE VEHICLES BY INHALATION OR ORAL DELIVE
         2.6.4.2. EVOLUTION OF BACTERIOPHAGE VEHICLES FOR EFFICIENT HOMING TO APCs
         2.6.4.3. EVOLUTION OF BACTERIOPHAGE FOR INVASION OF APCs
      2.6.5. EVOLUTION OF IMPROVED IMMUNOMODULATORY SEQUENCES
         2.6.5.1. IMMUNOSTIMULATORY DNA SEQUENCES
         2.6.5.2. CYTOKINES, CHEMOKINES, AND ACCESSORY MOLECULES
         2.6.5.3. AGONISTS OR ANTAGONISTS OF CELLULAR RECEPTORS
         2.6.5.4. COSTIMULATORY MOLECULES CAPABLE OF INHIBITING OR ENHANCING ACTIVATION, DIFFERENTIATION, OR ANERGY OF ANTIGEN-SPECIFIC T CELLS
      2.6.6. EVOLUTION OF GENETIC VACCINE VECTORS FOR INCREASED VACCINATION EFFICACY AND EASE OF VACCINATION
         2.6.6.1. TOPICAL APPLICATION OF GENETIC VACCINE VECTORS
         2.6.6.2. ENHANCED ABILITY TO ESCAPE HOST IMMUNE SYSTEM
         2.6.6.3. ENHANCED ANTIVIRAL ACTIVITY
         2.6.6.4. EVOLUTION OF VECTORS HAVING INCREASED COPY NUMBER IN PRODUCTION CELLS 2.7. OPTIMIZATION OF TRANSPORT AND PRESENTATION OF ANTIGENS
  2.7.1. PROTEASOMES
  2.7.2. ANTIGEN TRANSPORT
  2.7.3. CYTOTOXIC T-CELL INDUCING SEQUENCES AND IMMUNOGENIC AGONIST SEQUENCES
2.8. GENETIC VACCINE PHARMACEUTICAL COMPOSITIONS AND METHODS OF ADMINISTRATION
2.9. USES OF GENETIC VACCINES
  2.9.1. INFECTIOUS DISEASES
    2.9.1.1. BACTERIAL PATHOGENS AND TOXINS
    2.9.1.2. VIRAL PATHOGENS
  2.9.2. INFLAMMATORY AND AUTOIMMUNE DISEASES
  2.9.3. ALLERGY AND ASTHMA
  2.9.4. CANCER
  2.9.5. PARASITES
  2.9.6. CONTRACEPTION
2.10. MALARIAL ANTIGENS AND VACCINES
  2.10.1. MALARIAL POLYPEPTIDES
  2.10.2. MALARIAL NUCLEIC ACIDS AND CELLS CAPABLE OF EXPRESSING SAME
  2.10.3. ANTIBODIES
  2.10.4. METHODS OF USE
    2.10.4.1. DIAGNOSTIC APPLICATIONS
    2.10.4.2. SCREENING APPLICATIONS
    2.10.4.3. THERAPEUTIC AND PROPHYLACTIC APPLICATIONS
2.11. DIRECTED EVOLUTION METHODS
  2.11.1. SATURATION MUTAGENESIS
  2.11.2. CHIMERIZATIONS
    2.11.2.1. "SHUFFLING"
    2.11.2.2. EXONUCLEASE-MEDIATED REASSEMBLY
    2.11.2.3. NON-STOCHASTIC LIGATION REASSEMBLY
    2.11.2.4. END-SELECTION
  2.11.3. ADDITIONAL SCREENING METHODS
3. LITERATURE CITED

1. GENERAL

1.1. Field of the Invention

This invention pertains to the field of genetic vaccines. Specifically, the invention provides multi-component genetic vaccines that contain components that are optimized for a particular vaccination goal. In a particular aspect this invention provides methods for improving the efficacy of genetic vaccines by providing materials that facilitate targeting of a genetic vaccine to a particular tissue or cell type of interest.

This invention also pertains to the field of modulation of immune responses such as those induced by genetic vaccines and also pertains to the field of methods for developing immunogens that can induce efficient immune responses against a broad range of antigens.

Thus, the present invention also relates generally to novel proteins, and fragments thereof, as well as nucleic acids which encode these proteins, and methods of making and using these proteins in diagnostic, prophylactic and therapeutic applications. In a particular exemplification, the present invention relates to proteins from the Plasmodium falciparum erythrocyte membrane protein 1 ("PfEMP1") gene family and fragments thereof which are derived from malaria parasitized erythrocytes. In particular, these proteins are derived from the erythrocyte membrane protein of Plasmodium falciparum parasitized erythrocytes, also termed "PFEMP1". The present invention also provides nucleic acids encoding these proteins, which proteins and nucleic acids are associated with the pathology of malaria infections, and which may be used as vaccines or other prophylactic treatments for the prevention of malaria infections, and/or in diagnosing and treating the symptoms of patients who suffer from malaria and associated diseases.

This invention also relates to the field of protein engineering. Specifically, this invention relates to a directed evolution method for preparing a polynucleotide encoding a polypeptide. More specifically, this invention relates to a method of using mutagenesis to generate a novel polynucleotide encoding a novel polypeptide, which novel polypeptide is itself an improved biological molecule &/or contributes to the generation of another improved biological molecule. More specifically still, this invention relates to a method of performing both non-stochastic polynucleotide chimerization and non-stochastic site-directed point mutagenesis.

Thus, in one aspect, this invention relates to a method of generating a progeny set of chimeric polynucleotide(s) by means that are synthetic and non-stochastic, and where the design of the progeny polynucleotide(s) is derived by analysis of a parental set of polynucleotides &/or of the polypeptides correspondingly encoded by the parental polynucleotides. In another aspect this invention relates to a method of performing site-directed mutagenesis using means that are exhaustive, systematic, and non-stochastic.

Furthermore this invention relates to a step of selecting from among a generated set of progeny molecules a subset comprised of particularly desirable species, including by a process termed end-selection, which subset may then be screened further. This invention also relates to the step of screening a set of polynucleotides for the production of a polypeptide &/or of another expressed biological molecule having a useful property.

Novel biological molecules whose manufacture is taught by this invention include genes, gene pathways, and any molecules whose expression is affected thereby, including directly encoded polypetides &/or any molecules affected by such polypeptides. Said novel biological molecules include those that contain a carbohydrate, a lipid, a nucleic acid, &/or a protein component, and specific but non-limiting examples of these include antibiotics, antibodies, enzymes, and steroidal and non-steroidal hormones.

In a particular non-limiting aspect, the present invention relates to enzymes, particularly to thermostable enzymes, and to their generation by directed evolution. More particularly, the present invention relates to thermostable enzymes which are stable at high temperatures and which have improved activity at lower temperatures.

1.2. BACKGROUND

Providing Protective Immunity Even in Situations When the Pathogens are Poorly Characterized or Cannot be Isolated or Cultured in Laboratory Environment Genetic immunization represents a novel mechanism of inducing protective humoral and cellular immunity. Vectors for genetic vaccinations generally consist of DNA that includes a promoter/enhancer sequence, the gene of interest and a polyadenylation/transcriptional terminator sequence.

After intramuscular or intradermal injection, the gene of interest is expressed, followed by recognition of the resulting protein by the cells of the immune system. Genetic immunizations provide means to induce protective immunity even in situations when the pathogens are poorly characterized or cannot be isolated or cultured in laboratory environment.

Small Improvement in the Efficiency of Genetic Vaccine Vectors can Result in Dramatic Increase if the Level of Immune Response The efficacy of genetic vaccination is often limited by inefficient uptake of genetic vaccine vectors into cells. Generally, less than 1% of the muscle or skin cells at the sites of injections express the gene of interest. Even a small improvement in the efficiency of genetic vaccine vectors to enter the cells can result in a dramatic increase in the level of immune response induced by genetic vaccination. A vector typically has to cross many barriers which can result in only a very minor fraction of the DNA ever being expressed.

Various Limitations to Immunogenicity

Limitations to immunogenicity include: loss of vector due to nucleases present in blood and tissues; inefficient entry of DNA into a cell; inefficient entry of DNA into the nucleus of the cell and preference of DNA for other compartments; lack of DNA stability in the nucleus (factor limiting nuclear stability may differ from those affecting other cellular and extracellular compartments), and, for vectors that integrate into the chromosome, the efficiency of integration and the site of integration. Moreover, for many applications of genetic vaccines, it is preferable for the genetic vaccine to enter a particular target tissue or cell.

Thus, a need exists for genetic vaccines that can be targeted to specific cell and tissue types of interest, and which exhibit an increased ability to enter the target cells. The present invention fulfills these and other needs.

Pathways for Immune Responses Induced by Gentic Vaccines

Elicitation of a desired in vivo response by a genetic vaccine generally requires multiple cellular processes in a complex sequence. Several potential pathways exist along which a genetic vaccine can exert its effect on the mammalian immune system. In one pathway, the genetic vaccine vector enters cells that are the predominant cell type in the tissue that receives vaccine (e.g., muscle or epithelial cells). These cells express and release the antigen encoded by the vector. The vaccine vector can be engineered to have the antigen released as an intact protein from living transfected cells (i.e., via a secretion process) or directed to a membrane-bound form on the surface of these cells. Antigen can also be released from an intracellular compartment of such cells if those cells die.

The antigen derived from vaccine vector internalization and antigen expression within the predominant cell type in the tissue ends up within APC. which then process the antigen internally to prime MHC Class I and or Class II, essential steps in activation of CD4$^+$ T-helper cells and development of potent specific immune responses, Extracellular antigen derived from any of these situations interacts with antigen presenting cells (APC) either by binding to the cell surface (specifically via IgM or via other non-immunoglobulin receptors) and subsequent endocytosis of outer membrane, or by fluid phase micropinocytosis wherein the APC internalizes extracellular fluid and its contents into an endocytic compartment. Interaction with APC may occur before or after partial proteolytic cleavage in the extracellular environment. In any case, the antigen derived from vaccine vector internalization and antigen expression within the predominant cell type in the tissue ends up within APC. The APC then process the antigen internally to prime MHC Class I and or Class II, essential steps in activation of CD4$^+$ T-helper cells ($T_H1$ and/or $T_H2$) and development of potent specific immune responses.

The Genetic Vaccine Plasmid Enters APC and Antigen is Proteolytically Cleaved in the Cell Cytoplasm In a parallel pathway, the genetic vaccine plasmid enters APC (or the predominant cell type in the tissue) and, instead of antigen derived from plasmid expression being directed to extracellular export, antigen is proteolytically cleaved in the cell cytoplasm (in a proteasome dependent or independent process). Often, intracellular processing in such cells occurs via proteasomal degradation into peptides that are recognized by the TAP-1 and TAP-2 proteins and transported into the lumen of the rough endoplasmic reticulum (RER).

The Peptide Fragments are Transported Into the RER Complex, Expressed on the Cell Surface: in the Presence of Appropriate Additional Signals, can Differentiate Into Functional CTLs The peptide fragments transported into the RER complex with MHC Class I. Such antigen fragments are then expressed on the cell surface in association with Class I. CD8$^+$ cytotoxic T lymphocytes (CTL) bearing specific T cell receptor then recognize the complex and can, in the presence of appropriate additional signals, differentiate into functional CTLs.

By Virtue of Poorly Characterized Pathways for Trafficking of Cytoplasmically Generated Peptides Into Endosomal Compartments, a Genetic Vaccine Vector can Lead to CD4$^+$ T Cell Stimulation In addition, poorly characterized pathways, which are generally not dominant, exist in APC for trafficking of cytoplasmically generated peptides into endosomal compartments where they can end up complexed with MHC Class II, and thereby act to present antigen peptides to CD4$^+T_H1$ and $T_H2$ cells. Because activation, proliferation, differentiation and immunoglobulin isotype switching by B lymphocytes requires help of CD4$^+$T cells, antigen presentation in the context of MHC Class II molecules is crucial for induction of antigen-specific antibodies. By virtue of this pathway, a genetic vaccine vector can lead to CD4$^+$T cell stimulation in addition to the dominant CD8$^+$CTL activation process described above. This alternative pathway is, however, of little consequence in muscle cells where levels of MHC Class II expression are very low or zero.

In This Case Cytokines are Derived not Only From Processes Intrinsic to the Interaction of DNA With Cells, or Specific Cell Responses to the Antigen, but via Synthesis Directed by the Vaccine Plasmid Genetic vaccination can also elicit cytokine release from cells that bind to or take up DNA. So-called immunostimulatory or adjuvant properties of DNA are derived from its interaction with cells that internalize DNA. Cytokines can be released from cells that bind and/or internalize DNA in the absence of gene transcription. Separately, interaction of antigen with APC followed by presentation and specific recognition also stimulates release of cytokines that have positive feedback effects on these cells and other immune cells. Chief among these effects are the direction of $CD4^+T_H$ cells to differentiate/ proliferate preferentially to $T_H1$ or $TH_2$ phenotypes. Furthermore, cytokines released at the site of DNA vaccination, regardless of the mechanism of their release, contribute to recruitment of other immune cells from the immediate local area and more distant sites such as draining lymph nodes. In recognition of the importance of cytokines in elicitation of a potent immune response, some investigators have included the genes for one or more cytokines in the DNA vaccine plasmid along with the target antigen for immunization. In this case cytokines are derived not only from processes intrinsic to the interaction of DNA with cells, or specific cell responses to the antigen, but via synthesis directed by the vaccine plasmid.

Movement of Immune Cells From the Blood Stream and Different Sites to the Site of Immunization and Also From the Site of Immunization to Other Sites Immune cells are recruited to the site of immunization from distant sites or the bloodstream. Specific and non-specific immune responses are then greatly amplified. Immune cells, including APC, bearing antigen fragments complexed to MHC molecules or even expressing antigen from uptake of plasmid, also move from the immunization site to other sites (blood, hence to all tissues; lymph nodes; spleen) where additional immune recruitment and qualitative and quantitative development of the immune response ensue.

Current Genetic Vaccine Vectors Employ Simple Methods for Expression of the Desired Antigen With Few if Any Aesign Elements That Control the Precise Intracellular Fate of the Antigen or the Immunological Consequences of Antigen Expression While these pathways often compete, previously available genetic vaccines have incorporated all components for influencing each of the pathways into a single polynucleotide molecule. Because separate cell types are involved in the complex interactions required for a potent immune response to a genetic vaccine vector, mutually. incompatible consequences can arise from administration of a genetic vaccine that is incorporated in a single vector molecule. Current genetic vaccine vectors employ simple methods for expression of the desired antigen with few if any design elements that control the precise intracellular fate of the antigen or the immunological consequences of antigen expression. Thus, although genetic vaccines show great promise for vaccine research and development, the need for major improvements and several severe limitations of these technologies are apparent.

Existing Genetic Vaccine Vectors Have Not Been Optimized for Human Tissue, Providing Low and Short-lasting Expression of the Antigen of Interest, With Insufficient Stability, Inducibility or Levels of Expression in vivo, Among Other Things Largely due to the lack of suitable laboratory models, none of the existing genetic vaccine vectors have been optimized for human tissues. The existing genetic vaccine vectors typically provide low and short-lasting expression of the antigen of interest, and even large quantities of DNA do not always result in sufficiently high expression levels to induce protective immune responses. Because the mechanisms of the vector entry into the cells and transfer into the nucleus are poorly understood, virtually no attempts have been made to improve these key properties. Similarly, little is known about the mechanisms that regulate the maintenance of vector functions, including gene expression. Furthermore, although there is increasing amount of data indicating that specific sequences alter the immunostimulatory properties of the DNA, rational engineering is a very laborious and time-consuming approach when using this information to generate vector backbones with improved immunomodulatory properties.

Moreover, presently available genetic vaccine vectors do not provide sufficient stability, inducibility or levels of expression in vivo to satisfy the desire for vaccines which can deliver booster immunization without additional vaccine administration. Booster immunizations are typically required 3–4 weeks after the primary injection with existing genetic vaccines.

Therefore a need exists for improved genetic vaccine vectors and formulations, and methods for development of such vectors. The present invention fulfills these and other needs.

The interactions between pathogens and hosts are results of millions of years of evolution, during which the mammalian immune system has evolved sophisticated means to counterattack pathogen invasions. However, bacterial and viral pathogens have simultaneously gained a number of mechanisms to improve their virulence and survival in hosts, providing a major challenge for vaccine research and development despite the powers of modem techniques of molecular and cellular biology. Similar to the evolution of pathogen antigens, several cancer antigens are likely to have gained means to downregulate their immunogenicity as a mechanism to escape the host immune system.

Efficient vaccine development is also hampered by the antigenic heterogeneity of different strains of pathogens, driven in part by evolutionary forces as means for the pathogens to escape immune defenses. Pathogens also reduce their immunogenicity by selecting antigens that are difficult to express, process and/or transport in host cells, thereby reducing the availability of immunogenic peptides to the molecules initiating and modulating immune responses. The mechanisms associated with these challenges are complex, multivariate and rather poorly characterized. Accordingly, a need exists for vaccines that can induce a protective immune response against bacterial and viral pathogens. The present invention fulfills this and other needs.

Antigen processing and presentation is only one factor which determines the effectiveness of vaccination, whether performed with genetic vaccines or more classical methods. Other molecules involved in determining vaccine effectiveness include cytokines (interleukins, interferons, chemokines, hematopoietic growth factors, tumor necrosis factors and transforming growth factors), which are small molecular weight proteins that regulate maturation, activation, proliferation and differentiation of the cells of the immune system.

Characteristic features of cytokines are pleiotropy and redundancy; that is, one cytokine often has several functions and a given function is often mediated by more than one cytokine. In addition, several cytokines have additive or synergistic effects with other cytokines, and a number of cytokines also share receptor components.

Due to the complexity of the cytokine networks, studies on the physiological significance of a given cytokine have been difficult, although recent studies using cytokine gene-deficient mice have significantly improved our understanding on the functions of cytokines in vivo. In addition to soluble proteins, several membrane-bound costimulatory molecules play a fundamental role in the regulation of immune responses. These molecules include CD40, CD40 ligand, CD27, CD80, CD86 and CD 150 (SLAM), and they are typically expressed on lymphoid cells after activation via antigen recognition or through cell-cell interactions.

T helper ($T_H$) cells, key regulators of the immune system, are capable of producing a large number of different cytokines, and based on their cytokine synthesis pattern $T_H$ cells are divided into two subsets (Paul and Seder (1994) Cell 76: 241–251). THI cells produce high levels of IL-2 and IFN- and no or minimal levels of IL-4, IL-5 and IL-13. In contrast, $T_H2$ cells produce high levels of IL-4, IL-5 and IL-13, and IL-2 and IFN- production is minimal or absent. $T_H1$ cells activate macrophages, dendritic cells and augment the cytolytic activity of CD8+cytotoxic T lymphocytes and NK cells (Id.), whereas $T_H2$ cells provide efficient help for B cells and they also mediate allergic responses due to the capacity of $T_H2$ cells to induce IgE isotype switching and differentiation of B cells into IgE secreting cell (De Vries and Punnonen (1996) In Cytokine regulation of humoral immunity: basic and clinical aspects. Eds. Snapper, C. M., John Wiley & Sons, Ltd., West Sussex, UK, p. 195–215). The exact mechanisms that regulate the differentiation of T helper cells are not fully understood, but cytokines are believed to play a major role. IL-4 has been shown to direct $T_H2$ differentiation, whereas IL-12 induces development of $T_H1$ cells (Paul and Seder, supra.). In addition, it has been suggested that membrane bound costimulatory molecules, such as CD80, CD86 and CD150, can direct $T_H1$ and/or $T_H2$ development, and the same molecules that regulate $T_H$ cell differentiation also affect activation, proliferation and differentiation of B cells into Ig-secreting plasma cells (Cocks et al. (1995) Nature 376: 260–263; Lenschow et al. (1996) Immunity 5: 285–293; Punnonen et al. (1993) Proc. Nat'l. Acad. Sci. USA 90: 3730–3734; Punnonen et al. (1997) J Exp. Med. 185: 993–1004).

Studies in both man and mice have demonstrated that the cytokine synthesis profile of T helper ($T_H$) cells plays a crucial role in determining the outcome of several viral, bacterial and parasitic infections. High frequency of $T_H1$ cells generally protects from lethal infections, whereas dominant $T_H2$ phenotype often results in disseminated, chronic infections. For example, $T_H1$ phenotype is observed in tuberculoid (resistant) form of leprosy and $T_H2$ phenotype in lepromatous, multibacillary (susceptible) lesions (Yamamura et al. (1991) Science 254: 277–279). Similarly, late-stage HIV patients have $T_H2$-like cytokine synthesis profiles, and $T_H1$ phenotype has been proposed to protect from AIDS (Maggi et al. (1994) J Exp. Med. 180: 489–495). Furthermore, the survival from meningococcal septicemia is genetically determined based on the capacity of peripheral blood leukocytes to produce TNF- and IL-10. Individuals from families with high production of IL-10 have increased risk of fatal meningococcal disease, whereas members of families with high TNF- production were more likely to survive the infection (Westendorp et al. (1997) Lancet 349: 170–173).

Cytokine treatments can dramatically influence $T_H1/T_H2$ cell differentiation and macrophage activation, and thereby the outcome of infectious diseases. For example, BALB/c mice infected with Leishmania major generally develop a disseminated fatal disease with a $T_H2$ phenotype, but when treated with anti-IL-4 mAbs or IL-12, the frequency of $T_H1$ cells in the mice increases and they are able to counteract the pathogen invasion (Chatelain et al. (1992) J Immunol. 148: 1182–1187). Similarly, IFN- protects mice from lethal Herpes Simplex Virus (HSV) infection, and MCP-1 prevents lethal infections by Pseudomonas aeruginosa or Salmonella typhimurium. In addition, cytokine treatments, such as recombinant IL-2, have shown beneficial effects in human common variable immunodeficiency (Cunningham-Rundles et al. (1994) N. Engl. J Med. 331: 918–921).

The administration of cytokines and other molecules to modulate immune responses in a manner most appropriate for treating a particular disease can provide a significant tool for the treatment of disease. However, presently available immunomodulator treatments can have several disadvantages, such as insufficient specific activity, induction of immune responses against, the immunomodulator that is administered, and other potential problems. Thus, a need exists for immunomodulators that exhibit improved properties relative to those currently available. The present invention fulfills this and other needs.

Erythrocytes infected with the malaria parasite P. falciparum disappear from the peripheral circulation as they mature from the ring stage to trophozoites (Bignami and Bastianeli, Reforma Medica (1889) 6:1334–1335). This phenomenon, known as sequestration, results from parasitized erythrocyte ("PE") adherence to microvascular endothelial cells in diverse organs (Miller, Am. J Trop. Med. Hyg. (1969) 18:860–865). Sequestration is associated temporally with expression of knob protrusions (Leech et al., J. Cell. Biol. (1984) 98:1256–1264), expression of a very large antigenically variant surface protein, called PfEMPI (Aley et al., J. Exp. Med. (1984) 160:1585–1590; Leech et al., J. Exp. Med. (1984) 159:1567–1575; Howard et al., Molec. Biochem. Parasitol. (1988) 27:207–223), and expression of new receptor properties which mediate adherence to endothelial cells (Miller, supra; Udeinya et al., Science (1981) 213:555–557. Endothelial cell surface proteins such as CD36, thrombospondin (TSP) and ICAM-1 have been identified as major host receptors for mature PE. See, e.g., Barnwell et al., J. Immunol. (1985) 135:3494–3497; Roberts et al., Nature (1985) 318:64–66; and Berendt et al., Nature (1989) 341:57–59.

PE sequestration confers unique advantages for P. falciparum parasites (Howard and Gilladoga, Blood (1989) 74:2603–2618), but also contributes directly to the acute pathology of P. falciparum (Miller et al., Science (1994) 264:1878–1883). Of the four human malarias, only P. falciparum infection is associated with neurological impairment and cerebral pathology seen-increasingly in severe drug-resistant malaria (Howard and Gilladoga, supra).

Although the genesis of human cerebral malaria is likely due to a combination of factors including particular parasite phenotypes (Berendt et al., Parasitol. Today (1994) 10:412–414), inappropriate immune responses and the phenotype of endothelial cell surface molecules in the cerebral microvasculature (Pasloske and Howard, Ann. Rev. Med. (1994) :283–295), adherence of PE to cerebral blood vessels and consequent local microvascular occlusion is a major contributing factor. See, e.g., Berendt et al., supra; Patnaik et al., Am. J Trop. Med. Hyg. (1994) 51:642–647.

The capacity of P. falciparum PE to express variant forms of PFEMP1 contributes to the special virulence of this parasite. Variant parasites can evade variant-specific antibodies elicited by earlier infections. The *P. falciparum* variant antigens have been defined in vitro using antiserum prepared in Aotus monkeys infected with individual parasite strains (Howard et al., *Molec. Biochem. Parasitol.* (1988) 27:207–223). Antibodies raised against a particular parasite will only react by PE agglutination, indirect immunofluorescence or immunoelectronmicroscopy with PE from the same strain (van Schravendijk et al., *Blood* (1991) 78:226–236).

Such studies with PE from malaria patients in diverse geographic locations and sera from the same or different patients confirm that PE in natural isolates express variant surface antigens and that individual patients respond to infection by production of isolate-specific antibodies (Marsh and Howard, *Science* (1986) 231:150–153; Aguiar et al., Am. J. Trop. Med. Hyg. (1992) 47:621–632; Iqbal et al., Trans. R. Soc. Trop. Med. Hyg. (1993) 87:583–588. Expression of a variant antigen on PE has also been demonstrated in several simian, murine and human malaria species, including *P. knowlesi* (Brown and Brown, Nature (1965) 208:1286–1288; Barnwell et al., Infect. Immun. (1983) 40:985–994), *P. chabaudi* (Gilks et al., Parasite Immunol. (1990) 12:45–64; Brannan et al., Proc. R. Soc. Lond. Biol. Sci. (1994) 256:71–75), P. fragile (Handunnetti et al., J. Exp. Mod. (1987) 165:1269–1283) and *P. vivax* (Mendis et al., Am. J. Txop. Med. Hyg. (1988) 38:42–46). Laboratory studies with *P. knowlesi* (Brown and Brown, supra; Barnwell et al., supra) or *P. falciparum* (Hommel et al., J. Exp. Med. (1983) 157:1137–1148) in monkeys and *P. chabaudi* in mice (Gilks et al., supra) confirmed that antigenic variation at the PE surface is associated with prolonged or chronic infection and the capacity to repeatedly re-establish blood infection in previously infected animals. Studies with cloned parasites demonstrated that antigenic variants can arise with extraordinary frequency, e.g., 2% per generation with *P. falciparum* (Roberts et al., Nature (1992) 357:689–692) and 1.6% per generation with *P. chabaudi* (Brannan et al., supra).

PFEMP1 was identified as a $^{125}$I-labeled, size diverse protein (200–350 kD) on PE that is lacking from uninfected erythrocytes, and that is also labeled by biosynthetic incorporation of radiolabeled amino acids (Leech et al., J. Exp. Med. (1984) 159:1567–1575; Howard et al., Molec. Biochem. Parasitol. (1988) 27:207–223). PFEMP1 is not extracted from PE by neutral detergents such as Triton X-100 but is extracted by SDS, suggesting that it is linked to the erythrocyte cytoskeleton (Aley et al., J. Med. Exp. (1984) 160:1585–1590). After addition of excess Triton X-100, PfEMP1 is immunoreactive with appropriate serum antibodies (Howard et al., (1988), supra). Mild trypsinization of intact PE rapidly cleaves PfEMP1 from the cell surface (Leech et al., J. Exp. Mod. (1984) 159:1567–1575). PFEMP1 bears antigenically diverse epitopes since it is immunoprecipitated from particular strains of *P. falciparum* by antibodies from sera of Aotus monkeys infected with the same strain, but not by antibodies from animals infected with heterologous strains (Howard et al. (1988), supra). Knobless PE derived from parasite passage in splenectomized Aotus monkeys (Aley et al., supra) do not express surface PfEMPl and are not agglutinated with sera from immune individuals or infected monkeys (Howard et al. (1988), supra; Howard and Gilladoga, Blood (1989) 74:2603–2618). In general, sera that react with the PE surface by indirect immunofluorescence and antibody-mediated PE agglutination are the only sera to immunoprecipitate $^{125}$I-labeled PfEMP1 from any particular strain (Howard et al., (1988), supra; van Schravendijk et al., Blood (1991) 78:226–236; Biggs et al., J. Immunol. (1992) 149:2047–2054).

The adherence of parasitized erythrocytes to endothelial cells is mediated by multiple receptor/counter-receptor interactions, including CD36, thrombospondin and intracellular adhesion molecule-1 (ICAM_1) as the major host cell receptors (Howard and Gilladoga, Blood (1989) 74:2603–2618, Pasloske and Howard, Ann. Rev. Med. (1994) 45:283–295).

Vascular cell adhesion molecule-1 (VCAM-1) and endothelial leukocyte adhesion molecule-1 (ELAM-1) have also been implicated as additional endothelial cell receptors that can mediate adherence of a minority of *P. falciparum* PE (Ockenhouse, et al., J. Exp. Med. (1992) 176:1183–1189, and Howard and Paslaske, supra). The adherence receptors on the surface of PE has not yet been conclusively identified, and several molecules, including AG 332 (Udomsangpetch, et al., Nature (1989) 338:763–765), modified band 3 (Crandall, et al., Proc. Nat'l Acad. Sci. USA (1993) 90:4703–4707), Sequestrin (Ockenhouse, Proc. Nat'l Acad. Sci. USA (1991) 88:3175–3179), and PFEMP1 (Howard and Gilladoga, supra, and Pasloske and Howard, supra), have been proposed as candidates. Several pieces of indirect evidence have linked expression of PFEMP1 with the acquisition of new host protein receptor properties on the surface of PE (Howard and Gilladoga, supra; Pasloske and Howard, Ann. Rev. Med. (1994) 45:283–295). PE adherence is correlated with the expression of PFEMP1 on the surface of mature stage PE (Leech, et al., J. Exp. Med. (1984) 159:1567–1575). Alterations in the adherence phenotype of the PE selected for in vitro are usually associated with the emergence of new forms of PFEMP1 (Biggs, et al., J. Immunol. (1992) 149:2047–2054; Roberts, et al., Nature (1992) 357:689–692). Mild trypsinization of intact mature PE cleaves the extracellular portion of PFEMP1 and at the same time, reduces or eliminates PE cytoadherence (Leech, et al., supra) Previously described antibody mediated blockade or reversal of cytoadherence is strain specific and is correlated with the ability of the reacting sera to agglutinate the corresponding PE and to immunoprecipitate the surface labeled $^{125}$I-PfEMP1 (Howard, et al., Molec. Biochem. Parasitol. (1988) 27:207–224). Pfalhesin (modified band 3) have been shown to bind CD36 under non-physiological conditions (Crandall, et al., Exp. Parasitol. (1994) 78:203–209). Sequestrin, which appears to be homologous to PfEMP 1, extracted with TX 100 from knobless PE, was shown to bind to immobilized CD36 (Ockenhouse, Proc. Nat'l Acad. Sci. USA (1991) 88:3175–3179).

The complex nature and/or mechanism of malarial antigenic variation, and its particular virulence has created a need for methods and compositions which may be useful in the treatment diagnosis and prevention of malaria infections. The present invention meets these and other needs.

General Overview of Problems & Considerations in Directed Evolution

The approach, termed directed evolution, of experimentally modifying a biological molecule towards a desirable property, can be achieved by mutagenizing one or more parental molecular templates and by idendifying any desirable molecules among the progeny molecules. Currently available technologies in directed evolution include methods for achieving stochastic (i.e. random) mutagenesis and methods for achieving non-stochastic (non-random) mutagenesis. However, critical shortfalls in both types of methods are identified in the instant disclosure.

In prelude, it is noteworthy that it may be argued philosophically by some that all mutagenesis—if considered from an objective point of view—is non-stochastic; and furthermore that the entire universe is undergoing a process that—if considered from an objective point of view—is non-stochastic. Whether this is true is outside of the scope of the instant consideration. Accordingly, as used herein, the terms "randomness", "uncertainty", and "unpredictability" have subjective meanings, and the knowledge, particularly the predictive knowledge, of the designer of an experimental process is a determinant of whether the process is stochastic or non-stochastic.

By way of illustration, stochastic or random mutagenesis is exemplified by a situation in which a progenitor molecular template is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. In contrast, non-stochastic or non-random mutagenesis is exemplified by a situation in which a progenitor molecular template is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product.

Thus, as used herein, stochastic mutagenesis is manifested in processes such as error-prone PCR and stochastic shuffling, where the mutation(s) achieved are random or not predetermined. In contrast, as used herein, non-stochastic mutagenesis is manifested in instantly disclosed processes such as gene site-saturation mutagenesis and synthetic ligation reassembly, where the exact chemical structure(s) of the intended product(s) are predetermined.

In brief, existing mutagenesis methods that are non-stochastic have been serviceable in generating from one to only a very small number of predetermined mutations per method application, and thus produce per method application from one to only a few progeny molecules that have predetermined molecular structures. Moreover, the types of mutations currently available by the application of these non-stochastic methods are also limited, and thus so are the types of progeny mutant molecules.

In contrast, existing methods for mutagenesis that are stochastic in nature have been serviceable for generating somewhat larger numbers of mutations per method application—though in a random fashion & usually with a large but unavoidable contingency of undesirable background products. Thus, these existing stochastic methods can produce per method application larger numbers of progeny molecules, but that have undetermined molecular structures. The types of mutations that can be achieved by application of these current stochastic methods are also limited, and thus so are the types of progeny mutant molecules.

It is instantly appreciated that there is a need for the development of non-stochastic mutagenesis methods that:
1) Can be used to generate large numbers of progeny molecules that have predetermined molecular structures;
2) Can be used to readily generate more types of mutations;
3) Can produce a correspondingly larger variety of progeny mutant molecules;
4) Produce decreased unwanted background products;
5) Can be used in a manner that is exhaustive of all possibilities; and
6) Can produce progeny molecules in a systematic & non-repetitive way.

The instant invention satisfies all of these needs.

Directed Evolution Supplements Natural Evolution: Natural evolution has been a springboard for directed or experimental evolution, serving both as a reservoir of methods to be mimicked and of molecular templates to be mutagenized. It is appreciated that, despite its intrinsic process-related limitations (in the types of favored &/or allowed mutagenesis processes) and in its speed, natural evolution has had the advantage of having been in process for millions of years & and throughout a wide diversity of environments. Accordingly, natural evolution (molecular mutagenesis and selection in nature) has resulted in the generation of a wealth of biological compounds that have shown usefulness in certain commercial applications.

However, it is instantly appreciated that many unmet commercial needs are discordant with any evolutionary pressure &/or direction that can be found in nature. Moreover, it is often the case that when commercially useful mutations would otherwise be favored at the molecular level in nature, natural evolution often overrides the positive selection of such mutations, e.g. when there is a concurrent detriment to an organism as a whole (such as when a favorable mutation is accompanied by a detrimental mutation).

Additionally, natural evolution is often slow, and favors fidelity in many types of replication. Additionally still, natural evolution often favors a path paved mainly by consecutive beneficial mutations while tending to avoid a plurality of successive negative mutations, even though such negative mutations may prove beneficial when combined, or may lead—through a circuitous route—to final state that is beneficial.

Moreover, natural evolution advances through specific steps (e.g. specific mutagenesis and selection processes), with avoidance of less favored steps. For example, many nucleic acids do not reach close enough proximity to each other in a operative environment to undergo chimerization or incorporation or other types of transfers from one species to another. Thus, e.g., when sexual intercourse between 2 particular species is avoided in nature, the chimerization of nucleic acids from these 2 species is likewise unlikely, with parasites common to the two species serving as an example of a very slow passageway for inter-molecular encounters and exchanges of DNA. For another example, the generation of a molecule causing self-toxicity or self-lethality or sexual sterility is avoided in nature. For yet another example, the propagation of a molecule having no particular immediate benefit to an organism is prone to vanish in subsequent generations of the organism. Furthermore, e.g., there is no selection pressure for improving the performance of molecule under conditions other than those to which it is exposed in its endogenous environment; e.g. a cytoplasmic molecule is not likely to acquire functional features extending beyond what is required of it in the cytoplasm. Furthermore still, the propagation of a biological molecule is susceptible to any global detrimental effects—whether caused by itself or not—on its ecosystem. These and other characteristics greatly limit the types of mutations that can be propagated in nature.

On the other hand, directed (or experimental) evolution—particularly as provided herein—can be performed much more rapidly and can be directed in a more streamlined manner at evolving a predetermined molecular property that is commercially desirable where nature does not provide one &/or is not likely to provide. Moreover, the directed evolution invention provided herein can provide more wide-ranging possibilities in the types of steps that can be used in mutagenesis and selection processes. Accordingly, using templates harvested from nature, the instant directed evolution invention provides more wide-ranging possibilities in the types of progeny molecules that can be generated and in the speed at which they can be generated than often nature itself might be expected to in the same length of time.

In a particular exemplification, the instantly disclosed directed evolution methods can be applied iteratively to produce a lineage of progeny molecules (e.g. comprising successive sets of progeny molecules) that would not likely be propagated (i.e., generated &/or selected for) in nature, but that could lead to the generation of a desirable downstream mutagenesis product that is not achievable by natural evolution.

Previous Directed Evolution Methods Are Suboptimal: Mutagenesis has been attempted in the past on many occasions, but by methods that are inadequate for the purpose of this invention. For example, previously described non-stochastic methods have been serviceable in the generation of only very small sets of progeny molecules (comprised often of merely a solitary progeny molecule). By way of illustration, a chimeric gene has been made by joining 2 polynucleotide fragments using compatible sticky ends generated by restriction enzyme(s), where each fragment is derived from a separate progenitor (or parental) molecule. Another example might be the mutagenesis of a single codon position (i.e. to achieve a codon substitution, addition, or deletion) in a parental polynucleotide to generate a single progeny polynucleotide encoding for a single site-mutagenized polypeptide.

Previous non-stochastic approaches have only been serviceable in the generation of but one to a few mutations per method application. Thus, these previously described non-stochastic methods thus fail to address one of the central goals of this invention, namely the exhaustive and non-stochastic chimerization of nucleic acids. Accordingly previous non-stochastic methods leave untapped the vast majority of the possible point mutations, chimerizations, and combinations thereof, which may lead to the generation of highly desirable progeny molecules.

In contrast, stochastic methods have been used to achieve larger numbers of point mutations and/or chimerizations than non-stochastic methods; for this reason, stochastic methods have comprised the predominant approach for generating a set of progeny molecules that can be subjected to screening, and amongst which a desirable molecular species might hopefully be found. However, a major drawback of these approaches is that—because of their stochastic nature—there is a randomness to the exact components in each set of progeny molecules that is produced. Accordingly, the experimentalist typically has little or no idea what exact progeny molecular species are represented in a particular reaction vessel prior to their generation. Thus, when a stochastic procedure is repeated (e.g. in a continuation of a search for a desirable progeny molecule), the re-generation and re-screening of previously discarded undesirable molecular species becomes a labor-intensive obstruction to progress, causing a circuitous—if not circular—path to be taken. The drawbacks of such a highly suboptimal path can be addressed by subjecting a stochastically generated set of progeny molecules to a labor-incurring process, such as sequencing, in order to identify their molecular structures, but even this is an incomplete remedy.

Moreover, current stochastic approaches are highly unsuitable for comprehensively or exhaustively generating all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations. Accordingly, current stochastic approaches do not inherently enable the systematic elimination of unwanted mutagenesis results, and are, in sum, burdened by too many inherently shortcomings to be optimal for directed evolution.

In a non-limiting aspect, the instant invention addresses these problems by providing non-stochastic means for comprehensively and exhaustively generating all possible point mutations in a parental template. In another non-limiting aspect, the instant invention further provides means for exhaustively generating all possible chimerizations within a group of chimerizations. Thus, the aforementioned problems are solved by the instant invention.

Specific shortfalls in the technological landscape addressed by this invention include:

1) Site-directed mutagenesis technologies, such as sloppy or low-fidelity PCR, are ineffective for systematically achieving at each position (site) along a polypeptide sequence the full (saturated) range of possible mutations (i.e. all possible amino acid substitutions).
2) There is no relatively easy systematic means for rapidly analyzing the large amount of information that can be contained in a molecular sequence and in the potentially colossal number or progeny molecules that could be conceivably obtained by the directed evolution of one or more molecular templates.
3) There is no relatively easy systematic means for providing comprehensive empirical information relating structure to function for molecular positions.
4) There is no easy systematic means for incorporating internal controls, such as positive controls, for key steps in certain mutagenesis (e.g. chimerization) procedures. 5) There is no easy systematic means to select for a specific group of progeny molecules, such as full-length chimeras, from among smaller partial sequences.

An exceedingly large number of possibilities exist for the purposeful and random combination of amino acids within a protein to produce useful hybrid proteins and their corresponding biological molecules encoding for these hybrid proteins, i.e., DNA, RNA. Accordingly, there is a need to produce and screen a wide variety of such hybrid proteins for a desirable utility, particularly widely varying random proteins.

The complexity of an active sequence of a biological macromolecule (e.g., polynucleotides, polypeptides, and molecules that are comprised of both polynucleotide and polypeptide sequences) has been called its information content ("IC"), which has been defined as the resistance of the active protein to amino acid sequence variation (calculated from the minimum number of invariable amino acids (bits) required to describe a family of related sequences with the same function). Proteins that are more sensitive to random mutagenesis have a high information content.

Molecular biology developments, such as molecular libraries, have allowed the identification of quite a large number of variable bases, and even provide ways to select functional sequences from random libraries. In such libraries, most residues can be varied (although typically not all at the same time) depending on compensating changes in the context. Thus, while a 100 amino acid protein can contain only 2,000 different mutations, $20^{100}$ sequence combinations are possible.

Information density is the IC per unit length of a sequence. Active sites of enzymes tend to have a high information density. By contrast, flexible linkers of information in enzymes have a low information density.

Current methods in widespread use for creating alternative proteins in a library format are error-prone polymerase chain reactions and cassette mutagenesis, in which the specific region to be optimized is replaced with a synthetically mutagenized oligonucleotide. In both cases, a substantial number of mutant sites are generated around certain sites in the original sequence.

Error-prone PCR uses low-fidelity polymerization conditions to introduce a low level of point mutations randomly over a long sequence. In a mixture of fragments of unknown sequence, error-prone PCR can be used to mutagenize the mixture. The published error-prone PCR protocols suffer from a low processivity of the polymerase. Therefore, the protocol is unable to result in the random mutagenesis of an average-sized gene. This inability limits the practical application of error-prone PCR. Some computer simulations have suggested that point mutagenesis alone may often be too gradual to allow the large-scale block changes that are required for continued and dramatic sequence evolution. Further, the published error-prone PCR protocols do not allow for amplification of DNA fragments greater than 0.5 to 1.0 kb, limiting their practical application. In addition, repeated cycles of error-prone PCR can lead to an accumulation of neutral mutations with undesired results, such as affecting a protein's immunogenicity but not its binding affinity.

In oligonucleotide-directed mutagenesis, a short sequence is replaced with a synthetically mutagenized oligonucleotide. This approach does not generate combinations of distant mutations and is thus not combinatorial. The limited library size relative to the vast sequence length means that many rounds of selection are unavoidable for protein optimization. Mutagenesis with synthetic oligonucleotides requires sequencing of individual clones after each selection round followed by grouping them into families, arbitrarily choosing a single family, and reducing it to a consensus motif. Such motif is re-synthesized and reinserted into a single gene followed by additional selection. This step process constitutes a statistical bottleneck, is labor intensive, and is not practical for many rounds of mutagenesis.

Error-prone PCR and oligonucleotide-directed mutagenesis are thus useful for single cycles of sequence fine tuning, but rapidly become too limiting when they are applied for multiple cycles.

Another limitation of error-prone PCR is that the rate of down-mutations grows with the information content of the sequence. As the information content, library size, and mutagenesis rate increase, the balance of down-mutations to up-mutations will statistically prevent the selection of further improvements (statistical ceiling).

In cassette mutagenesis, a sequence block of a single template is typically replaced-by a (partially) randomized sequence. Therefore, the maximum information content that can be obtained is statistically limited by the number of random sequences (i.e., library size). This eliminates other sequence families which are not currently best, but which may have greater long term potential.

Also, mutagenesis with synthetic oligonucleotides requires sequencing of individual clones after each selection round. Thus, such an approach is tedious and impractical for many rounds of mutagenesis.

Thus, error-prone PCR and cassette mutagenesis are best suited, and have been widely used, for fine-tuning areas of comparatively low information content. One apparent exception is the selection of an RNA ligase ribozyme from a random library using many rounds of amplification by error-prone PCR and selection.

In nature, the evolution of most organisms occurs by natural selection and sexual reproduction. Sexual reproduction ensures mixing and combining of the genes in the offspring of the selected individuals. During meiosis, homologous chromosomes from the parents line up with one another and cross-over part way along their length, thus randomly swapping genetic material. Such swapping or shuffling of the DNA allows organisms to evolve more rapidly.

In recombination, because the inserted sequences were of proven utility in a homologous environment, the inserted sequences are likely to still have substantial information content once they are inserted into the new sequence.

Theoretically there are 2,000 different single mutants of a 100 amino acid protein. However, a protein of 100 amino acids has $20^{100}$ possible sequence combinations, a number which is too large to exhaustively explore by conventional methods. It would be advantageous to develop a system which would allow generation and screening of all of these possible combination mutations.

Some workers in the art have utilized an in vivo site specific recombination system to generate hybrids of combine light chain antibody genes with heavy chain antibody genes for expression in a phage system. However, their system relies on specific sites of recombination and is limited accordingly. Simultaneous mutagenesis of antibody CDR regions in single chain antibodies (scFv) by overlapping extension and PCR have been reported.

Others have described a method for generating a large population of multiple hybrids using random in vivo recombination. This method requires the recombination of two different libraries of plasmids, each library having a different selectable marker. The method is limited to a finite number of recombinations equal to the number of selectable markers existing, and produces a concomitant linear increase in the number of marker genes linked to the selected sequence(s).

In vivo recombination between two homologous, but truncated, insect-toxin genes on a plasmid has been reported as a method of producing a hybrid gene. The in vivo recombination of substantially mismatched DNA sequences in a host cell having defective mismatch repair enzymes, resulting in hybrid molecule formation has been reported.

1.3. SUMMARY OF THE INVENTION

Directing an Immune Response so as to Achieve an Optimal Response to Vaccination The present invention provides multicomponent genetic vaccines that include at least one, and preferably two or more genetic vaccine components that confer upon the vaccine the ability to direct an immune response so as to achieve an optimal response to vaccination. For example, the genetic vaccines can include a component that provides optimal antigen release; a component that provides optimal production of cytotoxic T lymphocytes; a component that directs release of an immunomodulator; a component that directs release of a chemokine; and/or a component that facilitates binding to, or entry into, a desired target cell type. For example, a component can confer improved improves binding to, and uptake of, the genetic vaccine to target cells such as antigen-expressing cells or antigen-presenting cells.

Additional components include those that direct antigen peptides derived from uptake of an antigen into a cell to presentation on either Class I or Class II molecules. For example, one can include a component that directs antigen peptides to presentation on Class I molecules and comprises a polynucleotide that encodes a protein such as tapasin, TAP-1 and TAP-2, and/or a component that directs antigen peptides to presentation on Class II molecules and comprises a polynucleotide that encodes a protein such as an endosomal or lysosomal protease.

In a particularly preferred aspect, this invention provides a method for obtaining an immunomodulatory polynucleotide that has an optimized modulatory effect on an immune response, or encodes a polypeptide that has an optimized modulatory effect on an immune response, the method comprising: creating a library of non-stochastically generated progeny polynucleotides from a parental polynucleotide set; wherein optimization can thus be achieved using one or more of the directed evolution methods as described herein in any combination, permutation and iterative manner; whereby these directed evolution methods include the introduction of mutations by non-stochastic methods, including by "gene site saturation mutagenesis" as described herein; and whereby these directed evolution methods also include the introduction mutations by non-stochastic polynucleotide reassembly methods as described herein; including by synthetic ligation polynucleotide reassembly as described herein.

In another particularly preferred aspect, this invention provides a method for obtaining an immunomodulatory polynucleotide that has an optimized modulatory effect on an immune response, or encodes a polypeptide that has an optimized modulatory effect on an immune response, the method comprising:
screening a library of non-stochastically generated progeny polynucleotides to identify an optimized non-stochastically generated progeny polynucleotide that has, or encodes a polypeptide that has, a modulatory effect on an immune response; wherein the optimized non-stochastically generated polynucleotide or the polypeptide encoded by the non-stochastically generated polynucleotide exhibits an enhanced ability to modulate an immune response compared to a parental polynucleotide from which the library was created.

In another particularly preferred aspect, this invention provides a method for obtaining an immunomodulatory polynucleotide that has an optimized modulatory effect on an immune response, or encodes a polypeptide that has an optimized modulatory effect on an immune response, the method comprising: a) creating a library of non-stochastically generated progeny polynucleotides from a parental polynucleotide set; and b) screening the library to identify an optimized non-stochastically generated progeny polynucleotide that has, or encodes a polypeptide that has, a modulatory effect on an immune response induced by a genetic vaccine vector; wherein the optimized non-stochastically generated polynucleotide or the polypeptide encoded by the non-stochastically generated polynucleotide exhibits an enhanced ability to modulate an immune response compared to a parental polynucleotide from which the library was created; whereby optimization can thus be achieved using one or more of the directed evolution methods as described herein in any combination, permutation, and iterative manner; whereby these directed evolution methods include the introduction of point mutations by non-stochastic methods, including by "gene site saturation mutagenesis" as described herein; and whereby these directed evolution methods also include the introduction mutations by non-stochastic polynucleotide reassembly methods as described herein; including by synthetic ligation polynucleotide reassembly as described herein.

In another particularly preferred aspect, this invention provides a method for obtaining an immunomodulatory polynucleotide that has, an optimized expression in a recombinant expression host, the method comprising: creating a library of non-stochastically generated progeny polynucleotides from a parental polynucleotide set; whereby optimization can thus be achieved using one or more of the directed evolution methods as described herein in any combination, permutation and iterative manner; whereby these directed evolution methods include the introduction of mutations by non-stochastic methods, including by "gene site saturation mutagenesis" as described herein; and whereby these directed evolution methods also include the introduction mutations by non-stochastic polynucleotide reassembly methods as described herein; including by synthetic ligation polynucleotide reassembly as described herein.

In another particularly preferred aspect, this invention provides a method for obtaining an immunomodulatory polynucleotide that has an optimized expression in a recombinant expression host, the method comprising: screening a library of non-stochastically generated progeny polynucleotides to identify an optimized non-stochastically generated progeny polynucleotide that has an optimized expression in a recombinant expression host when compared to the expression of a parental polynucleotide from which the library was created.

In another particularly preferred aspect, this invention provides a method for obtaining an immunomodulatory polynucleotide that has an optimized-expression in a recombinant expression host, the method comprising: a) creating a library of non-stochastically generated progeny polynucleotides from a parental polynucleotide set; and b) screening a library of non-stochastically generated progeny polynucleotides to identify an optimized non-stochastically generated progeny polynucleotide that has an optimized expression in a recombinant expression host when compared to the expression of a parental polynucleotide from which the library was created; whereby optimization can thus be achieved using one or more of the directed evolution methods as described herein in any combination, permutation, and iterative manner; whereby these directed evolution methods include the introduction of point mutations by non-stochastic methods, including by "gene site saturation mutagenesis" as described herein; and whereby these directed evolution methods also include the introduction mutations by non-stochastic polynucleotide reassembly methods as described herein; including by synthetic ligation polynucleotide reassembly as described herein.

In one aspect, this invention provides that the ability to a vaccine, for example a genetic vaccine, or a component of a vaccine, for example a component of a genetic vaccine by optimizing its immunogenicity. Moreover, the present invention provides for the modification of other properties, including its:
Catalysed reaction(s)
Reaction type
Natural substrate(s)
Substrate spectrum
Product spectrum
Inhibitor(s)

Cofactor(s)/prostetic group(s)
Metal compounds/salts that affect it
Turnover number
Specific activity
Km value
pH optimum
pH range
Temperature optimum
Temperature range It is also instantly appreciated that the serviceability of amolecule with an immunogenic effect can be affected by additional physical properties, which can likewise be modified by directed evolution as provided herein, such as how it is affected by subjection to:

Isolation/Preparation
Purification
Renaturating conditions (reversibility or retention of activity upon: heating and cooling, urea, salts, detergents, pH extremes)
Crystallization
pH
Temperature
Oxidation
Organic solvent(s)
Miscellaneous storage conditions Moreover, the instant invention provides for the modification of molecule's immunogenic properties properties such as Exposure to biological compartments (stomach acids, in vivo degradation)
Expression (e.g.Transcription &/or Translation) level
mRNA stability
Any in vivo interactions with other cells or biologicals Method for Obtaining the Genetic Components In some embodiments, one or more of the genetic vaccine components is obtained by a method that involves: (1) reassembling (&/or subjecting to one or more directed evolution methods described herein) at least first and second forms of a nucleic acid which can confer a desired property upon a genetic vaccine, wherein the first and second forms differ from each other in two or more nucleotides, to produce a library of recombinant nucleic acids; and (2) screening the library to identify at least one optimized recombinant component that exhibits an enhanced capacity to confer the desired property upon the genetic vaccine. If further optimization of the component is desired, the following additional steps can be conducted: (3) reassembling (&/or subjecting to one or more directed evolution methods described herein) at least one optimized recombinant component with a further form of the nucleic acid, which is the same or different from the first and second forms, to produce a further library of recombinant nucleic acids; (4) screening the further library to identify at least one further optimized recombinant component that exhibits an enhanced capacity to confer the desired property upon the genetic vaccine; and (5) repeating (3) and (4), as necessary, until the further optimized recombinant component exhibits a further enhanced capacity to confer the desired property upon the genetic vaccine.

Members of a Gene Family

In some embodiments of the invention, the first form of the nucleic acid is a first member of a gene family and the second form of the nucleic acid comprises a second member of the gene family. Additional forms of the module nucleic acid can also be members of the gene family. As an example, the first member of the gene family can be obtained from a first species of organism and the second member of the gene family obtained from a second species of organism. If desired, the optimized recombinant genetic vaccine component obtained by the methods of the invention can be backcrossed by, for example, reassembling (&/or subjecting to one or more directed evolution methods described herein) the optimized recombinant genetic vaccine component with a molar excess of one or both of the first and second forms of the substrate nucleic acids to produce a further library of recombinant genetic vaccine components; and screening the further library to identify at least one optimized recombinant genetic vaccine component that further enhances the capability of a genetic vaccine vector that includes the component to modulate the immune response.

Methods of Obtaining a Genetic Vaccine Component That Confers Upon a Genetic Vaccine Vector an Enhanced Ability to Replicate in a Host Cell.

Additional embodiments of the invention provide methods of obtaining a genetic vaccine component that confers upon a genetic vaccine vector an enhanced ability to replicate in a host cell. These methods involve creating a library of recombinant nucleic acids by subjecting to reassembly (&/or one or more additonal directed evolution methods described herein) at least two forms of a polynucleotide that can confer episomal replication upon a vector that contains the polynucleotide; introducing into a population of host cells a library of vectors, each of which contains a member of the library of recombinant nucleic acids and a polynucleotide that encodes a cell surface antigen; propagating the population of host cells for multiple generations; and identifying cells which display the cell surface antigen on a surface of the cell, wherein cells which display the cell surface antigen are likely to harbor a vector that contains a recombinant vector module which enhances the ability of the vector to replicate episomally.

Obtaining Genetic Vaccine Components That Confer Upon a Vector an Enhanced Ability to Replicate in a Host Cell Genetic vaccine components that confer upon a vector an enhanced ability to replicate in a host cell can also be obtained by creating a library of recombinant nucleic acids by subjecting to reassembly (&/or one or more additonal directed evolution methods described herein) at least two forms of a polynucleotide derived from a human papillomavirus that can confer episomal replication upon a vector that contains the polynucleotide; introducing a library of vectors, each of which contains a member of the library of recombinant nucleic acids, into a population of host cells; propagating the host cells for a plurality of generations; and identifying cells that contain the vector.

In additional embodiments, the invention provides methods obtaining a genetic vaccine component that confers upon a vector an enhanced ability to replicate in a human host cell by creating a library of recombinant nucleic acids by subjecting to reassembly (&/or one or more additonal directed evolution methods described herein) at least two forms of a polynucleotide that can confer episomal replication upon a vector that contains the polynucleotide; introducing a library of genetic vaccine vectors, each of which comprises a member of the library of recombinant nucleic acids, into a test system that mimics a human immune response; and determining whether the genetic vaccine vector replicates or induces an immune response in the test system. A suitable test system can involve human skin cells present as a xenotransplant on skin of an immunocompromised non-human host animal, for example, or a non-human mammal that comprises a functional human immune system. Replication in these systems can be detected by determining whether the animal exhibits an immune response against the antigen.

The invention also provides methods of obtaining a genetic vaccine component that confers upon a genetic vaccine an enhanced ability to enter an antigen-presenting cell. These methods involve creating a library of recombinant nucleic acids by subjecting to reassembly (&/or one or more additonal directed evolution methods described herein) at least two forms of a polynucleotide that can confer episomal replication upon a vector that contains the polynucleotide; introducing a library of genetic vaccine vectors, each of which comprises a member of the library of recombinant nucleic acids, into a population of antigen-presenting or antigen-processing cells; and determining the percentage of cells in the population which contain the nucleic acid vector. Antigen- presenting or antigen-processing cells of interest include, for example, B cells, monocytes/macrophages, dendritic cells, Langerhans cells, keratinocytes, and muscle cells.

The present invention provides methods of obtaining a polynucleotide that has a modulatory effect on an immune response that is induced by a genetic vaccine, either directly (i.e., as an immunomodulatory polynucleotide) or indirectly (i.e., upon translation of the polynucleotide to create an immunomodulatory polypeptide. The methods of the invention involve: creating a library of experimentally generated (in vitro &/or in vivo) polynucleotides; and screening the library to identify at least one optimized experimentally generated (in vitro &/or in vivo) polynucleotide that exhibits, either by itself or through the encoded polypeptide, an enhanced ability to modulate an immune response than a form of the nucleic acid from which the library was created. Examples include, for example, CpG-rich polynucleotide sequences, polynucleotide sequences that encode a costimulator (e.g., B7-1, B7-2, CD1, CD40, CD154 (ligand for CD40), CD150 (SLAM), or a cytokine. The screening step used in these methods can include, for example, introducing genetic vaccine vectors which comprise the library of recombinant nucleic acids into a cell, and identifying cells which exhibit an increased ability to modulate an immune response of interest or increased ability to express an immunomodulatory molecule. For example, a library of recombinant cytokine-encoding nucleic acids can be screened by testing the ability of cytokines encoded by the nucleic acids to activate cells which contain a receptor for the cytokine. The receptor for the cytokine can be native to the cell, or can be expressed from a heterologous nucleic acid that encodes the cytokine receptor. For example, the optimized costimulators can be tested to identify those for which the cells or culture medium are capable of inducing a predominantly $T_H2$ immune response, or a predominantly $T_H1$ immune response.

In some embodiments, the polynucleotide that has a modulatory effect on an immune response is obtained by: (1) reassembling (&/or subjecting to one or more directed evolution methods described herein) at least first and second forms of a nucleic acid that is, or encodes a molecule that is, involved in modulating an immune response, wherein the first and second forms differ from each other in two or more nucleotides, to produce a library of experimentally generated (in vitro &/or in vivo) polynucleotides; and (2) screening the library to identify at least one optimized experimentally generated (in vitro &/or in vivo) polynucleotide that exhibits, either by itself or through the encoded polypeptide, an enhanced ability to modulate an immune response than a form of the nucleic acid from which the library was created. If additional optimization is desired, the method can further involve: (3) reassembling (&/or subjecting to one or more directed evolution methods described herein) at least one optimized experimentally generated (in vitro &/or in vivo) polynucleotide with a further form of the nucleic acid, which is the same or different from the first and second forms, to produce a further library of experimentally generated (in vitro &/or in vivo) polynucleotides; (4) screening, the further library to identify at least one further optimized experimentally generated (in vitro &/or in vivo) polynucleotide that exhibits an enhanced ability to modulate an immune response than a form of the nucleic acid from which the library was created; and (5) repeating (3) and (4), as necessary, until the further optimized experimentally generated (in vitro &/or in vivo) polynucleotide exhibits an further enhanced ability to modulate an immune response than a form of the nucleic acid from which the library was created.

In some embodiments of the invention, the library of experimentally generated (in vitro &/or in vivo) polynucleotides is screened by: expressing the experimentally generated (in vitro &/or in vivo) polynucleotides so that the encoded peptides or polypeptides are produced as fusions with a protein displayed on the surface of a replicable genetic package; contacting the replicable genetic packages with a plurality of cells that display the receptor; and identifying cells that exhibit a modulation of an immune response mediated by the receptor.

The invention also provides methods for obtaining a polynucleotide that encodes an accessory molecule that improves the transport or presentation of antigens by a cell. These methods involve creating a library of experimentally generated (in vitro &/or in vivo) polynucleotides by subjecting to reassembly (&/or one or more additonal directed evolution methods described herein) nucleic acids that encode all or part of the accessory molecule; and screening the library to identify an optimized experimentally generated (in vitro &/or in vivo) polynucleotide that encodes a recombinant accessory molecule that confers upon a cell an increased or decreased ability to transport or present an antigen on a surface of the cell compared to an accessory molecule encoded by the non-recombinant nucleic acids. In some embodiments, the screening step involves: introducing the library of experimentally generated (in vitro &/or in vivo) polynucleotides into a genetic vaccine vector that encodes an antigen to form a library of vectors; introducing the library of vectors into mammalian cells; and identifying mammalian cells that exhibit increased or decreased immunogenicity to the antigen.

In some embodiments of the invention, the cytokine that is optimized is interleukin-12 and the screening is performed by growing mammalian cells which contain the genetic vaccine vector in a culture medium, and detecting whether T cell proliferation or T cell differentiation is induced by contact with the culture medium. In another embodiment, the cytokine is interferon- and the screening is performed by expressing the recombinant vector module as a fusion protein which is displayed on the surface of a bacteriophage to form a phage display library, and identifying phage library members which are capable of inhibiting proliferation of a B cell line. Another embodiment utilizes B7-1 (CD80) or B7-2 (CD86) as the costimulator and the cell or culture medium is tested for ability to modulate an immune response.

The invention provides methods of using stochastic (e.g. polynucleotide shuffling & interrupted synthesis) and non-stochastic polynucleotide reassembly to obtain optimized recombinant vector modules that encode cytokines and other costimulators that exhibit reduced immunogenicity compared to a corresponding polypeptide encoded by a non-optimized vector module. The reduced immunogenicity can be detected by introducing a cytokine or costimulator encoded by the recombinant vector module into a mammal and determining whether an immune response is induced against the cytokine.

The invention also provides methods of obtaining optimized immunomodulatory sequences that encode a cytokine antagonist. For example, suitable cytokine agonists include a soluble cytokine receptor and a transmembrane cytokine receptor having, a defective signal sequence. Examples include sIL-10R and sIL-4R, and the like.

The present invention provides methods for obtaining a cell-specific binding molecule that is useful for increasing uptake or specificity of a genetic vaccine to a target cell. The methods involve: creating a library of experimentally generated (in vitro &/or in vivo) polynucleotides that by reassembling (&/or subjecting to one or more directed evolution methods described herein) a nucleic acid that encodes a polypeptide that comprises a nucleic acid binding domain and a nucleic acid that encodes a polypeptide that comprises a cell-specific binding domain; and screening the library to identify a experimentally generated (in vitro &/or in vivo) polynucleotide that encodes a binding molecule that can bind to a nucleic acid and to a cell-specific receptor. Target cells of particular interest include antigen-presenting and antigen-processing cells, such as muscle cells, monocytes, dendritic cells, B cells, Langerhans cells, keratinocytes, and M-cells.

In some embodiments, the methods of the invention for obtaining a cell-specific binding moiety useful for increasing uptake or specificity of a genetic vaccine to a target cell involve:

(1) reassembling (&/or subjecting to one or more directed evolution methods described herein) at least first and second forms of a nucleic acid which comprises a polynucleotide that encodes a nucleic acid binding domain and at least first and second forms of a nucleic acid which comprises a cell-specific ligand that specifically binds to a protein on the surface of a cell of interest, wherein the first and second forms differ from each other in two or more nucleotides, to produce a library of recombinant binding moiety-encodingnucleic acids;

(2) transfecting into a population of host cells a library of vectors, each of which comprises: a) a binding site specific for the nucleic acid binding domain and b) a member of the library of recombinant binding moiety-encoding nucleic acids, wherein the recombinant binding moiety is expressed and binds to the binding site to form a vector-binding moiety complex;

(3) lysing the host cells under conditions that do not disrupt binding of the vector-binding moiety complex;

(4) contacting the vector-binding moiety complex with a target cell of interest; and (5) identifying target cells that contain a vector and isolating the optimized recombinant cell-specific binding moiety nucleic acids from these target cells.

If further optimization is desired, the methods can further involve:

(6) reassembling (&/or subjecting to one or more directed evolution methods described herein) at least one optimized recombinant binding moiety-encoding nucleic acid with a further form of the polynucleotide that encodes a nucleic acid binding domain and/or a further form of the polynucleotide that encodes a cell-specific ligand, which are the same or different from the first and second forms, to produce a further library of recombinant binding moiety-encoding nucleic acids;

(7) transfecting into a population of host cells a library of vectors that comprise: a) a binding site specific for the nucleic acid binding domain and 2) the recombinant binding moiety-encoding nucleic acids, wherein the recombinant binding moiety is expressed and binds to the binding site to form a vector-binding moiety complex;

(8) lysing the host cells under conditions that do not disrupt binding of the vector-binding moiety complex;

(9) contacting the vector-binding moiety complex with a target cell of interest and identifying target cells that contain the vector; and

(10) isolating the optimized recombinant binding moiety nucleic acids from the target cells which contain the vector; and

(11) repeating (6) through (10), as necessary, to obtain a further optimized cell-specific binding moiety useful for increasing uptake or specificity of a genetic vaccine vector to a target cell.

The invention also provides cell-specific recombinant binding moieties produced by expressing in a host cell an optimized recombinant binding moiety-encoding nucleic acid obtained by the methods of the invention.

In another embodiment, the invention provides genetic vaccines that include: a) an optimized recombinant binding moiety that comprises a nucleic acid binding domain and a cell-specific ligand, and b) a polynucleotide sequence that comprises a binding site, wherein the nucleic acid binding domain is capable of specifically binding to the binding site.

A further embodiment of the invention provides methods for obtaining an optimized cell-specific binding moiety useful for increasing uptake, efficacy, or specificity of a genetic vaccine for a target cell by:

(1) reassembling (&/or subjecting to one or more directed evolution methods described herein) at least first and second forms of a nucleic acid that comprises a polynucleotide which encodes a non-toxic receptor binding moiety-of an enterotoxin or other toxin, wherein the first and second forms differ from each other in two or more nucleotides, to produce a library of recombinant nucleic acids;

(2) transfecting vectors that contain the library of nucleic acids into a population of host cells, wherein the nucleic acids are expressed to form recombinant cell-specific binding moiety polypeptides;

(3) contacting the recombinant cell-specific binding moiety polypeptides with a cell surface receptor of a target cell; and (4) determining which recombinant cell-specific binding moiety polypeptides exhibit enhanced ability to bind to the target cell. Methods of enhancing uptake of a genetic vaccine vector by a target cell by coating the genetic vaccine vector with an optimized recombinant cell-specific binding moiety produced by these methods are also provided by the invention.

The present invention also provides methods for evolving a vaccine delivery vehicle, genetic vaccine vector, or a vector component to obtain an optimized delivery vehicle or component that has, or confers upon a vector, enhanced ability to enter a selected mammalian tissue upon administration to a mammal. These methods involve:

(1) reassembling (&/or subjecting to one or more directed evolution methods described herein) members of a pool of polynucleotides to produce a library of experimentally generated (in vitro &/or in vivo) polynucleotides;

(2) administering to a test animal a library of replicable genetic packages, each of which comprises a member of the library of experimentally generated (in vitro &/or in vivo) polynucleotides operably linked to a polynucleotide that encodes a display polypeptide, wherein the experimentally generated (in vitro &/or in vivo) polynucleotide and the display polypeptide are expressed as a fusion protein which is which is displayed on the surface of the replicable genetic package; and (3) recovering replicable genetic packages that are present in the selected tissue of the test animal at a suitable time after administration, wherein recovered replicable genetic packages have enhanced ability to enter the selected mammalian tissue upon administration to the mammal.

If further optimization of the delivery vehicle is desired, the methods of the invention further involve:

(4) reassembling (&/or subjecting to one or more directed evolution methods described herein) a nucleic acid that comprises at least one experimentally generated (in vitro &/or in vivo) polynucleotide obtained from a replicable genetic package recovered from the selected tissue with a further pool of polynucleotides to produce a further library of experimentally generated (in vitro &/or in vivo) polynucleotides;

(5) administering to a test animal a library of replicable genetic packages, each of which comprises a member of the further library of experimentally generated (in vitro &/or in vivo) polynucleotides operably linked to a polynucleotide that encodes a display polypeptide, wherein the experimentally generated (in vitro &/or in vivo) polynucleotide and the display polypeptide are expressed as a fusion protein which is which is displayed on the surface of the replicable genetic package;

(6) recovering replicable genetic packages that are present in the selected tissue of the test animal at a suitable time after administration; and (7) repeating (4) through (6), as necessary, to obtain a further optimized recombinant delivery vehicle that exhibits further enhanced ability to enter a selected mammalian tissue upon administration to a mammal. Methods of administration that are of particular interest include, for example, oral, topical, and inhalation. Where the administration is intravenous, mammalian tissues of interest include, for example, lymph node and spleen.

In another embodiment, the invention provides methods for evolving a vaccine delivery vehicle, genetic vaccine vector, or a vector component to obtain an optimized delivery vehicle or component to obtain an optimized delivery vehicle or vector component that has, or confers upon a vector containing the component, enhanced specificity for antigen-presenting cells by:

(1) reassembling (&/or subjecting to one or more directed evolution methods described herein) members of a pool of polynucleotides to produce a library of experimentally generated (in vitro &/or in vivo) polynucleotides;

(2) producing a library of replicable genetic packages, each of which comprises a member of the library of experimentally generated (in vitro &/or in vivo) polynucleotides operably linked to a polynucleotide that encodes a display polypeptide, wherein the experimentally generated (in vitro &/or in vivo) polynucleotide and the display polypeptide are expressed as a fusion protein which is which is displayed on the surface of the replicable genetic package;

(3) contacting the library of recombinant replicable genetic packages with a non-APC to remove replicable genetic packages that display non-APC-specific fusion polypeptides; and (4) contacting the recombinant replicable genetic packages that did not bind to the non-APC with an APC and recovering those that bind to the APC, wherein the recovered replicable genetic packages are capable of specifically binding to APCs.

In an additional embodiment, the invention provides methods for evolving a vaccine delivery vehicle, genetic vaccine vector, or a vector component to obtain an optimized delivery vehicle or component to obtain an optimized delivery vehicle or vector component that has, or confers upon. a vector containing the component, an enhanced ability to enter a target cell by:

(1) reassembling (&/or subjecting to one or more directed evolution methods described herein) at least first and second forms of a nucleic acid which encodes an invasin polypeptide, wherein the first and second forms differ from each other in two or more nucleotides, to produce a library of recombinant invasin nucleic acids;

(2) producing a library of recombinant bacteriophage, each of which displays on the bacteriophage surface a fusion polypeptide encoded by a chimeric gene that comprises a recombinant invasin nucleic acid operably linked to a polynucleotide that encodes a display polypeptide;

(3) contacting the library of recombinant bacteriophage with a population of target cells;

(4) removing unbound phage and phage which is bound to the surface of the target cells; and (5) recovering phage which are present within the target cells, wherein the recovered phage are enriched for phage that have enhanced ability to enter the target cells.

In some embodiments, the optimized recombinant genetic vaccine vectors, delivery vehicles, or vector components obtained using these methods exhibit improved ability to enter an antigen presenting cell. These methods can involve washing the cells after the transfection step to remove vectors which did not enter an antigen presenting cell; culturing the cells for a predetermined time after transfection; lysing the antigen presenting cells; and isolating the optimized recombinant genetic vaccine vector from the cell lysate.

Antigen Presenting Cells That Contain an Optimized Recombinant Genetic Vaccine Vectors can be Identified by, for Example, Detecting Expression of a Marker Gene That is Included in the Vectors The invention also provides methods of evolving a bacteriophage-derived vaccine delivery vehicle to obtain a delivery vehicle having enhanced ability to enter a target cell. These methods involve the steps of (1) reassembling (&/or subjecting to one or more directed evolution methods described herein) at least first and second forms of a nucleic acid which encodes an invasin polypeptide, wherein the first and second forms differ from each other in two or more nucleotides, to produce a library of recombinant invasin nucleic acids;

(2) producing a library of recombinant bacteriophage, each of which displays on the bacteriophage surface a fusion polypeptide encoded by a chimeric gene that comprises a recombinant invasin nucleic acid operably linked to a polynucleotide that encodes a display polypeptide;

(3) contacting the library of recombinant bacteriophage with a population of target cells;

(4) removing unbound phage and phage which is bound to the surface of the target cells; and (5) recovering phage which are present within the target cells, wherein the recovered phage are enriched for phage that have enhanced ability to enter the target cells. Again, if further optimization is desired, the methods can include the further steps of.

(6) reassembling (&/or subjecting to one or more directed evolution methods described herein) a nucleic acid which comprises at least one recombinant invasin nucleic acid obtained from a bacteriophage which is recovered from a target cell with a further pool of polynucleotides to produce a further library of recombinant invasin polynucleotides;

(7) producing a further library of recombinant bacteriophage, each of which displays on the bacteriophage surface a fusion polypeptide encoded by a chimeric gene that comprises a recombinant invasin nucleic acid operably linked to a polynucleotide that encodes a display polypeptide;

(8) contacting the library of recombinant bacteriophage with a population of target cells;

(9) removing unbound phage and phage which is bound to the surface of the target cells; and

(10) recovering phage which are present within the target cells; and

(11) repeating (6) through (10), as necessary, to obtain a further optimized recombinant delivery vehicle which exhibits further have enhanced ability to enter the target cells.

In some embodiments the methods of evolving a bacteriophage-derived vaccine delivery vehicle to obtain a delivery vehicle having enhanced ability to enter a target cell can include the additional steps of

(12) inserting into the optimized recombinant delivery vehicle a polynucleotide which encodes an antigen of interest, wherein the antigen of interest is expressed as a fusion polypeptide which comprises a second display polypeptide;

(13) administering the delivery vehicle to a test animal; and (14) determining whether the delivery vehicle is capable of inducing a CTL response in the test animal.

Alternatively, the following steps can be employed:

(12) inserting into the optimized recombinant delivery vehicle a polynucleotide which encodes an antigen of interest, wherein the antigen of interest is expressed as a fusion polypeptide which comprises a second display polypeptide;

(13) administering the delivery vehicle to a test animal; and

(14) determining whether the delivery vehicle is capable of inducing neutralizing antibodies against a pathogen which comprises the antigen of interest. An example of a target cell of interest for these methods is an antigen-presenting cell.

The present invention provides recombinant multivalent antigenic polypeptides that include a first antigenic determinant from a first disease-associated polypeptide and at least a second antigenic determinant from a second disease-associated polypeptide. The disease-associated polypeptides can be selected from the group consisting of cancer antigens, antigens associated with autoimmunity disorders, antigens associated with inflammatory conditions, antigens associated with allergic reactions, antigens associated with infectious agents, and other antigens that are associated with a disease condition.

In another embodiment, the invention provides a recombinant antigen library that contains recombinant nucleic acids that encode antigenic polypeptides. The libraries are typically obtained by reassembling (&/or subjecting to one or more directed evolution methods described herein), at least first and second forms of a nucleic acid which includes a polynucleotide sequence that encodes a disease-associated antigenic polypeptide, wherein the first and second forms differ from each other in two or more nucleotides, to produce a library of recombinant nucleic acids.

Another embodiment of the invention provides methods of obtaining a polynucleotide that encodes a recombinant antigen having improved ability to induce an immune response to a disease condition. These methods involve:

(1) reassembling (&/or subjecting to one or more directed evolution methods described herein) at least first and second forms of a nucleic acid which comprises a polynucleotide sequence that encodes an antigenic polypeptide that is associated with the disease condition, wherein the first and second forms differ from each other in two or more nucleotides, to produce a library of recombinant nucleic acids; and (2) screening the library to identify at least one optimized recombinant nucleic acid that encodes an optimized recombinant antigenic polypeptide that has improved ability to induce an immune response to the disease condition. These methods optionally further involve:

(3) reassembling (&/or subjecting to one or more directed evolution methods described herein) at least one optimized recombinant nucleic acid with a further form of the nucleic acid, which is the same or different from the first and second forms, to produce a further library of recombinant nucleic acids;

(4) screening the further library to identify at least one further optimized recombinant nucleic acid that encodes a polypeptide that has improved ability to induce an immune response to the disease condition; and (5) repeating (3) and (4), as necessary, until the further optimized recombinant nucleic acid encodes a polypeptide that has improved ability to induce an immune response to the disease condition.

In some embodiments, the optimized recombinant nucleic acid encodes a multivalent antigenic polypeptide and the screening is accomplished by expressing the library of recombinant nucleic acids in a phage display expression vector such that the recombinant antigen is expressed as a fusion protein with a phage polypeptide that is displayed on a phage particle surface; contacting the phage with a first antibody that is specific for a first serotype of the pathogenic agent and selecting those phage that bind to the first antibody; and contacting those phage that bind to the first antibody with a second antibody that is specific for a second serotype of the pathogenic agent and selecting those phage that bind to the second antibody; wherein those phage that bind to the first antibody and the second antibody express a multivalent antigenic polypeptide.

The Invention Also Provides Methods of Obtaining a Recombinant Viral Vector Which has an Enhanced Ability to Induce an Antiviral Response in a Cell

Methods of Obtaining a Recombinant Genetic Vaccine Component That Confers Upon a Genetic Vaccine an Enhanced Ability to Induce a Desired Immune Response in a Mammal In additional embodiments, the invention provides methods of obtaining a recombinant genetic vaccine component that confers upon a genetic vaccine an enhanced ability to induce a desired immune response in a mammal. These methods involve: (1) reassembling (&/or subjecting to one or more directed evolution methods described herein) at least first and second forms of a nucleic acid which comprise a genetic vaccine vector, wherein the first and second forms differ from each other in two or more nucleotides, to produce a library of recombinant genetic vaccine vectors; (2) transfecting the library of recombinant vaccine vectors into a population of mammalian cells selected from the group consisting of peripheral blood T cells, T cell clones, freshly isolated monocytes/macrophages and dendritic cells; (3) staining the cells for the presence of one or more cytokines and identifying cells which exhibit a cytokine staining pattern indicative of the desired immune response; and (4) obtaining recombinant vaccine vector nucleic acid sequences from the cells which exhibit the desired cytokine staining pattern.

Methods of Improving the Ability of a Genetic Vaccine Vector to Modulate an Immune Response Also provided by the invention are methods of improving the ability of a genetic vaccine vector to modulate an immune response by: (1) reassembling (&/or subjecting to one or more directed evolution methods described herein) at least first and second forms of a nucleic acid which comprise a genetic vaccine vector, wherein the first and second forms differ from each other in two or more nucleotides, to produce a library of recombinant genetic vaccine vectors; (2) transfecting the library of recombinant genetic vaccine vectors into a population of antigen presenting cells; and (3) isolating from the cells optimized recombinant genetic vaccine vectors which exhibit enhanced ability to modulate a desired immune response.

Methods of Obtaining a Recombinant Genetic Vaccine Vector That has an Enhanced Ability to Induce a Desired Immune Response in a Mammal Upon Administration to the Skin of the Mammal Another embodiment of the invention provides methods of obtaining a recombinant genetic vaccine vector that has an enhanced ability to induce a desired immune response in a mammal upon administration to the skin of the mammal. These methods involve: (1) reassembling (&/or subjecting to one or more directed evolution methods described herein) at least first and second forms of a nucleic acid which comprise a genetic vaccine vector, wherein the first and second forms differ from each other in two or more nucleotides, to produce a library of recombinant genetic vaccine vectors; (2) topically applying the library of recombinant genetic vaccine vectors to skin of a mammal; (3) identifying vectors that induce an immune response; and (4) recovering genetic vaccine vectors from the skin cells which contain vectors that induce an immune response.

Methods of Inducing an Immune Response in a Mammal by Topically Applying to Skin of the Mammal a Genetic Vaccine Vector, Wherein the Genetic Vaccine Vector is Optimized for Topical Application Through Use of Stochastic (e.g. Polynucleotide Shuffling & Interrupted Synthesis) and Non-stochastic Polynucleotide Reassembly The invention also provides methods of inducing an immune response in a mammal by topically applying to skin of the mammal a genetic vaccine vector, wherein the genetic vaccine vector is optimized for topical application through use of stochastic (e.g. polynucletide shuffling & interrupted synthesis) and non-stochastic polynucleotide reassembly. In some embodiments, the genetic vaccine is administered as a formulation selected from the group consisting of a transdermal patch, a cream, naked DNA, a mixture of DNA and a transfection-enhancing agent. Suitable transfection-enhancing agents include one or more agents selected from the group consisting of a lipid, a liposome, a protease, and a lipase.

Alternatively, or in addition, the genetic vaccine can be administered after pretreatment of the skin by abrasion or hair removal.

Methods of Obtaining an Optimized Genetic Vaccine Component That Confers Upon a Genetic Vaccine Containing the Component an Enhanced Ability to Induce or Inhibit Apoptosis of a Cell Into Which the Vaccine is Introduced In another embodiment, the invention provides methods of obtaining an optimized genetic vaccine component that confers upon a genetic vaccine containing the component an enhanced ability to induce or inhibit apoptosis of a cell into which the vaccine is introduced. These methods involve: (1) reassembling (&/or subjecting to one or more directed evolution methods described herein) at least first and second forms of a nucleic acid which comprise a nucleic acid that encodes an apoptosis-modulating polypeptide, wherein the first and second forms differ from each other in two or more nucleotides, to produce a library of recombinant nucleic acids; (2) transfecting the library of recombinant nucleic acids into a population of mammalian cells; (3) staining the cells for the presence of a cell membrane change which is indicative of apoptosis initiation; and (4) obtaining recombinant apoptosis-modulating genetic vaccine components from the cells which exhibit the desired apoptotic membrane changes.

Methods of Obtaining a Genetic Vaccine Component That Confers Upon a Genetic Vaccine Reduced Susceptibility to a CTL Immune Response in a Host Mammal Other embodiments of the invention provide methods of obtaining a genetic vaccine component that confers upon a genetic vaccine reduced susceptibility to a CTL immune response in a host mammal. These methods can involve: (1) reassembling (&/or subjecting to one or more directed evolution methods described herein) at least first and second forms of a nucleic acid which comprises a gene that encodes an inhibitor of a CTL immune response, wherein the first and second forms differ from each other in two or more nucleotides, to produce a library of recombinant CTL inhibitor nucleic acids; (2) introducing genetic vaccine vectors which comprise the library of recombinant CTL inhibitor nucleic acids into a plurality of human cells; (3) selecting cells which exhibit reduced MHC class I molecule expression; and (4) obtaining optimized recombinant CTL inhibitor nucleic acids from the selected cells. Methods of obtaining a genetic vaccine component that confers upon a genetic vaccine reduced susceptibility to a CTL immune response in a host mammal, The invention also provides methods of obtaining a genetic vaccine component that confers upon a genetic vaccine reduced susceptibility to a CTL immune response in a host mammal. These methods involve: (1) reassembling (&/or subjecting to one or more directed evolution methods described herein) at least first and second forms of a nucleic acid which comprises a gene that encodes an inhibitor of a CTL immune response, wherein the first and second forms differ from each other in two or more nucleotides, to produce a library of recombinant CTL inhibitor nucleic acids; (2) introducing viral vectors which comprise the library of recombinant CTL inhibitor nucleic acids into mammalian cells; (3) identifying mammalian cells which express a marker gene included in the viral vectors a predetermined time after introduction, wherein the identified cells are resistant to a CTL response; and (4) recovering as the genetic vaccine component the recombinant CTL inhibitor nucleic acids from the identified cells.

It is a general object of the invention to provide proteins and polypeptides that are derived from PfEMP1 proteins, nucleic acids encoding these proteins and antibodies that are specifically immunoreactive with these proteins. It is a further object to provide methods of using these various compositions in diagnosis, treatment or prevention of the onset of symptoms of a malaria parasite infection. It is a further object to provide methods of screening compounds to identify further compositions which may be used in these methods.

In one embodiment, the present invention provides substantially pure polypeptides which have amino acid sequences substantially homologous to the amino acid sequence of a PFEMP1 protein, or biologically active fragments thereof.

In preferred aspects, the polypeptides of the present invention are substantially homologous to the amino acid sequence shown, described &/or referenced herein (including incorporated by reference), biologically active fragments or analogues thereof. Also provided are pharmaceutical compositions comprising these polypeptides.

In another embodiment, the present invention provides nucleic acids which encode the above-described polypeptides. Particularly preferred nucleic acids will be substantially homologous to a part or whole of the nucleic acid sequence shown, described &/or referenced herein (including incorporated by reference) or the nucleic acid encoding for the sequences shown, described &/or referenced herein (including incorporated by reference). The present invention also provides expression vectors comprising these nucleic acid sequences and cells capable of expressing same.

In an additional embodiment, the present invention provides antibodies which recognize and bind PfEMP1 polypeptides or biologically active fragments thereof. More preferred are those peptides which recognize and bind PFEMP1 proteins associated with infection by more than one variant of *P. falciparum*.

In a further embodiment, the present invention provides methods of inhibiting the formation of PFEMP1/ligand complex, comprising contacting PFEMP1 or its ligands with polypeptides of the present invention.

In a related embodiment, the present invention provides methods of inhibiting sequestration of erythrocytes in a patient suffering from a malaria infection, comprising administering to said patient, an effective amount of a polypeptide of the present invention. such administration may be carried out prior to or following infection.

In still another embodiment, the present invention provides a method of detecting the presence or absence of PFEMP1 in a sample. The method comprises exposing the sample to an antibody of the invention, and detecting binding, if any, between the antibody and a component of the sample.

In an additional embodiment, the present invention provides a method of determining whether a test compound is an antagonist of PFEMP1/ligand complex formation. The method comprises incubating the test compound with PFEMP1 or a biologically active fragment thereof, and its ligand, under conditions which permit the formation of the complex. The amount of complex formed in the presence of the test compound is determined and compared with the amount of complex formed in the absence of the test compound. A decrease in the amount of complex formed in the presence of the test compound is indicative that the compound is an antagonist of PFEMP1/ligand complex formation.

Summary of Directed Evolution Approaches

This invention also relates generally to the field of nucleic acid engineering and correspondingly encoded recombinant protein engineering. More particularly, the invention relates to the directed evolution of nucleic acids and screening of clones containing the evolved nucleic acids for resultant activity(ies) of interest, such nucleic acid activity(ies) &/or specified protein, particularly enzyme, activity(ies) of interest.

Mutagenized molecules provided by this invention may have chimeric molecules and molecules with point mutations, including biological molecules that contain a carbohydrate, a lipid, a nucleic acid, &/or a protein component, and specific but non-limiting examples of these include antibiotics, antibodies, enzymes, and steroidal and non-steroidal hormones.

This invention relates generally to a method of: 1) preparing a progeny generation of molecule(s) (including a molecule that is comprised of a polynucleotide sequence, a molecule that is comprised of a polypeptide sequence, and a molecules that is comprised in part of a polynucleotide sequence and in part of a polypeptide sequence), that is mutagenized to achieve at least one point mutation, addition, deletion, &/or chimerization, from one or more ancestral or parental generation template(s); 2) screening the progeny generation molecule(s)—preferably using a high throughput method—for at least one property of interest (such as an improvement in an enzyme activity or an increase in stability or a novel chemotherapeutic effect); 3) optionally obtaining &/or cataloguing structural &/or and functional information regarding the parental &/or progeny generation molecules; and 4) optionally repeating any of steps 1) to 3).

In a preferred embodiment, there is generated (e.g. from a parent polynucleotide template)—in what is termed "codon site-saturation mutagenesis"—a progeny generation of polynucleotides, each having at least one set of up to three contiguous point mutations (i.e. different bases comprising a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"—one such mutant polypeptide for each of the 19 naturally encoded polypeptide-forming alpha-amino acid substitutions at each and every amino acid position along the polypeptide. This yield—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids Thus, in another aspect, this approach is also serviceable for generating mutants containing—in addition to &/or in combination with the 20 naturally encoded polypeptide-forming alpha-amino acids—other rare &/or not naturally-encoded amino acids and amino acid derivatives. In yet another aspect, this approach is also serviceable for generating mutants by the use of—in addition to &/or in combination with natural or unaltered codon recognition systems of suitable hosts—altered, mutagenized, &/or designer codon recognition systems (such as in a host cell with one or more altered tRNA molecules).

In yet another aspect, this invention relates to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In yet another preferred embodiment, this invention is serviceable for analyzing and cataloguing—with respect to any molecular property (e.g. an enzymatic activity) or combination of properties allowed by current technology—the effects of any mutational change achieved (including particularly saturation mutagenesis). Thus, a comprehensive method is provided for determining the effect of changing each amino acid in a parental polypeptide into each of at least 19 possible substitutions. This allows each amino acid in a parental polypeptide to be characterized and catalogued according to its spectrum of potential effects on a measurable property of the polypeptide.

In another aspect, the method of the present invention utilizes the natural property of cells to recombine molecules and/or to mediate reductive processes that reduce the complexity of sequences and extent of repeated or consecutive sequences possessing regions of homology.

It is an object of the present invention to provide a method for generating hybrid polynucleotides encoding biologically active hybrid polypeptides with enhanced activities. In accomplishing these and other objects, there has been provided, in accordance with one aspect of the invention, a method for introducing polynucleotides into a suitable host cell and growing the host cell under conditions that produce a hybrid polynucleotide.

In another aspect of the invention, the invention provides a method for screening for biologically active hybrid polypeptides encoded by hybrid polynucleotides. The present method allows for the identification of biologically active hybrid polypeptides with enhanced biological activities.

1.4. BRIEF DESCRIPTION OF THE DRAWINGS

FIG. 1. Exonuclease Activity. FIG. 1 shows the activity of the enzyme exonuclease III. This is an exemplary enzyme that can be used to shuffle, assemble, reassemble, recombine, and/or concatenate polynucleotide building blocks. The asterisk indicates that the enzyme acts from the 3' direction towards the 5' direction of the polynucleotide substrate.

Figure 2:
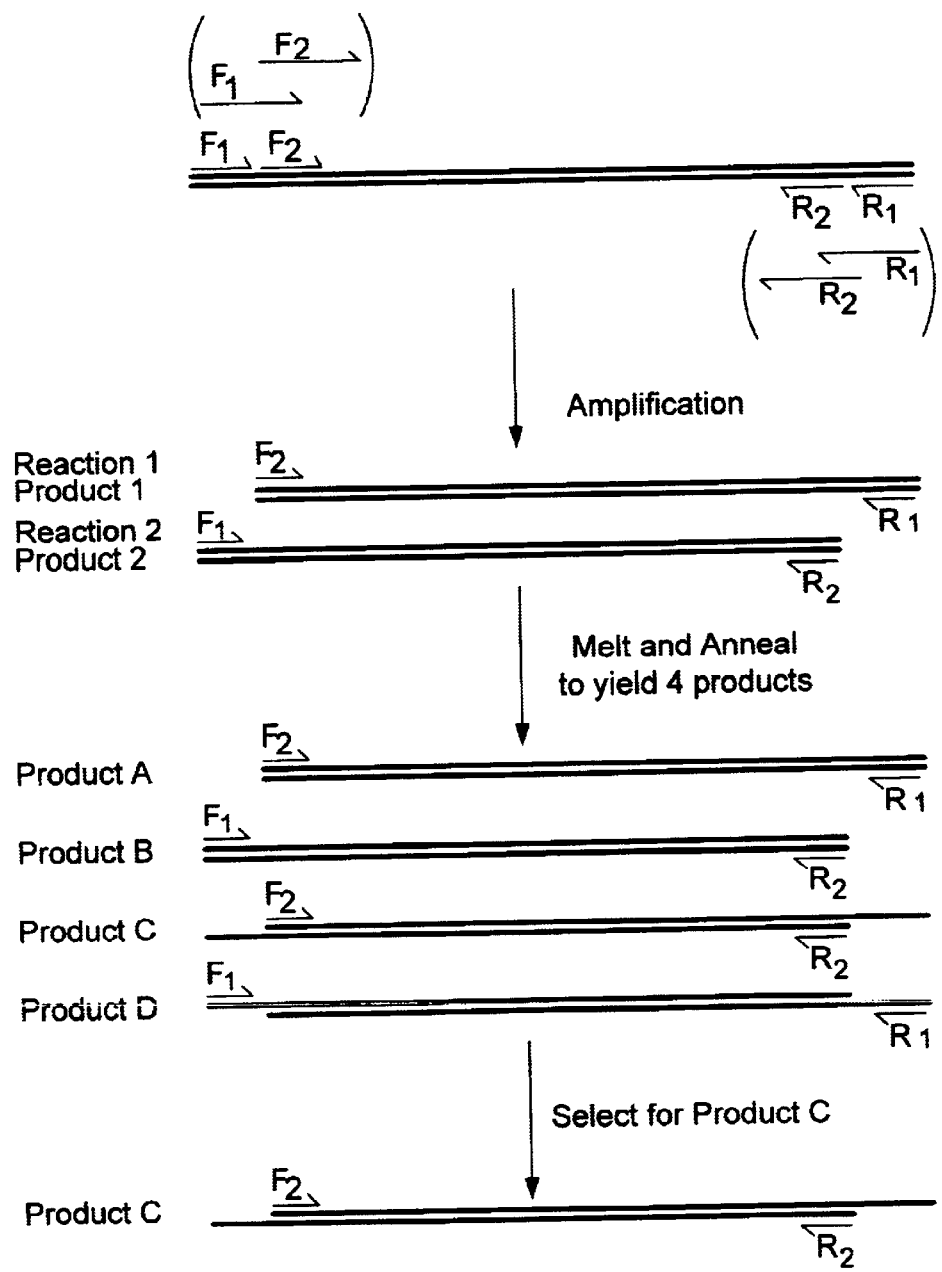

FIG. 2. Generation of A Nucleic Acid Building Block by Polymerase-Based Amplification. FIG. 2 illustrates a method of generating a double-stranded nucleic acid building block with two overhangs using a polymerase-based amplification reaction (e.g., PCR). As illustrated, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$ and $R_2$, is used to generate a blunt-ended product (labeled Reaction 2, Product 2), which is essentially identical to Product B. These two products are then mixed and allowed to melt and anneal, generating a potentially useful double-stranded nucleic acid building block with two overhangs. In the example of FIG. 1, the product with the 3' overhangs (Product C) is selected for by nuclease-based degradation of the other 3 products using a 3' acting exonuclease, such as exonuclease III. Alternate primers are shown in parenthesis to illustrate serviceable primers may overlap, and additionally that serviceable primers may be of different lengths, as shown.

FIG. 3. Unique Overhangs And Unique Couplings. FIG. 3 illustrates the point that the number of unique overhangs of each size (e.g. the total number of unique overhangs composed of 1 or 2 or 3, etc. nucleotides) exceeds the number of unique couplings that can result from the use of all the unique overhangs of that size. For example, total number of unique couplings that can be made using all the 8 unique single-nucleotide 3' overhangs and single-nucleotide 5' overhangs is 4. As shown in Panel A, 4 unique single-nucleotide 3' overhangs are possible (i.e. A, C, G, &T). For each of these there is a complementary 3' overhang with which it can pair (i.e. T, G, C, & A, respectively). However, the number of unique single-nucleotide 3' overhangs is greater than the number of unique couplings. Thus, only 2 intrinsically unique couplings exist using single-nucleotide 3' overhangs as shown in Panel B. Likewise, 4 unique single-nucleotide 5' overhangs are possible (i.e. A, C, G, & T). For each of these there is a complementary 5' overhang with which it can pair (i.e., T, G, C & A, respectively as shown in Panel C. The number of unique single-nucleotide 5' overhangs, however, is greater than the number of unique couplings. Thus, only 2 intrinsically unique couplings exist using single-nucleotide 5' overhangs as shown in Panel D.

FIG. 4. Unique Overall Assembly Order Achieved by Sequentially Coupling the Building Blocks. FIG. 4 illustrates that awareness of the degeneracy (between the number of unique overhangs and the number of unique couplings) is important in order to avoid the production of degeneracy in the overall assembly order of the finalized nucleic acid. However, a unique overall assembly order can also be achieved - despite the use of non-unique couplings—by using building blocks having distinct combinations of couplings, and/or by stepping the assembly of the building blocks in a deliberately chosen sequence. For example, on could attempt to assemble the nucleic acid product using the 5 nucleic acid building blocks as shown in Panel A. However, degeneracy in the overall assembly order of the 5' nucleic acid building blocks would be present if the assembly process were carried out in one step. For example, building block #2 and building block #3 could both couple to building block #1 as shown in Panel B. A unique overall assembly order, however, could be achieved by sequentially coupling the building blocks in 2 steps (rather than all at once) as shown in Panel C.

Figure 5:
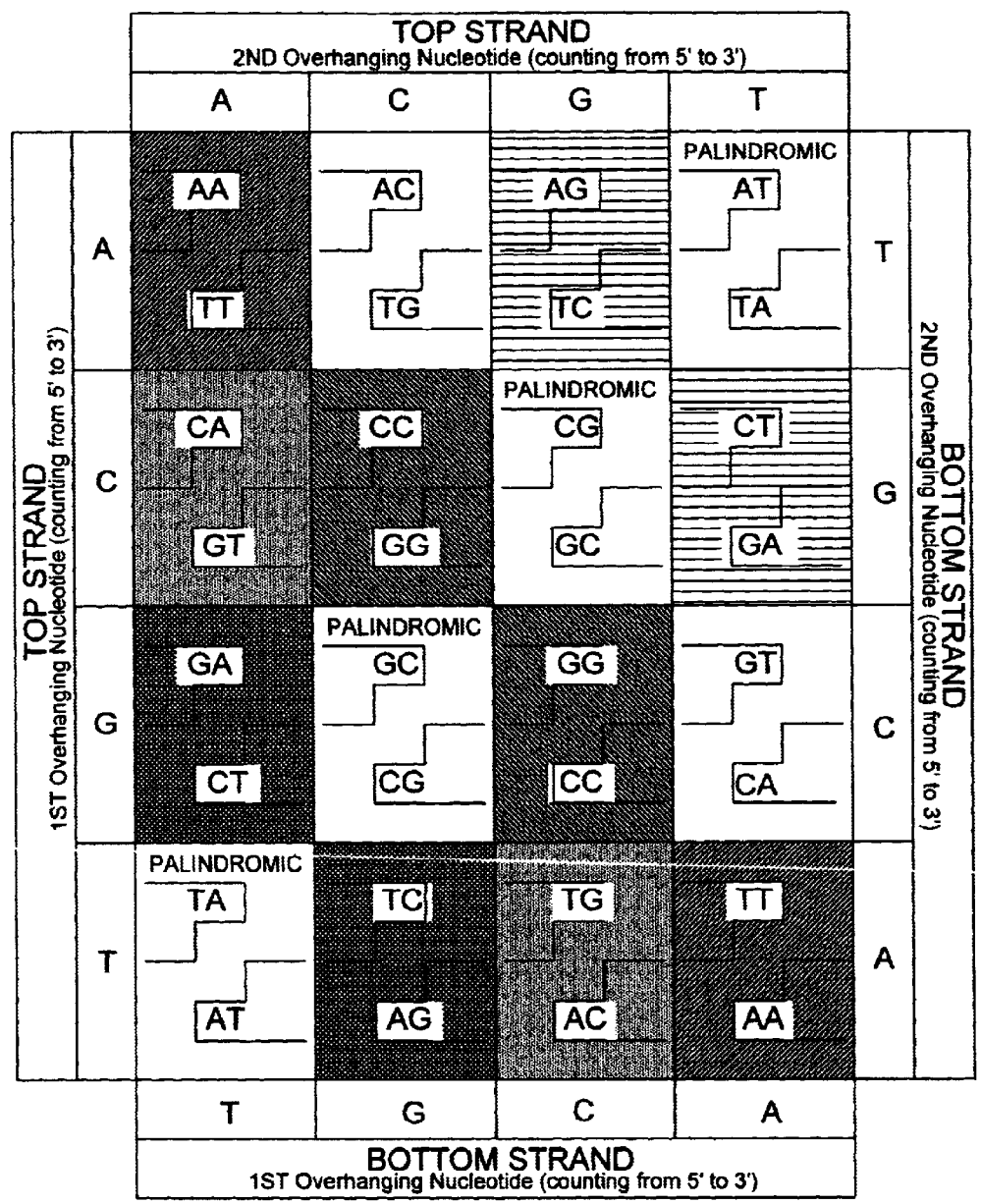

FIG. 5. Unique Couplings Available Using a Two-Nucleotide 3' Overhang. FIG. 5 further illustrates the point that the number of unique overhangs of each size (here, e.g. the total number of unique overhangs composed of 2 nucleotides) exceeds the number of unique couplings that can result from the use of all the unique overhangs of that size. For example, there are 16 unique 3' overhangs composed of two nucleotides, and another 16 unique 5' overhangs composed of two nucleotides, for a total of 32 as shown. Yet the total number of couplings that are unique and not self-binding that can be made using all the 32 unique double-nucleotide 3' overhangs and double-nucleotide 5' overhangs is 12. Some apparently unique couplings have "identical twins" (marked in the same shading), which are visually obvious in this illustration. Still other overhangs contain nucleotide sequences that can self-bind in a palindromic fashion, as shown and labeled in this figure; thus they not contribute the high stringency to the overall assembly order.

Figures 6, 6A:
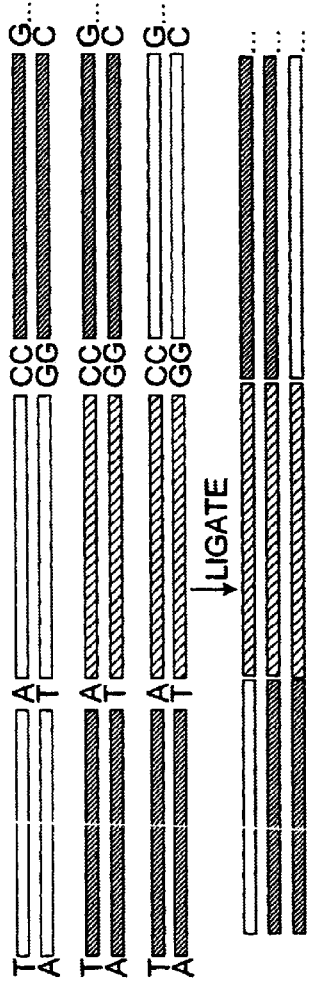

FIG. 6. Generation of an Exhaustive Set of Chimeric Combinations by Synthetic Ligation Reassembly. FIG. 6 showcases the power of this invention in its ability to generate exhaustively and systematically all possible combinations of the nucleic acid building blocks designed in this example. Particularly large sets (or libraries) of progeny chimeric molecules can be generated. Because this method can be performed exhaustively and systematically, the method application can be repeated by choosing new demarcation points and with correspondingly newly designed nucleic acid building blocks, bypassing the burden of re-generating and re-screening previously examined and rejected molecular species. It is appreciated that, codon wobble can be used to advantage to increase the frequency of a demarcation point. In other words, a particular base can often be substituted into a nucleic acid building block without altering the amino acid encoded by progenitor codon (that is now altered codon) because of codon degeneracy. As illustrated, demarcation points are chosen upon alignment of 8 progenitor templates. Nucleic acid building blocks including their overhangs (which are serviceable for the formation of ordered couplings) are then designed and synthesized. In this instance, 18 nucleic acid building blocks are generated based on the sequence of each of the 8 progenitor templates, for a total of 144 nucleic acid building blocks (or double-stranded oligos). Performing the ligation synthesis procedure will then produce a library of progeny molecules comprised of yield of $8^{18}$ (or over $1.8 \times 10^{16}$) chimeras.

FIG. 7. Synthetic genes from oligos. According to one embodiment of this invention, double-stranded nucleic acid building blocks are designed by aligning a plurality of progenitor nucleic acid templates. Preferably these templates contain some homology and some heterology. The nucleic acids may encode related proteins, such as related enzymes, which relationship may be based on function or structure or both. FIG. 7 shows the alignment of three polynucleotide progenitor templates and the selection of demarcation points (boxed) shared by all the progenitor molecules. In this particular example, the nucleic acid building blocks derived from each of the progenitor templates were chosen to be approximately 30 to 50 nucleotides in length.

Figure 8:
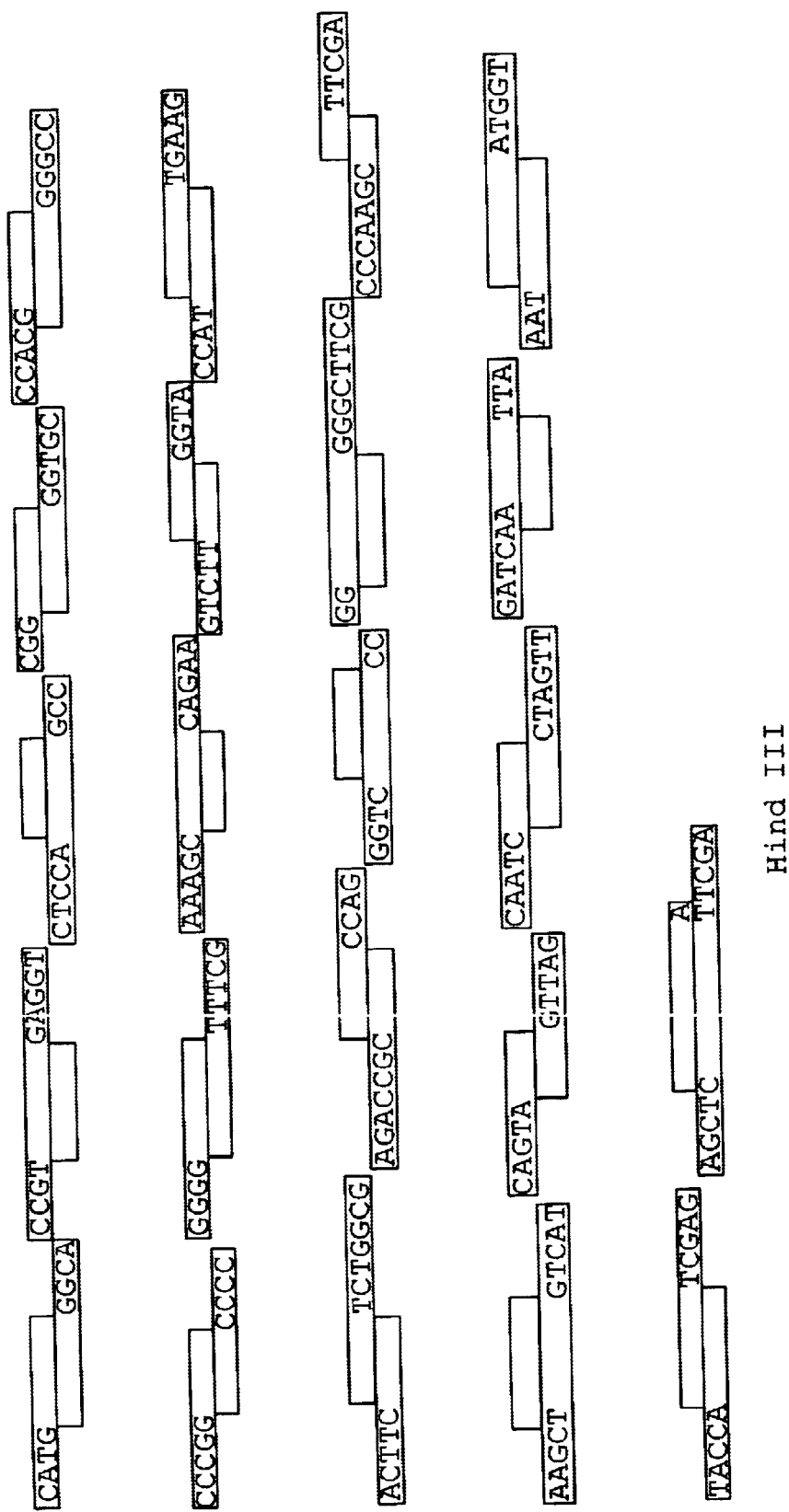

FIG. 8. Nucleic acid building blocks for synthetic ligation gene reassembly. FIG. 8 shows the nucleic acid building blocks from the example in FIG. 7. The nucleic acid building blocks are shown here in generic cartoon form, with their compatible overhangs, including both 5' and 3' overhangs. There are 22 total nucleic acid building blocks derived from each of the 3 progenitor templates. Thus, the ligation synthesis procedure can produce a library of progeny molecules comprised of yield of $3^{22}$ (or over $3.1 \times 10^{10}$) chimeras.

FIG. 9. Addition of Introns by Synthetic Ligation Reassembly. FIG. 9 shows in generic cartoon form that an intron may be introduced into a chimeric progeny molecule by way of a nucleic acid building block. It is appreciated that introns often have consensus sequences at both termini in order to render them operational. It is also appreciated that, in addition to enabling gene splicing, introns may serve an additional purpose by providing sites of homology to other nucleic acids to enable homologous recombination. For this purpose, and potentially others, it may be sometimes desirable to generate a large nucleic acid building block for introducing an intron. If the size is overly large easily genrating by direct chemical synthesis of two single stranded oligos, such a specialized nucleic acid building block may also be generated by direct chemical synthesis of more than two single stranded oligos or by using a polymerase-based amplification reaction as shown, described &/or referenced herein (including incorporated by reference).

Figure 10:
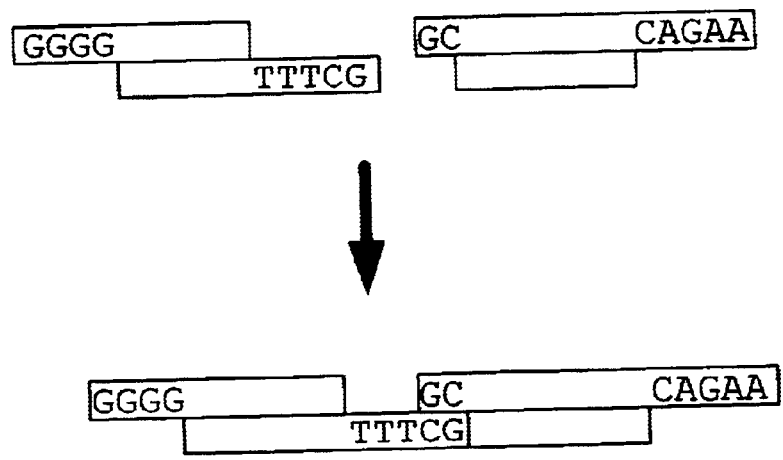

FIG. 10. Ligation Reassembly Using Fewer Than All The Nucleotides Of An Overhang. FIG. 10 shows that coupling can occur in a manner that does not make use of every nucleotide in a participating overhang. The coupling is particularly lively to survive (e.g. in a transformed host) if the coupling reinforced by treatment with a ligase enzyme to form what may be referred to as a "gap ligation" or a "gapped ligation". It is appreciated that, as shown, this type of coupling can contribute to generation of unwanted background product(s), but it can also be used advantageously increase the diversity of the progeny library generated by the designed ligation reassembly.

Figure 11:
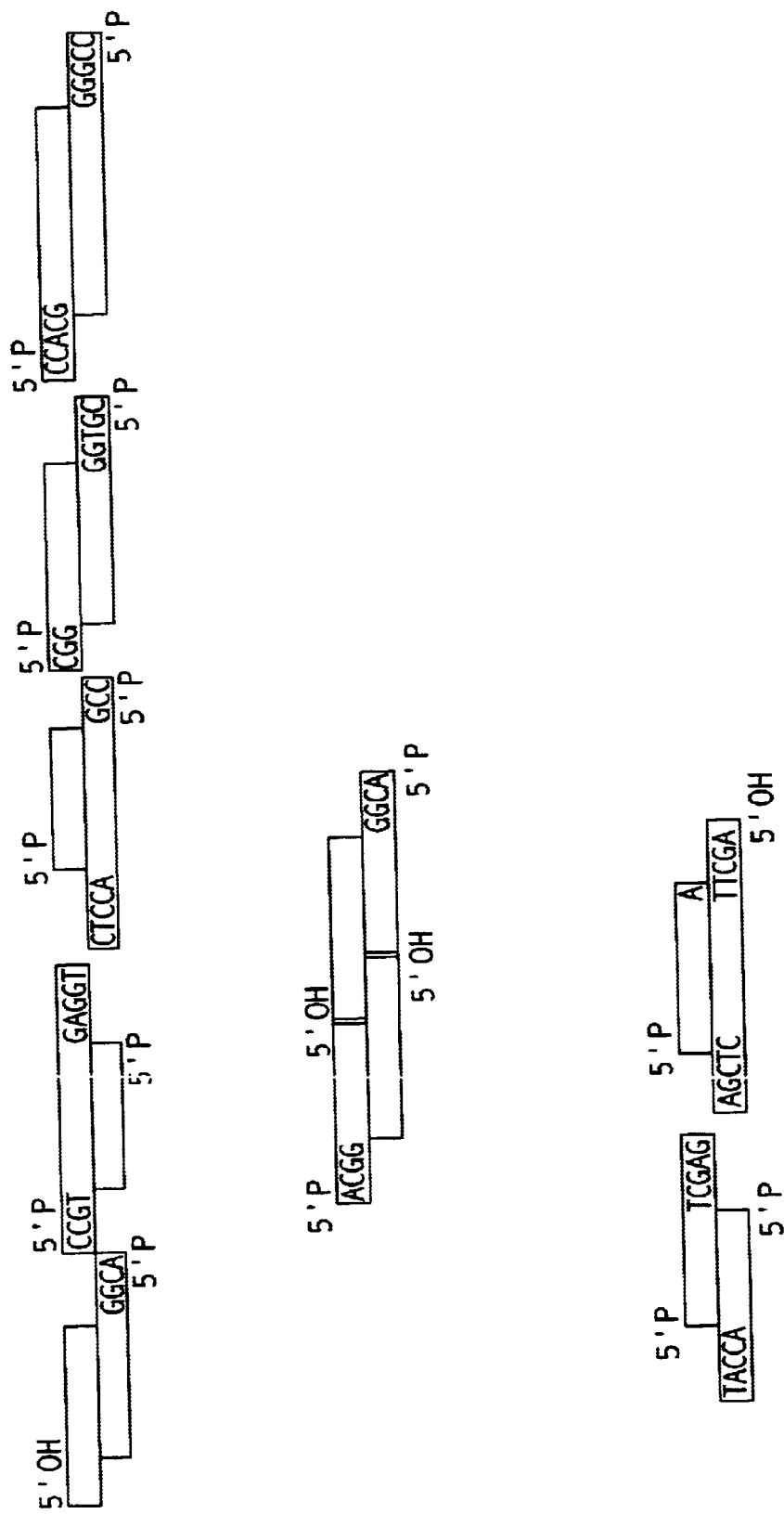

FIG. 11. Avoidance of unwanted self-ligation in palindromic couplings. As mentioned before and shown, described &/or referenced herein (including incorporated by reference), certain overhangs are able to undergo self-coupling to form a palindromic coupling. A coupling is strengthened substantially if it is reinforced by treatment with a ligase enzyme. Accordingly, it is appreciated that the lack of 5' phosphates on these overhangs, as shown, can be used advantageously to prevent this type of palindromic self-ligation. Accordingly, this invention provides that nucleic acid building blocks can be chemically made (or ordered) that lack a 5' phosphate group (or alternatively they can be remove—e.g. by treatment with a phosphatase enzyme such as a calf intestinal alkaline phosphatase (CIAP)—in order to prevent palindromic self-ligations in ligation reassembly processes.

FIG. 12. Site-directed mutagenesis by polymerase-based extension. Panel A. This figure shows one method of site-directed mutagenesis, among many methods of site-directed mutagenesis, that are serviceable for performing site-saturation mutagenesis. Section (1) shows the first and second mutagenic primer annealed to a circular closed double-stranded plasmid. The dot and the open-sided triangle indicate the mutagenic sites in the mutagenic primers. The arrows indicate the direction of synthesis. Section (2) shows the newly synthesized (mutagenized) DNA strands annealed to each other. The parental DNA can be treated with a selection enzyme. The mutagenized DNA strands are shown as being annealed to form a double-stranded mutagenized circular DNA intermediate. The dot and the open-sided triangle indicate the mutagenic sites in the experimentally generated progeny (mutagenized) DNA strands. Note that the staggered openings on the mutagenized DNA strands form "sticky" ends. Section (3) shows the first and second mutagenic primer annealed to the mutagenized DNA strands of Section (2). The arrows indicate the direction of synthesis. Note the opening on each of the mutagenized DNA strands (i.e. they have not been ligated). Section (4) shows a "Gapped Product", which is composed of second generation mutagenized DNA strands, synthesized using the mutagenized DNA strands (shown in Step (2)) as a template. The DNA strands of the "Gapped Product" are shown as being annealed to form a double-stranded mutagenized circular DNA intermediate. The dot and the open-sided triangle indicate the mutagenic sites in the mutagenized DNA strands. Note the large gap in each of the mutagenized DNA strands. Section (5) shows the "Gapped Product" annealed to the parental (non-mutated) plasmid, enabling polymerase-based synthesis to occur. The arrows indicate the direction of synthesis. Section (6) shows the newly synthesized DNA strands, as being annealed to form a double-stranded mutagenized circular DNA product. The dot and the open-sided triangle indicate the mutagenic sites in the mutagenized DNA strands. Note the staggered openings on the mutagenized DNA strands. Also note the presence of both mutagenic sites on each of the mutagenized DNA strands. Panel B. This figure shows two possible molecular structures produced from the amplification steps of FIG. 12A. Molecule (A) is shown also in Section (2) of FIG. 12A. Molecule (B) is also shown in Section (6) of FIG. 12A.

FIG. 13. Site-directed mutagenesis by polymerase-based extension and ligase-based ligation. Panel A. This figure shows one method of site-directed mutagenesis, among many methods of site-directed mutagenesis, that are serviceable for performing site-saturation mutagenesis. Section (1) shows the first and second mutagenic primer annealed to a circular closed double-stranded plasmid. The dot and the open-sided triangle indicate the mutagenic sites in the mutagenic primers. The arrows indicate the direction of synthesis. Section (2) shows the newly synthesized (mutagenized) DNA strands annealed to each other. The parental DNA can be treated with a selection enzyme. The mutagenized DNA strands are shown as being annealed to form a double-stranded mutagenized circular DNA intermediate. The dot and the open-sided triangle indicate the mutagenic sites in the experimentally generated progeny (mutagenized) DNA strands. Note that the staggered openings on the mutagenized DNA strands form "sticky" ends. Section (3) shows the resultant double-stranded mutagenized circular DNA molecule produced after the double-stranded mutagenized circular DNA intermediate of Section (2) is ligated (e.g. with T4 DNA ligase). Section (4) shows the first and second mutagenic primer annealed to the mutagenized DNA strands of Section (3). The arrows indicate the direction of synthesis. Section (5) shows the recently generated (blue) mutagenized DNA strands as being annealed to form a double-stranded mutagenized circular DNA intermediate. The dot and the open-sided triangle indicate the mutagenic sites in the recently generated mutagenized DNA strands (blue). Note that the staggered openings on the mutagenized DNA strands form "sticky ends". Also note the presence of both mutagenic sites on each of the two recently generated mutagenized DNA strands (blue). Note the opening on each of the mutagenized DNA strands (i.e. they have not been ligated). Section (6) shows the resultant double-stranded mutagenized circular DNA molecule produced after the double-stranded mutagenized circular DNA intermediate of Section (5) is ligated (e.g. using T4 DNA ligase). The dot and the open-sided triangle indicate the mutagenic sites in the mutagenized DNA molecules. Again, note the presence of both mutagenic sites on each of the mutagenized DNA strands.

Panel B. This figure shows two molecular structures produced from the amplification steps of FIG. 13A. Molecule (A) is also shown in Section (3) of FIG. 13A. Molecule (B) is produced in Section (6) of,Figure 1 3A.

Figure 14:
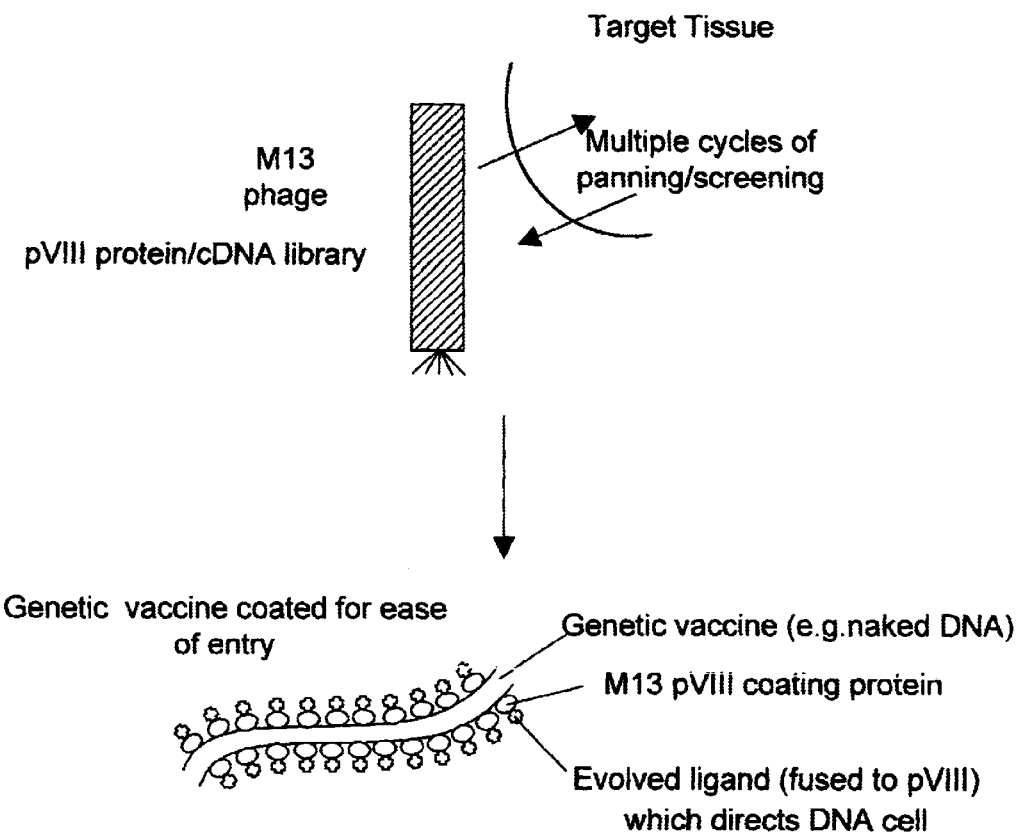

FIG. 14: Strategy for Obtaining and Using Nucleic Acid Binding Proteins that Facilitate Entry of Genetic Vaccines. Shown here is a strategy for obtaining and using nucleic acid binding proteins that facilitate entry of genetic vaccines, in particular, naked DNA, into target cells. Members of a library obtained by the directed evolution methods described herein are linked to a coding region of M 13 protein VIII so that a fusion protein is displayed on the surface of the phage particles. Phage that efficiently enter the desired target tissue are identified, and the fusion protein is then used to coat a genetic vaccine nucleic acid.

Figure 15:
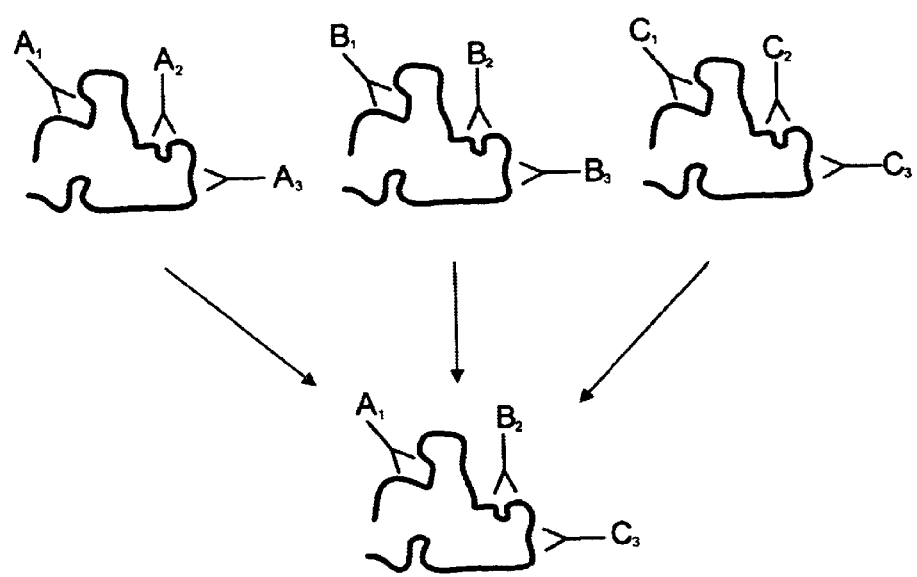

FIG. 15: A schematic representation of a method for generating a chimeric, multivalent antigen that has immunogenic regions from multiple antigens. Antibodies to each of the non-chimeric parental immunogenic polypeptides are specific for the respective organisms (A, B, C). After carrying out the directed evolution and selection methods of the invention, however, a chimeric immunogenic polypeptide is obtained that is recognized by antibodies raised against each of the three parental immunogenic polypeptides.

Figure 16:
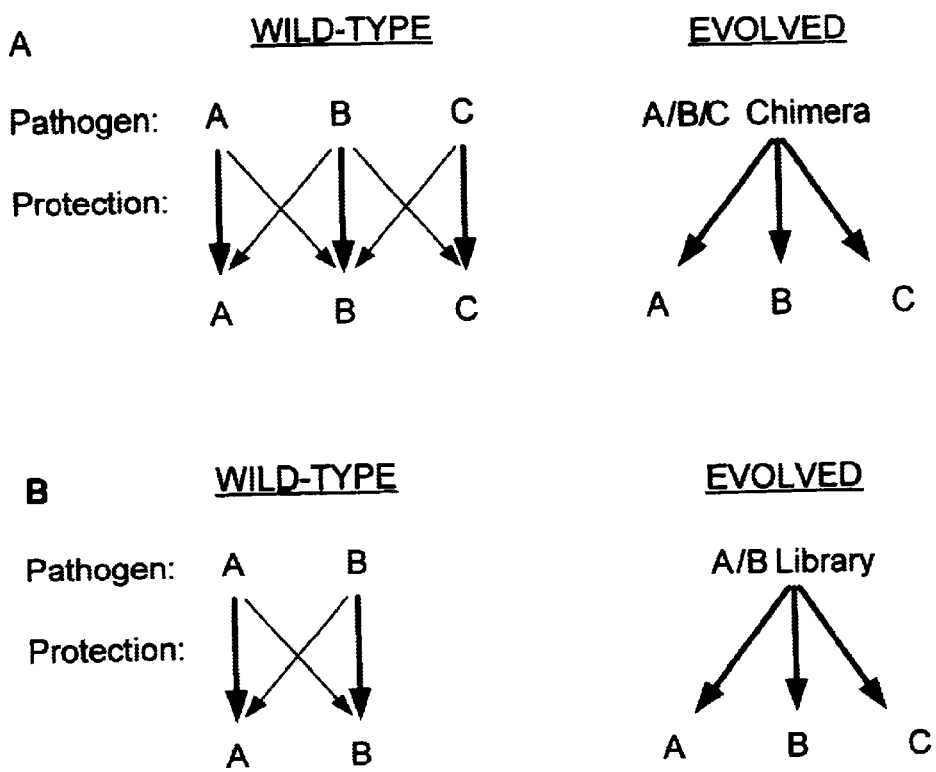

FIG. 16A and FIG. 16B: Method for Obtaining Non-Stochastically Generated Polypeptides that can induce a Broad-Spectrum Immune Response. Shown here is a schematic for a method by which one can obtain non-stochastically generated polypeptides that can induce a broad-spectrum immune response. In FIG. 16A, wild-type immunogenic polypeptides from the pathogens A, B, and C provide protection against the corresponding pathogen from which the polypeptide is derived, but little or no cross-protection against the other pathogens (left panel). After evolving, an A/B/C chimeric polypeptide is obtained that can induce a protective immune response against all three pathogen types (right panel). In FIG. 16B, directed evolution is used with substrate nucleic acids from two pathogen strains (A, B), which encode polypeptides that are protective only against the corresponding pathogen. After directed evolution, the resulting chimeric polypeptide can induce an immune response that is effective against not only the two parental pathogen strains, but also against a third strain of pathogen (C).

Figure 17:
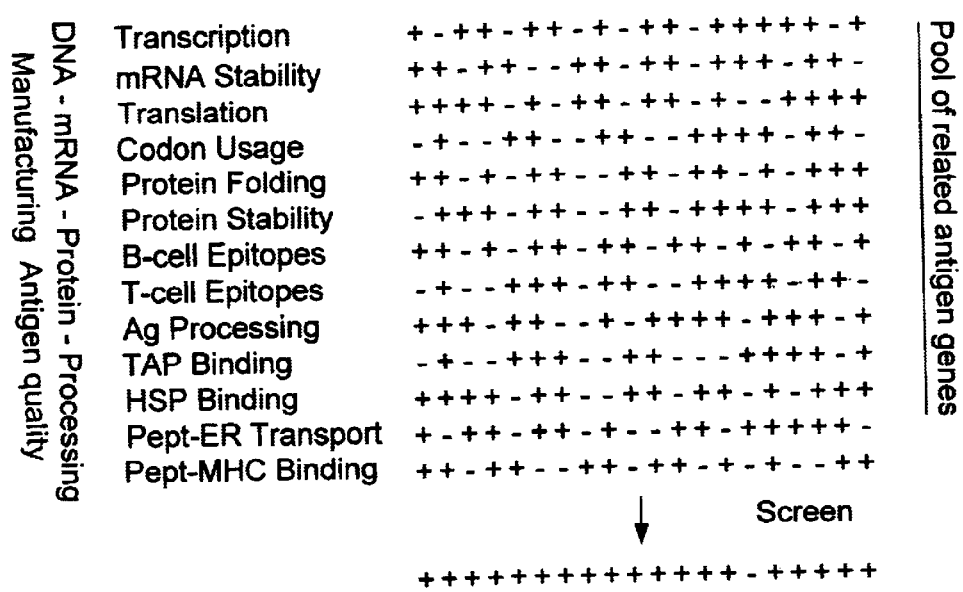

FIG. 17: Possible factors for determining whether a particular polynucleotide encodes an immunogenic polypeptide having a desired property. Shown here are some of the possible factors that can determine whether a particular polynucleotide encodes an immunogenic polypeptide having a desired property, such as enhanced immunogenicity and/or cross-reactivity. Those sequence regions that positively affect a particular property are indicated as plus signs along the antigen gene, while those sequence regions that have a negative effect are shown as minus signs. A pool of related antigen genes are non-stochastically generated using the methods described herein and screened to obtain those evolved nucleic acids that have gained positive sequence regions and lost negative regions. No pre-existing knowledge as to which regions are positive or negative for a particular trait is required.

Figure 18:
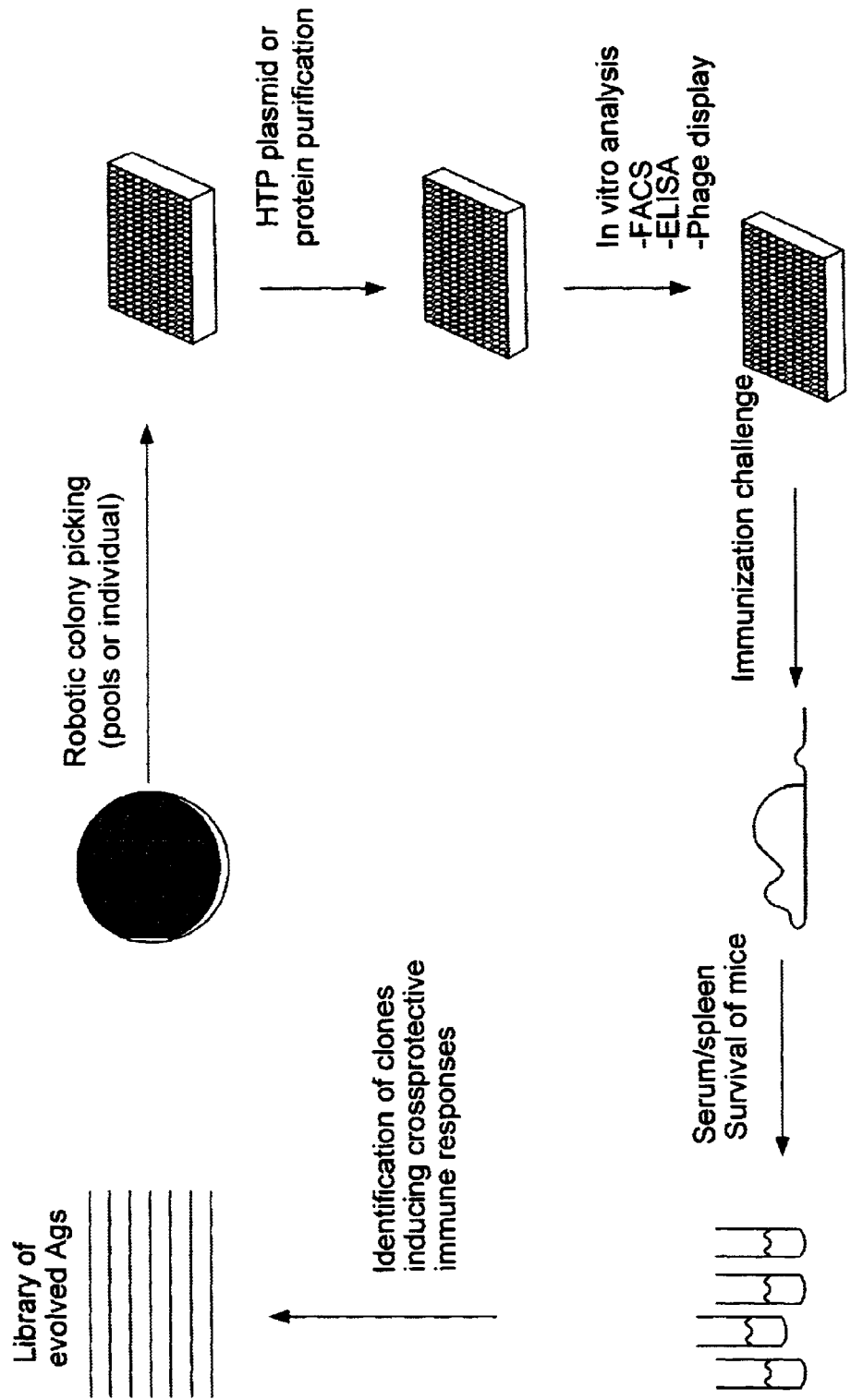

FIG. 18: Screening strategy for antigen library screening. Shown here is a schematic representation of the screening strategy for antigen library screening.

Figure 19:
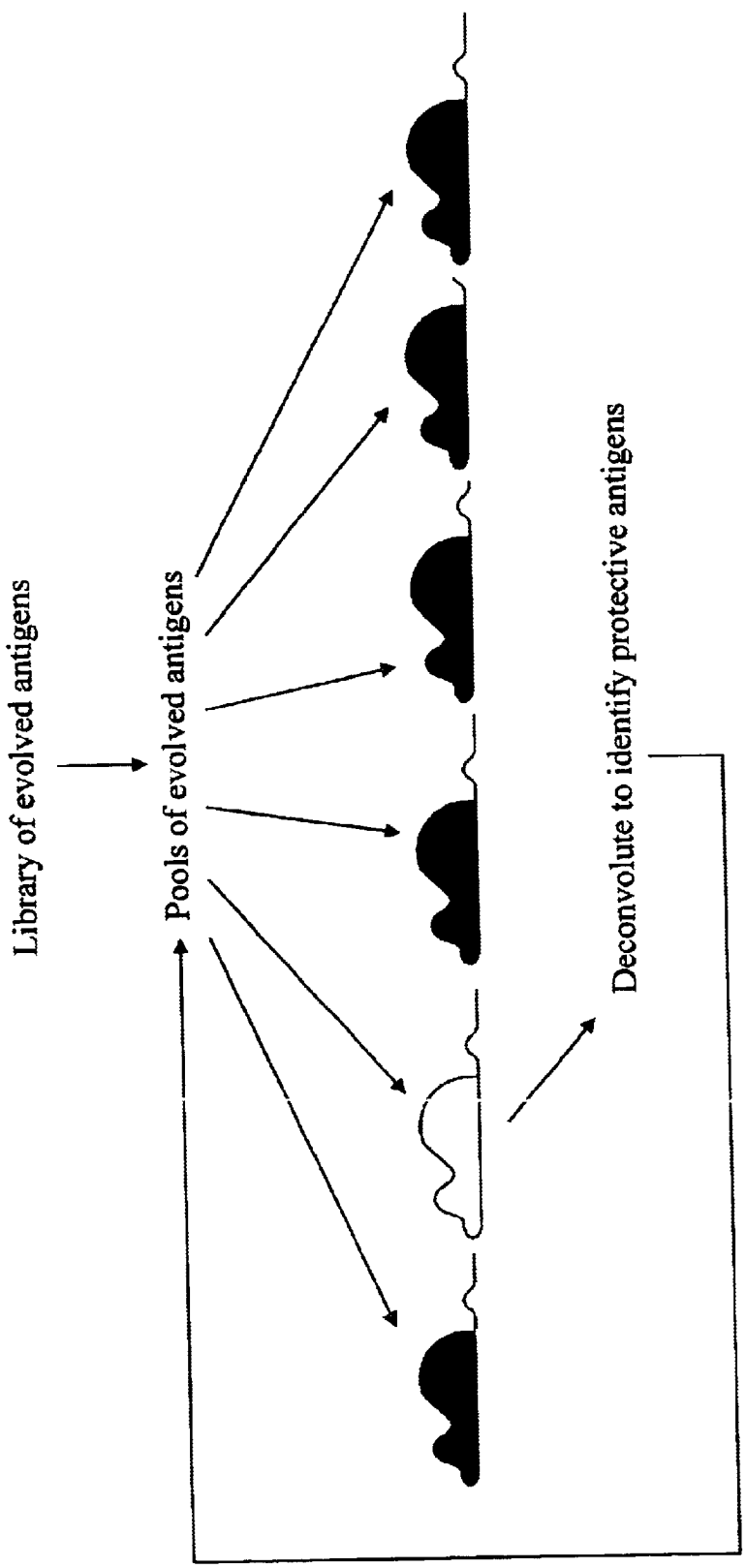

FIG. 19: Strategy for pooling and deconvolution as used in antigen library screening. Shown here is a schematic representation of a strategy for pooling and deconvolution as used in antigen library screening.

Figure 20:
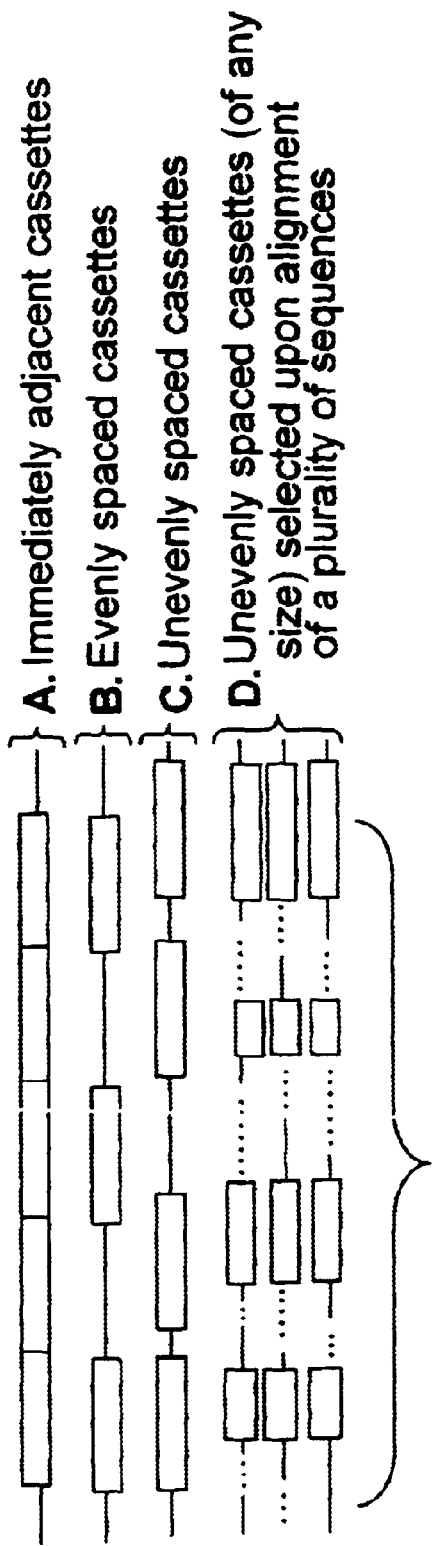

FIG. 20: Preferred Embodiments of Site-Saturation Mutagenesis.

Figure 21:
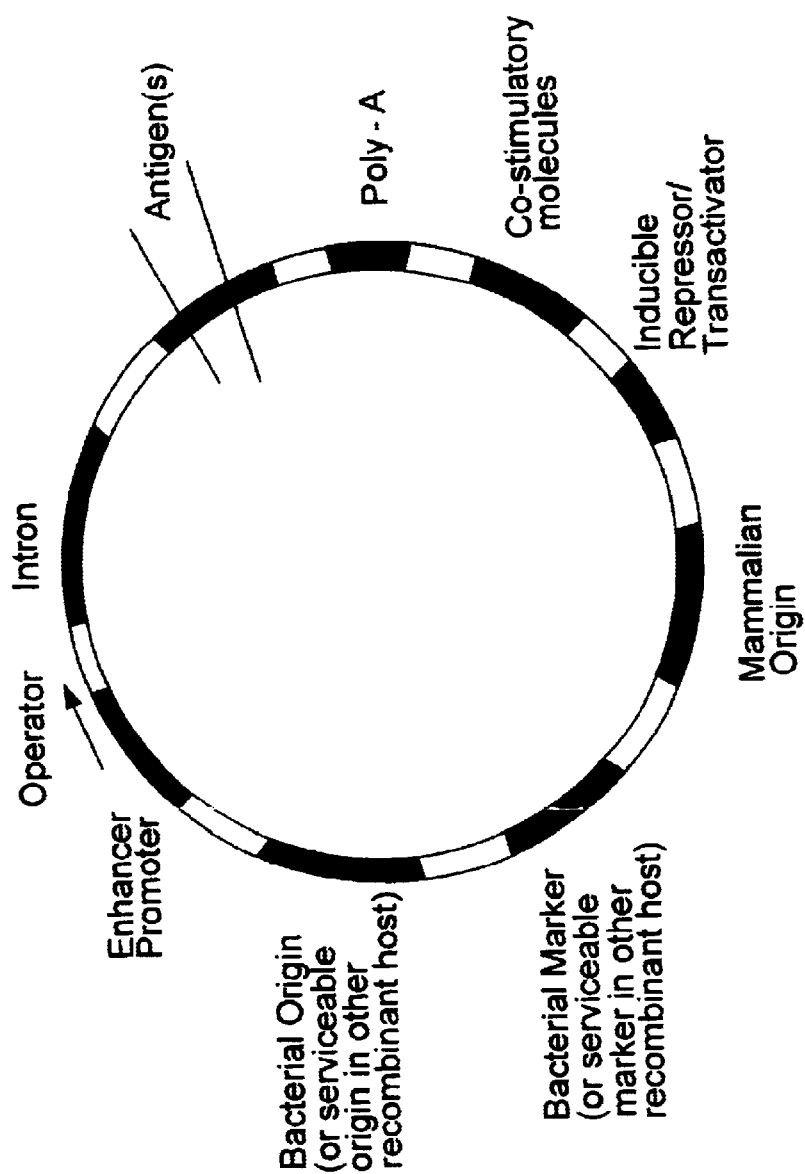

FIG. 21. Schematic representation of a multimodule genetic vaccine vector. Shown here is a schematic representation of a multimodule genetic vaccine vector. A typical genetic vaccine vector will include one or more of the components indicated, each of which can be native or optimized using the directed evolution methods described herein. These directed evolution methods can include the introduction of point mutations by stochastic methods &/or by non-stochastic methods, including "gene site saturation mutagenesis" as described herein. These directed evolution methods can also include stochastic polynucleotide reassembly methods, for example by interrupted synthesis (as described in U.S. Pat No. 5,965,408). These directed evolution methods can also include non-stochastic polynucleotide reassembly methods as described herein, including synthetic ligation polynucleotide reassembly as described herein. The components can be present on the same vaccine vector, or can be included in a genetic vaccine as separate molecules.

Figure 22A:
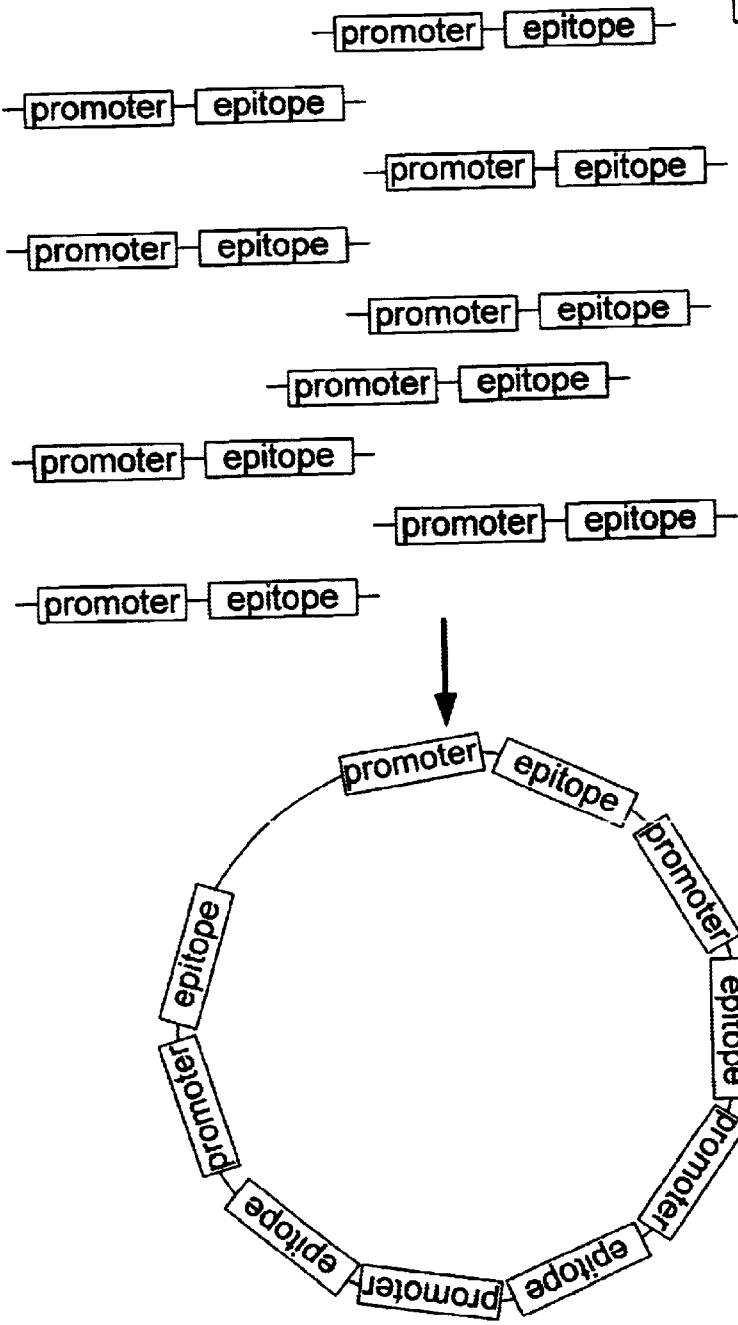
Figure 22B:
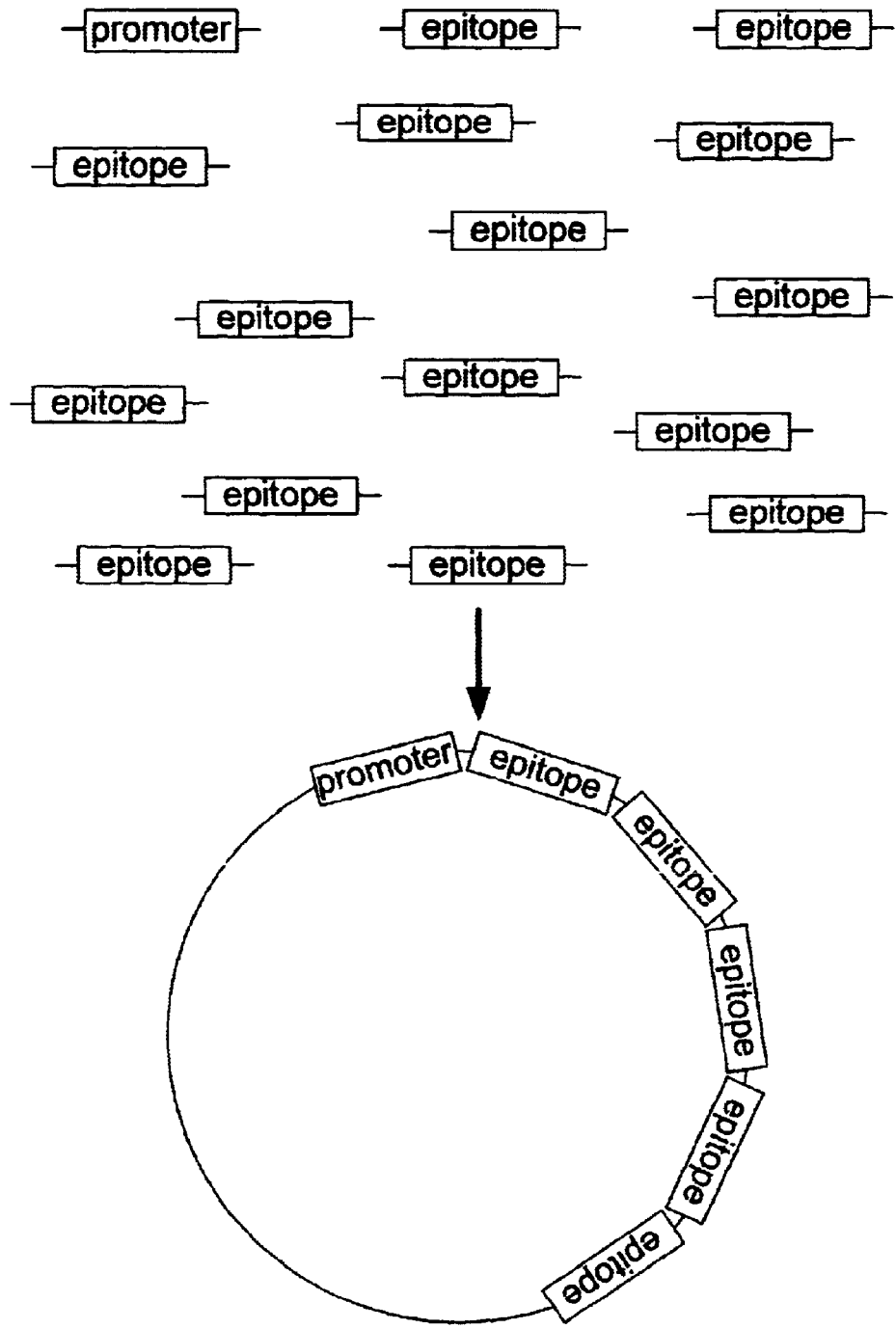

FIG. 22A and FIG. 22B. Generation of vectors with multiple T cell epitopes. Shown here are two different strategies for generating vectors that contain multiple T cell epitopes obtained, for example, by directed evolution. In FIG. 60A, each individual non-stochastically generated epitope-encoding gene is linked to a single promoter, and multiple promoter-epitope gene constructs can be placed in a single vector. The scheme shown, described &/or referenced herein (including incorporated by reference) involves linking multiple epitope-encoding genes to a single promoter.

Figure 23:
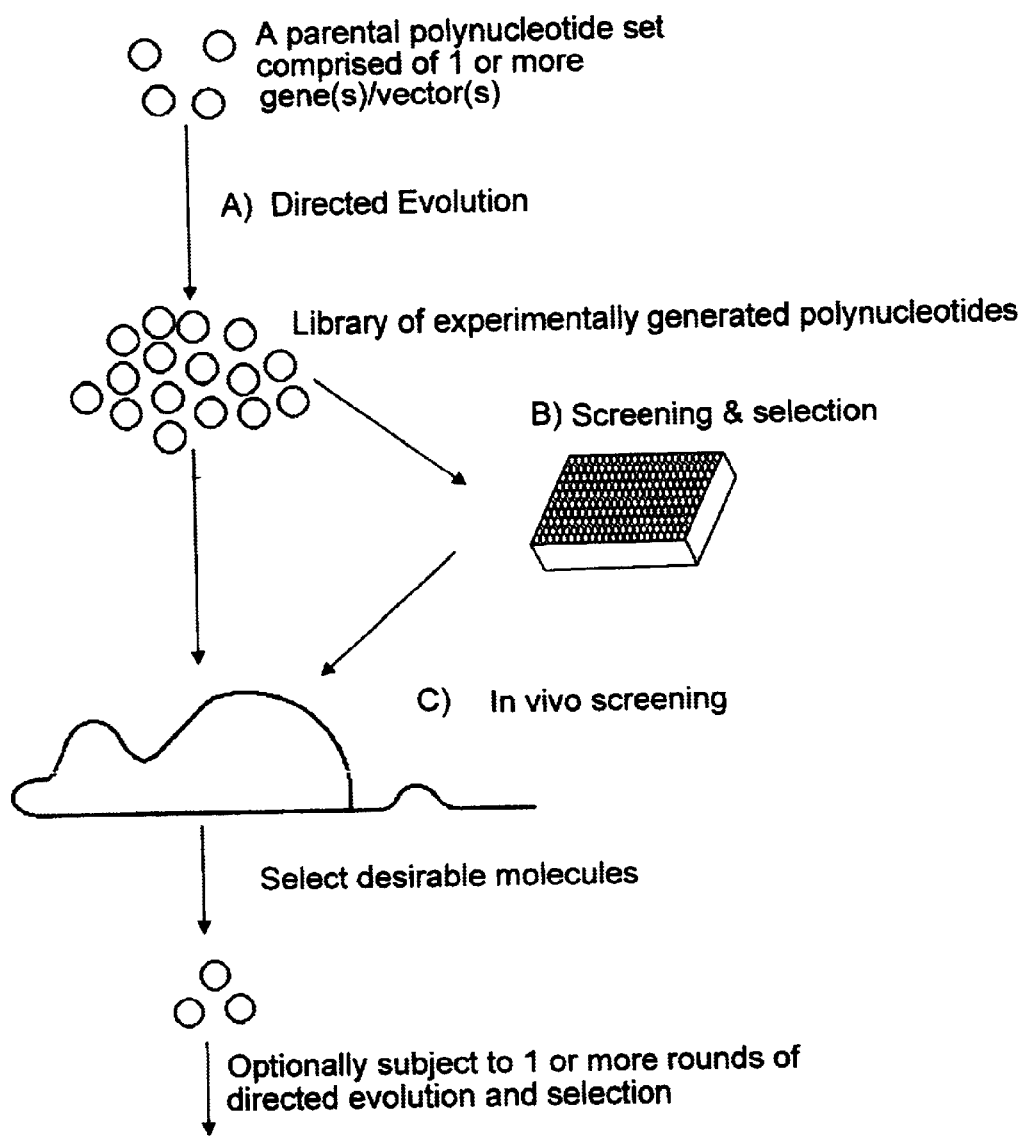

FIG. 23. Generation of optimized genetic vaccines by directed evolution. Shown here is a diagram of the application of directed evolution to the generation of optimized genetic vaccines. Different forms of polynucleotides having known functional properties (e.g., regulatory, coding, and the like) are evolved and screened to identify variants that exhibit improved properties for use as genetic vaccines.

Figure 24:
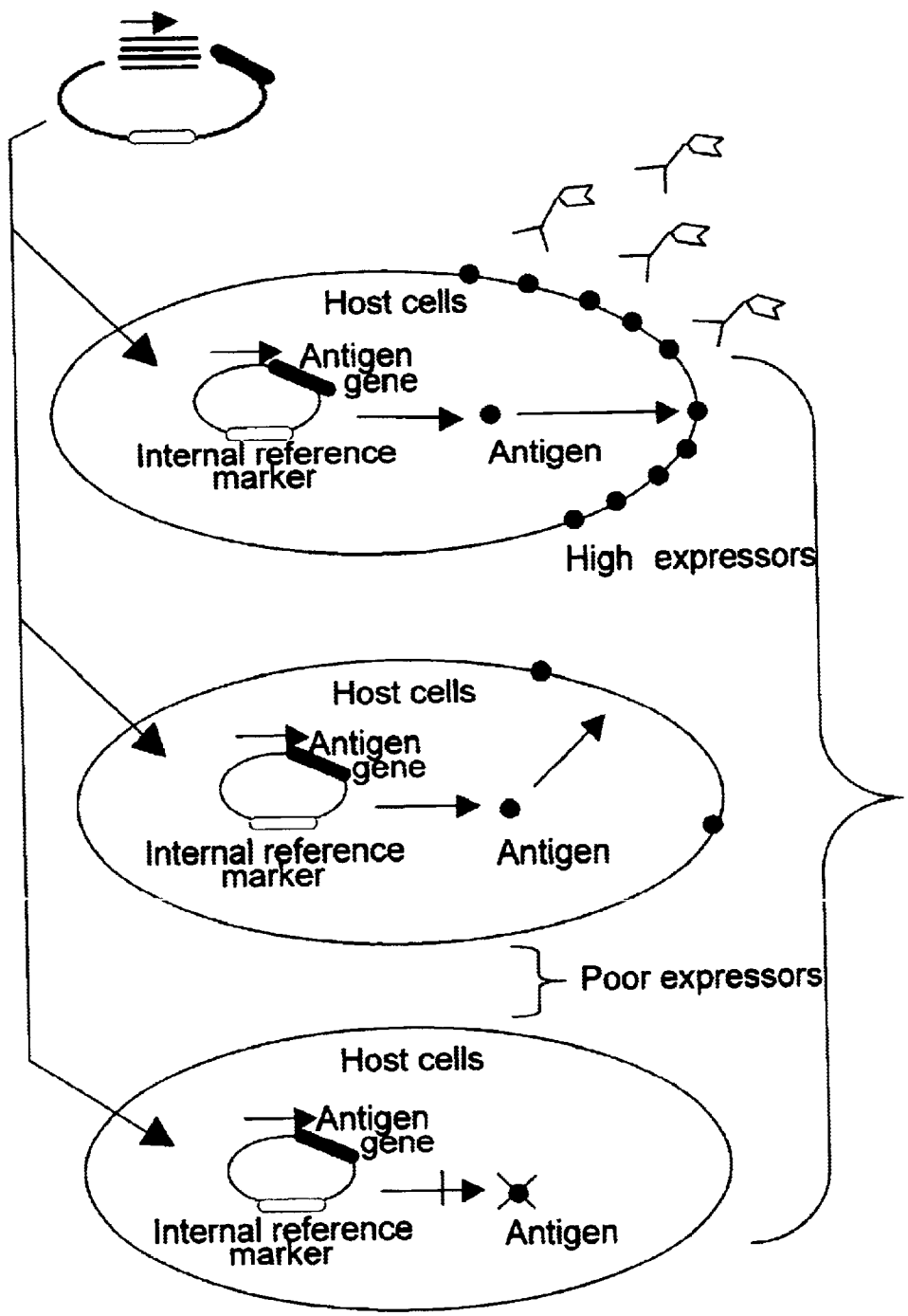

FIG. 24. Recursive application of directed evolution and selection of evolved promoter sequences as an example of flow cytometry-based screening methods. Shown here is a diagram of flow cytometry-based screening methods (FACS) for selection of optimized promoter sequences evolved using recursive applications of the directed evolution methods as described herein. A cytomegalovirus (CMV) promoter is used for illustrative purposes.

Figure 25:
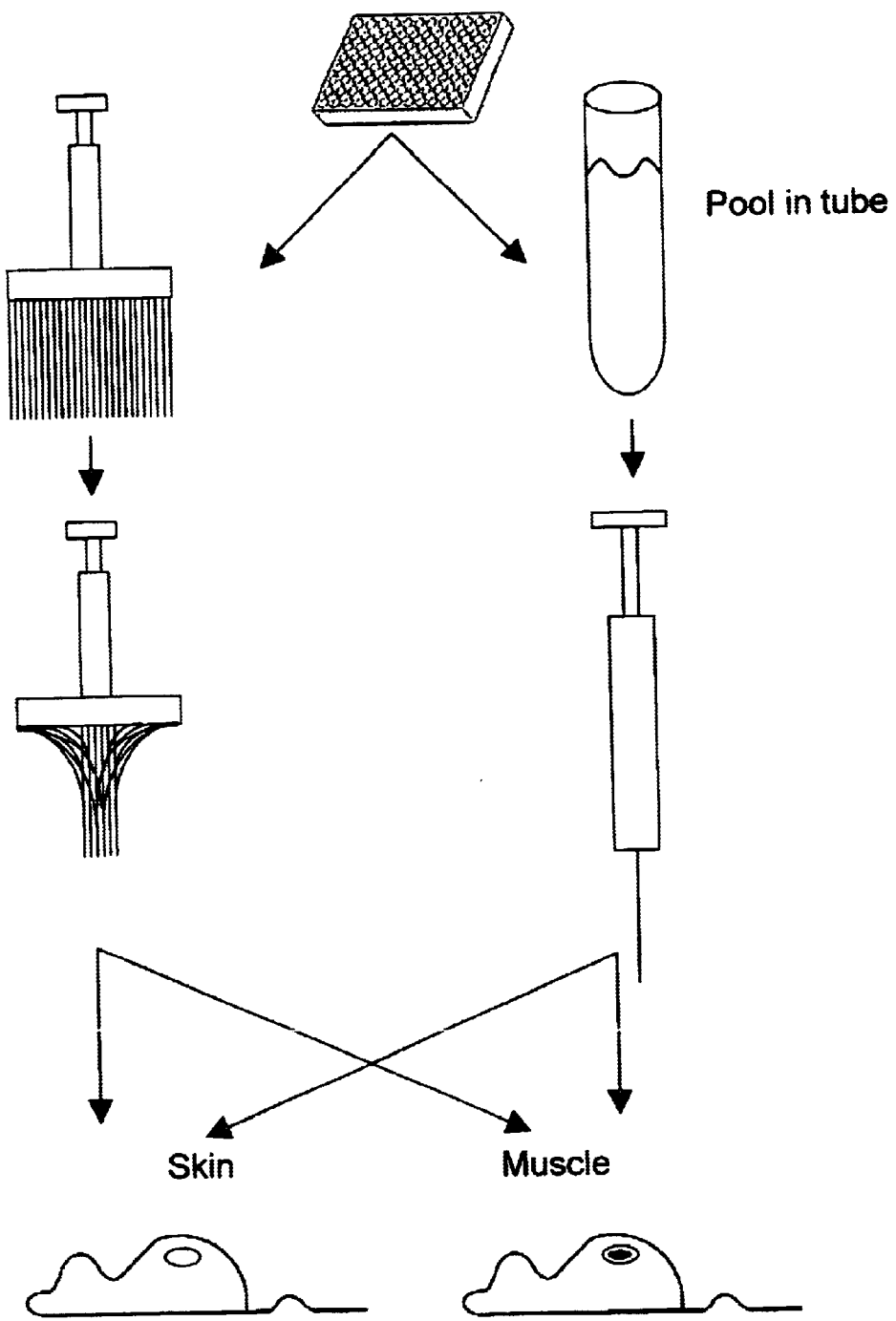

FIG. 25. An apparatus for microinjections of skin and muscle. Shown here is an apparatus that is suitable for microinjection of genetic vaccines and other reagents into tissue such as skin and muscle. The apparatus is particularly useful for screening large numbers of agents in vivo, being based on a 96-well format. The tips of the apparatus are movable to allow adjustment so that the tips fit into a microtiter plate. After obtaining a reagent of interest is obtained from a plate, the tips are adjusted to a distance of about 2–3 min apart, enabling transfer of 96 different samples to an area of about 1.6 cm by 2.4 cm to about 2.4 cm by 3.6 cm. If desired, the volume of each sample transferred can be electronically controlled; typically the volumes transferred range from about 2 $\mu$l to about 5 $\mu$ul. Each reagent can be mixed with a marker agent or dye to facilitate recognition of the injection site in the tissue. For example, gold particles of different sizes and shaped can be mixed with the reagent of interest, and microscopy and immunohistochemistry used to identify each injection site and to study the reaction induced by each reagent. When muscle tissue is injected, the injection site is first revealed by surgery.

Figure 26A:
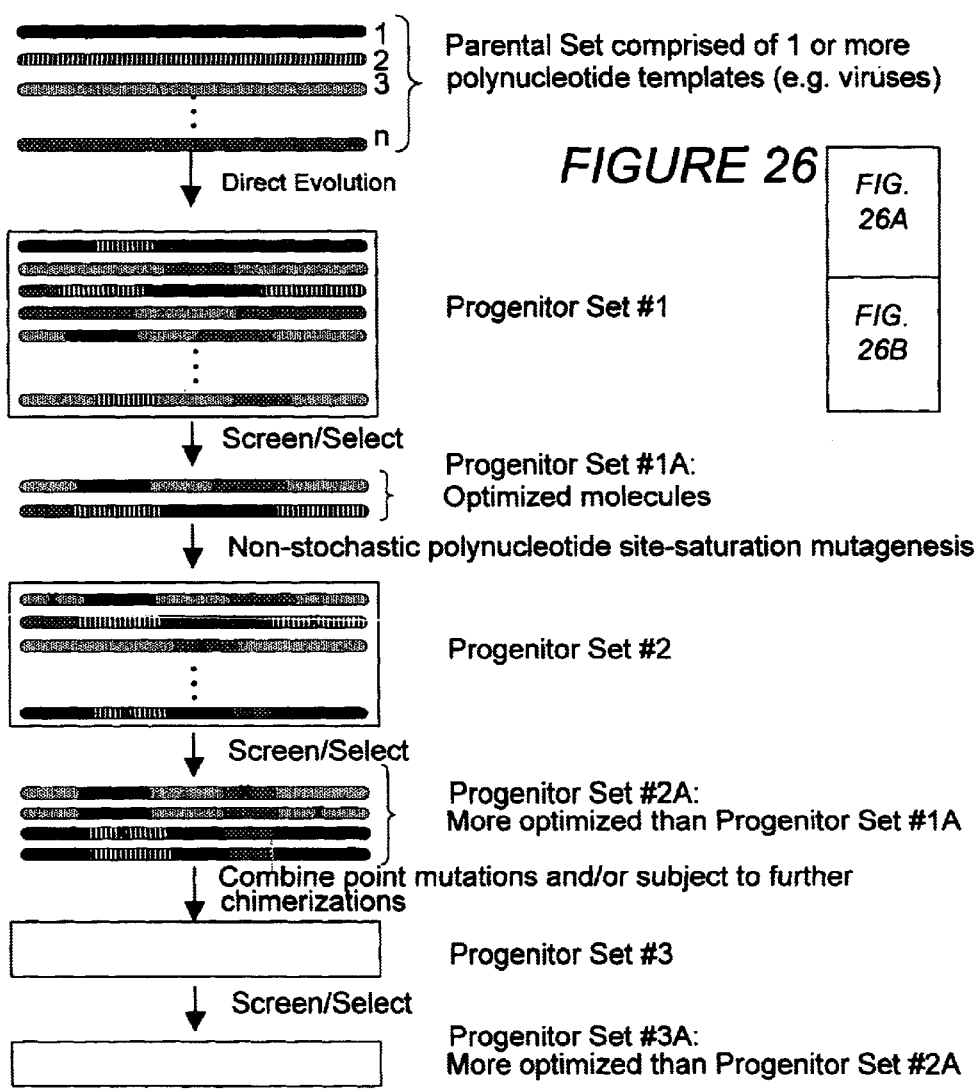
Figure 26B:
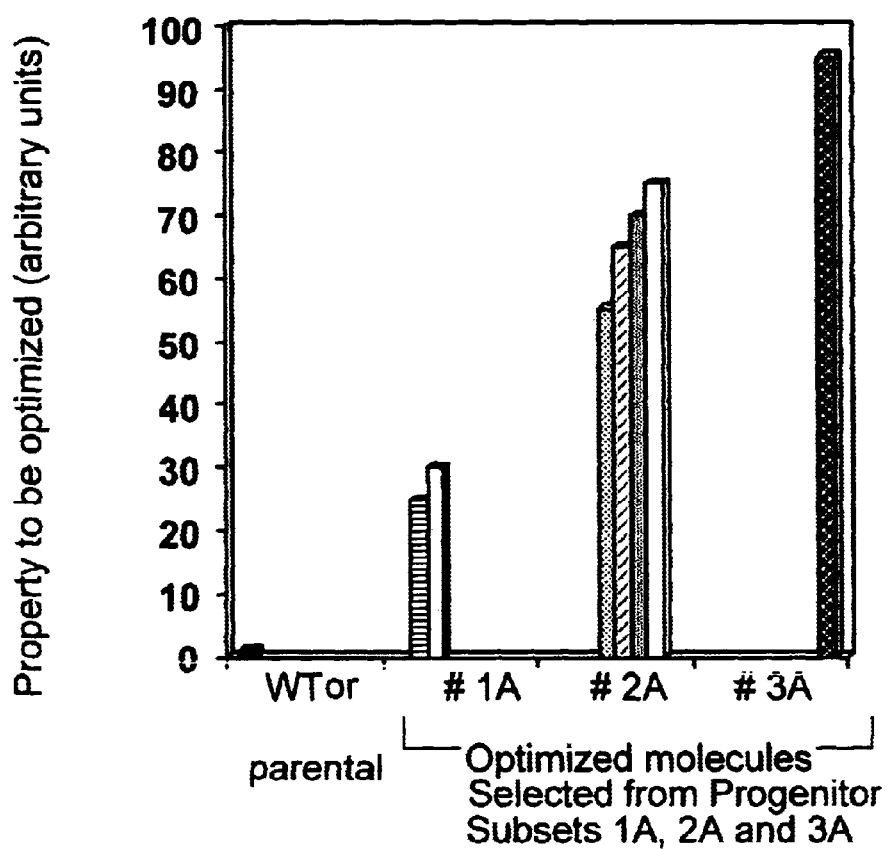

FIG. 26. Polynucleotide reassembly. Shown in Panel A is an example of directed evolution. n different strains of a virus are used in this illustration, but the technique is applicable to any single nucleic acid as well as to any nucleic acid for which different strains, species, or gene families have homologous nucleic acids that have one or more nucleotide changes compared to other homologous nucleic acids. The different variant nucleic acids are experimentally generated, preferably non-stochastically, as described herein, and screened or selected to identify those variants that exhibit the desired property. The directed evolution method(s) and screening can be repeated one or more times to obtain further improvement. Panel B shows that successive rounds of directed evolution can produce progressively enhanced properties, and that the combination of individual beneficial mutations can lead to an enhance improvement compared to the improvement achieved by an individual beneficial mutation.

Figure 27:
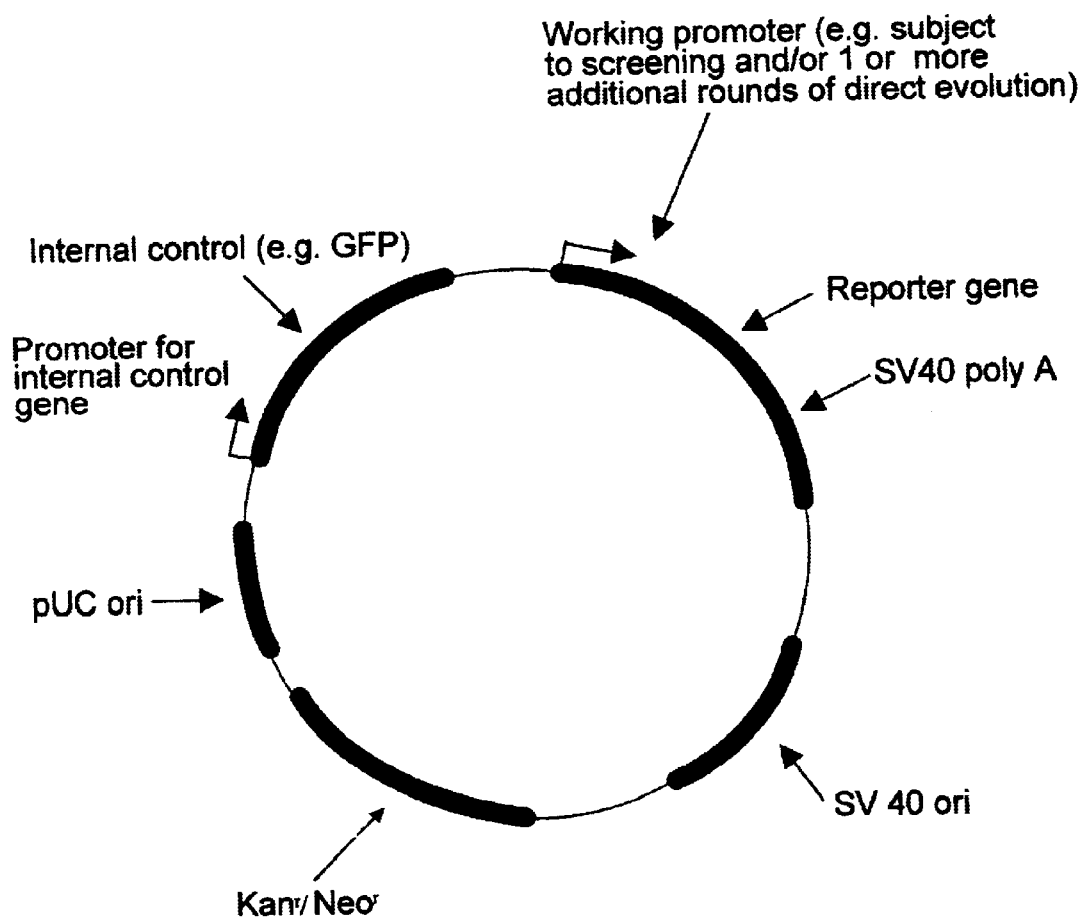

FIG. 27. Vector for promoter evolution. Shown here is an example of a vector that is useful for screening to identify improved promoters from a library of promoter nucleic acids evolved using the directed evolution methods as described herein. Experimentally generated putative promoters are inserted into the vector upstream of a reporter gene for which expression is readily detected. For many applications, it is desirable that the product of the reporter gene be a cell surface protein so that cells which express high levels of the reporter gene can be sorted using flow cytometry-based cell sorting using the reporter gene product. Examples of suitable reporter genes include, for example, B7-2 and mAb179 epitopes. A polyadenylation region is typically placed downstream of the reporter gene (SV40 polyA is illustrated). The vector can also include a second reporter gene an internal control (GFP; green fluorescent protein); this gene is linked to a promoter (SR p ). The vector also typically includes a selectable marker (kanamycin/neomycin resistance is shown), and origins of replication that are functional in mammalian (SV40 ori) and/or bacterial (pUC ori) cells.

Figure 28:
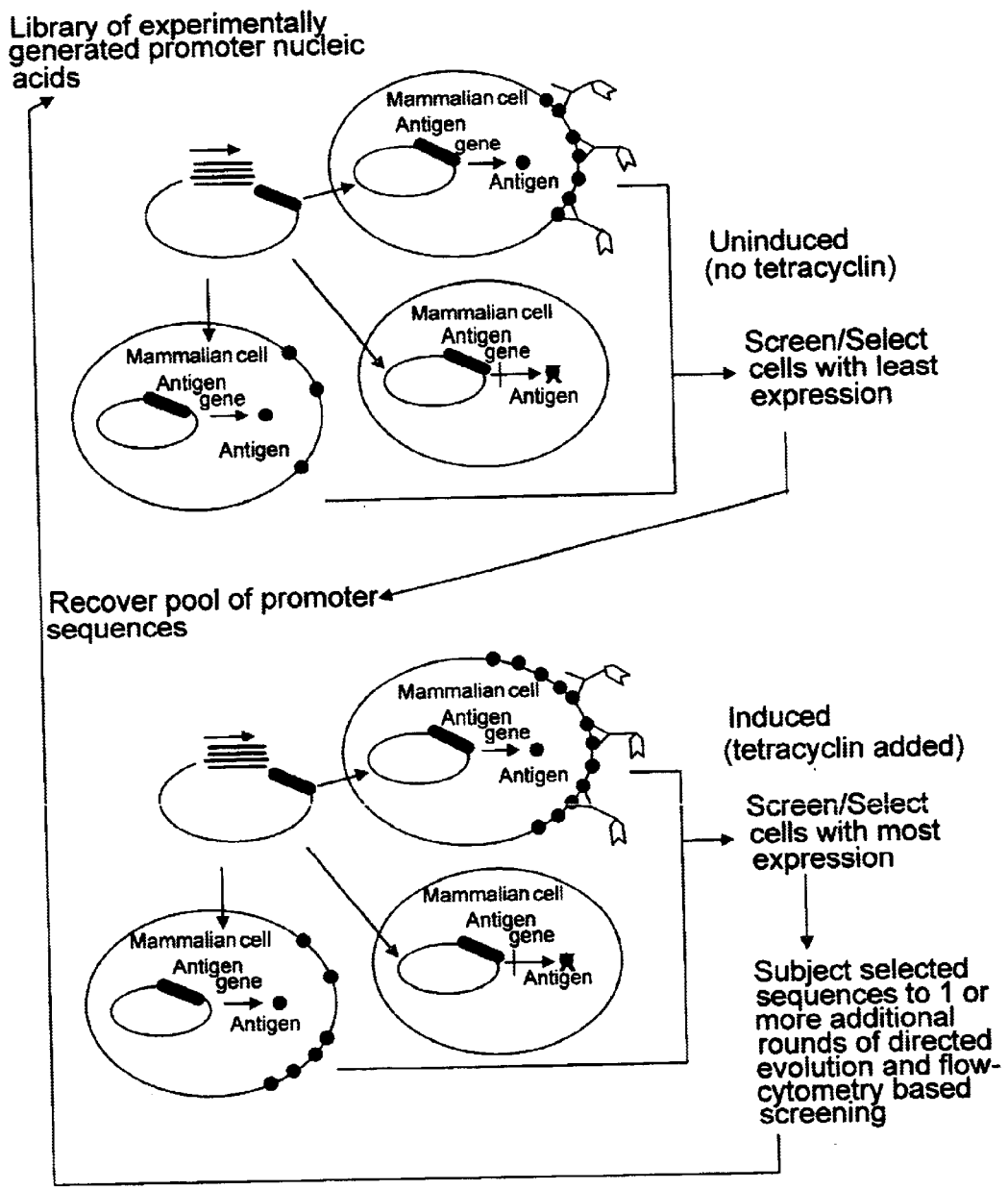

FIG. 28. Iterative evolution of inducible promoters using directed evolution and flow cytometry-based selection. Shown here is a diagram of a scheme for iterative evolution of inducible promoters using the directed evolution methods as described herein and flow cytometry-based selection. A library of experimentally generated (i.e. produced by one or more directed evolution methods as descried herein) promoter nucleic acids present in appropriate vectors is transfected into the cells, and those cells which exhibit the least expression of marker antigen when grown under uninduced conditions are selected. The vectors (&/or cells containing them) are recovered, and the vectors are introduced into cells (if not contained therein already), and grown under inducing conditions. Those cells that express the highest level of marker antigen are selected.

Figure 29:
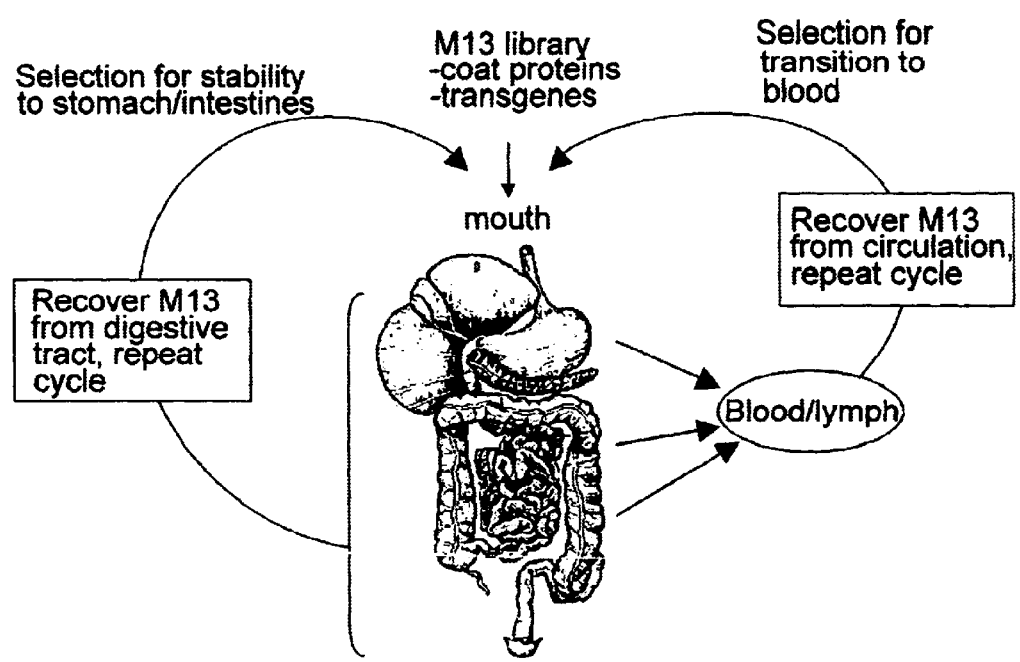
Figure 32:
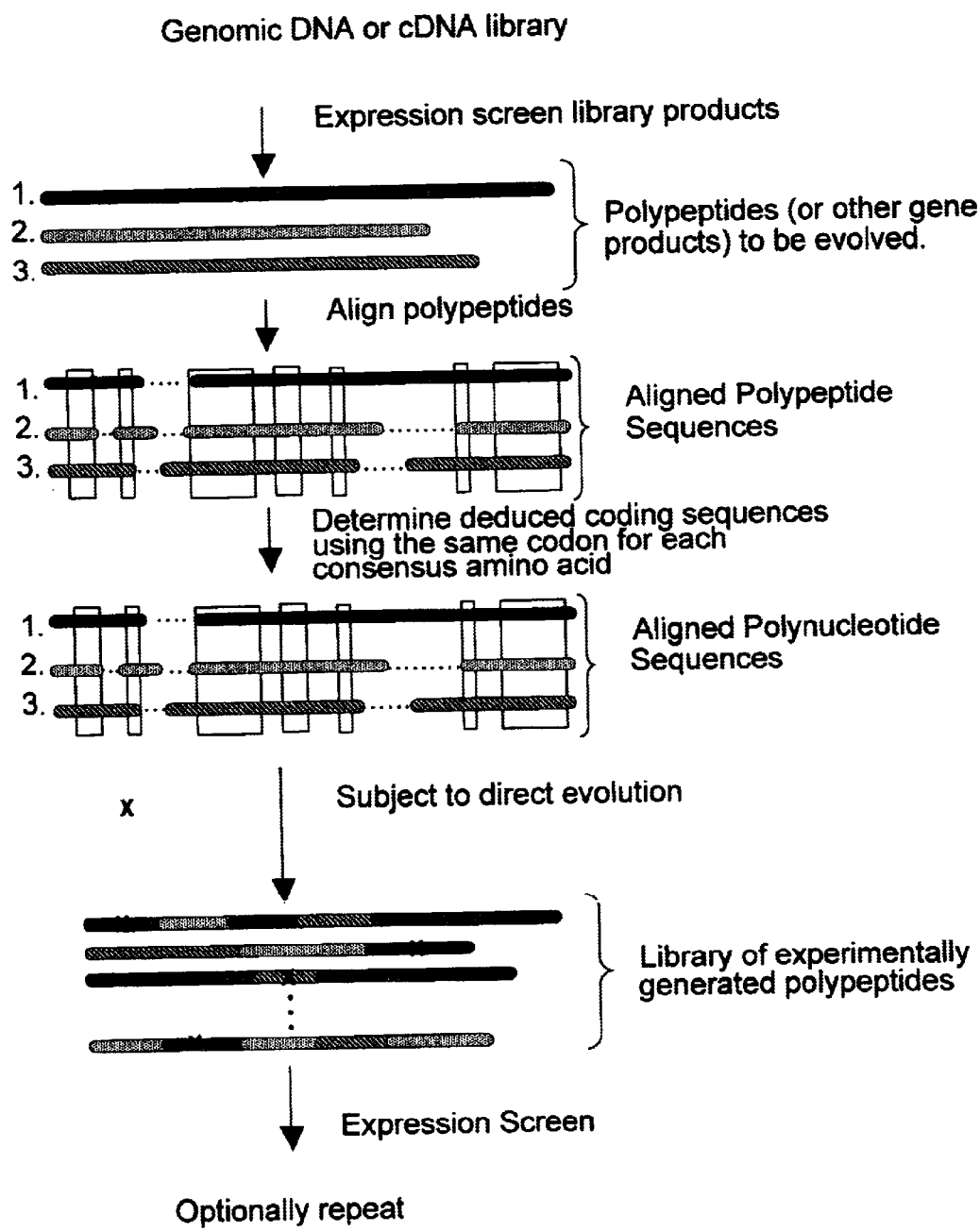
Figure 33:
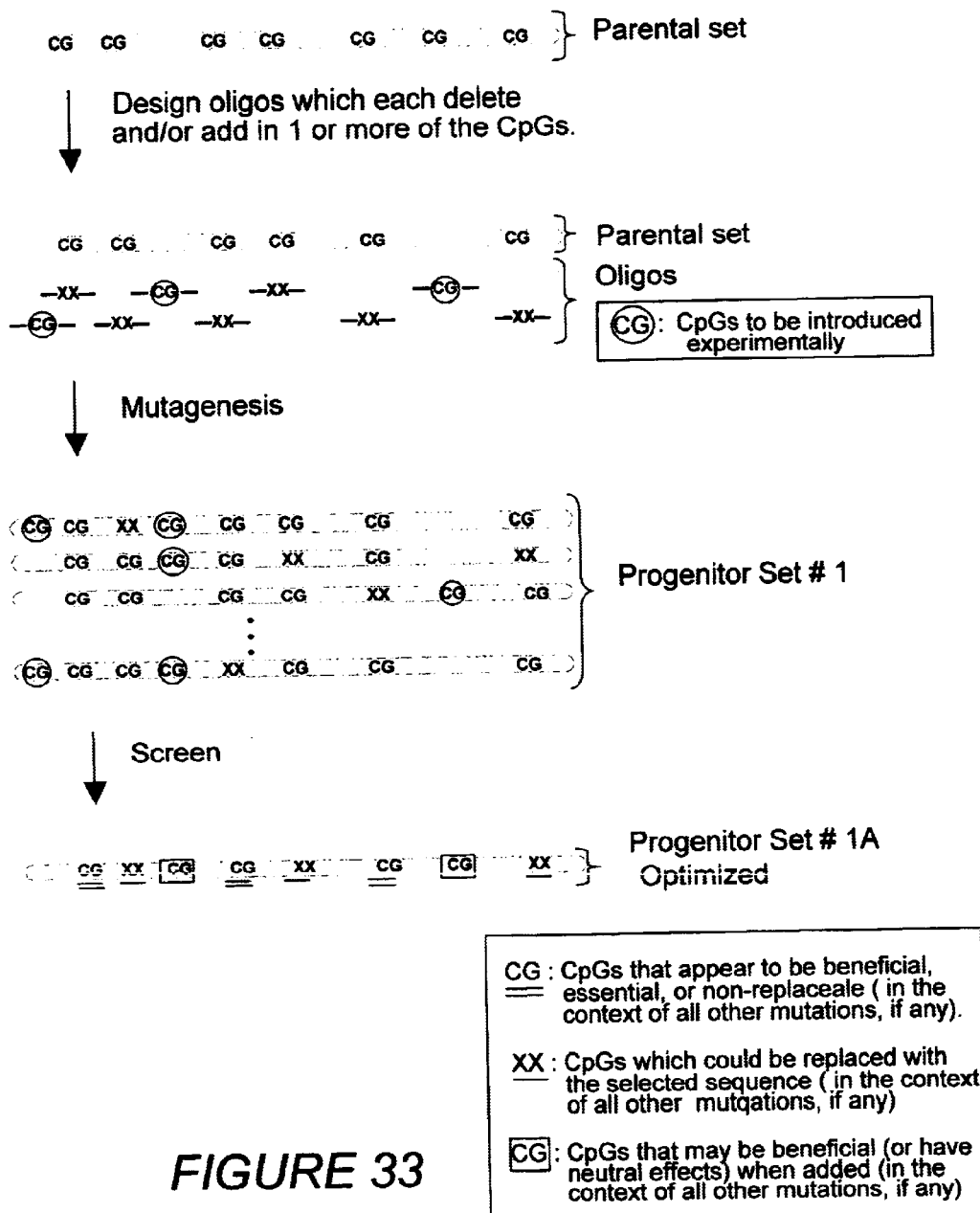
Figure 34:
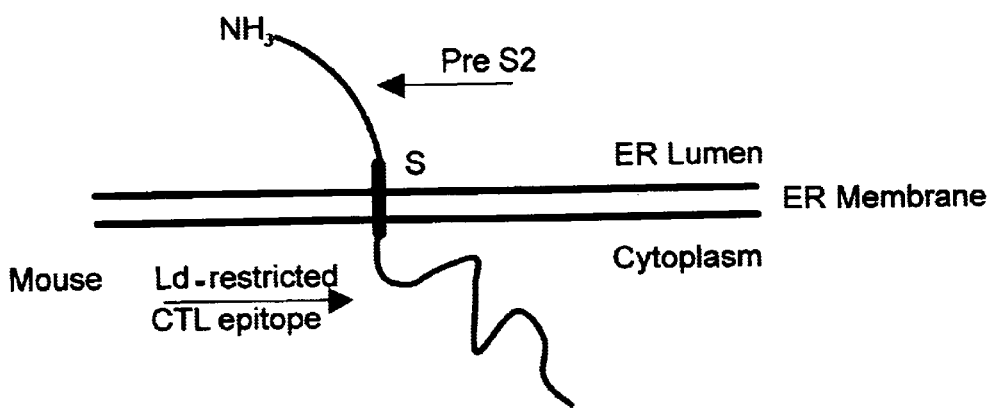
Figure 35:
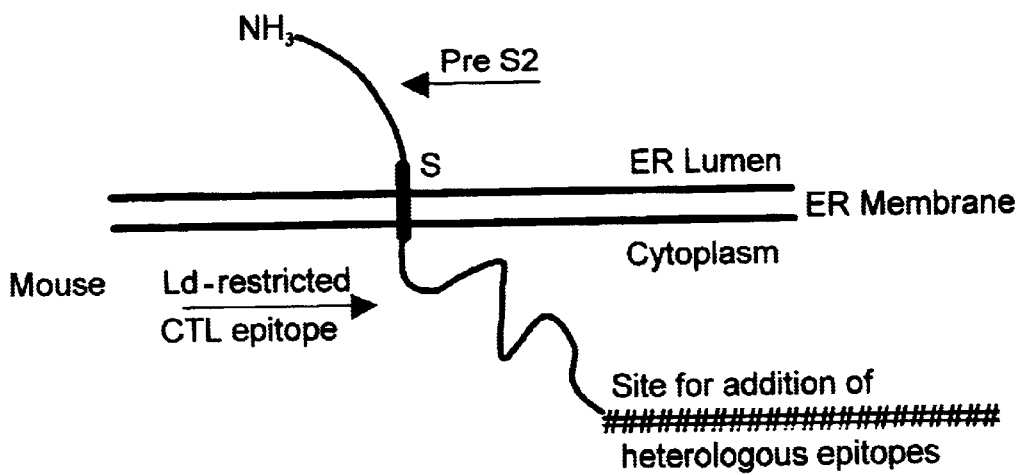
Figure 36:
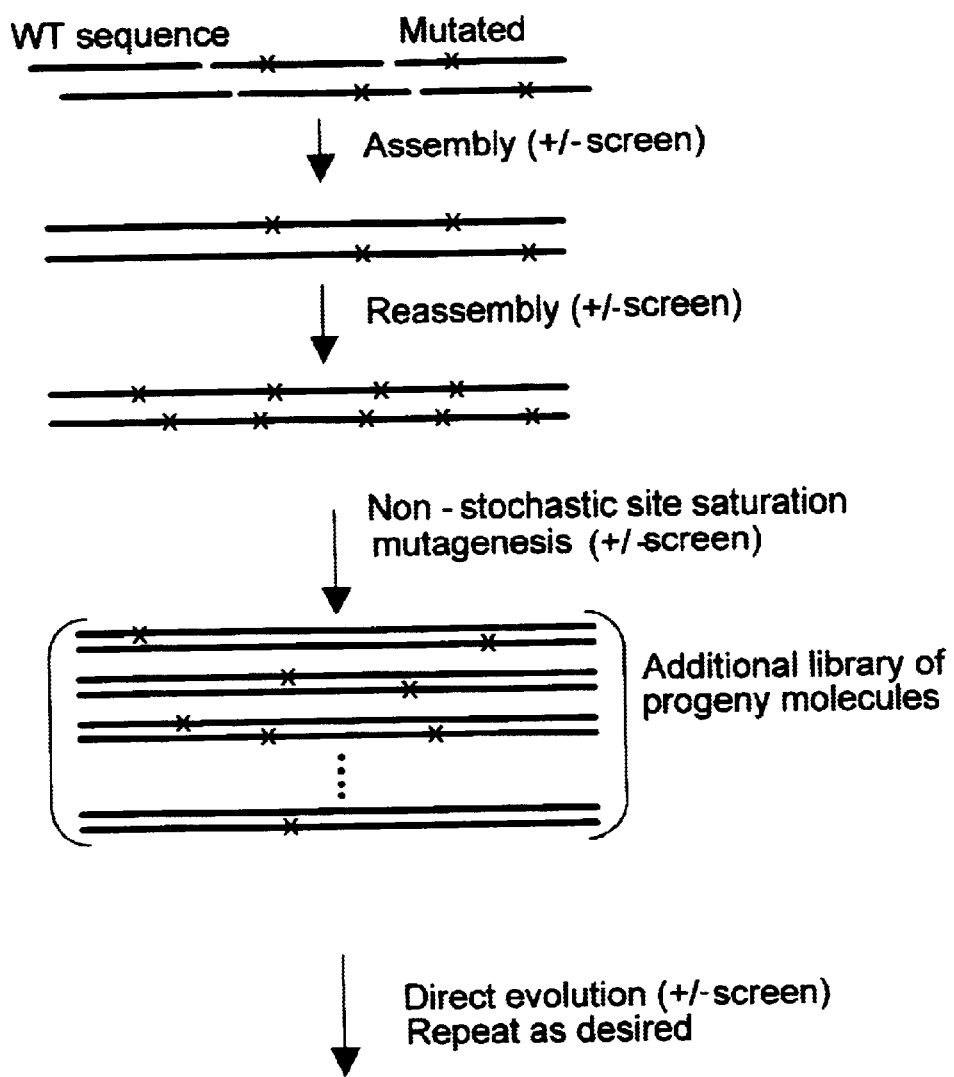
Figure 37:
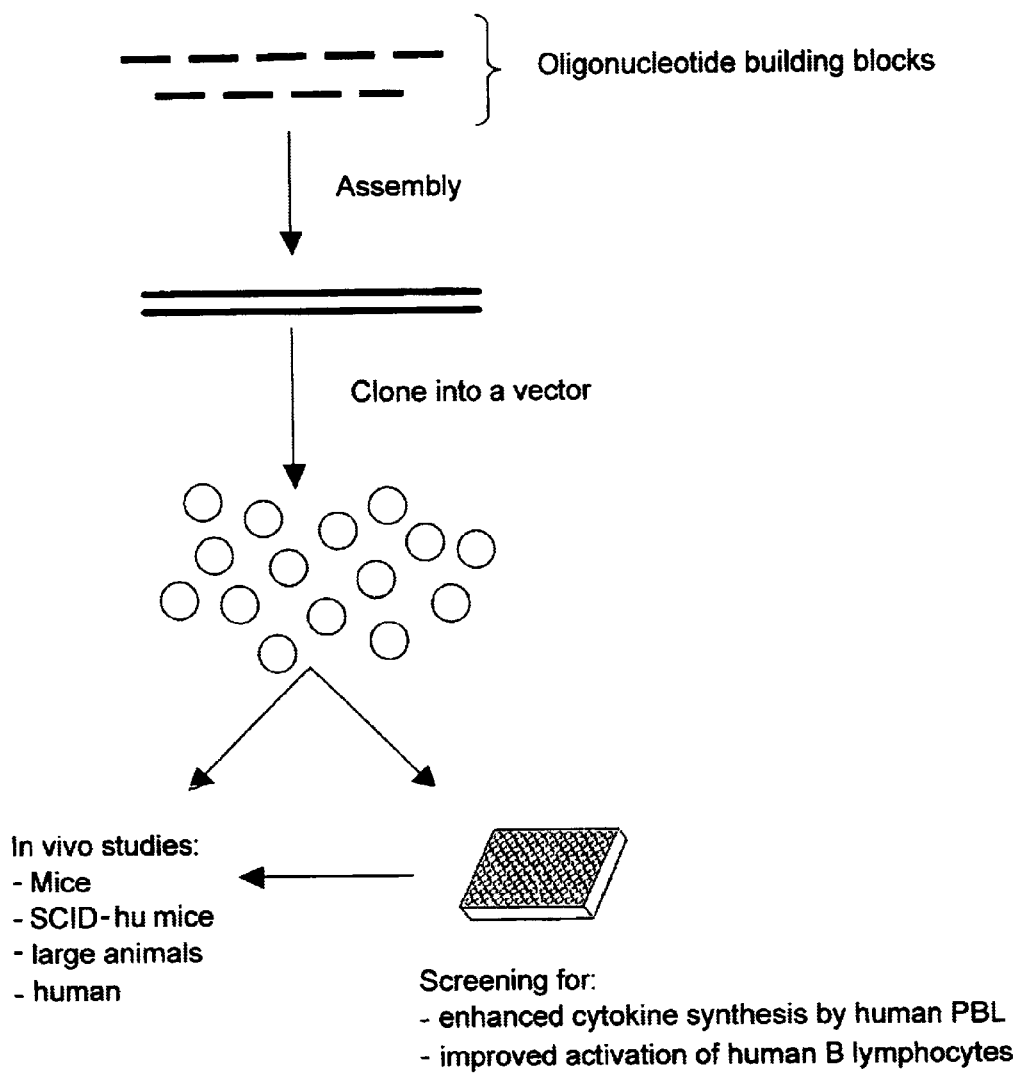
Figure 39:
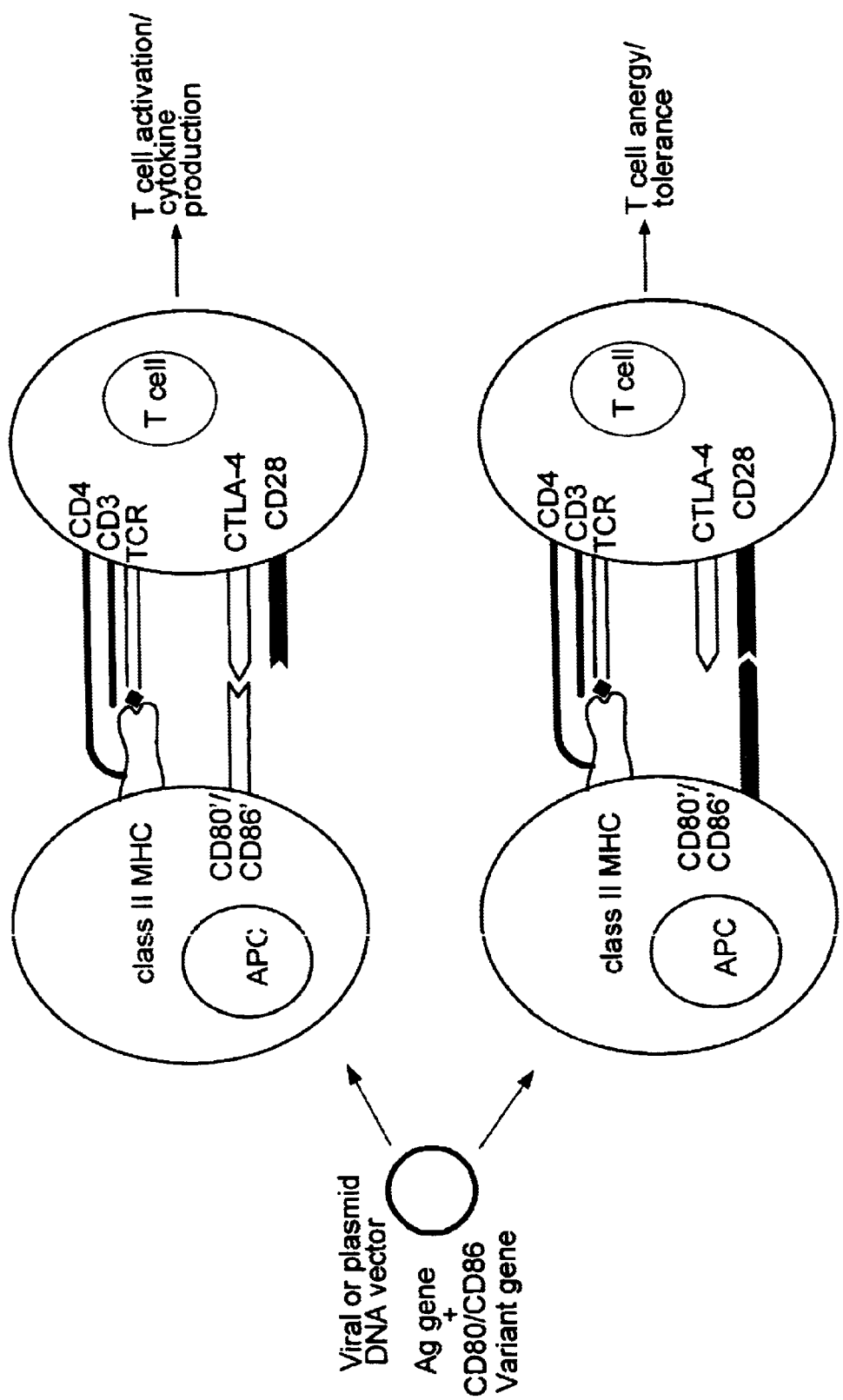

FIG. 29. Evolving a genetic vaccine vector for Oral, Intravenous, Intramuscular, Intradermal, Anal, Vaginal, or Topical Delivery. Illustrated is a strategy for screening of M13 libraries (e.g. generated experimentally using directed evolution as descried herein) for desired targeting of various tissues. The particular example shown here is a schematic diagram of a method for evolving a genetic vaccine vector for improved oral delivery. This may comprise selecting for stability under the acidic conditions of the stomach, and resistance to other degredatory factors of the digestive tract. The particular example illustrated relates to screening for improved oral delivery, but the same principle applies to libraries administered by other routes, including intravenously, intramuscularly, intradernally, anally, vaginally, or topically. After delivery to a test animal, the M1 3 phage (or a product thereof) is recovered from the tissue of interest. The procedure can be repeated to obtain further optimization.

Figure 30B:
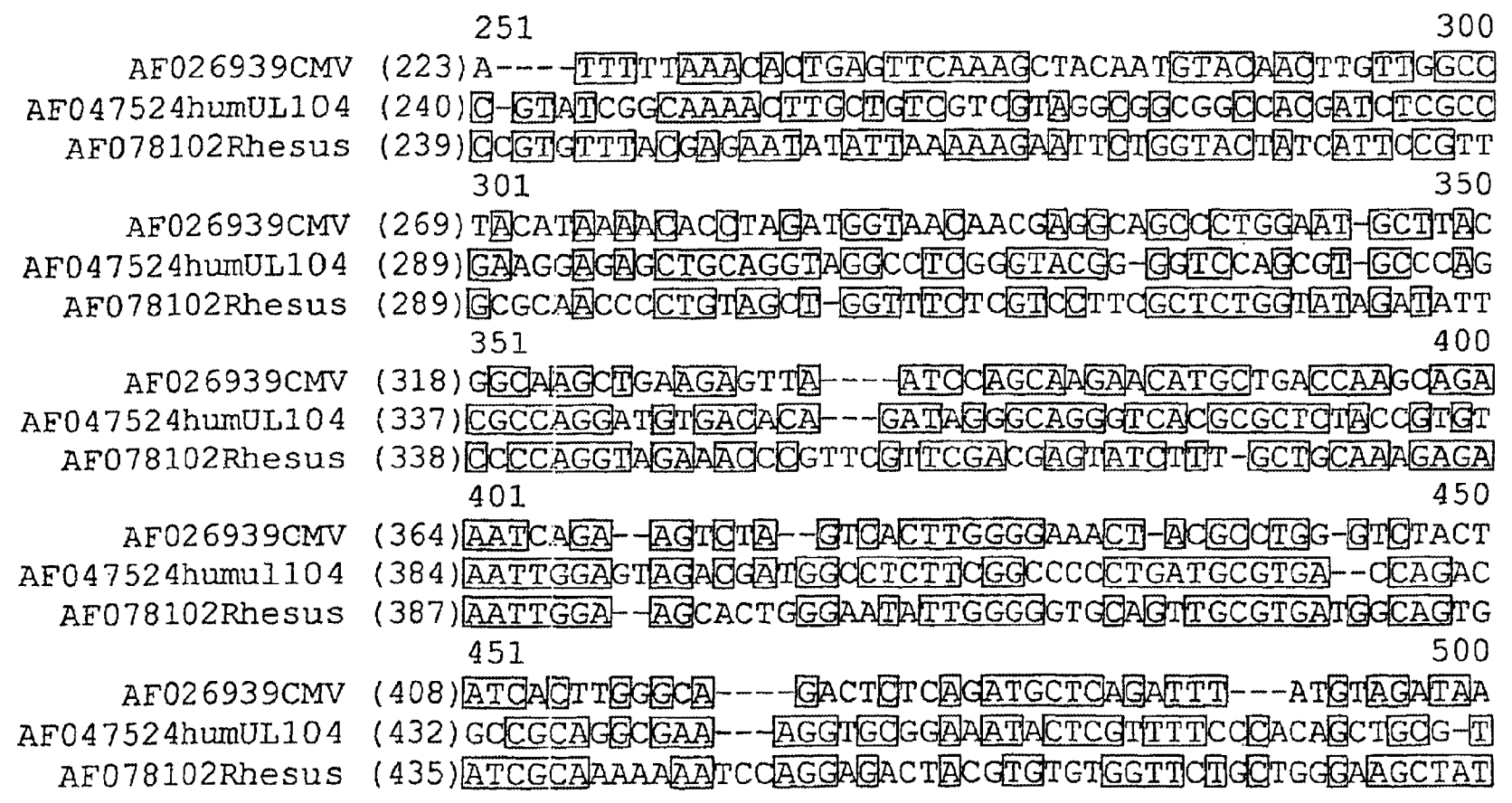
Figure 30C:
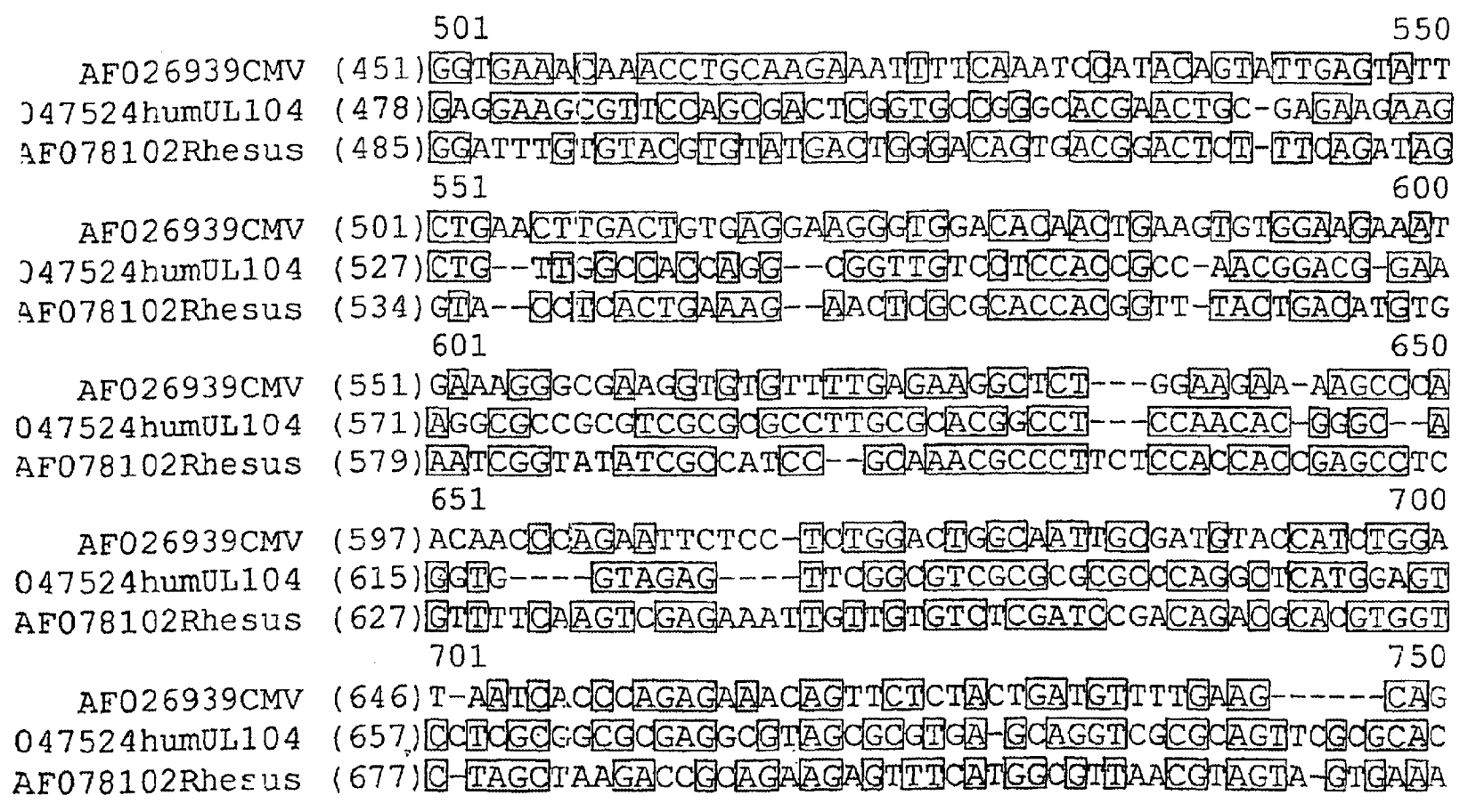
Figure 30D:
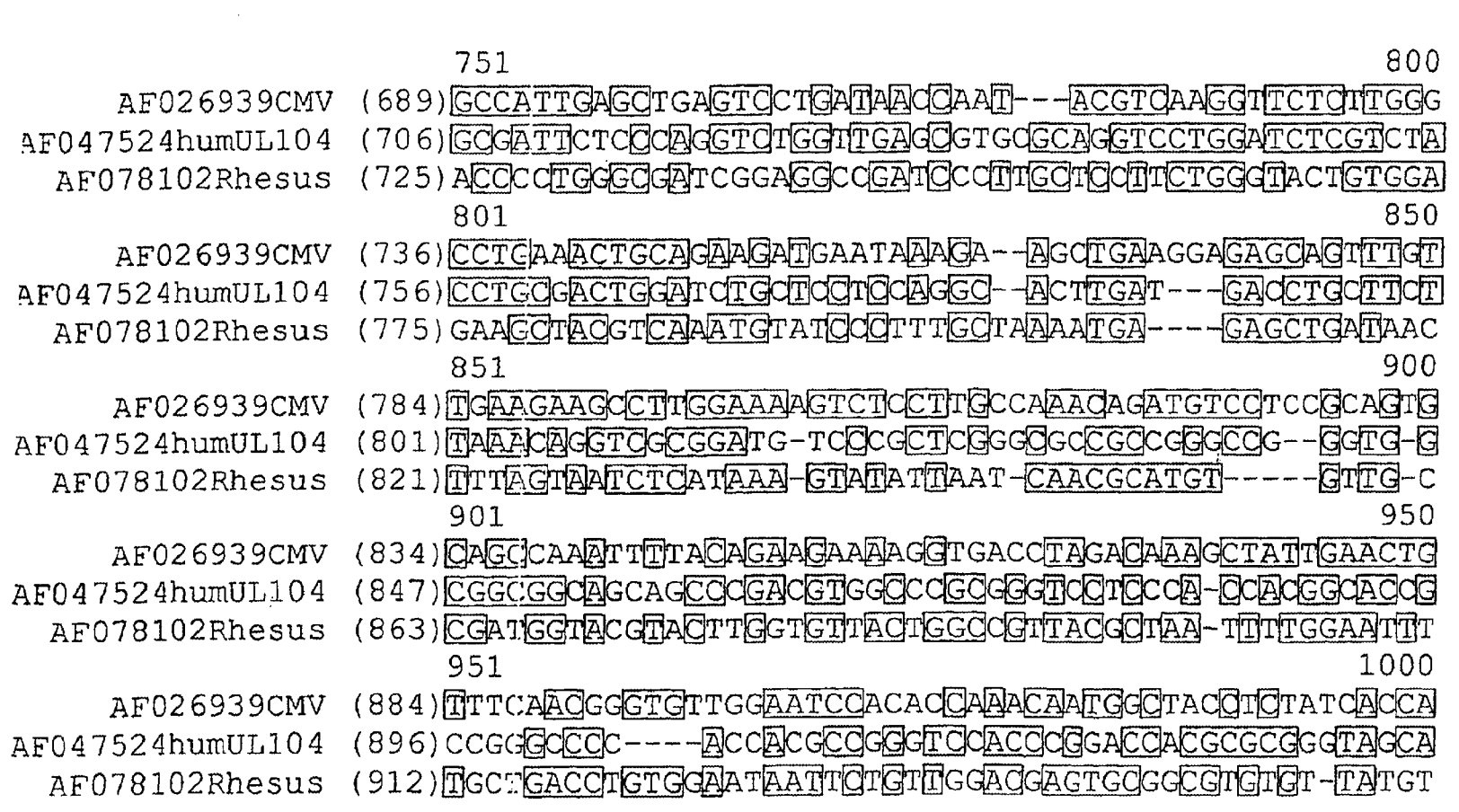
Figure 30F:
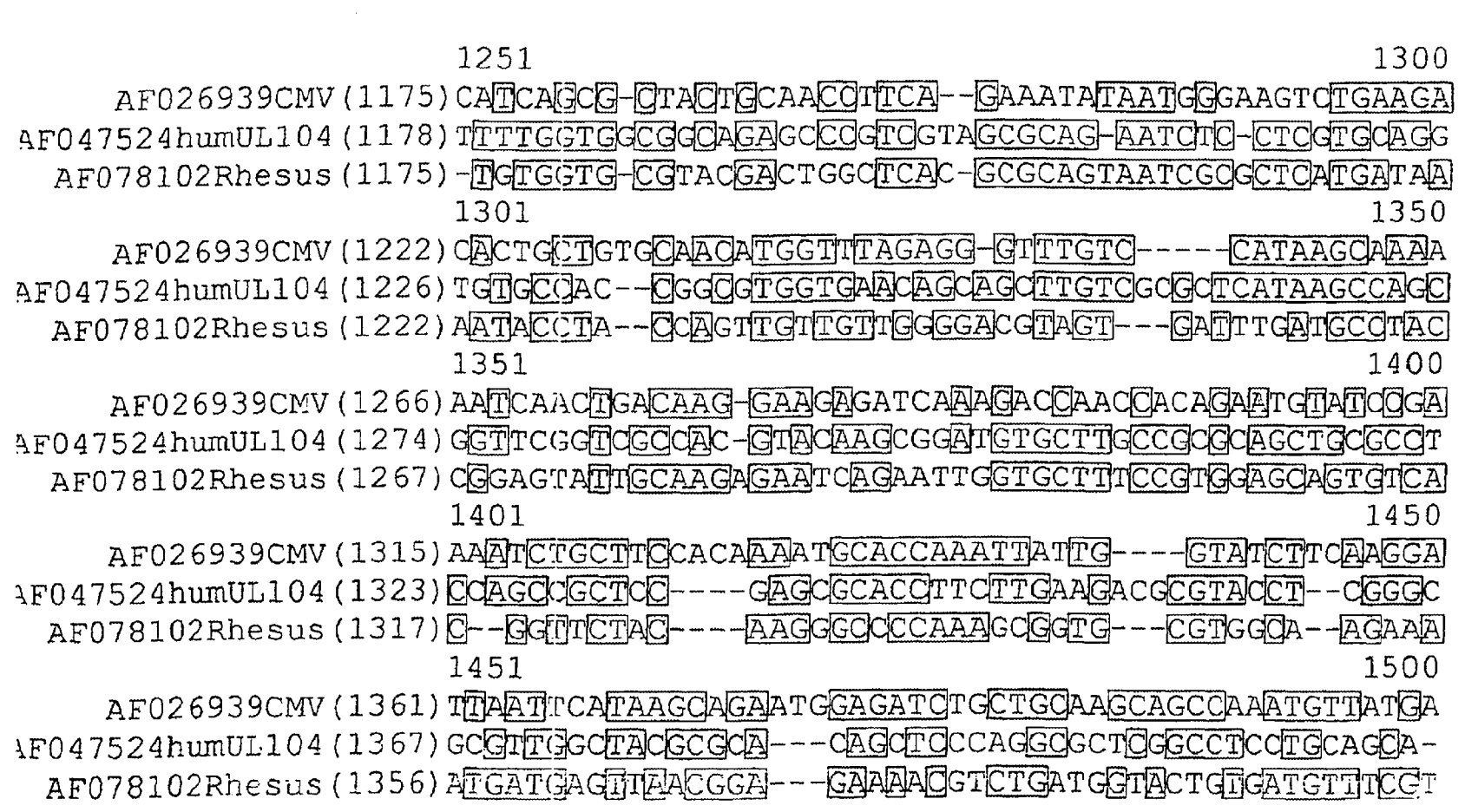
Figure 30G:
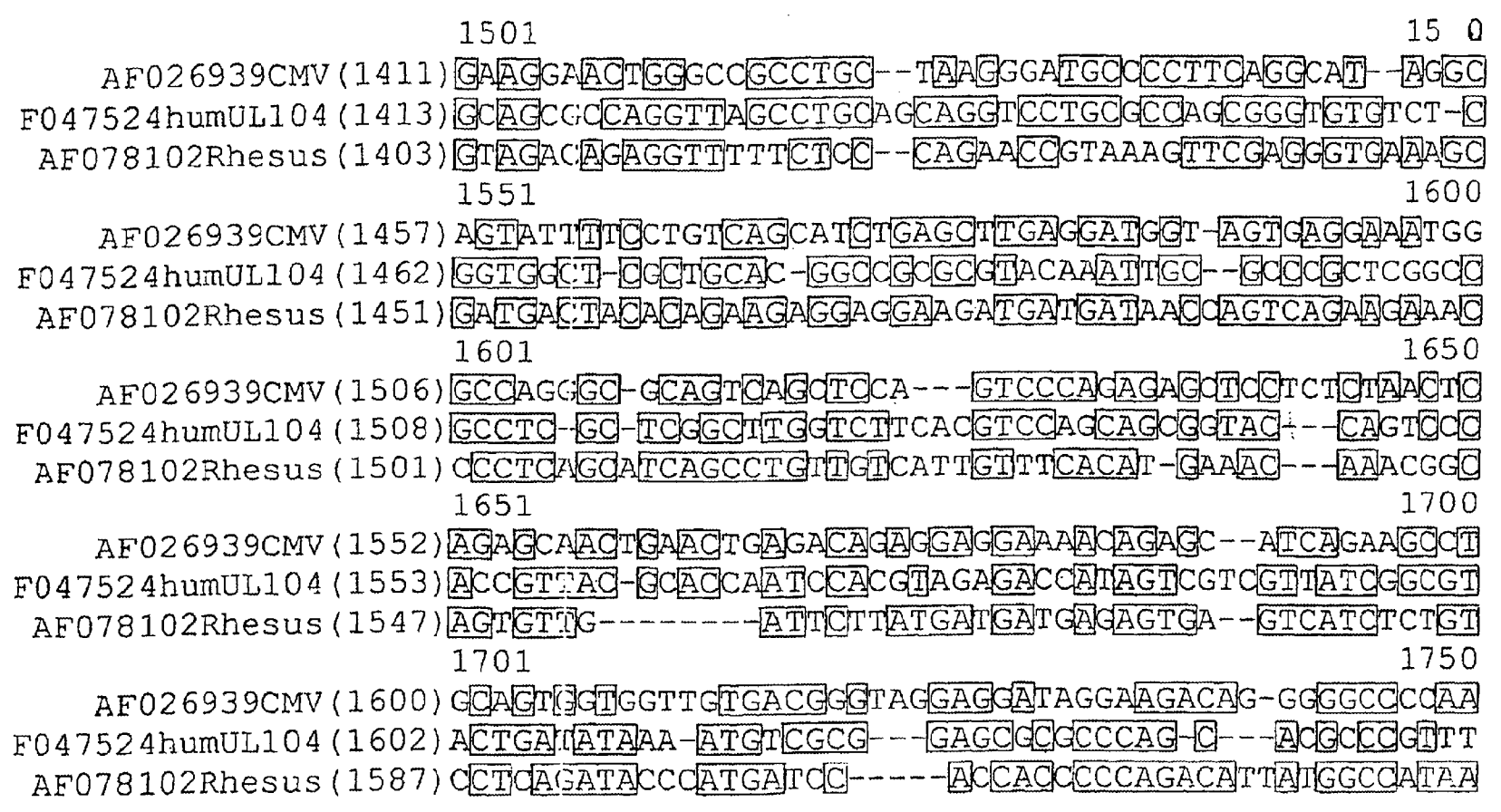
Figure 30H:
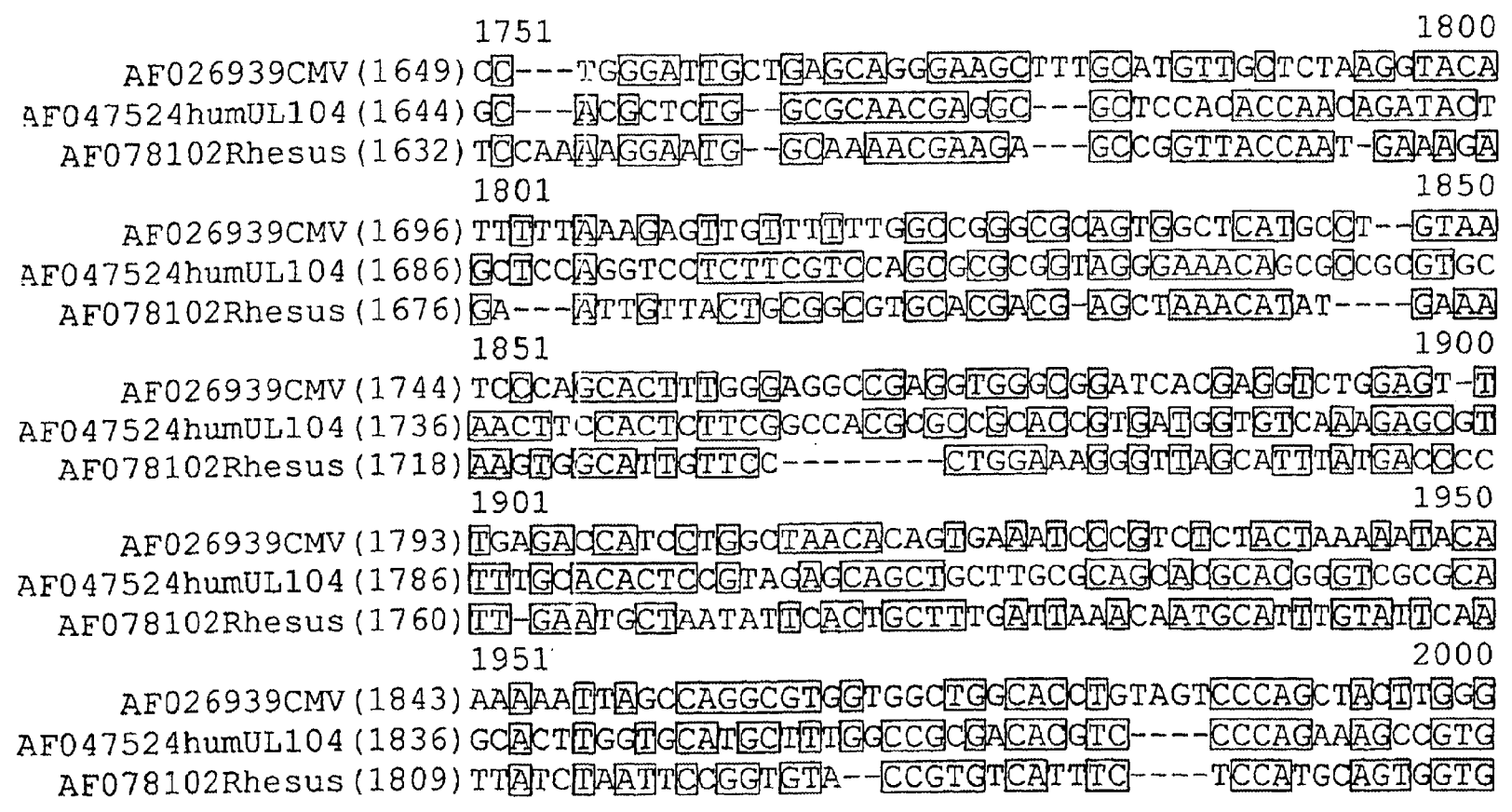

FIG. 30. An alignment of the nucleotide sequences of two human CMV strains and one monkey strain. Shown here is an alignment of the nucleotide sequences of two human cytomegalovirus (CMV) strains and one monkey (Rhesus) strain. This alignment is serviceable for performing non-stochastic polynucleotide reassembly. Nucleotide sequences shared by 2 sequences & nucleotides sequences shared by 3 sequences are boxed to illustrate preferred but non-limiting examples of reassembly points.

Figure 31B:
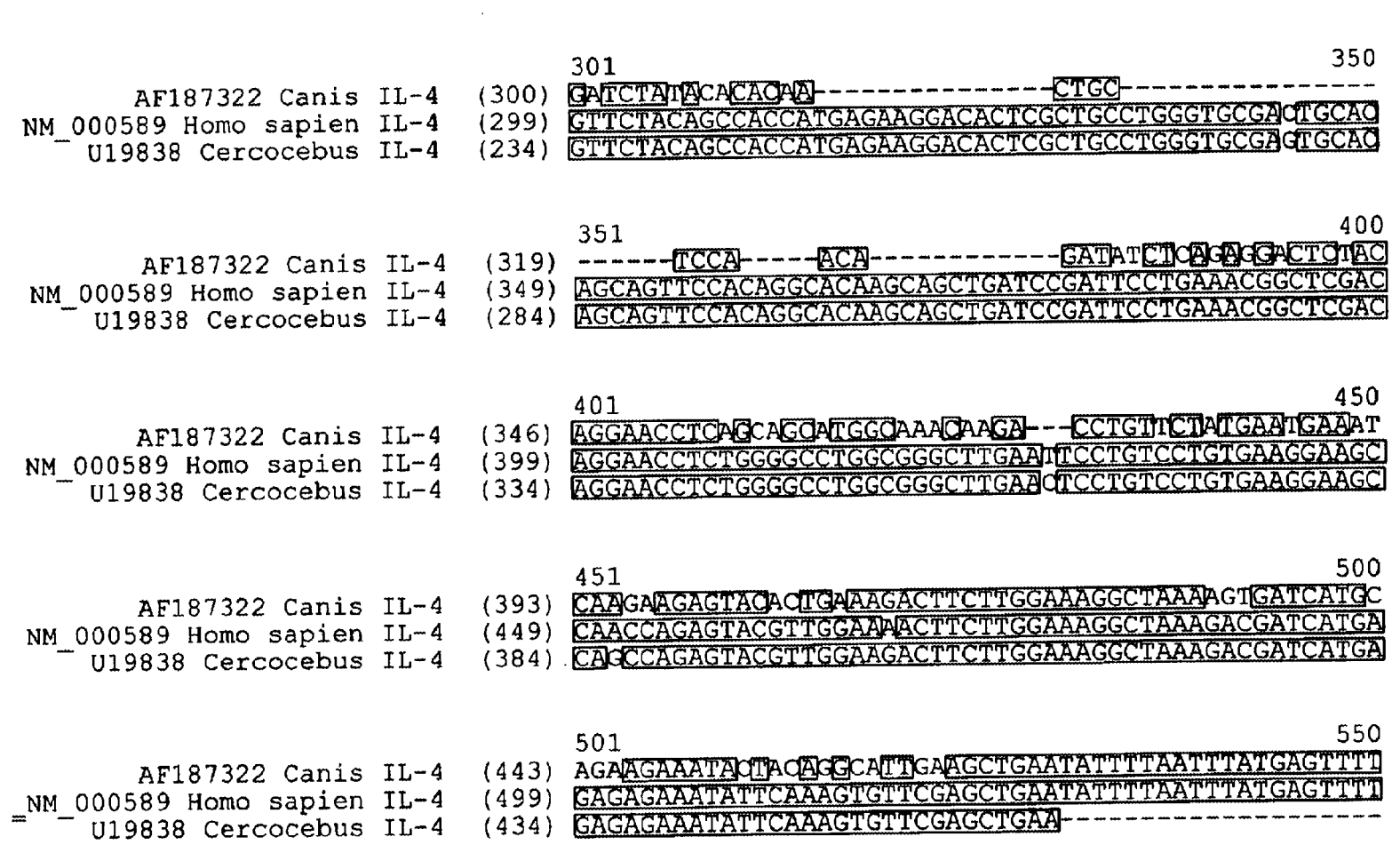

FIG. 31. An alignment of IL-4 nucleotide sequences from 3 species (human, primate, and canine). Shown here is an alignment of the IL-4 nucleotide sequences of human, dog and primate strains. This alignment is serviceable for performing non-stochastic polynucleotide reassembly. Nucleotide sequences shared by 2 sequences & nucleotide sequences shared by 3 sequences are boxed to illustrate preferred but non-limiting examples of reassembly points.

FIG. 32. Evolution of polypeptides by synthesizing (in vivo or in vitro) corresponding deduced polynucleotides and subjecting the deduced polynucleotides to directed evolution and expression screening subsequently expressed polypeptides. Expression screen library products such as polypeptides, promotors, or other gene products are aligned using, for example, software such as VECTOR NTI™ (Informax, Inc) or MACAW (Greg Schuler, NCBI, NLM, NIH). The coding sequences are deducted using the same codon foe each consensus amino acid and the nucleotide sequences aligned. The polynucleotide sequences are subjected to directed evolution by non-stochastic polynucleotide reassembly and/or non-stochastic site-saturation mutagenesis. Consensus amino acids and nucleotide bases are boxed.

FIG. 33. Non-stochastic Reassembly of oligo-directed CpG knock-outs. Shown here is a schematic representation of the use of the non-stochastic methods described herein to generate promoter sequences in which unnecessary CpG sequences are deleted, potentially useful CpG sequences are added, and non-replaceable CpG sequences are identified. Additionally, other sequences (aside from the CpG sequences) can be substituted into, added to, &/or deleted from working polynucleotides.

FIG. 34. An Example of a CTIS obtained from HbsAg polypeptide (PreS2 plus S regions). Shown here is an example of a cytotoxic T-cell inducing sequence (CTIS) obtained from HBsAg polypeptide (PreS2 plus S regions).

FIG. 35. A CTIS Having Heterologous Epitopes Attached to the Cytoplasmic Portion. Shown here is a CTIS having heterologous epitopes attached to the cytoplasmic portion.

FIG. 36. Method for preparing immunogenic agonist sequences (IAS). Shown here is a method for preparing immunogenic agonist sequences (IAS). Wild-type (WT) and mutated forms of nucleic acids encoding a polypeptide of interest are assembled and subjected to non-stochastic reassembly to obtain a nucleic acid encoding a poly-epitope region that contains potential agonist sequences.

FIG. 37. Improving Immunostimulatory Sequences (ISS) Using Directed Evolution. Shown here is a scheme for improving immunostimulatory sequences by the directed evolution methods described herein. Oligonucleotide building blocks (e.g. synthetically generated), oligos with known ISS, CpG containing hexamers &/or oligos containing CpG containing hexamers, poly A, C, G, T, etc. . . can be assembled. The resultant molecule(s) can then by subjected to 1 or more directed evolution methods as described herein.

FIG. 38. Screening to identify IL-12 genes that encode recombinant IL-12 having an increased ability to induce T Cell proliferation. Shown here is a diagram of a procedure by which experimentally generated molecules, e.g. non-stochastically generated libraries of human IL-12 genes can be screened to identify evolved IL-12 genes that encode evolved forms of IL-12 having increased ability to induce T cell proliferation.

FIG. 39. Model of induction of T cell activation or anergy by genetic vaccine vectors encoding different CD80 and/or CD86 variants. Shown here is a model of how T cell activation or anergy can be induced by genetic vaccine vectors that encode different B7-1 (CD80) and/or B7-2 (CD86) variants.

FIG. 40. Screening of CD80/CD86 variants that have improved capacity to induce T cell activation or anergy. Shown here is a method for using directed evolution as described herein to obtain CD80/CD86 variants that have improved capacity to induce T cell activation or anergy.

Figure 41B:
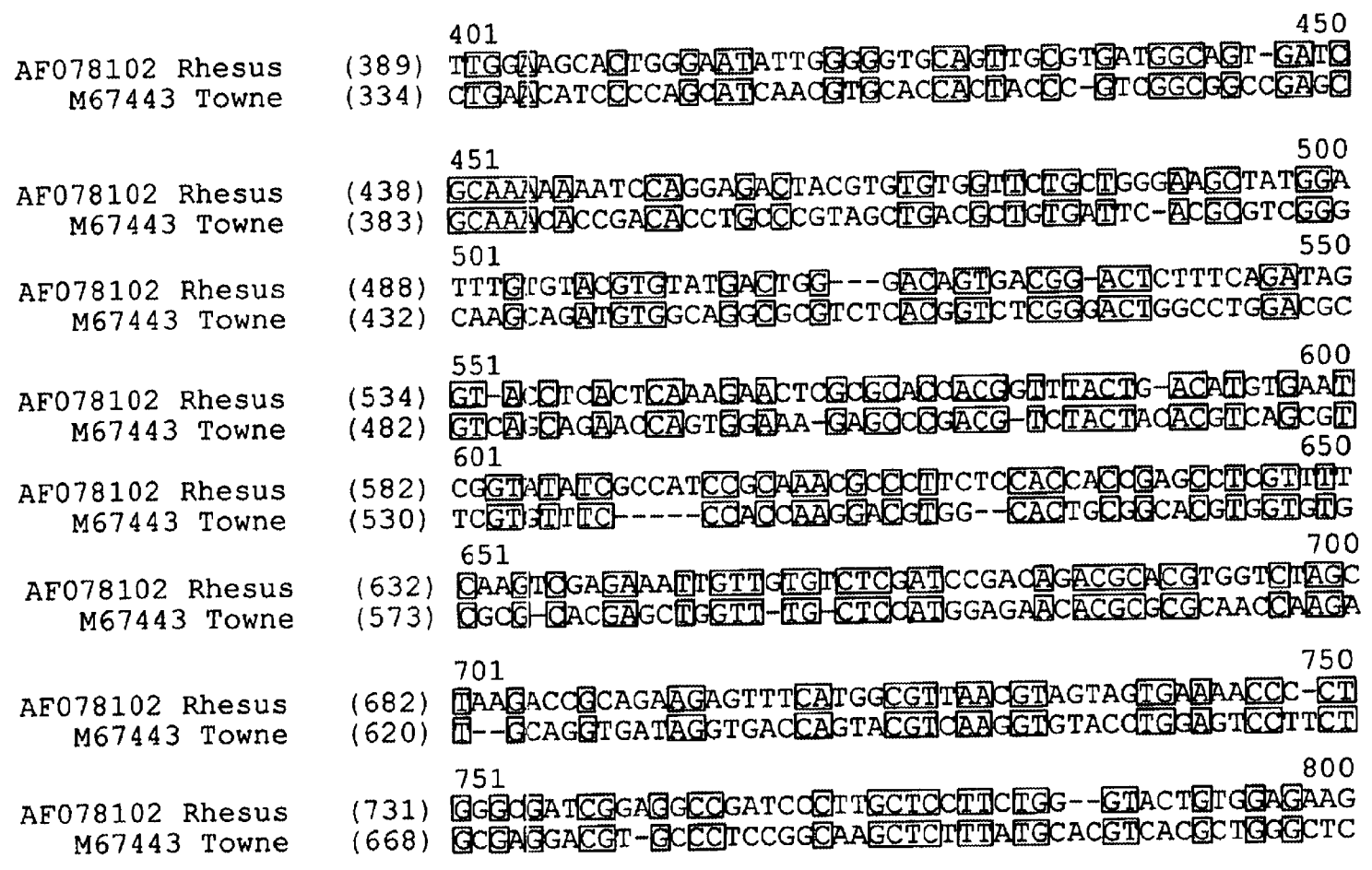
Figure 41C:
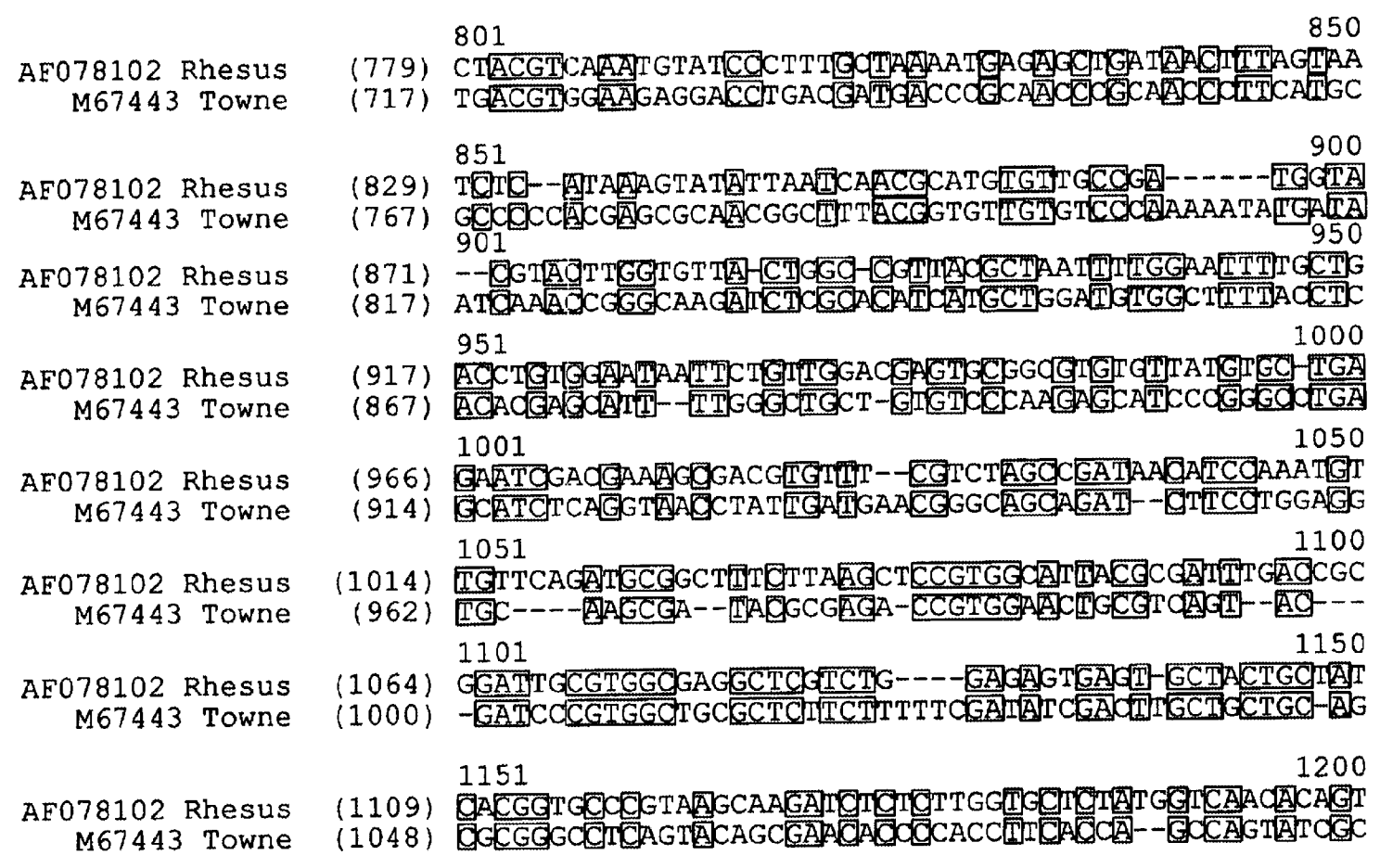
Figure 41D:
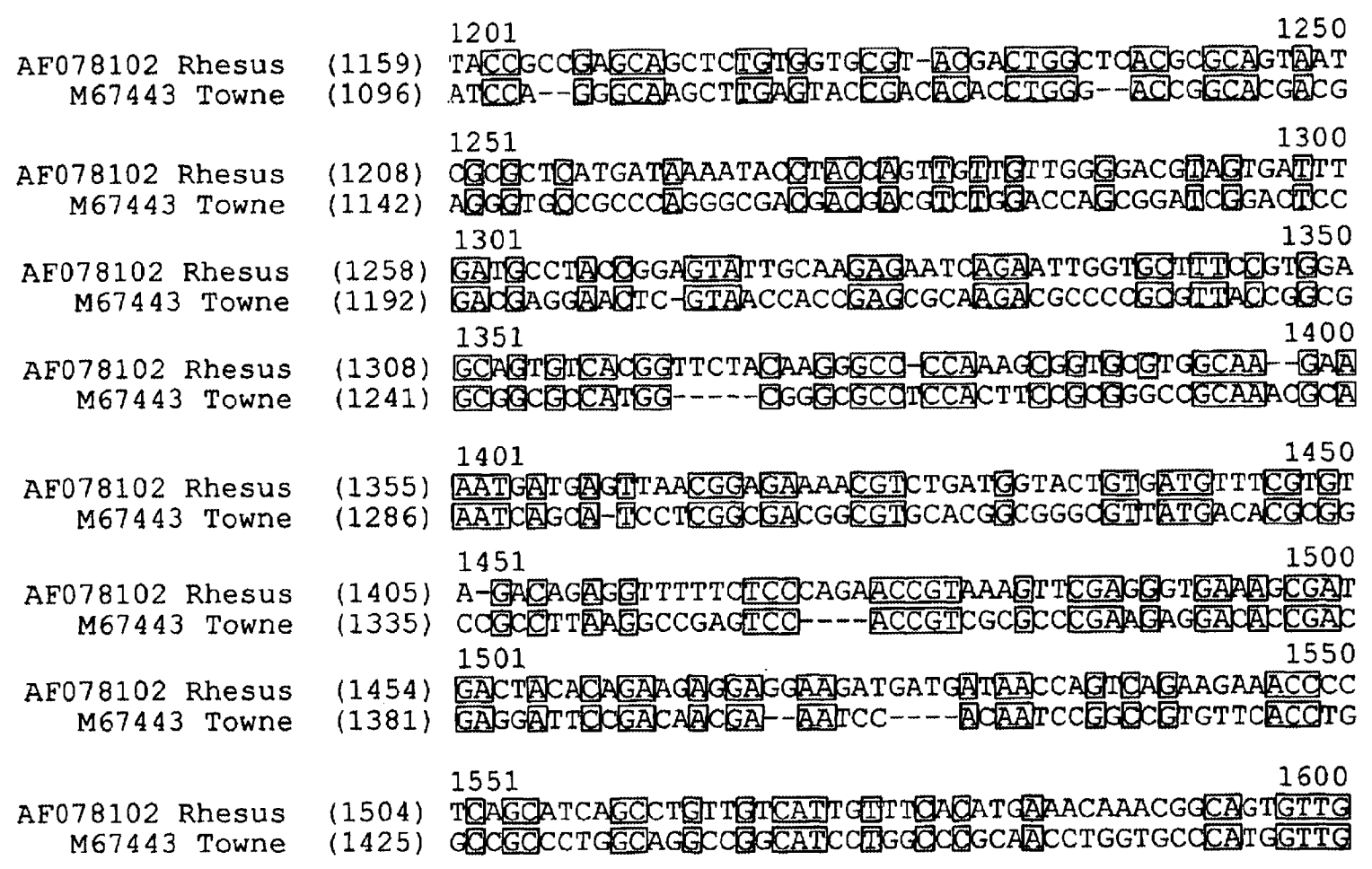
Figure 41E:
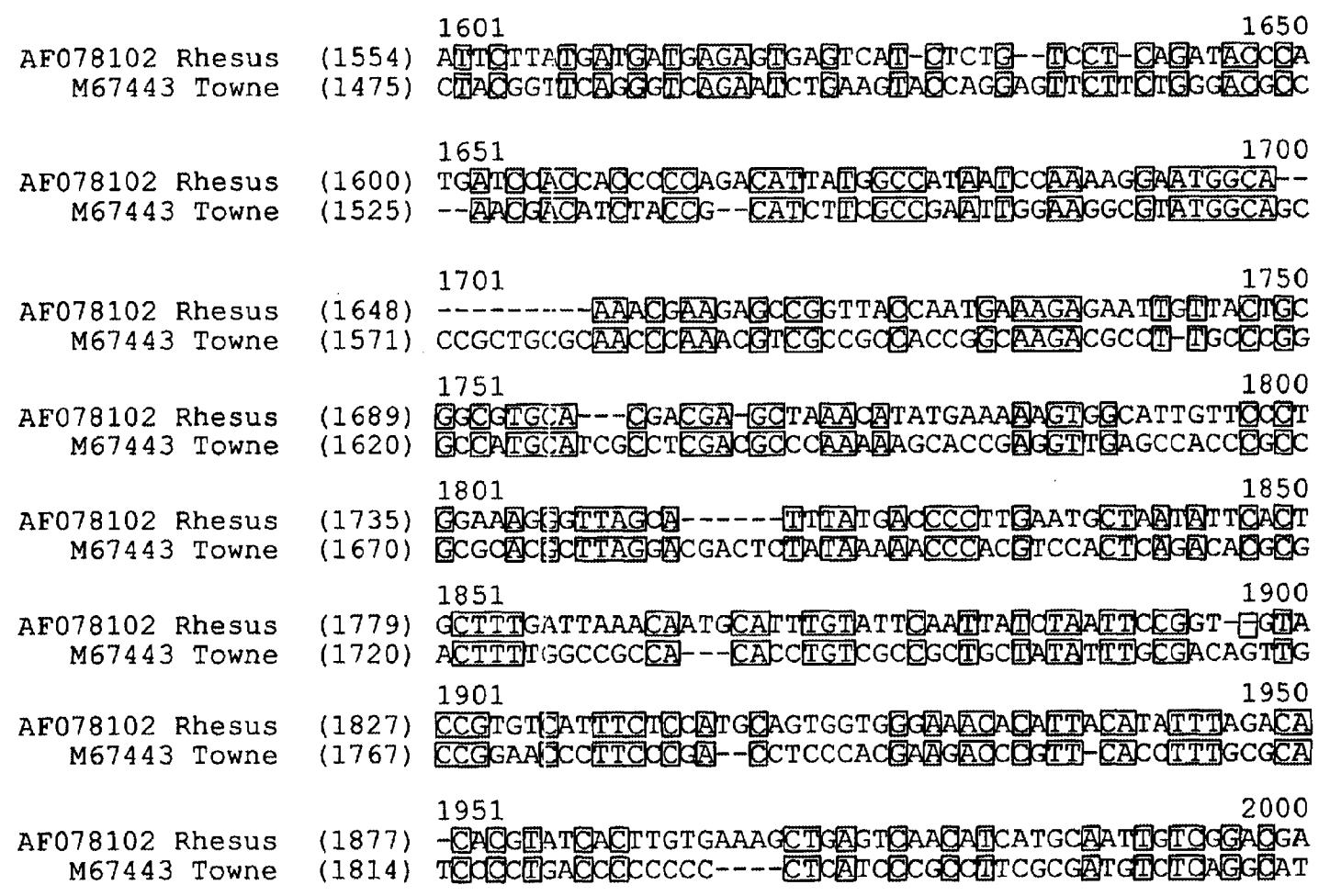

FIG. 41. An alignment of two CMV-derived nucleotide sequences from human and primate species. Shown here is an alignment of two CMV-derived nucleotide sequences of human and primate strains. This alignment is serviceable for performing non-stochastic polynucleotide reassembly. Nucleotide sequences shared by 2 sequences are boxed to illustrate preferred but non-limiting examples of reassembly points.

Figure 42B:
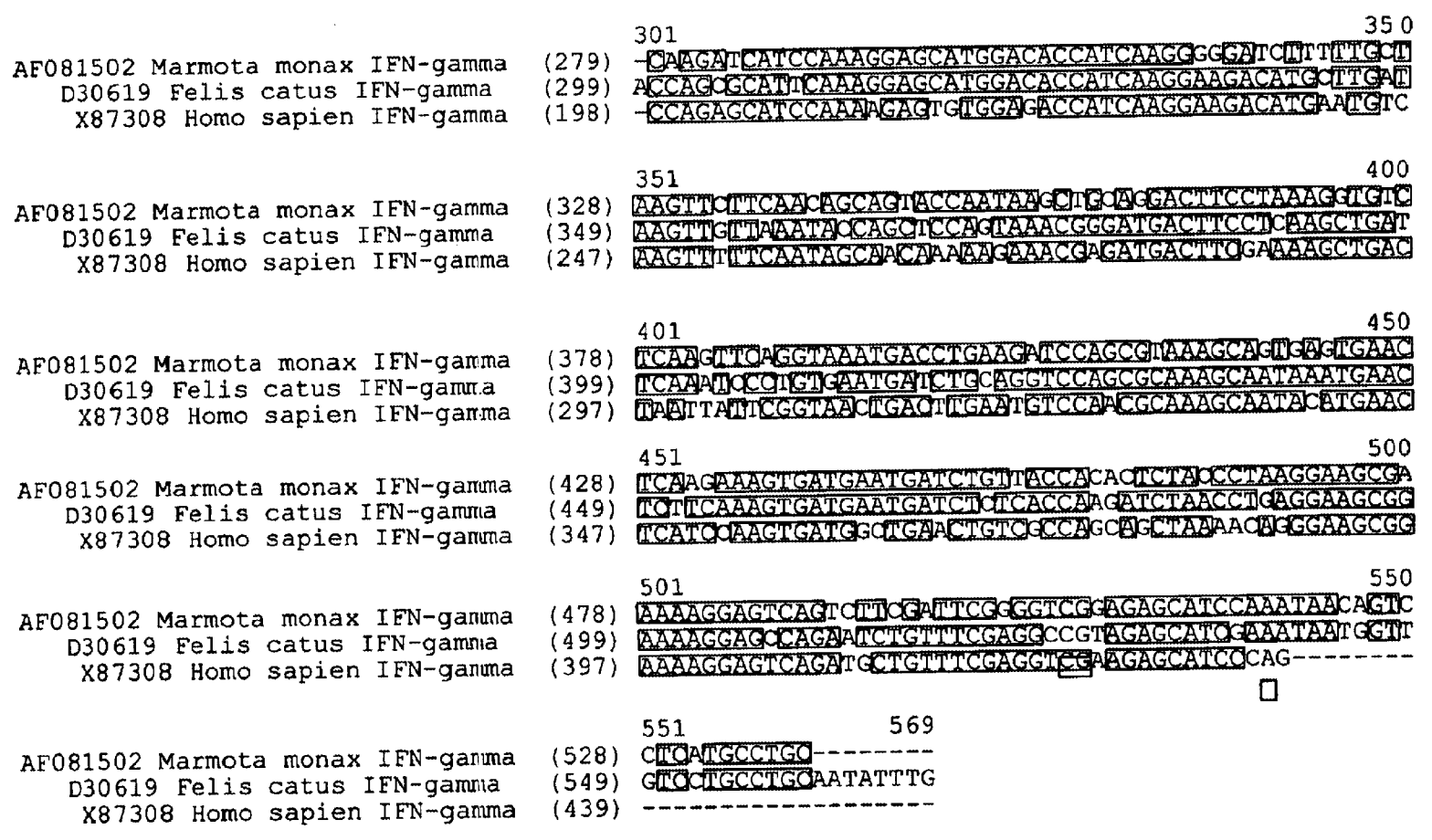

FIG. 42. An alignment of the IFN- gamma nucleotide sequences from human, cat, and rodent species. Shown here is an alignment of the IFN-gamma nucleotide sequences from human, cat, and rodent species. This alignment is serviceable for performing non-stochastic polynucleotide reassembly. Nucleotide sequences shared by 2 sequences & nucleotide sequences shared by 3 sequences are boxed to illustrate preferred but non-limiting examples of reassembly points.

2. DETAILED DESCRIPTION OF THE INVENTION

2.1. DEFINITIONS OF TERMS

In order to facilitate understanding of the examples provided herein, certain frequently occurring methods and/or terms will be described.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scfv) display library, a polysome peptide display library, or an extract made form biological materials such as bacteria, plants, fuingi, or animal (particular mammalian) cells or tissues. Agents are evaluated for potential activity as anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which doe snot substantially interfere with cell viability) by inclusion in screening assays described hereinbelow.

An "ambiguous base requirement" in a restriction site refers to a nucleotide base requirement that is not specified to the fullest extent, i.e. that is not a specific base (such as, in a non-limiting exemplification, a specific base selected from A, C, G, and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

"Alignment" with respect to molecular sequences is a way to determine similarity between 2 or more sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff& Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The term "amino acid" as used herein refers to any organic compound that contains an amino group (—$NH_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')$_2$, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

(1) An Fab-fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) An single chain antibody ("SCA") is a genetically engineered single chain molecule containing the variable region of a light chain and the variable region of a heavy chain, linked by a suitable, flexible polypeptide linker.

The term "Applied Molecular Evolution" ("AME") means the application of an evolutionary design algorithm to a specific, useful goal. While many different library formats for AME have been reported for polynucleotides, peptides and proteins (phage, lacd and polysomes), none of these formats have provided for recombination by random crossovers to deliberately create a combinatorial library.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assemblying a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, *Adv Appl Math*, 1981; Smith and Waterman, J Teor Biol, 1981; Smith and Waterman, *J Mol Biol*, 1981; Smith et al, J Mol Evol, 1981), by the homology alignment algorithm of Needleman (Needleman and Wunesch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia CDR definitions also generally known as supervariable regions or hypervariable loops (Chothia and Lesk, 1987; Clothia et al, 1989; Kabat et al, 1987; and Tramontano et al, 1990). Variable region domains typically comprise the amino-terminal approximately 105–115 amino acids of a naturally-occurring immunoglobulin chain (e.g., amino acids 1–110), although variable domains somewhat shorter or longer are also suitable for forming single-chain antibodies.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine.

Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted.

One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

Aliphatic: Glycine (G), Alanine (A), Valine (V), Leucine (L), Isoleucine (1);
Aromatic: Phenylalanine (F), Tyrosine (Y), Tryptophan (W);
Sulfir-containing: Methionine (M), Cysteine (C);
Basic: Arginine (R), Lysine (K), Histidine (H);
Acidic: Aspartic acid (D), Glutamic acid (E), Asparagine (N), Glutamine (Q).

See also, Creighton (1984) Proteins, W.H. Freeman and Company, for additional groupings of amino acids. In addition, individual substitutions, deletions or additions which alter, add or delete a single amino acid or a small percentage of amino acids in an encoded sequence are also "conservatively modified variations".

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "cytokine" includes, for example, interleukins, interferons, chemokines, hematopoietic growth factors, tumor necrosis factors and transforming growth factors. In general these are small molecular weight proteins that regulate maturation, activation, proliferation and differentiation of the cells of the immune system.

The term "degrading effective" amount refers to the amount of enzyme which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences $(NNK)_{10}$ and $(NNM)_{10}$, wherein N represents A, T, G, or C; K represents G or T; and M represents A or C, are defined sequence kernels.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment. "Directional ligation" refers to a ligation in which a 5' end and a 3' end of a polynuclotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically displayed when a digested PCR product having a 5' EcoR I-treated end and a 3' BamH I—is ligated into a cloning vector that has a multiple cloning site digested with EcoR I and BamH I.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

An "exogenous DNA segment", "heterologous sequence" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of stochastic (e.g. polynucleotide shuffling & interrupted synthesis) and non-stochastic polynucleotide reassembly. Thus, the terms refer to a DNA segment which is foreign or heterologous to the cell, or homologous to the cell but in a position within the host cell nucleic acid in which the element is not ordinarily found.

"Exogenous" DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

An "experimentally generated (in vitro &/or in vivo) polynucleotide" (which term includes a "recombinant polynucleotide") or an "experimentally (in vitro &/or in vivo) generated polypeptide" (which term includes a "experimentally generated polypeptide") is a non-naturally occurring polynucleotide or polypeptide that includes nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. The source polynucleotides or polypeptides from which the different nucleic acid or amino acid sequences are derived are sometimes homologous (i.e., have, or encode a polypeptide that encodes, the same or a similar structure and/or function), and are often from different isolates, serotypes, strains, species, of organism or from different disease states, for example.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

A method is provided herein for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly if repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

An immunoglobulin light or heavy chain variable region consists of a "framework" region interrupted by three hypervariable regions, also called CDR's. The extent of the framework region and CDR's have been precisely defined; see "Sequences of Proteins of Immunological Interest" (Kabat et al, 1987). The sequences of the framework regions of different light or heavy chains are relatively conserved within a specie. As used herein, a "human framework region" is a framework region that is substantially identical (about 85 or more, usually 90–95 or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

The benefits of this invention extend to "commercial applications" (or commercial processes), which term is used to include applications in commercial industry proper (or simply industry) as well as non-commercial commercial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

A further indication that two nucleic acid sequences or polypeptides are substantially "identical" is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Sambrook et al, 1982, p. 146; Sambrook, 1989). Unless otherwise provided, ligation may be accomplished using known buffers and conditions with 10 units of T4 DNA ligase ("ligase") per 0.5 $\mu$g of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, &/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

A "multivalent antigenic polypeptide" or a "recombinant multivalent antigenic polypeptide" is a non-naturally occurring polypeptide that includes amino acid sequences from more than one source polypeptide, which source polypeptide is typically a naturally occurring polypeptide. At least some of the regions of different amino acid sequences constitute epitopes that are recognized by antibodies found in a mammal that has been injected with the source polypeptide. The source polypeptides from which the different epitopes are derived are usually homologous (i.e., have the same or a similar structure and/or function), and are often from different isolates, serotypes, strains, species, of organism or from different disease states, for example.

The term "mutations" includes changes in the sequence of a wild-type or parental nucleic acid sequence or changes in the sequence of a peptide. Such mutations may be point mutations such as transitions or transversions. The mutations may be deletions, insertions or duplications. A mutation can also be a "chimerization", which is exemplified in a progeny molecule that is generated to contain part or all of a sequence of one parental molecule as well as part or all of a sequence of at least one other parental molecule. This invention provides for both chimeric polynucleotides and chimeric polypeptides.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses bacteria, protozoa, insects, plants or mammalian tissue) that can be isolated from a source in nature and which has not been intentionally modified by man in the laboratory is naturally occurring. Generally, the term naturally occurring refers to an object as present in a non-pathological (undiseased) individual, such as would be typical for the species.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences In in which the third position of one or more selected (or all) codons is substituted with mixed-base and/or deoxyinosine residues (Batzer et al. (1991) Nucleic Acid Res. 19: 5081; Ohtsuka et al. (1985) J Biol. Chem. 260: 2605–2608; Cassol et al. (1992) Rossolini et al. (1994) Mol. Cell. Probes 8: 91–98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an MRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

As used herein, a "nucleic acid molecule" is comprised of at least one base or one base pair, depending on whether it is single-stranded or double-stranded, respectively.

Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

A nucleic acid is "operably linked" when it is placed into a functional relationship with another nucleic acid sequence. For instance, a promoter or enhancer is operably linked to a coding sequence if it increases the transcription of the coding sequence.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set comprised of one or more distinct polynucleotide species. Usually this term fis used in reference to a progeny polynucleotide set which is preferably obtained by mutagenization of the parental set, in which case the terms "parental", "starting" and "template" are used interchangeably.

As used herein the term "physiological conditions" refers to temperature, pH, ionic strength, viscosity, and like biochemical parameters which are compatible with a viable organism, and/or which typically exist intracellularly in a viable cultured yeast cell or marnmalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20–45° C. and 0.001–10 mM divalent cation (e.g., Mg++, Ca+); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or non-ionic detergents and/or membrane fractions and/or anti-foam agents and/or scintillants.

Standard convention (5' to 3') is used herein to describe the sequence of double standed polynucleotides.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference proform molecule. When two or more chemical modification (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "pseudorandom" refers to a set of sequences that have limited variability, such that, for example, the degree of residue variability at another position, but any pseudorandom position is allowed some degree of residue variation, however circumscribed.

The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

"Recombinant enzymes" refer to enzymes produced by recombinant DNA techniques, i.e., produced from cells transformed by an exogenous DNA construct encoding the desired enzyme. "Synthetic" enzymes are those prepared by chemical synthesis.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoR I site) or an immediately adjacent cleavage site (e.g./CCWGG in the EcoR II site). In other cases, relevant restriction enzymes [e.g. the Eco57 I site or CTGAAG(16/14)] contain a low ambiguity sequence (e.g. the CTGAAG sequence in the Eco57 I site) with an external cleavage site (e.g. in the $N_{16}$ portion of the Eco57 I site). When an enzyme (e.g. a restriction enzyme) is said to "cleave" a polynucleotide, it is understood to mean that the restriction enzyme catalyzes or facilitates a cleavage of a polynucleotide.

The term "screening" describes, in general, a process that identifies optimal antigens. Several properties of the antigen can be used in selection and screening including antigen expression, folding, stability, immunogenicity and presence of epitopes from several related antigens. Selection is a form of screening in which identification and physical separation are achieved simultaneously by expression of a selection marker, which, in some genetic circumstances, allows cells expressing the marker to survive while other cells die (or vice versa). Screening markers include, for example, luciferase, beta-galactosidase and green fluorescent protein. Selection markers include drug and toxin resistance genes, and the like. Because of limitations in studying primary immune responses in vitro, in vivo studies are particularly useful screening methods. In these studies, the antigens are first introduced to test animals, and the immune responses are subsequently studied by analyzing protective immune responses or by studying the quality or strength of the induced immune response using lymphoid cells derived from the immunized animal. Although spontaneous selection can and does occur in the course of natural evolution, in the present methods selection is performed by man.

In a non-limiting aspect, a "selectable polynucleotide" is comprised of a 5' terminal region (or end region), an intermediate region (i.e. an internal or central region), and a 3' terminal region (or end region). As used in this aspect, a 5' terminal region is a region that is located towards a 5' polynucleotide terminus (or a 5' polynucleotide end); thus it is either partially or entirely in a 5' half of a polynucleotide. Likewise, a 3' terminal region is a region that is located towards a 3' polynucleotide terminus (or a 3' polynucleotide end); thus it is either partially or entirely in a 3' half of a polynucleotide. As used in this non-limiting exemplification, there may be sequence overlap between any two regions or even among all three regions.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25–50 nucleotides, wherein the percentage of sequence identity is calculated by comparing the reference sequence to the polynucleotide sequence which may include deletions or additions which total 20 percent or less of the reference sequence over the window of comparison.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

As used herein, the term "single-chain antibody" refers to a polypeptide comprising a $V_H$ domain and a $V_L$ domain in polypeptide linkage, generally liked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361–368, which is incorporated herein by reference), most frequently encoded by a rodent, non-human primate, avian, porcine bovine, ovine, goat, or human heavy chain or light chain gene sequence. A ftmctional single-chain antibody generally contains a sufficient portion of an immunoglobulin superfamily gene product so as to retain the property of binding to a specific target molecule, typically a receptor or antigen (epitope).

The phrase "specifically (or selectively) binds to an antibody" or "specifically (or selectively) immunoreactive with", when referring to a protein or peptide, refers to a binding reaction which is determinative of the presence of the protein, or an epitope from the protein, in the presence of a heterogeneous population of proteins and other biologics. Thus, under designated immunoassay conditions, the specified antibodies bind to a particular protein and do not bind in a significant amount to other proteins present in the sample. The antibodies raised against a multivalent antigenic polypeptide will generally bind to the proteins from which one or more of the epitopes were obtained. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) Antibodies, A Laboratory Manual, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

A "specific binding affinity" between two molecules, for example, a ligand and a receptor, means a preferential binding of one molecule for another in a mixture of molecules. The binding of the molecules can be considered specific if the binding affinity is about $1 \times 10^4 M^{-1}$ to about $1 \times 10^6 M^{-1}$ or greater.

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight.

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

An example of highly "stringent" wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na$^+$ ion, typically about 0.01 to 1.0 M Na+ ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures.

An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. Typically, under "stringent conditions" a probe will hybridize to its target subsequence, but to no other sequences.

Also included in the invention are polypeptides having sequences that are "substantially identical" to the sequence of a phytase polypeptide, such as one of SEQ ID 1. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In some embodiments, the sequences are substantially identical over the entire length of the coding regions.

A "subsequence" refers to a sequence of nucleic acids or amino acids that comprise a part of a longer sequence of nucleic acids or amino acids (e. g., polypeptide) respectively.

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, the term "variable segment" refers to a portion of a nascent peptide which comprises a random, pseudorandom, or defined kernal sequence. A variable segment" refers to a portion of a nascent peptide which comprises a random pseudorandom, or defined kernal sequence. A variable segment can comprise both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

The term "wild-type" means that the polynucleotide does not comprise any mutations. A "wild type" protein means that the protein will be active at a level of activity found in nature and will comprise the amino acid sequence found in nature.

The term "working", as in "working sample", for example, is simply a sample with which one is working. Likewise, a "working molecule", for example is a molecule with which one is working.

2.2. GENERAL CONSIDERATIONS & FORMATS FOR RECOMBINATION

Component Modules Provides Genetic Vaccine With the Acquisition of or Improvement in a Useful Property or Characteristic The present invention provides multicomponent genetic vaccines that include one or more component modules, each of which provides the genetic vaccine with the acquisition of or an improvement in a property or characteristic useful in genetic vaccination.

The invention provides significant advantages over previously used genetic vaccines. Through use of a multicomponent vaccine, one can obtain an immune response that is particularly effective for a particular application. A multicomponent genetic vaccine can, for example, contain a component that is optimized for optimal antigen expression, as well as a component that confers improved activation of cytotoxic T lymphocytes (CTLs) by enhancing the presentation of the antigen on dendritic cell MHC Class I molecules. Additional examples are described herein.

The invention provides a new approach to vaccine development, which is termed "antigen library immunization." No other technologies are available for generating libraries of related antigens or optimizing known protective antigens. The most powerful previously existing methods for identification of vaccine antigens, such as high throughput sequencing or expression library immunization, only explore the sequence space provided by the pathogen genome. These approaches are likely to be insufficient, because they generally only target single pathogen strains, and because natural evolution has directed pathogens to downregulate their own immunogenicity. In contrast, the immunization protocols of the invention, which use experimentally evolved (e.g. by polynucleotide reassembly &/or polynucleotide site-saturation mutagenesis) antigen libraries, provide a means to identify novel antigen sequences. Those antigens that are most protective can be selected from these pools by in vivo challenge models. Antigen library immunization dramatically expands the diversity of available immunogen sequences, and therefore, these antigen chimera libraries can also provide means to defend against newly emerging pathogen variants of the future. The methods of the invention enable the identification of individual chimeric antigens that provide efficient protection against a variety of existing pathogens, providing improved vaccines for troops and civilian populations.

The methods of the invention provide an evolution-based approach, such as stochastic (e.g. polynucleotide shuffling & interrupted synthesis) and non-stochastic polynucleotide reassembly in particular, that is an optimal approach to improve the immunogenicity of many types of antigens. For example, the methods provide means of obtaining optimized cancer antigens useful for preventing and treating malignant diseases. Furthermore, an increasing number of self-antigens, causing autoimmune diseases, and allergens, causing atopy, allergy and asthma, have been characterized. The immunogenicity and manufacturing of these antigens can likewise be improved with the methods of this invention.

The antigen library immunization methods of the invention provide a means by which one can obtain a recombinant antigen that has improved ability to induce an immune response to a pathogenic agent. A "pathogenic agent" refers to an organism or virus that is capable of infecting a host cell. Pathogenic agents typically include and/or encode a molecule, usually a polypeptide, that is immunogenic in that an immune response is raised against the immunogenic polypeptide. Often, the immune response raised against an immunogenic polypeptide from one serotype of the pathogenic agent is not capable of recognizing, and thus protecting against, a different serotype of the pathogenic agent, or other related pathogenic agents. In other situations, the polypeptide produced by a pathogenic agent is not produced in sufficient amounts, or is not sufficiently immunogenic, for the infected host to raise an effective immune response against the pathogenic agent.

These problems are overcome by the methods of the invention, which typically involve reassembling (&/or subjecting to one or more directed evolution methods described herein) two or more forms of a nucleic acid that encode a polypeptide of the pathogenic agent, or antigen involved in another disease or condition. These reassembly methods, including stochastic (e.g. polynucleotide shuffling & interrupted synthesis) and non-stochastic polynucleotide reassembly, use as substrates forms of the nucleic acid that differ from each other in two or more nucleotides, so a library of recombinant nucleic acids results. The library is then screened to identify at least one optimized recombinant nucleic acid that encodes an optimized recombinant antigen that has improved ability to induce an immune response to the pathogenic agent or other condition.

The resulting recombinant antigens often are chimeric in that they are recognized by antibodies (Abs) reacting against multiple pathogen strains, and generally can also elicit broad spectrum immune responses. Specific neutralizing antibodies are known to mediate protection against several pathogens of interest, although additional mechanisms, such as cytotoxic T lymphocytes, are likely to be involved. The concept of chimeric, multivalent antigens inducing broadly reacting antibody responses is further illustrated herein.

In preferred embodiments, the different forms of the nucleic acids that encode antigenic polypeptides are obtained from members of a family of related pathogenic agents.

This scheme of performing stochastic (e.g. polynucleotide shuffling & interrupted synthesis) and non-stochastic polynucleotide reassembly using nucleic acids from different organisms is shown schematically herein. Therefore, these stochastic (e.g. polynucleotide shuffling & interrupted synthesis) and non-stochastic polynucleotide reassembly methods provide an effective approach to generate multivalent, crossprotective antigens. The methods are useful for obtaining individual chimeras that effectively protect against most or all pathogen variants.

Moreover, immunizations using entire libraries or pools of experimentally evolved (e.g. by polynucleotide reassembly &/or polynucleotide site-saturation mutagenesis) antigen chimeras can also result in identification of chimeric antigens that protect against pathogen variants that were not included in the starting population of antigens (for example, protection against strain C by experimentally evolved (e.g. by polynucleotide reassembly &/or polynucleotide site-saturation mutagenesis) library of chimeras/mutants of strains A and B).

Accordingly, the antigen library immunization approach enables the development of immunogenic polypeptides that can induce immune responses against poorly characterized, newly emerging pathogen variants.

Sequence reassembly (&/or one or more additonal directed evolution methods described herein) can be achieved in many different formats and permutations of formats, as described in further detail below. These formats share some common principles. For example, the targets for modification vary in different applications, as does the property sought to be acquired or improved. Examples of candidate targets for acquisition of a property or improvement in a property include genes that encode proteins which have immunogenic and/or toxigenic activity when introduced into a host organism.

The methods use at least two variant forms of a starting target. The variant forms of candidate substrates can show substantial sequence or secondary structural similarity with each other, but they should also differ in at least one and preferably at least two positions. The initial diversity between forms can be the result of natural variation, e.g., the different variant forms (homologs) are obtained from different individuals or strains of an organism, or constitute related sequences from the same organism (e.g., allelic variations), or constitute homologs from different organisms (interspecific variants).

Alternatively, initial diversity can be induced, e.g., the variant forms can be generated by error-prone transcription, such as an error-prone PCR or use of a polymerase which lacks proof-reading activity (see, Liao (1990) Gene 88:107–111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umud, sbcb, recj, etc. The impairment is achieved by genetic mutation, allelic replacement, selective inhibition by an added reagent such as a small compound or an expressed antisense RNA, or other techniques. Impairment can be of the genes noted, or of homologous genes in any organism. Other methods of generating initial diversity include methods well known to those of skill in the art, including, for example, treatment of a nucleic acid with a chemical or other mutagen, through spontaneous mutation, and by inducing an error-prone repair system (e.g., SOS) in a cell that contains the nucleic acid. The initial diversity between substrates is greatly augmented in subsequent steps of reassembly (&/or one or more additonal directed evolution methods described herein) for library generation.

Properties Involved in Immunogenicity

Polynucleotide sequences that can positively or negatively affect the immunogenicity of an antigen encoded by the polynucleotide are often scattered throughout the entire antigen gene. Several of these factors are shown diagrammatically herein. By reassembling (&/or subjecting to one or more directed evolution methods described herein) different forms of polynucleotide that encode the antigen using stochastic (e.g. polynucleotide shuffling & interrupted synthesis) and non-stochastic polynucleotide reassembly, followed by selection for those chimeric polynucleotides that encode an antigen that can induce an improved immune response, one can obtain primarily sequences that have a positive influence on antigen immunogenicity. Those sequences that negatively affect antigen immunogenicity are eliminated. One need not know the particular sequences involved.

The present invention provides methods for obtaining polynucleotide sequences that, either directly or indirectly (i.e., through encoding a polypeptide), can modulate an immune response when present on a genetic vaccine vector. In another embodiment, the invention provides methods for optimizing the transport and presentation of antigens. The optimized immunomodulatory polynucleotides obtained using the methods of the invention are particularly suited for use in conjunction with vaccines, including genetic vaccines. One of the advantages of genetic vaccines is that one can incorporate genes encoding immunomodulatory molecules, such as cytokines, costimulatory molecules, and molecules that improve antigen transport and presentation into the genetic vaccine vectors. This provides opportunities to modulate immune responses that are induced against the antigens expressed by the genetic vaccines.

Obtaining Components for use in Genetic Vaccines That are more Effective Through the Creation of a Library, the Screening of the Library, and the Use of Recombinant Nucleic Acids That Exhibit Improved Properties In additional embodiments, the present invention provides methods of obtaining components for use in genetic vaccines, including the multicomponent vaccines, that are more effective in conferring a desired immune response property upon a genetic vaccine. The methods involve creating a library of recombinant nucleic acids and screening the library to identify those library members that exhibits an enhanced capacity to confer a desired property upon a genetic vaccine. Those recombinant nucleic acids that exhibit improved properties can be used as components in a genetic vaccine, either directly as a polynucleotide or as a protein that is obtained by expression of the component nucleic acid.

Improvement Goals

The properties or characteristics that can be sought to be acquired or improved vary widely, and, of course depend on the choice of substrate. For genetic vaccines, improvement goals include higher titer, more stable expression, improved stability, higher specificity targeting, higher or lower frequency of integration, reduced immunogenicity of the vector or an expression product thereof, increased immunogenicity of the antigen, higher expression of gene products, and the like. Other properties for which optimization is desired include the tailoring of an immune response to be most effective for a particular application. Examples of genetic vaccine components are shown, described &/or referenced herein (including incorporated by reference). Two or more components can be included in a single vector molecule, or each component can be present in a genetic vaccine formulation as a separate molecule.

Sequence Reassembly (&/or One or More Additonal Directed Evolution Methods Described Herein) can be Achieved Through Different Formats Which Share Some Common Principles In the methods of the invention, at least two variant forms of a nucleic acid are reassembled (&/or subjected to one or more directed evolution methods described herein) to produce a library of recombinant nucleic acids, which is then screened to identify at least one recombinant component that is optimized for the particular vaccine property. Often, improvements are achieved after one round of reassembly (&/or one or more additonal directed evolution methods described herein) and selection. Sequence reassembly (&/or one or more additonal directed evolution methods described herein) can be achieved in many different formats and permutations of formats, as described in further detail below. These formats share some common principles. A family of nucleic acid molecules that have some sequence identity to each other, but differ in the presence of mutations, is typically used as a substrate for reassembly (&/or one or more additonal directed evolution methods described herein). In any given cycle, reassembly (&/or one or more additonal directed evolution methods described herein) can occur in vivo or in vitro, intracellularly or extracellularly. Furthermore, diversity resulting from reassembly (&/or one or more additonal directed evolution methods described herein) can be augmented in any cycle by applying prior methods of mutagenesis (e.g., error-prone PCR or cassette mutagenesis) to either the substrates or products of reassembly (&/or one or more additonal directed evolution methods described herein). In some instances, a new or improved property or characteristic can be achieved after only a single cycle of in vivo or in vitro reassembly (&/or one or more additonal directed evolution methods described herein), as when using different, variant forms of the sequence, as homologs from different individuals or strains of an organism, or related sequences from the same organism, as allelic variations. However, recursive sequence reassembly (&/or one or more additonal directed evolution methods described herein), which entails successive cycles of reassembly (&/or one or more additonal directed evolution methods described herein), can also be employed to achieve still further improvements in a desired property, or to bring about new (or "distinct") properties, or to generate further molecular diversity.

In a presently preferred embodiment, polynucleotides that encode optimized recombinant antigens are subjected to molecular backcrossing, which provides a means to breed the experimentally evolved (e.g. by polynucleotide reassembly &/or polynucleotide site-saturation mutagenesis) chimeras/mutants back to a parental or wild-type sequence, while retaining the mutations that are critical to the phenotype that provides the optimized immune responses. In addition to removing the neutral mutations, molecular backcrossing can also be used to characterize which of the many mutations in an improved variant contribute most to the improved phenotype. This cannot be accomplished in an efficient library fashion by any other method. Backcrossing is performed by reassembling (optionally in combination with other directed evolution methods described herein) the improved sequence with a large molar excess of the parental sequences.

Stochastic (e.g. Polynucleotide Shuffling & Interrupted Synthesis) and Non-stochastic Polynucleotide Reassembly is Used to Obtain the Library of Recombinant Nucleic Acids, Using a Variety of Substrates to Acquire or Improve Various Properties for Different Applications Creation of Recombinant Libraries The invention involves creating recombinant libraries of polynucleotides that are then screened to identify those library members that exhibit a desired property. The recombinant libraries can be created using any of various methods.

Initial Diversity Between Substrates

The substrate nucleic acids used for the reassembly (&/or one or more additonal directed evolution methods described herein) can vary depending upon the particular application. For example, where a polynucleotide that encodes a nucleic acid binding domain or a ligand for a cell-specific receptor is to be optimized, different forms of nucleic acids that encode all or part of the nucleic acid binding domain or a ligand for a cell-specific receptor are subjected to reassembly (&/or one or more additonal directed evolution methods described herein).

In a presently preferred embodiment, stochastic (e.g. polynucleotide shuffling & interrupted synthesis) and non-stochastic polynucleotide reassembly is used to obtain the library of recombinant nucleic acids. stochastic (e.g. polynucleotide shuffling & interrupted synthesis) and non-stochastic polynucleotide reassembly, which is described herein, can result in optimization of a desired property even in the absence of a detailed understanding of the mechanism by which the particular property is mediated. The substrates for this modification, or evolution, vary in different applications, as does the property sought to be acquired or improved. Examples of candidate substrates for acquisition of a property or improvement in a property include viral and nonviral vectors used in genetic vaccination, as well as nucleic acids that are involved in mediating a particular aspect of an immune response. The methods require at least two variant forms of a starting substrate. The variant forms of candidate components can have substantial sequence or secondary structural similarity with each other, but they should also differ in at least two positions. The initial diversity between forms can be the result of natural variation, e.g., the different variant forms (homologs) are obtained from different individuals or strains of an organism (including geographic variants) or constitute related sequences from the same organism (e.g., allelic variations). Alternatively, the initial diversity can be induced, e.g., the second variant form can be generated by error-prone transcription, such as an error-prone PCR or use of a polymerase which lacks proof-reading activity (see, Liao (1990) Gene 88:107–111), of the first variant form, or, by replication of the first form in a mutator strain (mutator host cells are discussed in further detail below). The initial diversity between substrates is greatly augmented in subsequent steps of recursive sequence reassembly (&/or one or more additonal directed evolution methods described herein).

Screening or selection after a reassembly (&/or one or more additonal directed evolution methods described herein) cycle (screening after in vitro and in vivo reassembly (&/or one or more additonal directed evolution methods described herein) cycles)

Once one has performed stochastic (e.g. polynucleotide shuffling & interrupted synthesis) and non-stochastic polynucleotide reassembly to obtain a library of polynucleotides that encode recombinant antigens, the library is subjected to selection and/or screening to identify those library members that encode antigenic peptides that have improved ability to induce an immune response to the pathogenic agent. Selection and screening of experimentally generated polynucleotides that encode polypeptides having an improved ability to induce an immune response can involve either in vivo and in vitro methods, but most often involves a combination of these methods. For example, in a typical embodiment the members of a library of recombinant nucleic acids are picked, either individually or as pools. The clones can be subjected to analysis directly, or can be expressed to produce the corresponding polypeptides. In a presently preferred embodiment, an in vitro screen is performed to identify the best candidate sequences for the in vivo studies. Alternatively, the library can be subjected to in vivo challenge studies directly. The analyses can employ either the nucleic acids themselves (e.g., as genetic vaccines), or the polypeptides encoded by the nucleic acids. A schematic diagram of a typical strategy shown, described &/or referenced herein (including incorporated by reference). Both in vitro and in vivo methods are described in more detail below.

A cycle of reassembly (&/or one or more additonal directed evolution methods described herein) is usually followed by at least one cycle of screening or selection for molecules having a desired property or characteristic. If a cycle of reassembly (&/or one or more additonal directed evolution methods described herein) is performed in vitro, the products of reassembly (&/or one or more additonal directed evolution methods described herein), i.e., recombinant segments, are sometimes introduced into cells before the screening step. Recombinant segments can also be linked to an appropriate vector or other regulatory sequences before screening.

Alternatively, products of reassembly (&/or one or more additonal directed evolution methods described herein) generated in vitro are sometimes packaged as viruses (in viruses- e.g., bacteriophage) before screening. If reassembly (&/or one or more additonal directed evolution methods described herein) is performed in vivo, product of reassembly (&/or one or more additonal directed evolution methods described herein) can sometimes be screened in the cells in which reassembly (&/or one or more additional directed evolution methods described herein) occurred. In other applications, recombinant segments are extracted from the cells, and optionally packaged as viruses, before screening.

Component Sequences Having Different Roles Than the Product of Reassembly (&/or One or More Additional Directed Evolution Methods Described Herein)

The nature of screening or selection depends on what property or characteristic is to be acquired or the property or characteristic for which improvement is sought, and many examples are discussed below. It is not usually necessary to understand the molecular basis by which particular products of reassembly (&/or one or more additional directed evolution methods described herein) (recombinant segments) have acquired new or improved properties or characteristics relative to the starting substrates. For example, a genetic vaccine vector can have many component sequences each having a different intended role (e.g., coding sequence, regulatory sequences, targeting sequences, stability-conferring sequences, immunomodulatory sequences, sequences affecting antigen presentation, and sequences affecting integration). Each of these component sequences can be varied and reassembled (&/or subjected to one or more directed evolution methods described herein) simultaneously. Screening/selection can then be performed, for example, for recombinant segments that have increased episomal maintenance in a target cell without the need to attribute such improvement to any of the individual component sequences of the vector.

Initial Screenings in Bacterial Cells vs. Later Screening in Mammalian Cells

Depending on the particular screening protocol used for a desired property, initial round(s) of screening can sometimes be performed in bacterial cells due to high transfection efficiencies and ease of culture. However, especially for testing of immunogenic activity, test animals are used for library expression and screening. Later rounds, and other types of screening which are not amenable to screening in bacterial cells, are generally performed (in cells selected for use in an environment close to that of their intended use) in mammalian cells to optimize recombinant segments for use in an environment close to that of their intended use. Final rounds of screening can be performed in the cell type of intended use (e.g., a human antigen-presenting cell). In some instances, this cell can be obtained from a patient to be treated with a view, for example, to minimizing problems of immunogenicity in this patient. In some methods, use of a genetic vaccine vector in treatment can itself be used as a round of screening. That is, genetic vaccine vectors that are successively taken up and/or expressed by the intended target cells in one patient are recovered from those target cells and used to treat another patient. The genetic vaccine vectors that are recovered from the intended target cells in one patient are enriched for vectors that have evolved, i.e., have been modified by recursive reassembly (&/or one or more additional directed evolution methods described herein), toward improved or new properties or characteristics for specific uptake, immunogenicity, stability, and the like.

Identifying a Subpopulation of Recombinant Segments

The screening or selection step identifies a subpopulation of recombinant segments that have evolved toward acquisition of a new or improved desired property or properties useful in genetic vaccination. Depending on the screen, the recombinant segments can be screened as components of cells, components of viruses or other vectors, or in free form. More than one round of screening or selection can be performed after each round of reassembly (&/or one or more additional directed evolution methods described herein).

The Second Round of Reassembly (&/or One or More Additional Directed Evolution Methods Described Herein)

If further improvement in a property is desired, at least one and usually a collection of recombinant segments surviving a first round of screening/selection are subject to a further round of reassembly (&/or one or more additional directed evolution methods described herein). These recombinant segments can be reassembled (&/or subjected to one or more directed evolution methods described herein) with each other or with exogenous segments representing the original substrates or further variants thereof. Again, reassembly (&/or one or more additional directed evolution methods described herein) can proceed in vitro or in vivo. If the previous screening step identifies desired recombinant segments as components of cells, the components can be subjected to further reassembly (&/or one or more additional directed evolution methods described herein) in vivo, or can be subjected to further reassembly (&/or one or more additional directed evolution methods described herein) in vitro, or can be isolated before performing a round of in vitro reassembly (&/or one or more additional directed evolution methods described herein). Conversely, if the previous screening step identifies desired recombinant segments in naked form or as components of viruses or other vectors, these segments can be introduced into cells to perform a round of in vivo reassembly (&/or one or more additional directed evolution methods described herein). The second round of reassembly (&/or one or more additional directed evolution methods described herein), irrespective how performed, generates further recombinant segments which encompass additional diversity compared to recombinant segments resulting from previous rounds.

Additional Rounds of Reassembly (&/or One or More Additional Directed Evolution Methods Described Herein)/Screening to Sufficiently Evolve the Recombinant Segments The second round of reassembly (&/or one or more additional directed evolution methods described herein) can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired.

Additional rounds of reassembly (&/or one or more additional directed evolution methods described herein) and screening can then be performed until the recombinant segments have sufficiently evolved to acquire the desired new or improved property or function.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. General texts which describe molecular biological techniques useful herein, including mutagenesis, include Berger and Kimmel, Guide to Molecular Cloning Techniques, Methods in Enzymology volume 152 Academic Press, Inc., San Diego, Calif.(Berger); Sambrook et al., Molecular Cloning—A Laboratory Manual (2nd Ed.), Vol. 1–3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1998) ("Ausubel")).

Examples of techniques sufficient to direct persons of skill through in vitro amplification methods, including the polymerase chain reaction (PCR) the ligase chain reaction (LCR), Q-replicase amplification and other RNA polymerase mediated techniques (e. g., NASBA) are found in Berger, Sambrook, and Ausubel, as well as Mullis et al. (1987) U.S. Pat. No. 4,683,202; PCR Protocols A Guide to Methods and Applications (Innis et al. eds) Academic Press Inc. San Diego, Calif. (1990) (Innis); Antheirn & Levinson (Oct. 1, 1990) C&EN 36–47; The Journal Of NIH Research (1991) 3, 81–94; (Kwoh et al. (1989) Proc. Natl. Acad Sci. USA 86, 1173; Guatelli el al. (1990) Proc. Natl. Acad Sci. USA 87, 1874; Lowell et al. (1989) J Clin. Chem 35, 1826; Landegren et al. (1988) Science 241, 1077–1080; Van Brunt (1990) Biotechnology 8, 291–294; Wu and Wallace (1989) Gene 4, 560; Barringer et al. (1990) Gene 89, 117, and Sooknanan and Malek (1995) Biotechnology 13: 563–564.

Improved methods of cloning in vitro amplified nucleic acids are described in Wallace et al., U.S. Pat. No. 5,426, 039. Improved methods of amplifying large nucleic acids by PCR are summarized in Cheng et al. (1994) Nature 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as probes, e.g., in in vitro amplification methods, for use as gene probes, or as reassembly targets (e.g., synthetic genes or gene segments) are typically synthesized chemically according to the solid phase phosphoramidite triester method described by Beaucage and Caruthers (1981) Tetrahedron Letts., 22(20): 1859–1862, e.g., using an automated synthesizer, as described in Needham-VanDevanter et al. (1984) Nucleic Acids Res., 12:6159–6168. Oligonucleotides can also be custom made and ordered from a variety of commercial sources known to persons of skill.

Indeed, essentially any nucleic acid with a known sequence can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.) and many others. Similarly, peptides and antibodies can be custom ordered from any of a variety of sources, such as PeptidoGenic (pkim@ccnet.com), HTI Bioproducts, Inc. (http://www.htibio.com), BMA Biomedicals Ltd (U.K.), Bio-Synthesis, Inc., and many others.

Different Formats are Available for Performing Reassembly (&/or Additional Directed Evolution Methods Described Herein) and Screening/selection Which Allow for Large Numbers of Mutations in a Minimum Number of Selection Cycles and Does Not Require the Extensive Analysis and Computation Required by Conventional Methods A number of different formats are available by which one can create a library of recombinant nucleic acids for screening. In some embodiments, the methods of the invention entail performing reassembly (&/or one or more additional directed evolution methods described herein) and screening or selection to "evolve" individual genes, whole plasmids or viruses, multigene clusters, or even whole genomes (Stemmer (1995) Bio/Technology 13:549–553). Reiterative cycles of reassembly (&/or one or more additional directed evolution methods described herein) and screening/selection can be performed to further evolve the nucleic acids of interest. Such techniques do not require the extensive analysis and computation required by conventional methods for polypeptide engineering. Reassembly allows the combination of large numbers of mutations in a minimum number of selection cycles, in contrast to traditional, pair wise recombiantion events (e.g., as occur during sexual replication). Thus, the directed evolution techniques described herein provide particular advantages in that they provide reassembly (optionally in combination with one or more additional directed evolution methods described herein) between any or all of the mutations, thereby providing a very fast way of exploring the manner in which different combinations of mutations can affect a desired result. In some instances, however, structural and/or functional information is available which, although not required for sequence reassembly (&/or one or more additional directed evolution methods described herein), provides opportunities for modification of the technique.

Four Different Approaches to Improve Immunogenic Activity as Well as Broaden Specificity: Reassembly (Optionally in Combination With Other Directed Evolution Methods Described Herein) on Single Gene, Sequence Comparison of Homologous Genes, Whole Genome Reassembly, Codon Modification of Polypeptide-encoding Genes The stochastic (e.g. polynucleotide shuffling & interrupted synthesis) and non-stochastic polynucleotide reassembly methods can involve one or more of at least four different approaches to improve immunogenic activity as well as to broaden specificity. First, stochastic (e.g. polynucleotide shuffling & interrupted synthesis) and non-stochastic polynucleotide reassembly can be performed on a single gene. Secondly, several highly homologous genes can be identified by sequence comparison with known homologous genes. These genes can be synthesized and experimentally evolved (e.g. by polynucleotide reassembly &/or polynucleotide site-saturation mutagenesis) as a family of homologs, to select recombinants with the desired activity. The experimentally evolved (e.g. by polynucleotide reassembly &/or polynucleotide site-saturation mutagenesis) genes can be introduced into appropriate host cells, which can include *E. coli*, yeast, plants, fungi, animal cells, and the like, and those having the desired properties can be identified by the methods described herein. Third, whole genome reassembly can be performed to shuffle genes that can confer a desired property upon a genetic vaccine (along with other genomic nucleic acids). For whole genome reassembly approaches, it is not even necessary to identify which genes are being experimentally evolved (e.g. by polynucleotide reassembly &/or polynucleotide site-saturation mutagenesis). Instead, e.g., bacterial cell or viral genomes are combined and experimentally evolved (e.g. by polynucleotide reassembly &/or polynucleotide site-saturation mutagenesis) to acquire recombinant nucleic acids that, either itself or through encoding a polypeptide, have enhanced ability to induce an immune response, as measured in any of the assays described herein. Fourth, polypeptide- encoding genes can be codon modified to access mutational diversity not present in any naturally occurring gene.

References for Formats and Examples for Sequence Reassembly (&/or One or More Additional Directed Evolution Methods Described Herein) and for Other Methods Exemplary formats and examples for polynucleotide reassembly, gene site saturation mutagenesis, interrupted synthesis, and additional directed evolution methods described herein have been described by the present inventors and co-workers in issued and co-pending applications including U.S. Pat. No. 5,965,408 (issued Oct. 12, 1999), U.S. Pat. No. 5,830,696 (issued Nov. 3, 1998), and U.S. Pat. No. 5,939,250 (issued Aug. 17, 1999).

Other methods for obtaining libraries of experimentally generated polynucleotides and/or for obtaining diversity in nucleic acids used as the substrates for directed evolution including stochastic (e.g. polynucleotide shuffling & interrupted synthesis) and non-stochastic polynucleotide reassembly include, for example, W098/42727; Smith, Ann. Rev. Genet. 19: 423–462 (1985); Botstein and Shortle, Science 229: 1193–1201 (1985); Carter, Biochem. J 237: 1–7 (1986); Kunkel, "The efficiency of oligonucleotide directed mutagenesis" in Nucleic acids & Molecular Biology, Eckstein and Lilley, eds., Springer Verlag, Berlin (1987)). Included among these methods are oligonucleotide-directed mutagenesis (Zoller and Smith, Nucl. Acids Res. 10: 6487–6500 (1982), Methods in Enzymol. 100: 468–500 (1983), and Methods in Enzymol. 154: 329–350 (1987)) phosphothioate-modified DNA mutagenesis (Taylor et al., Nucl. Acids Res. 13: 8749–8764 (1985); Taylor et al., Nucl. Acids Res. 13: 8765–8787 (1985); Nakamaye and Eckstein, Nucl. Acids Res. 14: 9679–9698 (1986); Sayers et al., Nucl. Acids Res. 16: 791–802 (1988); Sayers et al., Nucl. Acids Res. 16: 803–814 (1988)), mutagenesis using uracil-containing templates (Kunkel, Proc. Nat'l. Acad. Sci. USA 82: 488–492 (1985) and Kunkel et al., Methods in Enzymol. 154: 367–382)); mutagenesis using gapped duplex DNA (Kramer et al., Nucl. Acids Res. 12: 9441–9456 (1984); Kramer and Fritz, Methods in Enzymol. 154: 350–367 (1987); Kramer et al., Nucl. Acids Res. 16: 7207 (1988)); and Fritz et al., Nucl. Acids Res. 16: 6987–6999 (1988)). Additional suitable methods include point mismatch repair (Kramer et al., Cell 38: 879–887 (1984)), mutagenesis using repair-deficient host strains (Carter et al., Nucl. Acids Res. 13: 4431–4443 (1985); Carter, Methods in Enzymol. 154: 382–403 (1987)), deletion mutagenesis (Eghtedarzadeh and Henikoff, Nucl. Acids Res. 14: 5115 (1986)), restriction-selection and restriction-purification (Wells et al., Phil. Trans. R. Soc. Lond. A 317: 415–423 (1986)), mutagenesis by total gene synthesis (Nambiar et al., Science 223: 1299–1301 (1984); Sakamar and Khorana, Nucl. Acids Res. 14: 6361–6372 (1988); Wells et al., Gene 34: 315–323 (1985); and Grundstrom et al., Nucl. Acids Res. 13: 3305–3316 (1985). Kits for mutagenesis are commercially available (e.g., Bio-Rad, Amersharn International, Anglian Biotechnology).

For Reassembly (&/or One or More Additional Directed Evolution Methods Described Herein) to Generate Increased Diversity Relative to the Starting Materials, the Starting Materials Must Differ from Each Other in at Least Two Nucleotide Positions The reassembly procedure starts with at least two substrates that generally show substantial sequence identity to each other (i.e., at least about 30%, 50%, 70%, 80% or 90% sequence identity), but differ from each other at certain positions. The difference can be any type of mutation, for example, substitutions, insertions and deletions. Often, different segments differ from each other in about 5–20 positions. For reassembly (&/or one or more additional directed evolution methods described herein) to generate increased diversity relative to the starting materials, the starting materials must differ from each other in at least two nucleotide positions. That is, if there are only two substrates, there should be at least two divergent positions. If there are three substrates, for example, one substrate can differ from the second at a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily, such as the family of Yersinia V-antigens, for example). The starting DNA segments can also be induced variants of each other. For example, one DNA segment can be produced by error-prone PCR replication of the other, the nucleic acid can be treated with a chemical or other mutagen, or by substitution of a mutagenic cassette. Induced mutants can also be prepared by propagating one (or both) of the segments in a mutagenic strain, or by inducing an error-prone repair system in the cells.

The Different Segments Forming the Starting Materials are Related, and Might or Might Not be of Similar Length In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The Starting DNA Segments are Reassembled (&/or Subjected to One or More Directed Evolution Methods Described Herein) to Generate a Library of Recombinant DNA Segments Varying in Size Which Will Include Full Length Coding Sequences and any Essential Regulatory The starting DNA segments are reassembled (&/or subjected to one or more directed evolution methods described herein) by any of the sequence reassembly (&/or one or more additional directed evolution methods described herein) formats provided herein to generate a diverse library of recombinant DNA segments. Such a library can vary widely in size from having fewer than 10 to more than $10^5$, $10^9$, $10^{12}$ or more members. In some embodiments, the starting segments and the recombinant libraries generated will include full-length coding sequences and any essential regulatory sequences, such as a promoter and polyadenylation sequence, required for expression. In other embodiments, the recombinant DNA segments in the library can be inserted into a common vector providing sequences necessary for expression before performing screening/selection.

Using Reassembly PCR to Assemble Multiple Segments That Have Been Separately Evolved Into a Full Length Nucleic Acid Template Such as a Gene A further technique for recombining mutations in a nucleic acid sequence utilizes "reassembly PCR". This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest.

Oligos are Synthesized for PCR Amplification of Segments of the Nucleic Acid Sequence of Interest So That the Oligos Overlap the Junctions of Two Segments by, Typically, About 10 to 100 Nucleotides Preferably, oligonucleotide primers (oligos) are synthesized for PCR amplification of segments of the nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols such as those discussed herein to assemble non-stochastically generated nucleic acid building blocks &/or randomly fragmented genes. In brief, in an assembly protocol the PCR products are first purified away from the primers, by, for example, gel electrophoresis or size exclusion chromatography. Purified products are mixed together and subjected to about 1–10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and experimentally evolved (e.g. by polynucleotide reassembly &/or polynucleotide site-saturation mutagenesis) genes.

PCR Primers Are Used to Introduce Variation Into the Gene of Interest and the Mutations at Sites of Interest are Screened or Selected by Sequencing Homologues of the Nucleic Acid Sequence In a further embodiment, PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on.

Using Oligonucleotide PCR Primers (Encoding Wild Type or Mutant Information) in PCR to Generate Libraries of Full Length Genes Encoding Permutations of Said Info, Where the Alternative Screening or Selection Process is Expensive, Cumbersome, or Impractical Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantageous in cases where the screening or selection process is expensive, cumbersome, or impractical relative to the cost of sequencing the genes of mutants of interest and synthesizing mutagenic oligonucleotides.

2.3. VECTORS USED IN GENETIC VACCINATION

Evolution of Genetic Vaccines and Components by Stochastic (e.g. Polynucleotide Shuffling & Interrupted Synthesis) and Non-stochastic Polynucleotide Reassembly The invention provides multicomponent genetic vaccines, and methods of obtaining genetic vaccine components that improve the capability of the genetic vaccine for use in nucleic acid-mediated immunomodulation. A general approach for evolution of genetic vaccines and components by stochastic (e.g. polynucleotide shuffling & interrupted synthesis) and non-stochastic polynucleotide reassembly is shown schematically herein.

Including an Origin of Replication is Useful to Obtain Sufficient Quantities of the Vector Prior to Administration to a Patient, but Might be Undesirable if the Vector is Designed to Integrate Into Host Chromosomal DNA or Bind to Host mRNA or DNA Broadly speaking, a genetic vaccine vector is an exogenous polynucleotide which produces a medically useful phenotypic effect upon the mammalian cell(s) and organisms into which it is transferred. A vector may or may not have an origin of replication. For example, it is useful to include an origin of replication in a vector to allow for propagation of the vector in order to obtain sufficient quantities of the vector prior to administration to a patient. If the vector is designed to integrate into host chromosomal DNA or bind to host mRNA or DNA, or if replication in the host is otherwise undesirable, the origin of replication can be removed before administration, or an origin can be used that functions in the cells used for vector production but not in the target cells. However, in certain situations, including some of those discussed herein, it is desirable that the genetic vaccine vector be capable of replicating in appropriate host cells.

Incorporating Nucleic Acids That are Modified by Stochastic (e.g. Polynucleotide Shuffling & Interrupted Synthesis) and Non-stochastic Polynucleotide Reassembly Into Viral Vectors to be Used in Genetic Vaccination Vectors used in genetic vaccination can be viral or non-viral. Viral vectors are usually introduced into a patient as components of a virus. Illustrative viral vectors into which one can incorporate nucleic acids that are modified by the stochastic (e.g. polynucleotide shuffling & interrupted synthesis) and non-stochastic polynucleotide reassembly methods of the invention include, for example, adenovirus-based vectors (Cantwell (1996) Blood 88:4676–4683; Ohashi (1997) Proc. Nat'l. Acad. Sci USA 94:1287–1292), Epstein-Barr virus-based vectors (Mazda (1997) J. Immunol. Methods 204:143–15 1), adenovirus-associated virus vectors, Sindbis virus vectors (Strong (1997) Gene Ther. 4: 624–627), herpes simplex virus vectors (Kennedy (1997) Brain 120: 1245–1259) and retroviral vectors (Schubert (1997) Curr. Eye Res. 16:656–662).

Techniques for Transferring DNA Into a Cell Useful in vivo (Naked DNA Delivered Using Liposomes Fusing to Cellular Membrane or Entering Through Endocytosis; Permeabilize the Cells and Use DNA Binding Protein to Transport Into Cell; and Bombardment of Skin with Particles Coated With DNA Delivered Mechanically)

Nonviral vectors, typically dsDNA, can be transferred as naked DNA or associated with a transfer-enhancing vehicle, such as a receptor- recognition protein, liposome, lipoamine, or cationic lipid. This DNA can be transferred into a cell using a variety of techniques well known in the art. For example, naked DNA can be delivered by the use of liposomes which fuse with the cellular membrane or are endocytosed, i.e., by employing ligands attached to the liposome, or attached directly to the DNA, that bind to surface membrane protein receptors of the cell resulting in endocytosis. Alternatively, the cells may be permeabilized to enhance transport of the DNA into the cell, without injuring the host cells. One can use a DNA binding protein, e.g., HBGF-1, known to transport DNA into a cell. Furthermore, DNA can be delivered by bombardment of the skin by gold or other particles coated with DNA which are delivered by mechanical means, e.g., pressure. These procedures for delivering naked DNA to cells are useful in vivo. For example, by using liposomes, particularly where the liposome surface carries ligands specific for target cells, or are otherwise preferentially directed to a specific organ, one may provide for the introduction of the DNA into the target cells/organs in vivo.

2.3.1. Viral Vectors

Structure of Viral Vectors Often Consist of a Modified Viral Genome and a Coat Structure Surrounding it, a Structure Which can be Changed in Many Ways for the Viral Nucleic Acid in a Vector Designed for Genetic Vaccination Various viral vectors, such as retroviruses, adenoviruses, adenoassociated viruses and herpes viruses, are commonly used in genetic vaccination. They are often made up of two components, a modified viral genome and a coat structure surrounding it (see generally Smith (1995) Annu. Rev. Microbiol. 49, 807–838), although sometimes viral vectors are introduced in naked form or coated with proteins other than viral proteins. Most current viral vectors have coat structures similar to a wild type virus. This structure packages and protects the viral nucleic acid and provides the means to bind and enter target cells. In contrast, the viral nucleic acid in a vector designed for genetic vaccination can be changed in many ways. The goals of these changes can be, for example, to enhance or reduce replication of the virus in target cells while maintaining its ability to grow in vector form in available packaging or helper cells, to incorporate new sequences that encode and enable appropriate expression of a gene of interest (e.g., an antigen-encoding gene), and to alter the immunogenicity of the viral vector itself Viral vector nucleic acids generally comprise two components: essential cis-acting viral sequences for replication and packaging in a helper line and a transcription unit for the exogenous gene. Other viral functions can be expressed in trans in a specific packaging or helper cell line.

2.3.1.1. Adenoviruses

The Normal Life Cycle and Production Infection Cycle of Adenoviruses

Adenoviruses comprise a large class of nonenveloped viruses that contain linear double-stranded DNA. The normal life cycle of the virus does not require dividing cells and involves productive infection in permissive cells during which large amounts of virus accumulate. The productive infection cycle takes about 32–36 hours in cell culture and comprises two phases, the early phase, prior to viral DNA synthesis, and the late phase, during which structural proteins and viral DNA are synthesized and assembled into virions.

In General, Adenovirus Infections are Associated With Mild Disease in Humans

E3-deletion Vectors Studied; Replication in Cultured Cells Does Not Require E3 Region, Allowing Insertion of Exogenous DNA Sequences to Yield Vectors Capable of Productive Infection and the Transient Synthesis of Relatively Large Amounts of Encoded Protein Adenovirus vectors are somewhat larger and more complex than retrovirus or AAV vectors, partly because only a small fraction of the viral genome is removed from most current vectors. If additional genes are removed, they are provided in trans to produce the vector, which so far has proved difficult. Instead, two general types of adenovirus-based vectors have been studied, E3-deletion and E1-deletion vectors. Some viruses in laboratory stocks of wild-type lack the E3 region and can grow in the absence of helper. This ability does not mean that the E3 gene products are not necessary in the wild, only that replication in cultured cells does not require them. Deletion of the E3 region allows insertion of exogenous DNA sequences to yield vectors capable of productive infection and the transient synthesis of relatively large amounts of encoded protein.

E1 Replacement Vectors Grown in 293 Cells Utilized in Most Gene Therapy Applications Involving Adenoviruses Deletion of the E1 region disables the adenovirus, but such vectors can still be grown because there exists an established human cell line (called "293") that contains the E1 region of Ad5 and that constitutively expresses the E1 proteins. Most recent gene-therapy applications involving adenovirus have utilized E1 replacement vectors grown in 293 cells.

Adenovirus Vectors Capable of Efficient Episomal Gene Transfer, Easy to Grow, can be Topically Applied to Skin for Antigen Delivery, Induction of Antigen Specific Immune Responses can be Observed, but Host Response Limits Duration of Expression and Ability to Repeat Dosing in Cases with High Doses of First Generation Vectors The main advantages of adenovirus vectors are that they are capable of efficient episomal gene transfer in a wide range of cells and tissues and that they are easy to grow in large amounts. Adenovirus-based vectors can also be used to deliver antigens after topical application onto the skin, and induction of antigen-specific immune responses can be observed following delivery to the skin (Tang et al. (1997) Nature 388: 729–730). The main disadvantage is that the host response to the virus appears to limit the duration of expression and the ability to repeat dosing, at least with high doses of first-generation vectors.

This Invention Provides for the First Time a Phagemid System Capable of Cloning Large DNA Inserts of Over 10 Kilobases and Generating ssDNA in vitro and in vivo Corresponding to Those Large Inserts In one embodiment, the directed evolution methods of the invention are used to construct a novel adenovirus-phagemid capable of packaging DNA inserts over 10 kilobases in size. Incorporation of a phage origin in a plasmid using the methods of the invention also generates a novel in vivo reassembly or shuffling format capable of evolving whole genomes of viruses, such as the 36 kb family of human adenoviruses. The widely used human adenovirus type 5 (Ad5) has a genome size of 36 kb. It is difficult to shuffle this large genome in vitro without creating an excessive number of changes which may cause a high percentage of nonviable recombinant variants. To minimize this problem and achieve whole genome reassembly of Ad5, an adenovirus-phagemid was constructed. The Ad-phagemid has been demonstrated to accept inserts as large as 15 and 24 kilobases and to effectively generate ssDNA of that size. In a further embodiment, larger DNA inserts, as large as 50 to 100 kb are inserted into the Ad-phagemid of the invention; with generation of full length ssDNA corresponding to those large inserts. Generation of such large ssDNA non-stochastically generated nucleic acid building blocks &/or fragments provides a means to evolve, i.e. modify by the recursive reassembly methods (&/or one or more additional recursive directed evolution methods described herein) of the invention, entire viral genomes. Thus, this invention provides for the first time a unique phagemid system capable of cloning large DNA inserts (>10 KB) and generating ssDNA in vitro and in vivo corresponding to those large inserts.

In vivo Reassembly or Shuffling of the Genomes of Related Serotypes of Human Adenoviruses Using System is Useful for Creation of Recombinant Adenovirus Variants With Changes in Multiple Genes The genomes of related serotypes of human adenovirus are experimentally evolved (e.g. by polynucleotide reassembly &/or polynucleotide site-saturation mutagenesis) in vivo using this unique phagemid system, as described in International Application No. PCT/US97/17302 (Publ. No. WO98/13485). The genomic DNA is first cloned into a phagemid vector, and the resulting plasmid, designated an "Admid," can be used to produce single-stranded (ss) Admid phage by using a helper M13 phage. To achieve in vivo reassembly (&/or one or more additional directed evolution methods described herein), ssAdmid phages containing the genome of homologous human adenoviruses are used to perform high multiplicity of infection (MOI) on $F^+$ MutS $E.$ $coli$ cells. The ssDNA is a better substrate for reassembly (&/or one or more additional directed evolution methods described herein) enzymes such as RecA. The high MOI ensures that the probability of having multiple cross-overs between copies of the infecting ssAdmid DNA is high. The experimentally evolved (e.g. by polynucleotide reassembly &/or polynucleotide site-saturation mutagenesis) adenovirus genome is generated by purification of the double stranded Admid DNA from the infected cells and is introduction into a permissive human cell line to produce the adenovirus library. This genomic reassembly strategy is useful for creation of recombinant adenovirus variants with changes in multiple genes. This allows screening or selection of recombinant variant phenotypes resulting from combinations of variations in multiple genes.

2.3.1.2. Adeno-associated Virus (AAV)

AAV is a small, simple, nonautonomous virus containing linear single-stranded DNA. See, Muzycka, Current Topics Microbiol. Immunol. 158, 97–129 (1992). The virus requires co-infection with adenovirus or certain other viruses in order to replicate. AAV is widespread in the human population, as evidenced by antibodies to the virus, but it is not associated with any known disease. AAV genome organization is straightforward, comprising only two genes: rep and cap. The termini of the genome comprises terminal repeats (ITR) sequences of about 145 nucleotides.

Growth of AAV is Cumbersome and Helper Virus Such as Adenovirus is Often Required AAV-based vectors typically contain only the ITR sequences flanking the transcription unit of interest. The length of the vector DNA cannot greatly exceed the viral genome length of 4680 nucleotides. Currently, growth of AAV vectors is cumbersome and involves introducing into the host cell not only the vector itself but also a plasmid encoding rep and cap to provide helper functions. The helper plasmid lacks ITRs and consequently cannot replicate and package. In addition, helper virus such as adenovirus is often required.

Advantage: Long-term Expression in Nondividing Cells

The potential advantage of AAV vectors is that they appear capable of long-term expression in nondividing cells, possibly, though not necessarily, because the viral DNA integrates. The vectors are structurally simple, and they may therefore provoke less of a host-cell response than adenovirus.

2.3.1.3. Papilloma Virus

Papillomaviruses are small, nonenveloped, icosahedral DNA viruses that replicate in the nucleus of squamous epithelial cells. Papillomaviruses consist of a single molecule of double-stranded circular DNA about 8,000 bp in size within a spherical protein coat of 72 capsomeres. Such papillomaviruses are classified by the species they infect (e.g., bovine, human, rabbit) and by type within species. Over 50 distinct human papillomaviruses ("HPV") have been described. See, e.g., Fields Virology (3rd ed., eds. Fields et al., Lippincott-Raven, Philadelphia, 1996).

Cellular Tropism for Epithelial Cells

Papillomaviruses display a marked degree of cellular tropism for epithelial cells. Specific viral types have a preference for either cutaneous or mucosal epithelial cells.

Benign, Low-risk, Intermediate-risk, and High-risk HPVs

All papillomaviruses have the capacity to induce cellular proliferation. The most common clinical manifestation of proliferation is the production of benign warts. However, many papillomaviruses have capacity to be oncogenic in some individuals and some papillomaviruses are highly oncogenic. Based on the pathology of the associated lesions, most human papillomaviruses (HPVs) can be classified in one of four major groups, benign, low-risk, intermediate-risk and high-risk (Fields Virology, (Fields et al., eds., Lippincott- Raven, Philadelphia, 3d ed. 1996); DNA Tumor Viruses: Papilloma in (Encyclopedia of Cancer, Academic Press) Vol. 1, p 520–531). For example, viruses HPV-1, HPV-2, HPV-3, HPV-4, and HPV-27 are associated with benign cutaneous lesions. Viruses HPV-6 and HPV-11 are associated with vulval, penile, and laryngeal warts and are considered low-risk viruses as they are rarely associated with invasive carcinomas. Viruses HPV-16, HPV-18, HPV-31, and HPV-45 are considered high risk virus as they are associated with a high frequency with adeno- and squamous carcinoma of the cervix. Viruses HPV-5 and HPV-8 are associated with benign cutaneous lesion in a multifactorial disease Epidermodysplasia Verruciformis (EV). Such lesions, however, can progress into squamous cell carcinomas.

HPVs Classified for Risk Based on Frequency of Cancerous Lesions Relative to Previously Classified HPVs These viruses do not fall under one of the four major risk groups. Newly discovered HPVs can classified for risk based on the frequency of cancerous lesions relative to that of HPVs that have already been classified for risk.

HPV vectors can be subjected to iterative cycles of reassembly (&/or one or more additional directed evolution methods described herein) and screening with a view to obtaining vectors with improved properties. Improved properties include increased tissue specificity, altered tissue specificity, increased expression level, prolonged expression, increased episomal copy number, increased or decreased capacity for chromosomal integration, increased uptake capacity, and other properties as discussed herein. The starting materials for reassembling (optionally in combination with other directed evolution methods described herein) are typically vectors of the kind described above constructed from different strains of human papillomaviruses, or segments or variants of such generated by e.g., error-prone PCR or cassette mutagenesis. The human papillomaviruses, or at least the E1 and E2 coding regions thereof are preferably human cutaneous papillomaviruses.

2.3.1.4. Retroviruses

Normal Viral Life Cycle and Viral Genome Organization

Retroviruses comprise a large class of enveloped viruses that contain single-stranded RNA as the viral genome.

During the normal viral life cycle, viral RNA is reverse-transcribed to yield double-stranded DNA that integrates into the host genome and is expressed over extended periods. As a result, infected cells shed virus continuously without apparent harm to the host cell. The viral genome is small (approximately 10 kb), and its prototypical organization is extremely simple, comprising three genes encoding gag, the group specific antigens or core proteins; pol, the reverse transcriptase; and env, the viral envelope protein. The termini of the RNA genome are called long terminal repeats (LTRs) and include promoter and enhancer activities and sequences involved in integration. The genome also includes a sequence required for packaging viral RNA and splice acceptor and donor sites for generation of the separate envelope mRNA. Most retroviruses can integrate only into replicating cells, although human immunodeficiency virus (HIV) appears to be an exception.

Providing the Missing Viral Functions to the Retrovirus Vector and Adding/removing Additional Features to Render the Vectors More Efficacious or Reduce the Possibility of Contamination by Helper Virus Retr recognized by antigen presenting cells (APC) and taken up by those cells for efficient intracellular processing and presentation to T helper (T$_H$) cells. Cells transfected with AR plasmid can be considered as an antigen factory for APC. AR plasmids typically have one or more of the following properties, each of which can be optimized using the stochastic (e.g. polynucleotide shuffling & interrupted synthesis) and non-stochastic polynucleotide reassembly methods of the invention.

Optimal Plasmid Binding to and Uptake by the Chosen Antigen Expressing Cells (e.g., Myocytes for Intramuscular Immunization or Epithelial Cells for Mucosal Immunization)

This is a critical property which differentiates AR from other vector components in the multicomponent DNA vaccine. Optimal vector binding to the target cell includes not only the concept of very avid binding and subsequent internalization into target cells, but relative inability to bind to and enter other cells. Optimization of this ratio of desired binding to undesired binding will significantly increase the number of target cells transfected. This property can be optimized using stochastic (e.g. polynucleotide shuffling & interrupted synthesis) and non-stochastic polynucleotide reassembly according to the present invention as described herein. For example, variant vector component sequences obtained by stochastic (e.g. polynucleotide shuffling & interrupted synthesis) and non-stochastic polynucleotide reassembly, combinatorial assembly of vector components, insertion of random oligonucleotide sequences, and the like, can first be selected for those that bind to target cells, after which this population of cells is depleted for those that bind to other cells. Vector components for targeting genetic vaccine vectors to particular cell types, and methods of obtaining improved targeting, are described in (a) optimal trafficking of the vector DNA to the nucleus.

Again, the present invention provides methods by which one can obtain genetic vaccine components that are optimal for such properties.

(b) optimal transcription of the antigen gene(s).

This can involve, for example, the use of optimized promoters, enhancers, introns, and the like. In a preferred embodiment, cell-specific promoters are used that only allow transcription of the genes when the vector is within the nucleus of the target cell type. In this case, specificity is derived not only from selective vector entry into target cells.

(c) optimal trafficking of mRNA to the cytoplasm and optimal longevity of the mRNA in the cytoplasm.

To achieve this property, the methods of the invention are used to obtain optimal 3' and 5' non-translated regions of the mRNA.

(d) optimal translation of the mRNA.

Again, the stochastic (e.g. polynucleotide shuffling & interrupted synthesis) and non-stochastic polynucleotide reassembly methods are used to obtain optimized recombinant sequences which exhibit optimal ribosome binding and assembly of translational machinery, plus optimal codon preference.

(e) optimal antigen structure for efficient uptake by APC.

Extracellular antigen is taken up by APC by at least five non-exclusive mechanisms. One mechanism is sampling of the external fluid phase by micropinocytosis and internalization of a vesicle.

Additional Mechanistic Considerations

The first mechanism has, as far as is presently known, no structural requirements for an antigen in the fluid phase and is therefore not relevant to considerations of designing antigen structure. A second mechanism involves binding of antigen to receptors on the APC surface; such binding occurs according to rules that are only now being studied (these receptors are not immunoglobulin family members and appear to represent several families of proteins and glycoproteins capable of binding different classes of extracellular proteins/glycoproteins). This type of binding is followed by receptor-mediated internalization, also in a vesicle. Because this mechanism is poorly understood at present, elements of antigen design cannot be incorporated in a rational design process. However, application of stochastic (e.g. polynucleotide shuffling & interrupted synthesis) and non-stochastic polynucleotide reassembly methods, an empirical approach of selection of variant DNA molecules most successful at entry into APC, can select for variants that are improved throughout this mechanism.

The other three mechanisms all relate to specific antibody recognition of the extracellular antigen. The first mechanism involves immunoglobulin-mediated recognition of the specific antigen via IgG that is bound to Fc receptors on the cell surface. APC such as monocytes, macrophages and dendritic cells can be decorated with surface membrane IgG of diverse specificities. In a primary response, this mechanism will not be operative. In previously immunized animals, IgG on the surface of APC can specifically bind extracellular antigen and mediate uptake of the bound antigen into an intracellular endosomal compartment. Another mechanism involves binding to clonally-derived surface membrane immunoglobulin which is present on each B cells (IgM in the case of primary B cells and IgG when the animal has been previously exposed to the antigen). B cells are efficient APC. Extracellular antigen can bind specifically to surface Ig and be internalized and processed in a membrane compartment for presentation on the B cell surface. Finally, extracellular antigen can be recognized by specific soluble immunoglobulin (IgM in the case of a primary immunization and IgG in the previously immunized animals). Complexing with Ig will elicit binding to the surface of APC (via Fc receptor recognition in the case of IgG) and internalization.

In each of these latter three mechanisms, the extent to which the conformation of the antigen is the same as the recognition specificity of the pre-existing antibody is critical to the efficiency of the process of antigen presentation. Antibodies can recognize linear protein epitopes as well as conformational epitopes determined by the three dimensional structure of the protein antigen. Protective antibodies that will recognize an extracellular virus or bacterial pathogen and by binding to its surface prevent infection or mediate its immune destruction (complement mediated lysis, immune complex formation and phagocytosis) are almost exclusively generated against conformational determinants on the proteins with native structure displayed on the surface of the pathogen. Hence, it is imperative for generation of host protective humoral immunity, to have those naive B cells which bear antibody specific for conformational epitopes present on the pathogen be stimulated by direct contact with T helper cells after intracellular processing of the antigen and presentation of degradation peptides in the context of MHC Class II. This T help will allow selective proliferation of the relevant B cells with consequent mutation of antibody and antigen driven selection for antibodies with increased specificity, as well as antibody class switching.

To summarize, optimal uptake of antigen by APC to elicit humoral immunity, as well as specific CD4$^+$ cytotoxic T cells, requires that the antigen be in native protein conformation (as presented subsequently to the immune system upon natural infection) and recognized by naive B cells bearing the appropriate membrane antibody. Native protein conformation includes appropriate protein folding, glycosylation and any other post-translational modifications necessary for optimal reactivity with the receptors (immunoglobulin and possibly non-immunoglobulin) on APC. In addition to the three dimensional structure of the expressed antigen required for recognition by specific antibody and elicitation of the required immune responses, the structure (and sequence) can be optimized for increased protein stability outside the expressing cell, until the time when it is recognized by immune cells, including APCs. The reassembly (&/or one or more additional directed evolution methods described herein) and screening methods of the invention can be used to optimize the antigen structure (and sequence) for subsequent processing after uptake by APC so that intracellular processing results in derivation of the required peptide fragments for presentation on Class I or Class II on APC and desired immune responses.

(f) optimal partitioning of the nascent antigen into the desired subcellular compartment or compartments.

This can be directed by signal and trafficking signals embodied in the antigen sequence. It may be desirable for all of the antigen to be secreted from these cells; alternatively, all or part of the antigen could be directed to be expressed on the cell surface of these factory cells. Signals to direct vesicles containing the antigen to other subcellular compartments for post-translational modifications, including glycosylation, can be embodied in the antigen sequence.

(g) optimal display of the antigen on the cell surface or optimal release of the antigen from the cells.

A variation on items (f) and (g) is to design the expression of the antigen within the cytoplasm of the factory cell followed by lysis of that cell to release soluble antigen. Cell death can be engineered by expression on the same genetic vaccine vector of an intracellular protein that will elicit apoptosis. In this case, the timing of cell death is balanced with the need for the cell to produce antigen, as well as the potential deleterious effect of killing some cells in a designed process.

In combination, items (a)–(h) lead to a variety of scenarios for the optimizing the longevity and extent of antigen expression. It is not always desirable that the antigen be expressed for the longest time at the highest level. In certain clinical applications, it will be important to have antigen expression that is short time-low expression, short time-high expression, long time-low expression, long time-high expression or somewhere in between. Plasmid AR can be designed to express one or more variants of a single antigen gene or several quite different targets for immunization. Methods for obtaining optimized antigens for use in genetic vaccines are described herein. Multiple antigens can be expressed from a monocistronic or multicistronic form of the vector.

2.4.2. Vector Components "CTL-DC", "CTL-LC" and "CTL-MM", Designed for Optimal Production of CTLs Genetic vector components "CTL-DC", "CTL-LC" and "CTL-MM" are designed to direct optimal production of cytotoxic $CD8^+$ lymphocytes (CTLs) by dendritic cells (CTL-DC), Langerhan's cells (CTL-LC), and monocytes and macrophages (CTL-MM) These vector components direct presentation of optimal antigen fragments in association with MHC Class I, thereby ensuring maximal cytotoxic T cell immune responses. Cells transfected with CTL vector components can be considered as the direct activators of this arm of specific immunity that is usually critically important for protection against viral diseases.

CTL vector components are typically designed to have one or more of the following properties, each of which can be optimized using the stochastic (e.g. polynucleotide shuffling & interrupted synthesis) and non-stochastic polynucleotide reassembly methods of the invention:

(a) optimal vector binding to, and uptake by, the chosen antigen presenting cells (e.g., dendritic cells, monocytes/macrophages, Langerhan's cells).

This is a critical property to differentiate CTL series vectors from other vectors in the multicomponent DNA vaccine. CTL series vectors preferably do not bind to or enter cells that are chosen to be the extracellular antigen expression host via AR vectors. This separation of functions is critical, as the intracellular fate and trafficking of antigen destined for stimulation of immune cells after release from an antigen expressing cell is quite different than the fate of antigen destined to be presented on the cell surface in association with MHC Class I. In the former case, antigen is directed via a signal secretion sequence to be delivered intact to the lumen of the rough endoplasmic reticulum (RER) and then secreted. In the latter case, antigen is directed to remain in the cytoplasm and there be degraded into peptide fragments by the proteasomal system followed by delivery to the lumen of the RER for association with MHC Class I. These complexes of peptide and MHC Class I are then delivered to the cell surface for specific interaction with $CD8^+$ cytotoxic T cells. Vector components, and methods for obtaining optimized vector components, that are optimized for targeting to desired cell types are described in Optimizing Transcription of the Antigen Gene(s)

This can be accomplished by optimizing promoters, enhancers, introns, and the like, as discussed herein. Cell specific promoters are valuable in such vectors as an additional level of selectivity.

(b) optimal longevity of the mRNA.

Optimal 3' and 5' non-translated regions of the mRNA can be obtained using the methods of the invention.

(c) optimal translation of the mRNA.

Again, the stochastic (e.g. polynucleotide shuffling & interrupted synthesis) and non-stochastic polynucleotide reassembly and selection methods of the invention can be used to obtain polynucleotide sequences for optimal ribosome binding and assembly of translational machinery, as well as optimal codon preference.

(d) optimal protein conformation.

In this case, the optimal protein conformation yields appropriate cytoplasmic proteolysis and production of the correct peptides for presentation on MHC Class I and elicitation of the desired specific CTL responses, rather than a conformation that will interact with specific antibody or other receptors on the surface of APC.

(e) optimal proteolysis to generate the correct peptides.

The order of specific proteolytic cleavages will depend on the nature of protein folding and the nature of proteases either in the cytoplasm or in the proteasome.

(f) optimal transport of the antigen peptides across the endoplasmic reticulum membrane to be delivered into the RER lumen.

This may be mediated by recognition of the peptides by TAP proteins or by other membrane transporters.

(h) optimal association of the peptides with the Class I-2 microglobulin complex and trafficking to the cell surface via the secretory pathway.

(i) optimal display of the MHC-peptide complex with associated accessory molecules for recognition by specific CTL.

Vector CTL can be designed to express one or more variants of a single antigen gene or several different targets for immunization. Multiple optimized antigens can be expressed from a monocistronic or multicistronic form of the vector.

2.4.3. Vectors "M" Designed for Optimal Release of Immune Modulators

Vectors "M" are designed to direct optimal release of immune modulators, such as cytokines and other growth factors, from target cells. Target cells can be either the predominant cell type in the immunized tissue or immune cells such dendritic cells (M-DC), Langerhan's cells (M-LC), monocytes & macrophages (M-MM)". These vectors direct simultaneous expression of optimal levels of several immune cell "modulators" (cytokines, growth factors, and the like) such that the immune response is of the desired type, or combination of types, and of the desired level. Cells transfected with M vectors can be considered as the directors of the nature of the vaccine immune response (CTL vs $T_H1$ vs $T_H2$ vs NK cell, etc.) and its magnitude. The properties of these vectors reflect the nature of the cell in which the vectors are designed to operate. For example, the vectors are designed to bind to and enter the desired cell type, and/or can have cell-specific regulated promoters that drive transcription in the desired cell type. The vectors can also be engineered to direct maximal synthesis and release of the cell modulator proteins from the target cells in the desired ratio.

"M" genetic vaccine vectors are typically designed to have one or more of the following properties, each of which can be optimized using the stochastic (e.g. polynucleotide shuffling & interrupted synthesis) and non-stochastic polynucleotide reassembly methods of the invention:

(a) optimal vector binding to and uptake by the chosen modulator expressing cell.

Suitable expressing cells include, for example, muscle cells, epithelial cells or other dominant (by number) cell types in the target tissue, antigen presenting cells (e.g. dendritic cells, monocytes/macrophages, Langerhans cells). This is a critical property which differentiates M series vectors from those designed to bind to and enter other cells.

(b) optimal transcription of the immune modulator gene(s).

Again, promoters, enhancers, introns, and the like can be optimized according to the methods of the invention. Cell specific promoters are very valuable here as an additional level of selectivity.

(c) optimal longevity of the mRNA.

Optimal 3' and 5' non-translated regions of the mRNA can be obtained using the methods of the invention.

(d) optimal translation of the mRNA.

Again, the stochastic (e.g. polynucleotide shuffling & interrupted synthesis) and non-stochastic polynucleotide reassembly and selection methods of the invention can be used to obtain polynucleotide sequences for optimal ribosome binding and assembly of translational machinery, as well as optimal codon preference.

(e) optimal trafficking of the modulator into the lumen of the RER (via a signal secretion sequence).

An alternative strategy for modulation of the immune response uses membrane anchored modulators rather than secretion of soluble modulator. Anchored modulator can be retained on the surface of the synthesizing cell by, for example, a hydrophobic tail and phosphoinositol glycan linkage.

(f) optimal protein conformation for each modulator.

In this case, the optimal protein conformation is that which allows extracellular modulator and/or cell membrane anchored modulator to interact with the relevant receptor.

(g) the ratio of modulators and their type can be determined empirically.

One will test sets of modulators that are known to work in concert to direct the immune response in the direction of a $T_H$ response (e.g., production of IL-2 and/or IFN) or $T_H2$ response (e.g., IL-4, IL-5, IL-13), for example. Vector M can be designed to express one or more modulators. Optimized immunomodulators, and methods for obtaining optimized immunomodulators, are described herein. These optimized immunomodulatory sequences are particularly suitable for use as components of the multicomponent genetic vaccines of the invention. Multiple modulators can be expressed from a monocistronic or multicistronic form of the vector.

2.4.4. Vectors "CK", Designed to Direct Release of Chemokines

Genetic vaccine vectors designated "CK" are designed to direct optimal release of chemokines from target cells. Target cells can be either the predominant cell type in the immunized tissue, or can be immune cells such as dendritic cells (CK-DC), Langerhan's cells (CK-LC), or monocytes and macrophages (CK-MM). These vectors typically direct simultaneous expression of optimal levels of several chemokines such that the recruitment of immune cells to the site of immunization is optimal. Cells transfected with CK vectors can be considered as the traffic police, regulating the immune cells critical for the vaccine immune response. The properties of these vectors reflect the nature of the cell in which the vectors are designed to operate. For example, the vectors are designed to bind to and enter the desired cell type, and/or can have cell-specific regulated promoters that drive transcription in the desired cell type. The vectors are also engineered to direct maximal synthesis and release of the chemokines from the target cells in the desired ratio. Genetic vaccine components, and methods for obtaining components, that provide optimal release of chemokines are described herein.

CK vectors are typically designed to have one or more of the following properties, each of which can be optimized using the stochastic (e.g. polynucleotide shuffling & interrupted synthesis) and non-stochastic polynucleotide reassembly methods of the invention:

(a) optimal vector binding to and uptake by the chosen chemokine expressing cell.

Suitable cells include, for example, muscle cells, epithelial cells, or cell types that are dominant (by number) in the particular tissue of interest. Also suitable are antigen presenting cells (e.g. dendritic cells, monocytes and macrophages, Langerhans cells). This is a critical property which differentiates CK series vectors from those designed to bind to and enter other cells.

(b) optimal transcription of the chemokine gene(s).

Again, promoters, enhancers, introns, and the like can be optimized according to the methods of the invention. Cell specific promoters are very valuable here as an additional level of selectivity.

(c) optimal longevity of the mRNA.

Optimal 3t and 5' non-translated regions of the mRNA can be obtained using the methods of the invention.

(d) optimal translation of the mRNA.

Again, the stochastic (e.g. polynucleotide shuffling & interrupted synthesis) and non-stochastic polynucleotide reassembly and selection methods of the invention can be used to obtain polynucleotide sequences for optimal ribosome binding and assembly of translational machinery, as well as optimal codon preference.

(e) optimal trafficking of the chemokine into the lumen of the RER (via a signal secretion sequence).

An alternative strategy for modulation of the immune response via recruitment of cells will use membrane anchored chemokine rather than secretion of soluble chemokine. Anchored chemokine will be retained on the surface of the synthesizing cell by a hydrophobic tail and phosphoinositol glycan linkage.

(f) optimal protein conformation for each chemokine.

In this case, the optimal protein conformation is that which allows extracellular chemokine/cell membrane anchored chemokine to interact with the relevant receptor.

(g) the ratio of diverse chemokines can be determined empirically.

One can test sets of chemokines that are known to work in concert to direct recruitment of CTL, $T_H$ cells, B cells, monocytes/macrophages, eosinophils, and/or neutrophils as appropriate. Vector CK can be designed to express one or more chemokines. Multiple chemokines can be expressed from a monocistronic or multicistronic form of the vector.

2.4.5. Other Vectors

Genetic vaccines which contain one or more additional component vector moieties are also provided by the invention. For example, the genetic vaccine can include a vector that is designed to specifically enter dendritic cells and Langerhans cells, and will migrate to the draining lymph nodes.

This Vector is Designed to Provide for Expression of the Target Antigen(s), as Well as a Cocktail of Cytokines and Chemokines Relevant to Elicitation of the Desired Immune Response in the Node Depending on the clinical goals and nature of the antigen, the vector can be optimized for relatively long lived expression of the target antigen so that stimulation of the immune system is prolonged at the node. Another example is a vector that specifically modulates MHC expression in B cells. Such vectors are designed to specifically bind to and enter B cells, cells either resident in the injection site or attracted into the site. Within the B cell, this vector directs the association of antigen peptides derived from specific uptake of antigen into the endocytic compartment of the cell to either association with Class I or Class II, hence directing the elicitation of specific immunity via $CD4^+$ T helper cells or $CD8^+$ cytotoxic lymphocytes. Numerous means exist for this intracellular direction of the fate of processed peptide that are discussed herein.

Examples of molecules that direct Class I presentation include tapasin, TAP-1 and TAP-2 (Koopman et al. (1997) Curr. Opin. Immunol. 9: 80–88), and those affecting Class II presentation include, for example, endosomal/lysosomal proteases (Peters (I1997) Curr. Opin. Immunol. 9: 89–96). Genetic vaccine components, and methods for obtaining components, that provide optimized Class I presentation are described herein. An optimal DNA vaccine could, for example, combine an AR vector (antigen release), a CTL-DC vector (CTL activation via dendritic cell presentation of antigen peptide on MHC Class I), an M-MM vector for release of IL-12 and IFNg from resident tissue macrophages, and a CK vector for recruitment of $T_H$ cells into the immunization site.

Directed Evolution Aid the Following DNA Vaccination Goals

DNA vaccination can be used for diverse goals that can include the following, among others:

stimulation of a CTL response and/or humoral response ready to react rapidly and aggressively against an invading bacterial or viral pathogen at some time in the distant future a continuous but non-aggressive response to prevent inappropriate responses to allergens a continuous non-aggressive and tolerization of immunity to an autoantigen in autoimmune disease elicitation of an aggressive CTL response as rapidly as possible against tumor cell antigens redirection of the immune response away from a strong but inappropriate immune response to an on-going chronic infection in the direction of desired responses to clear the pathogen and/or prevent pathology.

These goals cannot always be met by the format of a single vector DNA vaccine, particularly wherein competing goals are embodied within one DNA sequence. A multicomponent format allows the generation of a portfolio of DNA vaccine vectors, some of which will be reconstructed on each occasion (e.g., those vectors containing antigen) while others will be used as well characterized and understood reagents for numerous different clinical applications (e.g., the same chemokine-expressing vector can be used in different situations).

2.5. SCREENING METHODS

Screening Assay Varies Depending of Property for Which Improvement is Sought

Recombinant nucleic acid libraries that are obtained by the methods described herein are screened to identify those DNA segments that have a property which is desirable for genetic vaccination. The particular screening assay employed will vary, as described below, depending on the particular property for which improvement is sought. Typically, the experimentally evolved (e.g. by polynucleotide reassembly &/or polynucleotide site-saturation mutagenesis) nucleic acid library is introduced into cells prior to screening. If the stochastic (e.g. polynucleotide shuffling & interrupted synthesis) and non-stochastic polynucleotide reassembly format employed is an in vivo format, the library of recombinant DNA segments generated already exists in a cell. If the sequence reassembly (&/or one or more additional directed evolution methods described herein) is performed in vitro, the recombinant library is preferably introduced into the desired cell type before screening/selection. The members of the recombinant library can be linked to an episome or virus before introduction or can be introduced directly.

Cell Types

A wide variety of cell types can be used as a recipient of evolved genes. Cells of particular interest include many bacterial cell types that are used to deliver vaccines or vaccine antigens (Courvalin et al.(l995) C. R. Acad. Sci. 11118: 1207–12), both gram-negative and gram-positive, such as salmonella (Attridge et al. (1997) Vaccine 15: 155–62), clostridium. (Fox et al. (1996) Gene Ther. 3: 173–8), lactobacillus, shigella (Sizemore et al. (1995) Science 270: 299–302), *E. coli*, streptococcus (Oggioni and Pozzi (1996) Gene 169: 85–90), as well as mammalian cells, including human cells. In some embodiments of the invention, the library is amplified in a first host, and is then recovered from that host and introduced to a second host more amenable to expression, selection, or screening, or any other desirable parameter. The manner in which the library is introduced into the cell type depends on the DNA-uptake characteristics of the cell type, e.g., having viral receptors, being capable of conjugation, or being naturally competent. If the cell type is unsusceptible to natural and chemical-induced competence, but susceptible to electroporation, one would usually employ electroporation. If the cell type is unsusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells.

Competent or Potentially Competent Tissue

The process is applicable to a wide range of tissues, including plants, bacteria, fungi, algae, intact animal tissues, tissue culture cells, and animal embryos. One can employ electronic pulse delivery, which is essentially a mild electroporation format for live tissues in animals and patients (Zhao, Advanced Drug Delivery Reviews 17:257–262 (1995)). Novel methods for making cells competent are described in International Patent Application PCT/US97/04494 (Publ. No. WO97/35957). After introduction of the library of recombinant DNA genes, the cells are optionally propagated to allow expression of genes to occur.

Identifying Cells That Contain a Vector Through Inclusion of a Selectable Marker Gene In many assays, a means for identifying cells that contain a particular vector is necessary. Genetic vaccine vectors of all kinds can include a selectable marker gene. Under selective conditions, only those cells that express the selectable marker will survive.

Examples of Selectable Marker Genes

Examples of suitable markers include, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan � Southern & Berg (1982) J Mol. Appl. Genet. 1: 327).

Identifying Cells That Contain a Vector Through Inclusion of a Screenable Marker Gene As an alternative to, or in addition to, a selectable marker, a genetic vaccine vector can include a screenable marker which, when expressed, confers upon a cell containing the vector a readily identifiable phenotype. For example, gene that encodes a cell surface antigen that is not normally present on the host cell is suitable. The detection means can be, for example, an antibody or other ligand which specifically binds to the cell surface antigen. Examples of suitable cell surface antigens include any CD (cluster of differentiation) antigen (CD1 to CD163) from a species other than that of the host cell which is not recognized by host-specific antibodies. Other examples include green fluorescent protein (GFP, see, e.g., Chalfie et al. (1994) Science 263:802–805; Crameri et al. (1996) Nature Biotechnol. 14: 315–319; Chalfie et al. (1995) Photochem. Photobiol. 62:651–656; Olson et al. (1995) J Cell. Biol. 130:639–650) and related antigens, several of which are commercially available.

2.5.1. Screening for Vector Longevity or Translocation to Desired Tissue

For certain applications, it is desirable to identify those vectors with the greatest longevity as DNA, or to identify vectors which end up in tissues distant from the injection site. This can be accomplished by administering to an animal a population of recombinant genetic vaccine vectors by the chosen route of administration and, at various times thereafter excise the target tissue and recover vector from the tissue by standard molecular biology procedures. The recovered vector molecules can be amplified in, for example, *E. coli* and/or by PCR in vitro. The PCR amplification can involve further polynucleotide (e.g. gene, promoter, enhancer, intron, & the like) reassembly (optionally in combination with other directed evolution methods described herein), after which the derived selected population used for readministration to animals and further improvement of the vector. After several rounds of this procedure, the selected vectors can be tested for their capacity to express the antigen in the correct conformation under the same conditions as the vector was selected in vivo.

Methods for in vitro Identification of Cells Expressing the Desired Antigen

Because antigen expression is not part of the selection or screening process described above, not all vectors obtained are capable of expressing the desired antigen. To overcome this drawback, the invention provides methods for identifying those vectors in a genetic vaccine population that exhibit not only the desired tissue localization and longevity of DNA integrity in vivo, but retention of maximal antigen expression (or expression of other genes such as cytokines, chemokines, cell surface accessory molecules, MHC, and the like).

The methods involve in vitro identification of cells which express the desired molecule using cells purified from the tissue of choice, under conditions that allow recovery of very small numbers of cells and quantitative selection of those with different levels of antigen expression as desired.

Two embodiments of the invention are described, each of which uses a library of genetic vaccine vectors as the starting point. The goal of each method is to identify those vectors that exhibit the desired biological properties in vivo. The recombinant library represents a population of vectors that differ in known ways (e.g., a combinatorial vector library of different functional modules), or has randomly generated diversity generated either by insertion of random nucleotide stretches, or has been experimentally evolved (e.g. by polynucleotide reassembly &/or polynucleotide site-saturation mutagenesis) in vitro to introduce low level mutations across all or part of the vector.

2.5.1.1.Selection for Expression of Cell Surface-localized Antigen

In a first embodiment, the invention method involves selection for expression of cell surface-localized antigen. The antigen gene is engineered in the vaccine vector library such that it has a region of amino acids which is targeted to the cell membrane. For example, the region can encode a hydrophobic stretch of C-terminal amino acids which signals the attachment of a phosphoinositol-glycan (PIG) terminus on the expressed protein and directs the protein to be expressed on the surface of the transfected cell. With an antigen that is naturally a soluble protein, this method will likely not affect the three dimensional folding of the protein in this engineered fusion with a new C-terminus. With an antigen that is naturally a transmembrane protein (e.g., a surface membrane protein on pathogenic viruses, bacteria, protozoa or tumor cells) there are at least two possibilities. First, the extracellular domain can be engineered to be in fusion with the C-terminal sequence for signaling PIG-linkage. Second, the protein can be expressed in toto relying on the signaling of the host cell to direct it efficiently to the cell surface. In a minority of cases, the antigen for expression will have an endogenous PIG terminal linkage (e.g., some antigens of pathogenic protozoa).

Collection, Purification, Identification and Separation of Target Cells

The vector library is delivered in vivo and, after a suitable interval of time tissue and/or cells from diverse target sites in the animal are collected. Cells can be purified from the tissue using standard cell biological procedures, including the use of cell specific surface reactive monoclonal antibodies as affinity reagents. It is relatively facile to purify isolated epithelial cells from mucosal sites where epithelium may have been inoculated or myoblasts from muscle. In some embodiments, minimal physical purification is performed prior to analysis. It is sometimes desirable to identify and separate specific cell populations from various tissues, such as spleen, liver, bone marrow, lymph node, and blood. Blood cells can be fractionated readily by FACS to separate B cells, $CD4^+$ or $CD8^+$ T cells, dendritic cells, Langerhans cells, monocytes, and the like, using diverse fluorescent monoclonal antibody reagents.

Identification and Purification of Cells Expressing the Antigen

Those cells expressing the antigen can be identified with a fluorescent monoclonal antibody specific for the C-terminal sequence on PIG-linked forms of the surface antigen. FACS analysis allows quantitative assessment of the level of expression of the correct form of the antigen on the cell population. Cells expressing the maximal level of antigen are sorted and standard molecular biology methods used to recover the plasmid DNA vaccine vector that conferred this reactivity. An alternative procedure that allows purification of all those cells expressing the antigen (and that may be useful prior to loading onto a cell sorter since antigen expressing cells may be a very small minority population), is to rosette or pan-purify the cells expressing surface antigen. Rosettes can be formed between antigen expressing cells and erythrocytes bearing covalently coupled antibody to the relevant antigen. These are readily purified by unit gravity sedimentation. Panning of the cell population over petri dishes bearing immobilized monoclonal antibody specific for the relevant antigen can also be used to remove unwanted cells.

Cells expressing the required conformational structure of the target antigen can be identified using specific conformationally-dependent monoclonal antibodies that are known to react specifically with the same structure as expressed on the target pathogen.

Using Several Monoclonal Antibodies in the Selection Process to Minimize the Possibility of an Antigen Which Reacts With High Affinity to the Diagnostic Antibody but Does Not Yield the Correct Conformation Because one monoclonal antibody cannot define all aspects of correct folding of the target antigen, one can minimize the possibility of an antigen which reacts with high affinity to the diagnostic antibody but does not yield the correct conformation as defined by that in which the antigen is found on the surface of the target pathogen or as secreted from the target pathogen. One way to minimize this possibility is to use several monoclonal antibodies, each known to react with different conformational epitopes in the correctly folded protein, in the selection process. This can be achieved by secondary FACS sorting for example.

The enriched plasmid population that successfully expressed sufficient of the antigen in the correct body site for the desired time is then used as the starting population for another round of selection, incorporating gene reassembling (optionally in combination with other directed evolution methods described herein) to expand the diversity. In this manner, one recovers the desired biological activity encoded by plasmid from tissues in DNA vaccine-immunized animals.

This method can also provide the best in vivo selected vectors that express immune accessory molecules that one may wish to incorporate into DNA vaccine constructs. For example, if it is desired to express the accessory protein B7.1 or B7.2 in antigen-presenting-cells (APC) (to promote successful presentation of antigen to T cells) one can sort APC isolated from different tissues (at or different to the inoculation site) using commercially available monoclonal antibodies that recognize functional B7 proteins.

2.5.1.2.Selection for Expression of Secreted Antigen/Cytokine/Chemokine

Select Vectors That are Optimal in Inducing Secretion of Soluble Proteins That can Affect the Qualitative and Quantitative Nature of an Elicited Immune Response in vivo The invention also provides methods to identify plasmids in a genetic vaccine vector population that are optimal in secretion of soluble proteins that can affect the qualitative and quantitative nature of an elicited immune response. For example, the methods are useful for selecting vectors that are optimal for secretion of particular cytokines, growth factors and chemokines. The goal of the selection is to determine which particular combinations of cytokines, chemokines and growth factors, in combination with different promoters, enhancers, polyA tracts, introns, and the like, elicits the required immune response in vivo.

Genes Encoding the Polypeptides are Typically Present in the Vaccine Vector Library in Combination With Optimal Signal Secretion Sequences (Proteins are Secreted From the Cells.)

Combinations of the genes for the soluble proteins of interest can be present in the vectors; transcription can be either from a single promoter, or the genes can be placed in multicistronic arrangements. Typically, the genes encoding the polypeptides are present in the vaccine vector library in combination with optimal signal secretion sequences, such that the expressed proteins are secreted from the cells.

Generating Vectors Capable of Secreting Different Combinations of Soluble Factors in vitro and Capable of Expressing Those Factors for Desired Lengths of Time.

The first step in these methods is to generate vectors that are capable of secreting high (or in some case low) levels of different combinations of soluble factors in vitro and that will express those factors for a short or long time as desired. This method allows one to select for and retain an inventory of plasmids which can be characterized by known patterns of soluble protein expression in known tissues for a known time. These vectors can then be tested individually for in vivo efficacy, after being placed in combination with the genetic vaccine antigen in an appropriate expression construct.

Delivery of Vector Library and Subsequent Collection, Testing, and Purification Using FACS Sorting, Affinity Panning, Rosetting, or Magnetic Bead Separation to Separate Cell Populations Prior to Identification The vector library is delivered to a test animal and, after a chosen interval of time, tissue and/or cells from diverse sites on the animal are collected. Cells are purified from the tissue using standard cell biological procedures, which often include the use of cell specific surface reactive monoclonal antibodies as affinity reagents. As is the case for cell surface antigens described above, physical purification of separate cell populations can be performed prior to identification of cells which express the desired protein. For these studies, the target cells for expression of cytokines will most usually be APC or B cells or T cells rather than muscle cells or epithelial cells. In such cases FACS sorting by established methods will be preferred to separate the different cell types. The different cell types described above may also be separated into relatively pure fractions using affinity panning, rosetting or magnetic bead separation with panels of existing monoclonal antibodies known to define the surface membrane phenotype of murine immune cells.

Identifying and selecting purified cells through visual inspection or flow cytometry for use in another round of selection incorporating gene reassembling (optionally in combination with other directed evolution methods described herein) to expand the diversity Purified cells are plated onto agar plates under conditions that maintain cell viability. Cells expressing the required conformational structure of the target antigen are identified using conformationally-dependent monoclonal antibodies that are known to react specifically with the same structure as expressed on the target pathogen. Release of the relevant soluble protein from the cells is detected by incubation with monoclonal antibody, followed by a secondary reagent that gives a macroscopic signal (gold deposition, color development, fluorescence, luminescence). Cells expressing the maximal level of antigen can be identified by visual inspection, the cell or cell colony picked and standard molecular biology methods used to recover the plasmid DNA vaccine vector that conferred this reactivity. Alternatively, flow cytometry can be used to identify and select cells harboring plasmids that induce high levels of gene expression. The enriched plasmid population that successfully expressed sufficient of the soluble factor in the correct body site for the desired time is then used as the starting population for another round of selection, incorporating gene reassembling (optionally in combination with other directed evolution methods described herein) to expand the diversity, if further improvement is desired. In this manner, one recovers the desired biological activity encoded by plasmid from tissues in DNA vaccine-immunized animals.

Using Monoclonal Antibody to Confirm That the Initial Results From Sscreening Still Hold When Several Conformational Epitopes are Probed Several monoclonal antibodies, each known to react with different conformational epitopes in the correctly folded cytokine, chemokine or growth factor, can be used to confirm that the initial results from screening with one monoclonal antibody reagent still hold when several conformational epitopes are probed. In some cases the primary probe for functional cytokine released from the cell/cell colony in agar could be a soluble domain of the cognate receptor.

2.5.2. FLOW CYTOMETRY

Most of the Vector Module Libraries can be Assayed by Flow Cytometry to Select Individual Human Tissue Culture Cells That Contain the Experimentally Generated Nucleic Acid Sequences That Have the Greatest Improvement in the Desired Property Flow cytometry provides a means to efficiently analyze the functional properties of millions of individual cells. The cells are passed through an illumination zone, where they are hit by a laser beam; the scattered light and fluorescence is analyzed by computer-linked detectors. Flow cytometry provides several advantages over other methods of analyzing cell populations. Thousands of cells can be analyzed per second, with a high degree of accuracy and sensitivity. Gating of cell populations allows multiparameter analysis of each sample. Cell size, viability, and morphology can be analyzed without the need for staining. When dyes and labeled antibodies are used, one can analyze DNA content, cell surface and intracytoplasmic proteins, and identify cell type, activation state, cell cycle stage, and detect apoptosis. Up to four colors (thus, four separate antigens stained with different fluorescent labels) and light scatter characteristics can be analyzed simultaneously (four colors requires two-laser instrument; one-laser instrument can analyze three colors). The expression levels of several genes can be analyzed simultaneously, and importantly, flow cytometry-based cell sorting ("FACS sorting") allows selection of cells with desired phenotypes. Most of the vector module libraries, including the promoter, enhancer, intron, episomal origin of replication, expression level aspect of antigen, bacterial origin and bacterial marker, can be assayed by flow cytometry to select individual human tissue culture cells that contain the reassembled (&/or subjected to one or more directed evolution methods described herein) nucleic acid sequences that have the greatest improvement in the desired property. Typically the selection is for high level expression of a surface antigen or surrogate marker protein, as diagrammed herein. The pool of the best individual sequences is recovered from the cells selected by flow cytometry-based sorting. An advantage of this approach is that very large numbers ($>10^7$) can be evaluated in a single vial experiment.

2.5.3. Additional in vitro Screening Methods

Screening for Improved Vaccination Properties Using Various in vitro Testing Methods Such as Screening for Improved Adjuvant Activity and Immunostimulatory Properties.

Genetic vaccine vectors and vector modules can be screened for improved vaccination properties using various in vitro testing methods that are known to those of skill in the art. For example, the optimized genetic vaccines can be tested for their effect on induction of proliferation of the particular lymphocyte type of interest, e.g., B cells, T cells, T cell lines, and T cell clones. This type of screening for improved adjuvant activity and immunostimulatory properties can be performed using, for example, human or mouse cells.

Screening for Improved Vaccination Properties Using Various in vitro Testing Methods Such as Screening for Cytokine Production (ELISA and/or Cytoplasmic Cytokine Staining and Flow Cytometry) or for Alterations in the Capacity of the Vectors to Direct $T_H1/T_H2$ Differentiation A library of genetic vaccine vectors, e.g. obtained either from polynucleotide reassembly (optionally in combination with other directed evolution methods described herein), or of vectors harboring genes encoding cytokines, costimulatory molecules etc.) can be screened for cytokine production (e.g., IL-2, IL-4, IL-5, IL-6, IL-10, IL-12, IL-13, IL-15, IFN-, TNF-) by B cells, T cells, monocytes/macrophages, total human PBMC, or (diluted) whole blood. Cytokines can be measured by ELISA or and cytoplasmic cytokine staining and flow cytometry (single-cell analysis). Based on the cytokine production profile, one can screen for alterations in the capacity of the vectors to direct $T_H1/T_H2$ differentiation (as evidenced, for example, by changes in ratios of IL-4/IFN-, IL-4/IL-2, IL-SI IFN-, IL-5/IL-2, IL-13/IFN-, IL-13/IL-2). Induction of APC activation can be detected based on changes in surface expression levels of activation antigens, such as B7-1 (CD80), 137-2 (CD86), MHC class I and II, CD14, CD23, and Fc receptors, and the like.

Analyzing Genetic Vaccine Vectors for Their Capacity to Induce T Cell Activation Through Isolating Spleen Cell of Infected Mice and Studying the Capacity of Cytotoxic T Lymphocytes to lyse Infected, Autologous Target Cells In some embodiments, genetic vaccine vectors are analyzed for their capacity to induce T cell activation. More specifically, spleen cells from injected mice can be isolated and the capacity of cytotoxic T lymphocytes to lyse infected, autologous target cells is studied. The spleen cells are reactivated with the specific antigen in vitro. In addition, T helper cell differentiation is analyzed by measuring proliferation or production of $T_H1$ (IL-2 and IFN- ) and $T_H2$ (IL-4 and IL-5) cytokines by ELISA and directly in CD4$^+$ T cells by cytoplasmic cytokine staining and flow cytometry.

Testing for Ability to Induce Humoral Immune Responses With Assays Using, for Example, Peripheral B Lymphocytes From Immunized Individuals or Other Assays Involving Detection of Antigen Expression by the Target Cells Genetic vaccines and vaccine components can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays involve detection of antigen expression by the target cells. For example, FACS selection provides the most efficient method of identifying cells which produce a desired antigen on the cell surface. Another advantage of FACS selection is that one can sort for different levels of expression; sometimes lower expression may be desired. Another method involves panning using monoclonal antibodies on a plate. This method allows large numbers of cells to be handled in a short time, but the method only selects for highest expression levels. Capture by magnetic beads coated with monoclonal antibodies provides another method of identifying cells which express a particular antigen.

Screening for Ability to Inhibit Proliferation of Tumor Cell Lines in vitro

Genetic vaccines and vaccine components that are directed against cancer cells can be screened for their ability to inhibit proliferation of tumor cell lines in vitro. Such assays are known in the art. An indication of the efficacy of a genetic vaccine against, for example, cancer or an autoimmune disorder, is the degree of skin inflammation when the vector is injected into the skin of a patient or test animal. Strong inflammation is correlated with strong activation of antigen-specific T cells.

Improved activation of tumor-specific T cells may lead to enhanced killing of the tumors. In case of autoantigens, one can add immunomodulators that skew the responses towards $T_H2$. Skin biopsies can be taken, enabling detailed studies of the type of immune response that occurs at the sites of each injection (in mice large numbers of injections/vectors can be analyzed) Other suitable screening methods can involve detection of changes in expression of cytokines, chemokines, accessory molecules, and the like, by cells upon challenge by a library of genetic vaccine vectors.

Expressing the Recombinant Peptides or Polypeptides as Fusions with a Protein Displayed on the Surface of a Replicable Genetic Package Various screening methods for particular applications are described herein. In several instances, screening involves expressing the recombinant peptides or polypeptides encoded by the experimentally generated polynucleotides of the library as fusions with a protein that is displayed on the surface of a replicable genetic package. For example, phage display can be used. See, e.g., Cwirla et al., Proc. Natl. Acad. Sci. USA 87: 6378–6382 (1990); Devlin et al., Science 249: 404–406 (1990), Scott � Ladner et al., U.S. Pat. No. 5,571,698. Other replicable genetic packages include, for example, bacteria, eukaryotic viruses, yeast, and spores.

Purification and in vitro Analysis of Recombinant Nucleic Acids and Polypeptides Once stochastic (e.g. polynucleotide shuffling & interrupted synthesis) and/or non-stochastic polynucleotide reassembly has been performed, the resulting library of experimentally generated polynucleotides can be subjected to purification and preliminary analysis in vitro, in order to identify the most promising candidate recombinant nucleic acids. Advantageously, the assays can be practiced in a high-throughput format. For example, to purify individual experimentally evolved (e.g. by polynucleotide reassembly &/or polynucleotide site-saturation mutagenesis) recombinant antigens, clones can robotically picked into 96-well formats, grown, and, if desired, frozen for storage.

Whole cell lysates (V-antigen), periplasmic extracts, or culture supernatants (toxins) can be assayed directly by ELISA as described below, but high throughput purification is sometimes also needed. Affinity chromatography using immobilized antibodies or incorporation of a small nonimmunogenic affinity tag such as a hexahistidine peptide with immobilized metal affinity chromatography will allow rapid protein purification. High binding-capacity reagents with 96-well filter bottom plates provide a high throughput purification process. The scale of culture and purification will depend on protein yield, but initial studies will require less than 50 micrograms of protein. Antigens showing improved properties can be purified in larger scale by FPLC for re-assay and animal challenge studies.

In some embodiments, the experimentally evolved (e.g. by polynucleotide reassembly &/or polynucleotide site-saturation mutagenesis) antigen-encoding polynucleotides are assayed as genetic vaccines. Genetic vaccine vectors containing the experimentally evolved (e.g. by polynucleotide reassembly &/or polynucleotide site-saturation mutagenesis) antigen sequences can be prepared using robotic colony picking and subsequent robotic plasmid purification. Robotic plasmid purification protocols are available that allow purification of 600–800 plasmids per day. The quantity and purity of the DNA can also be analyzed in 96-well plates, for example. In a presently preferred embodiment, the amount of DNA in each sample is robotically normalized, which can significantly reduce the variation between different batches of vectors.

Once the proteins and/or nucleic acids are picked and purified as desired, they can be subjected to any of a number of in vitro analysis methods. Such screenings include, for example, phage display, flow cytometry, and ELISA assays to identify antigens that are efficiently expressed and have multiple epitopes and a proper folding pattern. In the case of bacterial toxins, the libraries may also be screened for reduced toxicity in mammalian cells.

As one example, to identify recombinant antigens that are cross-reactive, one can use a panel of monoclonal antibodies for screening. A humoral immune response generally targets multiple regions of antigenic proteins. Accordingly, monoclonal antibodies can be raised against various regions of immunogenic proteins (Alving et al. (1995) Immunol. Rev. 145: 5). In addition, there are several examples of monoclonal antibodies that only recognize one strain of a given pathogen, and by definition, different serotypes of pathogens are recognized by different sets of antibodies. For example, a panel of monoclonal antibodies have been raised against VEE envelope proteins, thus providing a means to recognize different subtypes of the virus (Roehrig and Bolin (1997) J Clin. Microbiol. 35: 1887). Such antibodies, combined with phage display and ELISA screening, can be used to enrich recombinant antigens that have epitopes from multiple pathogen strains. Flow cytometry based cell sorting will further allow for the selection of variants that are most efficiently expressed.

Phage display provides a powerful method for selecting proteins of interest from large libraries (Bass et al. (1990) Proteins: Struct. Funct. Genet. 8: 309; Lowman and Wells (1991) Methods: A Companion to Methods Enz. 3(3) ;205–216. Lowman and Wells (1993) J Mol. Biol. 234;564–578). Some recent reviews on the phage display technique include, for example, McGregor (1996) Mol Biotechnol. 6(2):155–62; Dunn (1996) Curr. Opin. Biotechnol. 7(5):547–53; Hill et al. (1996) Mol Microbiol 20(4):685–92; Phage Display of Peptides and Proteins: A Laboratory Manual. B K. Kay, J. Winter, J, McCafferty eds., Academic Press 1996; O'Neil et al. (1995) Curr. Opin. Struct. Biol. 5(4):443–9; Phizicky et al. (1995) Microbiol Rev. 59(1) :94–123; Clackson et al. (1994) Trends Biotechnol. 12(5) :173–84; Felici et al. (1995) Biotechnol. Annu. Rev. 1: 149–83; Burton (1995) Immunotechnology 1(2):87–94.) See, also, Cwirla et al., Proc. Natl. Acad Sci. USA 87: 6378–6382 (1990); Devlin et al., Science 249: 404–406 (1990), Scott & Smith, Science 249: 386–388 (1990); Ladner et al., U.S. Pat. No. 5,571,698. Each phage particle displays a unique variant protein on its surface and packages the gene encoding that particular variant. The experimentally evolved (e.g. by polynucleotide reassembly &/or polynucleotide site-saturation mutagenesis) genes for the antigens are fused to a protein that is expressed on the phage surface, e.g., gene III of phage M 13, and cloned into phagemid vectors. In a presently preferred embodiment, a suppressible stop codon (e.g., an amber stop codon) separates the genes so that in a suppressing strain of E. coli, the antigen-gIIIp fusion is produced and becomes incorporated into phage particles upon infection with M 13 helper phage. The same vector can direct production of the unfused antigen alone in a nonsuppressing E. coli for protein purification.

Most Frequently Used Genetic Packages for Display Libraries

The genetic packages most frequently used for display libraries are bacteriophage, particularly filamentous phage, and especially phage M13, Fd and F1. Most work has involved inserting libraries encoding polypeptides to be displayed into either gIII or gVIII of these phage forming a fusion protein. See, e.g., Dower, WO 91/19818; Devin, WO 91/18989; MacCafferty, WO 92/01047 (gene III); Huse, WO 92/06204; Kang, WO 92/18619 (gene VIII). Such a fusion protein comprises a signal sequence, usually but not necessarily, from the phage coat protein, a polypeptide to be displayed and either the gene III or gene VIII protein or a fragment thereof. Exogenous coding sequences are often inserted at or near the N-terminus of gene III or gene VIII although other insertion sites are possible.

Use of Eukaryotic Viruses to Display Polypeptides

Eukaryotic viruses can be used to display polypeptides in an analogous manner. For example, display of human heregulin fused to gp70of Moloney murine leukemia virus has been reported by Han et al., Proc. Natl. Acad. Sci. USA 92: 9747–9751 (1995). Spores can also be used as replicable genetic packages. In this case, polypeptides are displayed from the outer surface of the spore. For example, spores from B. subtilis have been reported to be suitable. Sequences of coat proteins of these spores are provided by Donovan et al., J. Mol. Biol. 196, 1–10 (1987). Cells can also be used as replicable genetic packages. Polypeptides to be displayed are inserted into a gene encoding a cell protein that is expressed on the cells surface. Bacterial cells including Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis, and especially Escherichia coli are preferred. Details of outer surface proteins are discussed by Ladner et al., U.S. Pat. No. 5,571,698 and references cited therein. For example, the lamB, protein of E. coli is suitable.

Establishment of a Physical Association Between Polypeptides and Their Genetic Material A basic concept of display methods that use phage or other replicable genetic package is the establishment of a physical association between DNA encoding a polypeptide to be screened and the polypeptide. This physical association is provided by the replicable genetic package, which displays a polypeptide as part of a capsid enclosing the genome of the phage or other package, wherein the polypeptide is encoded by the genome. The establishment of a physical association between polypeptides and their genetic material allows simultaneous mass screening of very large numbers of phage bearing different polypeptides. Phage displaying a polypeptide with affinity to a target, e.g., a receptor, bind to the target and these phage are enriched by affinity screening to the target. The identity of polypeptides displayed from these phage can be determined from their respective genomes.

Using these methods a polypeptide identified as having a binding affinity for a desired target can then be synthesized in bulk by conventional means, or the polynucleotide that encodes the peptide or polypeptide can be used as part of a genetic vaccine.

Variants with specific binding properties, in this case binding to family-specific antibodies, are easily enriched by panning with immobilized antibodies. Antibodies specific for a single family are used in each round of panning to rapidly select variants that have multiple epitopes from the antigen families. For example, A-family specific antibodies can be used to select those experimentally evolved (e.g. by polynucleotide reassembly &/or polynucleotide site-saturation mutagenesis) clones that display A-specific epitopes in the first round of panning. A second round of panning with B-specific antibodies will select from the "A" clones those that display both A- and B-specific epitopes. A third round of panning with C-specific antibodies will select for variants with A, B, and C epitopes. A continual selection exists during this process for clones that express well in *E. coli* and that are stable throughout the selection. Improvements in factors such as transcription, translation, secretion, folding and stability are often observed and will enhance the utility of selected clones for use in vaccine production.

Phage ELISA methods can be used to rapidly characterize individual variants. These assays provide a rapid method for quantitation of variants without requiring purification of each protein. Individual clones are arrayed into 96-well plates, gown, and frozen for storage. Cells in duplicate plates are infected with helper phage, grown overnight and pelleted by centrifugation. The supernatants containing phage displaying particular variants are incubated with immobilized antibodies and bound clones are detected by anti-M13 antibody conjugates. Titration series of phage particles, immobilized antigen, and/or soluble antigen competition binding studies are all highly effective means to quantitate protein binding. Variant antigens displaying multiple epitopes will be further studied in appropriate animal challenge models.

Several groups have reported an in vitro ribosome display system for the screening and selection of mutant proteins with desired properties from large libraries. This technique can be used similarly to phage display to select or enrich for variant antigens with improved properties such as broad cross reactivity to antibodies and improved folding (see, e.g., Hanes et al. (1997) Proc. Nat'l. A cad. Sci. USA 94(10):493 7–42; Mattheakis et al. (1994) Proc. Nat 7. Acad. Sci. USA 91(19):9022–6; He et al. (1997) Nucl. Acids Res. (24):5132–4; Nemoto et al. (1997) FEBS Lett. 414(2) :405–8).

Other display methods exist to screen antigens for improved properties such as increased expression levels, broad cross reactivity, enhanced folding and stability. These include, but are not limited to display of proteins on intact *E. coli* or other cells (e.g., Francisco et al. (1993) Proc. Nat'l. Acad. Sci. USA 90: 1044–10448; Lu et al. (1995) BiolTechnology 13: 366–372). Fusions of experimentally evolved (e.g. by polynucleotide reassembly &/or polynucleotide site-saturation mutagenesis) antigens to DNA-binding proteins can link the antigen protein to its gene in an expression vector (Schatz et al. (1996) Methods Enzymol. 267: 171–91; Gates et al. (1996) J Mol. Biol. 255: 373–86.) The various display methods and ELISA assays can be used to screen for experimentally evolved (e.g. by polynucleotide reassembly &/or polynucleotide site-saturation mutagenesis) antigens with improved properties such as presentation of multiple epitopes, improved immunogenicity, increased expression levels, increased folding rates and efficiency, increased stability to factors such as temperature, buffers, solvents, improved purification properties, etc. Selection of experimentally evolved (e.g. by polynucleotide reassembly &/or polynucleotide site-saturation mutagenesis) antigens with improved expression, folding, stability and purification profile under a variety of chromatographic conditions can be very important improvements to incorporate for the vaccine manufacturing process. To identify recombinant antigenic polypeptides that exhibit improved expression in a host cell, flow cytometry is a useful technique.

Flow cytometry provides a method to efficiently analyze the functional properties of millions of individual cells. One can analyze the expression levels of several genes simultaneously, and flow cytometry-based cell sorting allows for the selection of cells that display properly expressed antigen variants on the cell surface or in the cytoplasm. Very large numbers ($>10^7$) of cells can be evaluated in a single vial experiment, and the pool of the best individual sequences can be recovered from the sorted cells. These methods are particularly useful in the case of, for example, Hantaan virus glycoproteins, which are generally very poorly expressed in mammalian cells. This approach provides a general solution to improve expression levels of pathogen antigens in mammalian cells, a phenomenon that is critical for the function of genetic vaccines.

To use flow cytometry to analyze polypeptides that are not expressed on the cell surface, one can engineer the experimentally generated polynucleotides in the library such that the polynucleotide is expressed as a fusion protein that has a region of amino acids which is targeted to the cell membrane. For example, the region can encode a hydrophobic stretch of C-terminal amino acids which signals the attachment of a phosphoinositol-glycan (PIG) terminus on the expressed protein and directs the protein to be expressed on the surface of the transfected cell (Whitehorn et al. (1995) Biotechnology (N Y) 13:1215–9). With an antigen that is naturally a soluble protein, this method will likely not affect the three dimensional folding of the protein in this engineered fusion with a new C-terminus. With an antigen that is naturally a transmembrane protein (e.g., a surface membrane protein on pathogenic viruses, bacteria, protozoa or tumor cells) there are at least two possibilities.

First, the extracellular domain can be engineered to be in fusion with the C-terminal sequence for signaling PIG-linkage. Second, the protein can be expressed in toto relying on the signaling of the host cell to direct it efficiently to the cell surface. In a minority of cases, the antigen for expression will have an endogenous PIG terminal linkage (e.g., some antigens of pathogenic protozoa).

Those cells expressing the antigen can be identified with a fluorescent monoclonal antibody specific for the C-terminal sequence on PIG-linked forms of the surface antigen. FACS analysis allows quantitative assessment of the level of expression of the correct form of the antigen on the cell population. Cells expressing the maximal level of antigen are sorted and standard molecular biology methods are used to recover the plasmid DNA vaccine vector that conferred this reactivity. An alternative procedure that allows purification of all those cells expressing the antigen (and that may be useful prior to loading onto a cell sorter since antigen expressing cells may be a very small minority population), is to rosette or pan-purify the cells expressing surface antigen. Rosettes can be formed between antigen expressing cells and erythrocytes bearing covalently coupled antibody to the relevant antigen. These are readily purified by unit gravity sedimentation. Panning of the cell population over petri dishes bearing immobilized monoclonal antibody specific for the relevant antigen can also be used to remove unwanted cells.

In the high throughput assays of the invention, it is possible to screen up to several thousand different experimentally evolved (e.g. by polynucleotide reassembly &/or polynucleotide site-saturation mutagenesis) variants in a single day. For example, each well of a microtiter plate can be used to run a separate assay, or, if concentration or incubation time effects are to be observed, every 5–10 wells can test a single variant. Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Palo Alto, Calif.).

In one aspect, library members, e.g., cells, viral plaques, or the like, are separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes, optionally containing glass balls in the wells to prevent aggregation. The Q-bot does not pick an entire colony but rather inserts a pin through the center of the colony and exits with a small sampling of cells (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells dispersal of cells, or the like, similar to the blades of a fermentor. Clones from cultures of interest can be cloned by limiting dilution. Plaques or cells constituting libraries can also be screened directly for production of proteins, either by detecting hybridization, protein activity, protein binding to antibodies, or the like.

The ability to detect a subtle increase in the performance of a experimentally evolved (e.g. by polynucleotide reassembly &/or polynucleotide site-saturation mutagenesis) library member over that of a parent strain relies on the sensitivity of the assay. The chance of finding the organisms having an improvement in ability to induce an immune response is increased by the number of individual mutants that can be screened by the assay. To increase the chances of identifying a pool of sufficient size, a prescreen that increases the number of mutants processed by 10-fold can be used. The goal of the prescreen will be to quickly identify mutants having equal or better product titers than the parent strain(s) and to move only these mutants forward to liquid cell culture for subsequent analysis.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules encoded by codon-altered nucleic acids. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols the various high throughput. Thus, for example, Zymark Corp. provides technical bulletins describing screening systems for detecting the modulation of gene transcription, ligand binding, and the like. Microfluidic approaches to reagent manipulation have also been developed, e.g., by Caliper Technologies (Palo Alto, Calif.).

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. As noted above, in some applications, the signals resulting from assays are florescent, making optical detection approaches appropriate in these instances. A variety of commercially available peripheral equipment and software is available for digitizing, storing and analyzing a digitized video or digitized optical image, e.g., using PC (Intel x86 or Pentium chip-compatible DOS, OS2 WINDOWS, WINDOWS NT or VIMOWS95 based machines), MACINTOSH, or LTNIX based (e.g., SLJN work station) computers.

One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for analysis in the present invention typically include a digital computer with high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay component. The image scanner interfaces with the image analysis software to provide a measurement of optical intensity. Typically, the intensity measurement is interpreted by the data interpretation software to show whether the optimized recombinant antigenic polypeptide products are produced.

2.5.4. Antigen Library Immunization

In a presently preferred embodiment, antigen library immunization (ALI) is used to identify optimized recombinant antigens that have improved immunogenicity. ALI involves introduction of the library of recombinant antigen-encoding nucleic acids, or the recombinant antigens encoded by the experimentally evolved (e.g. by polynucleotide reassembly &/or polynucleotide site-saturation mutagenesis) nucleic acids, into a test animal. The animals are then subjected to in vivo challenge using live pathogens. Neutralizing antibodies and cross-protective immune responses are studied after immunization with the entire libraries, pools and/or individual antigen variants.

Methods of immunizing test animals are well known to those of skill in the art. In presently preferred embodiments, test animals are immunized twice or three times at two week intervals. One week after the last immunization, the animals are challenged with live pathogens (or mixtures of pathogens), and the survival and symptoms of the animals is followed. Immunizations using test animal challenge are described in, for example, Roggenkamp et al. (1997) Infect. Immun. 65: 446; Woody et al. (1997) Vaccine 2: 133; Agren et al. (1997) J Immunol. 158: 3936; Konishi et al. (1992) Virology 190: 454; Kinney et al. (1988) J Virol. 62: 4697; Iacono-Connors et al. (1996) Virus Res. 43: 125; Kochel et al. (1997) Vaccine 15: 547; and Chu et al. (1995) J Virol. 69: 6417.

The immunizations can be performed by injecting either the experimentally generated polynucleotides themselves, i.e., as a genetic vaccine, or by immunizing the animals with polypeptides encoded by the experimentally generated polynucleotides. Bacterial antigens are typically screened primarily as recombinant proteins, whereas viral antigens are preferably analyzed using genetic vaccinations.

To dramatically reduce the number of experiments required to identify individual antigens having improved immunogenic properties, one can use pooling and deconvolution, as diagrammed herein. Pools of recombinant nucleic acids, or polypeptides encoded by the recombinant nucleic acids, are used to immunize test animals. Those pools that result in protection against pathogen challenge are then subdivided and subjected to additional analysis. The high throughput in vitro approaches described above can be used to identify the best candidate sequences for the in vivo studies.

The challenge models that can be used to screen for protective antigens include pathogen and toxin models, such as Yersinia bacteria, bacterial toxins (such as Staphylococcal and Streptococcal enterotoxins, *E. coli/V. cholerae* enterotoxins), Venezuelan equine encephalitis virus (VEE), Flaviviruses (Japanese encephalitis virus, Tick-borne encephalitis virus, Dengue virus), Hantaan virus, Herpes simplex, influenza virus (e.g., Influenza A virus), Vesicular Steatites Virus, *Pseudomonas aeruginosa, Salmonella typhimurium, Escherichia coli, Klebsiella pneumoniae, Toxoplasma gondii, Plasmodium yoeliii*, Herpes simplex, influenza virus (e.g., Influenza A virus), and Vesicular Steatites Virus. However, the test animals can also be challenged with tumor cells to enable screening of antigens that efficiently protect against malignancies. Individual experimentally evolved (e.g. by polynucleotide reassembly &/or polynucleotide site-saturation mutagenesis) antigens or pools of antigens are introduced into the animals intradermally, intramuscularly, intravenously, intratracheally, anally, vaginally, orally, or intraperitoneally and antigens that can prevent the disease are chosen, when desired, for further rounds of reassembly (optionally in combination with other directed evolution methods described herein) and selection. Eventually, the most potent antigens, based on in vivo data in test animals and comparative in vitro studies in animals and man, are chosen for human trials, and their capacity to prevent and treat human diseases is investigated.

In some embodiments, antigen library immunization and pooling of individual clones is used to immunize against a pathogen strain that was not included in the sequences that were used to generate the library. The level of crossprotection provided by different strains of a given pathogen can significantly. However, homologous titer is always higher than heterologous titer. Pooling and deconvolution is especially efficient in models where minimal protection is provided by the wild-type antigens used as starting material for reassembly (optionally in combination with other directed evolution methods described herein). This approach can be taken, for example, when evolving the V-antigen of Yersinae or Hantaan virus glycoproteins.

In some embodiments, the desired screening involves analysis of the immune response based on immunological assays known to those skilled in the art. Typically, the test animals are first immunized and blood or tissue samples are collected for example one to two weeks after the last immunization. These studies enable one to one can measure immune parameters that correlate to protective immunity, such as induction of specific antibodies (particularly IgG) and induction of specific T lymphocyte responses, in addition to determining whether an antigen or pools of antigens provides protective immunity.

Spleen cells or peripheral blood mononuclear cells can be isolated from immunized test animals and measured for the presence of antigen-specific T cells and induction of cytokine synthesis. ELISA, ELISPOT and cytoplasmic cytokine staining, combined with flow cytometry, can provide such information on a single-cell level.

Common immunological tests that can be used to identify the efficacy of immunization include antibody measurements, neutralization assays and analysis of activation levels or frequencies of antigen presenting cells or lymphocytes that are specific for the antigen or pathogen. The test animals that can be used in such studies include, but are not limited to, mice, rats, guinea pigs, hamsters, rabbits, cats, dogs, pigs and monkeys.

Monkey is a particularly useful test animal because the MHC molecules of monkeys and humans are very similar. Virus neutralization assays are useful for detection of antibodies that not only specifically bind to the pathogen, but also neutralize the function of the virus. These assays are typically based on detection of antibodies in the sera of immunized animal and analysis of these antibodies for their capacity to inhibit viral growth in tissue culture cells. Such assays are known to those skilled in the art. One example of a virus neutralization assay is described by Dolin R (J. Infect. Dis. 1995, 172:1175–83). Virus neutralization assays provide means to screen for antigens that also provide protective immunity.

In some embodiments, experimentally evolved (e.g. by polynucleotide reassembly &/or polynucleotide site-saturation mutagenesis) antigens are screened for their capacity to induce T cell activation in vivo. More specifically, peripheral blood mononuclear cells or spleen cells from injected mice can be isolated and the capacity of cytotoxic T lymphocytes to lyse infected, autologous target cells is studied. The spleen cells can be reactivated with the specific antigen in vitro. In addition, T helper cell activation and differentiation is analyzed by measuring cell proliferation or production of $T_H$ (IL-2 and IFN- ) and $T_H2$ (IL-4 and IL-5) cytokines by ELISA and directly in $CD4^+$ T cells by cytoplasmic cytokine staining and flow cytometry. Based on the cytokine production profile, one can also screen for alterations in the capacity of the antigens to direct $T_H1/T_H2$ differentiation (as evidenced, for example, by changes in ratios of IL-4/IFN-, IL-4/IL-2, IL-5/IFN-, IL-5/IL-2, IL-13/IFN-, IL-13/IL-2). The analysis of the T cell activation induced by the antigen variants is a very useful screening method, because potent activation of specific T cells in vivo correlates to induction of protective immunity.

The frequency of antigen-specific CD8+ T cells in vivo can also be directly analyzed using tetramers of MHC class I molecules expressing specific peptides derived from the corresponding pathogen antigens (Ogg and McMichael, Curr. Opin. Immunol. 1998, 10:393–6; Altman et al., Science 1996, 274:94–6). The binding of the tetramers can be detected using flow cytometry, and will provide information about the efficacy of the experimentally evolved (e.g. by polynucleotide reassembly &/or polynucleotide site-saturation mutagenesis) antigens to induce activation of specific T cells. For example, flow cytometry and tetramer stainings provide an efficient method of identifying T cells that are specific to a given antigen or peptide. Another method involves panning using plates coated with tetramers with the specific peptides. This method allows large numbers of cells to be handled in a short time, but the method only selects for highest expression levels. The higher the frequency of antigen-specific T cells in vivo is, the more efficient the immunization has been, enabling identification of the antigen variants that have the most potent capacity to induce protective immune responses. These studies are particularly useful when conducted in monkeys, or other primates, because the MHC class I molecules of humans mimic those of other primates more closely than those of mice.

Measurement of the activation of antigen presenting cells (APC) in response to immunization by antigen variants is another useful screening method. Induction of APC activation can be detected based on changes in surface expression levels of activation antigens, such as 137–1 (CD80). 137-2 (CD86), MHC class I and 11, CD14, CD23, and Fc receptors, and the like.

Experimentally evolved (e.g. by polynucleotide reassembly &/or polynucleotide site-saturation mutagenesis) cancer antigens that induce cytotoxic T cells that have the capacity to kill cancer cells can be identified by measuring the capacity of T cells derived from immunized animals to kill cancer cells in vitro. Typically the cancer cells are first labeled with radioactive isotopes and the release of radioactivity is an indication of tumor cell killing after incubation in the presence of T cells from immunized animals. Such cytotoxicity assays are known in the art.

An indication of the efficacy of an antigen to activate T cells specific for, for example, cancer antigens, allergens or autoantigens, is also the degree of skin inflammation when the antigen is injected into the skin of a patient or test animal. Strong inflammation is correlated with strong activation of antigen-specific T cells. Improved activation of tumor-specific T cells may lead to enhanced killing of the tumors. In case of autoantigens, one can add immunomodulators that skew the responses towards $T_H2$, whereas in the case of allergens a $T_H1$ response is desired. Skin biopsies can be taken, enabling detailed studies of the type of immune response that occurs at the sites of each injection (in mice and monkeys large numbers of injections/antigens can be analyzed). Such studies include detection of changes in expression of cytokines, chemokines, accessory molecules, and the like, by cells upon injection of the antigen into the skin.

To screen for antigens that have optimal capacity to activate antigen-specific T cells, peripheral blood mononuclear cells from previously infected or immunized humans individuals can be used. This is a particularly useful method, because the MHC molecules that will present the antigenic peptides are human MHC molecules. Peripheral blood mononuclear cells or purified professional antigen-presenting cells (APCs) can be isolated from previously vaccinated or infected individuals or from patients with acute infection with the pathogen of interest. Because these individuals have increased frequencies of pathogen-specific T cells in circulation, antigens expressed in PBMCs or purified APCs of these individuals will induce proliferation and cytokine production by antigen-specific CD4+ and CD8+ T cells. Thus, antigens that simultaneously harbor epitopes from several antigens can be recognized by their capacity to stimulate T cells from various patients infected or immunized with different pathogen antigens, cancer antigens, autoantigens or allergens. One buffy coat derived from a blood donor contains lymphocytes from 0.5 liters of blood, and up to $10^4$ PBMC can be obtained, enabling very large screening experiments using T cells from one donor.

When healthy vaccinated individuals (lab volunteers) are studied, one can make EBV-transformed B cell lines from these individuals. These cell lines can be used as antigen presenting cells in subsequent experiments using blood from the same donor; this reduces interassay and donor-to-donor variation. In addition, one can make antigen-specific T cell clones, after which antigen variants are introduced to EBV transformed B cells. The efficiency with which the transformed B cells induce proliferation of the specific T cell clones is then studied. When working with specific T cell clones, the proliferation and cytokine synthesis responses are significantly higher than when using total PBMCs, because the frequency of antigen-specific T cells among PBMC is very low.

CTL epitopes can be presented by most cells types since the class I major histocompatibility complex (MHC) surface glycoproteins are widely expressed. Therefore, transfection of cells in culture by libraries of experimentally evolved (e.g. by polynucleotide reassembly &/or polynucleotide site-saturation mutagenesis) antigen sequences in appropriate expression vectors can lead to class I epitope presentation. If specific CTLs directed to a given epitope have been isolated from an individual, then the co-culture of the transfected presenting cells and the CTLs can lead to release by the CTLs of cytokines, such as IL-2, IFN-, or TNF, if the epitope is presented. Higher amounts of released TNF will correspond to more efficient processing and presentation of the class I epitope from the experimentally evolved (e.g. by polynucleotide reassembly &/or polynucleotide site-saturation mutagenesis), evolved sequence. Experimentally evolved (e.g. by polynucleotide reassembly &/or polynucleotide site-saturation mutagenesis) antigens that induce cytotoxic T cells that have the capacity to kill infected cells can also be identified by measuring the capacity of T cells derived from immunized animals to kill infected cells in vitro. Typically the target cells are first labeled with radioactive isotopes and the release of radioactivity is an indication of target cell killing after incubation in the presence of T cells from immunized animals. Such cytotoxicity assays are known in the art.

A second method for identifying optimized CTL epitopes does not require the isolation of CTLs reacting with the epitope. In this approach, cells expressing class I MHC surface glycoproteins are transfected with the library of evolved sequences as above. After suitable incubation to allow for processing and presentation, a detergent soluble extract is prepared from each cell culture and after a partial purification of the MHC-epitope complex (perhaps optional) the products are submitted to mass spectrometry (Henderson et al. (1993) Proc. Nat'l. Acad. Sci. USA 90: 10275–10279). Since the sequence is known of the epitope whose presentation to be increased, one can calibrate the mass spectrogram to identify this peptide. In addition, a cellular protein can be used for internal calibration to obtain a quantitative result; the cellular protein used for internal calibration could be the MHC molecule itself. Thus one can measure the amount of peptide epitope bound as a proportion of the N4HC molecules.

2.5.5. Screening for Optimal Induction of Protective Immunity

Vectors That Can Provide Efficient, Protective Immunity are Selected Using Lethal Infection Models to Choose Vectors That Can Prevent the Disease for Further Rounds of Reassembly (Optionally in Combination With Other Directed Evolution Methods Described herein) and Selection To select genetic vaccine vectors that provide efficient protective immunity, one can screen the vector libraries in a test mammal using lethal infection models, such as *Pseudomonas aeruginosa, Salmonella typhimurium, Escherichia coli, Klebsiella pneumoniae, Toxoplasma gondii, Plasmodium yoeliii*, Herpes simplex, influenza virus (e.g., Influenza A virus), and Vesicular Steatites Virus. Pools of genetic vaccine vectors or individual vectors are introduced into the animals intradermally, intramuscularly, intravenously, intratracheally, anally, vaginally, orally, or intraperitoneally and vectors that can prevent the disease are chosen for further rounds of reassembly (optionally in combination with other directed evolution methods described herein) and selection.

Examples: Anti-IL-4 mAbs or Recombinant IL-12; Recombinant IL-12 (Advantage of Latter Model is That Infection Occurs Through Lung, Common Route of Human Pathogen Invasion)

As an example, optimal vectors can be screened in mice infected with Leishmania major parasites. When injected into footpads of BALB/c mice, these parasites cause a progressive infection later resulting in a disseminated disease with fatal outcome, which can be prevented by anti-IL-4 mAbs or recombinant IL-12 (Chatelain et al. (1992) J. Immunol. 148: 1182–1187). Pools of plasmids can be injected intravenously, intraperitoneally or into footpads of these mice, and pools that can prevent the disease are chosen for further analysis and screened for vectors that can cure existing infections. The size of the footpad swelling can be followed visually providing simple yet precise monitoring of the disease progression. Mice can be infected intratracheally with Klebsiella pneumoniae resulting in lethal pneumonia, which can be prevented by recombinant IL-12 (Greenberger et al. (1996) J Immunol. 157: 3006–3012). The advantage of this model is that the infection occurs through the lung, which is a common route of human pathogen invasion. The vectors can be given to the lung together with the pathogen or they can be administered after symptoms are evident in order to screen for vectors that can cure established infections.

Example: Influenza-provides a way to Screen for Vectors That Provide Protection at Very Low Quantities of DNA and/or High Virus Concentrations, and it Also Allows one to Analyze the Levels of Antigen Specific Abs and CTLs Induced in vivo In another example, the genetic vaccines are a mouse vaccination model for Influenza A virus. Influenza was one of the first models in which the efficacy of genetic vaccines was demonstrated (Ulmer et al. (1993) Science 259: 1745–1749). Several Influenza strains are lethal in mice providing an easy means to screen for efficacy of genetic vaccines.

For example, Influenza virus strain A/PR/8/34, which is available through the American Type Culture Collection (ATCC VR-95), causes lethal infection, but 100% survival can be obtained when the mice are immunized with and influenza hemagglutinin (HA) genetic vaccine (Deck et al. (1997) Vaccine 15: 71–78). This model provides a way to screen for vectors that provide protection at very low quantities of DNA and/or high virus concentrations, and it also allows one to analyze the levels of antigen specific Abs and CTLs induced in vivo.

Example: Mycobacterium Tuberculosis (Partial Protection, Requires Major Improvements)

The genetic vaccine vectors can also be analyzed for their capacity to provide protection against infections by Mycobacterium tuberculosis. This is an example of a situation where genetic vaccines have provided partial protection, and where major improvements are required.

Identification of Candidate Vectors Followed by More Testing

Once a number of candidate vectors has been identified, these vectors can be subjected to more detailed analysis in additional models. Testing in other infectious disease models (such as HSV, Mycoplasma pulmonis, RSV and/or rotavirus) will allow identification of vectors that are optimal in each infectious disease.

Optimal Plasmids From the First Round of Screening are Used as the Starting Material for the Next Round, the Successful Vectors are Sequenced and the Corresponding Human Genes are Cloned Into Genetic Vaccine Vectors Which are Characterized in vitro for Their Capacity to Induce Differentiation of a Desired Trait In each case, the optimal plasmids from the first round of screening can be used as the starting material for the next round of reassembly (optionally in combination with other directed evolution methods described herein), assembly and selection. Vectors that are successful in animal models are sequenced and the corresponding human genes are cloned into genetic vaccine vectors. These vectors are then characterized in vitro for their capacity to induce differentiation of $T_H1/T_H2$ cells, activation of $T_H$ cells, cytotoxic T lymphocytes and monocytes/macrophages, or other desired trait. Eventually, the most potent vectors, based on in vivo data in mice and comparative in vitro studies in mice and man, are chosen for human trials, and their capacity to counteract various human infectious diseases is investigated.

Methods for Measuring Immune Parameters That Correlate to Protective Immunity

In addition to determining whether a vector pool provides protective immunity, one can measure immune parameters that correlate to protective immunity, such as induction of specific antibodies (particularly IgG) and induction of specific CTL responses. Spleen cells can be isolated from vaccinated mice and measured for the presence of antigen-specific T cells and induction of $T_H1$ cytokine synthesis profiles. ELISA and cytoplasmic cytokine staining, combined with flow cytometry, can provide such information on a single-cell level.

2.5.6. Screening of Genetic Vaccine Vectors That Activate Human Antigen-specific Lymphocyte Responses Isolation of PBMCs or APCs to Screen for Vectors With Optimal Immunostimulatory Properties for the Human Immune System To screen for vectors with optimal immunostimulatory properties for the human immune system, peripheral blood mononuclear cells (PBMCs) or purified professional antigen-presenting cells (APCs) can be isolated from previously vaccinated or infected individuals or from patients with acute infection with the pathogen of interest.

Genetic Vaccine Vectors Encoding the Antigen for Which the Individuals Have Specific T Cells can be Transfected Into PBMC and Induction of T Cell Proliferation and Cytokine Synthesis can be Measured; Also Possible to Screen for Spontaneous Entry of Genetic Vaccine Vector Into APCs Because these individuals have increased frequencies of pathogen-specific T cells in circulation, antigens expressed in PBMCs or purified APCs of these individuals will induce proliferation and cytokine production by antigen-specific CD4+ and CD8+ T cells. Thus, genetic vaccine vectors encoding the antigen for which the individuals have specific T cells can be transfected into PBMC of the individuals, after which induction of T cell proliferation and cytokine synthesis can be measured. Alternatively, one can screen for spontaneous entry of the genetic vaccine vector into A-PCs, thus providing a means by which to screen simultaneously for improved transfection efficiency, improved expression of antigen and improved induction of activation of specific T cells. Vectors with the most potent immunostimulatory properties can be screened based on their capacity to induce B cell proliferation and immunoglobulin synthesis. One buffy coat derived from a blood donor contains PBMC lymphocytes from 0.5 liters of blood, and up to $10^4$ PBMC can be obtained, enabling very large screening experiments using T cells from one donor.

Making EBV-transformed B Cell Lines From Healthy Vaccinated Individuals for Subsequent Experiments When healthy vaccinated individuals (lab volunteers) are studied, one can make EBV-transformed B cell lines from these individuals. These cell lines can be used as antigen presenting cells in subsequent experiments using blood from the same donor; this reduces interassay and donor-to-donor variation). In addition, one can make antigen-specific T cell clones, after which genetic vaccines are transfected into EBV transformed B cells.

Efficiency With Which the Transformed B Cells Induce Proliferation of the Specific T Cell Clones The efficiency with which the transformed B cells induce proliferation of the specific T cell clones is then studied. When working with specific T cell clones, the proliferation and cytokine synthesis responses are significantly higher than when using total PBMCs, because the frequency of antigen-specific T cells among PBMC is very low.

Transfection of Cells in Culture by Libraries of Experimentally Evolved (e.g. by Polynucleotide Reassembly &/or Polynucleotide Site-saturation Mutagenesis) DNA Sequences in Appropriate Expression Vectors can Lead to Class I Epitope Presentation CTL epitopes can be presented by most cells types since the class I major histocompatibility complex (MHC) surface glycoproteins are widely expressed. Therefore, transfection of cells in culture by libraries of experimentally evolved (e.g. by polynucleotide reassembly &/or polynucleotide site-saturation mutagenesis) DNA sequences in appropriate expression vectors can lead to class I epitope presentation. If specific CTLs directed to a given epitope have been isolated from an individual, then the co-culture of the transfected presenting cells and the CTLs can lead to release by the CTLs of cytokines, such as IL-2, IFN-, or TNF, if the epitope is presented. Higher amounts of released TNF . will correspond to more efficient processing and presentation of the class I epitope from the experimentally evolved (e.g. by polynucleotide reassembly &/or polynucleotide site-saturation mutagenesis), evolved sequence.

Transfecting Cells Expressing Class I MHC Surface Glycoproteins With Library of Evolved Sequences, Preparing a Detergent Soluble Extract, Performing a Partial Purification of the MHC-epitope Complex, and Then Submitting the Products to Mass Spectrometry A second method for identifying optimized CTL epitopes does not require the isolation of CTLs reacting with the epitope. In this approach, cells expressing class I MHC surface glycoproteins are transfected with the library of evolved sequences as above. After suitable incubation to allow for processing and presentation, a detergent soluble extract is prepared from each cell culture and after a partial purification of the MHC-epitope complex (perhaps optional) the products are submitted to mass spectrometry (Henderson et al. (1993) Proc. Nat'l. Acad. Sci. USA 90: 10275–10279). Since the sequence is known of the epitope whose presentation to be increased, one can calibrate the mass spectrogram to identify this peptide. In addition, a cellular protein can be used for internal calibration to obtain a quantitative result; the cellular protein used for internal calibration could be the MHC molecule itself. Thus one can measure the amount of peptide epitope bound as a proportion of the MHC molecules.

2.5.7. SCID-human Skin Model for Vaccination Studies

Use of Mouse Models in Vaccine Studies Limited in That the MHC Molecules in Mice and Man are Substantially Different, Meaning That Proteins and Peptides That Efficiently Induce Protective Immune Responses in Mice do not Necessarily Function in Humans Successful genetic vaccinations require transfection of the target cells after injection of the vector, expression of the desired antigen, processing the antigen in antigen presenting cells, presentation of the antigenic peptides in the context of MHC molecules, recognition of the peptide/MHC complex by T cell receptors, interactions of T cells with B cells and professional APCs and induction of specific T cell and B cell responses. All these events could be differentially regulated in mouse and man. A limitation of mouse models in vaccine studies is the fact that the MHC molecules of mice and man are substantially different. Therefore, proteins and peptides that effectively induce protective immune responses in mice do not necessarily function in humans.

Mouse Models can be Used to Study Human Tissues in Mice in vivo for Studies of Transfection Efficiency, Transfer Sequences, and Gene Expression Levels To overcome these limitations mouse models can be used to study human tissues in mice in vivo. Live pieces of human skin are xenotransplant onto the back of immunodeficient mice, such as SCID mice, allowing screening of the vector libraries for optimal properties in human cells in vivo. Recursive selection of episomal vectors provides strong selection pressure for vectors that remain episomal, yet provide high level of gene expression. These mice provide an excellent model for studies on transfection efficiency, transfer sequences and gene expression levels. In addition, antigen presenting cells (APCs) derived from these mice can also be used to assess the level of antigens delivered to professional APCs, and to study the capacity of these cells to present antigens and induce activation of antigen-specific CD4+ and CD8+ T cells in vitro. Significantly, although SCID mice have severely deficient T and B cell components, antigen presenting cells (dendritic cells and monocytes) are relatively normal in these mice.

Rendering Immunocompetent Mice Immunodeficient in Order to aid Transplantation of Human Tissue, Enabling Vaccine Studies in Human Skin Xenotransplanted Into Mice with Genetically Normal Immune Systems as Well, due to the Transient Nature of the in vivo Immunosuppression In one embodiment of this model system, immunocompetent mice are rendered immunodeficient in order to enable transplantation of human tissue. For example, blocking of CD28 and CD40 pathways promotes long-term survival of allogeneic skin grafts in mice (Larsen et al. (1996) Nature 381: 434). Because the in vivo immunosuppression is transient, this model also enables vaccine studies in human skin xenotransplanted into mice with genetically normal immune systems. Several methods of blocking CD28-137 interactions and CD40-CD40 ligand interactions are known to those of skill in the art, including, for example, administration of neutralizing anti-B7-1 and 137-2 antibodies, soluble CTLA-4, a soluble form of the extracellular portion of CTLA-4, a fusion protein that includes CTLA-4 and an Fc portion of an IgG molecule, and neutralizing anti-CD40 or anti-CD40 ligand antibodies. Additional methods by which one can improve transient immunosuppression include administration of one or more of the following reagents: cyclosporin A, anti-IL-2 receptor—chain Ab, soluble IL-2 receptor, IL-10, and combinations thereof.

A model in which SCID-mice transplanted with human skin are injected with HLA-matched PBMC can be used to analyze vectors that provide long lasting expression in vivo. In this model, the vectors are injected, or topically applied, into the human skin.

If the HLA-matched PBMC Injected Into Mice Contains Lymphocytes Specific for the Vector the Transfected Cells Will be Recognized, and Eventually Destroyed, by These Vector-specific Lymphocytes, Providing the Possibility to Screen for Vectors That Efficiently Escape Destruction Thereafter, HLA-matched PBMC are injected into these mice. If the PBMC contains lymphocytes specific for the vector, the transfected cells will be recognized, and eventually destroyed, by these vector-specific lymphocytes. Therefore, this model provides possibilities to screen for vectors that efficiently escape destruction by the immune cells. It has been shown that human PBLs injected into mice with human skin transplants reject the organ, indicating that the CTLs reach the skin in this model. Obtaining HLA-matching skin and blood is possible (e.g. blood sample and skin graft from a patient undergoing skin removal due to malignancy, or blood and foreskin from the same infant).

SCIDhu Mouse Model: Additionally, Transplanting Human Skin Allows Studies on the Efficacy of Genetic Vaccine Vectors Following Injection to the Skin An additional model that is suitable for screening as described herein is the modified SCIDhu mouse model, in which pieces of human fetal thymus, liver and bone marrow are transplanted into SCID mice providing functional human immune system in mice (Roncarolo et al. (1996) Semin. Immunol. 8: 207). Functional human B and T cells, and APCs can be observed in these mice. When additionally human skin is transplanted, it is likely to allow studies on the efficacy of genetic vaccine vectors following injection into the skin. Cotransplantation of skin is likely to improve the model because it will provide an additional source of professional APCs.

2.5.8. Mouse Model for Studying the Efficiancy of Genetic Vaccines in Transfecting Human Muscle Cells and Inducing Human Immune Responses in vivo There is a Lack of Suitable in vivo Models for Studies of the Efficiency of Genetic Vaccines and the Vast Majority of Studies are Performed on the Mouse Model, in Which it is Sometimes Difficult to Predict Whether the Results Obtained Reliably Predict Similar Vaccinations in Humans Because of the Complexity of Events Occurring After Genetic Vaccination A lack of suitable in vivo models has hampered studies of the efficiency of genetic vaccines in inducing antigen expression in human muscle cells and in inducing specific human immune responses. The vast majority of studies on the capacity of genetic vaccines to transfect muscle cells and to induce specific immune responses in vivo have employed a mouse model. Because of the complexity of events occurring after genetic vaccination, however, it is sometimes difficult to predict whether results obtained in the mouse model reliably predict the outcome of similar vaccinations in humans. The events required in successful genetic vaccination include transfection of the cells after delivery of the plasmid, expression of the desired antigen, processing the antigen in antigen presenting cells, presentation of the antigenic peptides in the context of MHC molecules, recognition of the peptide/MHC complex by T cell receptors, interactions of T cells with B cells and professional antigen presenting cells and finally induction of specific T cell and B cell responses. All these events are likely to be somewhat differentially regulated in mouse and man.

The Invention Provides an in vivo Model for Human Muscle Cell Transfection

Muscle tissue, obtained for example from cadavers, is transplanted subcutaneously into immunodeficient mice, which can be transplanted with tissues from other species without rejection. This model system is especially valuable because there is no in vitro culture system available for normal muscle cells. Muscle tissue, obtained for example from cadavers, is transplanted subcutaneously into immunodeficient mice. Immunodeficient mice can be transplanted with tissues from other species without rejection. Mice suitable for xenotransplantations include, but are not limited to, SCID mice, nude mice and mice rendered deficient in their genes encoding RAG1 or RAG2 genes. SCID mice and RAG deficient mice lack functional T and B cells, and therefore are severely immunocompromised and are unable to reject transplanted organs. Previous studies indicate that these mice can be transplanted with human tissues, such as skin, spleen, liver, thymus or bone, without rejection (Roncarolo et al. (1996) Semin. Immunol. 8: 207). After transplantation of human fetal lymphoid tissues into SCID mice, functional human immune system can be demonstrated in these mice, a model generally referred to as SCID-hu mice. When human muscle tissue is transplanted into SCID-hu mice, one can not only study transfection efficiency and expression of the desired antigen, but one can also study induction of specific human immune responses induced by genetic vaccines in vivo. In this case, muscle and lymphoid organs from the same donor are used. Fetal muscle also has an advantage in that it contains few mature lymphocytes of donor origin decreasing likelihood of graft versus host reaction.

Genetic Vaccine Vectors are Introduced Into the Human Muscle Tissue to Study the Expression of the Antigen of Interest Once the human muscle tissue is established in the mouse, genetic vaccine vectors are introduced into the human muscle tissue to study the expression of the antigen of interest. When studying transfection efficiency only, RAG deficient mice are preferred, because these mice never have mature B or T cells in the circulation, whereas "leakiness" of SCID phenotype has been demonstrated which may cause variation in the transplantation efficiency.

Model Provides an Efficient Means to Study Gene Expression in Human Muscle Cells in vivo, Despite the Limited Survival of the Tissue in Mice The survival of human muscle tissue in mice is likely to be limited even in immuno-compromised mice. However, because expression studies can be performed within one or two days, this model provides an efficient means to study gene expression in human muscle cells in vivo. A modified SCID-hu mouse model with human muscle transplanted into these mice can be used to study human immune responses in mice in vivo.

2.5.9. Screening for Improved Delivery of Vaccines

Identifying Genetic Vaccine Vectors That are Capable of Being Administered in a Particular Manner For certain applications, it is desirable to identify genetic vaccine vectors that are capable of being administered in a particular manner, for example, orally or through the skin. The following screening methods provide suitable assays; additional assays are also described herein in conjunction with particular genetic vaccine properties for which the assays are especially suitable.

Screening for Oral Delivery Either in vitro (Based on Caco-2 Cells) or in vivo Screening for oral delivery can be performed either in vitro or in vivo. An example of an in vitro method is based on Caco-2 (human colon adenocarcinoma) cells which are grown in tissue culture. When grown on semipermeable filters, these cells spontaneously differentiate into cells that resemble human small intestine epithelium, both structurally and functionally. Genetic vaccine libraries and/or vectors can be placed on one side of the Caco-2 cell layer, and vectors that are able to move through the cell layer are detected on the opposite side of the layer.

Libraries can also be screened for amenability to oral delivery in vivo. For example, a library of vectors can be administered orally, after which target tissues are assayed for presence of vectors. Intestinal epithelium, liver, and the bloodstream are examples of tissues that can be tested for presence of library members. Vectors that are successful in reaching the target tissue can be recovered and, if further improvement is desired, used in succeeding rounds of reassembly (optionally in combination with other directed evolution methods described herein) and selection.

Apparatus Which Permits Large Numbers of Vectors to be Screened Efficiently and Can be Used to Study the Effect of Large Numbers of Agents in vivo For screening a library of genetic vaccine vectors for ability to transfect cells upon injection into skin or muscle, the invention provides an apparatus which permits large numbers of vectors to be screened efficiently. This apparatus is based on 96-well format and is designed to transfer small volumes (2–5 $\mu$l) from a microtiter plate to skin or muscle of laboratory animals, such as mice and rats. Moreover, human muscle or skin transplanted into immunodeficient mice can be injected.

The apparatus is designed in such a way that the tips move to fit a microtiter plate. After the reagent of interest has been obtained from the plate, the distance of the tips from each other is decreased to 2–3 mm, enabling transfer of 96 reagents to an area of 1.6 cm×2.4 cm to 2.4 cm×3.6 cm. The volume of each sample transferred is electronically controlled. Each reagent is mixed with a marker agent or dye to enable recognition of injection site in the tissue. For example, gold particles of different sizes and shapes are mixed with the reagent of interest, and microscopy and immunohistochemistry can be used to identify each injection site and to study the reaction induced by each reagent. When muscle tissue is injected the injection site is first revealed by surgery.

This apparatus can be used to study the effects of large numbers of agents in vivo. For example, this apparatus can be used to screen efficiency of large numbers of different DNA vaccine vectors to transfect human skin or muscle cells transplanted into immunodeficient mice.

2.5.10. Enhanced Entry of Genetic Vaccine Vectors Into Cells

Using Stochastic (e.g. Polynucleotide Shuffling & Interrupted Synthesis) and Non-stochastic Polynucleotide Reassembly to Efficiently Improve the Capacity of DNA to Enter the Cytoplasm and Subsequently the Nucleus of Human Cells The methods involve subjecting to stochastic (e.g. polynucleotide shuffling & interrupted synthesis) and non-stochastic polynucleotide reassembly polynucleotides which are involved in cell entry. Such polynucleotides are referred to herein as "transfer sequences" or "transfer modules." Transfer modules can be obtained which increase transfer in a cell-specific manner, or which act in a more general manner. Because the exact sequences that affect DNA binding and transfer are not often known, stochastic (e.g. polynucleotide shuffling & interrupted synthesis) and non-stochastic polynucleotide reassembly may be the only efficient method to improve the capacity of DNA to enter the cytoplasm and subsequently the nucleus of human cells.

The Stochastic (e.g. Polynucleotide Shuffling & Interrupted Synthesis) and Non-stochastic Polynucleotide Reassembly Methods of the Invention Provide Means for Optimizing DNA Sequences and the Three-dimensional Structure of the Plasmids for Ability to Confer Upon a Vector the Ability to Enter a Cell Even in the Absence of Detailed Information as to the Mechanism by Which This Effect is Achieved The methods involve reassembling (&/or subjecting to one or more directed evolution methods described herein) at least first and second forms of a nucleic acid that comprises a transfer sequence. The first and second forms differ from each other in two or more nucleotides. Suitable substrates include, for example, transcription factor binding sites, CpG sequences, poly A, C, G, T oligonucleotides, non-stochastically generated nucleic acid building blocks ,and random DNA fragments such as, for example, genomic DNA, from human or other mammalian species. It has been suggested that cell surface proteins, such as the macrophage scavenger receptor, may act as receptors for specific DNA binding (Pisetsky (1996) Immunity 5: 303). It is not known whether these receptors recognize specific DNA sequences or whether they bind DNA in a sequence non-specific manner. However, GGGG tetrads have been shown to enhance DNA binding to cell surfaces (Id.). In addition to the DNA sequence, the three-dimensional structure of the plasmids may play a role in the capacity of these plasmids to enter cells. The stochastic (e.g. polynucleotide shuffling & interrupted synthesis) and non-stochastic polynucleotide reassembly methods of the invention provide means for optimizing such sequences for ability to confer upon a vector the ability to enter a cell even in the absence of detailed information as to the mechanism by which this effect is achieved.

Clonal Isolates of Vectors Bearing Recombinant Segments are Used to Infect Separate Cultures of Cells and the Percentage of Vectors Which Enter Cells is Then Determined by, for Example, Counting Cells Expressing a Marker Expressed by the Vectors in the Course of Transfection The resulting library of recombinant transfer modules are screened to identify at least one optimized recombinant transfer module that enhances the capability of a vector comprising the transfer module to enter a cell of interest. For example, vectors that include a recombinant transfer module can be contacted with a population of cells under conditions conducive to entry of the vector into the cells, after which the percentage of cells in the population which contain the nucleic acid vector is determined. Preferably, the vector will contain a selectable or screenable marker to facilitate identification of cells which contain the vector. In a preferred embodiment, clonal isolates of vectors bearing recombinant segments are used to infect separate cultures of cells. The percentage of vectors which enter cells can then be determined by, for example, counting cells expressing a marker expressed by the vectors in the course of transfection.

The Reassembly (&/or One or More Additional Directed Evolution Methods Described Herein) and Rescreening Process can be Repeated as Necessary, Until a Transfer Module That has Sufficient Ability to Enhance Transfer is Obtained Typically, the reassembly (&/or one or more additional directed evolution methods described herein) process is repeated by reassembling (&/or subjecting to one or more directed evolution methods described herein) at least one optimized transfer sequence with a further form of the transfer sequence to produce a further library of recombinant transfer modules. The further form can be the same or different from the first and second forms. The new library is screened to identify at least one further optimized recombinant vector module that exhibits an enhancement of the ability of a genetic vaccine vector that includes the optimized transfer module to enter a cell of interest.

The reassembly (&/or one or more additional directed evolution methods described herein) and rescreening process can be repeated as necessary, until a transfer module that has sufficient ability to enhance transfer is obtained. After one or more of reassembly (&/or one or more additional directed evolution methods described herein) and screening, vector modules are obtained which are capable of conferring upon a nucleic acid vector the ability to enter at least about 50 percent more target cells than a control vector which does not contain the optimized module, more preferably at least about 75 percent more, and most preferably at least about 95 or 99 percent more target cells than a control vector.

For Integration by Homologous Recombination, Important Factors are the Degree and Length of Homology to Chromosomal Sequences, the Frequency of Such Sequences in the Genome, and the Specific Sequence Mediating Homologous Recombination; for Nonhomologous, Illegitimate and Site-specific Recombination, Recombination is Mediated by Specific Sites on the Therapy Vector Which Interact With Cell Encoded Recombination Proteins Although for vaccine purposes non-integrating vectors are generally preferred, for some applications it may be desirable to use an integrating vector; for these applications DNA sequences that directly or indirectly affect the efficiency of integration can be included in the genetic vaccine vector. For integration by homologous recombination, important factors are the degree and length of homology to chromosomal sequences, as well as the frequency of such sequences in the genome (e.g., Alu repeats). The specific sequence mediating homologous recombination is also important, since integration occurs much more easily in transcriptionally active DNA. Methods and materials for constructing homologous targeting constructs are described by e.g., Mansour (1988) Nature 336:348; Bradley (1992) Bio/Technology 10:534. For nonhomologous, illegitimate and site-specific recombination, recombination is mediated by specific sites on the therapy vector which interact with cell encoded recombination proteins, e.g., Cre/Lox and Flp/Frt systems. See, e.g., Baubonis (1993) Nucleic Acids Res. 21:2025–2029, which reports that a vector including a LoxP site becomes integrated at a LoxP site in chromosomal DNA in the presence of Cre recombinase enzyme.

2.6. OPTIMIZATION OF GENETIC VACCINE COMPONENTS

Optimizing Properties That can Influence the Efficacy of a Genetic Vaccine in Modulating an Immune Response in a Mammalian System Many factors can influence the efficacy of a genetic vaccine in modulating an immune response. The ability of the vector to enter a cell, for example, has a significant effect on the ability of the vector to modulate an immune response. The strength of an immune response is also mediated by the immunogenicity of an antigen expressed by a genetic vaccine vector and the level at which the antigen is expressed. The presence or absence of costimulatory molecules produced by the genetic vaccine vector can affect not only the strength, but also the type of immune response that arises due to introduction of the vector into a mammal. An increase in the persistence of a vector in an organism can lengthen the time of immunomodulation, and also makes feasible self-boosting vectors which do not require multiple administrations to achieve long-lasting protection. The present invention provides methods for optimizing many of these properties, thus resulting in genetic vaccine vectors that exhibit improved ability to elicit the desired effect on a mammalian immune system.

The Selection From Large Libraries Using Recursive Cycles of Reassembly (Optionally in Combination With Other Directed Evolution Methods Described Herein) to Maximally Access all the Fortuitous but Complex Mechanisms That Cannot be Approached Rationally Genetic vaccines can contain a variety of functional components, whose preferred sequences are best determined by stochastic (e.g. polynucleotide shuffling & interrupted synthesis) and non-stochastic polynucleotide reassembly, the empirical sequence evolution described in detail herein. The methods of the invention involve, in general, constructing a separate library for each of the major vector components by stochastic (e.g. polynucleotide shuffling & interrupted synthesis) and non-stochastic polynucleotide reassembly of multiple homologous starting sequences, or other methods of generating a population of recombinants, resulting in a complex mixture of chimeric sequences. The best sequences are selected from these libraries using the high-throughput assays described below. After one or more cycles of selection from each of the single module libraries, the pools of the best sequences of different modules can be combined by stochastic (e.g. polynucleotide shuffling & interrupted synthesis) and non-stochastic polynucleotide reassembly as long as the screens are compatible. The screens for promoter, enhancer, intron, transfer sequences, mammalian ori, bacterial ori and bacterial marker, and the like, can eventually be combined, resulting in co-optimization of the context of each sequence. An important aspect in these experiments is the selection from large libraries using recursive cycles of reassembly (optionally in combination with other directed evolution methods described herein) to maximally access all the fortuitous but complex mechanisms that cannot be approached rationally, such as DNA transfer into the cell.

A Library of Different Vectors can be Generated by Assembling Vector Modules That Provide Promoters, Cytokines, Cytokine Antagonists, Chemokines, Immunostimulatory Sequences, and Costimulatory Molecules Using Assembly PCR and Combinatorial Molecular Biology Assembly PCR is a method for assembly of long DNA sequences, such as genes, non-stochastically generated nucleic acid building blocks, and fragments of plasmids. In contrast to PCR, there is no distinction between primers and template, because the non-stochastically generated nucleic acid building blocks &/or fragments to be assembled prime each other. The library of vector modules obtained as described herein can be fused with promoters, which can themselves be optimized by the stochastic (e.g. polynucleotide shuffling & interrupted synthesis) and non-stochastic polynucleotide reassembly methods of the invention. The resulting genes can be assembled combinatorially into DNA vaccine vectors, where each gene is expressed under a different promoter (e.g., a promoter derived from a library of experimentally evolved (e.g. by polynucleotide reassembly &/or polynucleotide site-saturation mutagenesis) CMV promoters), and the vector library is screened as described herein to identify vectors which exhibit the desired effect on the immune system.

Properies That Influence the Efficacy or Desirability of the Vaccine

The methods of the invention are useful for obtaining genetic vaccines that are optimized for one or more of many properties that influence the efficacy or desirability of the vaccine. These properties include, but are not limited to, the following.

2.6.1. Episomal Vector Maintenance

Episomally Replicating Vectors are Maintained in a Cell for a Longer Period of Time and Permit the Development of Self-boosting Vaccines One property that one can optimize using the sequence reassembly methods of the invention is the ability of a genetic vaccine vector to replicate episomally in a mammalian cell. Episomal replication of a vaccine vector is advantageous in many situations. For example, episomally replicating vectors are maintained in a cell for a longer period of time than non-replicating vectors, thus resulting in an increased length of immune response modulation or increased delivery of a therapeutically useful protein. Episomal replication also permits the development of self-boosting vaccines which, unlike traditional vaccines, do not require multiple vaccine, administrations. For example, a self-boosting vaccine vector can include an antigen-encoding gene which is under the control of an inducible control element which allows induction of antigen expression, and the corresponding immune response, in response to a specific stimulus. However, screening for naturally occurring vector modules which result in enhanced episomal maintenance using traditional approaches or attempts to rationally design mutants with improved properties would require many person-years of research. The invention provides methods for generating and screening orders of magnitude more diversity in a short time period.

Using Stochastic (e.g. Polynucleotide Shuffling & Interrupted Synthesis) and Non-stochastic Polynucleotide Reassembly to Recombine at Least Two Forms of a Nucleic Acid Which is Capable of Conferring Upon a Genetic Vector the Ability to Replicate Autonomously in Mammalian Cells The ability of a genetic vaccine vector to replicate episomally can be optimized by using stochastic (e.g. polynucleotide shuffling & interrupted synthesis) and non-stochastic polynucleotide reassembly to recombine at least two forms of a nucleic acid which is capable of conferring upon a genetic vector the ability to replicate autonomously in mammalian cells. The two or more forms of the episomal replication vector module differ from each other in two or more nucleotides. A library of recombinant episomal replication vector modules is produced, and the library is screened to identify one or more optimized replication vector modules which, when placed in a genetic vaccine vector, confer upon the vector an enhanced ability to replicate autonomously compared to a vector which contains a non-optimized episomal replication vector module.

Repetition of the Stochastic (e.g. Polynucleotide Shuffling & Interrupted Synthesis) and Non-stochastic Polynucleotide Reassembly Process at Least Once to Identify Modules Which Exhibit Enhanced Ability to Confer Episomal Maintenance Upon a Vector Containing the Module In one embodiment, the stochastic (e.g. polynucleotide shuffling & interrupted synthesis) and non-stochastic polynucleotide reassembly process is repeated at least once using as a substrate an optimized episomal replication vector module obtained from a previous round of stochastic (e.g. polynucleotide shuffling & interrupted synthesis) and non-stochastic polynucleotide reassembly. The optimized vector module obtained in the earlier round is reassembled (&/or subjected to one or more directed evolution methods described herein) with a further form of the vector module, which can be the same as one of the forms used in the earlier round, or can be a different form of a nucleic acid that functions as an episomal replication element. Again, a library of recombinant episomal replication vector modules is produced, and the screening process is repeated to identify those episomal replication modules which exhibit enhanced ability to confer episomal maintenance upon a vector containing the module.

Ability to Replicate Autonomously in Eukaryotic Cells-examples

Nucleic acids which are useful as substrates for the use of stochastic (e.g. polynucleotide shuffling & interrupted synthesis) and non-stochastic polynucleotide reassembly to optimize episomal replication ability include any nucleic acid that is involved in conferring upon a vector the ability to replicate autonomously in eukaryotic cells. For example, papillomavirus sequences E1 and E2, simian virus 40 (SV40) origin of replication, and the like.

Genes From Human Papillomaviruses are Exemplary Episomal Replication Vector Modules Exemplary episomal replication vector modules that can be optimized using the methods of the invention are genes from human papillomaviruses (HPV) which are involved in episomal replication. HPV are non-tumorigenic viruses which replicate episomally in skin and are stably expressed in vivo for years. Bernard and Apt (1994) Arch. Dermatol. 130: 210.

Increased Episomal Maintenance of the HPV Genes Involved in Episomal Replication Using Directed Evolution Despite these in vivo properties, it has not been possible to maintain HPV episomally in tissue culture due to under-replication. The invention provides methods by which HPV genes involved in episomal maintenance can be optimized for use in genetic vaccine vectors. HPV genes involved in episomal replication include, for example, the E1 and E2 genes. Thus, according to one embodiment of the invention, either or both of the HPV E1 and E2 genes are subjected to stochastic (e.g. polynucleotide shuffling & interrupted synthesis) and non-stochastic polynucleotide reassembly to obtain a recombinant episomal replication module which, when placed in a nucleic acid vaccine vector, results in increased maintenance of the vector in mammalian cells. In a preferred embodiment, the HPV E1 and E2 genes from different, but closely related, benign HPVs are used in a polynucleotide reassembly procedure, as shown, described &/or referenced herein (including incorporated by reference). For example, polynucletide shuffling of HPV E1 and E2 genes from closely related strains of HPV (such as, for example, HPV 2, 27, and 57) can be used to obtain a library of recombinant E1 and E2 genes which are then subjected to an appropriate screening method to identify those that exhibit improved episomal maintenance properties.

Identification, Selection, Enrichment of Recombinant Episomal Replication Vector Modules That Exhibit Improved Ability to Mediate Episomal Maintenance To identify recombinant episomal replication vector modules that exhibit improved ability to mediate episomal maintenance, members of the library of recombinant vector modules are inserted into vectors which are introduced into mammalian cells. The cells are propagated for at least several generations, after which cells that have maintained the vector are identified. Identification can be accomplished, for example, employing a vector that includes a selectable marker. Cells containing the library members are propagated in the absence of selection for the selectable marker for at least several generations, after which selective pressure is added. Cells which survive selection are enriched for cells that harbor vectors which contain a recombinant vector module which enhances the ability of the vector to replicate episomally. DNA is recovered from the selected cells and introduced into bacterial host cells, allowing recovery of episomal, non-integrated vectors.

Screening by Introducing to a Vector Containing a Polynucleotide Encoding an Antigen That is Present on the Surface of the Cell When Expressed In another embodiment of the invention, the screening step is accomplished by introducing members of the library of recombinant episomal replication vector modules into a vector that includes a polynucleotide that encodes an antigen-which, when expressed, is present on the surface of a cell. The library of vectors is introduced into mammalian cells which are propagated for at least several generations, after which cells which display the cell surface antigen on the surface of the cell are identified. Such cells most likely harbor a genetic vaccine vector which enhances the ability of the vector to replicate autonomously.

Use of Optimized Recombinant Episomal Replication Vector Module to Construct Genetic Vaccine Vectors Upon identifying cells which contain an episomally maintained vector, the optimized recombinant episomal replication vector module is obtained and used to construct genetic vaccine vectors. Cell surface antigens which are suitable for use in the screening methods are described above, and others are known to those of skill in the art. Preferably, an antigen is used for which a convenient means of detection is available.

Preferred Cells for use in the Screening Methods

Cells which are suitable for use in the screening methods include both cultured mammalian cells and cells which are present in an animal. To screen for recombinant vector modules that are intended for use in humans, the preferred cells for screening purposes are human cells. Generally, initial screening is accomplished in cell culture, where processing of large libraries of experimentally evolved (e.g. by polynucleotide reassembly &/or polynucleotide site-saturation mutagenesis) material is feasible. In a preferred embodiment, cells which display a vector-encoded cell surface antigen on the cell surface are identified by flow cytometry based cell sorting methods, such as fluorescence activated cell sorting. This approach allows very large numbers ($>10^7$) cells to be evaluated in a single vial experiment.

Further Testing for Durability in vivo in an Animal Model

Constructs which replicate autonomously in cell culture and give rise to strong marker gene expression can be further tested for durability in vivo in an animal model. For example, mouse models for studies of human tissues in mice in vivo are described herein. Live pieces of human skin are xenotransplanted onto the back of SCID mice, allowing screening of the vector libraries for optimal properties in human cells in vivo. Recursive selection of episomal vectors will provide strong selection pressure for vectors that remain episomal, yet provide high level of gene expression.

Introducing a Genetic Vaccine Vector Into a Mammal That has a Functional Human Immune System and Testing for the Existence of an Immune Response Against the Antigen In another embodiment, the screening step involves introducing a genetic vaccine vector which includes the recombinant episomal replication vector module, as well as polynucleotide that encodes an antigen or pharmaceutically useful protein, into a mammal that has a functional human immune system. The animal is then tested for the existence of an immune response against the antigen. In a preferred embodiment, the mammals used for such assays are non-human mammals that have a functional human immune system. For example, a functional human immune system can be created in an immunodeficient mouse by introducing one or more of a human fetal tissue selected from the group consisting of liver, thymus, and bone marrow (Roncarolo et al. (1996) Semin. Immunol. 8: 207).

Episomally Maintained Vectors Result in High Signal-to-noise Ratios Upon FACS Selection and Significantly Improve the Possibility to Recover the Plasmids From a Small Number of Selected Cells Stable episomal vectors which are obtained using the methods of the invention are useful not only as genetic vaccines, but also are useful tools in other library screening applications. In contrast to randomly integrating and transient vectors, episomally maintained vectors result in high signal-to-noise ratios upon FACS selection, and they also significantly improve the possibility to recover the plasmids from a small number of selected cells.

2.6.2. Evolution of Optimized Promoters for expression of an Antigen

Optimizing the Promoter and/or Other Control Sequence to Improve the Efficacy of Genetic Vaccinations, Reduce the Amount of DNA Required for Protective Immunity and Thereby the Cost of Vaccination, Control the Type of Cell in Which the Gene is Expressed, and/or the Timing of the Antigen Expression In another embodiment, the invention provides methods of optimizing vector modules such as promoters and other gene expression control signals. Usually, a coding sequence for an antigen that is delivered by a genetic vaccine is operably linked to an additional sequence, such as a regulatory sequence, to ensure its expression. These regulatory sequences can include one or more of the following: an enhancer, a promoter, a signal peptide sequence, an intron and/or a polyadenylation sequence. A desirable goal is to increase the level of expression of functional expression product relative to that achieved with conventional vectors. The efficacy of a genetic vaccine vector often depends on the level of expression of an antigen by the vaccine vector. An optimized promoter and/or other control sequence is likely to result in improved efficacy of genetic vaccinations, reduce the amount of DNA required for protective immunity and thereby the cost of vaccination.

Moreover, it is sometimes desirable to have control over the type of cell in which a gene is expressed, and/or the timing of antigen expression. The methods of the invention provide for optimization of these and other factors which are influenced by promoters and other control sequences.

Improving Expression by Increasing the Rate of Production of an Expression Product, Decreasing the rate of Degradation of the Expression Product, or Improving the Capacity of Expression Product to Perform its Intended Function Using Stochastic (e.g. Polynucleotide Shuffling & Interrupted Synthesis) and Non-stochastic Polynucleotide Reassembly of Polynucleotides Involved in Control of Gene Expression Improved expression of selection markers can be achieved by performing stochastic (e.g. polynucleotide shuffling & interrupted synthesis) and non-stochastic polynucleotide reassembly, for example. Expression can effectively be improved by a variety of means, including increasing the rate of production of an expression product, decreasing the rate of degradation of the expression product or improving the capacity of the expression product to perform its intended function. The methods involve subjecting to stochastic (e.g. polynucleotide shuffling & interrupted synthesis) and non-stochastic polynucleotide reassembly polynucleotides which are involved in control of gene expression. At least first and second forms of a nucleic acid that comprises a control sequence, which forms differ from each other in two or more nucleotides, are reassembled (&/or subjected to one or more directed evolution methods described herein) as described above. The resulting library of recombinant transfer modules are screened to identify at least one optimized recombinant control sequence that exhibits enhanced strength, inducibility, or specificity.

Introduction of the Recombinant Segments at the Level of Fragments (Non-tochastically Generated &/or Randomly Generated) and in vitro The substrates for reassembly (&/or one or more additional directed evolution methods described herein) can be the full-length vectors, or fragments thereof, which include a coding sequence and/or regulatory sequences to which the coding sequence is operably linked. The substrates can include variants of any of the regulatory and/or coding sequence(s) present in the vector. If reassembly (&/or one or more additional directed evolution methods described herein) is effected at the level of fragments, the recombinant segments should be reinserted into vectors before screening. If reassembly (&/or one or more additional directed evolution methods described herein) proceeds in vitro, vectors containing the recombinant segments are usually introduced into cells before screening. An example of a vector suitable for use in screening of experimentally evolved (e.g. by polynucleotide reassembly &/or polynucleotide site-saturation mutagenesis) promoters and other regulatory regions is shown, described &/or referenced herein (including incorporated by reference).

Using an Easily Detected Selection Marker (Green Fluorescent Protein, Cell Surface Protein) When an Additional or Substitute Marker is Required Cells containing the recombinant segments can be screened by detecting expression of the gene encoded by the selection marker. For purposes of selection and/or screening, a gene product expressed from a vector is sometimes an easily detected marker rather than a product having an actual therapeutic purpose, e.g., a green fluorescent protein (see, Crameri (1996) Nature Biotechnol. 14: 315–319) or a cell surface protein. For example, if this marker is green fluorescent protein, cells with the highest expression levels can be identified by flow cytometry-based cell sorting. If the marker is a cell surface protein, the cells are stained with a reagent having affinity for the protein, such as antibody, and again analyzed by flow cytometry-based cell sorting. However, some genes having a therapeutic purpose, e.g., drug resistance genes, themselves provide a selectable marker, and no additional or substitute marker is required. Alternatively, the gene product can be a fusion protein comprising any combination of detection and selection markers. Internal reference marker genes can be included on the vector to detect and compensate for variations in copy number or insertion site.

Further Round of Reassembly (&/or One or More Additional Directed Evolution Methods Described Herein) and Screening Recombinant segments from the cells showing highest expression of the marker gene can be used as some or all of the substrates in a further round of reassembly (&/or one or more additional directed evolution methods described herein) and screening, if additional improvement is desired.

2.6.2.1. Constitutive Promoters

Evolving Control Sequences (Promoters, Enhancers, etc.) to Express a Gene of Interest at a Higher Level Than is a Gene Operably Linked to a Non-evolved Control Sequences The invention provides methods of evolving nucleotide sequences that are capable of directing constitutive expression of a gene of interest which is operably linked to the control sequence. Typically, the control sequences, which can include promoters, enhancers, and the like, are evolved so that a gene of interest is expressed at a higher level than is a gene operably linked to a non-evolved control sequence. To screen for control sequences which are of increased strength, a recombinant library of control sequences can be introduced into a population of cells and the level of expression of a detectable marker operably linked to the control sequences determined. Preferably, the optimized promoter is capable of expressing an operably linked gene at a level that is at least about 30% greater than that of a control promoter construct, more preferably the optimized promoter is at least about 50% stronger than a control, and most preferably at least about 75% or more stronger than a control promoter.

Using Improved CMV Promoter/enhancer Elements (SV40 and Sra) to Express Foreign Genes Both in Animal Models and in Clinical Applications Examples of promoters which can be used as substrates in the methods include any constitutive promoter that functions in the intended host cell. The major immediate-early (IE) region transcriptional regulatory elements, including promoter and enhancer sequences (the promoter/enhancer region), of cytomegalovirus (CMV) is widely used for regulating transcription in vectors used for gene therapy because it is highly active in a broad range of cell types. Optimized CMV transcriptional regulatory elements which direct increased levels of antigen expression is generated by the recursive reassembly (&/or one or more additional directed evolution methods described herein) methods of the invention, resulting in improved efficacy of gene therapy. As the CMV promoter and enhancer is active in human and animal cells, the improved CMV promoter/enhancer elements are used to express foreign genes both in animal models and in clinical applications. Other constitutive promoters that are amenable to use in the claimed methods include, for example, promoters from SV40 and SR, and other promoters known to those of skill in the art.

Creating a Library of Chimeric Transcriptional Regulatory Elements Through Stochastic (e.g. Polynucleotide Shuffling & Interrupted Synthesis) and Non-stochastic Polynucleotide Reassembly of Wild-type Sequences From Two or More of the Five Related Strains of CMV, Obtaining the Promoter, Enhancer and First Intron Sequences of the IE Region Through PCR of the CMV Strains In a preferred embodiment, a library of chimeric transcriptional regulatory elements is created by stochastic (e.g. polynucleotide shuffling & interrupted synthesis) and non-stochastic polynucleotide reassembly of wild-type sequences from two or more of the five related strains of CMV. The promoter, enhancer and first intron sequences of the IE region are obtained by PCR from the CMV strains: human VR-538 strain AD169 (Rowe (1956) Proc. Soc. Exp. Biol. Med. 92:418; human V-977 strain Towne (Plotkin (1975) Infect. Immunol. 12:521–527); rhesus VR-677 strain 68–1 (Asher (1969) Bacteriol. Proc. 269:91); vervet VR-706 strain CSG (Black (1963) Proc. Soc. Exp. Biol. Med. 112:60 1); and, squirrel monkey VR-1398 strain SqSHV (Rangan (1980) Lab. Animal Sci. 30:532). The promoter/enhancer sequences of the human CMV strains are 95% homologous, and share 70% homology with the sequences of the monkey isolates, allowing the use of polynucleotide reassembly (optionally in combination with other directed evolution methods described herein) to generate a library great diversity. Following reassembly (optionally in combination with other directed evolution methods described herein), the library is cloned into a plasmid backbone and used to direct transcription of a marker gene in mammalian cells. An internal marker under the control of a native promoter is typically included in the plasmid vector, which will allow analysis and sorting of cells harboring equal numbers of vectors.

Expression markers, such as green fluorescent protein (GFP) and CD86 (also known as B7.2, see Freeman (1993) J Exp. Med 178:2185, Chen (1994) *J Immunol.* 152:4929) can also be used. In addition, transfection of SV40 T antigen-transformed cells can be used to amplify a vector which contains an SV40 origin of replication. The transfected cells are screened by FACS sorting to identify those which express high levels of the marker gene, normalized against the internal marker to account for differences in vector copy numbers per cell. If desired, vectors carrying optimal, recursively reassembled (&/or subjected to one or more directed evolution methods described herein) promoter sequences are recovered and subjected to further cycles of

2.6.2.2. Cell-specific Promoters

Reducing the Risk of Autoimmune Disorder Following Introduction of Foreign Antigens Into Host Cells and Providing for Efficient Induction of Protective Immunity Through the Expression of Genetic Vaccines in Professional APCs, Such as Dendritic Cells and Macrophages One of the safety concerns associated with genetic vaccines has been the possibility of autoimmune disorders following introduction of foreign antigens into host cells. This risk can be reduced if the pathogen antigen is specifically expressed in professional APCs that express the proper costimulatory molecules. Although it is somewhat debatable which cells are the most important cells expressing the pathogen antigen following genetic vaccinations, it is likely that professional APCs are involved. It has been shown that blood monocytes express antigen following intramuscular injection of genetic vaccine vectors, and dendritic cells derived from lymph nodes of vaccinated animals efficiently induced antigen-specific T cell activation (C. Bona, The First Gordon Conference on Genetic Vaccines, Plymouth, N.H., Jul. 21, 1997). These data, together with previous studies indicating that small number of dendritic cells expressing antigen or antigenic peptides is sufficient to induce activation of antigen-specific T cells (Thomas and Lipsky, Stem Cells 14: 196, 1996), support the conclusion that genetic vaccines specifically expressed in professional APC, such as dendritic cells and macrophages, are likely to provide efficient induction of protective immunity with minimized chance of adverse effects.

Methods for Obtaining Promoters and Enhancers That Induce High Expression Levels Specifically in Professional APCs, Exploiting Natural Diversity as a Source of Substrates for Stochastic (e.g. Polynucleotide Shuffling & Interrupted Synthesis) and Non-stochastic Polynucleotide Reassembly The present invention provides methods of obtaining promoters and enhancers that induce high expression levels specifically in professional APCs. Previously existing APC-specific vectors did not provide sufficient expression levels following genetic vaccinations. The methods involve performing stochastic (e.g. polynucleotide shuffling & interrupted synthesis) and non-stochastic polynucleotide reassembly as described above using as substrates different forms of a nucleic acid that comprises an APC-specific promoter or other control signal. Suitable promoters include, for example, the MHC Class II, and the CD11b, CD11c, and CD40 promoters. Natural diversity of the promoters can be exploited as a highly appropriate source of substrates for the stochastic (e.g. polynucleotide shuffling & interrupted synthesis) and non-stochastic polynucleotide reassembly. For example, genomic DNA from monkeys, pigs, dogs, cows, cats, rabbits, rats and mice, can be obtained, and the proper sequences obtained by using multiple PCR primers specific for the most conserved regions based on known sequence information. The selection of the optimal promoters can be done in monocytic or B cell lines, such as U937, HL60 or Jijoye, using FACS-sorting. In addition, $SV40^+$ cell lines, such as COS-1 and COS-7, can be used to improve the recovery of the plasmids. Further analysis can be undertaken in human dendritic cells obtained by culturing peripheral blood monocytes in the presence of IL-4 and GM-CSF as described (Chapuis et al. (1997) Eur. J Immunol. 27: 431).

2.6.2.3. Inducible Promoters

Using Stochastic (e.g. Polynucleotide Shuffling & Interrupted Synthesis) and Non-stochastic Polynucleotide Reassembly of Two Substrates, Such as Tetracycline and Hormone Inducible Expression Systems, to Increase the Expression Level and Inducibility in vivo of the Promoter Controlling Transgene Expression A particularly desirable property of a genetic vaccines would be an ability to induce the promoter controlling transgene expression simply by taking an innocuous oral drug, resulting in a boost of the immune response. Essential requirements for inducible promoters are low base-line expression and strong inducibility. Several promoters with exquisite in vitro regulation exist, but the expression level and inducibility of each is too low to be useable in vivo. The invention overcome these problems by stochastic (e.g. polynucleotide shuffling & interrupted synthesis) and non-stochastic polynucleotide reassembly using as substrates two or more variants of a nucleic acid that functions as an inducible control sequence. Suitable substrates include, for example, tetracycline and hormone inducible expression systems, and the like. Hormones that have been used to regulate gene expression include, for example, estrogen, tomoxifen, toremifen and ecdysone (Rarnkumar and Adler (1995) Endocrinology 136: 536–542). Libraries of recombinant inducible promoters are screened as described above in the presence and absence of the inducer.

Tetracycline Responsive System Provides Possibilities to Induce and Turn Off Gene Expression (Ecdysone Responsive Element Another Candidate)

The most commonly used inducible gene expression protocol is the tetracycline responsive system, which provides possibilities to both induce and turn off gene expression (Gossen and Bujard (1992) Proc. Nat'l. Acad. Sci. USA 89: 5547; Gossen et al. (1995) Science 268: 1766). A repressor gene is located on the plasmid and binds to an operator in the promoter. Tetracycline or doxycycline modulates the binding ability of the repressor. Interestingly, four amino acid changes convert the repressor into an activator. In addition to the tetracycline responsive system, other candidates for inducible promoter evolution include the ecdysone responsive element (No et al., Proc. Nat'l. Acad Sci. USA 93:3346,1997).

Inducible Promoters Provide a Means by Which a Vaccine Dose can be Administered Subsequent to the Initial Administration Simply by Ingestion of a Reagent That Causes Induction of the Inducible Promoter Inducible promoters such as those obtained using the methods of the invention are useful in autoboost vaccines. Particularly when combined with a stably maintained episomal vector obtained as described above, the inducible promoters provide a means by which a vaccine dose can be administered subsequent to the initial administration simply by ingestion of a reagent that causes induction of the inducible promoter. A flow cytometry-based screening protocol that is suitable for optimization of inducible promoters is diagrammed herein.

Testing the Functionality of Autoboosting Vaccines in a Mouse Model

The functionality of autoboosting vaccines can be tested in a mouse model such as that described above. Genetic vaccine vectors are injected into the skin of normal mice and into human skin in SCID-human skin mice. A gene encoding hepatitis B surface antigen (HBsAg) or other surface antigen is incorporated into these vectors enabling direct measurements of the levels of antigen produced, because HBsAg levels can be measured in cell culture supernates and in the circulation of the mice. The drug inducing the expression of the antigen is given after 1, 2, 4 and 6 weeks, and the expression levels of HBsAg are studied. Moreover, the levels of anti-HBsAg antibodies are measured. The mice are also injected with a vector containing a pathogen antigen discovered by ELI, and specific immune responses are followed.

In vivo Assessment of Functionality of Autoboosting Genetic Vaccines in Human Immune System Using SCID-human Skin Model With SCID-hu Mouse Model Combining the SCID-human skin model with traditional SCID-hu mouse model (Roncarolo et al., Semin. Immunol. 8: 207, 1996) allows the assessment of functionality of autoboosting genetic vaccines in human immune system in vivo, and also allows measurements of human Ab responses in vivo. This model can also be used to assess production of HBsAg after oral boosting of novel genetic vaccine vectors harboring the gene encoding HBsAg.

2.6.3. Evolution of Binding Polypeptides That Enhance Specificity and Efficiancy of Genetic Vaccines The present invention also provides methods for obtaining recombinant nucleic acids that encode polypeptides which can enhance the ability of genetic vaccines to enter target cells. Although the mechanisms involved in DNA uptake are not well understood, the methods of the invention enable one to obtain genetic vaccines that exhibit enhanced entry to cells, and to appropriate cellular compartments.

Enhancing the Efficiency and Specificity of a Genetic Vaccine Nucleic Acid Uptake by a Given Cell Type by Coating the Nucleic Acid With an Evolved Protein That Binds to the Genetic Vaccine Nucleic Acid, and is Also Capable of Binding to the Target Cell In one embodiment, the invention provides methods of enhancing the efficiency and specificity of a genetic vaccine nucleic acid uptake by a given cell type by coating the nucleic acid with an evolved protein that binds to the genetic vaccine nucleic acid, and is also capable of binding to the target cell. The vector can be contacted with the protein in vitro or in vivo. In the latter situation, the protein is expressed in cells containing the vector, optionally from a coding sequence within the vector. The nucleic acid binding proteins to be evolved usually have nucleic acid binding activity but do not necessarily have any known capacity to enhance or alter nucleic acid DNA uptake.

DNA Binding Proteins That can be Used in These Methods

DNA binding proteins which can be used in these methods include, but are not limited to, transcriptional regulators, enzymes involved in DNA replication (e.g., recA) and reassembly (&/or one or more additional directed evolution methods described herein), and proteins that serve structural functions on DNA (e.g., histones, protamines). Other DNA binding proteins that can be used include the phage 434 repressor, the lambda phage cl and cro repressors, the E. coli CAP protein, myc, proteins with leucine zippers and DNA binding basic domains such as fos and jun; proteins with 'POU' domains such as the Drosophila paired protein; proteins with domains whose structures depend on metal ion chelation such as $Cys_2His_2$ zinc fingers found in TFIIIA, $Zn_2(Cys)_6$ clusters such as those found in yeast Gal4, the $Cys_3$ His box found in retroviral nucleocapsid proteins, and the $Zn_2(Cys)_8$ clusters found in nuclear hormone receptor-type proteins; the phage P22 Arc and Mnt repressors (see Knight et al. (1989) J Biol. Chem. 264: 3639–3642 and Bowie & Sauerkl 989) J Biol. Chem. 264: 7596–7602. RNA binding proteins are reviewed by Burd & Dreyfuss (1994) Science 265: 615–62 1, and include HIV Tat and Rev.

Formats for Performing Reassembly (&/or One or More Additional Directed Evolution Methods Described Herein)

As in other methods of the invention, evolution of DNA binding proteins toward acquisition of improved or altered uptake efficiency is effective by one or more cycles of reassembly (&/or one or more additional directed evolution methods described herein) and screening. The starting substrates can be nucleic acid segments encoding natural or induced variants of one or nucleic acid binding proteins, such as those mentioned above. The nucleic acid segments can be present in vectors or in isolated form for the reassembly (&/or one or more additional directed evolution methods described herein) step. reassembly (&/or one or more additional directed evolution methods described herein) can proceed through any of the formats described herein.

For screening purposes, the reassembled (&/or subjected to one or more directed evolution methods described herein) nucleic acid segments are typically inserted into a vector, if not already present in such a vector during the reassembly (&/or one or more additional directed evolution methods described herein) step.

Including Binding Site in Vector for DNA Binding Protein Recognizingy a Specific Binding Site The vector generally encodes a selective marker capable of being expressed in the cell type for which uptake is desired. If the DNA binding protein being evolved recognizes a specific binding site (e.g., lacl binding protein recognizes lacO), this binding site can be included in the vector. Optionally, the vector can contain multiple binding sites in tandem.

Transforming Vectors Containing Recombinant Segments Into Host Cells and Lysing Cells Under Mild Conditions That do not Disrupt Binding of Vectors to DNA Binding Proteins The vectors containing different recombinant segments are transformed into host cells, usually E. coli, to allow recombinant proteins to be expressed and bind to the vector encoding their genetic material. Most cells take up only a single vector and so transformation results in a population of cells, most of which contain a single species of vector. After an appropriate period to allow for expression and binding, cells are lysed under mild conditions that do not disrupt binding of vectors to DNA binding proteins. For example, a lysis buffer of 35 mM HEPES (pH 7.5 with KOH), 0.1 mM EDTA, 100 mM Na glutamate, 5% glycerol, 0.3 mg/ml BSA, 1 mM DTT, and 0.1 mM PMSF) plus lysozyme (0.3-ml at 10 mg/ml) is suitable (see Schatz et al., U.S. Pat. No. 5,338,665). The complexes of vector and nucleic acid binding protein are then contacted with cells of the type for which improved or altered uptake is desired under conditions favoring uptake. Suitable recipient cells include the human cell types that are common targets in DNA vaccination. These cells include muscle cells, monocytes/ macrophages, dendritic cells, B cells, Langerhans cells, keratinocytes, and the M-cells of the gut. Cells from mammals including, for example, human, mouse, and monkey can be used for screening. Both primary cells and cells obtained from cell lines are suitable.

Recovery of Cells Expressing Marker and Enriching for Recombinant Segments for Further Rounds of Selection After incubation, cells are plated with selection for expression of the selective marker present in the vector containing the recombinant segments. Cells expressing the marker are recovered. These cells are enriched for recombinant segments encoding nucleic acid binding proteins that enhance uptake of vectors encoding the respective recombinant segments. The recombinant segments from cells expressing the marker can then be subjected to a further round of selection. Usually, the recombinant segments are first recovered from cells, e.g., by PCR amplification or by recovery of the entire vectors. The recombinant segments can then be reassembled (&/or subjected to one or more directed evolution methods described herein) with each other or with other sources of DNA binding protein variants to generate further recombinant segments. The further recombinant segments are screened in the same manner as before.

Using Stochastic (e.g. Polynucleotide Shuffling & Interrupted Synthesis) and Non-stochastic Polynucleotide Reassembly to Evolve, Particularly, the Carboxy- and Amino-terminal Peptide Extensions of the Histone Protein, to Increase the Efficiency of DNA Transfer Into the Cells One example of a method to evolve an optimized nucleic acid binding domain involves the reassembly (optionally in combination with other directed evolution methods described herein) of histone genes. Histone-condensed DNA can result in increased gene transfer into cells. See, e.g., Fritz et al. (1996) Human Gene Therapy 7: 1395–1404. Thus, stochastic (e.g. polynucleotide shuffling & interrupted synthesis) and non-stochastic polynucleotide reassembly can be used to evolve the histone protein, particularly the carboxy- and amino-termninal peptide extensions, to increase the efficiency of DNA transfer into cells. In this approach, the histone is encoded by the DNA to which it will be bound.

Construction of the Histone Library

The histone library can be constructed by, for example, 1) reassembly (optionally in combination with other directed evolution methods described herein) of many related histone genes from natural diversity, 2) addition of random or partially randomized peptide sequences at the N- and C-terminal sequences of the histone, 3) by addition of pre-selected protein-encoding regions to the N- or C-termini, such as whole cDNA libraries, nuclear protein ligand libraries, etc. These proteins can be partially randomized and linked to the histone by a library of linkers.

Starting Substrates for Evolving Nucleic Acid Binding Sites Contain Variant Binding Sites and Recombinant Forms of These Sites are Screened as a Component of a Vector That Also Encodes a Nucleic Acid Binding Protein In a variation of the above procedure, a binding site recognized by a nucleic acid binding protein can be evolved instead of, or as well as, the nucleic acid binding protein. Nucleic acid binding sites are evolved by an analogous procedure to nucleic acid binding proteins except that the starting substrates contain variant binding sites and recombinant forms of these sites are screened as a component of a vector that also encodes a nucleic acid binding protein.

When the Evolved DNA Binding Protein Does Not Have a High Degree of Sequence Specificity and it is Unknown Precisely Which Sites of the Vector Used in Screening are Bound by the Protein, the Vector Should Include All or Most of the Screening Vector Sequences Together With Additional Sequences Required to Effect Vaccination or Therapy Evolved nucleic acid segments encoding DNA binding proteins and/or evolved DNA binding sites can be included in genetic vaccine vectors. If the affinity of the DNA binding protein is specific to a known DNA binding site, it is sufficient to include that binding site and the sequence encoding the DNA binding protein in the genetic vaccine vector together with such other coding and regulatory sequences are required to effect gene therapy. In some instances, the evolved DNA binding protein may not have a high degree of sequence specificity and it may be unknown precisely which sites on the vector used in screening are bound by the protein. In these circumstances, the vector should include all or most of the screening vector sequences together with additional sequences required to effect vaccination or therapy. An exemplary selection scheme which employs M 13 protein VIII is shown, described &/or referenced herein (including incorporated by reference).

Target Cells of Interest

Target cells of interest include, for example, muscle cells, monocytes, dendritic cells, B cells, Langerhans cells, keratinocytes, M-cells of the gut, and the like. Cell-specific ligands that are suitable for use with each of the cell types are known to those of skill in the art. For example, suitable proteins to direct binding to antigen presenting cells include CD2, CD28, CTLA-4, CD40 ligand, fibrinogen, factor X, ICAM-1, -glycan (zymosan), and the Fc portion of immunoglobulin G. (Weir's Handbook of Experimental Immunology, Eds. L. A. Herzenberg, D. M. Weir, L. A. Herzenberg, C. Blackwell, 5th edition, volume IV, chapters 156 and 174) because their respective ligands are present on APCs, including dendritic cells, monocytes/macrophages, B cells, and Langerhans cells. Bacterial enterotoxins or subunits thereof are also of interest for targeting purposes.

LPS Ffacilitates the Interaction Between Vector and Monocytes and is Also Llikely to act as an Aadjuvant, Further Potentiating the Immune Responses The ability of the vectors to enter and activate APC, such as monocytes, can also be enhanced by coating the vectors with small quantities of lipopolysaccharide (LPS). This facilitates the interaction between vector and monocytes, which have a cell surface receptor for LPS. Due to its immunostimulatory activities, LPS is also likely to act as an adjuvant, thereby further potentiating the immune responses.

Receptor Binding Components of Enterotoxins can be Evolved for Improved Attachment to Cell Surface Receptors, Improved Entry to and Transport Across the Cells of the Intestinal Epithelium, and Improved Binding to, and Activation of, B Cells or Other APCs Enterotoxins produced by certain pathogenic bacteria are useful as agents that bind cells and thus enhance delivery of vaccines, antigens, gene therapy vectors and pharmaceutical proteins. In an exemplary embodiment of the invention, receptor binding components of enterotoxins derived from *Vibrio cholerae* and enterotoxigenic strains of *E. coli* are evolved for improved attachment to cell surface receptors and for improved entry to and transport across the cells of the intestinal epithelium. In addition, they can be evolved for improved binding to, and activation of, B cells or other APCs. An antigen of interest can be fused to these toxin subunits to illustrate the feasibility of the approach in oral delivery of proteins and to facilitate the screening of evolved enterotoxin subunits. Examples of such antigens include growth hormone, insulin, myelin basic protein, collagen and viral envelope proteins.

Vectors That Contain the Library of Recombinant Enterotoxin Binding Moiety Nucleic Acids are Transfected Into a Population of Host Cells, Wherein the Recombinant Enterotoxin Binding Moiety Nucleic Acids are Expressed to form Recombinant Enterotoxin Binding Moiety Polypeptides These methods involve reassembling (&/or subjecting to one or more directed evolution methods described herein) at least first and second forms of a nucleic acid which comprises a polynucleotide that encodes a preferably non-toxic receptor binding moiety of an enterotoxin. The first and second forms differ from each other in two or more nucleotides, so the stochastic (e.g. polynucleotide shuffling & interrupted synthesis) and non-stochastic polynucleotide reassembly results in production of a library of recombinant enterotoxin binding moiety nucleic acids. Suitable enterotoxins include, for example, a V cholerae enterotoxin, enterotoxins from enterotoxigenic strains of *E. coli*, salmonella toxin, shigella toxin and campylobacter toxin. Vectors that contain the library of recombinant enterotoxin binding moiety nucleic acids are transfected into a population of host cells, wherein the recombinant enterotoxin binding moiety nucleic acids are expressed to form recombinant enterotoxin binding moiety polypeptides. In a preferred embodiment, the recombinant enterotoxin binding moiety polypeptides are expressed as fusion proteins on the surface of bacteriophage particles. The recombinant enterotoxin binding moiety polypeptides can be screened by contacting the library with a cell surface receptor of a target cell and determining which recombinant enterotoxin binding moiety polypeptides exhibit enhanced ability to bind to the target cell receptor. The cell surface receptor can be present on the surface of a target cell itself, or can be attached to a different cell, or binding can be tested using cell surface receptor that is not associated with a cell. Examples of suitable cell surface receptors include, for example, Gm I. Similarly, one can evolve bacterial superantigens for altered (increased or decreased) binding to T cell receptor and MHC class H molecules. These superantigens activate T cells in an antigen nonspecific manner.

Superantigens binding to T cell receptor/MHC class II molecules include Staphylococcal enterotoxin B, *Urtica dioica* superantigen (Musette et al. (1996) Eur. J Immunol. 26:618–22) and Staphylococcal enterotoxin A (Bavari et al. (1996) J Infect. Dis. 174:338–45). Phage display has been shown to be effective when selecting superantigens that bind MHC class H molecules (Wung and Gascoigne (1997) J Immunol. Methods. 204:33–41).

Both CT and CT-B Have Been Shown to Have Potent Adjuvant Activities in vivo and They Enhance Immune Responses After Oral Delivery of Antigens and Vaccines Cholera toxin (CT) is an oligomeric protein of 84,000 daltons which consists of one toxic A subunit (CT-A) covalently linked to five B subunits (CT-B). CT-B functions as the-receptor binding component and binds to $G_{M1}$, ganglioside receptors on mammalian cell surfaces. The toxic A-subunit is not necessary for the flunction of CT, and in the absence of CT-A, functional CT-B pentamers can form (Lebens and Holingren (1994) Dev. Biol. Stand. 82: 215–227). Both CT and CT-B have been shown to have potent adjuvant activities in vivo and they enhance immune responses after oral delivery of antigens and vaccines (Czerkinsky et al. (1996) Ann. NY Acad.

Sci. 778: 185–93; Van Cott et al. (1996) Vaccine 14: 392–8). Moreover, a single dose of CT-B conjugated to myelin basic protein prevented onset of autoimmune encephalomyelitis (EAE), a murine model of multiple sclerosis (Czerkinsky et al., supra.). Furthermore, feeding animals with myelin basic protein conjugated to CT-B after the onset of clinical symptoms (7 days) attenuated the symptoms in these animals. Other bacterial toxins, such as enterotoxins of *E. coli*, Salmonella toxin, Shigella toxin and Campylobacter toxin, have structural similarities with CT. Enterotoxins of *E. coli* have the same A-B structure as CT and they also have sequence homology and share ftunctional similarities.

Family Stochastic (e.g. Polynucleotide Shuffling & Interrupted Synthesis) and Non-stochastic Polynucleotide Reassembly is Feasible Among Enterotoxin-encoding Nucleic Acids From Dfferent Bacterial Species Bacterial enterotoxins can be evolved for improved affinity and entry to cells by polynucleotide (e.g. gene, promoter, enhancer, intron, & the like) reassembly (optionally in combination with other directed evolution methods described herein). The similarity of *E. coli*-derived enterotoxin subunit and CT-B is 78%, and several completely conserved regions of more than eight nucleotides can be found. B subunits from two different strains of *E. coli* are 98% homologous both at sequence and protein levels. Thus, family stochastic (e.g. polynucleotide shuffling & interrupted synthesis) and non-stochastic polynucleotide reassembly is feasible among enterotoxin-encoding nucleic acids from different bacterial species.

Screen the Secretion of Chimeric Proteins by V cholerae by Culturing the Bacteria in Agar in the Presence of Monoclonal Antibodies Specific for the Antigen That was Fused to the Toxins The libraries of experimentally evolved (e.g. by polynucleotide reassembly &/or polynucleotide site-saturation mutagenesis) toxin subunits can be expressed in a suitable host cell, such as V cholerae. For safety reasons, strains in which the toxic CT-A is deleted are preferred. An antigen of interest can be fused to the receptor-binding subunit. Secretion of chimeric proteins by V cholerae can be screened by culturing the bacteria in agar in the presence of monoclonal antibodies specific for the antigen that was fused to the toxins and the level of secretion is detected as immunoprecipitation in the agar around the colonies.

Evolving for Improved Binding to the $G_{M1}$, Ganglioside Receptor and Other Receptors, Detecting Binding Between Receptor and Chimeric Fusion Proteins With a Monoclonal Antibody Specific for the Antigen That was Fused to the Toxin One can also add GMI, ganglioside receptors to the agar in order to detect colonies secreting functional enterotoxin subunits. Colonies producing significant levels of the fusion protein are then cultured in 96-well plates, and the culture medium is tested for the presence of molecules capable of binding to cells or receptors in solution. Binding of chimeric fusion proteins to $G_{M1}$, ganglioside receptors on cell surface or in solution can be detected by a monoclonal antibody specific for the antigen that was fused to the toxin. The assay using whole cells has the advantage that one may evolve for improved binding also to receptors other than the $G_{M1}$, ganglioside receptor. When increasing concentrations of wild-type enterotoxins are added to these assays, one can detect mutants that bind to receptors with improved affinities. Affinity and specificity of toxin binding can also be determined by surface plasmon resonance (Kuziemko et al. (1996) Biochemistry 35: 6375–84).

Advantage of large scale production and avoidance of problems associated with expression on phage in the bacterial expression system The advantage of the bacterial expression system is that the fusion protein is secreted by bacteria that could potentially be used in large scale production. Moreover, because the fusion protein is in solution during selection, possible problems associated with expression on phage (such as bias towards selection of mutants that only function on phage) can be avoided.

In Phage Display, Mutants can be Easily Further Selected in in vivo Assays When Screening to Identify Enterotoxins With Improved Affinities Nevertheless, phage display is useful for screening to identify enterotoxins with improved affinities. A library of experimentally evolved (e.g. by polynucleotide reassembly &/or polynucleotide site-saturation mutagenesis) mutants can be expressed on phage, such as M 13, and mutants with improved affinity are selected based on binding to, for example, $G_{M1}$ ganglioside receptors in solution or on a cell surface. The advantage of this approach is that the mutants can be easily further selected in in vivo assays as discussed below. A screening approach using fusion to M 13 protein VIII is diagrammed herein.

The Recombinant Binding Moiety is Expressed in the Cells and Binds to the Nucleic Acid Binding Domain to Form a Vector-binding Moiety Complex Finally, the resulting evolved enterotoxin can be fused with DNA binding protein, and genetic vaccine vectors are coated with this fusion protein. The stochastic (e.g. polynucleotide shuffling & interrupted synthesis) and non-stochastic polynucleotide reassembly can be done either separately, in which case the two domains are assembled after reassembly (optionally in combination with other directed evolution methods described herein), or in a combined reaction. reassembly (optionally in combination with other directed evolution methods described herein) results in production of a library of recombinant binding moiety nucleic acids which can be screened by transfecting vectors which contain the library, as well as a binding site specific for the nucleic acid binding domain, into a population of host cells. The binding moiety is expressed in the cells and binds to the nucleic acid binding domain to form a vector-binding moiety complex. Host cells can then be lysed under conditions that do not disrupt binding of the vector-binding moiety complex.

Optimized Recombinant Binding Moiety Nucleic Acids are Isolated From Cells Containing the Vector The vector-binding moiety complex can then be contacted with a cell of interest, after which cells are identified that contain a vector and the optimized recombinant binding moiety nucleic acids are isolated from the cells.

Increasing the Number of Copies of Target DNA Taken Into Those Cells That Initially Take Up the Same DNA (Mammalian Cells)

Another method for obtaining enhanced uptake of a target DNA by mammalian cells is also provided by the invention. Specifically, the method increases the number of copies of target DNA taken into those cells that initially take up the same DNA.

Cells That Take up the Target Molecule of DNA (Cell Surface Expression of Membrane-associated DNA Binding Domains) Will Express the Factor and Have Increased Specific Affinity for Target DNA That Remains Extracellular, While Cells That did not Take up DNA Will be at a Competitive Disadvantage as They Will not Bear the Cell Surface Target DNA-specific Binding Domain, Which is Required for Specifically Mediated DNA Uptake The method uses cell surface expression of membrane-associated DNA binding domains of, for example, transcription factors, that are encoded in the target DNA sequence, which also includes the cognate recognition sequence for the binding domain. Uptake of one molecule of target DNA into a cell (by any process, passive uptake, electroporation, osmotic shock, other stress) will lead to transcription of the gene encoding the polynucleotide binding domain. The gene encoding the binding domain is engineered so that the binding domain is expressed in a membrane anchored form. For example, a hydrophobic stretch of amino acids can be encoded at the carboxyl terminus of the binding domain, thus leading to phospho-inositol-glycan (PIG) conjugation after partial cleavage of this terminal sequence. This, in turn, leads to trafficking and positioning of the binding domain on the cell surface. The same cells that took up the first molecule of DNA will express the factor and have increased specific affinity for target DNA that remains extracellular. Cells that did not take up DNA will be at a competitive disadvantage as they will not bear the cell surface target DNA-specific binding domain, which is required for specifically mediated DNA uptake.

Enhanced binding of the target DNA to the target cell will increase the efficiency of DNA internalization and desired intracellular function. This process represents a positive feedback for increased DNA uptake into cells that take up DNA first.

Practical Means for Determining Which Transcription Factor or Combination of Factors to Use With Any Particular Target DNA The target DNA, whether a circular or linear plasmid, oligonucleotide, bacterial or mammalian chromosomal fragment, is engineered to bear one or more copies of a DNA recognition sequence for a mammalian or bacterial transcription factor. Many target sequences will already bear one or more such motifs; these can be identified by sequence analysis. Endogenous motifs recognized by these factors also can be identified experimentally by demonstrating that the target DNA binds to one or more of a panel of transcription factors in an appropriate assay format. This provides a practical means for determining which factor or combination of factors to use with any particular target DNA.

Motif(s) in the Case of a Small Oligonucleotide or a DNA Plasmid and in the Cases Where More Than One DNA Binding Protein Will be Expressed on the Cell Surface In the case of a small oligonucleotide or a DNA plasmid (such as used for a DNA vaccine), appropriate motifs can be engineered into the sequence. A particular motif can be engineered in one or more copies, in tandem or dispersed in the target sequence. Alternatively, a set of different motifs can be engineered, in tandem or separated, in cases where more than one DNA binding protein will be expressed on the cell surface.

2.6.4. Evolution of Bacteriophage Vectors

Using Stochastic (e.g. Polynucleotide Shuffling & Interrupted Synthesis) and Non-stochastic Polynucleotide Rreassembly, Phage Genetics and Display Technologies to Rapidly Evolve Highly Novel, Potent, and Generic Vaccine Vehicles The invention provides methods of obtaining bacteriophage vectors that exhibit desirable properties for use as genetic vaccine vectors. The principle behind the approach provided by the invention is to combine the power of stochastic (e.g. polynucleotide shuffling & interrupted synthesis) and non-stochastic polynucleotide reassembly with the extraordinary power of bacteriophage genetics and the wealth of recent advances in phage display technologies to rapidly evolve highly novel, potent, and generic vaccine vehicles.

Methods for Delivery of Antigens From Pathogens to Professional APCs, Maximizing Efficiency Through Increasing the Kinetics and Potency of the Immune Response to the Vaccine The evolved vaccine vehicles can present antigen either (1) in native form on the surface of these APCs for the induction of an antibody response or (2) selectively invade APCs and deliver DNA vaccine constructs to APCs for intracellular expression, processing and presentation to CTLs. More efficient methods for delivery of antigens from pathogens to professional APCs will increase the kinetics and potency of the immune response to the vaccine.

Affinity Maturation Process, Essential for the Generation of Antibodies With Sufficient Affinity to Neutralize Pathogenic Antigens, Occurs in Germinal Centers (Spleen) Where Follicular Dendritic Cells Present Protein Antigens to B Cells and Processed Antigen Fragments to T Cells, Making Efficient Delivery of Antigens to FDCs Essential in Increasing the Kinetics and Potency of the Immune Response to the Immunizing Antigen Genetic vaccine delivery vehicles that are evolved according to the methods of the invention are particularly valuable for the rapid induction of high affinity antibodies which can effectively neutralize viral epitopes or pathogenic toxins such as superantigens or cholera toxin. High affinity antibodies are generated by somatic mutation of low affinity primary response antibodies. This so-called affinity maturation process is essential for the generation of antibodies with sufficient affinity to neutralize pathogenic antigens. Affinity maturation occurs in the spleen in germinal centers where follicular dendritic cells (FDCs), professional antigen presenting cells, present protein antigens to B cells and processed antigen fragments to T cells. Clonally expanding B cell populations which have undergone somatic mutation are selected for those mutant B cells expressing antibodies with improved affinity for antigen. Thus, efficient delivery of antigen to FDCs will increase the kinetics and potency of the immune response to the immunizing antigen. Additionally, processed antigen bound to MHC is required to stimulate antigen specific T cells. Genetic vaccines are particularly efficient at priming class I MHC restricted responses due to intracellular expression of antigen, with a resultant trafficking of antigen fragments to the class I MHC pathway. Thus, invasive bacteriophage vectors capable of delivery of genetic vaccine constructs or protein antigens to FDCs are useful.

Preferred Bacteriophage for the Purpose of Evolution are Those That Have Been Genetically Wwell Characterized and Developed for the Display of Foreign Protein Epitopes (of Special Note was M13 Bacteriophage, a Small Filamentous Phage Which is a Versatile, Highly Evolvable Vehicle for Efficient and Targeted Delivery of Protein or DNA Vaccine Vehicles to Cellular Targets of Interest Any of several bacteriophage can be evolved according to the methods of the invention. Preferred bacteriophage for these purposes are those that have been genetically well characterized and developed for the display of foreign protein epitopes; these include, for example, lambda, T7, and M13 bacteriophage. The filamentous phage M13 is a particularly preferred vector for use in the methods of the invention. M 13 is a small filamentous bacteriophage that has been used widely to display polypeptide fragments in functional, folded form on the surface of bacteriophage particles. Polypeptides have been fused to both the gene III and gene VIII coat proteins for such display purposes. Thus,M 13 is a versatile, highly evolvable vehicle for efficient and targeted delivery of protein or DNA vaccine vehicles to cellular targets of interest.

Improvements in Methods (Efficient Delivery of Phage, Homing to APCs, and Invasion of Target Cells Using Experimentally Evolved (e.g. by Polynucleotide Reassembly &/or Polynucleotide Site-saturation Mutagenesis) Bacterial Invasion Proteins) Exemplified for Bacteriophage Vectors and Applicable to Other Types of Genetic Vaccine Vectors The following three properties are examples of the type of improvements that can be achieved by use of the methods of the invention to evolve bacteriophage genetic vaccine vectors: (1) efficient delivery of phage to the bloodstream by inhalation or oral delivery, (2) efficient homing to APCs, and (3) efficient invasion of target cells using experimentally evolved (e.g. by polynucleotide reassembly &/or polynucleotide site-saturation mutagenesis) bacterial invasion proteins. Where Ml 3 is used, fusions can be made to both gene III and gene VIII coat proteins so that two evolved properties can be combined into a single phage particle. These studies can be performed in test animals such as laboratory mice so that the evolved constructs can be rapidly characterized with respect to their potency as vaccine vehicles. Evolved inhalable and/or orally deliverable vehicles and evolved invasins will translate directly for use in human cells, while the principles developed in evolving the ability to home to test animal APCs are readily transferable to human cells by performing analogous selections on human APCs. While these methods are exemplified for bacteriophage vectors, the methods are also applicable to other types of genetic vaccine vectors.

1 5 2.6.4.1. Evolution of Efficient Delivery of Bacteriophage Vehicles by Inhalation or Oral Delivery Method for the Formulation of Proteins Into Inhalable Colloids That can be Absorbed Into the Blood Stream Through the Lung (Preparation Involved in the Invention)

The invention provides methods for obtaining genetic vaccine vectors that are capable of efficient delivery to the bloodstream upon administration by inhalation or by oral administration. Methods have been developed for the formulation of proteins into inhalable colloids that can be absorbed into the blood stream through the lung. The mechanisms by which proteins are transported into the blood stream are not clearly understood, and thus improvements are readily approached by evolutionary methods. Using M 13 as an example, the invention involves preparation of a library of, for example, peptide ligands, adhesion molecules, bacterial enterotoxins, and 30 randomly fragmented cDNA, which are fused to gene 111, for example, of M13. Libraries of $>10^{10}$ individual fusions are readily achievable with this technology.

> M13 Phage Enters the Blood Stream, can be Recovered and Amplified in E. coli Cells, Pass Through Several Rounds of Enrichment, and be Further Characterized and Evolved by Sequencing and Reassembling (Optionally in Combination With Other Directed Evolution Methods Described Herein) the Entire Phage Genome and Subjecting the Phage to Reiterated Cycles of Delivery, Recovery, Amplification, and Reassembly (Optionally in Combination With Other Directed Evolution Methods Described Herein)

Screening involves preparation of high titer stocks (preferably $>10^{12}$ phage particles) in standard colloidal formulations which are delivered intranasally to test animals, such as mice. Blood samples are taken over the course of the ensuing day and circulating phage are amplified in E. coli. It has been established that M13 circulates for long periods in the blood after injection intravenously, and thus it is reasonable to expect that phage that successfully enter the blood stream through the lung can be efficiently recovered and amplified E. coli cells. In a preferred embodiment, several rounds of enrichment are applied to the initial libraries in order to enrich for phage that can efficiently enter the blood stream when delivered intranasally. Candidate clones are typically tested individually for their relative efficiency of entry, and the best clones can be further characterized by sequencing to identify the nature of the fusions that confer efficient delivery (of particular interest from the cDNA libraries). Selected clones can be further evolved and for improved entry by reassembling (optionally in combination with other directed evolution methods described herein) the entire phage genome and subjecting the phage to reiterated cycles of delivery, recovery, arnplification, and reassembly (optionally in combination with other directed evolution methods described herein).

> To Obtain Vaccine Vectors That are Effective When Taken Orally, Recombinant Vectors Prepared Through Reassembly (Optionally in Combination With Other Directed Evolution Methods Described Herein) are Administered, Surviving, Stable Vectors are Recovered From the Stomach, and Vectors That Efficiently Enter the Bloodstream and/or Lymphatic Tissue can be Recovered From the Blood/lymph An analogous procedure is used to obtain vaccine vectors that are effective when delivered orally. A genetic vaccine vector library is prepared by stochastic (e.g. polynucleotide shuffling & interrupted synthesis) and non-stochastic polynucleotide reassembly. The recombinant vectors are packaged and administered to a test animal. Vectors that are stable in the stomach/intestinal environment are recovered, for example, by recovering surviving vectors from the stomach. Vectors that efficiently enter the bloodstream and/or lymphatic tissue can be identified by recovering vectors that reach the blood/lymph. A schematic of this selection method is shown, described &/or referenced herein (including incorporated by reference).

2.6.4.2. Evolution of Bacteriophage Vehicles for Efficient Homing to APCs

> Two Selection Formats: the First Consisting of Enriching the Libraries of Random Peptide Ligands and cDNAs Used in (A) Above for Phage Which Selectively Bind to APCs and Using Either Negative or Positive Selection; the Second Consists of Injecting Phage Libraries Intravenously, Collecting Target Organs of Interest, Liberating the Phage by Sonication, Further Amplifying and Enriching The invention also provides methods of evolving bacteriophage vectors, as well as other types of genetic vaccine vectors, for efficient homing to professional antigen presenting cells. Libraries of random peptide ligands and cDNAs used in (A) above are enriched for phage which selectively bind to APCs by first negatively selecting for binding to non-APC cell types, and then positively selecting for binding to APCs. The selections is typically performed by mixing high titer stocks of phage from the libraries ($>10^{12}$ phage particles) with cells (~$10^7$ cells per selection cycle) and either taking the nonbinding phage (negative selection) or the binding phage from cell pellets (positive selection). An alternative selection format consists of injecting phage libraries intravenously, allowing the libraries to circulate for several hours, collecting target organs of interest (lymph node, spleen), and liberating the phage by sonication. The positively selected phage can be amplified in E. coli and further rounds of enrichment are performed (3–5 rounds) if further optimization is desired. After the chosen number of rounds, individual phage are characterized for their ability to home to lymphoid organs. The best few candidates can be subjected to further evolution through iterated rounds of selection, amplification, and reassembly (optionally in combination with other directed evolution methods described herein).

2.6.4.3. Evolution of Bacteriophage for Invasion of APCs

The methods of the invention are also useful for evolving bacteriophage and other genetic vaccine vehicles for invasion of target cells. This opens up the possibility of targeting the class I MHC antigen processing pathways with either internalized protein antigen or antigen expressed by DNA vaccine vehicles carried in by the evolved vector.

> Efficient Internalization of Pathogenic Bacteria Through Invasin Interaction With Integrins Invasins comprise a large family of bacterial proteins which interact with integrins and promote the efficient internalization of pathogenic bacteria such as Salmonella.

> Reassembly (Optionally in Combination With Other Directed Evolution Methods Described Herein) of Different Forms of Polynucleotides Encoding Invasins, Cloning as Fusions to the M13 Gene VIII Coat Protein Gene, Preparing Libraries and Mixing These Libraries With Target APCs This embodiment of the invention involves reassembling (optionally in combination with other directed evolution methods described herein) different forms of polynucleotides that encode invasins. For example, two or more genes which encode the invasin family of proteins can be experimentally evolved (e.g. by polynucleotide reassembly &/or polynucleotide site-saturation mutagenesis). The experimentally evolved (e.g. by polynucleotide reassembly &/or polynucleotide site-saturation mutagenesis) polynucleotides can be cloned as fusions to the M 13 gene VIII coat protein gene, for example, and high titer stock of such libraries will be prepared. These libraries of bacteriophage can be mixed with target APCs.

Removing Free Phage and Phage Bound to the Cell Surface

After incubation, the cells are exhaustively washed to remove free phage and phage bound to the surface of the cells can be removed by panning against polyclonal anti-M13 antibodies.

Obtaining Successful Phage, Amplifying, Reassembling (Optionally in Combination With Other Directed Evolution Methods Described Herein), and Selecting, Characterizing for Relative Invasiveness, Combing With Gene III Fusions (Encoding Pathogenic Epitopes of Interest) and Testing for Relative Abilities to Induce a CTL Response to the Pathogenic Antigens The cells are then sonicated, thus releasing phage that have successfully entered the target cells (thus protecting them from the polyclonal anti-M13 antiserum). These phage can, if desired, be amplified, experimentally evolved (e.g. by polynucleotide reassembly &/or polynucleotide site-saturation mutagenesis), and the selective cycle will be iteratively applied for, e.g., 3-times. Individual phage from the final cycle can then be characterized with respect to their relative invasiveness. The best candidates can then be combined with gene III fusions that encode pathogenic epitopes of interest. These phage can be injected into mice and tested for their relative abilities to induce a CTL response to the pathogenic antigens.

Bacteriophage vaccine vehicles evolved for activity in mice according to the above methods will establish the principles for the evolution of similar vehicles for potent human vaccines. The ability to induce more rapid and potent CTL and neutralizing antibody responses with such vehicles is an important new tool for the evolution of improved countermeasures against pathogens of interest.

2.6.5. Evolution of Improved Immunomodulatory Sequences

Cytokines can dramatically influence macrophage activation and $T_H1/T_H2$ cell differentiation, and thereby the outcome of infectious diseases. In addition, recent studies strongly suggest that DNA itself can act as adjuvant by activating the cells of the immune system. Specifically, unmethylated CpG-rich DNA sequences were shown to enhance $T_H1$ cell differentiation, activate cytokine synthesis by monocytes and induce proliferation of B lymphocytes. The invention thus provides methods for enhancing the immunomodulatory properties of genetic vaccines (a) by evolving the stimulatory properties of DNA itself and (b) by evolving genes encoding cytokines and related molecules that are involved in immune system regulation. These genes are then used in genetic vaccine vectors.

Of particular interest are IFN- (x and IL-12, which skew immune responses towards a T helper I ($T_H1$) cell phenotype and, thereby, improve the host's capacity to counteract pathogen invasions. Also provided are methods of obtaining improved immunomodulatory nucleic acids that are capable of inhibiting or enhancing activation, differentiation, or anergy of antigen-specific T cells. Because of the limited information about the structures and mechanisms that regulate these events, molecular breeding C71 techniques of the invention provide much faster solutions than rational design.

The methods of the invention typically involve the use of stochastic (e.g. polynucleotide shuffling & interrupted synthesis) and non-stochastic polynucleotide reassembly or other methods to create a library of experimentally generated (in vitro &/or in vivo) polynucleotides. The library is then screened to identify experimentally generated polynucleotides in the library, when included in a genetic vaccine vector or administered in conjunction with a genetic vaccine, are capable of enhancing or otherwise altering an immune response induced by the vector. The screening step, in some embodiments, can involve introducing a genetic vaccine vector that includes the experimentally generated polynucleotides into mammalian cells and determining whether the cells, or culture medium obtained by growing the cells, is capable of modulating an immune response.

Optimized recombinant vector modules obtained through polynucleotide reassembly (&/or one or more additional directed evolution methods described herein) are useful not only as components of genetic vaccine vectors, but also for production of polypeptides, e.g., modified cytokines and the like, that can be administered to a mammal to enhance or shift an immune response. Polynucleotide sequences obtained using the stochastic (e.g. polynucleotide shuffling & interrupted synthesis) and non-stochastic polynucleotide reassembly methods of the invention can be used as a component of a genetic vaccine, or can be used for production of cytokines and other immunomodulatory polypeptides that are themselves used as therapeutic or prophylactic reagents. If desired, the sequence of the optimized immunomodulatory polypeptide-encoding polynucleotides can be determined and the deduced amino acid sequence used to produce polypeptides using methods known to those of skill in the art.

2.6.5.1 Immunostimulatory DNA Sequences

The invention provides methods of obtaining polynucleotides that are immunostimulatory when introduced into a mammal. Oligonucleotides that contain hexamers with a central CpG flanked by two 5' purines (GpA or ApA) and two 3' pyrimidines (TpC or TpT) efficiently induce cytokine synthesis and B cell proliferation (Krieg et al. (1995) Nature 374: 546; Klinman et al. (1996) Proc. Nat'l. Acad. Sci. USA 93: 2879; Pisetsky (1996) Immunity 5: 303–10) in vitro and act as adjuvants in vivo. Genetic vaccine vectors in which immunostimulatory sequence-(ISS) containing oligos are inserted have increased capacity to enhance antigen-specific antibody responses after DNA vaccination. The minimal length of an ISS oligonucleotide for functional activity in vitro is eight (Klinman et al., supra.). Twenty-mers with three CG motifs were found to be significantly more efficient in inducing cytokine synthesis than a 15-mer with two CG motifs (1d.). GGGG tetrads have been suggested to be involved in binding of DNA to cell surfaces (macrophages express receptors. for example scavenger receptors, that bind DNA) (Pisetsky et al., supra.).

According to the invention, a library is generated by subjecting to reassembly (&/or one or more additional directed evolution methods described herein) random DNA (e.g., fragments of human, murine, or other genomic DNA), oligonucleotides that contain known ISS, poly A, C, G or T sequences, or combinations thereof. The DNA, which includes at least first and second forms which differ from each other in two or more nucleotides, are reassembled (&/or subjected to one or more directed evolution methods described herein) to produce a library of experimentally generated polynucleotides.

The library is then screened to identify those experimentally generated polynucleotides that exhibit immunostimulatory properties, For example, the library can be screened for induction cytokine production in vitro upon introduction of the library into an appropriate cell type. A diagram of this procedure is shown, described &/or referenced herein (including incorporated by reference). Among the cytokines that can be used as an indicator of immunostimulatory activity are, for example, IL-2, IL-4, IL-5, IL-6, IL-10, IL-12, IL-13, IL-15, and IFN-. One can also test for changes in ratios of IL-4/IFN- y, IL-4/IL-2, IL-5/IFN-, IL-5/IL-2, IL-I 3/IFN-, IL-13/IL-2. An alternative screening method is the determination of the ability to induce proliferation of cells involved in immune responses, such as B cells, T cells, monocytes/macrophages, total PBL, and the like. Other screens include detecting induction of APC activation based on changes in expression levels of surface antigens, such as B7-1 (CD80), B7-2 (CD86), MHC class I and II, and CD14.

Other useful screens include identifying, experimentally generated polynucleotides that induce T cell proliferation. Because ISS sequences induce B cell activation, and because of several homologies between surface antigens expressed by T cells and B cells, polynucleotides can be obtained that have stimulatory activities on T cells.

Libraries of experimentally generated polynucleotides can also be screened for improved CTL and antibody responses in vivo and for improved protection from infection, cancer, allergy or autoimmunity. Experimentally generated polynucleotides that exhibit the desired property can be recovered from the cell and, if further improvement is desired, the reassembly (optionally in combination with other directed evolution methods described herein) and screening, can be repeated. Optimized ISS sequences can used as an adjuvant separately from an actual vaccine, or the DNA sequence of interest can be fused to a genetic vaccine vector.

2.6.5.2. Cytokines, Chemokines, and Accessory Molecules

The invention also provides methods for obtaining optimized cytokines, cytokine antagonists, chemokines, and other accessory molecules that direct, inhibit, or enhance immune responses. For example, the methods of the invention can be used to obtain genetic vaccines and other reagents (e.g., optimized cytokines, and the like) that, when administered to a mammal, improve or alter an immune response. These optimized immunomodulators are useful for treating infectious diseases, as well as other conditions such as inflammatory disorders, in an antigen non-specific manner.

For example, the methods of the invention can be used to develop optimized immunomodulatory molecules for treating allergies. The optimized immunomodulatory molecules can be used alone or in conjunction with antigen-specific genetic vaccines to prevent or treat allergy. Four basic mechanisms are available by which one can achieve specific immunotherapy of allergy. First, one can administer a reagent that causes a decrease in allergen-specific $T_H2$ cells. Second, a reagent can be administered that causes an increase in allergen-specific $T_H1$ cells. Third, one can direct an increase in suppressive $CD8^+$ T cells.

Finally, allergy can be treated by inducing anergy of allergen-specific T cells. In this Example, cytokines are optimized using the methods of the invention to obtain reagents that are effective in achieving one or more of these immunotherapeutic goals. The methods of the invention are used to obtain anti-allergic cytokines that have one or more properties such as improved specific activity, improved secretion after introduction into target cells, are effective at a lower dose than natural cytokines, and fewer side effects. Targets of particular interest include interferon-/, IL-10, IL-12, and antagonists of IL-4 and IL-13.

The optimized immunomodulators, or optimized experimentally generated polynucleotides that encode the immunomodulators, can be administered alone, or in combination with other accessory molecules. Inclusion of optimal concentrations of the appropriate molecules can enhance a desired immune response, and/or direct the induction or repression of a particular type of immune response. The polynucleotides that encode the optimized molecules can be included in a genetic vaccine vector, or the optimized molecules encoded by the genes can be administered as polypeptides.

In the methods of the invention, a library of experimentally generated polynucleotides that encode immunomodulators is created by subjecting substrate nucleic acids to a reassembly (&/or one or more additional directed evolution methods described herein) protocol, such as stochastic (e.g. polynucleotide shuffling & interrupted synthesis) and non-stochastic polynucleotide reassembly or other method known to those of skill in the art. The substrate nucleic acids are typically two or more forms of a nucleic acid that encodes an immunomodulator of interest.

Cytokines are among the immunomodulators that can be improved using the 0 methods of the invention. Cytokine synthesis profiles play a crucial role in the capacity of the host to counteract viral, bacterial and parasitic infections, and cytokines can dramatically influence the efficacy of genetic vaccines and the outcome of infectious diseases. Several cytokines, for example IL-I, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, IFN-, IFN-, TGF-, TNF-, TNF-, IL-20 (MDA-7), and flt-3 ligand have been shown stimulate immune responses in vitro or in vivo. Immune functions that can be enhanced using appropriate cytokines include, for example, B cell proliferation, Ig synthesis, Ig isotype switching, T cell proliferation and cytokine synthesis, differentiation of $T_H1$ and $T_H2$ cells, activation and proliferation of CTLs, activation and cytokine production by monocytes/macrophages/ dendritic cells, and differentiation of dendritic cells from monocytes/ macrophages.

In some embodiments, the invention provides methods of obtaining optimized immummomodulators that can direct an immune response towards a $T_H1$ or a $TH^2$ response. The ability to influence the direction of immune responses in this manner is of great importance in development of genetic vaccines. Altering the type of $T_H$ response can fundamentally change the outcome of an infectious disease. A high frequency of $T_H1$ cells generally protects from lethal infections with intracellular pathogens, whereas a dominant $T_H2$ phenotype often results in disseminated, chronic infections. For example, in human, the $T_H1$ phenotype is present in the tuberculoid (resistant) form of leprosy, while the $T_H2$ phenotype is found in lepromatous, multibacillary (susceptible) lesions (Yamamura et al. (1991) Science 254: 277). Late-stage AIDS patients have the $T_H2$ phenotype. Studies in family members indicate that survival from meningococcal septicemia depends on the cytokine synthesis profile of PBL, with high IL-10 synthesis being associated with a high risk of lethal outcome and high TNF-being associated with a low risk. Similar examples are found in mice. For example, BALB/c mice are susceptible to Leishmania major infection; these mice develop a disseminated fatal disease with a $TH^2$ phenotype. Treatment with anti-IL-4 monoclonal antibodies or with IL-12 induces a $T_H1$ response, resulting in healing. Anti-interferon-monoclonal antibodies exacerbate the disease. For some applications, it is preferable to direct an immune response in the direction of a $T_H2$ response.

For example, where increased mucosal immunity is desired, including protective immunity, enhancing the $T_H2$ response can lead to increased antibody production, particularly IgA. T helper ($T_H$) cells are probably the most important regulators of the immune system. $T_H$ cells are divided into two subsets, based on their cytokine synthesis pattern (Mosmann and Coffman (1989) Adv. Immunol. 46: 111). $T_H1$ cells produce high levels of the cytokines IL-2 and IFN- and no or minimal levels of IL-4, IL-5 and IL-13. In contrast, TH2 cells produce high levels of IL-4, IL-5 and IL-13, and IEL-2 and IFN- production is minimal or absent. $T_H1$ cells activate macrophages, dendritic cells and augment the cytolytic activity of $CD8^+$ cytotoxic T lymphocytes and natural killer (NK) cells (Paul and Seder (1994) Cell 76: 24 1), whereas $TH^2$ cells provide efficient help for B cells and also mediate allergic responses due to the capacity of $T_H2$ cells to induce IgE isotype switching and differentiation of B cells into IgE secreting cells (Punnonen et al. (1993) Proc. Nat'l. Acad. Sci. USA 90: 3730).

The screening methods for improved cytokines, chemokines, and other accessory molecules are generally based on identification of modified molecules that exhibit improved specific activity on target cells that are sensitive to the respective cytokine, chemokine, or other accessory molecules. A library of recombinant cytokine, chemokine, or accessory molecule nucleic acids can be expressed on phage or as purified protein and tested using in vitro cell culture assays, for example. Importantly, when analyzing the recombinant nucleic acids as components of DNA vaccines, one can identify the most optimal DNA sequences (in addition to the functions of the protein products) in terms of their immunostimulatory properties, transfection efficiency, and their capacity to improve the stabilities of the vectors. The identified optimized recombinant nucleic acids can then be subjected to new rounds of reassembly (optionally in combination with other directed evolution methods described herein) and selection.

In one embodiment of the invention, cytokines are evolved that direct differentiation of $T_H1$ cells. Because of their capacities to skew immune responses towards a $T_H1$ phenotype, the genes encoding interferon-(IFN- ) and interleukin-12 (IL-12) are preferred substrates for reassembly (&/or one or more additional directed evolution methods described herein) and selection in order to obtain maximal specific activity and capacity to act as adjuvants in genetic vaccinations. IFN- is a particularly preferred target for optimization using the methods of the invention because of its effects on the immune system, tumor cells growth and viral replication. Due to these activities, IFN- was the first cytokine to be used in clinical practice. Today, IFN- is used for a wide variety of applications, including several types of cancers and viral diseases. IFN- also efficiently directs differentiation of human T cells into $T_H1$ phenotype (Parronchi et al. (1992) J Immunol. 149: 2977). However, it has not been thoroughly investigated in vaccination models, because, in contrast to human systems, it does not affect $T_H1$ differentiation in mice.

The species difference was recently explained by data indicating that, like IL-12, IFN- induces STAT4 activation in human cells but not in murine cells, and STAT4 has been shown to be required in IL-12 mediated $T_H1$ differentiation (Thierfelder et al. (1996) Nature 382: 171).

Family stochastic (e.g. polynucleotide shuffling & interrupted synthesis) and non-stochastic polynucleotide reassembly is a preferred method for optimizing IFN-, using as substrates the mammalian IFN- genes, which are 85%–97% homologous. Greater $10^{26}$ distinct recombinants can be generated from the natural diversity in these genes. To allow rapid parallel analysis of recombinant interferons, one can employ high throughput methods for their expression and biological assay as fusion proteins on bacteriophage.

Recombinants with improved potency and selectivity profiles are being selectively bred for improved activity. Variants which demonstrate improved binding to IFN- receptors can be selected for further analysis using a screen for mutants with optimal capacity to direct $T_H1$ differentiation. More specifically, the capacities of IFN- mutants to induce IL-2 and IFN- production in in vitro human T lymphocyte cultures can be studied by cytokine-specific ELISA and cytoplasmic cytokine staining and flow cytometry.

IL-12 is perhaps the most potent cytokine that directs $T_H1$ responses, and it has also been shown to act as an adjuvant and enhance $T_H1$ responses following genetic vaccinations (Kim et al. (1997) J Immunol. 15 8: 816). IL-12 is both structurally and functionally a unique cytokine. It is the only heterodimeric cytokine known to date, composed of a 35 kD light chain (p35) and a 40 kD heavy chain (p40) (Kobayashi et al (1989) J Exp. Med. 170: 827; Stem et al. (1990) Proc. Nat'l. Acad. Sci. USA 87: 6808).

Recently Lieschke et al. ((1997) Nature Biotech. 15: 35) demonstrated that a fusion between p35 and p40 genes results in a single gene that has activity comparable to that of the two genes expressed separately. These data indicate that it is possible to reassemble IL-12 genes as one entity, which is beneficial in designing the reassembly protocol (optionally in combination with other directed evolution methods described herein). Because of its T cell growth promoting activities, one can use normal human peripheral blood T cells in the selection of the most active IL-12 genes, enabling direct selection of IL-12 mutants with the most potent activities on human T cells. IL-12 mutants can be expressed in CHO cells, for example, and the ability of the supernatants to induce T cell proliferation determined. The concentrations of IL-12 in the supernatants can be normalized based on a specific ELISA that detects a tag fused to the experimentally evolved (e.g. by polynucleotide reassembly &/or polynucleotide site-saturation mutagenesis) IL-12 molecules.

Incorporation of evolved IFN- and/or IL-12 genes into genetic vaccine vectors is expected to be safe. The safety of IFN- has been demonstrated in numerous clinical studies and in everyday hospital practice. A Phase II trial of IL-12 in the treatment of patients with renal cell cancer resulted in several unexpected adverse effects (Tahara et al. (1995) Human Gene Therapy 6: 1607). However, IL-12 gene as a component of genetic vaccines alms at high local expression levels, whereas the levels observed in circulation are minimal compared to those observed after systemic bolus injections. In addition, some of the adverse effects of systemic IL-12 treatments are likely to be related to its unusually long half-life (up to 48 hours in monkeys). stochastic (e.g. polynucleotide shuffling & interrupted synthesis) and non-stochastic polynucleotide reassembly may allow selection for a shorter half-life, thereby reducing the toxicity even after high bolus doses.

In other cases, genetic vaccines that can induce $T_H2$ responses are preferred, especially when improved antibody production is desired. As an example, IL-4 has been shown to direct differentiation of $T_H2$ cells (which produce high levels of IL-4, IL-5 and IL-13, and mediate allergic immune responses). Immune responses that are skewed towards $T_H2$ phenotype are preferred when genetic vaccines are used to immunize against autoimmune diseases prophylactically. $T_H1$ responses are also preferred when the vaccines are used to treat and modulate existing autoimmune responses, because autoreactive T cells are generally of $T_H1$ phenotype (Liblau et al. (1995) Immunol. Today 16:34–38). IL-4 is also the most potent cytokine in induction of IgE synthesis; IL-4 deficient mice are unable to produce IgE. Asthma and allergies are associated with an increased frequency of IL-4 producing cells, and are genetically linked to the locus encoding IL-4, which is on chromosome 5 (in close proximity to genes encoding IL-3, IL-5, IL-9, IL-13 and GM-CSF). IL-4, which is produced by activated T cells, basophils and mast cells, is a protein that has 153 amino acids and two potential N-glycosylation sites. Human IL-4 is only approximately 50% identical to mouse IL-4, and IL-4 activity is species-specific. In human, IL-13 has activities similar to those of IL-4, but IL-13 is less potent than IL-4 in inducing IgE synthesis. IL-4 is the only cytokine known to direct $T_H2$ differentiation.

Improved IL-2 agonists are also useful in directing $T_H2$ cell differentiation, whereas improved IL-4 antagonists can direct $T_H1$ cell differentiation. Improved IL-4 agonists and antagonists can be generated by the reassembly (optionally in combination with other directed evolution methods described herein) of IL-4 or soluble IL-4 receptor. The IL-4 receptor consists of an IL-4R-chain (140 kD high-affinity binding unit) and an IL-2R-chain (these cytokine receptors share a common 7-chain). The IL-4R-chain is shared by IL-4 and IL-13 receptor complexes. Both IL-4 and IL-13 induce phosphorylation of the IL-4R-chain, but expression of IL-4R-chain alone on transfectants is not sufficient to provide a functional IL-4R. Soluble IL-4 receptor currently in clinical trials for the treatment of allergies. Using the stochastic (e.g. polynucleotide shuffling & interrupted synthesis) and non-stochastic polynucleotide reassembly methods of the invention, one can evolve a soluble IL-4 receptor that has improved affinity for IL-4. Such receptors are useful for the treatment of asthma and other $T_H2$ cell mediated diseases, such as severe allergies. The reassembly (optionally in combination with other directed evolution methods described herein) reactions can take advantage of natural diversity present in cDNA libraries from activated T cells from human and other primates. In a typical embodiment, a experimentally evolved (e.g. by polynucleotide reassembly &/or polynucleotide site-saturation mutagenesis) IL-4R-chain library is expressed on a phage, and mutants that bind to IL-4 with improved affinity are identified. The biological activity of the selected mutants is then assayed using cell-based assays.

IL-2 and IL-15 are also of particular interest for use in genetic vaccines. IL-2 acts as a growth factor for activated B and T cells, and it also modulates the functions of NK-cells. IL-2 is predominantly produced by $T_H1$-like T cell clones, and, therefore, it is considered mainly to function in delayed type hypersensitivity reactions. However, IL-2 also has potent, direct effects on proliferation and Ig-synthesis by B cells. The complex immunoregulatory properties of IL-2 are reflected in the phenotype of IL-2 deficient mice, which have high mortality at young age and multiple defects in their immune functions including spontaneous development of inflammatory bowel disease. IL-15 is a more recently identified cytokine produced by multiple cell types. IL-15 shares several, but not all, activities with IL-2. Both IL-2 and IL-15 induce B cell growth and differentiation. However, assuming that IL-15 production in IL-2 deficient mice is normal, it is clear that IL-15 cannot substitute for the function of IL-2 in vivo, since these mice have multiple immunodeficiencies. IL-2 has been shown to synergistically enhance IL-10-induced human Ig production in the presence of anti-CD40 mAbs, but it antagonized the effects of IL-4. IL-2 also enhances IL-4-dependent IgE synthesis by purified B cells. On the other hand, IL-2 was shown to inhibit IL-4-dependent murine IgGI and IgE synthesis both in vitro and in vivo. Similarly, IL-2 inhibited IL-4-dependent human IgE synthesis by unfractionated human PBMC, but the effects were less significant than those of IFN- or IFN-. Due to their capacities to activate both B and T cells, IL-2 and IL-15 are useful in vaccinations. In fact, IL-2, as protein and as a component of genetic vaccines, has been shown to improve the efficacy of the vaccinations. Improving the specific activity and/or expression levels/kinetics of IL-2 and IL-15 through use of the stochastic (e.g. polynucleotide shuffling & interrupted synthesis) and non-stochastic polynucleotide reassembly methods of the invention increases the advantageous effects compared to wild-type IL-2 and IL-1 5.

Another cytokine of particular interest for optimization and use in genetic vaccines according to the methods of the invention is interleukin-6. IL-6 is a monocyte-derived cytokine that was originally described as a B cell differentiation factor or B cell stimulatory factor-2 because of its ability to enhance Ig levels secreted by activated B cells.

IL-6 has also been shown to enhance IL-4-induced I-E synthesis. It has also been suggested that IL-6 is an obligatory factor for human IgE synthesis, because neutralizing anti-IL-6 mAbs completely blocked IL-4-induced IgE synthesis. IL-6 deficient mice have impaired capacity to produce IgA. Because of its potent activities on the differentiation of B cells, IL-6 can enhance the levels of specific antibodies produced following vaccination. It is particularly useful as a component of DNA vaccines because high local concentrations can be achieved, thereby providing the most potent effects on the cells adjacent to the transfected cells expressing the immunogenic antigen. IL-6 with improved specific activity and/or with improved expression levels, obtained by stochastic (e.g. polynucleotide shuffling & interrupted synthesis) and non-stochastic polynucleotide reassembly, will have more beneficial effects than the wild-type IL-6.

Interleukin-8 is another example of a cytokine that, when modified according to the methods of the invention, is useful in genetic vaccines. IL-8 was originally identified as a monocyte-derived neutrophil chemotactic and activating factor. Subsequently, IL-8 was also shown to be chemotactic for T cells and to activate basophils resulting in enhanced histamine and leukotriene release from these cells. Furthermore, IL-8 inhibits adhesion of neutrophils to cytokine-activated endothelial cell monolayers, and it protects these cells from neutrophil-mediated damage. Therefore, endothelial cell derived IL-8 was suggested to 3_31 attenuate inflammatory events occurring in the proximity of blood vessel walls. IL-8 also modulates immunoglobulin production, and inhibits IL-4-induced IgG4 and IgE synthesis by both unfractionated human PBMC and purified B cells in vitro. This inhibitory effect was independent of IFN-, IFN- or prostaglandin E2. In addition, IL-8 inhibited spontaneous IgE synthesis by PBMC derived from atopic patients. Due to its capacity to attract inflammatory cells, IL-8, like other chemotactic agents, is useful in potentiating the functional properties of vaccines, including DNA vaccines (acting as an adjuvant). The beneficial effects of IL-8 can be improved by using the stochastic (e.g. polynucleotide shuffling & interrupted synthesis) and non-stochastic polynucleotide reassembly methods of the invention to obtain IL-8 with improved specific activity and/or with improved expression in target cells.

Interleukin-5, and antagonists thereof, can also be optimized using the methods of the invention for use in genetic vaccines. IL-5 is primarily produced by $T_H2$-type T cells and appears to play an important role in the pathogenesis of allergic disorders because of its ability to induce eosinophilia. IL-5 acts as an eosinophil differentiation and survival factor in both mouse and man. Blocking IL-5 activity by use of neutralizing monoclonal antibodies strongly inhibits pulmonary eosinophilia and hyperactivity in mouse models, and IL-5 deficient mice do not develop eosinophilia. These data also suggest that IL-5 antagonists may have therapeutic potential in the treatment of allergic eosinophilia.

IL-5 has also been shown to enhance both proliferation of, and Ig synthesis by, activated mouse and human B cells. However, other studies suggested that IL-5 has no effect on proliferation of human B cells, whereas it activated eosinophils. IL-5 apparently is not crucial for maturation or differentiation of conventional B cells, because antibody responses in IL-5 deficient mice are normal. However, these mice have a developmental defect in their $CD5^+$ B cells indicating that IL-5 is required for normal differentiation of this B cell subset in mice. At suboptimal concentrations of IL-4, IL-5 was shown to enhance IgE synthesis by human B cells in vitro. Furthermore, a recent study suggested that the effects of IL-5 on human B cells depend on the mode of B cell stimulation. IL-5 significantly enhanced IgM synthesis by B cells stimulated with *Moraxella catarrhalis*. In addition, IL-5 synergized with suboptimal concentrations of IL-2, but had no effect on I-synthesis by SAC-activated B cells. Activated human B cells also expressed IL-5 mRNA suggesting that IL-5 may also regulate B cell function, including I-E synthesis, by autocrine mechanisms.

The invention provides methods of evolving an IL-5 antagonist that efficiently binds to and neutralizes IL-5 or its receptor. These antagonists are useful as a component of vaccines used for prophylaxis and treatment of allergies. Nucleic acids encoding IL-5, for example, from human and other mammalian species, are experimentally evolved (e.g. by polynucleotide reassembly &/or polynucleotide site-saturation mutagenesis) and screened for binding to immobilized IL-5R for the initial screening. Polypeptides that exhibit the desired effect in the initial screening assays can then be screened for the highest biological activity using assays such as inhibition of growth of IL-5 dependent cells lines cultured in the presence of recombinant wild-type IL-5. Alternatively, experimentally evolved (e.g. by polynucleotide reassembly &/or polynucleotide site-saturation mutagenesis) IL-5R—chains are screened for improved binding to IL-5.

Tumor necrosis factors (and) and their receptors are also suitable targets for modification and use in genetic vaccines. TNF-, which was originally described as cachectin because of its ability to cause necrosis of tumors, is a 17 kDa protein that is produced in low quantities by almost all cells in the human body following activation. TNF-acts as an endogenous pyrogen and induces the synthesis of several proinflammatory cytokines, stimulates the production of acute phase proteins, and induces proliferation of fibroblasts. TNF-plays a major role in the pathogenesis of endotoxin shock. A membrane-bound form of TNF- (mTNF-), which is involved in interactions between B- and T-cells, is rapidly upregulated within four hours of T cell activation. mTNF-plays a role in the polyclonal B cell activation observed in patients infected with HIV. Monoclonal antibodies specific for mTNF- or the p55 TNF-receptor strongly inhibit IgE synthesis induced by activated $CD4^+$ T cell clones or their membranes. Mice deficient for p55 TNF-R are resistant to endotoxic shock, and soluble TNF-R prevents autoimmune diabetes mellitus in NOD mice. Phase III trials using sTNF-R in the treatment of rheumatoid arthritis are in progress, after promising results obtained in the phase II trials.

The methods of the invention can be used to, for example, evolve a soluble TNF-R that has improved affinity, and thus is capable of acting as an antagonist for TNF activity. Nucleic acids that encode TNF-R and exhibit sequence diversity, such as the natural diversity observed in cDNA libraries from activated T cells of human and other primates, are experimentally evolved (e.g. by polynucleotide reassembly &/or polynucleotide site-saturation mutagenesis). The experimentally evolved (e.g. by polynucleotide reassembly &/or polynucleotide site-saturation mutagenesis) nucleic acids are expressed, e.g., on phage, after which mutants are selected that bind to TNF- with improved affinity. If desired, the improved mutants can be subjected to further assays using biological activity, and the experimentally evolved (e.g. by polynucleotide reassembly &/or polynucleotide site-saturation mutagenesis) genes can be subjected to one or more rounds of reassembly (optionally in combination with other directed evolution methods described herein) and screening.

Another target of interest for application of the methods of the invention is interferon-y, and the evolution of antagonists of this cytokine. The receptor for IFN- consists of a binding component glycoprotein of 90 kD, a 228 amino acid extracellular portion, a transmembrane region, and a 222 amino acid intracellular region. Glycosylation is not required for functional activity. A single chain provides high affinity binding ($10^{-9}$–$10^{-10}$ M), but is not sufficient for signaling. Receptor components dimerize upon ligand binding.

The mouse IFN- receptor is 53% identical to that of mouse at the amino acid level. The human and mouse receptors only bind human and mouse IFN-, respectively. Vaccinia, cowpox and camelpox viruses have homologues of sIFN- R, which have relatively low amino acid sequence similarity (Q20%), but are capable of efficient neutralization of IFN- in vitro. These homologues bind human, bovine, rat (but not mouse) IFN-, and may have in vivo activity as IFN-antagonists. All eight cysteines are conserved in human, mouse, myxoma and Shope fibroma virus (6 in vaccinia virus) IFN-R polypeptides, indicating similar 3-D structures. An extracellular portion of mIFN-R with a kD of 100–300 pM has been expressed in insect cells. Treatment of NZB/W mice (a mouse model of human SLE) with msIFN- receptor (100 mg/three times a week i.p.) inhibits the onset of glomerulonephritis. All mice treated with sIFN- or anti-IFN-niAbs were alive 4 weeks after the treatment was discontinued, compared with 50% in a placebo group, and 78% of IFN- treated mice died.

The methods of the invention can be used to evolve soluble IFN-R receptor polypeptides with improved affinity, and to evolve IFN-w ith improved specific activity and improved capacity to activate cellular immune responses. In each case nucleic acids encoding the respective polypeptide, and which exhibit sequence diversity (e.g., that observed in cDNA libraries from activated T cells from human and other primates), are subjected to reassembly (&/or one or more additional directed evolution methods described herein) and screened to identify those recombinant nucleic acids that encode a polypeptide having improved activity. In the case of experimentally evolved (e.g. by polynucleotide reassembly &/or polynucleotide site-saturation mutagenesis) IFN-R, the library of experimentally evolved (e.g. by polynucleotide reassembly &/or polynucleotide site-saturation mutagenesis) nucleic acids can be expressed on phage, which are screened to identify mutants that bind to IFN- with improved affinity. In the case of IFN-, the experimentally evolved (e.g. by polynucleotide reassembly &/or polynucleotide site-saturation mutagenesis) library is analyzed for improved specific activity and improved activation of the immune system, for example, by using activation of monocytes/macrophages as an assay. The evolved IFN- molecules can improve the efficacy of vaccinations (e.g. when used as adjuvants). Diseases that can be treated using high-affinity sIFN-R polypeptides obtained using the methods of the invention include, for example, multiple sclerosis, systemic lupus erythematosus (SLE), organ rejection after treatment, and graft versus host disease. Multiple sclerosis, for example, is characterized by increased expression of IFN- in the brain of the patients, and increased production of IFN- by patients' T cells in vitro. IFN- treatment has been shown to significantly exacerbate the disease (in contrast to EAE in mice).

Transforming growth factor (TGF)- is another cytokine that can be optimized for use in genetic vaccines using the methods of the invention. TGF- has growth regulatory activities on essentially all cell types, and it has also been shown to have complex modulatory effects on the cells of the immune system. TGF- inhibits proliferation of both B and T cells, and it also suppresses development of and differentiation of cytotoxic T cells and NK cells, TGF- has been shown to direct IgA switching in both murine and human B cells. It was also shown to induce germline a transcription in murine and human B cells, supporting the conclusion that TGF-can specifically induce IgA switching.

Due to its capacity to direct IgA switching, TGF- is useful as a component of DNA vaccines which aim at inducing potent mucosal immunity, e.g vaccines for diarrhea. Also, because of its potent anti-proliferative effects TGF- is useful as a component of therapeutical cancer vaccines. TGF- with improved specific activity and/or with improved expression levels/kinetics will have increased beneficial effects compared to the wild-type TGF- Cytokines that can be optimized using the methods of the invention also include granulocyte colony stimulating factor (G-CSF) and granulocyte/macrophage colony stimulating factor (GM-CSF). These cytokines induce differentiation of bone marrow stem cell into granulocytes/macrophages. Administration of G-CSF and GM-CSF significantly improve recovery from bone marrow (BM) transplantation and radiotherapy, reducing infections and time the patients have to spend in hospitals. GM-CSF enhances antibody production following DNA vaccination. G-CSF is a 175 amino acid protein, while GM-CSF has 127 amino acids. Human G-CSF is 73% identical at the amino acid level to murine G-CSF and the two proteins show species cross-reactivity. G-CSF has a homodimeric receptor (dimeric with kD of ~200 pM, monomeric ~2.4 nM), and the receptor for GM-CSF is a three subunit complex. Cell lines transfected with cDNA encoding G-CSF R proliferate in response to G-CSF. Cell lines dependent of GM-CSF available (such as TF-1). G-CSF is nontoxic and is presently working very well as a drug. However, the treatment is expensive, and more potent G-CSF might reduce the cost for patients and to the health care. Treatments with these cytokines are typically short-lasting and the patients are likely to never need the same treatment again reducing likelihood of problems with immunogenicity.

The methods of the invention are useful for evolving G-CSF and/or GM-CSF which have improved specific activity, as well as other polypeptides that have G-CSF and/or GM-CSF activity. G-CSF and/or GM-CSF nucleic acids having sequence diversity, e.g., those obtained from cDNA libraries from diverse species, are experimentally evolved (e.g. by polynucleotide reassembly &/or polynucleotide site-saturation mutagenesis) to create a library of experimentally evolved (e.g. by polynucleotide reassembly &/or polynucleotide site-saturation mutagenesis) G-CSF and/or GM-CSF genes. These libraries can be screened by, for example, picking colonies, transfecting the plasmids into a suitable host cell (e.g., CHO cells), and assaying the supernatants using receptor-positive cell lines. Alternatively, phage display or related techniques can be used, again using receptor-positive cell lines. Yet another screening method involves transfecting the experimentally evolved (e.g. by polynucleotide reassembly &/or polynucleotide site-saturation mutagenesis) genes into G-CSF/GM-CSF-dependent cell lines. The cells are grown one cell per well and/or at very low density in large flasks, and the cells that grow fastest are selected. Experimentally evolved (e.g. by polynucleotide reassembly &/or polynucleotide site-saturation mutagenesis) genes from these cells are isolated; if desired, these genes can be used for additional rounds of reassembly (optionally in combination with other directed evolution methods described herein) and selection.

Ciliary neurotrophic factor (CNTF) is another suitable target for application of the methods of the invention. CNTF has 200 amino acids which exhibit 80% sequence identity between rat and rabbit CNTF polypeptides. CNTF has IL-6-like inflammatory effects, and induces synthesis of acute phase proteins. CNTF is a cytosolic protein which belongs to the IL-6/IL-11I/LIF/oncostatin M-family, and becomes biologically active only after becoming available either by cellular lesion or by an unknown release mechanism. CNTF is expressed by myelinating Schwann cells, astrocytes and sciatic nerves.

Structurally, CNTF is a dimeric protein, with a novel anti-parallel arrangement of the subunits. Each subunit adopts a double crossover four-helix bundle fold, in which two helices contribute to the dimer interface. Lys-155 mutants lose activity, and some Glu-153 mutants have 5–10 higher biological activity. The receptor for CNTF consists of a specific CNTF receptor chain, gpl 30, and a LIF-r eceptor. The CNTFR-chain lacks a transmembrane domain portion, instead being GPI-anchored. At high concentration, CNTF can mediate CNTFR-independent responses. Soluble CNTFR binds CNTF and thereafter can bind to LIFR and induce signaling through gp 130. CNTF enhances survival of several types of neurons, and protects neurons in an animal model of Huntington disease (in contrast to NGF, neurotrophic factor, and neurotrophin-3). CNTF receptor knockout mice have severe motor neuron deficits at birth, and CNTF knockout mice exhibit such deficits postnatally. CNTF also reduces obesity in mouse models. Decreased expression of CNTF is sometimes observed in psychiatric patients. Phase I studies in patients with ALS (annual incidence ~1/100 000, 5% familiar cases, 90% die within 6 years) found significant side effects after doses higher than 5 mg/kg/day subcutaneously (including anorexia, weight loss, reactivation of herpes simplex virus (HSV1), cough, increased oral secretions). Antibodies against CNTF were detected in almost all patients, thus illustrating the need for alternative CNTF with different immunological properties.

The reassembly (&/or one or more additional directed evolution methods described herein) and screening methods of the invention can be used to obtain modified CNTF polypeptides that exhibit decreased immunogenicity in vivo; higher also obtainable using the methods. reassembly (optionally in combination with other directed evolution methods described herein) is conducted using nucleic acids encoding CNTF. In a preferred embodiment, an IL-6/LIF/ (CNTF) hybrid is obtained by reassembly (optionally in combination with other directed evolution methods described herein) using an excess of oliconucleotides that encode to the receptor binding sites of CNTF. Phage display can then be used to test for lack of binding to the IL-6/LIF receptor.

This initial screen is followed by a test for high affinity binding to the CNTF receptor, and, if desired, functional assays using CNTF responsive cell lines. The experimentally evolved (e.g. by polynucleotide reassembly &/or polynucleotide site-saturation mutagenesis) CNTF polypeptides can be tested to identify those that exhibit reduced immunogenicity upon administration to a mammal.

Another way in which the reassembly (&/or one or more additional directed evolution methods described herein) and screening methods of the invention can be used to optimize CNTF is to improve secretion of the polypeptide. When a CNTF cDNA is operably linked to a leader sequence of HNGF, only 35–40 percent of the total CNTF produced is secreted.

Target diseases for treatment with optimized CNTF, using either the experimentally evolved (e.g. by polynucleotide reassembly &/or polynucleotide site-saturation mutagenesis) gene in an expression vector as in DNA vaccines, or a purified protein, include obesity, amyotrophic lateral sclerosis (ALS, Lou Gehrig's disease), diabetic neuropathy, stroke, and brain surgery.

Polynucleotides that encode chemokines can also be optimized using the methods of the invention and included in a genetic vaccine vector. At least three classes of chemokines are known, based on structure: C chemokines (such as lymphotactin), C-C chemokines (such as MCP-1, MCP-2, MCP-3, MCP-4, MIP-1a, MIP-1b, RANTES), C-X-C chemokines (such as IL-8, SDF-1, ELR, Mig, IP 10) (Premack and Schall (1996) Nature Med. 2: 1174). Chemokines can attract other cells that mediate immune and inflammatory functions, thereby potentiating the immune response. Cells that are attracted by different types of chemokines include, for example, lymphocytes, monocytes and neutrophils. Generally, C-X-C chemokines are chemoattractants for neutrophils but not for monocytes, C-C chemokines attract monocytes and lymphocytes but not neutrophils, C chemokine attracts lymphocytes.

Genetic vaccine vectors can also include optimized experimentally generated polynucleotides that encode surface-bound accessory molecules, such as those that are involved in modulation and potentiation of immune responses. These molecules, which include, for example, B7-1 (CD80), B7-2 (CD86), CD40, ligand for CD40, CTLA-4, CD28, and CD 150 (SLAM), can be subjected to stochastic (e.g. polynucleotide shuffling & interrupted synthesis) and non-stochastic polynucleotide reassembly to obtain variants have altered and/or improved activities.

Optimized experimentally generated polynucleotides that encode CD1 molecules are also useful in a genetic vaccine vector for certain applications. CD1 are nonpolymorphic molecules that are structurally and functionally related to MEC molecules. Importantly, CD I has MHC-like activities, and it can function as an antigen presenting molecule (Porcelli (1995) Adv. Immunol. 59: 1). CD1 is highly expressed on dendritic cells, which are very efficient antigen presenting cells. Simultaneous transfection of target cells with DNA vaccine vectors encoding CD1 and an antigen of interest is likely to boost the immune response. Because CD1 cells, in contrast to MHC molecules, exhibit limited allelic diversity in an outbred population (Porcelli, supra.), large populations of individuals with different genetic backgrounds can be vaccinated with one CD 1 allele. The functional properties of CD1 molecules can be improved by the stochastic (e.g. polynucleotide shuffling & interrupted synthesis) and non-stochastic polynucleotide reassembly methods of the invention.

Optimized recombinant TAP genes and/or gene products can also be included in a genetic vaccine vector. TAP genes and their optimization for various purposes are discussed in more detail below. Moreover, heat shock proteins (HSP), such as HSP70, can also be evolved for improved presentation and processing of antigens. HSP70 has been shown to act as adjuvant for induction of $CD8^+$ T cell activation and it enhances immunogenicity of specific antigenic peptides (Blachere et al. (1997) J Exp. Med. 186:1315–22). When HSP70 is encoded by a genetic vaccine vector, it is likely to enhance presentation and processing of antigenic peptides and thereby improve the efficacy of the genetic vaccines. stochastic (e.g. polynucleotide shuffling & interrupted synthesis) and non-stochastic polynucleotide reassembly can be used to further improve the properties, including adjuvant activity, of heat shock proteins, such as HSP70.

Recombinantly produced cytokine, chemokine, and accessory molecule polypeptides, as well as antagonists of these molecules, can be used to influence the type of immune response to a given stimulus. However, the administration of polypeptides sometimes has shortcomings, including short half life, high expense, difficult to store (must be stored at 4° C.), and a requirement for large volumes. Also, bolus injections can sometimes cause side effects. Administration of polynucleotides that encode the recombinant cytokines or other molecules overcomes most or all of these problems. DNA, for example, can be prepared in high purity, is stable, temperature resistant, noninfectious, easy to manufacture. In addition, polynucleotide-mediated administration of cytokines can provide long-lasting, consistent expression, and administration of polynucleotides in general is regarded as being safe.

The functions of cytokines, chemokines and accessory molecules are redundant and pleiotropic, and therefore can be difficult to determine which cytokines or cytokine combinations are the most potent in inducing and enhancing antigen specific immune responses following vaccination. Furthermore, the most useful combination of cytokines and accessory molecules is typically different depending on the type of immune C, response that is desired following vaccination. As an example, IL-4 has been shown to direct differentiation of $T_H2$ cells (which produce high levels of IL-4, IL-S and IL-13, and mediate allergic immune responses), whereas IFN- a n d IL-12 direct differentiation of $T_H1$ cells (which produce high levels of IL-2 and IFN-), and mediate delayed type immune responses. Moreover, the most useful combination of cytokines and accessory molecules is also likely to depend on the antigen used in the vaccination. The invention provides a solution to this problem of obtaining an optimized genetic vaccine cocktail. Different combinations of cytokines, chemokines and accessory molecules are assembled into vectors using the methods described herein. These vectors are then screened for their capacity to induce immune responses in vivo and in vitro.

Large libraries of vectors, generated by polynucleotide (e.g. gene, promoter, enhancer, intron, & the like) reassembly (optionally in combination with other directed evolution methods described herein) and combinatorial molecular biology, are screened for maximal capacity to direct immune responses towards, for example, a $T_H1$ or $T_H2$ phenotype, as desired. A library of different vectors can be generated by assembling different evolved promoters, (evolved) cytokines, (evolved) cytokine antagonists, (evolved) chemokines, (evolved) accessory molecules and immunostimulatory sequences, each of which can be prepared using methods described herein. DNA sequences and compounds that facilitate the transfection and expression can be included. If the pathogen(s) is known, specific DNA sequences encoding immunogenic antigens from the pathogen can be incorporated into these vectors providing protective immunity against the pathogen(s) (as in genetic vaccines).

Initial screening is preferably carried out in vitro. For example, the library can be introduced into cells which are tested for ability to induce differentiation of T cells capable of producing cytokines that are indicative of the type of immune response desired. For a $T_H1$ response, for example, the library is screened to identify experimentally generated polynucleotides that are capable of inducing T cells to produce IL-2 and IFN-, while screening for induction of T cell production of IL-4, IL-5, and IL-13 is performed to identify experimentally generated polynucleotides that favor a $T_H2$ response.

Screening can also be conducted in vivo, using animal models. For example, vectors produced using the methods of the invention can be tested for ability to protect against a lethal infection. Another screening method involves injection of Leishmania major parasites into footpads of BALB/c mice (nonhealer). Pools of plasmids are injected i.v., i.p. or into footpads of these mice and the size of the footpad swelling is followed. Yet another in vivo screening method involves detection of IgE levels after infection with Nippostrongylus brasiliensis. High levels indicate a $T_H2$ response, while low levels of IgE indicate a $T_H1$ response.

Successful results in animal models are easy to verify in humans. In vitro screening can be conducted to test for human $T_H1$ or $T_H2$ phenotype, or for other desired immune response. Vectors can also be tested for ability to induce protection against infection in humans. Because the principles of immune functions are similar in a wide variety of infections, immunostimulating DNA vaccine vectors may not only be useful in the treatment of a number of infectious diseases but also in prevention of the infections, when the vectors are delivered to the sites of the entry of the pathogen (e.g., the lung or gut).

2.6.5.3. Agonists or Antagonists of Cellular Receptors

The invention also provides methods for obtaining optimized experimentally generated polynucleotides that encode a peptide or polypeptide that can interact with a cellular receptor that is involved in mediating an immune response. The optimized experimentally generated polynucleotides can act as an agonist or an antagonist of the receptor.

Cytokine Antagonists can be Used as Components of Genetic Vaccine Cocktails

Blocking immunosuppressive cytokines, rather than adding single proinflammatory cytokines, is likely to potentiate the immune response in a more general manner, because several pathways are potentiated at the same time. By appropriate choice of antagonist, one can tailor the immune response induced by a genetic vaccine in order to obtain the response that is most effective in achieving the desired effect. Antagonists against any cytokine can be used as appropriate; particular cytokines of interest for blocking include, for example, IL-4, IL-13, IL-10, and the like.

The invention provides methods of obtaining cytokine antagonists that exhibit greater effectiveness in blocking the action of the respective cytokine. Polynucleotides that encode improved cytokine antagonists can be obtained by using polynucleotide (e.g. gene, promoter, enhancer, intron, & the like) reassembly (optionally in combination with other directed evolution methods described herein) to generate a recombinant library of polynucleotides which are then screened to identify those that encode an improved antagonist. As substrates for the stochastic (e.g. polynucleotide shuffling & interrupted synthesis) and non-stochastic polynucleotide reassembly, one can use, for example, polynucleotides that encode receptors for the respective cytokine. At least two forms of the substrate will be present in the reassembly (&/or one or more additional directed evolution methods described herein) reaction, with each form differing from the other in at least one nucleotide position. In a preferred embodiment, the different forms of the polynucleotide are homologous cytokine receptor genes from different organisms. The resulting library of experimentally generated polynucleotides is then screened to identify those that encode cytokine antagonists with the desired affinity and biological activity.

As one example of the type of effect that one can achieve by including a cytokine antagonist in a genetic vaccine cocktail, as well as how the effect can be improved using the stochastic (e.g. polynucleotide shuffling & interrupted synthesis) and non-stochastic polynucleotide reassembly methods of the invention. IL-10 is discussed. The same rationale can be. applied to obtaining and using antagonists of other cytokines. Interleukin-10 (IL-10) is perhaps the most potent anti-inflammatory cytokine known to date. IL-10 inhibits a number of pathways that potentiate inflammatory responses. The biological activities of IL-10 include inhibition of MHC class II expression on monocytes, inhibition of production of IL-1, IL-6, IL-12, TNF- by monocytes/macrophages, and inhibition of proliferation and IL-2 production by T lymphocytes. The significance of IL-10 as a regulatory molecule of immune and inflammatory responses was clearly demonstrated in IL-10 deficient mice.

These mice are growth-retarded, anemic and spontaneously develop an inflammatory bowel disease (Kuhn et al. (1993) Cell 75: 263). In addition, both innate and acquired immunity to *Listeria monocytogenes* were shown to be elevated in IL-10 deficient mice (Dai et al. (1997) J Immunol. 158: 2259). It has also been suggested that genetic differences in the levels of IL-10 production may affect the risk of patients to die from complications meningococcal. infection. Families with high IL-10 production had 20-fold increased risk of fatal outcome of meningococcal. disease (Westendorp et al. (1997) Lancet 349: 170).

IL-10 has been shown to activate normal and malignant B cells in vitro, but it does not appear to be a major growth promoting cytokine for normal B cells in vivo, because IL-I0 deficient mice have normal levels of B lymphocytes and Ig in their circulation. In fact, there is evidence that IL-10 can indirectly downregulate B cell function through inhibition of the accessory cell function of monocytes. However, IL-10 appears to play a role in the growth and expansion of malignant B cells. Anti-IL-10 monoclonal antibodies and IL-10 antisense oligonucleotides have been shown to inhibit transformation of B cells by EBV in vitro. In addition, B cell lymphomas are associated with EBV and most EBV+ lymphomas produce high levels of IL-10; which is derived both from the human gene and the homologue of IL-10 encoded by EBV. AIDS-related B cell lymphomas also secrete high levels of IL-10. Furthermore, patients with detectable serum IL-10 at the time of diagnosis of intermediate/high-grade non-Hodgkin's lymphoma have short survival, further suggesting IDID in a role for IL-10 in the pathogenesis of B cell malignancies.

Antagonizing IL-10 in vivo can be beneficial in several infectious and malignant diseases, and in vaccination. The effect of blocking of IL-10 is an enhancement of immune responses that is independent of the specificity of the response. This is useful in vaccinations and in the treatment of serious infectious diseases. Moreover, an IL-10 antagonist is useful in the treatment of B cell malignancies which exhibit overproduction of IL-10 and viral IL-10, and it may also be useful in boosting general anti-tumor immune response in cancer patients. Combining an IL-10 antagonist with gene therapy vectors may be useful in gene therapy of tumor cells in order to obtain maximal immune response against the tumor cells. If the reassembly (optionally in combination with other directed evolution methods described herein) of IL-10 results in IL-10 with improved specific activity, this IL-10 molecule would have potential in the treatment of autoimmune diseases and inflammatory bowel diseases. IL-10 with improved specific activity may also be useful as a component of gene therapy vectors in reducing the immune response against vectors which are recognized by memory cells and it may also reduce the immunogenicity of these vectors.

An antagonist of IL-10 has been made by generating a soluble form of IL-10 receptor (sIL-10R; Tan et al. (1995) J Biol. Chem. 270: 12906). However, sIL-10R binds IL-10 with Kd of 560 pM, whereas the wild-type, surface-bound receptor has affinity of 35–200 pM. Consequently, 150-fold molar excess of sIL-10R is required for half-maximal inhibition of biological function of IL-10. Moreover, affinity of viral IL-10 (IL-10 homologue encoded by Epstein-Barr virus) to sIL-10R is more than 1000 fold less than that of hIL-10, and in some situations, such as when treating EBV-associated B cell malignancies, it may be beneficial if one can also block the function of viral IL-10. Taken together, this soluble form of IL-10R is unlikely to be effective in antagonizing IL-10 in vivo.

To obtain an IL-10 antagonist that has sufficient affinity and antagonistic activity to function in vivo, stochastic (e.g. polynucleotide shuffling & interrupted synthesis) and non-stochastic polynucleotide reassembly can be performed using polynucleotides that encode IL-10 receptor. IL-10 receptor with higher than normal affinity will function as an IL-10 antagonist, because it strongly reduces the amount of IL-10 available for binding to functional, wild-type IL-10R. In a preferred embodiment, IL-10R is experimentally evolved (e.g. by polynucleotide reassembly &/or polynucleotide site-saturation mutagenesis) using homologous cDNAs encoding IL-10R derived from human and other mammalian species.

An alignment of human and mouse IL-10 receptor sequences is shown, described &/or referenced herein (including incorporated by reference) to illustrate the feasibility of family stochastic (e.g. polynucleotide shuffling & interrupted synthesis) and non-stochastic polynucleotide reassembly when evolving IL-10 receptors with improved affinity. A phage library of IL-10 receptor recombinants can be screened for improved binding of experimentally evolved (e.g. by polynucleotide reassembly &/or polynucleotide site-saturation mutagenesis) IL-10R to human or viral IL-10. Wild-type IL-10 and/or viral IL-0 are added at increasing concentrations to demand for higher affinity. Phage bound to IL-10 can be recovered using anti-IL-10 monoclonal antibodies. If desired, the shuffling can be repeated one or more times, after which the evolved soluble IL-10R is analyzed in functional assays for its capacity to neutralize the biological activities of IL-10/viral IL-10. More specifically, evolved soluble IL-10R is studied for its capacity to block the inhibitory effects of IL-10 on cytokine synthesis and MHC class II expression by monocytes, proliferation by T cells, and for its capacity to inhibit the enhancing effects of IL-10 on proliferation of B cells activated by anti-CD40 monoclonal antibodies.

An IL-10 antagonist can also be generated by evolving IL-10 to obtain variants that bind to IL-10R with higher than wild-type affinity, but without receptor activation. The advantage of this approach is that one can evolve an IL-10 molecule with improved specific activity using the same methods. In a preferred embodiment, IL-10 is experimentally evolved (e.g. by polynucleotide reassembly &/or polynucleotide site-saturation mutagenesis) using homologous cDNAs encoding IL-10 derived from human and other mammalian species. In addition, a gene encoding viral IL-10 can be included in the reassembly (optionally in combination with other directed evolution methods described herein). A library of IL-10 recombinants is screened for improved binding to human IL-10 receptor. Library members bound to IL-10R can be recovered by anti-IL-10R monoclonal antibodies. This screening protocol is likely to result in IL-10 molecules with both antagonistic and agonistic activities. Because initial screen demands for higher affinity, a proportion of the agonists are likely to have improved specific activity when compared to wild-type human IL-10. The functional properties of the mutant IL-10 molecules are determined in biological assays similar to those described above for ultrahigh-affinity IL-10 receptors (cytokine synthesis and MHC class II expression by monocytes, proliferation of B and T cells). An antagonistic IL-4 mutant has been previously generated illustrating the general feasibility of the approach (Kruse et al. (1992) EMBO J. 11: 3237–3244.). One amino acid mutation in IL-4 resulted in a molecule that efficiently binds to IL-4R a-chain but has minimal IL-4-like agonistic activity.

Another example of an IL-10 antagonist is IL-20/mda-7, which is a 206 amino acid secreted protein. This protein was originally characterized as mda-7, which is a melanoma cell-derived negative regulator of tumor cell growth (Jiang et al. (1995) Oncogene 11: 2477; (1996) Proc. Nat'l. Acad. Sci. USA 93: 9160). IL-20/mda-7 is structurally related to IL-10, and it antagonizes several functions of IL-10 (Abstract of the 13th European Immunology Meeting, Amsterdam, Jun. 22–25, 1997). In contrast to IL-10, IL-20/mda-7 enhances expression of CD80 (B7-1) and CD86 (B7-2) on human monocytes and it upregulates production of TNF- and IL-6. IL-20/mda-7 also enhances production of IFN- by PHA-activated PBMC. The invention provides methods of improving genetic vaccines by incorporation of IL-20/mda-7 genes into the genetic vaccine vectors. The methods of the invention can be used to obtain IL-20/mda-7 variants that exhibit improved ability to antagonize IL-10 activity.

When a cytokine antagonist is used as a component of DNA vaccine or gene therapy vectors, maximal local effect is desirable. Therefore, in addition to a soluble form of a cytokine antagonist, a transmembrane form of the antagonist can be generated. The soluble form can be given in purified polypeptide form to patients by, for example, intravenous injection. Alternatively, a polynucleotide encoding the cytokine antagonist can be used as a component as a component of a genetic vaccine or a gene therapy vector. In this case, either or both of the soluble and transmembrane forms can be used. Where both soluble and transmembrane forms of the antagonist are encoded by the same vector, the target cells express both forms, resulting in maximal inhibition of cytokine function on the target cell surface and in their immediate vicinity.

The peptides or polypeptides obtained using these methods can substitute for the natural ligands of the receptors, such as cytokines or other costimulatory molecules in their ability to exert an effect on the immune system via the receptor. A potential disadvantage of administering cytokines or other costimulatory molecules themselves is that an autoimmune reaction could be induced against the natural molecule, either due to breaking tolerance (if using a natural cytokine or other molecule) or by inducing cross-reactive immunity (humoral or cellular) when using related but distinct molecules. Through using the methods of the invention, one can obtain agonists or antagonists that avoid these potential drawbacks. For example, one can use relatively small peptides as agonists that can mimic the activity of the natural immunomodulator, or antagonize the activity, without inducing cross-reactive immunity to the natural molecule. In a presently preferred embodiment, the optimized agonist or antagonist obtained using the methods of the invention is about 50 amino acids or length or less, more preferably about 30 amino acids or less, and most preferably is about 20 amino acids in length, or less. The agonist or antagonist peptide is preferably at least about 4 amino acids in length, and more preferably at least about 8 amino acids in length. Polynucleotides that flank the coding sequence of the mimetic peptide can also be optimized using the methods of the invention in order to optimize the expression, conformation, or activity of the mimetic peptide.

The optimized agonist or antagonist peptides or polypeptides are obtained by generating a library of experimentally generated polynucleotides and screening the library to identify those that encode a peptide or polypeptide that exhibits an enhanced ability to modulate an immune response. The library can be produced using methods such as stochastic (e.g. polynucleotide shuffling & interrupted synthesis) and non-stochastic polynucleotide reassembly or other methods described herein or otherwise known to those of skill in the art. Screening is conveniently conducted by expressing the peptides encoded by the library members on the surface of a population of replicable genetic packages and identifying those members that bind to a target of interest, e.g., a receptor.

The optimized experimentally generated polynucleotides that are obtained using the methods of the invention can be used in several ways. For example, the polynucleotide can be placed in a genetic vaccine vector, under the control of appropriate expression control sequences, so that the mimetic peptide is expressed upon introduction of the vector into a mammal. If desired, the polynucleotide can be placed in the vector embedded in the coding sequence of the surface protein (e.g., geneIII or geneVIII) in order to preserve, the conformation of the mimetic. Alternatively, the mimetic-encoding polynucleotide can be inserted directly into the antigen-encoding sequence of the genetic vaccine to form a coding sequence for a "mimotope-on-antigen" structure. The polynucleotide that encodes the mimotope-on-antigen structure can be used within a genetic vaccine, or can be used to express a protein that is itself administered as a vaccine. As one example of this type of application, a coding sequence of a mimetic peptide is introduced into a polynucleotide that encodes the "M-loop" of the hepatitis B surface antigen (HBsAg) protein. The M-loop is a six amino acid peptide sequence bounded by cysteine residues, which is found at amino acids 139–147 (numbering within the S protein sequence). The M-loop in the natural HBsAg protein is recognized by the monoclonal antibody RFHB7 (Chen et al., Proc. Nat'l. Acad. Sci. USA, 93: 1997–2001 (1996)). According to Chen et al., the M-loop forms an epitope of the HBsAg that is non-overlapping and separate from at least four other HBsAg epitopes.

Because of the probable Cys-Cys disulfide bond in this hydrophilic part of the protein, amino acids 139–147 are likely in a cyclic conformation. This structure is therefore similar to that found in the regions of the filamentous phage proteins pIII and pVIII where mimotope sequences are placed. Therefore, one can insert a mimotope obtained using the methods of the invention into this region of the HBsAg amino acid sequence.

The chemokine receptor CCR6 is an example of a suitable target for a peptide mimetic obtained using the methods. The CCR6 receptor is a 7-transmembrane domain protein (Dieu et al., Biochem. Biophys. Res. Comm. 236: 212–217 (1997) and J. Biol. Chem. 272: 14893–14898 (1997)) that is involved in the chemoattraction of immature dendritic cells, which are found in the blood and migrate to sites of antigen uptake (Dieu et al., J Exp. Med. 188: 373–386 (1998)). CCR6 binds the chemokine MIP-3, so a mimetic peptide that is capable of activating CCR6 can provide a further chemoattractant function to a given antigen and thus promote uptake by dendritic cells after immunization with the antigen antigen-mimetic fusion or a DNA vector that expresses the antigen.

Another application of this method of the invention is to obtain molecules that can act as an agonist for the macrophage scavenger receptor (MSR; see, Wloch et al., Hum. Gene Ther. 9: 1439–1447 (1998)). The MSR is involved in mediating the effects of various immunomodulators. Among these are bacterial DNA, including the plasmids used in DNA vaccination, and oligonucleotides, which are often potent immunostimulators.

Oligonucleotides of certain chemical structure (e.g., phosphothio-oligonucleotides) are particularly potent, while bacterial or plasmid DNA must be used in relatively large quantities to produce an effect. Also mediated by the MSR is the ability of oligonucleotides that contain dG residues to stimulate B cells and enhance the activity of immunostimulatory CpG motifs, and of lipopolysaccharides to activate macrophages. Some of these activities are toxic. Each of these immunomodulators, along with a variety of polyanionic ligands, binds to the MSR. The methods of the invention can be used to obtain mimetics of one or more of these immunomodulators that bind to the MSR with high affinity but are devoid of toxic properties. Such mimetic peptides are useful as immunostimulators or adjuvants.

The MSR is a trimeric integral membrane glycoprotein. The three extracellular C-terminal cysteine-rich regions are connected to the transmembrane domain by a fibrous region that is composed of an (x-helical coil and a collagen-like triple helix (see, Kodama et al., Nature 343: 531–535 (1990)). Therefore, screening of the library of experimentally generated polynucleotides can be accomplished by expressing the extracellular receptor structure and artificially attaching it to plastic surfaces. The libraries can be expressed, e.g., by phage display, and screened to identify those that bind to the receptors with high affinity.

The optimized experimentally generated polynucleotides identified by this method can be incorporated into antigen-encoding sequences to evaluate their modulatory effect on the immune response.

2.6.5.4. Costimulatory Molecules Capable of Inhibiting or Enhancing Activation, Differentiation, or Anergy of Antigen-specific T Cells Also provided are methods of obtaining optimized experimentally generated polynucleotides that, when expressed, are capable of inhibiting or enhancing the activation, differentiation, or anergy of antigen-specific T cells. T cell activation is initiated when T cells recognize their specific antigenic peptides in the context of MHC molecules on the plasma membrane of antigen presenting cells (APC), such as monocytes, dendritic cells (DC), Langerhans cells or B cells. Activation of $CD4^+$ T cells requires recognition by the T cell receptor (TCR) of an antigenic peptide in the context of MHC class II molecules, whereas $CD8^+$ T cells recognize peptides in the context of MHC class I molecules.

Importantly, however, recognition of the antigenic peptides is not sufficient for induction of T cell proliferation and cytokine synthesis. An additional costimulatory signal, "the second signal", is required. The costimulatory signal is mediated via CD28, which binds to its ligands B7-1 (CD80) or B7-2 (CD86), typically expressed on the antigen presenting cells. In the absence of the costimulatory signal, no T cell activation occurs, or T cells are rendered anergic. In addition to CD28, CTLA-4 (CD152) also functions as a ligand for B7-1 and B7-2. However, in contrast to CD28, CTLA-4 mediates a negative regulatory signal to T cells and/or to induce anergy and tolerance (Walunas et al. (1994) Immunity 1: 405; Karandikar et al. (1996) J Exp. Med. 184: 783).

B7-1 and B7-2 have been shown to be able to regulate several immunological responses, and they have been implicated to be of importance in the immune regulation in vaccinations, allergy, autoimmunity and cancer. Gene therapy and genetic vaccine vectors expressing B7-1 and/or B7-2 have also been shown to have therapeutic potential in the treatment of the above mentioned diseases and in improving the efficacy of genetic vaccines.

FIG. 39 illustrates interaction of APC and $CD4^+$ T cells, but the same principle is true with $CD8^+$ T cells, with the exception that the T cells recognize the antigenic peptides in the context of MHC class I molecules. Both B7-1 and B7-2 bind to CD28 and CTLA-4, even though the sequence similarities between these four molecules are very limited (20–30%). It is desirable to obtain mutations in B7-1 and B7-2 that only influence binding to one ligand but not to the other, or improve activity through one ligand while decreasing the activity through the other. Moreover, because the affinities of B7 molecules to their ligands appear to be relatively low, it would also be desirable to find mutations that improve/alter the activities of the molecules. However, rational design does not enable predictions of useful mutations because of the complexity of the molecules.

The invention provides methods of overcoming these difficulties, enabling one to generate and identify functionally different B7 molecules with altered relative capacities to induce T cell activation, differentiation, cytokine production, anergy and/or tolerance. Through use of the methods of the invention, one can find mutations in B7-1 and B7-2 that only influence binding to one ligand but not to the other, or that improve activity through one ligand while decreasing the activity through the other by stochastic (e.g. polynucleotide shuffling & interrupted synthesis) and non-stochastic polynucleotide reassembly is likely to be the most powerful method in discovering new B7 variants with altered relative binding capacities to CD28 and CTLA-4. B7 variants which act through CD28 with improved activity (and with decreased activity through CTLA-4) are expected to have improved capacity to induce activation of T cells. In contrast, B7 variants which bind and act through CTLA-4 with improved activity (and with decreased activity through CD28) are expected to be potent negative regulators of T cell functions and to induce tolerance and anergy. stochastic (e.g. polynucleotide shuffling & interrupted synthesis) and non-stochastic polynucleotide reassembly or other reassembly (&/or one or more additional directed evolution methods described herein) method is used to generate B7 (e.g., B7-1/CD80 and B7-2/CD86) variants which have altered relative capacity to act through CD28 and CTLA-4 when compared to wild-type B7 molecules. In a preferred embodiment, the different forms of substrate used in the reassembly (&/or one or more additional directed evolution methods described herein) reaction are B7 cDNAs from various species. Such cDNAs can be obtained by methods known to those of skill in the art, including RT-PCR-Typically, genes encoding these variant B7 molecules are incorporated into genetic vaccine vectors encoding an antigen, so that one the vectors can be used to modify antigen-specific T cell responses. Vectors that harbor B7 genes that efficiently act through CD28 are useful in inducing, for example, protective immune responses, whereas vectors that harbor genes encoding B7 genes that efficiently act through CTLA-4 are useful in inducing, for example, tolerance and anergy of allergen- or autoantigen-specific T cells. In some situations, such as in tumor cells or cells inducing autoimmune reactions, the antigen may already be present on the surface of the target cell, and the variant B7 molecules may be transfected in the absence of additional exogenous antigen gene. A screening protocol that one can use to identify B7-1 (CD80) and/or B7-2 (CD86) variants that have increased capacity to induce T cell activation or anergy is diagrammed herein, and the application of this strategy is described in more detail herein.

Several approaches for screening of the variants can be taken. For example, one can use a flow cytometry-based selection systems. The library of B7-1 and B7-2 molecules is transfected into cells that normally do not express these molecules (e.g., COS-7 cells or any cell line from a different species with limited or no cross-reactivity with man regarding B7 ligand binding). An internal marker gene can be incorporated in order to analyze the copy number per cell. Soluble CTLA-4 and CD28 molecules can be generated to for use in the flow cytometry experiments. Typically, these will be fused with the Fc portion of IgG molecule to improve the stability of the molecules and to enable easy staining by labeled anti-IgG mAbs, as described by van der Merwe et al. (J. Exp. Med: 185: 393, 1997). The cells transfected with the library of B7 molecules are then stained with the soluble CTLA-4 and CD28 molecules. Cells demonstrating increased or decreased CTLA-4/CD28 binding ratio will be sorted. The plasmids are then recovered and the experimentally evolved (e.g. by polynucleotide reassembly &/or polynucleotide site-saturation mutagenesis) B7 variant-encoding sequences identified. These selected B7 variants can then be subjected to new rounds of reassembly (optionally in combination with other directed evolution methods described herein) and selection, and/or they can be further analyzed using functional assays as described below.

The B7 variants can also be directly selected based on their functional properties. For in vivo studies, the B7 molecules can also be evolved to function on mouse cells. Bacterial colonies with plasmids with mutant B7 molecules are picked and the plasmids are isolated. These plasmids are then transfected into antigen presenting cells, such as dendritic cells, and the capacities of these mutants to activate T cells is analyzed. One of the advantages of this approach is that no assumptions on the binding affinities or specificities to the known ligands are made, and possibly new activities through yet to be identified ligands can be found. In addition to dendritic cells, other cells that are relatively easy to transfect (e.g., U937 or COS-7) can be used in the screening, provided that the "first T cell signal" is induced by, for example, anti-CD3 monoclonal antibodies. T cell activation can be analyzed by methods known to those of skill in the art, including, for example, measuring proliferation, cytokine production, CTL activity or expression of activation antigens such as IL-2 receptor, CD69 or HLA-DR molecules. Usage of antigen-specific T, cell clones, such as T cells specific for house dust mite antigen Der p I, will allow analysis of antigen-specific T cell activation (Yssel et al. (1992) J Immunol. 148: 738–745). Mutants are identified that can enhance or inhibit T cell proliferation or enhance or inhibit CTL responses. Similarly variants that have altered capacity to induce cytokine production or expression of activation antigens as measured by, for example, cytokine-specific ELISAs or flow cytometry can be identified.

The B7 variants are useful in modulating immune responses in autoimmune diseases, allergy, cancer, infectious disease and vaccination. B7 variants which act through CD28 with improved activity (and with decreased activity through CTLA-4) will have improved capacity to induce activation of T cells. In contrast, B7 variants which bind and act through CTLA-4 with improved activity (and with decreased activity through CD28) will be potent negative regulators of T cell functions and to induce tolerance and anergy. Thus, by incorporating genes encoding these variant B7 molecules into genetic vaccine vectors encoding an antigen, it is possible to modify antigen-specific T cell responses. Vectors that harbor B7 genes that efficiently act through CD28 are useful in inducing, for example, protective immune responses, whereas vectors that harbor genes encoding B7 genes that efficiently act through CTLA-4 are useful in inducing, for example, tolerance and anergy of allergen- or autoantigen-specific T cells. In some situations, such as in tumor cells or cells inducing autoimmune reactions, the antigen may already be present on the surface of the target cell, and the variant B7 molecules may be transfected in the absence of additional exogenous antigen gene.

The methods of the invention are also useful for obtaining B7 variants that have increased effectiveness in directing either $T_H1$ or $T_H2$ cell differentiation. Differential roles have been observed for B7-1 and B7-2 molecules in the regulation of T helper ($T_H$) cell differentiation (Freeman et al. (1995) Immunity 2: 523; Kuchroo et al. (1995) Cell 80: 707). $T_H$ cell differentiation can be measured by analyzing, the cytokine production profiles induced by each particular variant. High levels of IL-4, IL-5 and/or IL-13 are an indication of efficient $T_H2$ cell differentiation whereas high levels of IFN- or IL-2 production can be used as a marker of $T_H1$ cell differentiation. B7 variants with altered capacity to induce $T_H1$ or $T_H2$ cell differentiation are useful, for example, in the treatment of allergic, malignant, autoimmune and infectious diseases and in vaccination.

Also provided by the invention are methods of obtaining B7 variants that have enhanced capacity to induce IL-10 production by antigen-specific T cells. Elevated production of IL-10 is a characteristic of regulatory T cells, which can suppress proliferation of antigen-specific CD4$^+$ T cells (Groux et al. (1997) Nature 389: 737). stochastic (e.g. polynucleotide shuffling & interrupted synthesis) and non-stochastic polynucleotide reassembly is performed as described above, after which recombinant nucleic acids encoding B7 variants having enhanced capability of inducing IL-10 can be identified by, for example, ELISA or flow cytometry using intracytoplasmic cytokine staining. The variants that induce high levels of IL-10 production are useful in the treatment of allergic and autoimmune diseases.

2.6.6. Evolution of Genetic Vaccine Vectors for Increased Vaccination Efficacy and Ease of Vaccination This section discusses the application of the invention to some specific goals in genetic vaccination. Many of these goals relate to improvements in vectors used in vaccine delivery. Unless otherwise indicated the methods are applicable to both viral and nonviral vectors.

2.6.6.1. Topical Application of Genetic Vaccine Vectors

Low Efficiency of Topical Application; Protective Immune Responses Have not Been Demonstrated The invention provides methods of improving the ability of genetic vaccine vectors to induce a desired response after topical application of the vector. Adenoviral vectors topically applied to bare skin have been shown to be capable of acting as vaccine antigen delivery vehicles (Tang et al. (1997) Nature 388: 729–730). An adenoviral vector that encoded carcinoembryonic antigen (CA) was shown to induce antibodies specific for CA after application to the skin. However, the efficiency of topical application is generally quite low, and protective immune responses have not been demonstrated after topical application.

Optimizing the Topical Application Efficiency Using the Methods of the Invention The invention provides methods of obtaining vectors that exhibit improved efficiency when topically administered. Several factors can influence topical application efficiency, each of which can be optimized using the methods of the invention. For example, the invention provides methods of improving vector affinity for skin cells, improved skin cell transfection efficiency, improved persistence of the vector in skin cells (both through improved replication or through avoidance of destruction by immune cells), and improved antigen expression in skin cells, and improved induction of an immune response.

Methods of Reassembly (Optionally in Combination With Other Directed Evolution Methods Described Herein), Selection, and Screening These methods involve performing stochastic (e.g. polynucleotide shuffling & interrupted synthesis) and non-stochastic polynucleotide reassembly using as substrates plasmid, naked DNA vectors, or viral vector nucleic acids, including, for example, adenoviral vectors. Libraries of experimentally evolved (e.g. by polynucleotide reassembly &/or polynucleotide site-saturation mutagenesis) nucleic acids are screened to identify those nucleic acids that confer upon a vector an enhanced ability to induce an immune response upon topical administration. Screening can be conducted by, for example, topically applying a library of experimentally evolved (e.g. by polynucleotide reassembly &/or polynucleotide site-saturation mutagenesis) vectors to skin, either mouse skin, monkey skin, or human skin that has been transplanted to immunodeficient mice, or to normal human skin in vivo. Vectors that persist and/or provide efficient and long-lasting expression of marker gene are recovered from the skin samples. In a preferred embodiment, the desired cells are first selected by cell sorting, magnetic beads, or panning. For example, recovery can be effected through expression of a marker gene (e.g., GFP) and detecting cells that are transfected using fluorescence microscopy or flow cytometry. Cells that express the marker gene can be isolated using flow cytometry based cell sorting. Screening can also involve selection of vectors that induce the highest specific antibody or CTL responses upon administration to a test mammal, or the identification of vectors that provide an enhanced protective immune response to challenge with a corresponding pathogen. Experimentally evolved (e.g. by polynucleotide reassembly &/or polynucleotide site-saturation mutagenesis) polynucleotides are then recovered, e.g., by polymerase chain reaction, or the entire vectors can be purified from these selected cells. If desired, further optimization of topical application efficiency can be obtained by subjecting the recovered experimentally evolved (e.g. by polynucleotide reassembly &/or polynucleotide site-saturation mutagenesis) polynucleotides to new rounds of reassembly (optionally in combination with other directed evolution methods described herein) and selection.

Administration of Genetic Vaccine Vectors Optimized for Topical Application

Genetic vaccine vectors that are optimized for topical application can be applied topically to the skin, or by intramuscular, intravenous, intradermal, oral, anal, or vaginal delivery. The vector can be delivered in any of the suitable forms that are known to those of skill in the art, such as a patch, a cream, as naked DNA, or as a mixture of DNA and one or more transfection-enhancing agents such as liposomes and/or lipids. In preferred embodiments, the genetic vaccine vector is applied after the skin or other target is rendered more susceptible to uptake of the vector by, for example, mechanical abrasion, removal of hair (e.g., by treatment with a commercially available product such as Nair™, Neet™, and the like). In one embodiment, the skin is pretreated with proteases or lipases to make it more susceptible to DNA delivery. In addition, the DNA can be mixed with the proteases or lipases to enhance gene transfer. Alternatively, a droplet containing the vector and other vaccine components, if any, can simply be administered to the skin.

2.6.6.2. Enhanced Ability to Escape Host Immune System

Limitations of Host Immune Responses Directed Against the Viral Vector Sometimes Even Before Target Cells are Entered Immunogenicity is a particular concern with viral vectors, since a host immune response can prevent a virus from reaching its intended target particularly in repeated administrations. The efficacy of some viral vectors which are used for genetic vaccination and gene delivery is limited by host immune responses directed against the viral vector. For example, most individuals have pre-existing antibodies against adenovirus. Adenoviral vectors can sometimes induce strong immune responses which can destroy cells harboring adenoviral vectors or clear adenoviral vectors from the host even before target cells are entered. Cellular immune responses can also be induced against nonviral vectors administered in naked form or shielded with a coat such as liposomes.

Methods to Create Genetic Vaccine Vectors With Improved Ability to Avoid the Humoral and Cellular Immune Systems The invention provides methods to create genetic vaccine vectors that can escape immune responses that would otherwise be detrimental to obtaining the desired effect. These methods are useful for prolonging expression and secretion of pathogen antigen or pharmaceutically useful protein by genetic vaccine vectors. Several strategies are provided by which one can improve a genetic vaccine vector's ability to avoid the humoral (Ab) and cellular (CTL) immune systems. These strategies can be used in combination to obtain optimal avoidance such as may be required for highly immunogenic vectors such as adenovirus.

Incorporating Into Genetic Vaccines One or More Components That Inhibit Peptide Transport and/or MHC Class I Expression in Order to Obtain Viral Vectors That are Capable of Escaping a Host CTL Immune Response In one embodiment, the invention provides methods of obtaining viral vectors that are capable of escaping a host CTL immune response. This method can be used in conjunction with methods for obtaining genetic vaccine vectors that can escape the humoral response; the combination of approaches is often desirable, as different viral serotypes often have CTL epitopes in common, suggesting that virus variants which are not recognized by antibodies still are likely to be recognized by CTLs. This embodiment of the invention involves incorporating into genetic vaccines one or more components that inhibit peptide transport and/or MHC class I expression. An essential element in the activation of cytotoxic T lymphocyte (CTL) responses is an interaction between T cell receptors on CTLs and antigenic peptide-MH(class I molecule complexes on antigen presenting cells. Expression of MHC class I molecules on thymocytes and antigen presenting cells is a requirement for maturation and activation of antigen-specific $CD8^+$ T lymphocytes. Thus, genes that encode inhibitors of MHC class I-mediated antigen presentation can be experimentally evolved (e.g. by polynucleotide reassembly &/or polynucleotide site-saturation mutagenesis) as described herein and placed into viral vectors to obtain vectors that, when present in target cells, do not induce destruction of the target cells by the cells of the immune system. This can result in prolonged survival of cells harboring genetic vaccine vectors, including those that express a pathogen antigen, as well as vectors that express a pharmaceutically useful protein. In the case of genetic vaccines, reduced expression of MHC class I molecules will allow secretion of the pathogen antigen, which then will be presented by professional antigen presenting cells elsewhere. In the case of vectors encoding pharmaceutical proteins, reduced expression of MHC class I molecules prevents recognition by the immune system prolonging the survival of the cells expressing the gene.

Reassembly (Optionally in Combination With Other Directed Evolution Methods Described Herein) Genes That Encode Inhibitors of TAP Activity to Obtain Genes That Encode Optimized TAP Inhibitors Among the proteins involved in MHC class I molecule expression and antigen presentation are those encoded by TAP genes (transporters associated with antigen processing), which are described above. In one embodiment of the invention, genes that encode inhibitors of TAP activity are experimentally evolved (e.g. by polynucleotide reassembly &/or polynucleotide site-saturation mutagenesis) to obtain genes that encode optimized TAP inhibitors. The substrates for these methods can include, for example, one or more of the viral genes that are known to regulate levels of MHC class I molecule expression. TAP I and TAP2 gene expression is 5–10-fold and 100-fold reduced, respectively, in cells transformed by adenovirus 12, which results in reduced class I expression and thus leads to reduced virus-specific cytotoxic T lymphocyte responses. Similarly, TAP gene expression is downregulated in 49% of HPV-16$^+$ cervical carcinomas (Seliger et al. (1997) Immunol. Today 18: 292). Thus, adenovirus and HPV viral nucleic acids provide examples of suitable substrates for carrying out the methods of the invention. Additional examples of suitable stochastic (e.g. polynucleotide shuffling & interrupted synthesis) and non-stochastic polynucleotide reassembly substrates for this embodiment of the invention include the human cytomegalovirus (CMV) encoded genes US2, US3 and US 11, which can downregulate MHC class I expression (Wiertz et al. (1996) Nature 384: 432 and Cell (1996) 84: 769; Ahn et al. (1996) Proc. Nat'l. Acad Sci. USA 93: 10990). Another human CMV gene that encodes an inhibitor of TAP-dependent peptide translocation is US6 (Lehner et al. (1997) Proc. Nat'l. Acad Sci. USA 94: 6904–9). Cells transfected with US6 had reduced expression of MHC class I molecules on their surface and reduced capacity to activate cytotoxic T lymphocytes.

Reassembly (Optionally in Combination With Other Directed Evolution Methods Described Herein) This 7 kb Cluster of Genes in Order to Find the Most Potent Sequence for Inhibiting the Expression of MHC Class I Molecules, Which can also be Used for Generation of Animal Models Thus, in one embodiment, the invention involves stochastic (e.g. polynucleotide shuffling & interrupted synthesis) and non-stochastic polynucleotide reassembly of this cluster of genes (approximately 7 kb), or fragments thereof, in order to identify the sequences that are most potent in inhibiting the expression of MHC class I molecules. Such optimized TAP inhibitor polynucleotide sequences are useftil not only for use in constructing vectors that can escape CTL immune responses, but also for generation of animal models for use with human viruses that normally are eliminated in laboratory animals due to their immunogenicity. The desired expression levels and functional properties of TAP inhibitors may vary depending on whether genetic vaccine vector, gene therapy vector or animal model is evolved.

Reassembly (Optionally in Combination With Other Directed Evolution Methods Described Herein) Other Genes Involved in Downregulating Expression of MHC Class I Molecules and/or Antigen Presentation Alternative embodiments of the invention involve stochastic (e.g. polynucleotide shuffling & interrupted synthesis) and non-stochastic polynucleotide reassembly of other genes that are involved in downregulating expression of MHC class I molecules and/or antigen presentation. Examples of other possible target genes include genes encoding adenoviral E3 protein, herpes simplex ICP47 protein, and tapasin antagonists (Seliger et al. (1997) Immunol. Today 18:292–299; Galoncha et al. (1997) J Exp. Med. 185: 1565–1572; Li et al. (1997) Proc. Nat'l. Acad. Sci. USA 94: 8708–8713; Ortmann et al. (1997) Science 277: 1306–1309.

A Gene That Encodes an MHC-like Molecule That Inhibits NK Cell Function but is Unable to Present Antigens to T Lymphocytes Because reduced expression of MHC class I molecules on cell surfaces may act as a stimulus for NK cells, it may be useful to include in genetic vaccine vectors a gene that encodes an MHC like molecule that inhibits NK cell function but is unable to present antigens to T lymphocytes. An example of such molecule is MHC class I homologue encoded by cytomegalovirus (Farrell et al. (1997) Nature 3 86: 510–514).

Obtaining Viral Vectors That Exhibit an Enhanced Capability of Avoiding Attack by CD4+ T Lymphocytes The invention also provides methods of obtaining viral vectors that exhibit an enhanced capability of avoiding attack by CD4$^+$ T lymphocytes. Such vectors are particularly useful in situations where the target cells are capable of expressing MHC class II molecules, such as in the case of vaccinations and gene therapy targeted to the cells of the immune system. Substrates for stochastic (e.g. polynucleotide shuffling & interrupted synthesis) and non-stochastic polynucleotide reassembly include genes that encode inhibitors of MHC class II molecules such as, for example, IL-10 and antagonists of IFN- (such as soluble IFN- receptor).

Improving Sequences That Result in Inhibition of MHC Class I Expression, MHC Class II Expression, and Additional Sequences That Encode Homologs of MHC Class I Molecules Vectors that have the greatest capability of escaping the host immune system, will typically include DNA sequences that result in inhibition of MHC class I expression and MHC class II expression, and additional sequences that encode homologs of MHC class I molecules. The properties of all these can be further improved by stochastic (e.g. polynucleotide shuffling & interrupted synthesis) and non-stochastic polynucleotide reassembly according to the methods of the invention.

Methods for Screening the Library to Identify Those Polynucleotides That Exhibit the Desired Effect on the Host Immune Response Once a library of experimentally evolved (e.g. by polynucleotide reassembly &/or polynucleotide site-saturation mutagenesis) DNA molecules is obtained, any of several methods are available for screening the library to identify those polynucleotides that, when present in a viral vector (or in an animal model) exhibit the desired effect on the host immune response. For example, to obtain experimentally evolved (e.g. by polynucleotide reassembly &/or polynucleotide site-saturation mutagenesis) polynucleotides that inhibit MHC class I expression and/or antigen presentation, a library of experimentally evolved (e.g. by polynucleotide reassembly &/or polynucleotide site-saturation mutagenesis) genes can be incorporated into genetic vaccine or gene therapy vectors and transfected into human cell lines, such as, for example, HeLa, U937 or Jijoye, in a single tube transfection. Primary human monocytes, or dendritic cells generated by culturing human cord blood cells or monocytes in the presence of IL-4 and GM-CSF, are also suitable. Initial screening can be done using FACS-sorting.

Cells Expressing the Lowest Levels of MHC Class I Molecules are Expected to have the Lowest Capacity to Induce CTL Responses Cells expressing the lowest levels of MHC class I molecules are selected, the polynucleotides that encode the MHC inhibitors, or whole plasmids containing the sequences, are recovered. If desired, the selected sequences can be subjected to new rounds of reassembly (optionally in combination with other directed evolution methods described herein) and selection. Cells expressing the lowest levels of MHC class I molecules are expected to have the lowest capacity to induce CTL responses.

Screening Method: Injecting Library of Experimentally Evolved (e.g. by Polynucleotide Reassembly &/or Polynucleotide Site-saturation Mutagenesis) Polynucleotides That Encode Inhibitors of MHC Class I Expression Incorporated Into HPV Vectors Another screening method involves incorporating libraries of experimentally evolved (e.g. by polynucleotide reassembly &/or polynucleotide site-saturation mutagenesis) polynucleotides that encode inhibitors of MHC class I expression are incorporated into human papillomavirus (HPV) vectors. This library is injected into the skin of mice.

Normally Murine Cells Expressing HPV are Destroyed by the Host Immune System, Cells Expressing Potent Inhibitors of Peptide Transportation and/or MHC Class Expression Will be Able to Escape the Immune Response However, cells expressing potent inhibitors of peptide transportation and/or MHC class expression will be able to escape the immune response. The cells that express a marker gene present on the vector, such as GFP, for extended periods of time are selected, the sequences or whole plasmids are recovered, and, if further optimization is desired, the selected sequences are subjected to new rounds of reassembly (optionally in combination with other directed evolution methods described herein) and selection. Long-lasting maintenance of HPV in mice will allow drug screening and vaccine studies, which to date have not been possible due to high immunogenicity of HPV in mice.

Evolved Inhibitors Will Block Efficient Presentation of Immunogenic Peptides, and Hence, Will Strongly Downregulate Activation of Antigen-specific CTLs Allowing Long-lasting Transgene Expression in vivo In another embodiment, the libraries of experimentally evolved (e.g. by polynucleotide reassembly &/or polynucleotide site-saturation mutagenesis) polynucleotides encoding inhibitors of MHC class I expression are incorporated into human adenovirus vectors. This library is transfected into human cell lines, such as HeLa cells, and cells expressing the lowest levels of MHC class I molecules are selected as described above. The sequences that provide the lowest levels of MHC class I expression are further tested by analyzing the capacity of antigen-presenting cells transfected with adenovirus harboring evolved inhibitors of MHC class I expression to activate specific T cell lines or clones.

These inhibitors will block efficient presentation of immunogenic peptides, and hence, will strongly downregulate activation of antigen-specific CTLs allowing long-lasting transgene expression in vivo.

Methods to Screen for Inhibitors

Methods to screen for improved inhibitors of MHC class II expression include detection of MHC class II molecules on the surface of the target cells by fluorescent labeled specific monoclonal antibodies, fluorescence microscopy, and flow cytometry. In addition, the inhibitors can be analyzed in fuinctional assays by studying the capacity of the inhibitors to block activation of MHC class II restricted antigen-specific CD4$^+$ T lymphocytes. For example, one can determine the capacity of the inhibitor to inhibit induction of CD4$^+$ T cell proliferation induced by autologous antigen presenting cells, such as monocytes, dendritic cells, B cells or EBV-transformed B cell lines, that harbor genes encoding the MHC class II inhibitor or have been treated with supernatant containing the inhibitor.

2.6.6.3. Enhanced Antiviral Activity

Obtaining a Recombinant Viral Vector Which has an Enhanced Ability to Induce an Antiviral Response in a Cell The invention also provides methods of obtaining a recombinant viral vector which has an enhanced ability to induce an antiviral response in a cell. These methods can include the steps of:
(1) reassembling (&/or subjecting to one or more directed evolution methods described herein) at least first and second forms of a nucleic acid which comprise a viral vector, wherein the first and second forms differ from each other in two or more nucleotides, to produce a library of recombinant viral vectors;
(2) transfecting the library of recombinant viral vectors into a population of mammalian cells;
(3) staining the cells for the presence of Mx protein; and
(4) isolating recombinant viral vectors from cells which stain positive for Mx protein, wherein recombinant viral vectors from positive staining cells exhibit enhanced ability to induce an antiviral response.

Stochastic (e.g. polynucleotide shuffling & interrupted synthesis) and non-stochastic polynucleotide reassembly is used to produce a library of recombinant viral vectors. The library is transfected into a population of mammalian cells, which are then tested for ability to induce an antiviral response. One suitable test involves staining the cells for the presence of Mx protein, which is produced by cells that are exhibiting an antiviral response (see, e.g., Hallirnen et al. (1997) Pediatric Research 41: 647–650; Melen et al. (1994) J Biol. Chem. 269: 2009–2015).

Recombinant viral vectors can be isolated from cells which stain positive for Mx protein. These recombinant viral vectors from positive staining cells are enriched for those that exhibit enhanced ability to induce an antiviral response. Viral vectors for which this method is useful include, for example, influenza virus.

2.6.6.4. Evolution of Vectors Having Increased Copy Number in Production Cells

Desirability of Method to Increase the Plasmid Copy Number After all Elements Have Been Cloned in the Vector, Especially When the Plasmid is to be Manufactured on a Large Scale The invention provides methods for obtaining vector components that, when present in a genetic vaccine vector (such as a plasmid) the ability to replicate to a high copy number in a cell used to produce the vector. Plasmids can incorporate various heterologous DNA sequences, however the size or the nature of the cloned sequences in a given plasmid vector may render that vector less able to grow to high copy number in the bacteria in which it is propagated. It is therefore desirable to have a method to increase the plasmid copy number after all elements have been cloned into the vector. This is especially important when the plasmid is to be manufactured on a large scale as will be the case for genetic vaccines.

Incorporating Into the Plasmid One or More Polynucleotide Sequences That Bind Proteins Which Would Otherwise be Toxic to the Bacterium The methods of the invention involve incorporating into the plasmid one or more polynucleotide sequences that bind proteins which would otherwise be toxic to the bacterium. One suitable toxic moiety and binding site combination is the transcription factor GATA-1 and its recognition site. It has been shown that expression of a DNA-binding fragment of GATA-1 is toxic to bacteria; this toxicity apparently results from inhibition of bacterial DNA replication. Trudel et al. ((1996) Biotechniques 20: 684–693) have described a plasmid (PGATA) that expresses the Z2B2 region of GATA-1 as a GST fusion protein. The expression of the fusion protein in this plasmid is under the control of the IPTG-inducible lac promoter. The GST-GATA-1 fragment also binds strongly to a sequence from the mouse -globin gene promoter as well as to the C-oligonucleotide from the -globin gene 3' enhancer; either or both of these are suitable for use as binding sites in the methods of the invention.

Including Only a Single Form of the Selectable Marker in the Shuffling Reaction to Achieve Significant Diversity in the Experimentally Evolved (e.g. by Polynucleotide Reassembly &/or Polynucleotide Site-saturation Mutagenesis) Library to Recover a Plasmid Which is Improved in its Growth Properties While Fully Retaining the Appropriate Selection Function of the Plasmid The plasmids preferably also include a selectable marker such as, for example, kanamycin resistance (aminoglycoside 3'-phosphotransferase (EC 2.7.1.95)) and the like. The plasmid backbone polynucleotide sequence is subjected to stochastic (e.g. polynucleotide shuffling & interrupted synthesis) and non-stochastic polynucleotide reassembly as described herein to generate a library of plasmids which have different backbone sequences and possibly different supercoil densities. In order to introduce sufficient sequence diversity to search for improved function, it is preferable to perform family stochastic (e.g. polynucleotide shuffling & interrupted synthesis) and non-stochastic polynucleotide reassembly. This can be accomplished in the context of the present invention by including in the reassembly (optionally in combination with other directed evolution methods described herein) reaction(s) only a single form of the selectable marker. In this way, significant diversity can be achieved in the experimentally evolved (e.g. by polynucleotide reassembly &/or polynucleotide site-saturation mutagenesis) library to recover a plasmid which is improved in its growth properties while fully retaining the appropriate selection function of the plasmid.

Selecting for Hgh Copy Number Plasmids

The selection for high copy number plasmids is performed by introducing the library of experimentally evolved (e.g. by polynucleotide reassembly &/or polynucleotide site-saturation mutagenesis) recombinant plasmids into the desired host cell. The host cells also express the toxic moiety, preferably under the control of a promoter which is inducible. For example, the pGATA plasmid is suitable for use in *E. coli* host cells. The experimentally evolved (e.g. by polynucleotide reassembly &/or polynucleotide site-saturation mutagenesis) plasmids are introduced into the cells under non-inducing conditions. Transformed cells are then placed under conditions which induce expression of the toxic moiety. For example, *E. coli* cells that contain pGATA can be placed on media containing increasing concentrations of IPTG. Those target plasmids which grow to high copy number in the bacteria will express correspondingly higher numbers of the binding sequences for GATA-1. The target plasmids will bind the GST-GATA-1 fusion protein and thus neutralize the toxic effects on the bacteria. Plasmids with the highest copy number are detected as those which confer the best growth to bacteria on the inducer-containing growth media. Such plasmids can be recovered and transformed into bacteria which lack the gene that encodes the toxic moiety; these plasmids should retain their high copy number characteristics. Further rounds of reassembly (optionally in combination with other directed evolution methods described herein) can be used to isolate high copy numnber plasmids by the above selection procedure. Alternatively, manual screening can be done in the bacterial host of choice, lacking the toxic moiety-encoding plasmid, to avoid any effects due to the presence of this extraneous plasmid.

2.7. OPTIMIZATION OF TRANSPORT AND PRESENTATION OF ANTIGENS

The invention also provides methods of obtaining genetic vaccines and accessory molecules that can improve the transport and presentation of antigenic peptides. A library of experimentally generated polynucleotides is created and screened to identify those that encode molecules that have improved properties compared to the wild-type counterparts. The polynucleotides themselves can be used in genetic vaccines, or the gene products of the polynucleotides can be utilized for therapeutic or prophylactic applications.

2.7.1. Proteasomes

The class I peptides presented on major histocompatibility complex molecules are generated by cellular proteasomes. Interferon-gamma can stimulate antigen presentation, and part of the mechanism of action of interferon may be due to induction of the proteasome beta-subunits LMP2 and LMP7, which replace the homologous beta-subunits Y (delta) and X (epsilon). Such a replacement changes the peptide cleavage specificity of the proteasome and can enhance class I epitope immunogenicity. The Y (delta) and X (epsilon) subunits, as well as other recently discovered proteasome subunits such as the MECL-1 homologue MC 14, are characteristic of cells which are not specialized in antigen presentation. Thus, the incorporation into cells by DNA transfer of LMP2, LMP7, MECL-1 and/or other epitope presentation-specific and potentially interferon-inducible subunits can enhance epitope presentation. It is likely that the peptides generated by the proteasome containing the interferon-inducible subunits are transported to the endoplasmic reticulum by the TAP molecules.

The invention provides methods of obtaining proteasomes that exhibit increased or decreased ability to specifically process MHC class I epitopes. According to the methods, stochastic (e.g. polynucleotide shuffling & interrupted synthesis) and non-stochastic polynucleotide reassembly is used to obtain evolved proteins that can either have new specificities which might enhance the immunogenicity of some proteins and/or enhance the activity of the subunits once they are bound to the proteasome. Because the transition from a non-specific proteasome to a class I epitope-specific proteasome can pass through several states (in which some but not all of the interferon-inducible subunits are associated with the proteasome), many different proteolytic specificities can potentially be achieved. Evolving the specific LMP-like subunits can therefore create new proteasome compositions which have enhanced functionality for the presentation of epitopes.

The methods involve performing stochastic (e.g. polynucleotide shuffling & interrupted synthesis) and non-stochastic polynucleotide reassembly using as substrates two or more forms of polynucleotides which encode proteasome components, where the forms of polynucleotides differ in at least one nucleotide. reassembly (optionally in combination with other directed evolution methods described herein) is performed as described herein, using polynucleotides that encode any one or more of the various proteasome components, including, for example, LMP2, LMP7, MECL-1 and other individual proteasome components that are specifically involved in class I epitope presentation. Examples of suitable substrates are described in, e.g., Stoliwasser et al. (1997) Eur. J Immunol. 27: 1182–1187 and Gaczynska et al. (1996) J Biol. Chem. 271: 17275–17280. In a preferred embodiment, polynucleotide reassembly (optionally in combination with other directed evolution methods described herein) is used, in which the different substrates are proteasome component-encoding polynucleotides from different species.

After the reassembly (&/or one or more additional directed evolution methods described herein) reaction is completed, the resulting library of experimentally generated polynucleotides is screened to identify those which encode proteasome components having the desired effect on class I epitope production. For example, the experimentally generated polynucleotides can be introduced into a genetic vaccine vector which also encodes a particular antigen of interest. The library of vectors can then be introduced into mammalian cells which are then screened to identify cells which exhibit increased antigen-specific imrmunogenicity. Methods of analyzing proteasome activity are described in, for example, Groettrup et al. (1997) Proc. Nat'l. Acad. Sci. USA 94: 8970–8975 and Groettrup et al. (1997) Eur. J. Immunol. 26: 863–869.

Alternatively, one can use the methods of the invention to evolve proteins which bind strongly to the proteasome but have decreased or no activity, thus antagonizing the proteasome activity and diminishing a cells ability to present class I molecules. Such molecules can be applied to gene therapy protocols in which it is desirable to lower the immunogenicity of exogenous proteins expressed in the cells as a result of the gene therapy, and which would otherwise be processed for class I presentation allowing the cell to be recognized by the immune system. Such high-affinity low-activity LMP-like subunits will demonstrate immuno suppressive effects which are also of use in other therapeutic protocols where cells expressing a non-self protein need to be protected from an immune response. The specificity of the proteasome and the TAP molecules (discussed below) may have co-evolved naturally. Thus it may be important that the two pathways of the class I processing system be functionally matched. A further aspect of the invention involves performing stochastic (e.g. polynucleotide shuffling & interrupted synthesis) and non-stochastic polynucleotide reassembly simultaneously on the two gene families followed by random combinations of the two in order to discover appropriate matched proteolytic and transport specificities.

2.7.2. Antigen Transport

The invention provides methods of improving transport of antigenic peptides from the cytosolic compartment to the endoplasmic reticulum. and thereby to the cell surface in the context of MHC class I molecules. Enhanced expression of antigenic peptides results in enhanced immune response, particularly in improved activation of $CD8^+$ cytotoxic lymphocytes. This is useful in the development of DNA vaccines and in gene therapy.

In one embodiment, the invention involves evolving TAP-genes (transporters associated with antigen processing) to obtain genes that exhibit improved antigen presentation. TAP genes are members of ATP-binding cassette family of membrane translocators. These proteins transport antigenic peptides to MHC class I molecules and are involved in the expression and stability of MHC class I molecules on the cell surface. Two TAP genes, TAP1 and TAP2, have been cloned to date (Powis et al. (1996) Proc. Nat'l. Acad. Sci. USA 89: 1463–1467; Koopman et al. (1997) Curr. Opin. Immunol. 9: 80–88; Monaco (1995) J Leukocyte Biol. 57: 543–57). TAP1 and TAP2 form a heterodimer and these genes are required for transport of peptides into the endoplasmic reticulum, where they bind to MHC class I molecules. The essential role of TAP gene products in presentation of antigenic peptides was demonstrated in mice with disrupted TAP genes. TAP 1-deficient mice have drastically reduced levels of surface expression of MHC class I, and positive selection of $CD8^+$ T cells in the thymus is strongly reduced. Therefore, the number of $CD8^+$ T lymphocytes in the periphery of TAP-deficient mice is extremely low. Transfection of TAP genes back into these cells restores the level of MHC class I expression.

TAP genes are a good target for polynucleotide (e.g. gene, promoter, enhancer, intron, & the like) reassembly (optionally in combination with other directed evolution methods described herein) because of natural polymorphism and because these genes of several mammalian species have been cloned and sequenced, including human (Beck et al. (1992) J Mol. Biol. 228: 433–441; Genbank Accession No. Y13582; Powis et al., supra.), gorilla TAP1 (Laud et al. (1996) Human Immunol. 50: 91–102), mouse (Reiser et al. (1988) Proc. Nat'l. Acad. Sci. USA 85: 2255–2259; Marusina et al. (1997) J Immunol, 158: 5251–5256, TAP1: Genbank Accession Nos. U60018, U60019, U60020, U60021, U60022, and L76468-L67470; TAP2: Genbank Accession Nos. U60087, U60088, U6089, U60090, U60091 and U60092), hamster (TAP1, Genbank Accession Nos. AF001154 and AF001157; TAP2, Genbank Accession Nos. AFOOI 156 and AFOOI 155). Furthermore, it has been shown that point mutations in TAP genes may result in altered peptide specificity and peptide presentation. Also, functional differences in TAP genes derived from different species have been observed. For example, human TAP and rat TAP containing the rTA.P2a allele are rather promiscuous, whereas mouse TAP is restrictive and select against peptides with C-terminal small polar/hydrophobic or positively charged amino acids. The basis for this selectivity is unknown.

The methods of the invention involve performing stochastic (e.g. polynucleotide shuffling & interrupted synthesis)

and non-stochastic polynucleotide reassembly of TAP1 and TAP2 genes using as substrates at least two forms of TAP1 and/or TAP2 polynucleotide sequences which differ in at least one nucleotide position. In a preferred embodiment, TAP sequences derived from several mammalian species are used as the substrates for reassembly (optionally in combination with other directed evolution methods described herein).

Natural polymorphism of the genes can provide additional diversity of substrate. If desired, optimized TAP genes obtained from one round of reassembly (optionally in combination with other directed evolution methods described herein) and screening can be subjected to additional reassembly (optionally in combination with other directed evolution methods described herein)/screening rounds to obtain further optimized TAP-encoding polynucleotides.

To identify optimized TAP-encoding polynucleotides from a library of recombinant TAP genes, the genes can be expressed on the same plasmid as a target antigen of interest. If this step is limiting the extent of antigen presentation, then enhanced presentation to $CD8^+$ CTL will result. Mutants of TAPs may act selectively to increase expression of a particular antigen peptide fragment for which levels of expression are otherwise limiting, or to cause transport of a peptide that would normally never be transferred into the RER and made available to bind to MHC Class I.

When used in the context of gene therapy vectors in cancer treatment, evolved TAP genes provide a means to enhance expression of MHC class I molecules on tumor cells and obtain efficient presentation of antigenic tumor-specific peptides. Thus, vectors that contain the evolved TAP genes can induce potent immune responses against the malignant cells. Experimentally evolved (e.g. by polynucleotide reassembly &/or polynucleotide site-saturation mutagenesis) TAP genes can be transfected into malignant cell lines that express low levels of MHC class I molecules usina retroviral vectors or electroporation.

Transfection efficiency can be monitored using marker genes, such as green fluorescent protein, encoded by the same vector as the TAP genes. Cells expressing equal levels of green fluorescent protein but the highest levels of MHC class I molecules, as a marker of efficient TAP genes, are then sorted using flow cytometry, and the evolved TAP genes are then recovered from these cells by, for example, PCR or by recovering the entire vectors.

These sequences can then subjected into new rounds of reassembly (optionally in combination with other directed evolution methods described herein), selection and recovery, if further optimization is desired. Molecular evolution of TAP genes can be combined with simultaneous evolution of the desired antigen. Simultaneous evolution of the desired antigen can further improve the efficacy of presentation of antigenic peptides following DNA vaccination. The antigen can be evolved, using polynucleotide reassembly (optionally in combination with other directed evolution methods described herein), to contain structures that allow optimal presentation of desired antigenic peptides when optimal TAP genes are expressed. TAP genes that are optimal for presentation of antigenic peptides of one given antigen may be different from TAP genes that are optimal for presentation of antigenic peptide of another antigen. Polynucleotide (e.g. gene, promoter, enhancer, intron, & the like) reassembly (optionally in combination with other directed evolution methods described herein) technique is ideal, and perhaps the only, method to solve this type of problems. Efficient presentation of desired antigenic peptides can be analyzed using specific cytotoxic T lymphocytes, for example, by measuring the cytokine production or CTL activity of the T lymphocytes using methods known to those of skill in the art.

2.7.3. CYTOTOXIC T-CELL INDUCING SEQUENCES AND IMMUNOGENIC AGONIST SEQUENCES

Certain proteins are better able than others to carry MHC class I epitopes because they are more readily used by the cellular machinery involved in the necessary processing for class I epitope presentation. The invention provides methods of identifying expressed polypeptides that are particularly efficient in traversing the various biosynthetic and degradative steps leading to class I epitope presentation and the use of these polypeptides to enhance presentation of CTL epitopes from other proteins.

In one embodiment, the invention provides Cytotoxic T-cell Inducing Sequences (CTIS), which can be used to carry heterologous class I epitopes for the purpose of vaccinating against the pathogen from which the heterologous epitopes are derived. One example of a CTIS is obtained from the hepatitis B surface antigen (HBsAg), which has been shown to be an effective carrier for its own CTL epitopes when delivered as a protein under certain conditions. DNA immunization with plasmids expressing the HBsAg also induces high levels of CTL activity. The invention provides a shorter, truncated fragment of the HBsAg polypeptide which functions very efficiently in inducing CTL activity, and attains CTL induction levels that are higher than with the HBsAg protein or with the plasmids encoding the full-length HBsAg polypeptide. Synthesis of a CTIS derived from HBsAg is described in Example 3; and a diagram of a CTIS is shown, described &/or referenced herein (including incorporated by reference).

The ER localization of the truncated polypeptide may be important in achieving suitable proteolytic liberation of the peptide(s) containing the CTL epitopes (see Cresswell � Craiu et al. (1997) Proc. Nat'l. Acad. Sei. USA 94: 10850–10855). The preS2 region and the transmembrane region provide T-helper epitopes which may be important for the induction of a strong cytotoxic immune response. Because the truncated CTIS polypeptide has a simple structure, it is possible to attach one or more heterologous class I epitope sequences to the C-terminal end of the polypeptide without having to maintain any specific protein conformation. Such sequences are then available to the class I epitope processing mechanisms. The size of the polypeptide is not subject to the normal constraints of the native HBsAg structure. Therefore the length of the heterologous sequence and thus the number of included CTL epitopes is flexible. This is shown schematically herein. The ability to include a long sequence containing either multiple and distinct class I sequences, or alternatively different variations of a single CTL sequence, allows stochastic (e.g. polynucleotide shuffling & interrupted synthesis) and non-stochastic polynucleotide reassembly methodology to be applied.

The invention also provides methods of obtaining Immunogenic Agonist Sequences (IAS) which induce CTLs capable of specific lysis of cells expressing the natural epitope sequence. In some cases, the reactivity is greater than if the CTL response is induced by the natural epitope. Such IAS-induced CTL may be drawn from a T-cell repertoire different from that induced by the natural sequence. In this way, poor responsiveness to a given epitope can be overcome by recruiting T cells from a larger pool. In order to discover such IAS, the amino acid at each position of a CTL-inducing peptide (excluding perhaps the positions of the so-called anchor residues) can be varied over the range of the 19 amino acids not normally present at the position stochastic (e.g. polynucleotide shuffling & interrupted synthesis) and non-stochastic polynucleotide reassembly methodology can be used to scan a large range of sequence possibilities.

A synthetic gene segment containing multiple copies of the original epitope sequence can be prepared such that each copy possesses a small number of nucleotide changes. The gene segment can be experimentally evolved (e.g. by polynucleotide reassembly &/or polynucleotide site-saturation mutagenesis) to create a diverse range of CTL epitope sequences, some of which should function as IAS. This process is illustrated herein.

In practice, oligonucleotides are typically constructed in accordance with the above design and polymerized enzymatically to form the synthetic gene segment of the concatenated epitopes. Restriction sites can be incorporated into a fraction of the oligonucleotides to allow for cleavage and selection of given size ranges of the concatenated epitopes, most of which will have different sequences and thus will be potential IAS. The epitope-containing gene segment can be joined by appropriate cloning methods to a CTIS, such as that of HBsAg. The resulting plasmid constructions can be used for DNA-based C immunization and CTL induction.

2.8. GENETIC VACCINE PHARMACEUTICAL COMPOSITIONS AND METHODS OF ADMINISTRATION

Using Genetic Vaccines in Prophylaxis and Therapy of Infectious Diseases, Autoimmune Diseases, Other Inflammatory Conditions, Allergies, Asthma, and Cancer and the Prevention of Metastasis The vector components and multicomponent genetic vaccines of the invention are useful for treating and/or preventing various diseases and other conditions. For example, genetic vaccines that employ the reagents obtained according to the methods of the invention are useful in both prophylaxis and therapy of infectious diseases, including those caused by any bacterial, fungal, viral, or other pathogens of mammals. The reagents obtained using the invention can also be used for treatment of autoimmune diseases including, for example, rheumatoid arthritis, SLE, diabetes mellitus, myasthenia gravis, reactive arthritis, ankylosing spondylitis, and multiple sclerosis. These and other inflammatory conditions, including IBD, psoriasis, pancreatitis, and various immunodeficiencies, can be treated using genetic vaccines that include vectors and other components obtained using the methods of the invention. Genetic vaccine vectors and other reagents obtained using the methods of the invention can be used to treat allergies and asthma. Moreover, the use of genetic vaccines have great promise for the treatment of cancer and prevention of metastasis. By inducing an immune response against cancerous cells, the body's immune system can be enlisted to reduce or eliminate cancer.

Use of Recombinant Multivalent Antigens

The multivalent antigens of the invention are useful for treating and/or preventing the various diseases and conditions with which the respective antigens are associated. For example, the multivalent antigens can be expressed in a suitable host cell and are administered in polypeptide form. Suitable formulations and dosage regimes for vaccine delivery are well known to those of skill in the art. The improved immunomodulatory polynucleotides and polypeptides of the invention are useful for treating and/or preventing the various diseases and conditions with which the respective antigens are associated.

An Antigen for a Particular Condition can be Optimized Using Reassembly (&/or one or More Additional Directed Evolution Methods Described Herein) and Selection Methods Analogous to Those Described Herein In presently preferred embodiments, the reagents obtained using the invention (e.g. optimized experimentally generated polynucleotides that encode improved allergens), are used in conjunction with a genetic vaccine. The choice of vector and components can also be optimized for the particular purpose of treating allergy or other conditions. In presently preferred embodiments, the optimized genetic vaccine components are used in conjunction with other optimized genetic vaccine reagents. For example, an antigen that is useful for a particular condition can be optimized by methods analogous to the reassembly (&/or one or more additional directed evolution methods described herein) and screening methods described herein.

The polynucleotide that encodes the recombinant antigenic polypeptide can be placed under the control of a promoter, e.g., a high activity or tissue-specific promoter. The promoter used to express the antigenic polypeptide can itself be optimized using reassembly (&/or one or more additional directed evolution methods described herein) and selection methods analogous to those described herein, as described in International Application No. PCTIUS97/17300 (International Publication No. WO 98/13487).

The vector can contain immunostimulatory sequences such as are described herein. A vector engineered to direct a $T_H1$ response is preferred for many of the immune responses mediated by the antigens described herein. The reagents obtained using the methods of the invention can also be used in conjunction with multicomponent genetic vaccines, which are capable of tailoring an immune response as is most appropriate to achieve a desired effect. It is sometimes advantageous to employ a genetic vaccine that is targeted for a particular target cell type (e.g., an antigen presenting cell or an antigen processing cell); suitable targeting methods are described herein.

Delivery of Genetic Vaccines and Delivery Vehicles to Mammals in vivo and ex vivo Genetic vaccines, (e.g. genetic vaccines that include the optimized experimentally generated polynucleotides obtained as described herein, such as genetic vaccines that encode the multivalent antigens described herein, including the multicomponent genetic vaccines described herein), can be delivered to a mammal (including humans) to induce a therapeutic or prophylactic immune response. Vaccine delivery vehicles can be delivered in vivo by administration to an individual patient, typically by systemic administration (e.g., intravenous, intraperitoneal, intramuscular, subdermal, intracranial, anal, vaginal, oral, buccal route or they can be inhaled) or they can be administered by topical application.

Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Delivery Methods and References

A large number of delivery methods are well known to those of skill in the art. Such methods include, for example liposome-based gene delivery (Debs and Zhu (1993) WO 93/24640; Mannino and Gould-Fogerite (1988) BioTechniques 6(7): 682–691; Rose U.S. Pat No. 5,279,833; Brigham (1991) WO 91/06309; and Felgner et al. (1987) Proc. Natl. Acad. Sci. USA 84: 7413–7414), as well as use of viral vectors (e.g., adenoviral (see, e.g., Berns et al. (1995) Ann. NYAcad Sci. 772: 95–104; Ali et al. (1994) Gene Ther. 1: 367–3 84; and Haddada et al. (1995) Curr. Top. Microbiol. Immunol. 199 (Pt 3): 297–306 for review), papillomaviral, retroviral (see, e.g., Buchscher et al. (1992) J Virol. 66(5) 2731–2739; Johann et al. (1992) J Virol. 66 (5):163 5–1640 (1992); Sommerfelt et al., (1990) Virol. 176:58–59; Wilson et al. (1989) J Virol. 63:2374–2378; Miller et al., J Virol. 65:2220–2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra.), and adeno-associated viral vectors (see, West et al. (1987) Virology 160:3 8–47; Carter et al. (1989) U. S. Pat. No. 4,797,3 68; Carter et al. WO 93/24641 (1993); Kotin (1994) Human Gene Therapy 5:793–801; Muzyczka (1994) J Clin. Invst. 94:1351 and Samulski (supra) for an overview of AAV vectors; see also, Lebkowski, U.S. Pat. No. 5,173,414; Tratschin et al. (1985) Mol. Cell. Biol. 5(11):3251–3260; Tratschin, et al. (1984) Mol. Cell. Biol., 4:2072–2081; Hermonat and Muzyczka (1984) Proc. Natl. Acad Sci. USA, 81:6466–6470; McLaughlin et al. (1988) and Samulski et al. (1989) J Virol., 63:03 822–3 828), and the like.

Introduction of "Naked" DNA and/or RNA That Comprises a Genetic Vaccine Directly Into a Tissue or Using "Biolistic" or Particle-Mediated Transformation, Both in vivo and ex vivo "Naked" DNA and/or RNA that comprises a genetic vaccine can be introduced directly into a tissue, such as muscle. See, e.g., U.S. Pat. No. 5,580, 859. Other methods such as "biolistic" or particle-mediated transformation (see, e.g., Sanford et al., U.S. Pat. No. 4,945,050; U.S. Pat. No. 5,036,006) are also suitable for introduction of genetic vaccines into cells of a mammal according to the invention. These methods are useful not only for in vivo introduction of DNA into a mammal, but also for ex vivo modification of cells for reintroduction into a mammal. As for other methods of delivering genetic vaccines, if necessary, vaccine administration is repeated in order to maintain the desired level of immunomodulation.

Methods of Administering Packaged Nucleic Acids in Mammals for Transduction of Cells in vivo Genetic vaccine vectors (e.g., adenoviruses, liposomes, papillomaviruses, retroviruses, etc.) can be administered directly to the mammal for transduction of cells in vivo. The genetic vaccines obtained using the methods of the invention can be formulated as pharmaceutical compositions for administration in any suitable manner, including parenteral (e.g., subcutaneous, intramuscular, intradermal, or intravenous), topical, oral, rectal, intrathecal, buccal (e.g., sublingual), or local administration, such as by aerosol or transdermally, for prophylactic and/or therapeutic treatment. Pretreatment of skin, for example, by use of hair-removing agents, may be useful in transdermal delivery. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of genetic vaccine vector in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet fonns can include one or more of lactose, sucrose, mannitol, sorbitol, calcium phosphates, corn starch, potato starch, tragacanth, microcrystalline cellulose, acacia, gelatin, colloidal silicon dioxide, croscannellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the genetic vaccines, when administered orally, must be protected from digestion. This is typically accomplished either by complexing the vaccine vector with a composition to render it resistant to acidic and enzymatic hydrolysis or by packaging the vector in an appropriately resistant carrier such as a liposome. Means of protecting vectors from digestion are well known in the art. The pharmaceutical compositions can be encapsulated, e.g., in liposomes, or in a formulation that provides for slow release of the active ingredient.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral. administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally.

Parenteral Administration and Intravenous Administration are the Preferred Methods of Administration The formulations of packaged nucleic acid can be presented in unit-dose or multi-dose sealed containers, such as ampoules and vials. Injection solutions and suspensions can be prepared from sterile powders, granules, and tablets of the kind previously described. Cells transduced by the packaged nucleic acid can also be administered intravenously or parenterally.

Dose Size

The dose administered to a patient, in the context of the present invention should be sufficient to effect a beneficial therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of an infection or other condition, the physician evaluates vector toxicities, progression of the disease, and the production of anti-vector antibodies, if any. In general, the dose equivalent of a naked nucleic acid from a vector is from about 1 $\mu$g to 1 mg for a typical 70 kilogram patient, and doses of vectors used to deliver the nucleic acid are calculated to yield an equivalent amount of therapeutic nucleic acid. Administration can be accomplished via single or divided doses.

In therapeutic applications, compositions are administered to a patient suffering from a disease (e.g., an infectious disease or autoimmune disorder) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

In prophylactic applications, compositions are administered to a human or other mammal to induce an immune response that can help protect against the establishment of an infectious disease or other condition.

Ability to Determine Toxicity Therapeutic Efficacy

The toxicity and therapeutic efficacy of the genetic vaccine vectors provided by the invention are determined using standard pharmaceutical procedures in cell cultures or experimental animals. One can determine the $LD_{50}$ (the dose lethal to 50% of the population) and the $ED_{50}$ (the dose therapeutically effective in 50% of the population) using procedures presented herein and those otherwise known to those of skill in the art.

More on Dosage

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

Packaging/Dispenser Devices

The genetic vaccines obtained using the methods of the invention (e.g. the multivalent antigenic polypeptides of the invention, and genetic vaccines that express the polypeptides) can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, autoimmune disorder, tumor, or for preventing or treating other diseases or conditions that are mediated by, or potentially susceptible to, a mammalian immune response.

2.9. USES OF GENETIC VACCINES

Genetic vaccines which include optimized vector modules and other reagents provided by the invention are useful for treating many diseases and other conditions that are either mediated by a mammalian immune system or are susceptible to treatment by an appropriate immune response. Representative examples of these diseases & antigens appropriate for each are listed below, described herein, or incorporated by reference.

Substrates for Eolution of Otimized Rcombinant Atigens

The invention provides methods of obtaining experimentally generated polynucleotides that encode antigens that exhibit improved ability to induce an immune response to a pathogenic agent. The methods are applicable to a wide range of pathogenic agents, including potential biological warfare agents and other organisms and polypeptides that can cause disease and toxicity in humans and other animals. The following examples are merely illustrative, and not limiting.

2.9.1. Infectious Diseases

Genetic vaccine vectors obtained according to the methods of the invention are useful in both prophylaxis and therapy of infectious diseases, including those caused by any bacterial, fungal, viral, or other pathogens of mammals. In some embodiments, protection is conferred by use of a genetic vaccine vector that will express an antigen (either or both of a humoral antigen or a T cell antigen) of the pathogen of interest. In preferred embodiments, the antigen is evolved using the methods of the invention in order to obtain optimized antigens as described herein. The vector induces an immune response against the antigen. One or several antigens or antigen fragments can be included in one genetic vaccine delivery vehicle. Examples of pathogens and corresponding polypeptides from which an antigen can be obtained include, but are not limited to, HIV (gp120, gp160), hepatitis B, C, D, E (surface antigen), rabies (glycoprotein), Schistosoma mansoni (calpain; Jankovic (1996) *J Immunol.* 157: 806–14). Other pathogen infections that are treatable using genetic vaccine vectors include, for example, herpes zoster, herpes simplex-1 and -2, tuberculosis (including chronic, drug-resistant), lyme disease (*Borrelia burgorferii*), syphilis, parvovirus, rabies, human papillomavirus, and the like.

2.9.1.1 Bacterial Pathogens and Toxins

In some embodiments, the methods of the invention are applied to bacterial pathogens, as well as to toxins produced by bacteria and other organisms. One can use the methods to obtain experimentally generated polypeptides that can induce an immune response against the pathogen, as well as recombinant toxins that are less toxic than native toxin polypeptides. Often, the polynucleotides of interest encode polypeptides that are present on the surface of the pathogenic organism. Among the pathogens for which the methods of the invention are useful for producing protective immunogenic experimentally generated polypeptides are the Yersinia species.

*Yersinia pestis*, the causative agent of plague, is one of the most virulent bacteria known with $LD_{50}$ values in mouse of less than 10 bacteria. The pneumonic form of the disease is readily spread between humans by aerosol or infectious droplets and can be lethal within days. A particularly preferred target for obtaining a experimentally generated polypeptide that can protect against Yersinia infection is the V antigen, which is a 37 kDa virulence factor, induces protective immune responses and is currently being evaluated as a subunit vaccine (Brubaker (1991) Current Investigations of the Microbiology of Yersinae, 12: 127). The V-antigen alone is not toxic, but *Y. pestis* isolates that lack the V-antigen are avirulent. The Yersinia V-antigen has been successfully produced in *E. coli* by several groups (Leary et al. (1995) Infect. Immun. 3: 2854). Antibodies that recognize the V-antigen can provide passive protection against homologous strains, but not against heterologous strains. Similarly, immunization with purified V antigen protects against only homologous strains. To obtain cross-protective recombinant V antigen, in a preferred embodiment, V antigen genes from various Yersinia species are subjected to polynucleotide reassembly (optionally in combination with other directed evolution methods described herein). The genes encoding the V antigen from *Y. pestis, Y. enterocolitica*, and *Y. pseudotuberculosis*, for example, are 92–99% identical at the DNA level, making them ideal for optimization using family reassembly (optionally in combination with other directed evolution methods described herein) according to the methods of the invention. After reassembly (optionally in combination with other directed evolution methods described herein), the library of recombinant nucleic acids is screened and/or selected for those that encode recombinant V antigen polypeptides that can induce an improved immune response and/or have greater cross-protectivity.

*Bacillus anthracis*, the causative agent of anthrax, is another example of a bacterial target against which the methods of the invention are useful. The anthrax protective antigen (PA) provides protective immune responses in test animals, and antibodies against PA also provide some protection. However, the immunogenicity of PA is relatively poor, so multiple injections are typically required when wild-type PA is used. Co- vaccination with lethal factor (LF) can improve the efficacy of wild-type PA vaccines, but toxicity is a limiting factor. Accordingly the stochastic (e.g. polynucleotide shuffling & interrupted synthesis) and non-stochastic polynucleotide reassembly and antigen library immunization methods of the invention can be used to obtain nontoxic LF. Polynucleotides that encode LF from various *B. anthracis* strains are subjected to family reassembly (optionally in combination with other directed evolution methods described herein). The resulting library of recombinant LF nucleic acids can then be screened to identify those that encode recombinant LF polypeptides that exhibit reduced toxicity. For example, one can inoculate tissue culture cells with the recombinant LF polypeptides in the presence of PA and select those clones for which the cells survive. If desired, one can then backcross the nontoxic LF polypeptides to retain the immunogenic epitopes of LF. Those that are selected through the first screen can then be subjected to a secondary screen. For example, one can test for the ability of the recombinant nontoxic LF polypeptides to induce an immune response (e.g., CTL or antibody response) in a test animal such as mice. In preferred embodiments, the recombinant nontoxic LF polypeptides are then tested for ability to induce protective immunity in test animals against challenge by different strains of *B. anthracis*.

The protective antigen (PA) of *B. anthracis* is also a suitable target for the methods of the invention. PA-encoding nucleic acids from various strains of *B. anthracis* are subjected to stochastic (e.g. polynucleotide shuffling & interrupted synthesis) and non-stochastic polynucleotide reassembly. One can then screen for proper folding in, for example, *E. coli*, using polyclonal antibodies. Screening for ability to induce broad-spectrum antibodies in a test animal is also typically used, either alone or in addition to a preliminary screening method. In presently preferred embodiments, those experimentally generated polynucleotides that exhibit the desired properties can be backcrossed so that the immunogenic epitopes are maintained. Finally, the selected recombinants are tested for ability to induce protective immunity against different strains of *B. anthracis* in a test animal.

The *Staphylococcus aureus* and Streptococcus toxins are another example of a target polypeptide that can be altered using the methods of the invention. Strains of *Stapkvlococcus aureus* and group A Streptococci are involved in a range of diseases, including food poisoning, toxic shock syndrome, scarlet fever and various autoimmune disorders. They secrete a variety of toxins, which include at least five cytolytic toxins, a coagulase, and a variety of enterotoxins. The enterotoxins are classified as superantigens in that they crosslink MHC class II molecules with T cell receptors to cause a constitutive T cell activation (Fields et al. (1996) Nature 3 84: 188). This results in the accumulation of pathogenic levels of cytokines that can lead to multiple organ failure and death. At least thirty related, yet distinct enterotoxins have been sequenced and can be phylogenetically grouped into families. Crystal structures have been obtained for several members alone and in complex with MHC class II molecules. Certain mutations in the MHC class II binding site of the toxins strongly reduce their toxicity and can form the basis of attenuated vaccines (Woody et al. (1997) Vaccine 15: 133). However, a successful immune response to one type of toxin may provide protection against closely related family members, whereas little protection against toxins from the other families is observed. Family reassembly (optionally in combination with other directed evolution methods described herein) of enterotoxin genes from various family members can be used to obtain recombinant toxin molecules that have reduced toxicity and can induce a cross-protective immune response. Experimentally evolved (e.g. by polynucleotide reassembly &/or polynucleotide site-saturation mutagenesis) antigens can also be screened to identify antigens that elicit neutralizing antibodies in an appropriate animal model such as mouse or monkey. Examples of such assays can include ELISA formats in which the elicited antibodies prevent binding of the enterotoxin to the MHC complex and/or T cell receptors on cells or purified forms. These assays can also include formats where the added antibodies would prevent T cells from being cross-linked to appropriate antigen presenting cells.

Cholera is an ancient, potentially lethal disease caused by the bacterium *Vibrio cholerae* and an effective vaccine for its prevention is still unavailable. Much of the pathogenesis of this disease is caused by the cholera enterotoxin. Ingestion of microgram quantities of cholera toxin can induce severe diarrhea causing loss of tens of liters of fluid.

Cholera toxin is a complex of a single catalytic A subunit with a pentameric ring of identical B subunits. Each subunit is inactive on its own. The B subunits bind to specific ganglioside receptors on the surface of intestinal epithelial cells and trigger the entry of the A subunit into the cell. The A subunit ADP-ribosylates a regulatory G protein initiating a cascade of events causing a massive, sustained flow of electrolytes and water into the intestinal lumen resulting in extreme diarrhea.

The B subunit of cholera toxin is an attractive vaccine target for a number of reasons. It is a major target of protective antibodies generated during cholera infection and contains the epitopes for antitoxin neutralizing antibodies. It is nontoxic without the A subunit, is orally effective, and stimulates production of a strong IgA-dominated gut mucosal immune response, which is essential in protection against cholera and cholera toxin. The B subunit is also being investigated for use as an adjuvant in other vaccine preparations, and therefore, evolved toxins may provide general improvements for a variety of different vaccines. The heat-labile enterotoxins (LT) from enterotoxigenic *E. coli* strains are structurally related to cholera toxin and are 75% identical at the DNA sequence level. To obtain optimized recombinant toxin molecules that exhibit reduced toxicity and increased ability to induce an immune response that is protective against *V. cholerae* and *E. coli*, the genes that encode the related toxins are subjected to stochastic (e.g. polynucleotide shuffling & interrupted synthesis) and non-stochastic polynucleotide reassembly.

The recombinant toxins are then tested for one or more of a several desirable traits. For example, one can screen for improved cross-reactivity of antibodies raised against the recombinant toxin polypeptides, for lack of toxicity in a cell culture assay, and for ability to induce a protective immune response against the pathogens and/or against the toxins themselves. The experimentally evolved (e.g. by polynucleotide reassembly &/or polynucleotide site-saturation mutagenesis) clones can be selected by phage display and/or screened by phage ELISA and ELISA assays for the presence of epitopes from the different serotypes. Variant proteins with multiple epitopes can then be purified and used to immunize mice or other test animal. The animal serum is then assayed for antibodies to the different B chain subtypes and variants that elicit a broad cross-reactive response will be evaluated further in a virulent challenge model. The *E. coli* and *V. cholerae* toxins can also act as adjuvants that are capable of enhancing mucosal immunity and oral delivery of vaccines and proteins.

Accordingly, one can Test the Library of Recombinant Toxins for Enhancement of the Adjuvant Activity Experimentally evolved (e.g. by polynucleotide reassembly &/or polynucleotide site-saturation mutagenesis) antigens can also be screened for improved expression levels and stability of the B chain pentamer, which may be less stable than when in the presence of the A chain in the hexameric complex. Addition of a heat treatment step or denaturing agents such as salts, urea, and/or guanidine hydrochloride can be included prior to ELISA assays to measure yields of correctly folded molecules by appropriate antibodies. It is sometimes desirable to screen for stable monomeric B chain molecules, in an ELISA format, for example, using antibodies that bind monomeric, but not pentameric B chains. Additionally, the ability of experimentally evolved (e.g. by polynucleotide reassembly &/or polynucleotide site-saturation mutagenesis) antigens to elicit neutralizing antibodies in an appropriate animal model such as mouse or monkey can be screened. For example, antibodies that bind to the B chain and prevent its binding to its specific ganglioside receptors on the surface of intestinal epithelial cells may prevent disease. Similarly antibodies that bind to the B chain and prevent its pentamerization or block A chain binding may be useful in preventing disease.

The bacterial antigens that can be improved by stochastic (e.g. polynucleotide shuffling & interrupted synthesis) and non-stochastic polynucleotide reassembly for use as vaccines also include, but are not limited to, Helicobacter pylori antigens CagA and VacA (Blaser (1996) Aliment. Pharmacol. Ther. 1: 73–7; Blaser and Crabtree (1996) Am. J Clin. Pathol. 106: 565–7; Censini et al. (1996) Proc. Nat'l. Acad. Sci. USA 93: 14648–14643).

Other suitable H. pylori antigens include, for example, four immunoreactive proteins of 45–65 kDa as reported by Chatha et al. (1997) Indian J Med. Res. 105: 170–175 and the *H. pylori* GroES homologue (HspA) (Kansau et al. (1996) Mol. Microbiol. 22: 1013–1023. Other suitable bacterial antigens include, but are not limited to, the 43-kDa and the fimbrilin (41 kDa) proteins of P. gingivalis (Boutsl et al. (1996) Oral Microbiol. Immunol. 11: 236–241); pneumococcal surface protein A (Briles et al. (1996) Ann. NYAcad. Sci. 797: 118–126); Chlamydia psittaci antigens, 80–90 kDa protein and 110 kDa protein (Buendia et al. (1997) FEMS-Microbiol. Lett. 150: 113–9); the chlainydial exoglycolipid antigen (GLXA) (Whittum-Hudson et al. (1996) Nature Med. 2: 1116–112 1); *Chlamlydia pneumoniae* species-specific antigens in the molecular weight ranges 92–98, 51–55, 43–46 and 31.5–33 kDa and genus-specific antigens in the ranges 12, 26 and 65–70 kDa (Halme et al. (1997) Scand. J Immunol. 45: 378–84); Neisseria gonorrhoeae (GC) or *Escherichia coli* phase-variable opacity (Opa) proteins (Chen and Gotschlich (1996) Proc. Nat'l. Acad. Sci. USA 93: 14851–14856), any of the twelve immunodominant proteins of Schistosoma mansoni (ranging in molecular weight from 14 to 208 kDa) as described by Cutts and Wilson (1997) Parasitolog-v 114: 245–55; the 17-kDa protein antigen of Brucella abortus (De Mot et al. (1996) Curr. Microbiol. 33: 26–30); a gene homolog of the 17-kDa protein antigen of the Gram-negative pathogen Brucella abortus identified in the nocardioform actinomycete Rhodococcus sp. N186/21 (De Mot et al. (1996) Curr. Microbiol. 33: 26–30); the staphylococcal enterotoxins (SEs) (Wood et al. (1997) FEMS Immunol. Med. Microbiol. 17: 1–10), a 42-kDa *M. hy,opneunionіае* NrdF ribonucleotide reductase R2 protein or 15-kDa subunit protein of *M. hyopneumoniae* (Fagan et al. (1997) Infect. Immun. 65: 2502–2507), the meningococcal antigen PorA protein (Feavers et al. (1997) Clin. Diagn. Lab. Immunol. 3: 444–50); pneumococcal surface protein A (PspA) (McDaniel et al. (1997) Gene Ther. 4: 375–377); *F. tularensis* outer membrane protein FopA (Fulop et al. (1996) FEMSImmunol. Med. Microbiol. 13: 245–247); the major outer membrane protein within strains of the genus Actinobacillus (Hartmann et al. (1996) Zentralbl. Bakteriol. 284: 255–262); p60 or listeriolysin (Hly) antigen of *Listeria monocytogenes* (Hess et al. (1996) Proc. Nat'l. Acad. Sci. USA 93: 1458–1463); flagellar (G) antigens observed on *Salmonella enteritidis* and *S. pullorum* (Holt and Chaubal (1997) J. Clin. Microbiol. 35: 1016–1020); *Bacillus anthracis* protective antigen (PA) (Ivins et al. (1995) Vaccine 13: 1779–1784); *Echinococcus granulosus* antigen 5 (Jones et al. (1 996) Parasitology 113: 213–222); the rol genes of *Shigella dvsenteriae* I and *Escherichia coli* K-12 (Klee et al. (1997) J. Bacteriol. 179: 2421–2425); cell surface proteins Rib and alpha of group B streptococcus (Larsson et al. (1996) Infect. Immun. 64: 3518–3523); the 37 kDa secreted polypeptide encoded on the 70 kb virulence plasmid of pathogenic Yersinia spp. (Leary et al. (1995) Contrib. Microbiol. Immunol. 13: 216–217 and Roggenkamp et al. (1997) Infect. Immun. 65: 446–5 1); the OspA (outer surface protein A) of the Lyme disease spirochete *Borrelia burgdorferi* (Li et al. (1997) Proc. Nat'l. Acad Sci. USA 94: 3584–3589, Padilla et al. (1996) J Infect. Dis. 174: 739–746, and Wallich et al. (1996) Infection 24: 396–397); the Brucella melitensis group 3 antigen gene encoding Omp28 (Lindler et al. (1996) Infect. Immun. 64: 2490–2499); the PAc antigen of *Streptococcus mutans* (Murakami et al. (1997) Infect. Immun. 65: 794–797); pneumolysin, *Pneumococcal neuraminidases*, autolysin, hyaluronidase, and the 37 kDa pneumococcal surface adhesin A (Paton et al. (1997) Microb. Drug Resist. 3: 1–10); 29–32, 41–45, 63–71×10(3) MW antigens of Salmonella typhi (Perez et al. (1996) Immunology 89: 262–267); K-antigen as a marker of Klebsiella pneumoniae (Priamukhina and Morozova (1996) Klin. Lab. Diagn. 47–9); nocardial antigens of molecular mass approximately 60, 40, and 15–10 kDa (Prokesova et al. (1996) Int. J Immunopharmacol. 18: 661–668); Staphylococcus aureus antigen ORF-2 (Rieneck et al. (1997) Biochim Biophys Acta 1350: 128–132); GlpQ antigen of *Borrelia hermsii* (Schwan et al. (1996) J Clin. Microbiol. 34: 2483–2492); cholera protective antigen (CPA) (Sciortino (1996) J. Diarrhoeal Dis. Res. 14: 16–26); a 190-kDa protein antigen of *Streptococcus mutans* (Senpuku et al. (1996) Oral Microbiol. Immunol. 11: 121–128); Anthrax toxin protective antigen (PA) (Sharma et al. (1996) Protein Expr. Purif. 7: 33–38); Clostridium perfringens antigens and toxoid (Strom et al. (1995) Br. J. Rheumatol. 34: 1095–1096); the SEF14 fimbrial antigen of Salmonella enteritidis (Thorns et al. (1996) Microb. Pathog. 20: 235–246); the *Yersinia pestis* capsular antigen (F I antigen) (Titball et al. (1997) Infect. Immun. 65: 1926–1930); a 35-kilodalton protein of *Mycobacterium leprae* (Triccas et al. (1996) Infect. Immun. 64: 5171–5177); the major outer membrane protein, CD, extracted from Moraxella (Branhamella) catarrhalis (Yang et al. (1997) FEMS Immunol. Med. Microbiol. 17:–199); pH6 antigen (PsaA protein) of *Yersinia pestis* (Zav'yalov et al. (1996) FEMS Immunol. Med. Microbiol. 14: 53–57); a major surface glycoprotein, gp63, of Leishmania major (Xu and Liew (1994) Vaccine 12: 1534–1536; Xu and Liew (1995) Immunology 84: 173–176); mycobacterial heat shock protein 65, mycobacterial antigen (*Mycobacterium leprae* hsp65) (Lowrie et al. (1994) Vaccine 12: 1537–1540; Ragno et al. (1997) Arthritis Rheum. 40: 277–283; Silva (1995) Braz. J Med. Biol. Res. 28: 843–851); *Mycobacterium tuberculosis* antigen 85 (Ag85) (Huygen et al. (1996) Nat. Med. 2: 893–898); the 45/47 kDa antigen complex (APA) of *Mycobacterium tuberculosis, M. bovis* and BCG (Horn et al. (1996) J Immunol. Methods 197: 151–159); the mycobacterial antigen, 65-kDa heat shock protein, hsp65 (Tascon et al. (1996) Nat. Med. 2: 888–892); the mycobacterial antigens MPB64, MPB70, MPB57 and alpha antigen (Yamada et al. (1995) Kekkaku 70: 639–644); the *M. tuberculosis* 38 kDa protein (Vordenneier et al. (1995) Vaccine 13: 1576–1582); the MPT63, MPT64 and MPT- 59 antigens from *Mycobacterium tuberculosis* (Manca et al. (1997) Infect. Immun. 65: 16–23; Oettinger et al. (1997) Scand. J Immunol. 45: 499–503; Wilcke et al. (1996) Tuber. Lung Dis. 77: 250–256); the 35–kilodalton protein of *Mycobacterium leprae* (Triccas et al. (1996) Infect. Immun. 64: 5171–5177); the ESAT-6 antigen of virulent mycobacteria (Brandt et al. (1996) J Immunol. 157: 3527–3533; Pollock and Andersen (1997) J Infect. Dis. 175: 1251–1254); A~vcobacterium tuberculosis 16-kDa antigen (Hspl6.3) (Chang et al. (1996) J Biol. Chem. 271: 7218–7223); and the 18-kilodalton protein of Mycobacterium leprae (Baumgart et al. (1996) Infect. Immun. 64: 2274–228 1).

2.9.1.2. Viral Pathogens

The methods of the invention are also useful for obtaining recombinant nucleic acids and polypeptides that have enhanced ability to induce an immune response against viral pathogens. While the bacterial recombinants described above are typically administered in polypeptide form, recombinants that confer viral protection are preferably administered in nucleic acid form, as genetic vaccines.

One illustrative example is the Hantaan virus. Glycoproteins of this virus typically accumulate at the membranes of the Golgi apparatus of infected cells. This poor expression of the glycoprotein prevents the development of efficient genetic vaccines against these viruses. The methods of the invention solve this problem by performing stochastic (e.g. polynucleotide shuffling & interrupted synthesis) and non-stochastic polynucleotide reassembly on nucleic acids that encode the glycoproteins and identifying those recombinants that exhibit enhanced expression in a host cell, and/or for improved immunogenicity when administered as a genetic vaccine. A convenient screening method for these methods is to express the experimentally generated polynucleotides as fusion proteins to PIG, which results in display of the polypeptides on the surface of the host cell (Whitehorn et al. (1995) Biotechnology (N Y) 13:1215–9). Fluorescence-activated cell sorting is then used to sort and recover those cells that express an increased amount of the antigenic polypeptide on the cell surface. This preliminary screen can be followed by immunogenicity tests in mammals, such as mice. Finally, in preferred embodiments, those recombinant nucleic acids are tested as genetic vaccines for their ability to protect a test animal against challenge by the virus.

The flaviviruses are another example of a viral pathogen for which the methods of the invention are useful for obtaining a experimentally generated polypeptide or genetic vaccine that is effective against a viral pathogen. The flaviviruses consist of three clusters of antigenically related viruses: Dengue 1–4 (62–77% identity), Japanese, St. Louis and Murray Valley encephalitis viruses (75–82% identity), and the tick-borne encephalitis viruses (77–96% identity). Dengue virus can induce protective antibodies against SLE and Yellow fever (40–50% identity), but few efficient vaccines are available. To obtain genetic vaccines and experimentally generated polypeptides that exhibit enhanced cross-reactivity and immunogenicity, the polynucleotides that encode envelope proteins of related viruses are subjected to stochastic (e.g. polynucleotide shuffling & interrupted synthesis) and non-stochastic polynucleotide reassembly. The resulting experimentally generated polynucleotides can be tested, either as genetic vaccines or by using the expressed polypeptides, for ability to induce a broadly reacting neutralizing antibody response. Finally, those clones that are favorable in the preliminary screens can be tested for ability to protect a test animal against viral challenge.

Viral antigens that can be evolved by stochastic (e.g. polynucleotide shuffling & interrupted synthesis) and non-stochastic polynucleotide reassembly for improved activity as vaccines include, but are not limited to, influenza A virus N2 neuraminidase (Kilbourne et al. (1995) Vaccine 13: 1799–1803); Dengue virus envelope (E) and premembrane (prM) antigens (Feighny et al. (1994) Am. J Trop. Med. Hyg. 50: 322–328; Putnak et al. (1996) Am. J Trop. Med. Hyg. 5 5: 504–10); HIV antigens Gag, Pol, Vif and Nef (Vogt et al. (1995) Vaccine 13: 202–208); HIV antigens gp 120 and gp 160 (Achour et al. (1995) Cell. Mol. Biol. 41: 395–400; Hone et al. (1994) Dev. Biol. Stand. 82: 159–162); gp41 epitope of human immunodeficiency virus (Eckhart et al. (1996) J Gen. Virol. 77: 2001–2008); rotavirus antigen VP4 (Mattion et al. (1995) J Virol. 69: 5132–5137); the rotavirus protein VP7 or VP7sc (Emslie et al. (1995) J Virol. 69: 1747–1754; Xu et al. (1995) J Gen. Virol. 76: 1971–1980); herpes simplex virus (HSV) glycoproteins gB, gC, gD, gE, gG, gH, and gl (Fleck et al. (1994) Med. Microbiol. Immunol. (Berl) 183: 87–94 [Mattion, 1995]; Ghiasi et al. (1995) Invest. Ophthalmol. Vis. Sci. 36: 1352–1360; McLean et al. (1994) J Infect. Dis. 170: 1100–1109); immediate-early protein ICP47 of herpes simplex virus-type 1 (HSV-1) (Banks et al. (1994) Virology 200: 23 6–245); immediate-early (IE) proteins ICP27, ICPO, and ICP4 of herpes simplex virus (Manickan et al. (1995) J Virol. 69: 4711–4716); influenza virus nucleoprotein and hemagglutinin (Deck et al. (1997) Vaccine 15: 71–78; Fu et al. (1997) J Virol. 71: 2715–272 1); B 19 parvovirus capsid proteins VPI (Kawase et al. (1995) Virology 211: 359–366) or VP2 (Brown et al. (1994) Virology 198: 477–488); Hepatitis B virus core and e antigen (Schodel et al. (1996) Intervirology 39:104–106); hepatitis B surface antigen (Shiau and Murray (1997) J. Med. Virol. 51: 159–166); hepatitis B surface antigen fused to the core antigen of the virus (Id.); Hepatitis B virus core-preS2 particles (Nemeckova et al. (1996) Acta Virol. 40: 273–279); HBV preS2-S protein (Kutinova et al. (1996) Vaccine 14: 1045–1052); VZV glycoprotein I (Kutinova et al. (1996) Vaccine 14: 1045–1052); rabies virus glycoproteins (Xiang et al. (1994) Virology 199: 132–140; Xuan et al. (1995) Virus Res. 36: 151–161) or ribonucleocapsid (Hooper etal. (1994) Proc. Nat'l. Acad. Sci. USA 91: 10908–10912); human cytomegalovirus (HCMV) glycoprotein B (LTL55) (Britt et al. (1995) J Infect. Dis. 171: 18–25); the hepatitis C virus (HCV) nucleocapsid protein in a secreted or a nonsecreted form, or as a fusion protein with the middle (pre-S2 and S) or major (S) surface antigens of hepatitis B virus (HBV) (Inchauspe et al. (1 997) DNA Cell Biol. 16: 185–195; Major et al. (1995) J Virol. 69: 5798–5805); the hepatitis C virus antigens: the core protein (pC); E1 (pE1) and E2 (pE2) alone or as fusion proteins (Saito et al. (1997) Gastroenterology 112: 1321–1330); the gene encoding respiratory syncytial virus fusion protein (PFP-2) (Falsey and Walsh (1996) Vaccine 14: 1214–1218; Piedra et al. (1996) Pediatr. Infect. Dis. J. 15: 23–3 1); the VP6 and VP7 genes of rotaviruses (Choi et al. (1997) Virology 232: 129–13 8; Jin et al. (1996) Arch. Virol. 141: 2057–2076); the E 1, E2, E3, E4, E5, E6 and E7 proteins of human papillomavirus (Brown et al. (1994) Virology 201: 46–54; Dillner et al. (1995) Cancer Detect. Prev. 19: 3 81–393; Krul et al. (1996) Cancer Immunol. Immunother. 43: 44–48; Nakagawa et al. (1997) J Infect. Dis. 175: 927–93 1); a human T-lymphotropic virus type 1 gag protein (Porter et al. (1995) J Med Virol. 45: 469–474); Epstein-Barr virus (EBV) gp340 (Mackett et al. (1996) J Med. Virol. 50: 263–271); the Epstein-Barr virus (EBV) latent membrane protein LMP2 (Lee et al. (1996) Eur. J Immunol. 26: 1875–1883); Epstein-Barr virus nuclear antigens 1 and 2 (Chen and Cooper (1996) J Virol. 70: 4849–4853; Khanna et al. (1995) Virology 214: 633–637); the measles virus nucleoprotein (N) (Fooks et al. (1995) Virology 210: 456–465); and cytomegalovirus glycoprotein gB (Marshall et al. (1994) J Med. Virol. 43: 77–83) or glycoprotein gH (Rasmussen et al. (1994) J Infect. Dis. 170: 673–677).

2.9.2. Inflammatory and Autoimmune Diseases

Autoimmune diseases are characterized by immune response that attacks tissues or cells of ones own body, or pathogen-specific immune responses that also are harmful for ones own tissues or cells, or non-specific immune activation which is harmful for ones own tissues or cells. Examples of autoinimune diseases include, but are not limited to, rheumatoid arthritis, SLE, diabetes mellitus, myasthenia gravis, reactive arthritis, ankylosing spondylitis, and multiple sclerosis. These and other inflammatory conditions, including IBD, psoriasis, pancreatitis, and various immunodeficiencies, can be treated using genetic vaccines that include vectors and other components obtained using the methods of the invention (e.g. using antigens that are optimized using the methods of the invention).

These conditions are often characterized by an accumulation of inflammatory cells, such as lymphocytes, macrophages, and neutrophils, at the sites of inflammation. Altered cytokine production levels are often observed, with increased levels of cytokine production. Several autoimmune diseases, including diabetes and rheumatoid arthritis, are linked to certain MHC haplotypes. Other autoimmune-type disorders, such as reactive arthritis, have been shown to be triggered by bacteria such as Yersinia and Shigella, and evidence suggests that several other autoimmune diseases, such as diabetes, multiple sclerosis, rheumatoid arthritis, may also be initiated by viral or bacterial infections in genetically susceptible individuals.

Current strategies of treatment generally include anti-inflammatory drugs, such as NSAID or cyclosporin, and antiproliferative drugs, such as methotrexate. These therapies are non-specific, so a need exists for therapies having greater specificity, and for means to direct the immune responses towards the direction that inhibits the autoimmune process.

The present invention provides several strategies by which these needs can be fulfilled. First, the invention provides methods of obtaining vaccines which exhibit improved delivery of tolerogenic antigens (e.g. methods of obtaining antigens having greater tolerogenicity and/or have improved antigenicity), antigens which have improved antigenicity, genetic vaccine-mediated tolerance, and modulation of the immune response by inclusion of appropriate accessory molecules. In a preferred embodiment, the vaccines (e.g. optimized antigens) prepared according to the invention exhibit improved induction of tolerance by oral delivery.

Oral tolerance is characterized by induction of immunological tolerance after oral administration of large quantities of antigen (Chen et al. (1 995) Science 265: 123 7–1240; Haq et al. (1995) Science 268: 714–716). In animal models, this approach has proven to be a very promising approach to treat autoimmune diseases, and clinical trials are in progress to address the efficacy of this approach in the treatment of human autoimmune diseases, such as rheumatoid arthritis and multiple sclerosis (Chen et al. (1994) Science 265:123 7–40; Whitacre et al. (1996) Clin. Immunol. Immunopathol. 80: S31–9; Hohol et al. (1996) Ann. N.Y Acad Sci. 778:243–50). It has also been suggested that induction of oral tolerance against viruses used in gene therapy might reduce the immunogenicity of gene therapy vectors.

However, the amounts of antigen required for induction of oral tolerance are very high and improved methods for oral delivery of antigenic proteins would significantly improve the efficacy of induction of oral tolerance.

Expression library immunization (Barry et al. (1995) Nature 3 77: 632) is a particularly useful method of screening for optimal antigens for use in genetic vaccines. For example, to identify autoantigens present in Yersinia, Shigella, and the like, one can screen for induction of T cell responses in HLA-B27 positive individuals. Complexes that include epitopes of bacterial antigens and MHC molecules associated with autoimmune diseases, e.g., HLA-B27 in association with Yersinia antigens can be used in the prevention of reactive arthritis and ankylosing spondylitis in HLA-B27 positive individuals.

Treatment of autoimmune and inflammatory conditions can involve not only administration of tolerogenic antigens, but also the use of a combination of cytokines, costimulatory molecules, and the like. Such cocktails are formulated for induction of a favorable immune response, typically induction of autoantigen-specific tolerance. Cocktails can also include, for example, CD1, which is crucially involved in recognition of self antigens by a subset of T cells (Porcelli (1995) Adv. Immunol. 5 9: 1). Genetic vaccine vectors and cocktails that skew immune responses towards the $T_H2$ are often used in treating autoimmune and inflammatory conditions, both with antigen-specific and antigen non-specific vectors.

Screening of genetic vaccines and accessory molecules (e.g. and optimized antigens) can be done in animal models which are known to those of skill in the art. Examples of suitable models for various conditions include collagen induced arthritis, the NFS/sld mouse model of human Siogren's syndrome; a 120 kD organ-specific autoantigen recently identified as an analog of human cytoskeletal. protein -fod r in (Haneji et al. (1997) Science 276: 604), the New Zealand Black/White F1 hybrid mouse model of human SLE, NOD mice, a mouse model of human diabetes mellitus, fas/fas ligand mutant mice, which spontaneously develop autoimmune and lymphoproliferative disorders (Watanabe-Fukunaga et al. (1992) Nature 356: 314), and experimental autoimmune encephalomyelitis (EAE), in which myelin basic protein induces a disease that resembles human multiple sclerosis.

Autoantigens (that can be experimentally evolved (e.g. by polynucleotide reassembly &/or polynucleotide site-saturation mutagenesis) according to the methods of the invention) that are useful in genetic vaccines for treating multiple sclerosis include, but are not limited to, myelin basic protein (Stinissen et al. (1996) J Neurosci. Res. 45: 500–511) or a fusion protein of myelin basic protein and proteolipid protein in multiple sclerosis (Elliott et al. (1996) J Clin. Invest. 98: 1602–1612), proteolipid protein (PLP) (Rosener et al. (1997) J Neuroimmunol. 75: 28–34), 2',3'-cyclic nucleotide 3'-phosphodiesterase (CNPase) (Rosener et al. (1997) J Neuroimmunol. 75: 28–34), the Epstein Barr virus nuclear antigen-1 (EBNA-1) in multiple sclerosis (Vaughan et al. (1996) J Neuroimmunol. 69: 95–102), HSP70 in multiple sclerosis (Salvetti et al. (1996) J Neuroimmunol. 65: 143–53; Feldmann et al. (1996) Cell 85: 307).

Target antigens that, after reassembly (optionally in combination with other directed evolution methods described herein) according to the methods of the invention, can be used to treat scleroderma, systemic sclerosis, and systemic lupus erythematosus include, for example, (-2-GPI, 50 kDa glycoprotein (Blank et al. (1994) J Autoimmun. 7: 441–455), Ku (p70/p80) autoantigen, or its 80-kd subunit protein (Hong et al. (1 994) Invest. Ophthalmol. Vis. Sei. 35: 4023–4030; Wang et al. (1994) J Cell Sci. 107: 3223–3233), the nuclear autoantigens La (SS-B) and Ro (SS-A) (Huang et al. (1 997) J Clin. Immunol. 17: 212–219; lgarashi et al. (1995) Autoimmunity 22: 33–42; Keech et al. (1996) Clin. Exp. Immunol. 104: 255–263; Manoussakis et al. (1995) J Autoimmun. 8: 959–969; Topfer et al. (1995) Proc. Nat'l. Acad. Sci. USA 92: 875–879), proteasome (-type subunit C9 (Feist et al. (1996) J Exp. Med. 184: 1313–1318), Scleroderma antigens Rpp 30, Rpp 38 or Scl-70 (Eder et al. (1997) Proc. Nat'l. Acad. Sci. USA 94: 1101–1106; Hietarinta et al. (1994) Br. J Rheumatol. 33: 323–326), the centrosome autoantigen PCM-1 (Bao et al. (1995) Autoimmunity 22: 219–228), polymyositis-scleroderma autoantigen (PM-Scl) (Kho et al. (1997) J Biol. Chem. 272: 13426–1343 1), scleroderma (and other systemic autoimmune disease) autoantigen CENP-A (Muro et al. (1996) Clin. Immunol. Immunopathol. 78: 86–89), U5, a small nuclear ribonucleoprotein (snRNP) (Okano et al. (1 996) Clin. Immunol. Immunopathol. 81: 41–47), the I 00-kd protein of PM-Scl autoantigen (Ge et al. (1996) Arthritis Rheum. 39: 1588–1595), the nucleolar U3- and Th(7–2) ribonucleoproteins (Verheijen et al. (1994) J. Immunol. Methods 169: 173–182), the ribosomal protein L7 (Neu et al. (1995) Clin. Exp. Immunol. 100: 198–204), hpop 1 (Lygerou et al. (1996) EMBO J. 15: 5936–5948), and a 36-kd protein from nuclear matrix antigen (Deng et al. (1996) Arthritis Rheum. 39: 1300–1307).

Hepatic autoimmune disorders can also be treated using improved recombinant antigens that are prepared according to the methods described herein. Among the antigens that are useful in such treatments are the cytochromes P450 and UDP- glucuronosyl-transferases (Obermayer-Straub and Manns (1996) Baillieres Clin. Gastroenterol. 10: 501–532), the cytochromes P450 2C9 and P450 1A2 (Bourdi et al. (1996) Chem. Res. Toxicol. 9: 1159–1166; Clemente et al. (1997) J Clin. Endocrinol. Metab. 82: 1353–1361), LC-1 antigen (Klein et al. (1996) J Pediatr. Gastroenterol. Nutr. 23: 461–465), and a 230-kDa Golgi-associated protein (Funaki et al. (1996) Cell Struct. Funct. 21: 63–72).

For treatment of autoimmune disorders of the skin, useful antigens include, but are not limited to, the 450 kD human epidermal autoantigen (Fujiwara et al. (1996) J Invest. Dermatol. 106: 1125–1130), the 230 kD and 180 kD bullous pemphigoid antigens (Hashimoto (1995) Keio J Med. 44: 115–123; Murakami et al. (1996) J Dermatol. Sci. 13: 112–117), pemphigus foliaceus antigen (desmoglein 1), pemphigus vulgaris antigen (desmoglein 3), BPAg2, BPAg1, and type VII collagen (Batteux et al. (1997) J Clin. Immunol. 17: 228–233; Hashimoto et al. (1996) J Dermatol. Sci. 12: 10–17), a 168-kDa mucosal antigen in a subset of patients with cicatricial pemphigoid (Ghohestani et al. (1996) J Invest. Dermatol. 107: 136–139), and a 218-kd nuclear protein (218-kd Mi-2) (Seelig et al. (1995) Arthritis Rheum. 38: 1389–1399).

The methods of the invention are also useful for obtaining improved antigens for treating insulin dependent diabetes mellitus, using one or more of antigens which include, but are not limited to, insulin, proinsulin, GAD65 and GAD67, heat-shock protein 65 (hsp65), and islet-cell antigen 69 (ICA69) (French et al. (1997) Diabetes 46: 34–39; Roep (1996) Diabetes 45: 1147–1156; Schloot et al. (1997) Diabetologia 40: 332–338), viral proteins homologous to GAD65 (Jones and Crosby (1996) Diabetologia 39: 1318–1324), islet cell antigen-related protein-tyrosine phosphatase (PTP) (Cui et al. (1996) J Biol. Chem. 271: 24817–24823), GM2-1 ganglioside (Cavallo et al. (1996) J Endocrinol. 150: 113–120; Dotta et al. (1996) Diabetes 45: 1193–1196), glutarnic acid decarboxylase (GAD) (Nepom (1995) Curr. Opin. Immunol. 7: 825–830; Panina-Bordignon et al. (1995) J Exp. Med. 181: 1923–1927), an islet cell antigen (ICA69) (Karges et al. (1997) Biochim. Biophys. Acta 1360: 97–101; Roep et al. (1996) Eur. J Immunol. 26: 1285–1289), Tep69, the single T cell epitope recognized by T cells from diabetes patients (Karges et al. (1997) Biochim. Biopkys. Acta 1360: 97–101), ICA 512, an autoantigen of type I diabetes (Solimena et al. (1996) EMBO J. 15: 2102–2114), an islet-cell protein tyrosine phosphatase and the 37- kDa autoantigen derived from it in type I diabetes (including IA-2, IA-2) (La Gasse et al. (1997) Mol. Med. 3: 163–173), the 64 kDa protein from In- 111 cells or human thyroid follicular cells that is immunoprecipitated with sera from patients with islet cell surface antibodies (ICSA) (Igawa et al. (1996) Endocr. J. 43: 299–306), phogrin, a homologue of the human transmembrane protein tyrosine phosphatase, an autoantigen of type I diabetes (Kawasaki et al. (1996) Biochem. Biophys. Res. Commun. 227: 440–447), the 40 kDa and 37 kDa tryptic fragments and their precursors IA-2 and IA-2 in IDDM (Lampasona et al. (1996) J Immunol. 157: 2707–2711; Notkins et al. (1996) J A utoimmun. 9: 677–682), insulin or a cholera toxoid-insulin conjugate (Bergerot et al. (1997) Proc: Nat'l. Acad. Sci. USA 94: 4610–4614), carboxypeptidase H, the human homologue of gp330, which is a renal epithelial glycoprotein involved in inducing Heymann nephritis in rats, and the 38- kD islet mitochondrial autoantigen (Arden et al. (1996) J Clin. Invest. 97: 551–561.

Rheumatoid arthritis is another condition that is treatable using optimized antigens prepared according to the present invention. Useful antigens for rheumatoid arthritis treatment include, but are not limited to, the 45 kDa DEK nuclear antigen, in particular onset juvenile rheumatoid arthritis and iridocyclitis (Murray et al. (1997) J Rheumatol. 24: 560–567), human cartilage glycoprotein-39, an autoantigen in rheumatoid arthritis (Verheijden et al. (1997) Arthritis Rheum. 40: 1115–1125), a 68k autoantigen in rheumatoid arthritis (Blass et al. (1997) Ann. Rheum. Dis. 56: 317–322), collagen (Rosloniec et al. (1995) J Immunol. 155: 4504–4511), collagen type II (Cook et al. (1996) Arthritis Rheum. 39: 1720–1727; Trentham (1996) Ann. N. Y. Acad. Sci. 778: 306–314), cartilage link protein (Guerassimov et al. (1997) J Rheumatol. 24: 95 9–964), ezrin, radixin and moesin, which are auto-immune antigens in rheumatoid arthritis (Wagatsuma et al. (1996) Mol. Immunol. 33: 1171–1176), and mycobacterial heat shock protein 65 (Ragno et al. (1997) Arthritis Rheum. 40: 277–283).

Also among the conditions for which one can obtain an improved antigen suitable for treatment are autoimmune thyroid disorders. Antigens that are useful for these applications include, for example, thyroid peroxidase and the thyroid stimulating hormone receptor (Tandon and Weetman (1994) J R. Coll. Physicians Lond. 28: 10–18), thyroid peroxidase from human Graves' thyroid tissue (Gardas et al. (1997) Biochem. Biophys. Res. Commun. 234: 366–370; Zimmer et al. (1997) Histochem. Cell. Biol. 107: 115–120), a 64-kDa antigen associated with thyroid-associated ophthalmopathy (Zhang et al. (1996) Clin. Immunol. Immunopathol. 80: 23 6–244), the human TSH receptor (Nicholson et al. (1996) J Mol. Endocrinol. 16: 159–170), and the 64 kDa protein from In- 111 cells or human thyroid follicular cells that is immunoprecipitated with sera from patients with islet cell surface antibodies (ICSA) (Igawa et al. (1996) Endocr. J. 43: 299–306).

Other conditions and associated antigens include, but are not limited to, Sjogren's syndrome (-fodrin; Haneji et al. (1997) Science 276: 604–607), myastenia gravis (the human M2 acetylcholine receptor or fragments thereof, specifically the second extracellular loop of the human M2 acetylcholine receptor; Fu et al. (1996) Clin. Immunol. Immunopathol. 78: 203–207), vitiligo (tyrosinase; Fishman et al. (1997) Cancer 79: 1461–1464), a 450 kD human epidermal autoantigen recognized by serum from individual with blistering skin disease, and ulcerative colitis (chromosomal proteins HMG1 and HMG2; Sobajima et al. (199 7) Clin. Exp. Immunol. 107: 135–140).

2.9.3. Allergy and Astham

The invention also provides methods of obtaining reagents that are useful for treating allergy. In one embodiment, the methods involve making a library of experimentally generated polynucleotides that encode an allergen, and screening the library to identify those experimentally generated polynucleotides that exhibit improved properties when used as immunotherapeutic reagents for treating allergy. For example, specific immunotherapy of allergy using natural antigens carries a risk of inducing anaphylaxis, which can be initiated by cross-linking of high-affinity IgE receptors on mast cells. Therefore, allergens that are not recognized by pre-existing IgE are desirable. The methods of the invention provide methods by which one can obtain such allergen variants. Another improved property of interest is induction of broader immune responses, increased safety and efficacy.

Genetic vaccine vectors and other reagents obtained using the methods of the invention can be used to treat allergies and asthma. Allergic immune responses are results of complex interactions between B cells, T cells, professional antigen-presenting cells (APC), eosinophils and mast cells. These cells take part in allergic immune responses both as modulators of the immune responses and are also involved in producing factors directly involved in initiation and maintenance of allergic responses.

Synthesis of Polyclonal and Allergen-Specific IgE Requires Multiple Interactions Between B Cells, T Cells and Professional Antigen-Presenting Cells (APC).

Activation of naive, unprimed B cells is initiated when specific B cells recognize the allergen by cell surface immunoglobulin (sIg). However, costimulatory molecules expressed by activated T cells in both soluble and membrane-bound forms are necessary for differentiation of B cells into IgE-secreting plasma cells. Activation of T helper cells requires recognition of an antigenic peptide in the context of MHC class II molecules on the plasma membrane of APC, such as monocytes, dendritic cells, Langerhans cells or primed B cells. Professional APC can efficiently capture the antigen and the peptide-MHC class II complexes are formed in a post-Golgi, proteolytic intracellular compartment and subsequently exported to the plasma membrane, where they are recognized by T cell receptor (TCR) (Monaco (1995) J Leuk. Biol. 57: 543–547). In addition, activated B cells express CD80 (B7-1) and CD86 (B7-2, B70), which are the counter receptors for CD28 and which provide a costimulatory signal for T cell activation resulting in T cell proliferation and cytokine synthesis (Bluestone (1995) Immunity 2: 555–559). Since allergen-specific T cells from atopic individuals generally belong to the TH2 cell subset, activation of these cells also leads to production of IL-4 and IL-13, which, together with membrane-bound costimulatory molecules expressed by activated T helper cells, direct B cell differentiation into IgE-secreting plasma cells (de Vries and Punnonen, In Cytokine Regulation of Humoral Immunity: Basic and Clinical Aspects, Ed. CM Snapper, John Wiley & Sons Ltd, West Sussex, UK, p. 195–215, 1996).

Mast cells and eosinophils are key cells in inducing allergic symptoms in target organs. Recognition of specific antigen by IgE bound to high-affinity IgE receptors on mast cells, basophils or eosinophils results in crosslinking of the receptors leading to degranulation of the cells and rapid release of mediator molecules, such as histamine, prostaglandins and leukotrienes, causing allergic symptoms.

Immunotherapy of allergic diseases currently includes hyposensibilization treatments using increasing doses of allergen injected to the patient. These treatments result skewing of immune responses towards $T_H1$ phenotype and increase the ratio of IgG/IgE antibodies specific for allergens. Because these patients have circulating IgE antibodies specific for the allergens, these treatments include significant risk of anaphylactic reactions.

In these reactions, free circulating allergen is recognized by IgE molecules bound to high-affinity IgE receptors on mast cells and eosinophils. Recognition of the allergen results in crosslinking of the receptors leading to release of mediators, such as histamine, prostaglandins, and leukotrienes, which cause the allergic symptoms, and occasionally anaphylactic reactions. Other problems associated with hyposensibilization include low efficacy and difficulties in producing allergen extracts reproducibly.

Genetic vaccines provide a means of circumventing the problems that have limited the usefulness of previously known hyposensibilization treatments. For example, by expressing antigens on the surface of cells, such as muscle cells, the risk of anaphylactic reactions is significantly reduced. This can be achieved by using genetic vaccine vectors that encode transmembrane forms of allergens. The allergens can also be modified in such a way that they are efficiently expressed in transmembrane forms, further reducing the risk of anaphylactic reactions. Another advantage provided by the use of genetic vaccines for hyposensibilization is that the genetic vaccines can include cytokines and accessory molecules which further direct the immune responses towards the $T_H1$ phenotype, thus reducing the amount of IgE antibodies produced and increasing the efficacy of the treatments. Vectors can also be evolved to induce primarily IgG and IgM responses, with little or no IgE response.

Furthermore, stochastic (e.g. polynucleotide shuffling & interrupted synthesis) and non-stochastic polynucleotide reassembly can be used to generate allergens that are not recognized by the specific IgE antibodies preexisting in vivo, yet are capable of inducing efficient activation of allergen-specific T cells. For example, using phage display selection, one can express experimentally evolved (e.g. by polynucleotide reassembly &/or polynucleotide site-saturation mutagenesis) allergens on phage, and only those that are not recognized by specific IgE antibodies are selected. These are further screened for their capacity to induce activation of specific T cells. An efficient T cell response is an indication that the T cell epitopes are functionally intact, although the B cell epitopes were altered, as indicated by lack of binding of specific antibodies.

In these methods, polynucleotides encoding known allergens, or homologs or fragments thereof (e.g., immunogenic peptides) are inserted into DNA vaccine vectors and used to immunize allergic and asthmatic individuals. Alternatively, the experimentally evolved (e.g. by polynucleotide reassembly &/or polynucleotide site-saturation mutagenesis) allergens are expressed in manufacturing cells, such as *E. coli* or yeast cells, and subsequently purified and used to treat the patients or prevent allergic disease. stochastic (e.g. polynucleotide shuffling & interrupted synthesis) and non-stochastic polynucleotide reassembly can be used to obtain antigens that activate T cells but cannot induce anaphylactic reactions. For example, a library of experimentally generated polynucleotides that encode allergen variants can be expressed in cells, such as antigen presenting cells, which are than contacted with PBMC or T cell clones from atopic patients. Those library members that efficiently activate TH cells from the atopic patients can be identified by assaying for T cell proliferation, or by cytokine synthesis (e.g., synthesis of IL-2, IL-4, IFN- . Those recombinant allergen variants that are positive in the in vitro tests can then be subjected to in vivo testing.

Examples of Allergies That can be Treated Include, but are not Limited to, Allergies Against House Dust Mite, Grass Pollen, Birch Pollen, Ragweed Pollen, Hazel Pollen, Cockroach, Rice, Olive Tree Pollen, Ftmgi, Mustard, Bee Venom Antigens of interest include those of animals, including the mite (e.g., Dermatophagoides pteronyssinus, Dermatophagoidesfarinae, Blomia tropicalis), such as the allergens der p1 (Scobie et al. (1994) Biochem. Soc. Trans. 22: 448S; Yssel et al. (1 992) J Immunol. 148: 738–745), der p2 (Chua et al. (1996) Clin. Exp. Allergy 26: 829–83 7), der p3 (Smith and Thomas (1996) Clin. Exp. Allergy 26: 571–579), der p5, der p V (Lin et al. (1994) J Allergy Clin. Immunol. 94: 989–996), der p6 (Bennett and Thomas (1996)

Clin. Exp. Allergy 26: 1150–1154), der p7 (Shen et al. (1995) Clin. Exp. Allergy 25: 416–422), der f2 (Yuuki et al. (1997) Int. Arch. Allergy Immunol. 112: 44–48), der f3 (Nishiyarna et al. (1995) FEBSLett. 377: 62–66), der f7 (Shen et al. (1995) Clin. Exp. Allergy 25: 1000–1006); Mag 3 (Fujikawa et al. (1996) Mol. Immunol. 33: 311–319). Also of interest as antigens are the house dust mite allergens Tyr p2 (Eriksson et al. (1998) Eur. J Biochem. 251: 443–447), Lep d I (Schmidt et al. (1995) FEBS Lett. 3 70: 11–14), and glutathione S-transferase (O'Neill et al. (1995) Immunol Lett. 48: 103–107); the 25,589 Da, 219 amino acid polypeptide with homology with glutathione S- transferases (ONeill et al. (1994) Biochim. Biophys. Acta. 1219: 521–528); Blo t 5 (Arruda et al. (1995) Int. Arch. Allergy Immunol. 107: 456–45 7); bee venom phospholipase A2 (Carballido et al. (1994) J Allergy Clin. Immunol. 93: 758–767; Jutel et al. (1995) J Immunol. 154: 4187–4194); bovine dermal/dander antigens BDA 11 (Rautiainen et al. (1995) J. Invest. Dermatol. 105: 660–663) and BDA20 (Mantyj arvi et al. (1996) J Allergy Clin. Immunol. 97: 1297–1303); the major horse allergen Equ cI (Gregoire et al. (1996) J Biol. Chem. 271: 32951–32959); Jumper ant M. pilosula allergen Myr p 1 and its homologous allergenic polypeptides Myr p2 (Donovan et al. (1996) Biochem. Mol. Biol. Int. 39: 877–885); 1–13, 14, 16 kD allergens of the mite Blomia tropicalis (Caraballo et al. (1996)J Allergy Clin. Immunol. 98: 573–579); the cockroach allergens Bla g Bd9OK (Helm et al. (1996) J Allergy Clin. Immunol. 98: 172–80) and Bla g 2 (Arruda et al. (1995) J Biol. Chem. 270: 19563–19568); the cockroach Cr-PI allergens (Wu et al. (1996) J Biol. Chem. 271: 1793 7–17943); fire ant venom allergen, Sol i 2 (Schmidt et al. (1996) J Allergy Clin. Immunol. 98: 82–88); the insect Chironomus thumini major allergen Chi t 1–9 (Kipp et al. (1996) Int. Arch. Allergy Immunol. 110: 348–353); dog allergen Can f 1 or cat allergen Fel d 1 (Ingram et al. (1995) J Allergy Clin. Immunol. 96: 449–456); albumin, derived, for example, from horse, dog or cat (Goubran Botros et al. (1996) Immunology 88: 340–347); deer allergens with the molecular mass of 22 kD, 25 kD or 60 kD (Spitzauer et al. (1997) Clin. Exp. Allergy 27: 196–200); and the 20 kd major allergen of cow (Ylonen et al. (1994) J Allergy Clin. Immunol. 93: 851–858). Pollen and grass allergens are also useful in vaccines, particularly after optimization of the antigen by the methods of the invention. Such allergens include, for example, Hor v9 (Astwood and Hill (1996) Gene 182: 53–62, Lig v 1 (Batanero et al. (1996) Clin. Exp. Allergy 26: 1401–1410); Lol p 1 (Muller et al. (1996) Int. Arch. Allergy Immunol. 109: 352–355), Lol p II (Tamborini et al. (1995) Mol. Immunol. 32: 505–513), Lol pVA, Lol pVB (Ong et al. (1995) Mol. Immunol. 32: 295–302), Lol p 9 (Blaher et al. (1 996) J Allergy Clin. Immunol. 98: 124–132); Par J I (Costa et al. (1994) FEBS Lett. 341: 182–186; Sallusto et al. (1996) J Allergy Clin. Immunol. 97: 627–637), Par j 2.0101 (Duro et al. (1996) FEBS Lett. 399: 295–298); Bet v1 (Faber et al. (1 996) J Biol. Chem. 271: 19243–19250), Bet v2 (Rihs et al. (1994) Int. Arch. Allergy Immunol. 105: 190–194); Dac g3 (Guerin-Marchand et al. (1996) Mol. Immunol. 33: 797–806); Phl p 1 (Petersen et al. (1995) J Allergy Clin. Immunol. 95: 987–994), Phl p 5 (Muller et al. (1996) Int. Arch. Allergy Immunol. 109: 352–355), Phl p 6 (Petersen et al. (1995) Int. Arch. Allergy Immunol. 108: 55–59); Cry j I (Sone et al. (1994) Biochem. Biophys. Res. Commun. 199: 619–625), Cry j II (Namba et al. (1994) FEBS Lett. 353: 124–128); Cor a 1 (Schenk et al. (1994) Eur. J Biochem. 224: 717–722); cyn d 1 (Smith et al. (1996) J Allergy Clin. Immunol. 98: 331–343), cyn d 7 (Suphioglu et al. (1997) FEBS Lett. 402: 167–172); Pha a 1 and isoforms of Pha a 5 (Suphioglu and Singh (1995) Clin. Exp. Allergy 25: 853–865); Cha o 1 (Suzuki et al. (1996) Mol. Immunol. 33: 451–460); profilin derived, e.g, from timothy grass or birch pollen (Valenta et al. (1994) Biochem. Biopkys. Res. Commun. 199:106–118); P0149(Wuet al. (1996) Plant Mol.Biol. 32: 1037–1042); Ory s1 (Xuet al. (1995) Gene 164:255–259); and Amb a V and Amb t5 (Kim et al. (1996) Mol. Immunol. 33: 873–880; Zhu et al. (1995) J Immunol. 155: 5064–5073).

Vaccines against food allergens can also be developed using the methods of the invention. Suitable antigens for reassembly (optionally in combination with other directed evolution methods described herein) include, for example, profilin (Rihs et al. (1994) Int. Arch. Allergy Immunol. 105: 190–194); rice allergenic cDNAs belonging to the alpha-amylase/trypsin inhibitor gene family (Alvarez et al. (1995) Biochim Biophys Acta 1251: 201–204); the main olive allergen, Ole e I (Lombardero et al. (1994) Clin Exp Allergy 24: 765–770); Sin a 1, the major allergen from mustard (Gonzalez De La Pena et al. (1996) Eur J Biochem. 237: 827–832); parvalbumin, the major allergen of salmon (Lindstrom et al. (1996) Scand. J Immunol. 44: 335–344); apple allergens, such as the major allergen Mal d 1 (Vanek-Krebitz et al. (1995) Biochem. Biophys. Res. Commun. 214: 538–551); and peanut allergens, such as Ara h I (Burks et al. (1995) J Clin. Invest. 96: 1715–1721).

The methods of the invention can also be used to develop recombinant antigens that are effective against allergies to ftngi. Fungal allergens useful in these vaccines include, but are not limited to, the allergen, Cla h III, of Cladosporium herbarum (Zhang et al. (1995) J Immunol. 154: 710–717); the allergen Psi c 2, a fungal cyclophilin, from the basidiomycete Psilocybe cubensis (Homer et al. (1995) Int. Arch. Allergy Immunol. 107: 298–300); hsp 70 cloned from a cDNA library of Cladosporium herbarum (Zhang et al. (1996) Clin Exp Allergy 26: 88–95); the 68 kD allergen of Penicillium notatum (Shen et al. (1995) Clin. Exp. Allergy 26: 350–356); aldehyde dehydrogenase (ALDH) (Achatz et al. (1995) Mol Immunol. 32: 213–227); enolase (Achatz et al. (1995) Mol. Immunol. 32: 213–227); YCP4 (Id.); acidic ribosomal protein P2 (Id.).

Other allergens that can be used in the methods of the invention include latex allergens, such as a major allergen (Hev b 5) from natural rubber latex (Akasawa et al. (1996) J Biol. Chem. 271: 25389–25393; Slater et al. (1996) J Biol. Chem. 271: 25394–25399).

The. invention also provides a solution to another shortcoming of genetic vaccination as a treatment for allergy and asthma. While genetic vaccination primarily induces CD8$^+$ T cell responses, induction of allergen-specific IgE responses is dependent on CD4$^+$ T cells and their help to B cells. T$_H$2-type cells are particularly efficient in inducing IgE synthesis because they secrete high levels of IL-4, IL-5 and IL-1 3, which direct Ig isotype switching to IgE synthesis. IL-5 also induces eosinophilia. The methods of the invention can be used to develop genetic vaccines that efficiently induce CD4$^+$ T cell responses, and direct differentiation of these cells towards the T$_H$1 phenotype.

The invention also provides methods by which the level of antigen release by a genetic vaccine-vector is regulated. Regulation of the antigen dose is crucial at the onset of hyposensibilization for safety reasons. Low antigen levels are preferably used at first, with the antigen level increasing once evidence has been obtained that the antigen does not induce adverse effects in the individual. The stochastic (e.g. polynucleotide shuffling & interrupted synthesis) and non-stochastic polynucleotide reassembly methods of the invention allow generation of genetic vaccine vectors that induce expression of different (high and low) levels of antigen. For example, two or more different evolved promoters can be used for antigen expression. Alternatively, the antigen gene itself can be evolved for different levels of expression by, for example, altering codon usage. Vectors that induce different levels of antigen expression can be screened by use of specific monoclonal antibodies, and cell sorting (e.g, FACS).

2.9.4. Cancer

Immunotherapy has great promise for the treatment of cancer and prevention of metastasis. By inducing an immune response against cancerous cells, the body's immune system can be enlisted to reduce or eliminate cancer. (e.g. using the improved antigens obtained using the methods of the invention). Genetic vaccines prepared using the methods of the invention, as well as accessory molecules described herein, provide cancer immunotherapies of increased effectiveness compared to those that are presently available.

One approach to cancer immunotherapy is vaccination using genetic vaccines that include or encode antigens that are specific for tumor cells or by injecting the patients with purified recombinant cancer antigens. The methods of the invention can be used for (obtaining antigens that exhibit an) enhancement of immune responses against known tumor-specific antigens, and also to search for novel protective antigenic sequences. Genetic vaccines that exhibit optimized antigen expression, processing, and presentation can be obtained as described herein. The methods of the invention are also suitable for obtaining optimized cytokines, costimulatory molecules, and other accessory molecules that are effective in induction of an antitumor immune response, as well as for obtaining genetic vaccines and cocktails that include these and other components present in optimal combinations. The approach used for each particular cancer can vary. For treatment of hormone-sensitive cancers (for example, breast cancer and prostate cancer), methods of the invention can be used to obtain optimized hormone antagonists. For highly immunogenic tumors, including melanoma, one can screen for genetic vaccine vectors (recombinant antigens) that optimally boost the immune response against the tumor.

Breast Cancer, in Contrast, is of Relatively Low Immunogenicity and Exhibits Slow Progression so Individual Treatments can be Designed for Each Patient, Prevention of Metastasis is Also a Goal in Design of Genetic Vaccines Among the tumor-specific antigens that can be used in the antigen reassembly (optionally in combination with other directed evolution methods described herein) methods of the invention are: bullous pemphigoid antigen 2, prostate mucin antigen (PMA) (Beckett and Wright (1995) Int. J Cancer 62: 703–710), tumor associated Thomsen-Friedenreich antigen (Dahlenborg et al. (1997) Int. J Cancer 70: 63–71), prostate-specific antigen (PSA) (Dannull and Belldegrun (1997) Br. J Urol. 1: 97–103), luminal epithelial antigen (LEA. 135) of breast carcinoma and bladder transitional cell carcinoma (TCC) (Jones et al. (1997) Anticancer Res. 17: 685–687), cancer-associated serum antigen (CASA) and cancer antigen 125 (CA 125) (Kierkegaard et al. (1995) Gynecol. Oncol. 59: 251–254), the epithelial glycoprotein 40 (EGP40) (Kievit et al. (1997) Int. J Cancer 71: 237–245), squamous cell carcinoma antigen (SCC) (Lozza et al. (1997) Antican-cer Res. 17: 525–529), cathepsin E (Mota et al. (1997) Ant. J Pathol. 150: 1223–1229), tyrosinase in melanoma (Fishman et al. (1997) Cancer 79: 1461–1464), cell nuclear antigen (PCNA) of cerebral cavemomas (Notelet et al. (1997) Surg. Neurol. 47: 364–370), DF3/MUCI breast cancer antigen (Apostolopoulos et al. (1996) Immunol. Cell. Biol. 74: 45 7–464; Pandey et al. (1995) Cancer Res. 5 5: 4000–4003), carcinoembryonic antigen (Paone et al. (1996) J Cancer Res. Clin. Oncol. 122: 499–503; Schlom et al. (1996) Breast Cancer Res. Treat. 38: 27–39), tumor-associated antigen CA 19–9 (Tolliver and O'Brien (1997) South Med. J. 90: 89–90; Tsuruta et al. (1997) Urol. Int. 5 8: 20–24), human melanoma antigens MART-I/Melan-A27- and gplOO (Kawakami and Rosenberg (1997) Int. Rev. Immunol. 14: 173–192; Zajac et al. (1997) Int. J Cancer 71: 491–496), the T and Tn pancarcinoma (CA) glycopeptide epitopes (Springer (1995) Crit. Rev. Oncog. 6: 57–85), a 35 kD tumor-associated autoantigen in papillary thyroid carcinoma (Lucas et al. (1996) Anticancer Res. 16: 2493–2496), KH-I adenocarcinoma antigen (Deshpande and Danishefsky (1997) Nature 387: 164–166), the A60 mycobacterial antigen (Maes et al. (1996) J Cancer Res. Clin. Oncol. 122: 296–300), heat shock proteins (HSPs) (Blachere and Srivastava (1995) Semin. Cancer Biol. 6: 349–355), and MAGE, tyrosinase, melan-A and gp75 and mutant oncogene products (e.g., p53, ras, and HER-2/neu (Bueler and Mulligan (1996) Mol. Med. 2: 545–555; Lewis and Houghton (1995) Semin. Cancer Biol. 6: 321–327; Theobald et al. (1995) Proc. Nat'l. Acad. Sci. USA 92: 11993–11997).

2.9.5. Parasites

Antigens from parasites can also be optimized by the methods of the invention. These include, but are not limited to, the schistosome gut-associated antigens CAA (circulating anodic antigen) and CCA (circulating cathodic antigen) in *Schistosoma mansoni, S. haematobium* or *S. japonicum* (Deelder et al. (1996) Parasitology 112: 21–35); a multiple antigen peptide (MAP) composed of two distinct protective antigens derived from the parasite *Schistosoma mansoni (Ferru et al.* (1997) Parasite Immunol. 19: 1–11); Leishmania parasite surface molecules (Lezama-Davila (1997) Arch. Med Res. 28: 47–53); third-stage larval (L3) antigens of L. loa (Akue et al. (1997) J Infect. Dis. 175: 158–63); the genes, Tams 1-1 and Tams 1–2, encoding the 30-and 32-kDa major merozoite surface antigens of Theileria annulata (Ta) (d'Oliveira et al. (1996) Gene 172: 33–39); Plasmodium falciparum merozoite surface antigen 1 or 2 (al-Yaman et al. (1995) Trans. R. Soc. Trop. Med. Hyg. 89: 555–559; Beck et al. (1997) J Infect. Dis. 175: 921–926; Rzepczyk et al. (1997) Infect. Immun. 65: 1098–1100); circumsporozoite (CS) protein-based B-epitopes from *Plasmodium berghei*, (PPPPNPND)2 and Plasmodium yoelii, (QGPGAP)3QG, along with a P. berghei T-helper epitope KQIRDSITEEWS (Reed et al. (1997) Vaccine 15: 482–488); NYVAC-Pf7 encoded *Plasmodium falciparum* antigens derived from the sporozoite (circumsporozoite protein and sporozoite surface protein 2), liver (liver stage antigen 1), blood (merozoite surface protein 1, serine repeat antigen, and apical membrane antigen 1), and sexual (25-kDa sexual-stage antigen) stages of the parasite life cycle were inserted into a single NYVAC genome to generate NYVAC-Pf7 (Tine et al. (1996) Infect. Immun. 64: 3833–3844); *Plasmodium falciparum* antigen Pfs230 (Williamson et al. (1996) Mol. Biochem. Parasitol. 78: 161–169); *Plasmodium falciparum* apical membrane antigen (AMA-1) (Lal et al. (1996) Infect. Immun. 64: 1054–1059); *Plasmodium falciparum* proteins Pfs28 and Pfs25 (Duffy and Kaslow (1997) Infect. Immun. 65: 1109–1113); *Plasmodium falciparum* merozoite surface protein, MSP1 (Hui et al. (1996) Infect. Immun. 64: 1502–1509); the malaria antigen Pf332 (Ahlborg et al. (1996) Immunology 88: 630–635); *Plasmodium falciparum* erythrocyte membrane protein I (Baruch et al. (1995) Proc. Nat'l. Acad. Sci. USA 93: 3497–3502; Baruch et al. (1995) Cell 82: 77–87); *Plasmodium falciparum* merozoite surface antigen, PfMSP-I (Egan et al. (1996) J Infect. Dis. 173: 765–769); *Plasmodium falciparum* antigens SERA, EBA-175, RAPI and RAP2 (Riley (1997) J Pharm. Pharmacol. 49: 21–27); Schistosoma japonicum paramyosin (Sj97) or fragments thereof (Yang et al. (1995) Biochem. Biophys. Res. Commun. 212: 1029–1039); and Hsp70 in parasites (Maresca and Kobayashi (1994) Experientia 50: 1067–1074).

2.9.6. Contraception

Genetic vaccines that contain optimized antigens obtained by the methods of the invention are also useful for contraception. For example, genetic vaccines can be obtained that encode sperm cell specific antigens, and thus induce anti-sperm immune responses. Vaccination can be achieved by, for example, administration of recombinant bacterial strains, e.g. Salmonella and the like, which express sperm antigen, as well as by induction of neutralizing anti-hCG antibodies by vaccination by DNA vaccines encoding human chorionic gonadotropin (hCG), or a fragment thereof.

Sperm antigens which can be used in the genetic vaccines include, for example, lactate dehydrogenase (LDH-C4), galactosyltransferase (GT), SP-10, rabbit sperm autoantigen (RSA), guinea pig (g)PH-20, cleavage signal protein (CS-1), HSA-63, human (h)PH-20, and AgX-1 (Zhu and Naz (1994) Arch. Androl. 33: 141–144), the synthetic spenn peptide, P10G (O'Rand et al. (1993) J Reprod. Immunol. 25: 89–102), the 135 kD, 95 kD, 65 kD, 47 kD, 41 kD and 23 kD proteins of sperm, and the FA-1 antigen (Naz et al. (1995) Arch. Androl. 35: 225–23 1), and the 35 kD fragment of cytokeratin 1 (Lucas et al. (1996) Anticancer Res. 16: 2493–2496).

The methods of the invention can also be used to obtain genetic vaccines that are expressed specifically in testis. For example, polynucleotide sequences that direct expression of genes that are specific to testis can be used (e.g., fertilization antigen-1 and the like). In addition to sperm antigens, antigens expressed on oocytes or hormones regulating reproduction may be useful targets of contraceptive vaccines. For example, genetic vaccines can be used to generate antibodies against gonadotropin releasing hormone (GnRH) or zona pellucida proteins (Miller et al. (1997) Vaccine 15:185 8–1862). Vaccinations using these molecules have been shown to be efficacious in animal models (Miller et al. (1997) Vaccine 15:1858–1862). Another example of a useful component of a genetic contraceptive vaccine is the ovarian zona pellucida glycoprotein ZP3 (Tung et al. (1994) Reprod Fertil. Dev. 6:349–355).

2.10. Malarial Antigens and Vaccines

The present invention generally relates to the *Plasmodium falciparum* erythrocyte membrane protein 1 ("PfEMP 1"), nucleic acids. which encode PfEMP 1, and antibodies which specifically recognize PfEMP1. The polypeptides, antibodies and nucleic acids are useful in a variety of applications including therapeutic, prophylactic, including vaccination, diagnostic and screening applications.

The data described herein, indicates that PfEMP1 is responsible for both antigenic variation and receptor properties on PE, both of which are central to the special virulence and pathology of *P. falciparum*. The central role of PfEMP1 in P. falciparum biology, as the malarial adherence receptor for host proteins on microvascular endothelium, as described herein, indicates its usefulness in a malaria vaccine, in modelling prophylactic drugs, and also as a target for therapeutics to reverse PE adherence in acute cerebral malaria (Howard and Gilladoga, 1989).

2.10.1. Malarial Polypeptides

Soluble PfEMP1 has been reported to bind to CD36, TSP and ICAM-1, and tryptic fragments of PfEMP1 cleaved from the PE surface have been shown to bind to TSP or CD36 (Baruch, et al., Molecular Parasitology Meeting at Woods Hole, Sep. 18–22, 1994). Accordingly, in one aspect, the present invention provides substantially pure PfEMP1 polypeptides, analogs or biologically active fragments thereof.

The terms "substantially pure" or "isolated" refer, interchangeably, to proteins, polypeptides and nucleic acids which are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure protein will make up from about 75 to about 90% of the total protein. Preferably, the protein will make up greater than about 90%, and more preferably, greater than about 95% of the total protein in the composition.

The term "biologically active fragment" as used herein, refers to portions of the proteins or polypeptides, e.g., a PfEMP1 derived polypeptide, which portions possess a particular biological activity, e.g., one or more activities found in a full length PfEMP1 polypeptide. For example, such biological activity may include the ability to bind a particular protein, substrate or ligand, to elicit antibodies reactive with PE, PfEMP1, the recombinant proteins or fragments thereof, to block, reverse or otherwise inhibit an interaction between two proteins, between an enzyme and its substrate, between an epitope and an antibody, or may include a particular catalytic activity. With regard to the polypeptides of the present invention, particularly preferred polypeptides or biologically active fragments include, e.g., polypeptides that possess one or more of the biological activities described above, such as the ability to bind a ligand of PfEMP1 or inhibit the binding of PfEMP1 to one or more of its ligands, e.g., CD36, TSP, ICAM-1, VCAM-1, ELAM-1, Chondroitin sulfate or by the presence within the polypeptide fragment of antigenic determinants which permit the raising of antibodies to that fragment.

The polypeptides of the present invention may also be characterized by their immunoreactivity with antibodies raised against PfEMP1 proteins or polypeptides. In particularly preferred aspects, the polypeptides are capable of inhibiting an interaction between a PfEMP1 protein and an antibody raised against a PfEMP1 protein. Additionally or alternatively, such fragments may be specifically immunoreactive with an antibody raised against a PfEMP1 protein. Such fragments are also referred to herein as "immunologically active fragments." Generally, such biologically active fragments will be from about 5 to about 500 amino acids in length.

Typically, these peptides will be from about 20 to about 250 amino acids in length, and preferably from about 50 to about 200 amino acids in length. Generally, the length of the fragment may depend, in part, upon the application for which the particular peptide is to be used. For example, for raising antibodies, the peptides may be of a shorter length, e.g., from about 5 to about 50 amino acids in length, whereas for binding applications, the peptides may have a greater length, e.g., from about 50 to about 500 amino acids in length, preferably, from about 100 to about 250 amino acids in length, and more preferably, from about 100 to about 200 amino acids in length.

The polypeptides of the present invention may generally be prepared using recombinant or synthetic methods well known in the art. Recombinant techniques are generally described in Sambrook, et al., Molecular Cloning: A Laboratory Manual, (2nd ed.) Vols. 1–3, Cold Spring Harbor Laboratory, (1989). Techniques for the synthesis of polypeptides are generally described in Merrifield, J. Amer. Chem. Soc. 85:2149–2456 (1963), Atherton, et al., Solid Phase Peptide Synthesis: A Practical Approach, IRL Press (1989), and. Merrifield, Science 232:341–347 (1986).

In preferred aspects, the polypeptides of the present invention may be expressed by a suitable host cell that has been transfected with a nucleic acid of the invention, as described in greater detail below. Isolation and purification of the polypeptides of the present invention can be carried out by methods that are generally well known in the art. For example, the polypeptides may be purified using readily available chromatographic methods, e.g., ion exchange, hydrophobic interaction, HPLC or affinity chromatography, to achieve the desired purity. Affinity chromatography may be particularly attractive in allowing the investigator to take advantage of the specific biological activity of the desired peptide, e.g., ligand binding, presence of antigenic determinants, or the like.

Exemplary polypeptides of the present invention will generally comprise an amino acid sequence that is substantially homologous to the amino acid sequence of a PfEMP1 protein, or biologically active fragments thereof, or may include sequences that may take on a homologous conformation. In particularly preferred aspects, the polypeptides of the present invention will comprise an amino acid sequence that is substantially homologous to the amino is acid sequence shown, described &/or referenced herein (including incorporated by reference), or a biologically active fragment thereof.

By "substantially homologous" is meant an amino acid sequence which is at least about 50% homologous to the amino acid sequence of PfEMP1 or a biologically active fragment thereof, preferably at least about 90% homologous, and wore preferably at least about 95% homologous. In some aspects, substantially homologous may include a sequence that is at least 50% homologous, but that presents a homologous structure in three dimensions, i.e., includes a substantially similar surface charge or presentation of hydrophobic groups.

Examples of preferred polypeptides include polypeptides having an amino acid sequence substantially homologous to the MC PfEMP1 amino acid sequence as shown, described &/or referenced herein (including incorporated by reference), and PfEMP1 of other P. falciparum strains as shown, described &/or referenced herein (including incorporated by reference), as well as biologically active fragments of these polypeptides. Preferred peptides include those peptide fragments of PfEMP1 that are involved in the sequestration of parasitized erythrocytes. Examples of these preferred peptides include peptides which comprise an amino acid sequence which is substantially homologous to amino acids 576 through 755 of the PfEMP1 amino acid sequence shown, described &/or referenced herein (including incorporated by reference).

Also among the particularly preferred peptides of the present invention are those peptides and peptide fragments of PfEMP1 which are relatively conserved among the variant strains of P. falciparum or which contain regions of high homology to PfEMP1 proteins from other strains. The term "relatively conserved" generally refers to amino acid sequences that are substantially homologous to portions of the amino acid sequence shown, described &/or referenced herein (including incorporated by reference). However, also included within the definition of this term are peptides which are encoded by a nucleic acid which is a PCR product of primer probes, and particularly, universal primers, derived from the PfEMP1 nucleic acid sequence. In particular, primer is probes derived from the nucleic acid sequence shown, described &/or referenced herein (including incorporated by reference), may be used to amplify nucleic acids from other strains of P. falciparum. Particularly preferred primer sequences include the primer sequences shown in Table 1, below. Similarly, universal primer compositions, described in greater detail below and also shown in Table 1, may be used to amplify sequences that encode the peptides of the present invention.

Specific examples of relatively conserved peptides include those that are contained in a region of PfEMP1 proteins that corresponds to amino acids 576 through 755 of the amino acid sequence of MC PfEMP1, as shown, described &/or referenced herein (including incorporated by reference).

Similar regions have been specifically elucidated in a number of P. falciparum strains (as described herein). In general, these corresponding regions may be described as containing amino acid sequences that are encoded by the universal primer sequences described below. Generally, these amino acid sequences have one or more of the following general structures:

TTIDKX$_1$LX$_2$HE and/or FFWX$_3$WVX4X$_5$ML where X$_1$ is selected from leucine or isoleucine, X$_2$ is selected from glutamine and asparagine, X$_3$ is selected from the methionine, lysine and aspartic acid, X4 is selected from histidine, threanine and tyrosine and X$_5$ is selected from aspartic acid, glutamic acid and histidine. In particularly preferred aspects, the polypeptides may contain both of the above general amino acid sequences. Particularly preferred amino acid sequences will possess the conserved amino acids shown in the various fragments shown, described &/or referenced herein (including incorporated by reference). In particular, conserved amino acid sequences of six amino acids or greater, shown, described &/or referenced herein (including incorporated by reference), may be used as epitopes for generation of antibodies that cross react with multiple P. falciparum strains.

The peptides of the invention may be free or tethered, or may include labeled groups for detection of the presence of the polypeptides. Suitable labels include radioactive, fluorescent and catalytic labeling groups that are well known in the art and that are substantially described herein, e.g., signaling enzymes, chemical reporter groups, polypeptide signals, biotin and the like. Additionally, the peptides may include modifications to the N and C-termini of the peptide, e.g., an acylated N-terminus or amidated C-terminus.

Also included within the present invention are amino acid variants of the above described polypeptides. These variants may include insertions, deletions and substitutions with other amino acids. For example, in some aspects, amino acids may be substituted with different amino acids having similar structural characteristics, e.g., net charge, hydrophobicity, or the like. For example, phenylalanine may be substituted with tyrosine, as a similarly hydrophobic residue. Glycosylation modifications, either changed, increased amounts or decreased amounts, as well as other sequence modifications are also envisioned.

In addition to the above polypeptides which consist only of naturally-occurring amino acids, peptidomimetics of the polypeptides of the present invention are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15:29; Veber and Freidinger (1985) TINS p.392; and Evans et al. (1987) J. Med. Chem 30:1229, and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M., J Chem Soc Perkin Trans I (1982) 307–314 (—CH—CH—, cis and trans); Almquist, R.G. et al., J Med Chem (1980) 23:1392–1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedxon Lett (1983) 24:4401–4404 (—C(OH)CH$_2$—); and Hruby, V. J., Life Sci (1982) 31:189–199 (—CH$_2$—S—)' Peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the molecules to which the peptidomimetic binds (e.g., CD36) to produce the therapeutic effect. Derivitization (e.g., labeling) of peptidomimetics should not substantially interfere with the desired biological or pharmacological activity of the peptidomimetic. Generally, peptidomimetics of peptides of the invention bind to their ligands (e.g., CD36) with high affinity and possess detectable biological activity (i.e., are agonistic or antagonistic to one or more ligand-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Blochem. 61: 387; for example, by adding internal cysteine residues capable of forming intramolecular disulfide bridges which cyclize the peptide.

Polypeptides of the present invention may also be characterized by their ability to bind antibodies raised against PfEMP1, or fragments thereof. Preferably, these antibodies recognize polypeptide domains that are homologous to the PfEMP1 proteins from a number of variants of *P. falciparum*. These homologous domains will generally be present throughout the family of PfEMP1 proteins. A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Antibodies to PfEMP1 and its fragments are discussed in greater detail, below. As used herein, the terms "polypeptide" or "peptide" are used interchangeably to refer to peptides, peptidomimetics, analogs, and the like, as described above.

The polypeptides of the present invention may be used as isolated polypeptides, or may exist as fusion proteins. A "fusion protein" generally refers to a composite protein made up of two or more separate, heterologous proteins which are normally not fused together as a single protein.

Thus, a fusion protein may comprise a fusion of two or more heterologous or homologous sequences, provided these sequences are not normally fused together. Fusion proteins will generally be made by either recombinant nucleic acid methods, i.e., as a result of transcription and translation of a gene fusion comprising a segment encoding a polypeptide comprising a PfEMP1 protein and a segment which encodes one or more heterologous proteins, or by chemical synthesis methods well known in the art.

2.10.2. Malarial Nucleic Acids and Cells Capable of Exdressing Same

Also provided in the present invention are isolated nucleic acid sequences which encode the above described polypeptides and biologically active fragments. Typically, such nucleic acid sequences will comprise a segment that is substantially homologous to a portion or fragment of the nucleic acid sequence shown, described &/or referenced herein (including incorporated by reference). Preferably, the nucleic acids of the present invention will comprise at least about 15 consecutive nucleotides of the nucleic acid, more preferably, at least about 20 contiguous nucleotides, still more preferably, at least about 30 contiguous nucleotides, and still more preferably, at least about 50 contiguous nucleotides from the nucleotide sequence.

Substantial homology in the nucleic acid context means that the segments, or their complementary strands, when compared, are the same when properly aligned with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments will hybridize under selective hybridization conditions to a strand, or its complement, typically using a sequence of at least about 15 contiguous nucleotides derived from the PfEMP1 nucleic acid sequence. However, larger segments will usually be preferred, e.g., at least about 20 or contiguous nucleotides, more usually about 40 contiguous nucleotides, and preferably more than about 50 contiguous nucleotides. Selective hybridization exists when hybridization occurs which is more selective than total lack of specificity. See, Kanchisa, Nucleic Acid Res. 12:203–213 (1984).

Nucleic acids of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids included in the present invention will typically comprise RNA or DNA or mixed polymers. The DNA compositions will generally include a coding region which encodes a polypeptide comprising an amino acid sequence substantially homologous to the amino acid sequence of a PfEMP1 protein. More preferred are those DNA segments comprising a nucleotide sequence which encodes a CD36 binding fragment of the PfEMP1 protein.

cDNA encoding the polypeptides of the present invention, or fragments thereof, may be readily employed as a probe useful for obtaining genes which encode the PfEMP1 polypeptides of the present invention. Preparation of these probes may be carried out by generally well known methods. For example, the cDNA probes may be prepared from the amino acid sequence of the PfEMP1 protein. In particular, probes may be prepared based upon segments of the amino acid sequence which possess relatively low levels of degeneracy, i.e., few or one possible nucleic acid sequences which encode therefor.

Suitable synthetic DNA fragments may then be prepared, e.g., by the phosphoramidite method described by Beaucage and Carruthers, Tetra. Letts. 22:1859–1862 (1981). Alternatively, nucleotide sequences which are relatively conserved among the PfEMP1 coding sequences for the various P. falciparum strains may be used as suitable probes. A double stranded probe may then be obtained by either synthesizing the complementary strand and hybridizing the strands together under appropriate conditions or by adding the complementary strand using DNA polymerase with an appropriate primer sequence. Such cDNA probes may be used in the design of oligonucleotide probes and primers for screening and cloning such genes, e.g., using well known PCR techniques, or, alternatively, may be used to detect the presence or absence of a PfEMP1 gene in a cell. Such nucleic acids, or fragments may comprise part or all of the cDNA sequence that encodes the polypeptides of the present invention. Effective cDNA probes may comprise as few as 15 consecutive nucleotides in the cDNA sequence, but will often comprise longer segments. Further, these probes may further comprise an additional nucleotide sequence, such as a transcriptional primer sequence for cloning, or a detectable group for easy identification and location of complementary sequences.

cDNA or genomic libraries of various types may be screened for new alleles or related sequences using the above probes. The choice of cDNA libraries normally corresponds to tissue sources which are abundant in mRNA for the desired polypeptides. Phage libraries are normally preferred, e.g., g t 11, but plasmid or YAC libraries may also be used. Clones of a library are spread onto plates, transferred to a substrate for screening, denatured, and probed for the presence of the desired sequences.

In a related aspect, the nucleic acids of the present invention also include the PCR product or RT-PCR product, produced using the above described primer probes. For example, primer probes derived from the nucleotide sequence shown, described &/or referenced herein (including incorporated by reference), may be used to amplify sequences from different malaria parasites, and in particular, different strains of P. falciparum.

The nucleic acids of the present invention may be present in whole cells, cell lysates or in partially pure or substantially pure or isolated form. Such "substantially pure" or "isolated" forms of these nucleic acids generally refer to the nucleic acid separated from contaminants with which it is generally associated, e.g., lipids, proteins and other nucleic acids. The nucleic acids of the present invention will be greater than about 50% pure. Typically, the nucleic acids will be more than about 60% pure, more typically, from about 75% to about 90% pure, and preferably, from about 95% to about 98% pure.

The present invention also provides substantially similar nucleic acid sequences, allelic variations and natural or induced sequences of the above described nucleic acids, as well as chemically modified and substituted nucleic acids, e.g., those which incorporate modified nucleotide bases or which incorporate a labeling group. In addition to comprising a segment which encodes a PfEMP1 protein or fragment thereof, the nucleic acids of the present invention may also comprise a segment encoding a heterologous protein, such that the gene is expressed to produce the two proteins as a fusion protein, as substantially described above.

In addition to their use as probes, the nucleic acids of the present invention may also be used in the preparation of the polypeptides of the present invention, as described above. DNA encoding the polypeptides of the present invention will typically be incorporated into DNA constructs capable of introduction to and expression in an in vitro cell culture. Often, the nucleic acids of the present invention may be used to produce a suitable recombinant host cell.

Specifically, DNA constructs will be suitable for replication in a unicellular host, such as bacteria, e.g., E. coli, viruses or yeast, but may also be intended for introduction into a cultured mammalian, plant, insect, or other eukaryotic cell lines. DNA constructs prepared for introduction into bacteria or yeast will typically include a replication system recognized by the host, the intended DNA segment encoding the desired polypeptide, transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence; DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment.

Examples of suitable promoter sequences include prokaryotic, and eukaryotic promoters well known in the art. See, e.g., Sambrook et al., supra. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., supra.

Conveniently available expression vectors which include the replication system and transcriptional and translational regulatory sequences together with the insertion site for the PfEMP1 polypeptide encoding segment may be employed. Examples of workable combinations of cell lines and expression vectors are described in Sambrook et al., supra, and in Metzger et al., Nature 334:31–36 (1988).

The vectors containing the DNA segments of interest, e.g., those encoding polypeptides comprising a PfEMP1 protein or fragments thereof, can be transferred into the host cell by well known methods, which may vary depending upon the type of host used. For example, calcium chloride transfection is commonly used for prokaryotic cells, whereas calcium phosphate treatment may be used for other hosts. See, Sambrook et al., supra. The term "transformed cell" as used herein, includes the progeny of originally transformed cells.

Techniques for manipulation of nucleic acids which encode the polypeptides of the present invention, i.e., subcloning the nucleic acids into expression vectors, labeling probes, DNA hybridization and the like, are generally described in Sambrook, et al., supra. In recombinant methods, generally the nucleic acid encoding a peptide of the present invention is first cloned or isolated in a form suitable for ligation into an expression vector. After ligation, the vectors containing the nucleic acids fragments or inserts are introduced into a suitable host cell, for the expression of the polypeptide of the invention. The polypeptides may then be purified or isolated from the host cells. Methods for the synthetic preparation of oligonucleotides are generally described in Gait, oligonucleotide Synthesis: A Practical Approach, IRL Press (1990).

There are various methods of isolating the nucleic acids which encode the polypeptides of the present invention. Typically, the DNA is isolated from a genomic or cDNA library using labeled oligonucleotide probes specific for sequences in the desired DNA. Restriction endonuclease digestion of genomic DNA or cDNA containing the appropriate genes can be used to isolate the DNA encoding the binding domains of these proteins. From the PfEMP1 sequence given (as shown herein), a panel of restriction endonucleases can be constructed to give cleavage of the DNA in desired regions, i.e., to obtain segments which encode biologically active fragments of the PfEMP1 protein. Following restriction endonuclease digestion, DNA encoding the polypeptides of the present invention is identified by its ability to hybridize with a nucleic acid probe in, for example a Southern blot format. These regions are then isolated using standard methods. See, e.g., Sambrook, et al., supra.

The polymerase chain reaction, or "PCR" can also be used to prepare nucleic acids which encode the polypeptides of the present invention. PCR technology is used to amplify nucleic acid sequences of the desired nucleic acid, e.g., the DNA which encodes the polypeptides of the invention, directly from mRNA, cDNA, or genomic or cDNA libraries. Appropriate primers and probes for amplifying the nucleic acids described herein, may be generated from analysis of the PfEMP1 oligonucleotide sequence, such as those shown, described &/or referenced herein (including incorporated by reference) and Table 1. Briefly, oligonucleotide primers complementary to the two 31 borders of the DNA region to be amplified are synthesized. The PCR is then carried out using the two primers. See, e.g., PCR Protocols: A Guide to Methods and Applications (Innis, M., Gelfand, D., Sninsky, J. and White, T., eds.) Academic Press (1990). Primers can be selected to amplify various sized segments from the PfEMP1 oligonucleotide sequence. The primers may also contain a restriction site and additional bases to permit "in-frame" cloning of the insert into an appropriate expression vector, using the restriction sites present on the primers.

2.10.3. Antibodies

The nucleic acids and polypeptides of the present invention, or fragments thereof, are also useful in producing antibodies, either polyclonal or monoclonal. These antibodies are produced by immunizing an appropriate vertebrate host, e.g., rat, mouse, rabbit or goat, with a polypeptide of the invention, or its fragment, or plasmid DNA containing a nucleic acid of the invention, alone or in conjunction with an adjunct. Usually, two or more immunizations are involved, and a few days following the last injection, the blood or spleen of the host will be harvested.

For production of polyclonal antibodies, an appropriate target immune system is selected, typically a mouse or rabbit, but also including goats, sheep, cows, guinea pigs, monkeys and rats. The substantially purified antigen or plasmid is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., Monoclonal Antibodies: Principles and Practice (2d ed.) Acad. Press, N. Y., and Harlow and Lane, Antibodies: A Laboratory Manual, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, Science 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, e.g., as probes in immunoassays, for inhibiting PfEMP1 binding to its ligands, thereby inhibiting or reducing erythrocyte sequestration, in diagnostics or therapeutics, or in research to further elucidate the mechanism of various aspects of malarial infection, and particularly, *P. falciparum* infection. The antibodies of the present invention can be used with or without modification. Frequently, the antibodies will be labeled by joining, either covalently or non-covalently, a substance which provides for a detectable signal. Such labels include those that are well known in the art, such as the labels described previously for the polypeptides of the invention. Additionally, the antibodies of the invention may be chimeric, human-like or humanized, in order to reduce their potential antigenicity, without reducing their affinity for their target. Chimeric, human-like and humanized antibodies have generally been described in the art. Generally, such chimeric, human-like or humanized antibodies comprise variable regions, e.g., complementarity determining regions (CDR) (for humanized antibodies), from a mammalian animal, i.e., a mouse, and a human framework region. By incorporating as little foreign sequence as possible in the hybrid antibody, the antigenicity is reduced. Preparation of these hybrid antibodies may be carried out by methods well known in the art.

Preferred antibodies are those that are specifically immunoreactive with the polypeptides of the present invention and their immunologically active fragments. The phrase "specifically immunoreactive," when referring to the interaction between an antibody of the invention and a particular protein, refers to an antibody that specifically recognizes and binds with relatively high affinity to the particular protein, such that this binding is determinative of the presence of the protein in a heterogeneous population of proteins and other biologics. Thus, under designated immunoassay conditions, the specified antibodies bind to a particular protein and do not bind in a significant amount to other proteins present in the sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The antibodies generated can be used for a number of purposes, e.g., as probes in immunoassays, for inhibiting interaction between a PfEMP1 protein and its ligand, e.g., CD-36, TSP, ICAM-1, VCAM-1, ELAM-1, or Chondroitin sulfate, thereby inhibiting or reducing the level of PfEMP1-ligand interaction, in diagnostics or therapeutics, or in research to further elucidate the mechanism of malarial pathology, e.g., erythrocyte sequestration. Where the antibodies are used to block or reverse the interaction between a polypeptide of the invention and an associating ligand or PE, the antibody will generally be referred to as a "blocking antibody." Preferred antibodies are those monoclonal or polyclonal antibodies which specifically recognize and bind the polypeptides of the invention. Accordingly, these preferred antibodies will specifically recognize and bind the polypeptides which have an amino acid sequence that is substantially homologous to the relevant amino acid sequence shown, described &/or referenced herein (including incorporated by reference), or immunologically active fragments thereof. Still more preferred are antibodies which are capable of forming an antibody-ligand complex with the relatively conserved polypeptide fragments of PfEMP1 sequences, and are thereby capable of blocking an interaction of PfEMP1 from a variety of *P. falciparum* strains, and PfEMP1 ligands.

2.10.4. Methods of Use

The polypeptides, antibodies, and nucleic acids of the present invention have a variety of important uses, including, but not limited to, diagnostic, screening, prophylactic, including vaccination, and therapeutic applications.

2.10.4.1. Diagnostic Application

In a particularly preferred aspect, the present invention provides methods and reagents useful in detecting the presence of PfEMP1 in a sample. These detection methods are particularly useful in diagnosing malarial infections in a patient. For example, in a particularly preferred aspect, the antibodies of the present invention may be used to assay for the presence or absence of PfEMP1 in a sample. Immunoassay techniques for the detection of the particular antigen are very well known in the art. For a review of immunological and immunoassay procedures in general, see Basic and Clinical Immunology 7th Edition (D. Stites and A. Terr ed.) 1991.

Moreover, the immunoassays of the present invention can be performed in any of several configurations, which are reviewed extensively in Enzyme Immunoassay, E. T. Maggio, ed., CRC Press, Boca Raton, Fla. (1980); "Practice and Theory of Enzyme Immunoassays," P. Tijssen, Laboratory Techniques in Biochemistry and Molecular Biology, Elsevier Science Publishers B. V. Amsterdam (1985); and, Harlow and Lane, Antibodies, A Laboratory Manual, supra. Generally, these methods comprise contacting the antibody with a sample to be tested, and detecting any specific binding between the antibody and a protein within the sample. Typically, this will be in a blot format, e.g., western blot, or in an ELISA format. Methods of performing these assay formats are well known in the art. See, e.g., Basic and Clinical Immunology, 7th ed. (D. Stites and A Terr, eds., 1991).

Typically, these diagnostic methods comprise contacting a sample with an antibody to PfEMP1, as described herein, and determining whether the antibody binds to any portion of the sample. In the case of human diagnostic techniques, the sample may be a whole blood sample, or some fraction thereof, e.g. an erythrocyte containing sample. Generally, such diagnostic methods are well known in the art, and are described in the above described references. The immunoreactivity of the antibody with the sample, indicates the presence of PfEMP1 in the sample, and, in the case of a sample derived from a patient, a possible malarial infection.

Alternatively, labeled polypeptides of the present invention may be used as diagnostic reagents in detecting the presence or absence of antibodies to PfEMP1, in a patient. The presence of antibodies within a patient would be indicative that the patient had been exposed to a malaria parasite sufficiently to result in an antigenic response.

Similarly, the nucleic acid probes of the invention may be used in a similar manner, i.e., to identify the presence in a sample of a DNA segment encoding a PfEMP1 polypeptide, or as PCR or RT-PCR primers to amplify and then detect PfEMP1 encoding nucleic acid segments. Such assays typically involve the immobilization of nucleic acids in the sample, followed by interrogation?? of the immobilized sequences with a chemically labeled oligonucleotide probe, as described herein. Hybridization of the probe to the immobilized sample indicates the presence of a DNA segment encoding PfEMP1, and thus, a malarial infection. As described above, assays may be further designed to indicate not only the presence of a Malarial parasite, but also indicate the strain of parasite present. Although described in terms of an immobilized sample probed with a solution based oligonucleotide probe, a wide variety of assay conformations may be adopted, which conformations are generally well known in the art.

2.10.4.2. Screening Application

In another particularly preferred aspect, the present invention provides methods for screening compounds to determine whether or not the particular compound is an antagonist of a symptom of a malarial infection. In particular, the screening methods of the present invention can be used to determine whether a test compound is an antagonist of the sequestration of erythrocytes which is associated with *P. falciparum* malaria. More particularly, the screening methods can determine whether a compound is an antagonist of the PfEMP1l/ligand interaction. Ligands of PfEMP1 generally include, e.g., CD36, TSP, ELAM-1, ICAM-1, VCAM-1 or Chondroitin sulfate.

Generally, the screening methods of the present invention comprise contacting PfEMP1 protein, or a fragment thereof, and/or ligand protein, with a compound which is to be screened ("test compound"). The level of PfEMP1/ligand complex formed may then be detected and compared to a control, e.g., in the absence of the test compound. A decrease in the level of PfEMP1/ligand interaction is indicative that the test compound is an antagonist of that interaction.

A test compound may be a chemical compound, a mixture of chemical compounds, a biological macromolecule, or an extract made from biological materials, such as bacteria, phage, yeast, plants, fungi, animal cells or tissues. Test compounds are evaluated for potential activity as antagonists of PfEMP1/ligand interaction by inclusion in the screening assays described herein. An "antagonist" refers to a compound which will diminish the level of PfEMP1/ligand interaction, over a control.

It will often be desirable in the screening assays of the present invention, to provide one of the PfEMP1 or ligand proteins immobilized on a solid support. Suitable solid supports include, e.g., agarose, cellulose, dextran, Sephadex, Sepharose, carboxymethyl cellulose, polystyrene, filter paper, nitrocellulose, ion exchange resins, plastic films, glass beads, polyaminemethylvinylether maleic acid copolymer, amino acid copolymer, ethylene-maleic acid copolymer, nylon, silk, etc. The support may be in the form of, e.g., a test tube, microtiter plate, beads, test strips, flat surface, e.g., for blotting formats, or the like. The reaction of the PfEMP1 polypeptide or its ligand with the particular solid support may be carried out by methods well known in the art, e.g., binding to an immobilized anti-PfEMP1 antibody, or binding to prederivatized solid support.

In addition to the foregoing, it may also be desirable to provide either the PfEMP1 or its ligand linked to a suitable detectable group to make detection of binding of one protein to the other, simpler. Useful detectable groups, or labels, are generally well known in the art. For example, a detectable group may be a radiolabel, such as, $^{125}I$, $^{32}P$ or $^{35}S$, or a fluorescent or chemiluminescent group.

Alternatively, the detectable group may be a substrate, cofactor, inhibitor, affinity ligand, antibody binding epitope tag, or an enzyme which is capable of being assayed. Suitable enzymes include, e.g., horseradish peroxidase, luciferase, or another readily assayable enzymes. These enzyme groups may be attached to the PfEMP1 polypeptide, or its ligand by chemical means or maybe expressed as a fusion protein, as already described.

Generally, where one of the above proteins, e.g., the PfEMP1 ligand, is immobilized on a solid support, the other protein, e.g., PfEMP1 or its fragment, will be labeled with an appropriate detectable group. Assaying whether a compound is an antagonist of the interaction of the two proteins is then a matter of contacting the labeled PfEMP1 polypeptide or fragment with the immobilized ligand, in the presence of the test compound, under conditions which allow specific binding of the two proteins. The amount of label bound to the solid support is compared to a control, where no test compound was added. Where a test compound results in a reduction of the amount of label which binds to a solid support, that compound is an antagonist of the PfEMP1/ligand interaction.

2.10.4.3. Therapeutic and Prophylactic Application

In addition to the above described uses, the polypeptides of the present invention may also be used in therapeutic applications, for the treatment of human and/or non-human mammalian patients. The therapeutic uses of the polypeptides of the present invention include the treatment of symptoms of existing disorders, as well as prophylactic applications. The term "prophylactic" refers to the prevention of a particular disorder, or symptoms of a particular disorder. Thus, prophylactic treatments will generally include drugs which actively participate in the prevention of a particular disorder such as a malaria infection, or symptoms thereof. Prophylactic applications will also include treatments which elicit a preventative response from a patient, including, for example, an immunological response as in the case of vaccination.

Typically, both therapeutic and prophylactic applications will comprise administering an effective amount of the compositions of the present invention to a patient, to treat or prevent symptoms, or the onset of a malarial parasite infection. An "effective amount", as the term is used herein, is defined as the amount of the composition which is necessary to achieve the desired goal, i.e. alleviation of symptoms, prevention of symptoms or infection, or treatment of disease.

In prophylactic applications, the polypeptides of the present invention may be used in a variety of treatments. For example, the polypeptides of the invention are particularly useful as a vaccine, to elicit an immunological response by a patient, e.g., production of antibodies specific for PfEMP1. In particular, such vaccine applications generally involve the administration of the PFEMP1 protein or biologically active fragments thereof, to the host or patient.

In response to this administration, the patient's immune system will generate antibodies to the particular PfEMP1 protein or fragment introduced. An amount of the polypeptides sufficient to produce an immunological response in a patient is termed "an immunogenically effective amount." Thus, the vaccines of the present invention will contain an immunogenically effective amount of the polypeptides of the present invention. The immune response of the patient may include generation of antibodies, activation of cytotoxic T-lymphocytes against cells expressing the polypeptides, e.g., PE, or other mechanisms known to the skilled artisan. See, e.g., Paul, Fundamental Immunology, 2d Edition, Raven Press. Useful carriers are well known in the art, and include for example, thyroglobulin, albumins such as human serum albumin, tetanus toxoid, polyamino acids such as poly(D-lysine; D-glutamic acid), influenza, hepatitis B virus core protein, hepatitis B virus recombinant vaccine. The vaccines can also contain a physiologically tolerable diluent, such as water, buffered water, buffered saline, saline and typically may further include an adjuvant, such as incomplete Freunds adjuvant, aluminum phosphate, aluminum hydroxide, alum, or other materials well known in the art.

Alternatively, the nucleic acids of the present invention may also be used as vaccines for the prevention of malaria symptoms, and/or infection by malaria parasites. See Sedegah, et al. Proc. Nat'l Acad. Sci. (1994) 91:9866–9870.

For example, plasmid DNA comprising the nucleic acids of the present invention may be directly administered to a patient. Expression of this "naked" DNA will have effects similar to the injection of. the actual polypeptides, as described above. Specifically, the patient's immune response to the presence of the proteins expressed from the DNA, will result in the production of antibodies to that protein. The nucleic acids may also be used to design antisense probes to interrupt transcription of PfEMP1 peptides in parasitized erythrocytes.

Antisense methods are generally well known in the art. The polypeptides of the present invention, and analogs thereof, may also be used as prophylactic treatments to prevent the onset of symptoms of malarial infection. For example, administration of the polypeptides can directly inhibit, block or reverse the sequestration of erythrocytes in patients suffering from *P. falciparuin* malaria infections. In particular, the polypeptides of the invention may be used to compete with or displace PE associated PfEMP1 in binding CD36.

The blockage or reversal of sequestration will reduce or eliminate the microvascular occlusion generally associated with the pathology of this type of malaria, which, again, can lead to destruction of the PE by the host. The antibodies of the invention may also be used in a similar fashion. In particular, the antibodies, which are capable of binding the polypeptides of the present invention, may be directly administered to a patient. By binding PfEMP1, the antibodies of the present invention are effective in blocking, reducing or reversing PfEMP1 mediated interactions, e.g., erythrocyte sequestration. Chimeric, human-like or humanized antibodies are particularly useful for administration to human patients. Additionally, such antibodies may also be used as a passive vaccination method to provide a subject with a short term immunization, much as anti-hepatitis A injections have been used previously.

In alternative aspects, the polypeptides, antibodies and nucleic acids of the invention may be used to treat a patient already suffering from a malarial infection. In particular, the compositions of the present invention may be administered to a patient suffering from a malarial infection to treat symptoms associated with that infection. More particularly, these compositions may be administered to the patient to prevent or reduce erythrocyte sequestration and the resulting microvascular occlusion associated with malarial, and more specifically, *P. falciparum*, infections.

Although the polypeptides, nucleic acids and antibodies of the present invention may be administered alone, for therapeutic and prophylactic applications, these elements will generally be administered as part of a pharmaceutical composition, e.g., in combination with a pharmaceutically acceptable carrier. Typically, a single composition may be used in both therapeutic and prophylactic applications. Pharmaceutical formulations suitable for use in the present invention are generally described in Remington's Pharmaceutical Sciences, Mack Publishing Co., 17th ed. (1985).

The pharmaceutical compositions of the present invention are intended for parenteral, topical, oral, or local administration. Where the pharmaceutical compositions are administered parenterally, the invention provides pharmaceutical compositions that comprise a solution of the agents described above, e.g., polypeptides of the invention, dissolved or suspended in a pharmaceutically acceptable carrier, preferably an aqueous carrier. A variety of aqueous carriers may be used, e.g., water, buffered water, saline glycine, and the like. These compositions may be sterilized by conventional, well known methods, e.g., sterile filtration. The resulting aqueous solutions may be packaged for use as is, or lyophilized for combination with a sterile solution prior to administration. The compositions may contain pharmaceutically acceptable auxiliary substances as required to approximate physiological conditions, such as pH adjusting and buffering agents, tonicity adjusting agents, wetting agents, and the like, for example sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose starch, magnesium stearate, sodium saccharin, talcum, cellulose, glucose, sucrose, magnesium carbonate, and the like. For oral administration, a pharmaceutically acceptable nontoxic composition may be formed by incorporating any of the normally employed excipients, such as the previously listed carriers, and generally, 10–95% of active ingredient, and more preferably 25–75% active ingredient. In addition, for oral administration of peptide based compounds, the pharmaceutical compositions may include the active ingredient as part of a matrix to prevent proteolytic degradation of the active ingredient by digestive process, e.g., by providing the pharmaceutical composition within a liposomal composition, according to methods well known in the art. See, e.g., Remington's Pharmaceutical Sciences, Mack Publishing Co., 17th Ed. (1985).

For aerosol administration, the polypeptides are generally supplied in finely divided form along with a surfactant or propellant. Preferably, the surfactant will be soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids, with an aliphatic polyhydric alcohol or its cyclic anhydride. Mixed esters, such as mixed or natural glycerides may be employed. A carrier can also be included, as desired, as with, e.g., lecithin for intranasal delivery. The above described compositions are suitable for a single administration or a series of administrations. When given as a series, e.g., as a vaccine booster, the inoculations subsequent to the initial administration are given to boost the immune response, and are typically referred to as booster inoculations.

The amount of the above compositions to be administered to the patient will vary depending upon what is to be administered to the patient, the state of the patient, the manner of administration, and the particular application, e.g., therapeutic or prophylactic. In therapeutic applications, the compositions are administered to the patient already suffering from a malarial infection, in an amount sufficient to inhibit the spread of the parasite through the erythrocytes, and thereby cure or at least partially arrest the symptoms of the disease and its associated complications.

An amount adequate to accomplish this is termed "a therapeutically effective amount." Amounts effective for this use will depend upon the severity of the disease and the weight and general state of the patient, but will generally be in the range of from about 1 mg to about 5 g of active agent per day, preferably from about 50 mg per day to about 500 mg per day, and more preferably, from about 50 mg to about 100 mg per day, for a 70 kg patient.

For prophylactic applications, immunogenically effective amounts will also depend upon the composition, the manner of administration and the weight and general state of the patient, as well as the judgment of the prescribing physician.

For the peptide, peptide analog and antibody based pharmaceutical compositions, the general range for the initial immunization (for either prophylactic or therapeutic applications) will be from about 100 µg to about 1 g of polypeptide for a 70 kg patient, followed by boosting dosages of from about 1 µg to about 1 gm of polypeptide pursuant to a boosting regimen over weeks to months, depending upon the patient's response and condition, e.g., by measuring the level of parasite or antibodies in the patient's blood. For nucleic acids, typically from about 30 to about 100 µg of nucleic acid is injected into a 70 kg patient, more typically, about 50 to 150 µg of nucleic acid is injected, followed by boosting treatments as appropriate.

The present invention is further illustrated by the following examples. These examples are merely to illustrate aspects of the present invention and are not intended as limitations of this invention.

2.11. Directed Evolution Methods

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a preferred embodiment, the invention relates to a method for producing a hybrid polynucleotide from at least a first polynucleotide and a second polynucleotide. The present invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides. In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism may, for example, finction effectively under a particular environmental condition, e.g. high salinity. An enzyme encoded by a second polynucleotide from a different organism may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the original polynucleotides of the invention include, but are not limited to; oxidoreductases, transferases, hydrolases, lyases, isomerases and ligases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e. proteases; (b) ester bonds, i.e. esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa: Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al, 1986).

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides, or fragments thereof, and postpolyketide biosynthesis genes for generation of novel polyketides for study is appealing. The method of the present invention makes it possible to facilitate the production of novel polyketide synthases through intermolecular recombination.

Preferably, gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a preferred embodiment, the present invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;

3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and discussed throughout the present specification. Such methods may be employed when isolating the polypeptides and polynucleotides of the present invention.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in $E.$ $coli$ is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from $E.$ $coli$ f-factor which is able to stably integrate large segments of genomic DNA. When integrated with DNA from a mixed uncultured environmental sample, this makes it possible to achieve large genomic fragments in the form of a stable "environmental DNA library." Another preferred type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al, 1989).

The DNA sequence in the expression vector is operatively linked to an appropriate expression control sequence(s) (promoter) to direct RNA synthesis. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), $\alpha$-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not ftnction in $E.$ $coli.$ The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The selection of the cloning vector depends upon the approach taken, for example, the vector can be any cloning vector with an adequate capacity for multiply repeated copies of a sequence, or multiple sequences that can be successfully transformed and selected in a host cell. One example of such a vector is described in "Polycos vectors: a system for packaging filamentous phage and phagemid vectors using lambda phage packaging extracts" (Alting-Mecs and Short, 1993). Propagation/maintenance can be by an antibiotic resistance carried by the cloning vector. After a period of growth, the naturally abbreviated molecules are recovered and identified by size fractionation on a gel or column, or amplified directly. The cloning vector utilized may contain a selectable gene that is disrupted by the insertion of the lengthy construct. As reductive reassortment progresses, the number of repeated units is reduced and the interrupted gene is again expressed and hence selection for the processed construct can be applied. The vector may be an expression/selection vector which will allow for the selection of an expressed product possessing desirable biologically properties. The insert may be positioned downstream of a ftmctional promotor and the desirable property screened by appropriate means.

In vivo reassortment is focused on "inter-molecular" processes collectively referred to as "recombination" which in bacteria, is generally viewed as a "RecA-dependent" phenomenon. The present invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the present invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates the method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact (e.g., such as catalytic antibodies) with a predetermined macromolecule, such as for example a proteinaceous receptor, peptide oligosaccharide, viron, or other predetermined compound or structure.

The displayed polypeptides, antibodies, peptidomimetic antibodies, and variable region sequences that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or affinity selection. The method can be modified such that the step of selecting for a phenotypic characteristic can be other than of binding affinity for a predetermined molecule (e.g., for catalytic activity, stability oxidation resistance, drug resistance, or detectable phenotype conferred upon a host cell).

The present invention provides a method for generating libraries of displayed antibodies suitable for affinity interactions screening. The method comprises (1) obtaining first a plurality of selected library members comprising a displayed antibody and an associated polynucleotide encoding said displayed antibody, and obtaining said associated polynucleotide encoding for said displayed antibody and obtaining said associated polynucleotides or copies thereof, wherein said associated polynucleotides comprise a region of substantially identical variable region framework sequence, and (2) introducing said polynucleotides into a suitable host cell and growing the cells under conditions which promote recombination and reductive reassortment resulting in shuffled polynucleotides. CDR combinations comprised by the shuffled pool are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Further, the plurality of selectively shuffled library members can be shuffled and screened iteratively, from 1 to about 1000 cycles or as desired until library members having a desired binding affinity are obtained.

In another aspect of the invention, it is envisioned that prior to or during recombination or reassortment, polynucleotides generated by the method of the present invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine, see Sun and Hurley, 1992); an N-acelylated or deacetylated 4'-fluro-4-aminobiphenyl adduct capable of inhibiting DNA synthesis (see, for example, van de Poll et al, 1992); or a N-acetylated or deacetylated 4-aminobiphenyl adduct capable of inhibiting DNA synthesis (see also, van de Poll et al, 1992, pp. 751–758); trivalent chromium, a trivalent chromium salt, a polycyclic aromatic hydrocarbon ("PAH") DNA adduct capable of inhibiting DNA replication, such as 7-bromomethyl-benz[α]anthracene ("BMA"), tris(2,3-dibromopropyl)phosphate ("Tris-BP"), 1,2-dibromo-3-chloropropane ("DBCP"), 2-bromoacrolein (2BA), benzo[α]pyrene-7,8-dihydrodiol-9–10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred "means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the present invention is directed to a method of producing recombinant proteins having biological activity by treating a sample comprising double-stranded template polynucleotides encoding a wild-type protein under conditions according to the present invention which provide for the production of hybrid or re-assorted polynucleotides.

The invention also provides the use of polynucleotide shuffling to shuffle a population of viral genes (e.g., capsid proteins, spike glycoproteins, polymerases, and proteases) or viral genomes (e.g., paramyxoviridae, orthomyxoviridae, herpesviruses, retroviruses, reoviruses and rhinoviruses). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes as well as novel epitopes created by recombination; such shuffled viral proteins may comprise epitopes or combinations of epitopes which are likely to arise in the natural environment as a consequence of viral evolution; (e.g., such as recombination of influenza virus strains).

The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other general therapy formats.

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

2.11.1. Saturation Mutagenesis

In one aspect, this invention provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position. The oligos used are comprised contiguously of a first homologous sequence, a degenerate N,N,G/T sequence, and preferably but not necessarily a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In a particular exemplification, it is possible to simultaneously mutagenize two or more contiguous amino acid positions using an oligo that contains contiguous N,N,G/T triplets, i.e. a degenerate (N,N,G/T)n sequence.

In another aspect, the present invention provides for the use of degenerate cassettes having less degeneracy than the N,N,G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the instant invention provides a way to systematically and fairly easily generate 2000 distinct species (i.e. 20 possible amino acids per position×100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g. cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, AIC/G, or E, where E is any base that is not A, C, G, or T (E can be referred to as a designer oligo). The tables below show exemplary tri-nucleotide cassettes (there are over 3000 possibilities in addition to N,N,G/T and N,N,N and N,N,A/C).

In a general sense, saturation mutagenesis is comprised of mutagenizing a complete set of mutagenic cassettes (wherein each cassette is preferably 1–500 bases in length) in defined polynucleotide sequence to be mutagenized (wherein the sequence to be mutagenized is preferably from 15 to 100,000 bases in length). Thusly, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized (see FIG. 20) include preferably a whole gene, pathway, cDNA, an entire open reading frame (ORF), and intire promoter, enhancer, repressor/transactivator, origin of replication, intron, operator, or any polynucleotide functional group. Generally, a preferred "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette (see Tables 1–85), this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

SUMMARY OF TABLES 1–85

These tables show preferred, but non-limiting, examples of 3-base long mutagenic cassettes that are non-stochastic and degenerate.

| Table# | triplet sequence | Site 1 | Site 2 | Site 3 |
|---|---|---|---|---|
| 1. | N,N,G/T | N | N | G/T |
| 2. | N,N,G/C | N | N | G/C |
| 3. | N,N,G/A | N | N | G/A |
| 4. | N,N,A/C | N | N | A/C |
| 5. | N,N,A/T | N | N | A/T |
| 6. | N,N,C/T | N | N | C/T |
| 7. | N,N,N | N | N | N |
| 8. | N,N,G | N | N | G |
| 9. | N,N,A | N | N | A |
| 10. | N,N,C | N | N | C |
| 11. | N,N,T | N | N | T |
| 12. | N,N,C/G/T | N | N | C/G/T |
| 13. | N,N,A/G/T | N | N | A/G/T |
| 14. | N,N,A/C/T | N | N | A/C/T |
| 15. | N,N,A/C/G | N | N | A/C/G |
| 16. | N,A,A | N | A | A |
| 17. | N,A,C | N | A | C |
| 18. | N,A,G | N | A | G |
| 19. | N,A,T | N | A | T |
| 20. | N,C,A | N | C | A |
| 21. | N,C,C | N | C | C |
| 22. | N,C,G | N | C | G |
| 23. | N,C,T | N | C | T |
| 24. | N,G,A | N | G | A |
| 25. | N,G,C | N | G | C |
| 26. | N,G,G | N | G | G |
| 27. | N,G,T | N | G | T |
| 28. | N,T,A | N | T | A |
| 29. | N,T,C | N | T | C |
| 30. | N,T,G | N | T | G |
| 31. | N,T,T | N | T | T |
| 32. | N,A/C,A | N | A/C | A |
| 33. | N,A/G,A | N | A/G | A |
| 34. | N,A/T,A | N | A/T | A |
| 35. | N,C/G,A | N | C/G | A |
| 36. | N,C/T,A | N | C/T | A |
| 37. | N,T/G,A | N | T/G | A |
| 38. | N,C/G/T,A | N | C/G/T | A |
| 39. | N,A/G/T,A | N | A/G/T | A |
| 40. | N,A/C/T,A | N | A/C/T | A |
| 41. | N,A/C/G,A | N | A/C/G | A |
| 42. | A,N,N | A | N | N |

-continued

| Table# | triplet sequence | Site 1 | Site 2 | Site 3 |
|---|---|---|---|---|
| 43. | C,N,N | C | N | N |
| 44. | G,N,N | G | N | N |
| 45. | T,N,N | T | N | N |
| 46. | A/C,N,N | A/C | N | N |
| 47. | A/G,N,N | A/G | N | N |
| 48. | A/T,N,N | A/T | N | N |
| 49. | C/G,N,N | C/G | N | N |
| 50. | C/T,N,N | C/T | N | N |
| 51. | G/T,N,N | G/T | N | N |
| 52. | N,A,N | N | A | N |
| 53. | N,C,N | N | C | N |
| 54. | N,G,N | N | G | N |
| 55. | N,T,N | N | T | N |
| 56. | N,A/C,N | N | A/C | N |
| 57. | N,A/G,N | N | A/G | N |
| 58. | N,A/T,N | N | A/T | N |
| 59. | N,C/G,N | N | C/G | N |
| 60. | N,C/T,N | N | C/T | N |
| 61. | N,G/T,N | N | G/T | N |
| 62. | N,A/C/G,N | N | A/C/G | N |
| 63. | N,A/C/T,N | N | A/C/T | N |
| 64. | N,A/G/T,N | N | A/G/T | N |
| 65. | N,C/G/T,N | N | C/G/T | N |
| 66. | C,C,N | C | C | N |
| 67. | G,G,N | G | G | N |
| 68. | G,C,N | G | C | N |
| 69. | G,T,N | G | T | N |
| 70. | C,G,N | C | G | N |
| 71. | C,T,N | C | T | N |
| 72. | T,C,N | T | C | N |
| 73. | A,C,N | A | C | N |
| 74. | G,A,N | G | A | N |
| 75. | A,T,N | A | T | N |
| 76. | C,A,N | C | A | N |
| 77. | T,T,N | T | T | N |
| 78. | A,A,N | A | A | N |
| 79. | T,A,N | T | A | N |
| 80. | T,G,N | T | G | N |
| 81. | A,G,N | A | G | N |
| 82. | G/C,G,N | G/C | G | N |
| 83. | G/C,C,N | G/C | C | N |
| 84. | G/C,A,N | G/C | A | N |
| 85. | G/C,T,N | G/C | T | N |

TABLE 1

Mutagenic Cassette: N, N, G/T

| CO-DON | Represented | AMINO ACID | (Frequency) | CATEGORY | (Frequency) |
|---|---|---|---|---|---|
| GGT | YES | GLYCINE | 2 | NONPOLAR (NPL) | 15 |
| GGC | NO | | | | |
| GGA | NO | | | | |
| GGG | YES | | | | |
| GCT | YES | ALANINE | 2 | | |
| GCC | NO | | | | |
| GCA | NO | | | | |
| GCG | YES | | | | |
| GTT | YES | VALINE | 2 | | |
| GTC | NO | | | | |
| GTA | NO | | | | |
| GTG | YES | | | | |
| TTA | NO | LEUCINE | 3 | | |
| TTG | YES | | | | |
| CTT | YES | | | | |
| CTC | NO | | | | |
| CTA | NO | | | | |
| CTG | YES | | | | |
| ATT | YES | ISOLEUCINE | 1 | | |
| ATC | NO | | | | |
| ATA | NO | | | | |

TABLE 1-continued

Mutagenic Cassette: N, N, G/T

| CO-DON | Represented | AMINO ACID | (Frequency) | CATEGORY | (Frequency) |
|---|---|---|---|---|---|
| ATG | YES | METHIONINE | 1 | | |
| TTT | YES | PHENYLAL-ANINE | 1 | | |
| TTC | NO | | | | |
| TGG | YES | TRYPTO-PHAN | 1 | | |
| CCT | YES | PROLINE | 2 | | |
| CCC | NO | | | | |
| CCA | NO | | | | |
| CCG | YES | | | | |
| TCT | YES | SERINE | 3 | POLAR NON-IONIZABLE (POL) | 9 |
| TCC | NO | | | | |
| TCA | NO | | | | |
| TCG | YES | | | | |
| AGT | YES | | | | |
| AGC | NO | | | | |
| TGT | YES | CYSTEINE | 1 | | |
| TGC | NO | | | | |
| AAT | YES | ASPARAGINE | 1 | | |
| AAC | NO | | | | |
| CAA | NO | GLUTAMINE | 1 | | |
| CAG | YES | | | | |
| TAT | YES | TYROSINE | 1 | | |
| TAC | NO | | | | |
| ACT | YES | THREONINE | 2 | | |
| ACC | NO | | | | |
| ACA | NO | | | | |
| ACG | YES | | | | |
| GAT | YES | ASPARTIC ACID | 1 | IONIZABLE: ACIDIC NEGATIVE CHARGE (NEG) | 2 |
| GAC | NO | | | | |
| GAA | NO | GLUTAMIC ACID | 1 | | |
| GAG | YES | | | | |
| AAA | NO | LYSINE | 1 | IONIZABLE: BASIC POSITIVE CHARGE (POS) | 5 |
| AAG | YES | | | | |
| CGT | YES | ARGININE | 3 | | |
| CGC | NO | | | | |
| CGA | NO | | | | |
| CGG | YES | | | | |
| AGA | NO | | | | |
| AGG | YES | | | | |
| CAT | YES | HISTIDINE | 1 | | |
| CAC | NO | | | | |
| TAA | NO | STOP CODON | 1 | STOP SIGNAL (STP) | 1 |
| TAG | YES | | | | |
| TGA | NO | | | | |
| TOTAL | | | | | |
| 64 | 32 | 20 Amino Acids Are Represented | | NPL: POL: NEG: POS: STP= 15: 9: 2: 5: 1 | |

TABLE 2

Mutagenic Cassette: N, N, G/C

| CO-DON | Represented | AMINO ACID | (Frequency) | CATEGORY | (Frequency) |
|---|---|---|---|---|---|
| GGT | NO | GLYCINE | 2 | NONPOLAR (NPL) | 15 |
| GGC | YES | | | | |
| GGA | NO | | | | |
| GGG | YES | | | | |
| GCT | NO | ALANINE | 2 | | |
| GCC | YES | | | | |
| GCA | NO | | | | |
| GCG | YES | | | | |
| GTT | NO | VALINE | 2 | | |
| GTC | YES | | | | |
| GTA | NO | | | | |
| GTG | YES | | | | |
| TTA | NO | LEUCINE | 3 | | |
| TTG | YES | | | | |
| CTT | NO | | | | |
| CTC | YES | | | | |
| CTA | NO | | | | |
| CTG | YES | | | | |
| ATT | NO | ISOLEUCINE | 1 | | |
| ATC | YES | | | | |
| ATA | NO | | | | |
| ATG | YES | METHIONINE | 1 | | |
| TTT | NO | PHENYLAL-ANINE | 1 | | |
| TTC | YES | | | | |
| TGG | YES | TRYPTO-PHAN | 1 | | |
| CCT | NO | PROLINE | 2 | | |
| CCC | YES | | | | |
| CCA | NO | | | | |
| CCG | YES | | | | |
| TCT | NO | SERINE | 3 | POLAR NON-IONIZABLE (POL) | 9 |
| TCC | YES | | | | |
| TCA | NO | | | | |
| TCG | YES | | | | |
| AGT | NO | | | | |
| AGC | YES | | | | |
| TGT | NO | CYSTEINE | 1 | | |
| TGC | YES | | | | |
| AAT | NO | ASPARAGINE | 1 | | |
| AAC | YES | | | | |
| CAA | NO | GLUTAMINE | 1 | | |
| CAG | YES | | | | |
| TAT | NO | TYROSINE | 1 | | |
| TAC | YES | | | | |
| ACT | NO | THREONINE | 2 | | |
| ACC | YES | | | | |
| ACA | NO | | | | |
| ACG | YES | | | | |
| GAT | NO | ASPARTIC ACID | 1 | IONIZABLE: ACIDIC NEGATIVE CHARGE (NEG) | 2 |
| GAC | YES | | | | |
| GAA | NO | GLUTAMIC ACID | 1 | | |
| GAG | YES | | | | |
| AAA | NO | LYSINE | 1 | IONIZABLE: BASIC POSITIVE CHARGE (POS) | 5 |
| AAG | YES | | | | |
| CGT | NO | ARGININE | 3 | | |
| CGC | YES | | | | |
| CGA | NO | | | | |
| CGG | YES | | | | |
| AGA | NO | | | | |
| AGG | YES | | | | |
| CAT | NO | HISTIDINE | 1 | | |
| CAC | YES | | | | |
| TAA | NO | STOP CODON | 1 | STOP SIGNAL (STP) | 1 |
| TAG | YES | | | | |
| TGA | NO | | | | |
| TOTAL | | | | | |
| 64 | 32 | 20 Amino Acids Are Represented | | NPL: POL: NEG: POS: STP= 15: 9: 2: 5: 1 | |

TABLE 3

Mutagenic Cassette: N, N, G/A

| CODON | Represented | AMINO ACID | (Frequency) | CATEGORY | (Frequency) |
|---|---|---|---|---|---|
| GGT | NO | GLYCINE | 2 | NONPOLAR (NPL) | 15 |
| GGC | NO | | | | |
| GGA | YES | | | | |
| GGG | YES | | | | |
| GCT | NO | ALANINE | 2 | | |
| GCC | NO | | | | |
| GCA | YES | | | | |
| GCG | YES | | | | |
| GTT | NO | VALINE | 2 | | |
| GTC | NO | | | | |
| GTA | YES | | | | |
| GTG | YES | | | | |
| TTA | YES | LEUCINE | 4 | | |
| TTG | YES | | | | |
| CTT | NO | | | | |
| CTC | NO | | | | |
| CTA | YES | | | | |
| CTG | YES | | | | |
| ATT | NO | ISOLEUCINE | 1 | | |
| ATC | NO | | | | |
| ATA | YES | | | | |
| ATG | YES | METHIONINE | 1 | | |
| TTT | NO | PHENYLALANINE | 0 | | |
| TTC | NO | | | | |
| TGG | YES | TRYPTOPHAN | 1 | | |
| CCT | NO | PROLINE | 2 | | |
| CCC | NO | | | | |
| CCA | YES | | | | |
| CCG | YES | | | | |
| TCT | NO | SERINE | 2 | POLAR NON-IONIZABLE (POL) | 6 |
| TCC | NO | | | | |
| TCA | YES | | | | |
| TCG | YES | | | | |
| AGT | NO | | | | |
| AGC | NO | | | | |
| TGT | NO | CYSTEINE | 0 | | |
| TGC | NO | | | | |
| AAT | NO | ASPARAGINE | 0 | | |
| AAC | NO | | | | |
| CAA | YES | GLUTAMINE | 2 | | |
| CAG | YES | | | | |
| TAT | NO | TYROSINE | 0 | | |
| TAC | NO | | | | |
| ACT | NO | THREONINE | 2 | | |
| ACC | NO | | | | |
| ACA | YES | | | | |
| ACG | YES | | | | |
| GAT | NO | ASPARTIC ACID | 0 | IONIZABLE: ACIDIC NEGATIVE CHARGE (NEG) | 2 |
| GAC | NO | | | | |
| GAA | YES | GLUTAMIC ACID | 2 | | |
| GAG | YES | | | | |
| AAA | YES | LYSINE | 2 | IONIZABLE: BASIC POSITIVE CHARGE (POS) | 6 |
| AAG | YES | | | | |
| CGT | NO | ARGININE | 4 | | |
| CGC | NO | | | | |
| CGA | YES | | | | |
| CGG | YES | | | | |
| AGA | YES | | | | |
| AGG | YES | | | | |
| CAT | NO | HISTIDINE | 0 | | |
| CAC | NO | | | | |
| TAA | YES | STOP CODON | 3 | STOP SIGNAL (STP) | 3 |
| TAG | YES | | | | |
| TGA | YES | | | | |
| TOTAL | | | | | |
| 64 | 32 | 14 Amino Acids Are Represented | | NPL: POL: NEG: POS: STP= 15: 6: 2: 6: 3 | |

TABLE 4

Mutagenic Cassette: N, N, A/C

| CODON | Represented | AMINO ACID | (Frequency) | CATEGORY | (Frequency) |
|---|---|---|---|---|---|
| GGT | NO | GLYCINE | 2 | NONPOLAR (NPL) | 14 |
| GGC | YES | | | | |
| GGA | YES | | | | |
| GGG | NO | | | | |
| GCT | NO | ALANINE | 2 | | |
| GCC | YES | | | | |
| GCA | YES | | | | |
| GCG | NO | | | | |
| GTT | NO | VALINE | 2 | | |
| GTC | YES | | | | |
| GTA | YES | | | | |
| GTG | NO | | | | |
| TTA | YES | LEUCINE | 3 | | |
| TTG | NO | | | | |
| CTT | NO | | | | |
| CTC | YES | | | | |
| CTA | YES | | | | |
| CTG | NO | | | | |
| ATT | NO | ISOLEUCINE | 2 | | |
| ATC | YES | | | | |
| ATA | YES | | | | |
| ATG | NO | METHIONINE | 0 | | |
| TTT | NO | PHENYLALANINE | 1 | | |
| TTC | YES | | | | |
| TGG | NO | TRYPTOPHAN | 0 | | |
| CCT | NO | PROLINE | 2 | | |
| CCC | YES | | | | |
| CCA | YES | | | | |
| CCG | NO | | | | |
| TCT | NO | SERINE | 3 | POLAR NON-IONIZABLE (POL) | 9 |
| TCC | YES | | | | |
| TCA | YES | | | | |
| TCG | NO | | | | |
| AGT | NO | | | | |
| AGC | YES | | | | |
| TGT | NO | CYSTEINE | 1 | | |
| TGC | YES | | | | |
| AAT | NO | ASPARAGINE | 1 | | |
| AAC | YES | | | | |
| CAA | YES | GLUTAMINE | 1 | | |
| CAG | NO | | | | |
| TAT | NO | TYROSINE | 1 | | |
| TAC | YES | | | | |
| ACT | NO | THREONINE | 2 | | |
| ACC | YES | | | | |
| ACA | YES | | | | |
| ACG | NO | | | | |
| GAT | NO | ASPARTIC ACID | 1 | IONIZABLE: ACIDIC NEGATIVE CHARGE (NEG) | 2 |
| GAC | YES | | | | |
| GAA | YES | GLUTAMIC ACID | 1 | | |
| GAG | NO | | | | |
| AAA | YES | LYSINE | 1 | IONIZABLE: BASIC POSITIVE CHARGE (POS) | 5 |
| AAG | NO | | | | |
| CGT | NO | ARGININE | 3 | | |
| CGC | YES | | | | |
| CGA | YES | | | | |
| CGG | NO | | | | |
| AGA | YES | | | | |
| AGG | NO | | | | |
| CAT | NO | HISTIDINE | 1 | | |
| CAC | YES | | | | |
| TAA | YES | STOP CODON | 2 | STOP SIGNAL (STP) | 2 |
| TAG | NO | | | | |
| TGA | YES | | | | |
| TOTAL | | | | | |
| 64 | 32 | 18 Amino Acids Are Represented | | NPL: POL: NEG: POS: STP= 14: 9: 2: 5: 2 | |

TABLE 5

Mutagenic Cassette: N, N, A/T

| CODON | Represented | AMINO ACID | (Frequency) | CATEGORY | (Frequency) |
|---|---|---|---|---|---|
| GGT | YES | GLYCINE | 2 | NONPOLAR (NPL) | 14 |
| GGC | NO | | | | |
| GGA | YES | | | | |
| GGG | NO | | | | |
| GCT | YES | ALANINE | 2 | | |
| GCC | NO | | | | |
| GCA | YES | | | | |
| GCG | NO | | | | |
| GTT | YES | VALINE | 2 | | |
| GTC | NO | | | | |
| GTA | YES | | | | |
| GTG | NO | | | | |
| TTA | YES | LEUCINE | 3 | | |
| TTG | NO | | | | |
| CTT | YES | | | | |
| CTC | NO | | | | |
| CTA | YES | | | | |
| CTG | NO | | | | |
| ATT | YES | ISOLEUCINE | 2 | | |
| ATC | NO | | | | |
| ATA | YES | | | | |
| ATG | NO | METHIONINE | 0 | | |
| TTT | YES | PHENYLALANINE | 1 | | |
| TTC | NO | | | | |
| TGG | NO | TRYPTOPHAN | 0 | | |
| CCT | YES | PROLINE | 2 | | |
| CCC | NO | | | | |
| CCA | YES | | | | |
| CCG | NO | | | | |
| TCT | YES | SERINE | 3 | POLAR NON-IONIZABLE (POL) | 9 |
| TCC | NO | | | | |
| TCA | YES | | | | |
| TCG | NO | | | | |
| AGT | YES | | | | |
| AGC | NO | | | | |
| TGT | YES | CYSTEINE | 1 | | |
| TGC | NO | | | | |
| AAT | YES | ASPARAGINE | 1 | | |
| AAC | NO | | | | |
| CAA | YES | GLUTAMINE | 1 | | |
| CAG | NO | | | | |
| TAT | YES | TYROSINE | 1 | | |
| TAC | NO | | | | |
| ACT | YES | THREONINE | 2 | | |
| ACC | NO | | | | |
| ACA | YES | | | | |
| ACG | NO | | | | |
| GAT | YES | ASPARTIC ACID | 1 | IONIZABLE: ACIDIC NEGATIVE CHARGE (NEG) | 2 |
| GAC | NO | | | | |
| GAA | YES | GLUTAMIC ACID | 1 | | |
| GAG | NO | | | | |
| AAA | YES | LYSINE | 1 | IONIZABLE: BASIC POSITIVE CHARGE (POS) | 5 |
| AAG | NO | | | | |
| CGT | YES | ARGININE | 3 | | |
| CGC | NO | | | | |
| CGA | YES | | | | |
| CGG | NO | | | | |
| AGA | YES | | | | |
| AGG | NO | | | | |
| CAT | YES | HISTIDINE | 1 | | |
| CAC | NO | | | | |
| TAA | YES | STOP CODON | 2 | STOP SIGNAL (STP) | 2 |
| TAG | NO | | | | |
| TGA | YES | | | | |
| TOTAL | | | | | |
| 64 | 32 | 18 Amino Acids Are Represented | | NPL: POL: NEG: POS: STP= 14: 9: 2: 5: 2 | |

TABLE 6

Mutagenic Cassette: N, N, C/T

| CODON | Represented | AMINO ACID | (Frequency) | CATEGORY | (Frequency) |
|---|---|---|---|---|---|
| GGT | YES | GLYCINE | 2 | NONPOLAR (NPL) | 14 |
| GGC | YES | | | | |
| GGA | NO | | | | |
| GGG | NO | | | | |
| GCT | YES | ALANINE | 2 | | |
| GCC | YES | | | | |
| GCA | NO | | | | |
| GCG | NO | | | | |
| GTT | YES | VALINE | 2 | | |
| GTC | YES | | | | |
| GTA | NO | | | | |
| GTG | NO | | | | |
| TTA | NO | LEUCINE | 2 | | |
| TTG | NO | | | | |
| CTT | YES | | | | |
| CTC | YES | | | | |
| CTA | NO | | | | |
| CTG | NO | | | | |
| ATT | YES | ISOLEUCINE | 2 | | |
| ATC | YES | | | | |
| ATA | NO | | | | |
| ATG | NO | METHIONINE | 0 | | |
| TTT | YES | PHENYLALANINE | 2 | | |
| TTC | YES | | | | |
| TGG | NO | TRYPTOPHAN | 0 | | |
| CCT | YES | PROLINE | 2 | | |
| CCC | YES | | | | |
| CCA | NO | | | | |
| CCG | NO | | | | |
| TCT | YES | SERINE | 4 | POLAR NON-IONIZABLE (POL) | 12 |
| TCC | YES | | | | |
| TCA | NO | | | | |
| TCG | NO | | | | |
| AGT | YES | | | | |
| AGC | YES | | | | |
| TGT | YES | CYSTEINE | 2 | | |
| TGC | YES | | | | |
| AAT | YES | ASPARAGINE | 2 | | |
| AAC | YES | | | | |
| CAA | NO | GLUTAMINE | 0 | | |
| CAG | NO | | | | |
| TAT | YES | TYROSINE | 2 | | |
| TAC | YES | | | | |
| ACT | YES | THREONINE | 2 | | |
| ACC | YES | | | | |
| ACA | NO | | | | |
| ACG | NO | | | | |
| GAT | YES | ASPARTIC ACID | 2 | IONIZABLE: ACIDIC NEGATIVE CHARGE (NEG) | 2 |
| GAC | YES | | | | |
| GAA | NO | GLUTAMIC ACID | 0 | | |
| GAG | NO | | | | |
| AAA | NO | LYSINE | 0 | IONIZABLE: BASIC POSITIVE CHARGE (POS) | 4 |
| AAG | NO | | | | |
| CGT | YES | ARGININE | 2 | | |
| CGC | YES | | | | |
| CGA | NO | | | | |
| CGG | NO | | | | |
| AGA | NO | | | | |
| AGG | NO | | | | |
| CAT | YES | HISTIDINE | 2 | | |
| CAC | YES | | | | |
| TAA | NO | STOP CODON | 0 | STOP SIGNAL (STP) | 0 |
| TAG | NO | | | | |
| TGA | NO | | | | |
| TOTAL | | | | | |
| 64 | 32 | 15 Amino Acids Are Represented | | NPL: POL: NEG: POS: STP= 14: 12: 2: 4: 0 | |

TABLE 7

Mutagenic Cassette: N, N, N

| CODON | Represented | AMINO ACID | (Frequency) | CATEGORY | (Frequency) |
|---|---|---|---|---|---|
| GGT | YES | GLYCINE | 4 | NONPOLAR (NPL) | 29 |
| GGC | YES | | | | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| TGG | YES | TRYPTOPHAN | 1 | | |
| CCT | YES | PROLINE | 4 | | |
| CCC | YES | | | | |
| CCA | YES | | | | |
| CCG | YES | | | | |
| TCT | YES | SERINE | 6 | POLAR NON-IONIZABLE (POL) | 18 |
| TCC | YES | | | | |
| TCA | YES | | | | |
| TCG | YES | | | | |
| AGT | YES | | | | |
| AGC | YES | | | | |
| TGT | YES | CYSTEINE | 2 | | |
| TGC | YES | | | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| ACT | YES | THREONINE | 4 | | |
| ACC | YES | | | | |
| ACA | YES | | | | |
| ACG | YES | | | | |
| GAT | YES | ASPARTIC ACID | 2 | IONIZABLE: ACIDIC NEGATIVE CHARGE (NEG) | 4 |
| GAC | YES | | | | |
| GAA | YES | GLUTAMIC ACID | 2 | | |
| GAG | YES | | | | |
| AAA | YES | LYSINE | 2 | IONIZABLE: BASIC POSITIVE CHARGE (POS) | 10 |
| AAG | YES | | | | |
| CGT | YES | ARGININE | 6 | | |
| CGC | YES | | | | |
| CGA | YES | | | | |
| CGG | YES | | | | |
| AGA | YES | | | | |
| AGG | YES | | | | |
| CAT | YES | HISTIDINE | 2 | | |
| CAC | YES | | | | |
| TAA | YES | STOP CODON | 3 | STOP SIGNAL (STP) | 3 |
| TAG | YES | | | | |
| TGA | YES | | | | |
| TOTAL | | | | | |
| 64 | 64 | 20 Amino Acids Are Represented | | NPL: POL: NEG: POS: STP= 29: 18: 4: 10: 3 | |

TABLE 8

Mutagenic Cassette: N, N, G

| CODON | Represented | AMINO ACID | (Frequency) | CATEGORY | (Frequency) |
|---|---|---|---|---|---|
| GGT | NO | GLYCINE | 1 | NONPOLAR (NPL) | 8 |
| GGC | NO | | | | |
| GGA | NO | | | | |
| GGG | YES | | | | |
| GCT | NO | ALANINE | 1 | | |
| GCC | NO | | | | |
| GCA | NO | | | | |
| GCG | YES | | | | |
| GTT | NO | VALINE | 1 | | |
| GTC | NO | | | | |
| GTA | NO | | | | |
| GTG | YES | | | | |
| TTA | NO | LEUCINE | 2 | | |
| TTG | YES | | | | |
| CTT | NO | | | | |
| CTC | NO | | | | |
| CTA | NO | | | | |
| CTG | YES | | | | |
| ATT | NO | ISOLEUCINE | 0 | | |
| ATC | NO | | | | |
| ATA | NO | | | | |
| ATG | YES | METHIONINE | 1 | | |
| TTT | NO | PHENYLALANINE | 0 | | |
| TTC | NO | | | | |
| TGG | YES | TRYPTOPHAN | 1 | | |
| CCT | NO | PROLINE | 1 | | |
| CCC | NO | | | | |
| CCA | NO | | | | |
| CCG | YES | | | | |
| TCT | NO | SERINE | 1 | POLAR NON-IONIZABLE (POL) | 3 |
| TCC | NO | | | | |
| TCA | NO | | | | |
| TCG | YES | | | | |
| AGT | NO | | | | |
| AGC | NO | | | | |
| TGT | NO | CYSTEINE | 0 | | |
| TGC | NO | | | | |
| AAT | NO | ASPARAGINE | 0 | | |
| AAC | NO | | | | |
| CAA | NO | GLUTAMINE | 1 | | |
| CAG | YES | | | | |
| TAT | NO | TYROSINE | 0 | | |
| TAC | NO | | | | |
| ACT | NO | THREONINE | 1 | | |
| ACC | NO | | | | |
| ACA | NO | | | | |
| ACG | YES | | | | |
| GAT | NO | ASPARTIC ACID | 0 | IONIZABLE: ACIDIC NEGATIVE CHARGE (NEG) | 1 |
| GAC | NO | | | | |
| GAA | NO | GLUTAMIC ACID | 1 | | |
| GAG | YES | | | | |
| AAA | NO | LYSINE | 1 | IONIZABLE: BASIC POSITIVE CHARGE (POS) | 3 |
| AAG | YES | | | | |
| CGT | NO | ARGININE | 2 | | |
| CGC | NO | | | | |
| CGA | NO | | | | |
| CGG | YES | | | | |
| AGA | NO | | | | |
| AGG | YES | | | | |
| CAT | NO | HISTIDINE | 0 | | |
| CAC | NO | | | | |
| TAA | NO | STOP CODON | 1 | STOP SIGNAL (STP) | 1 |
| TAG | YES | | | | |
| TGA | NO | | | | |
| TOTAL | | | | | |
| 64 | 16 | 13 Amino Acids Are Represented | | NPL: POL: NEG: POS: STP= 8: 3: 1: 3: 1 | |

TABLE 9

Mutagenic Cassette: N, N, A

| CODON | Represented | AMINO ACID | (Frequency) | CATEGORY | (Frequency) |
|---|---|---|---|---|---|
| GGT | NO | GLYCINE | 1 | NONPOLAR (NPL) | 7 |
| GGC | NO | | | | |
| GGA | YES | | | | |
| GGG | NO | | | | |
| GCT | NO | ALANINE | 1 | | |
| GCC | NO | | | | |
| GCA | YES | | | | |
| GCG | NO | | | | |
| GTT | NO | VALINE | 1 | | |
| GTC | NO | | | | |
| GTA | YES | | | | |
| GTG | NO | | | | |
| TTA | YES | LEUCINE | 2 | | |
| TTG | NO | | | | |
| CTT | NO | | | | |
| CTC | NO | | | | |
| CTA | YES | | | | |
| CTG | NO | | | | |
| ATT | NO | ISOLEUCINE | 1 | | |
| ATC | NO | | | | |
| ATA | YES | | | | |
| ATG | NO | METHIONINE | 0 | | |
| TTT | NO | PHENYL-ALANINE | 0 | | |
| TTC | NO | | | | |
| TGG | NO | TRYPTOPHAN | 0 | | |
| CCT | NO | PROLINE | 1 | | |
| CCC | NO | | | | |
| CCA | YES | | | | |
| CCG | NO | | | | |
| TCT | NO | SERINE | 1 | POLAR NON-IONIZABLE (POL) | 3 |
| TCC | NO | | | | |
| TCA | YES | | | | |
| TCG | NO | | | | |
| AGT | NO | | | | |
| AGC | NO | | | | |
| TGT | NO | CYSTEINE | 0 | | |
| TGC | NO | | | | |
| AAT | NO | ASPARAGINE | 0 | | |
| AAC | NO | | | | |
| CAA | YES | GLUTAMINE | 1 | | |
| CAG | NO | | | | |
| TAT | NO | TYROSINE | 0 | | |
| TAC | NO | | | | |
| ACT | NO | THREONINE | 1 | | |
| ACC | NO | | | | |
| ACA | YES | | | | |
| ACG | NO | | | | |
| GAT | NO | ASPARTIC ACID | 0 | IONIZABLE: ACIDIC NEGATIVE CHARGE (NEG) | 1 |
| GAC | NO | | | | |
| GAA | YES | GLUTAMIC ACID | 1 | | |
| GAG | NO | | | | |
| AAA | YES | LYSINE | 1 | IONIZABLE: BASIC POSITIVE CHARGE (POS) | 3 |
| AAG | NO | | | | |
| CGT | NO | ARGININE | 2 | | |
| CGC | NO | | | | |
| CGA | YES | | | | |
| CGG | NO | | | | |
| AGA | YES | | | | |
| AGG | NO | | | | |
| CAT | NO | HISTIDINE | 0 | | |
| CAC | NO | | | | |
| TAA | YES | STOP CODON | 2 | STOP SIGNAL (STP) | 2 |
| TAG | NO | | | | |
| TGA | YES | | | | |
| TOTAL | | | | | |
| 64 | 16 | 12 Amino Acids Are Represented | | NPL: POL: NEG: POS: STP= 7: 3: 1: 3: 2 | |

TABLE 10

Mutagenic Cassette: N, N, C

| CODON | Represented | AMINO ACID | (Frequency) | CATEGORY | (Frequency) |
|---|---|---|---|---|---|
| GGT | NO | GLYCINE | 1 | NONPOLAR (NPL) | 7 |
| GGC | YES | | | | |
| GGA | NO | | | | |
| GGG | NO | | | | |
| GCT | NO | ALANINE | 1 | | |
| GCC | YES | | | | |
| GCA | NO | | | | |
| GCG | NO | | | | |
| GTT | NO | VALINE | 1 | | |
| GTC | YES | | | | |
| GTA | NO | | | | |
| GTG | NO | | | | |
| TTA | NO | LEUCINE | 1 | | |
| TTG | NO | | | | |
| CTT | NO | | | | |
| CTC | YES | | | | |
| CTA | NO | | | | |
| CTG | NO | | | | |
| ATT | NO | ISOLEUCINE | 1 | | |
| ATC | YES | | | | |
| ATA | NO | | | | |
| ATG | NO | METHIONINE | 0 | | |
| TTT | NO | PHENYL-ALANINE | 1 | | |
| TTC | YES | | | | |
| TGG | NO | TRYPTOPHAN | 0 | | |
| CCT | NO | PROLINE | 1 | | |
| CCC | YES | | | | |
| CCA | NO | | | | |
| CCG | NO | | | | |
| TCT | NO | SERINE | 2 | POLAR NON-IONIZABLE (POL) | 6 |
| TCC | YES | | | | |
| TCA | NO | | | | |
| TCG | NO | | | | |
| AGT | NO | | | | |
| AGC | YES | | | | |
| TGT | NO | CYSTEINE | 1 | | |
| TGC | YES | | | | |
| AAT | NO | ASPARAGINE | 1 | | |
| AAC | YES | | | | |
| CAA | NO | GLUTAMINE | 0 | | |
| CAG | NO | | | | |
| TAT | NO | TYROSINE | 1 | | |
| TAC | YES | | | | |
| ACT | NO | THREONINE | 1 | | |
| ACC | YES | | | | |
| ACA | NO | | | | |
| ACG | NO | | | | |
| GAT | NO | ASPARTIC ACID | 1 | IONIZABLE: ACIDIC NEGATIVE CHARGE (NEG) | 1 |
| GAC | YES | | | | |
| GAA | NO | GLUTAMIC ACID | 0 | | |
| GAG | NO | | | | |
| AAA | NO | LYSINE | 0 | IONIZABLE: BASIC POSITIVE CHARGE (POS) | 2 |
| AAG | NO | | | | |
| CGT | NO | ARGININE | 1 | | |
| CGC | YES | | | | |
| CGA | NO | | | | |
| CGG | NO | | | | |
| AGA | NO | | | | |
| AGG | NO | | | | |
| CAT | NO | HISTIDINE | 1 | | |
| CAC | YES | | | | |
| TAA | NO | STOP CODON | 0 | STOP SIGNAL (STP) | 0 |
| TAG | NO | | | | |
| TGA | NO | | | | |
| TOTAL | | | | | |
| 64 | 16 | 15 Amino Acids Are Represented | | NPL: POL: NEG: POS: STP= 7: 6: 1: 2: 0 | |

TABLE 11

Mutagenic Cassette: N, N, T

| CO-DON | Represented | AMINO ACID | (Frequency) | CATEGORY | (Frequency) |
|---|---|---|---|---|---|
| GGT | YES | GLYCINE | 1 | NONPOLAR (NPL) | 7 |
| GGC | NO | | | | |
| GGA | NO | | | | |
| GGG | NO | | | | |
| GCT | YES | ALANINE | 1 | | |
| GCC | NO | | | | |
| GCA | NO | | | | |
| GCG | NO | | | | |
| GTT | YES | VALINE | 1 | | |
| GTC | NO | | | | |
| GTA | NO | | | | |
| GTG | NO | | | | |
| TTA | NO | LEUCINE | 1 | | |
| TTG | NO | | | | |
| CTT | YES | | | | |
| CTC | NO | | | | |
| CTA | NO | | | | |
| CTG | NO | | | | |
| ATT | YES | ISOLEUCINE | 1 | | |
| ATC | NO | | | | |
| ATA | NO | | | | |
| ATG | NO | METHIONINE | 0 | | |
| TTT | YES | PHENYLALANINE | 1 | | |
| TTC | NO | | | | |
| TGG | NO | TRYPTOPHAN | 0 | | |
| CCT | YES | PROLINE | 1 | | |
| CCC | NO | | | | |
| CCA | NO | | | | |
| CCG | NO | | | | |
| TCT | YES | SERINE | 2 | POLAR NON-IONIZABLE (POL) | 6 |
| TCC | NO | | | | |
| TCA | NO | | | | |
| TCG | NO | | | | |
| AGT | YES | | | | |
| AGC | NO | | | | |
| TGT | YES | CYSTEINE | 1 | | |
| TGC | NO | | | | |
| AAT | YES | ASPARAGINE | 1 | | |
| AAC | NO | | | | |
| CAA | NO | GLUTAMINE | 0 | | |
| CAG | NO | | | | |
| TAT | YES | TYROSINE | 1 | | |
| TAC | NO | | | | |
| ACT | YES | THREONINE | 1 | | |
| ACC | NO | | | | |
| ACA | NO | | | | |
| ACG | NO | | | | |
| GAT | YES | ASPARTIC ACID | 1 | IONIZABLE: ACIDIC NEGATIVE CHARGE (NEG) | 1 |
| GAC | NO | | | | |
| GAA | NO | GLUTAMIC ACID | 0 | | |
| GAG | NO | | | | |
| AAA | NO | LYSINE | 0 | IONIZABLE: BASIC POSITIVE CHARGE (POS) | 2 |
| AAG | NO | | | | |
| CGT | YES | ARGININE | 1 | | |
| CGC | NO | | | | |
| CGA | NO | | | | |
| CGG | NO | | | | |
| AGA | NO | | | | |
| AGG | NO | | | | |
| CAT | YES | HISTIDINE | 1 | | |
| CAC | NO | | | | |
| TAA | NO | STOP CODON | 0 | STOP SIGNAL (STP) | 0 |
| TAG | NO | | | | |
| TGA | NO | | | | |
| TOTAL | | | | | |
| 64 | 16 | 15 Amino Acids Are Represented | | NPL: POL: NEG: POS: STP= 7: 6: 1: 2: 0 | |

TABLE 12

Mutagenic Cassette: N, N, C/G/T

| CO-DON | Represented | AMINO ACID | (Frequency) | CATEGORY | (Frequency) |
|---|---|---|---|---|---|
| GGT | YES | GLYCINE | 3 | NONPOLAR (NPL) | 22 |
| GGC | YES | | | | |
| GGA | NO | | | | |
| GGG | YES | | | | |
| GCT | YES | ALANINE | 3 | | |
| GCC | YES | | | | |
| GCA | NO | | | | |
| GCG | YES | | | | |
| GTT | YES | VALINE | 3 | | |
| GTC | YES | | | | |
| GTA | NO | | | | |
| GTG | YES | | | | |
| TTA | NO | LEUCINE | 4 | | |
| TTG | YES | | | | |
| CTT | YES | | | | |
| CTC | YES | | | | |
| CTA | NO | | | | |
| CTG | YES | | | | |
| ATT | YES | ISOLEUCINE | 2 | | |
| ATC | YES | | | | |
| ATA | NO | | | | |
| ATG | YES | METHIONINE | 1 | | |
| TTT | YES | PHENYLALANINE | 2 | | |
| TTC | YES | | | | |
| TGG | YES | TRYPTOPHAN | 1 | | |
| CCT | YES | PROLINE | 3 | | |
| CCC | YES | | | | |
| CCA | NO | | | | |
| CCG | YES | | | | |
| TCT | YES | SERINE | 5 | POLAR NON-IONIZABLE (POL) | 15 |
| TCC | YES | | | | |
| TCA | NO | | | | |
| TCG | YES | | | | |
| AGT | YES | | | | |
| AGC | YES | | | | |
| TGT | YES | CYSTEINE | 2 | | |
| TGC | YES | | | | |
| AAT | YES | ASPARAGINE | 2 | | |
| AAC | YES | | | | |
| CAA | NO | GLUTAMINE | 1 | | |
| CAG | YES | | | | |
| TAT | YES | TYROSINE | 2 | | |
| TAC | YES | | | | |
| ACT | YES | THREONINE | 3 | | |
| ACC | YES | | | | |
| ACA | NO | | | | |
| ACG | YES | | | | |
| GAT | YES | ASPARTIC ACID | 2 | IONIZABLE: ACIDIC NEGATIVE CHARGE (NEG) | 3 |
| GAC | YES | | | | |
| GAA | NO | GLUTAMIC ACID | 1 | | |
| GAG | YES | | | | |
| AAA | NO | LYSINE | 1 | IONIZABLE: BASIC POSITIVE CHARGE (POS) | 7 |
| AAG | YES | | | | |
| CGT | YES | ARGININE | 4 | | |
| CGC | YES | | | | |
| CGA | NO | | | | |
| CGG | YES | | | | |
| AGA | NO | | | | |
| AGG | YES | | | | |
| CAT | YES | HISTIDINE | 2 | | |
| CAC | YES | | | | |
| TAA | NO | STOP CODON | 1 | STOP SIGNAL (STP) | 1 |
| TAG | YES | | | | |
| TGA | NO | | | | |
| TOTAL | | | | | |
| 64 | 48 | 20 Amino Acids Are Represented | | NPL: POL: NEG: POS: STP= 22: 15: 3: 7: 1 | |

TABLE 13

Mutagenic Cassette: N, N, A/G/T

| CODON | Represented | AMINO ACID | (Frequency) | CATEGORY | (Frequency) |
|---|---|---|---|---|---|
| GGT | YES | GLYCINE | 3 | NONPOLAR (NPL) | 22 |
| GGC | NO | | | | |
| GGA | YES | | | | |
| GGG | YES | | | | |
| GCT | YES | ALANINE | 3 | | |
| GCC | NO | | | | |
| GCA | YES | | | | |
| GCG | YES | | | | |
| GTT | YES | VALINE | 3 | | |
| GTC | NO | | | | |
| GTA | YES | | | | |
| GTG | YES | | | | |
| TTA | YES | LEUCINE | 5 | | |
| TTG | YES | | | | |
| CTT | YES | | | | |
| CTC | NO | | | | |
| CTA | YES | | | | |
| CTG | YES | | | | |
| ATT | YES | ISOLEUCINE | 2 | | |
| ATC | NO | | | | |
| ATA | YES | | | | |
| ATG | YES | METHIONINE | 1 | | |
| TTT | YES | PHENYLALANINE | 1 | | |
| TTC | NO | | | | |
| TGG | YES | TRYPTOPHAN | 1 | | |
| CCT | YES | PROLINE | 3 | | |
| CCC | NO | | | | |
| CCA | YES | | | | |
| CCG | YES | | | | |
| TCT | YES | SERINE | 4 | POLAR NON-IONIZABLE (POL) | 12 |
| TCC | NO | | | | |
| TCA | YES | | | | |
| TCG | YES | | | | |
| AGT | YES | | | | |
| AGC | NO | | | | |
| TGT | YES | CYSTEINE | 1 | | |
| TGC | NO | | | | |
| AAT | YES | ASPARAGINE | 1 | | |
| AAC | NO | | | | |
| CAA | YES | GLUTAMINE | 2 | | |
| CAG | YES | | | | |
| TAT | YES | TYROSINE | 1 | | |
| TAC | NO | | | | |
| ACT | YES | THREONINE | 3 | | |
| ACC | NO | | | | |
| ACA | YES | | | | |
| ACG | YES | | | | |
| GAT | YES | ASPARTIC ACID | 1 | IONIZABLE: ACIDIC NEGATIVE CHARGE (NEG) | 3 |
| GAC | NO | | | | |
| GAA | YES | GLUTAMIC ACID | 2 | | |
| GAG | YES | | | | |
| AAA | YES | LYSINE | 2 | IONIZABLE: BASIC POSITIVE CHARGE (POS) | 8 |
| AAG | YES | | | | |
| CGT | YES | ARGININE | 5 | | |
| CGC | NO | | | | |
| CGA | YES | | | | |
| CGG | YES | | | | |
| AGA | YES | | | | |
| AGG | YES | | | | |
| CAT | YES | HISTIDINE | 1 | | |
| CAC | NO | | | | |
| TAA | YES | STOP CODON | 3 | STOP SIGNAL (STP) | 3 |
| TAG | YES | | | | |
| TGA | YES | | | | |
| TOTAL | | | | | |
| 64 | 48 | 20 Amino Acids Are Represented | | NPL: POL: NEG: POS: STP= 22: 12: 3: 8: 3 | |

TABLE 14

Mutagenic Cassette: N, N, A/C/T

| CODON | Represented | AMINO ACID | (Frequency) | CATEGORY | (Frequency) |
|---|---|---|---|---|---|
| GGT | YES | GLYCINE | 3 | NONPOLAR (NPL) | 21 |
| GGC | YES | | | | |
| GGA | YES | | | | |
| GGG | NO | | | | |
| GCT | YES | ALANINE | 3 | | |
| GCC | YES | | | | |
| GCA | YES | | | | |
| GCG | NO | | | | |
| GTT | YES | VALINE | 3 | | |
| GTC | YES | | | | |
| GTA | YES | | | | |
| GTG | NO | | | | |
| TTA | YES | LEUCINE | 4 | | |
| TTG | NO | | | | |

TABLE 14-continued

Mutagenic Cassette: N, N, A/C/T

| CODON | Represented | AMINO ACID | (Frequency) | CATEGORY | (Frequency) |
|---|---|---|---|---|---|
| CTT | YES | | | | |
| CTC | YES | | | | |
| CTA | YES | | | | |
| CTG | NO | | | | |
| ATT | YES | ISOLEUCINE | 3 | | |
| ATC | YES | | | | |
| ATA | YES | | | | |
| ATG | NO | METHIONINE | 0 | | |
| TTT | YES | PHENYLALANINE | 2 | | |
| TTC | YES | | | | |
| TGG | NO | TRYPTOPHAN | 0 | | |
| CCT | YES | PROLINE | 3 | | |
| CCC | YES | | | | |
| CCA | YES | | | | |
| CCG | NO | | | | |
| TCT | YES | SERINE | 5 | POLAR | 15 |
| TCC | YES | | | NONIONIZABLE | |
| TCA | YES | | | (POL) | |
| TCG | NO | | | | |
| AGT | YES | | | | |
| AGC | YES | | | | |
| TGT | YES | CYSTEINE | 2 | | |
| TGC | YES | | | | |
| AAT | YES | ASPARAGINE | 2 | | |
| AAC | YES | | | | |
| CAA | YES | GLUTAMINE | 1 | | |
| CAG | NO | | | | |
| TAT | YES | TYROSINE | 2 | | |
| TAC | YES | | | | |
| ACT | YES | THREONINE | 3 | | |
| ACC | YES | | | | |
| ACA | YES | | | | |
| ACG | NO | | | | |
| GAT | YES | ASPARTIC ACID | 2 | IONIZABLE: ACIDIC | 3 |
| GAC | YES | | | NEGATIVE CHARGE | |
| GAA | YES | GLUTAMIC ACID | 1 | (NEG) | |
| GAG | NO | | | | |
| AAA | YES | LYSINE | 1 | IONIZABLE: BASIC | 7 |
| AAG | NO | | | POSITIVE CHARGE | |
| CGT | YES | ARGININE | 4 | (POS) | |
| CGC | YES | | | | |
| CGA | YES | | | | |
| CGG | NO | | | | |
| AGA | YES | | | | |
| AGG | NO | | | | |
| CAT | YES | HISTIDINE | 2 | | |
| CAC | YES | | | | |
| TAA | YES | STOP CODON | 2 | STOP SIGNAL | 2 |
| TAG | NO | | | (STP) | |
| TGA | YES | | | | |
| TOTAL 64 | 48 | 18 Amino Acids Are Represented | NPL: 21: | POL: 15: NEG: 3: POS: 7: | STP = 2 |

TABLE 15

Mutagenic Cassette: N, N, A/C/G

| CODON | Represented | AMINO ACID | (Frequency) | CATEGORY | (Frequency) |
|---|---|---|---|---|---|
| GGT | NO | GLYCINE | 3 | NONPOLAR | 22 |
| GGC | YES | | | (NPL) | |
| GGA | YES | | | | |
| GGG | YES | | | | |
| GCT | NO | ALANINE | 3 | | |
| GCC | YES | | | | |
| GCA | YES | | | | |
| GCG | YES | | | | |
| GTT | NO | VALINE | 3 | | |

TABLE 15-continued

Mutagenic Cassette: N, N, A/C/G

| CODON | Represented | AMINO ACID | (Frequency) | CATEGORY | (Frequency) |
|---|---|---|---|---|---|
| GTC | YES | | | | |
| GTA | YES | | | | |
| GTG | YES | | | | |
| TTA | YES | LEUCINE | 5 | | |
| TTG | YES | | | | |
| CTT | NO | | | | |
| CTC | YES | | | | |
| CTA | YES | | | | |
| CTG | YES | | | | |
| ATT | NO | ISOLEUCINE | 2 | | |
| ATC | YES | | | | |
| ATA | YES | | | | |
| ATG | YES | METHIONINE | 1 | | |
| TTT | NO | PHENYLALANINE | 1 | | |
| TTC | YES | | | | |
| TGG | YES | TRYPTOPHAN | 1 | | |
| CCT | NO | PROLINE | 3 | | |
| CCC | YES | | | | |
| CCA | YES | | | | |
| CCG | YES | | | | |
| TCT | NO | SERINE | 4 | POLAR | 12 |
| TCC | YES | | | NONIONIZABLE | |
| TCA | YES | | | (POL) | |
| TCG | YES | | | | |
| AGT | NO | | | | |
| AGC | YES | | | | |
| TGT | NO | CYSTEINE | 1 | | |
| TGC | YES | | | | |
| AAT | NO | ASPARAGINE | 1 | | |
| AAC | YES | | | | |
| CAA | YES | GLUTAMINE | 2 | | |
| CAG | YES | | | | |
| TAT | NO | TYROSINE | 1 | | |
| TAC | YES | | | | |
| ACT | NO | THREONINE | 3 | | |
| ACC | YES | | | | |
| ACA | YES | | | | |
| ACG | YES | | | | |
| GAT | NO | ASPARTIC ACID | 1 | IONIZABLE: ACIDIC | 3 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 8 |
| AAG | YES | | | POSITIVE CHARGE | |
| CGT | NO | ARGININE | 5 | (POS) | |
| CGC | YES | | | | |
| CGA | YES | | | | |
| CGG | YES | | | | |
| AGA | YES | | | | |
| AGG | YES | | | | |
| CAT | NO | HISTIDINE | 1 | | |
| CAC | YES | | | | |
| TAA | YES | STOP CODON | 3 | STOP SIGNAL | 3 |
| TAG | YES | | | (STP) | |
| TGA | YES | | | | |
| TOTAL 64 | 48 | 20 Amino Acids Are Represented | | NPL: POL: NEG: POS: STP = 22:   12:   3:   8:   3 | |

TABLE 16

Mutagenic Cassette: N, A, A

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |

TABLE 16-continued

Mutagenic Cassette: N, A, A

| CODON | Represented | AMINO ACID | (Frequency) | CATEGORY | (Frequency) |
|---|---|---|---|---|---|
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 1 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| | | THREONINE | 0 | | |
| | | ASPARTIC ACID | 0 | IONIZABLE: ACIDIC | 1 |
| GAA | YES | GLUTAMIC ACID | 1 | NEGATIVE CHARGE (NEG) | |
| AAA | YES | LYSINE | 1 | IONIZABLE: BASIC | 1 |
| | | ARGININE | 0 | POSITIVE CHARGE | |
| | | HISTIDINE | 0 | (POS) | |
| TAA | YES | STOP CODON | 1 | STOP SIGNAL (STP) | 1 |
| TOTAL | | 4 | 3 Amino Acids Are Represented | NPL: 0: POL: 1: NEG: 1: POS: 1: | STP = 1 |

TABLE 17

Mutagenic Cassette: N, A, C

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| AAC | YES | ASPARAGINE | 1 | (POL) | |
| | | GLUTAMINE | 0 | | |
| TAC | YES | TYROSINE | 1 | | |
| | | THREONINE | 0 | | |
| GAC | YES | ASPARTIC ACID | 1 | IONIZABLE: ACIDIC | 1 |
| | | GLUTAMIC ACID | 0 | NEGATIVE CHARGE (NEG) | |
| | | LYSINE | 0 | IONIZABLE: BASIC | 1 |
| | | ARGININE | 0 | POSITIVE CHARGE | |
| CAC | YES | HISTIDINE | 1 | (POS) | |
| | | STOP CODON | 0 | STOP SIGNAL (STP) | 0 |
| TOTAL | | 4 | 4 Amino Acids Are Represented | NPL: 0: POL: 2: NEG: 1: POS: 1: | STP = 0 |

TABLE 18

Mutagenic Cassette: N, A, G

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 1 |
| | | CYSTEINE | 0 | NONIONIZABLE | |
| | | ASPARAGINE | 0 | (POL) | |
| CAG | YES | GLUTAMINE | 1 | | |
| | | TYROSINE | 0 | | |
| | | THREONINE | 0 | | |
| | | ASPARTIC ACID | 0 | IONIZABLE: ACIDIC | 1 |
| GAG | YES | GLUTAMIC ACID | 1 | NEGATIVE CHARGE (NEG) | |
| AAG | YES | LYSINE | 1 | IONIZABLE: BASIC | 1 |
| | | ARGININE | 0 | POSITIVE CHARGE | |
| | | HISTIDINE | 0 | (POS) | |
| TAG | YES | STOP CODON | 1 | STOP SIGNAL (STP) | 1 |
| TOTAL | 4 | 3 Amino Acids Are Represented | | NPL: 0: POL: 1: NEG: 1: POS: 1: | STP = 1 |

TABLE 19

Mutagenic Cassette: N, A, T

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| AAT | YES | ASPARAGINE | 1 | (POL) | |
| | | GLUTAMINE | 0 | | |
| TAT | YES | TYROSINE | 1 | | |
| | | THREONINE | 0 | | |
| GAT | YES | ASPARTIC ACID | 1 | IONIZABLE: ACIDIC | 1 |
| | | GLUTAMIC ACID | 0 | NEGATIVE CHARGE (NEG) | |
| | | LYSINE | 0 | IONIZABLE: BASIC | 1 |
| | | ARGININE | 0 | POSITIVE CHARGE | |
| CAT | YES | HISTIDINE | 1 | (POS) | |
| | | STOP CODON | 0 | STOP SIGNAL (STP) | 0 |
| TOTAL | 4 | 4 Amino Acids Are Represented | | NPL: 0: POL: 2: NEG: 1: POS: 1: | STP = 0 |

TABLE 20

Mutagenic Cassette: N, C, A

| CODON | Represented | AMINO ACID | (Frequency) | CATEGORY | (Frequency) |
|---|---|---|---|---|---|
| | | GLYCINE | 0 | NONPOLAR | 2 |
| GCA | YES | ALANINE | 1 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 2 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| ACA | YES | THREONINE | 1 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 4 Amino Acids Are Represented | NPL: 2: POL: 2: NEG: 0: POS: 0: | STP = 0 |

TABLE 21

Mutagenic Cassette: N, C, C

| CODON | Represented | AMINO ACID | (Frequency) | CATEGORY | (Frequency) |
|---|---|---|---|---|---|
| | | GLYCINE | 0 | NONPOLAR | 2 |
| GCC | YES | ALANINE | 1 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCC | YES | PROLINE | 1 | | |
| TCC | YES | SERINE | 1 | POLAR | 2 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| ACC | YES | THREONINE | 1 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 4 Amino Acids Are Represented | NPL: 2: POL: 2: NEG: 0: POS: 0: | STP = 0 |

TABLE 22

Mutagenic Cassette: N, C, G

| CODON | Represented | AMINO ACID | (Frequency) | CATEGORY | (Frequency) |
|---|---|---|---|---|---|
|  |  | GLYCINE | 0 | NONPOLAR | 2 |
| GCG | YES | ALANINE | 1 | (NPL) |  |
|  |  | VALINE | 0 |  |  |
|  |  | LEUCINE | 0 |  |  |
|  |  | ISOLEUCINE | 0 |  |  |
|  |  | METHIONINE | 0 |  |  |
|  |  | PHENYLALANINE | 0 |  |  |
|  |  | TRYPTOPHAN | 0 |  |  |
| CCG | YES | PROLINE | 1 |  |  |
| TCG | YES | SERINE | 1 | POLAR | 2 |
|  |  | CYSTEINE | 0 | NONIONIZABLE |  |
|  |  | ASPARAGINE | 0 | (POL) |  |
|  |  | GLUTAMINE | 0 |  |  |
|  |  | TYROSINE | 0 |  |  |
| ACG | YES | THREONINE | 1 |  |  |
|  |  | ASPARTIC ACID | 0 | IONIZABLE: ACIDIC | 0 |
|  |  | GLUTAMIC ACID | 0 | NEGATIVE CHARGE (NEG) |  |
|  |  | LYSINE | 0 | IONIZABLE: BASIC | 0 |
|  |  | ARGININE | 0 | POSITIVE CHARGE |  |
|  |  | HISTIDINE | 0 | (POS) |  |
|  |  | STOP CODON | 0 | STOP SIGNAL (STP) | 0 |
| TOTAL |  | 4 | 4 Amino Acids Are Represented | NPL: 2: POL: 2: NEG: 0: POS: 0: | STP = 0 |

TABLE 23

Mutagenic Cassette: N, C, T

| CODON | Represented | AMINO ACID | (Frequency) | CATEGORY | (Frequency) |
|---|---|---|---|---|---|
|  |  | GLYCINE | 0 | NONPOLAR | 2 |
| GCT | YES | ALANINE | 1 | (NPL) |  |
|  |  | VALINE | 0 |  |  |
|  |  | LEUCINE | 0 |  |  |
|  |  | ISOLEUCINE | 0 |  |  |
|  |  | METHIONINE | 0 |  |  |
|  |  | PHENYLALANINE | 0 |  |  |
|  |  | TRYPTOPHAN | 0 |  |  |
| CCT | YES | PROLINE | 1 |  |  |
| TCT | YES | SERINE | 1 | POLAR | 2 |
|  |  | CYSTEINE | 0 | NONIONIZABLE |  |
|  |  | ASPARAGINE | 0 | (POL) |  |
|  |  | GLUTAMINE | 0 |  |  |
|  |  | TYROSINE | 0 |  |  |
| ACT | YES | THREONINE | 1 |  |  |
|  |  | ASPARTIC ACID | 0 | IONIZABLE: ACIDIC | 0 |
|  |  | GLUTAMIC ACID | 0 | NEGATIVE CHARGE (NEG) |  |
|  |  | LYSINE | 0 | IONIZABLE: BASIC | 0 |
|  |  | ARGININE | 0 | POSITIVE CHARGE |  |
|  |  | HISTIDINE | 0 | (POS) |  |
|  |  | STOP CODON | 0 | STOP SIGNAL (STP) | 0 |
| TOTAL |  | 4 | 4 Amino Acids Are Represented | NPL: 2: POL: 2: NEG: 0: POS: 0: | STP = 0 |

TABLE 24

Mutagenic Cassette: N, G, A

| CODON | Represented | AMINO ACID | (Frequency) | CATEGORY | (Frequency) |
|---|---|---|---|---|---|
| GGA | YES | GLYCINE | 1 | NONPOLAR | 1 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE | |
| | | | | (NEG) | |
| | | LYSINE | 0 | IONIZABLE: BASIC | 2 |
| CGA | YES | ARGININE | 2 | POSITIVE CHARGE | |
| AGA | YES | | | (POS) | |
| | | HISTIDINE | 0 | | |
| TGA | YES | STOP CODON | 1 | STOP SIGNAL | 1 |
| | | | | (STP) | |
| TOTAL | | 4 | 2 Amino Acids Are Represented | NPL: POL: NEG: POS: 1: 0: 0: 2: | STP = 1 |

TABLE 25

Mutagenic Cassette: N, G, C

| CODON | Represented | AMINO ACID | (Frequency) | CATEGORY | (Frequency) |
|---|---|---|---|---|---|
| GGC | YES | GLYCINE | 1 | NONPOLAR | 1 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| AGC | YES | SERINE | 1 | POLAR | 2 |
| TGC | YES | CYSTEINE | 1 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE | |
| | | | | (NEG) | |
| | | LYSINE | 0 | IONIZABLE: BASIC | 1 |
| CGC | YES | ARGININE | 1 | POSITIVE CHARGE | |
| | | HISTIDINE | 0 | (POS) | |
| | | STOP CODON | 0 | STOP SIGNAL | 0 |
| | | | | (STP) | |
| TOTAL | | 4 | 4 Amino Acids Are Represented | NPL: POL: NEG: POS: 1: 2: 0: 1: | STP = 0 |

TABLE 26

Mutagenic Cassette: N, G, G

| CODON | Represented | AMINO ACID | (Frequency) | CATEGORY | (Frequency) |
|---|---|---|---|---|---|
| GGG | YES | GLYCINE | 1 | NONPOLAR | 2 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 2 |
| CGG | YES | ARGININE | 2 | POSITIVE CHARGE | |
| AGG | YES | | | (POS) | |
| | | HISTIDINE | 0 | | |
| | | STOP CODON | 0 | STOP SIGNAL (STP) | 0 |
| TOTAL | | 4 | 3 Amino Acids Are Represented | NPL: 2: POL: 0: NEG: 0: POS: 2: | STP = 0 |

TABLE 27

Mutagenic Cassette: N, G, T

| CODON | Represented | AMINO ACID | (Frequency) | CATEGORY | (Frequency) |
|---|---|---|---|---|---|
| GGT | YES | GLYCINE | 1 | NONPOLAR | 1 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| AGT | YES | SERINE | 1 | POLAR | 2 |
| TGT | YES | CYSTEINE | 1 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 1 |
| CGT | YES | ARGININE | 1 | POSITIVE CHARGE | |
| | | HISTIDINE | 0 | (POS) | |
| | | STOP CODON | 0 | STOP SIGNAL (STP) | 0 |
| TOTAL | | 4 | 4 Amino Acids Are Represented | NPL: 1: POL: 2: NEG: 0: POS: 1: | STP = 0 |

TABLE 28

Mutagenic Cassette: N, T, A

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| GTA | YES | VALINE | 1 | | |
| TTA | YES | LEUCINE | 2 | | |
| CTA | YES | | | | |
| ATA | YES | ISOLEUCINE | 1 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 3 Amino Acids Are Represented | | NPL: POL: NEG: POS: STP = 4: 0: 0: 0: 0 | |

TABLE 29

Mutagenic Cassette: N, T, C

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| GTC | YES | VALINE | 1 | | |
| CTC | YES | LEUCINE | 1 | | |
| ATC | YES | ISOLEUCINE | 1 | | |
| | | METHIONINE | 0 | | |
| TTC | YES | PHENYLALANINE | 1 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 4 Amino Acids Are Represented | | NPL: POL: NEG: POS: STP = 4: 0: 0: 0: 0 | |

TABLE 30

Mutagenic Cassette: N, T, G

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| GTG | YES | VALINE | 1 | | |
| TTG | YES | LEUCINE | 2 | | |
| CTG | YES | | | | |
| | | ISOLEUCINE | 0 | | |
| ATG | YES | METHIONINE | 1 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 3 Amino Acids Are Represented | | NPL: 4: POL: 0: NEG: 0: POS: 0: STP = 0 | |

TABLE 31

Mutagenic Cassette: N, T, T

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| GTT | YES | VALINE | 1 | | |
| CTT | YES | LEUCINE | 1 | | |
| ATT | YES | ISOLEUCINE | 1 | | |
| | | METHIONINE | 0 | | |
| TTT | YES | PHENYLALANINE | 1 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 4 Amino Acids Are Represented | | NPL: 4: POL: 0: NEG: 0: POS: 0: STP = 0 | |

TABLE 32

Mutagenic Cassette: N, A/C, A

| CODON | Represented | AMINO ACID | (Frequency) | CATEGORY | (Frequency) |
|---|---|---|---|---|---|
| | | GLYCINE | 0 | NONPOLAR | 2 |
| GCA | YES | ALANINE | 1 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 3 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| ACA | YES | THREONINE | 1 | | |
| | | ASPARTIC ACID | 0 | IONIZABLE: ACIDIC | 1 |
| GAA | YES | GLUTAMIC ACID | 1 | NEGATIVE CHARGE (NEG) | |
| AAA | YES | LYSINE | 1 | IONIZABLE: BASIC | 1 |
| | | ARGININE | 0 | POSITIVE CHARGE | |
| | | HISTIDINE | 0 | (POS) | |
| TAA | YES | STOP CODON | 1 | STOP SIGNAL (STP) | 1 |
| TOTAL | 8 | 7 Amino Acids Are Represented | | NPL: 2: POL: 3: NEG: 1: POS: 1: STP = 1 | |

TABLE 33

Mutagenic Cassette: N, A/G, A

| CODON | Represented | AMINO ACID | (Frequency) | CATEGORY | (Frequency) |
|---|---|---|---|---|---|
| GGA | YES | GLYCINE | 1 | NONPOLAR | 1 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 1 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| | | THREONINE | 0 | | |
| | | ASPARTIC ACID | 0 | IONIZABLE: ACIDIC | 1 |
| GAA | YES | GLUTAMIC ACID | 1 | NEGATIVE CHARGE (NEG) | |
| AAA | YES | LYSINE | 1 | IONIZABLE: BASIC | 3 |
| CGA | YES | ARGININE | 2 | POSITIVE CHARGE | |
| AGA | YES | | | (POS) | |
| | | HISTIDINE | 0 | | |
| TAA | YES | STOP CODON | 2 | STOP SIGNAL | 2 |
| TGA | YES | | | (STP) | |
| TOTAL | 8 | 5 Amino Acids Are Represented | | NPL: 1: POL: 1: NEG: 1: POS: 3: STP = 2 | |

TABLE 34

Mutagenic Cassette: N, A/T, A

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| GTA | YES | VALINE | 1 | | |
| TTA | YES | LEUCINE | 2 | | |
| CTA | YES | | | | |
| ATA | YES | ISOLEUCINE | 1 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 1 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| | | THREONINE | 0 | | |
| | | ASPARTIC ACID | 0 | IONIZABLE: ACIDIC | 0 |
| GAA | YES | GLUTAMIC ACID | 1 | NEGATIVE CHARGE (NEG) | |
| AAA | YES | LYSINE | 1 | IONIZABLE: BASIC | 1 |
| | | ARGININE | 0 | POSITIVE CHARGE | |
| | | HISTIDINE | 0 | (POS) | |
| TAA | YES | STOP CODON | 1 | STOP SIGNAL (STP) | 1 |
| TOTAL | 8 | 6 Amino Acids Are Represented | | NPL: 4: POL: 1: NEG: 1: POS: 1: STP = 1 | |

TABLE 35

Mutagenic Cassette: N, C/G, A

| CODON | Represented | AMINO ACID | (Frequency) | CATEGORY | (Frequency) |
|---|---|---|---|---|---|
| GGA | YES | GLYCINE | 1 | NONPOLAR | 3 |
| GCA | YES | ALANINE | 1 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 2 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| ACA | YES | THREONINE | 1 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 2 |
| CGA | YES | ARGININE | 2 | POSITIVE CHARGE | |
| AGA | YES | | | (POS) | |
| | | HISTIDINE | 0 | | |
| TGA | YES | STOP CODON | 1 | STOP SIGNAL (STP) | 1 |
| TOTAL | 8 | 6 Amino Acids Are Represented | | NPL: 3: POL: 2: NEG: 0: POS: 2: STP = 1 | |

TABLE 36

Mutagenic Cassette: N, C/T, A

| CODON | Represented | AMINO ACID | (Frequency) | CATEGORY | (Frequency) |
|---|---|---|---|---|---|
| | | GLYCINE | 0 | NONPOLAR | 6 |
| GCA | YES | ALANINE | 1 | (NPL) | |
| GTA | YES | VALINE | 1 | | |
| TTA | YES | LEUCINE | 2 | | |
| CTA | YES | | | | |
| ATA | YES | ISOLEUCINE | 1 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 2 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| ACA | YES | THREONINE | 1 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 8 | 7 Amino Acids Are Represented | | NPL: 6: POL: 2: NEG: 0: POS: 0: STP = 0 | |

TABLE 37

Mutagenic Cassette: N, T/G, A

| CODON | Represented | AMINO ACID | (Frequency) | CATEGORY | (Frequency) |
|---|---|---|---|---|---|
| GGA | YES | GLYCINE | 1 | NONPOLAR | 5 |
| | | ALANINE | 0 | (NPL) | |
| GTA | YES | VALINE | 1 | | |
| TTA | YES | LEUCINE | 2 | | |
| CTA | YES | | | | |
| ATA | YES | ISOLEUCINE | 1 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 2 |
| CGA | YES | ARGININE | 2 | POSITIVE CHARGE | |
| AGA | YES | | | (POS) | |
| | | HISTIDINE | 0 | | |
| TGA | YES | STOP CODON | 1 | STOP SIGNAL (STP) | 1 |
| TOTAL | 8 | 5 Amino Acids Are Represented | | NPL: 5: POL: 0: NEG: 0: POS: 2: STP = 1 | |

TABLE 38

| | CODON | Represented | AMINO ACID | (Frequency) | CATEGORY | (Frequency) |
|---|---|---|---|---|---|---|
| | GGA | YES | GLYCINE | 1 | NONPOLAR | 7 |
| | GCA | YES | ALANINE | 1 | (NPL) | |
| | GTA | YES | VALINE | 1 | | |
| | TTA | YES | LEUCINE | 2 | | |
| | CTA | YES | | | | |
| | ATA | YES | ISOLEUCINE | 1 | | |
| | | | METHIONINE | 0 | | |
| | | | PHENYLALANINE | 0 | | |
| | | | TRYPTOPHAN | 0 | | |
| | CCA | YES | PROLINE | 1 | | |
| | TCA | YES | SERINE | 1 | POLAR | 2 |
| | | | CYSTEINE | 0 | NONIONIZABLE | |
| | | | ASPARAGINE | 0 | (POL) | |
| | | | GLUTAMINE | 0 | | |
| | | | TYROSINE | 0 | | |
| | ACA | YES | THREONINE | 1 | | |
| | | | ASPARTIC ACID | 0 | IONIZABLE: ACIDIC | 0 |
| | | | GLUTAMIC ACID | 0 | NEGATIVE CHARGE (NEG) | |
| | | | LYSINE | 0 | IONIZABLE: BASIC | 2 |
| | CGA | YES | ARGININE | 2 | POSITIVE CHARGE | |
| | AGA | YES | | | (POS) | |
| | | | HISTIDINE | 0 | | |
| | TGA | YES | STOP CODON | 1 | STOP SIGNAL (STP) | 1 |
| TOTAL | | 12 | 9 Amino Acids Are Represented | | NPL: 7: POL: 2: NEG: 0: POS: 2: | STP = 1 |

TABLE 39

| | CODON | Represented | AMINO ACID | (Frequency) | CATEGORY | (Frequency) |
|---|---|---|---|---|---|---|
| | GGA | YES | GLYCINE | 1 | NONPOLAR | 5 |
| | | | ALANINE | 0 | (NPL) | |
| | GTA | YES | VALINE | 1 | | |
| | TTA | YES | LEUCINE | 2 | | |
| | CTA | YES | | | | |
| | ATA | YES | ISOLEUCINE | 1 | | |
| | | | METHIONINE | 0 | | |
| | | | PHENYLALANINE | 0 | | |
| | | | TRYPTOPHAN | 0 | | |
| | | | PROLINE | 0 | | |
| | | | SERINE | 0 | POLAR | 1 |
| | | | CYSTEINE | 0 | NONIONIZABLE | |
| | | | ASPARAGINE | 0 | (POL) | |
| | CAA | YES | GLUTAMINE | 1 | | |
| | | | TYROSINE | 0 | | |
| | | | THREONINE | 0 | | |
| | | | ASPARTIC ACID | 0 | IONIZABLE: ACIDIC | 1 |
| | GAA | YES | GLUTAMIC ACID | 0 | NEGATIVE CHARGE (NEG) | |
| | AAA | YES | LYSINE | 1 | IONIZABLE: BASIC | 3 |
| | CGA | YES | ARGININE | 2 | POSITIVE CHARGE | |
| | AGA | YES | | | (POS) | |
| | | | HISTIDINE | 0 | | |
| | TAA | YES | STOP CODON | 2 | STOP SIGNAL | 2 |
| | TGA | YES | | | (STP) | |
| TOTAL | | 12 | 8 Amino Acids Are Represented | | NPL: 5: POL: 1: NEG: 1: POS: 3: | STP = 2 |

TABLE 40

Mutagenic Cassette: N, A/C/T, A

| CODON | Represented | AMINO ACID | (Frequency) | CATEGORY | (Frequency) |
|---|---|---|---|---|---|
| | | GLYCINE | 0 | NONPOLAR | 6 |
| GCA | YES | ALANINE | 1 | (NPL) | |
| GTA | YES | VALINE | 1 | | |
| TTA | YES | LEUCINE | 2 | | |
| CTA | YES | | | | |
| ATA | YES | ISOLEUCINE | 1 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 3 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| ACA | YES | THREONINE | 1 | | |
| | | ASPARTIC ACID | 0 | IONIZABLE: ACIDIC | 1 |
| GAA | YES | GLUTAMIC ACID | 1 | NEGATIVE CHARGE (NEG) | |
| AAA | YES | LYSINE | 1 | IONIZABLE: BASIC | 1 |
| | | ARGININE | 0 | POSITIVE CHARGE | |
| | | HISTIDINE | 0 | (POS) | |
| TAA | YES | STOP CODON | 1 | STOP SIGNAL (STP) | 1 |
| TOTAL | 12 | 10 Amino Acids Are Represented | | NPL: 6: POL: 3: NEG: 1: POS: 1: STP = 1 | |

TABLE 41

Mutagenic Cassette: N, A/C/G, A

| CODON | Represented | AMINO ACID | (Frequency) | CATEGORY | (Frequency) |
|---|---|---|---|---|---|
| GGA | YES | GLYCINE | 1 | NONPOLAR | 3 |
| GCA | YES | ALANINE | 1 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCA | YES | PROLINE | 1 | | |
| TCA | YES | SERINE | 1 | POLAR | 3 |
| | | CYSTEINE | 0 | NONIONIZABLE | |
| | | ASPARAGINE | 0 | (POL) | |
| CAA | YES | GLUTAMINE | 1 | | |
| | | TYROSINE | 0 | | |
| ACA | YES | THREONINE | 1 | | |
| | | ASPARTIC ACID | 0 | IONIZABLE: ACIDIC | 1 |
| GAA | YES | GLUTAMIC ACID | 1 | NEGATIVE CHARGE (NEG) | |
| AAA | YES | LYSINE | 1 | IONIZABLE: BASIC | 3 |
| CGA | YES | ARGININE | 2 | POSITIVE CHARGE | |
| AGA | YES | | | (POS) | |
| | | HISTIDINE | 0 | | |
| TAA | YES | STOP CODON | 2 | STOP SIGNAL | 2 |
| TGA | YES | | | (STP) | |
| TOTAL | 12 | 9 Amino Acids Are Represented | | NPL: 3: POL: 3: NEG: 1: POS: 3: STP = 2 | |

TABLE 42

Mutagenic Cassette: A, N, N

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| | | VALINE | 0 | | |
| | | LEUCINE | 0 | | |
| ATT | YES | ISOLEUCINE | 3 | | |
| ATC | YES | | | | |
| ATA | YES | | | | |
| ATG | YES | METHIONINE | 1 | | |
| | | PHENYLALANINE | 0 | | |
| | | TRYPTOPHAN | 0 | | |
| | | PROLINE | 0 | | |
| AGT | YES | SERINE | 2 | POLAR | 8 |
| AGC | YES | | | NONIONIZABLE | |
| | | CYSTEINE | 0 | (POL) | |
| AAT | YES | ASPARAGINE | 2 | | |
| AAC | YES | | | | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE (NEG) | |
| AAA | YES | LYSINE | 2 | IONIZABLE: BASIC POSITIVE CHARGE | 4 |
| AAG | YES | | | | |
| AGA | YES | ARGININE | 2 | (POS) | |
| AGG | YES | | | | |
| | | HISTIDINE | 0 | | |
| | | STOP CODON | 0 | STOP SIGNAL (STP) | 0 |
| TOTAL | 16 | 7 Amino Acids Are Represented | | NPL: 4: POL: 8: NEG: 0: POS: 4: STP = 0 | |

35

TABLE 43

Mutagenic Cassette: C, N, N

| CODON | Represented | AMINO ACID | (Frequency) | CATEGORY | (Frequency) |
|---|---|---|---|---|---|
| | | GLYCINE | 0 | NONPOLAR | 8 |
| | | ALANINE | 0 | (NPL) | |
| | | VALINE | 0 | | |
| CTT | YES | LEUCINE | 4 | | |
| CTC | YES | | | | |
| CTA | YES | | | | |
| CTG | YES | | | | |
| | | ISOLEUCINE | 0 | | |
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| | | SERINE | 0 | POLAR | 2 |
| | | CYSTEINE | 0 | NONIONIZABLE | |
| | | ASPARAGINE | 0 | (POL) | |
| CAA | YES | GLUTAMINE | 2 | | |
| CAG | YES | | | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 6 |
| CGT | YES | ARGININE | 4 | POSITIVE CHARGE | |
| CGC | YES | | | (POS) | |

TABLE 43-continued

Mutagenic Cassette: C, N, N

| CODON | Represented | AMINO ACID | (Frequency) | CATEGORY | (Frequency) |
|---|---|---|---|---|---|
| CGA | YES | | | | |
| CGG | YES | | | | |
| CAT | YES | HISTIDINE | 2 | | |
| CAC | YES | | | | |
| | | STOP CODON | 0 | STOP SIGNAL (STP) | 0 |
| TOTAL | 16 | 5 Amino Acids Are Represented | | NPL: 8: POL: 2: NEG: 0: POS: 6: STP = 0 | |

TABLE 44

Mutagenic Cassette: G, N, N

| CODON | Represented | AMINO ACID | (Frequency) | CATEGORY | (Frequency) |
|---|---|---|---|---|---|
| GGT | YES | GLYCINE | 4 | NONPOLAR (NPL) | 12 |
| GGC | YES | | | | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| GAT | YES | ASPARTIC ACID | 2 | IONIZABLE: ACIDIC NEGATIVE CHARGE | 4 |
| GAC | YES | | | | |
| GAA | YES | GLUTAMIC ACID | 2 | (NEG) | |
| GAG | YES | | | | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 16 | 5 Amino Acids Are Represented | | NPL: 12: POL: 0: NEG: 4: POS: 0: STP = 0 | |

TABLE 45

Mutagenic Cassette: T, N, N

| CODON | Represented | AMINO ACID | (Frequency) | CATEGORY | (Frequency) |
|---|---|---|---|---|---|
| | | GLYCINE | 0 | NONPOLAR (NPL) | 5 |
| | | ALANINE | 0 | | |
| | | VALINE | 0 | | |
| TTA | YES | LEUCINE | 2 | | |
| TTG | YES | | | | |
| | | ISOLEUCINE | 0 | | |
| | | METHIONINE | 0 | | |

TABLE 45-continued

Mutagenic Cassette: T, N, N

| CODON | Represented | AMINO ACID | (Frequency) | CATEGORY | (Frequency) |
|---|---|---|---|---|---|
| TTT | YES | PHENYLALANINE | 2 | | |
| TTC | YES | | | | |
| TGG | YES | TRYPTOPHAN | 1 | | |
| | | PROLINE | 0 | | |
| TCT | YES | SERINE | 4 | POLAR | 8 |
| TCC | YES | | | NONIONIZABLE | |
| TCA | YES | | | (POL) | |
| TCG | YES | | | | |
| TGT | YES | CYSTEINE | 2 | | |
| TGC | YES | | | | |
| | | ASPARAGINE | 0 | | |
| | | GLUTAMINE | 0 | | |
| TAT | YES | TYROSINE | 2 | | |
| TAC | YES | | | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| TAA | YES | STOP CODON | 3 | STOP SIGNAL | 3 |
| TAG | YES | | | (STP) | |
| TGA | YES | | | | |
| TOTAL | 16 | 6 Amino Acids Are Represented | | NPL: 5: POL: 8: NEG: 0: POS: 0: STP = 3 | |

TABLE 46

Mutagenic Cassette: A/C, N, N

| CODON | Represented | AMINO ACID | (Frequency) | CATEGORY | (Frequency) |
|---|---|---|---|---|---|
| | | GLYCINE | 0 | NONPOLAR | 12 |
| | | ALANINE | 0 | (NPL) | |
| | | VALINE | 0 | | |
| CTT | YES | LEUCINE | 4 | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| AGT | YES | SERINE | 2 | POLAR | 10 |
| AGC | YES | | | NONIONIZABLE | |
| | | CYSTEINE | 0 | (POL) | |
| AAT | YES | ASPARAGINE | 2 | | |
| AAC | YES | | | | |
| CAA | YES | GLUTAMINE | 2 | | |
| CAG | YES | | | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE (NEG) | |
| AAA | YES | LYSINE | 2 | IONIZABLE: BASIC | 10 |
| AAG | YES | | | POSITIVE CHARGE | |
| CGT | YES | ARGININE | 6 | (POS) | |
| CGC | YES | | | | |

TABLE 46-continued

Mutagenic Cassette: A/C, N, N

| CODON | Represented | AMINO ACID | (Frequency) | CATEGORY | (Frequency) |
|---|---|---|---|---|---|
| CGA | YES | | | | |
| CGG | YES | | | | |
| AGA | YES | | | | |
| AGG | YES | | | | |
| CAT | YES | HISTIDINE | 2 | | |
| CAC | YES | | | | |
| | | STOP CODON | 0 | STOP SIGNAL (STP) | 0 |
| TOTAL | 32 | 11 Amino Acids Are Represented | | NPL: 12: POL: 10: NEG: 0: | POS: 10: STP = 0 |

TABLE 47

Mutagenic Cassette: A/G, N, N

| CODON | Represented | AMINO ACID | (Frequency) | CATEGORY | (Frequency) |
|---|---|---|---|---|---|
| GGT | YES | GLYCINE | 4 | NONPOLAR | 16 |
| GGC | YES | | | (NPL) | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| | | LEUCINE | 0 | | |
| ATT | YES | ISOLEUCINE | 3 | | |
| ATC | YES | | | | |
| ATA | YES | | | | |
| ATG | YES | METHIONINE | 1 | | |
| | | PHENYLALANINE | 0 | | |
| | | TRYPTOPHAN | 0 | | |
| | | PROLINE | 0 | | |
| AGT | YES | SERINE | 2 | POLAR | 8 |
| AGC | YES | | | NONIONIZABLE | |
| | | CYSTEINE | 0 | (POL) | |
| AAT | YES | ASPARAGINE | 2 | | |
| AAC | YES | | | | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 4 |
| AAG | YES | | | POSITIVE CHARGE | |
| AGA | YES | ARGININE | 2 | (POS) | |
| AGG | YES | | | | |
| | | HISTIDINE | 0 | | |
| | | STOP CODON | 0 | STOP SIGNAL (STP) | 0 |
| TOTAL | 32 | 12 Amino Acids Are Represented | | NPL: 16: POL: 8: NEG: 4: | POS: 4: STP = 0 |

TABLE 48

| Mutagenic Cassette: A/T, N, N | | | | | |
|---|---|---|---|---|---|
| CODON | Represented | AMINO ACID | (Frequency) | CATEGORY | (Frequency) |
|  |  | GLYCINE | 0 | NONPOLAR | 9 |
|  |  | ALANINE | 0 | (NPL) |  |
|  |  | VALINE | 0 |  |  |
| TTA | YES | LEUCINE | 2 |  |  |
| TTG | YES |  |  |  |  |
| ATT | YES | ISOLEUCINE | 3 |  |  |
| ATC | YES |  |  |  |  |
| ATA | YES |  |  |  |  |
| ATG | YES | METHIONINE | 1 |  |  |
| TTT | YES | PHENYLALANINE | 2 |  |  |
| TTC | YES |  |  |  |  |
| TGG | YES | TRYPTOPHAN | 1 |  |  |
|  |  | PROLINE | 0 |  |  |
| TCT | YES | SERINE | 6 | POLAR | 16 |
| TCC | YES |  |  | NONIONIZABLE |  |
| TCA | YES |  |  | (POL) |  |
| TCG | YES |  |  |  |  |
| AGT | YES |  |  |  |  |
| AGC | YES |  |  |  |  |
| TGT | YES | CYSTEINE | 2 |  |  |
| TGC | YES |  |  |  |  |
| AAT | YES | ASPARAGINE | 2 |  |  |
| AAC | YES |  |  |  |  |
|  |  | GLUTAMINE | 0 |  |  |
| TAT | YES | TYROSINE | 2 |  |  |
| TAC | YES |  |  |  |  |
| ACT | YES | THREONINE | 4 |  |  |
| ACC | YES |  |  |  |  |
| ACA | YES |  |  |  |  |
| ACG | YES |  |  |  |  |
|  |  | ASPARTIC ACID | 0 | IONIZABLE: ACIDIC | 0 |
|  |  | GLUTAMIC ACID | 0 | NEGATIVE CHARGE |  |
|  |  |  |  | (NEG) |  |
| AAA | YES | LYSINE | 2 | IONIZABLE: BASIC | 4 |
| AAG | YES |  |  | POSITIVE CHARGE |  |
| AGA | YES | ARGININE | 2 | (POS) |  |
| AGG | YES |  |  |  |  |
|  |  | HISTDINE | 0 |  |  |
| TAA | YES | STOP CODON | 3 | STOP SIGNAL | 3 |
| TAG | YES |  |  | (STP) |  |
| TGA | YES |  |  |  |  |
| TOTAL | 32 | 12 Amino Acids Are Represented | | NPL: POL: NEG: POS: STP = 9: 16: 0: 4: 3 | |

TABLE 49

| Mutagenic Cassette: C/G, N, N | | | | | |
|---|---|---|---|---|---|
| CODON | Represented | AMINO ACID | (Frequency) | CATEGORY | (Frequency) |
| GGT | YES | GLYCINE | 4 | NONPOLAR | 20 |
| GGC | YES |  |  | (NPL) |  |
| GGA | YES |  |  |  |  |
| GGG | YES |  |  |  |  |
| GCT | YES | ALANINE | 4 |  |  |
| GCC | YES |  |  |  |  |
| GCA | YES |  |  |  |  |
| GCG | YES |  |  |  |  |
| GTT | YES | VALINE | 4 |  |  |
| GTC | YES |  |  |  |  |
| GTA | YES |  |  |  |  |
| GTG | YES |  |  |  |  |
| CTT | YES | LEUCINE | 4 |  |  |
| CTC | YES |  |  |  |  |
| CTA | YES |  |  |  |  |
| CTG | YES |  |  |  |  |
|  |  | ISOLEUCINE | 0 |  |  |

TABLE 49-continued

Mutagenic Cassette: C/G, N, N

| CODON | Represented | AMINO ACID | (Frequency) | CATEGORY | (Frequency) |
|---|---|---|---|---|---|
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| | | SERINE | 0 | POLAR | 2 |
| | | CYSTEINE | 0 | NONIONIZABLE | |
| | | ASPARAGINE | 0 | (POL) | |
| CAA | YES | GLUTAMINE | 2 | | |
| CAG | YES | | | | |
| | | TYROSINE | 0 | | |
| | | THREONINE | 0 | | |
| GAT | YES | ASPARTIC ACD | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| | | LYSINE | 0 | IONIZABLE: BASIC | 6 |
| CGT | YES | ARGININE | 4 | POSITIVE CHARGE | |
| CGC | YES | | | (POS) | |
| CGA | YES | | | | |
| CGG | YES | | | | |
| CAT | YES | HISTIDINE | 2 | | |
| CAC | YES | | | | |
| | | STOP CODON | 0 | STOP SIGNAL | 0 |
| | | | | (STP) | |
| TOTAL | 32 | 10 Amino Acids Are Represented | | NPL: POL: NEG: POS: STP = 20: 2: 4: 6: 0 | |

TABLE 50

Mutagenic Cassette: C/T, N, N

| CODON | Represented | AMINO ACID | (Frequency) | CATEGORY | (Frequency) |
|---|---|---|---|---|---|
| | | GLYCINE | 0 | NONPOLAR | 13 |
| | | ALANINE | 0 | (NPL) | |
| | | VALINE | 0 | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| | | ISOLEUCINE | 0 | | |
| | | METHIONINE | 0 | | |
| TTT | YES | PHENYLALANINE | 2 | | |
| TTC | YES | | | | |
| TGG | YES | TRYPTOPHAN | 1 | | |
| CCT | YES | PROLINE | 4 | | |
| CCC | YES | | | | |
| CCA | YES | | | | |
| CCG | YES | | | | |
| TCT | YES | SERINE | 4 | POLAR | 10 |
| TCC | YES | | | NONIONIZABLE | |
| TCA | YES | | | (POL) | |
| TCG | YES | | | | |
| TGT | YES | CYSTEINE | 2 | | |
| TGC | YES | | | | |
| | | ASPARAGINE | 0 | | |
| CAA | YES | GLUTAMINE | 2 | | |
| CAG | YES | | | | |
| TAT | YES | TYROSINE | 2 | | |
| TAC | YES | | | | |
| | | THREONINE | 0 | | |
| | | ASPARTIC ACID | 0 | IONIZABLE: ACIDIC | 0 |
| | | GLUTAMIC ACID | 0 | NEGATIVE CHARGE | |
| | | | | (NEG) | |

TABLE 50-continued

Mutagenic Cassette: C/T, N, N

| CODON | Represented | AMINO ACID | (Frequency) | CATEGORY | (Frequency) |
|---|---|---|---|---|---|
| | | LYSINE | 0 | IONIZABLE: BASIC | 6 |
| CGT | YES | ARGININE | 4 | POSITIVE CHARGE | |
| CGC | YES | | | (POS) | |
| CGA | YES | | | | |
| CGG | YES | | | | |
| CAT | YES | HISTDINE | 2 | | |
| CAC | YES | | | | |
| TAA | YES | STOP CODON | 3 | STOP SIGNAL | 3 |
| TAG | YES | | | (STP) | |
| TGA | YES | | | | |
| TOTAL | 32 | 10 Amino Acids Are Represented | | NPL: 13: POL: 10: NEG: 0: POS: 6: STP = 3 | |

TABLE 51

Mutagenic Cassette: G/T, N, N

| CODON | Represented | AMINO ACID | (Frequency) | CATEGORY | (Frequency) |
|---|---|---|---|---|---|
| GGT | YES | GLYCINE | 4 | NONPOLAR | 17 |
| GGC | YES | | | (NPL) | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| TTA | YES | LEUCINE | 2 | | |
| TTG | YES | | | | |
| | | ISOLEUCINE | 0 | | |
| | | METHIONINE | 0 | | |
| TTT | YES | PHENYLALANINE | 2 | | |
| TTC | YES | | | | |
| TGG | YES | TRYPTOPHAN | 1 | | |
| | | PROLINE | 0 | | |
| TCT | YES | SERINE | 4 | POLAR | 8 |
| TCC | YES | | | NONIONIZABLE | |
| TCA | YES | | | (POL) | |
| TCG | YES | | | | |
| TGT | YES | CYSTEINE | 2 | | |
| TGC | YES | | | | |
| | | ASPARAGINE | 0 | | |
| | | GLUTAMINE | 0 | | |
| TAT | YES | TYROSINE | 2 | | |
| TAC | YES | | | | |
| | | THREONINE | 0 | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| | | LYSINE | 0 | IONIZABLE: BASIC | 0 |
| | | ARGININE | 0 | POSITIVE CHARGE | |
| | | HISTIDINE | 0 | (POS) | |
| TAA | YES | STOP CODON | 3 | STOP SIGNAL | 3 |
| TAG | YES | | | (STP) | |
| TGA | YES | | | | |
| TOTAL | 32 | 11 Amino Acids Are Represented | | NPL: 17: POL: 8: NEG: 4: POS: 0: STP = 3 | |

TABLE 52

Mutagenic Cassette: N, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 6 |
| | | CYSTEINE | 0 | NONIONIZABLE | |
| AAT | YES | ASPARAGINE | 2 | (POL) | |
| AAC | YES | | | | |
| CAA | YES | GLUTAMINE | 2 | | |
| CAG | YES | | | | |
| TAT | YES | TYROSINE | 2 | | |
| TAC | YES | | | | |
| | | THREONINE | 0 | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 4 |
| AAG | YES | | | POSITIVE CHARGE | |
| | | ARGININE | 0 | (POS) | |
| CAT | YES | HISTIDINE | 2 | | |
| CAC | YES | | | | |
| TAA | YES | STOP CODON | 2 | STOP SIGNAL | 2 |
| TAG | YES | | | (STP) | |
| TOTAL | 16 | 7 Amino Acids Are Represented | | NPL: 0: POL: 6: NEG: 4: POS: 4: STP = 2 | |

TABLE 53

Mutagenic Cassette: N, C, N

| CODON | Represented | AMINO ACID | (Frequency) | CATEGORY | (Frequency) |
|---|---|---|---|---|---|
| | | GLYCINE | 0 | NONPOLAR | 8 |
| GCT | YES | ALANINE | 4 | (NPL) | |
| GCC | YES | | | | |
| GCA | YES | | | | |
| GCG | YES | | | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| TCT | YES | SERINE | 4 | POLAR | 8 |
| TCC | YES | | | NONIONIZABLE | |
| TCA | YES | | | (POL) | |
| TCG | YES | | | | |
| | | CYSTEINE | 0 | | |
| | | ASPARAGINE | 0 | | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE | |

TABLE 53-continued

Mutagenic Cassette: N, C, N

| CODON | Represented | AMINO ACID | (Frequency) | CATEGORY | (Frequency) |
|---|---|---|---|---|---|
| | | | | (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL | 0 |
| | | | | (STP) | |
| TOTAL | 16 | 4 Amino Acids Are Represented | | NPL: POL: NEG: POS: STP = | |
| | | | | 8:   8:   0:   0: | 0 |

TABLE 54

Mutagenic Cassette: N, G, N

| CODON | Represented | AMINO ACID | (Frequency) | CATEGORY | (Frequency) |
|---|---|---|---|---|---|
| GGT | YES | GLYCINE | 4 | NONPOLAR | 5 |
| GGC | YES | | | (NPL) | |
| GGA | YES | | | | |
| GGG | YES | | | | |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| | | PROLINE | 0 | | |
| AGT | YES | SERINE | 2 | POLAR | 4 |
| AGC | YES | | | NONIONIZABLE | |
| TGT | YES | CYSTEINE | 2 | (POL) | |
| TGC | YES | | | | |
| | | ASPARAGINE | 0 | | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CNARGE | |
| | | | | (NEG) | |
| | | LYSINE | 0 | IONIZABLE: BASIC | 6 |
| CGT | YES | ARGININE | 6 | POSITIVE CHARGE | |
| CGC | YES | | | (POS) | |
| CGA | YES | | | | |
| CGG | YES | | | | |
| AGA | YES | | | | |
| AGG | YES | | | | |
| | | HISTIDINE | 0 | | |
| TGA | YES | STOP CODON | 1 | STOP SIGNAL | 1 |
| | | | | (STP) | |
| TOTAL | 16 | 5 Amino Acids Are Represented | | NPL: POL: NEG: POS: STP = | |
| | | | | 5:   4:   0:   6: | 1 |

TABLE 55

Mutagenic Cassette: N, T, N

| CODON | Represented | AMINO ACID | (Frequency) | CATEGORY | (Frequency) |
|---|---|---|---|---|---|
| | | GLYCINE | 0 | NONPOLAR | 16 |
| | | ALANINE | 0 | (NPL) | |
| GTT | YES | VALINE | 4 | | |
| GTC | YES | | | | |
| GTA | YES | | | | |
| GTG | YES | | | | |
| TTA | YES | LEUCINE | 6 | | |

TABLE 55-continued

Mutagenic Cassette: N, T, N

| CODON | Represented | AMINO ACID | (Frequency) | CATEGORY | (Frequency) |
|---|---|---|---|---|---|
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE; BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 16 | 5 Amino Acids Are Represented | | NPL: POL: NEG: POS: STP = 16: 0: 0: 0: 0 | |

TABLE 56

Mutagenic Cassette: N, A/C, N

| CODON | Represented | AMINO ACID | (Frequency) | CATEGORY | (Frequency) |
|---|---|---|---|---|---|
| | | GLYCINE | 0 | NONPOLAR | 8 |
| GCT | YES | ALANINE | 4 | (NPL) | |
| GCC | YES | | | | |
| GCA | YES | | | | |
| GCG | YES | | | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| TCT | YES | SERINE | 4 | POLAR | 14 |
| TCC | YES | | | NONIONIZABLE | |
| TCA | YES | | | (POL) | |
| TCG | YES | | | | |
| | | CYSTEINE | 0 | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| ACT | YES | THREONINE | 4 | | |
| ACC | YES | | | | |
| ACA | YES | | | | |
| ACG | YES | | | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |

TABLE 56-continued

Mutagenic Cassette: N, A/C, N

| CODON | Represented | AMINO ACID | (Frequency) | CATEGORY | (Frequency) |
|---|---|---|---|---|---|
| GAG | YES | | | | |
| AAA | YES | LYSINE | 2 | IONIZABLE: BASIC | 4 |
| AAG | YES | | | POSITIVE CHARGE | |
| | | ARGININE | 0 | (POS) | |
| CAT | YES | HISTIDINE | 2 | | |
| CAC | YES | | | | |
| TAA | YES | STOP CODON | 2 | STOP SIGNAL | 2 |
| TAG | YES | | | (STP) | |
| TOTAL | 32 | 11 Amino Acids Are Represented | | NPL: 8: POL: 14: NEG: 4: POS: 4: STP = 2 | |

TABLE 57

Mutagenic Cassette: N, A/G, N

| CODON | Represented | AMINO ACID | (Frequency) | CATEGORY | (Frequency) |
|---|---|---|---|---|---|
| GGT | YES | GLYCINE | 4 | NONPOLAR | 5 |
| GGC | YES | | | (NPL) | |
| GGA | YES | | | | |
| GGG | YES | | | | |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| | | PROLINE | 0 | | |
| AGT | YES | SERINE | 2 | POLAR | 10 |
| AGC | YES | | | NONIONIZABLE | |
| TGT | YES | CYSTEINE | 2 | (POL) | |
| TGC | YES | | | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| | | THREONINE | 0 | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 10 |
| AAG | YES | | | POSITIVE CHARGE | |
| CGT | YES | ARGININE | 6 | (POS) | |
| CGC | YES | | | | |
| CGA | YES | | | | |
| CGG | YES | | | | |
| AGA | YES | | | | |
| AGG | YES | | | | |
| CAT | YES | HISTIDINE | 2 | | |
| CAC | YES | | | | |
| TAA | YES | STOP CODON | 3 | STOP SIGNAL | 3 |
| TAG | YES | | | (STP) | |
| TGA | YES | | | | |
| TOTAL | | 32 | 12 Amino Acids Are Represented | NPL: 5: POL: 10: NEG: 4: POS: 10: STP = 3 | |

TABLE 58

Mutagenic Cassette: N, A/T, N

| CODON | Represented | AMINO ACID | (Frequency) | CATEGORY | (Frequency) |
|---|---|---|---|---|---|
| | | GLYCINE | 0 | NONPOLAR | 16 |
| | | ALANINE | 0 | (NPL) | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| | | TRYPTOPHAN | 0 | | |
| | | PROLINE | 0 | | |
| | | SERINE | 0 | POLAR | 6 |
| | | CYSTEINE | 0 | NONIONIZABLE | |
| AAT | YES | ASPARAGINE | 2 | (POL) | |
| AAC | YES | | | | |
| CAA | YES | GLUTAMINE | 2 | | |
| CAG | YES | | | | |
| TAT | YES | TYROSINE | 2 | | |
| TAC | YES | | | | |
| | | THREONINE | 0 | | |
| GAT | YES | ASPARTIC ACID | 2 | IONIZABLE: ACIDIC | 4 |
| GAC | YES | | | NEGATIVE | |
| GAA | YES | GLUTAMIC ACID | 2 | CHARGE (NEG) | |
| GAG | YES | | | | |
| AAA | YES | LYSINE | 2 | IONIZABLE: BASIC | 4 |
| AAG | YES | | | POSITIVE CHARGE | |
| | | ARGININE | 0 | (POS) | |
| CAT | YES | HISTIDINE | 2 | | |
| CAC | YES | | | | |
| TAA | YES | STOP CODON | 2 | STOP SIGNAL | 2 |
| TAG | YES | | | (STP) | |
| TOTAL | 32 | 3 Amino Acids Are Represented | | NPL: POL: NEG: POS: STP = | |
| | | | | 16:   6:   4:   4:   2 | |

TABLE 59

Mutagenic Cassette: N, C/G, N

| CODON | Represented | AMINO ACID | (Frequency) | CATEGORY | (Frequency) |
|---|---|---|---|---|---|
| GGT | YES | GLYCINE | 4 | NONPOLAR | 13 |
| GGC | YES | | | (NPL) | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| | | VALINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| CCT | YES | PROLINE | 4 | | |
| CCC | YES | | | | |
| CCA | YES | | | | |
| CCG | YES | | | | |
| TCT | YES | SERINE | 6 | POLAR | 12 |

TABLE 59-continued

Mutagenic Cassette: N, C/G, N

| CODON | Represented | AMINO ACID | (Frequency) | CATEGORY | (Frequency) |
|---|---|---|---|---|---|
| TCC | YES | | | NONIONIZABLE | |
| TCA | YES | | | (POL) | |
| TCG | YES | | | | |
| AGT | YES | | | | |
| AGC | YES | | | | |
| TGT | YES | CYSTEINE | 2 | | |
| TGC | YES | | | | |
| | | ASPARAGINE | 0 | | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 6 |
| CGT | YES | ARGININE | 6 | POSITIVE CHARGE (POS) | |
| CGC | YES | | | | |
| CGA | YES | | | | |
| CGG | YES | | | | |
| AGA | YES | | | | |
| AGG | YES | | | | |
| | | HISTIDINE | 0 | | |
| TGA | YES | STOP CODON | 1 | STOP SIGNAL (STP) | 1 |
| TOTAL | 32 | 8 Amino Acids Are Represented | | NPL: POL: NEG: POS: STP = 13: 12: 0: 6: 1 | |

TABLE 60

Mutagenic Cassette: N, C/T, N

| CODON | Represented | AMINO ACID | (Frequency) | CATEGORY | (Frequency) |
|---|---|---|---|---|---|
| | | GLYCINE | 0 | NONPOLAR | 24 |
| GCT | YES | ALANINE | 4 | (NPL) | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| | | TRYPTOPHAN | 0 | | |
| CCT | YES | PROLINE | 4 | | |
| CCC | YES | | | | |
| CCA | YES | | | | |
| CCG | YES | | | | |
| TCT | YES | SERINE | 4 | POLAR NONIONIZABLE (POL) | 8 |
| TCC | YES | | | | |
| TCA | YES | | | | |
| TCG | YES | | | | |
| | | CYSTEINE | 0 | | |
| | | ASPARAGINE | 0 | | |
| | | GLUTAMINE | 0 | | |

TABLE 60-continued

Mutagenic Cassette: N, C/T, N

| CODON | Represented | AMINO ACID | (Frequency) | CATEGORY | (Frequency) |
|---|---|---|---|---|---|
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 32 | 9 Amino Acids Are Represented | NPL:POL:NEG:POS:STP = 24:8:0:0:0 | |

TABLE 61

Mutagenic Cassette: N, G/T, N

| CODON | Represented | AMINO ACID | (Frequency) | CATEGORY | (Frequency) |
|---|---|---|---|---|---|
| GGT | YES | GLYCINE | 4 | NONPOLAR (NPL) | 21 |
| GGC | YES | | | | |
| GGA | YES | | | | |
| GGG | YES | | | | |
| | | ALANINE | 0 | | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| TGG | YES | TRYPTOPHAN | 1 | | |
| | | PROLINE | 0 | | |
| AGT | YES | SERINE | 2 | POLAR NONIONIZABLE (POL) | 4 |
| AGC | YES | | | | |
| TGT | YES | CYSTEINE | 2 | | |
| TGC | YES | | | | |
| | | ASPARAGINE | 0 | | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 6 |
| CGT | YES | ARGININE | 6 | POSITIVE CHARGE (POS) | |
| CGC | YES | | | | |
| CGA | YES | | | | |
| CGG | YES | | | | |
| AGA | YES | | | | |
| AGG | YES | | | | |
| | | HISTIDINE | 0 | | |
| TGA | YES | STOP CODON | 1 | STOP SIGNAL (STP) | 1 |
| TOTAL | | 32 | 10 Amino Acids Are Represented | NPL:POL:NEG:POS:STP = 21:4:0:6:1 | |

TABLE 62

Mutagenic Cassette: N, A/C/G, N

| CODON | Represented | AMINO ACID | (Frequency) | CATEGORY | (Frequency) |
|---|---|---|---|---|---|
| GGT | YES | GLYCINE | 4 | NONPOLAR | 13 |
| GGC | YES | | | (NPL) | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| CCT | YES | PROLINE | 4 | | |
| CCC | YES | | | | |
| CCA | YES | | | | |
| CCG | YES | | | | |
| TCT | YES | SERINE | 6 | POLAR | 18 |
| TCC | YES | | | NONIONIZABLE | |
| TCA | YES | | | (POL) | |
| TCG | YES | | | | |
| AGT | YES | | | | |
| AGC | YES | | | | |
| TGT | YES | CYSTEINE | 2 | | |
| TGC | YES | | | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| ACT | YES | THREONINE | 4 | | |
| ACC | YES | | | | |
| ACA | YES | | | | |
| ACG | YES | | | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 10 |
| AAG | YES | | | POSITIVE CHARGE | |
| CGT | YES | ARGININE | 6 | (POS) | |
| CGC | YES | | | | |
| CGA | YES | | | | |
| CGG | YES | | | | |
| AGA | YES | | | | |
| AGG | YES | | | | |
| CAT | YES | HISTIDINE | 2 | | |
| CAC | YES | | | | |
| TAA | YES | STOP CODON | 3 | STOP SIGNAL | 3 |
| TAG | YES | | | (STP) | |
| TGA | YES | | | | |
| TOTAL | 48 | 15 Amino Acids Are Represented | | NPL:POL:NEG:POS:STP = 13:18:4:10:3 | |

TABLE 63

Mutagenic Cassette: N, A/C/T, N

| CODON | Represented | AMINO ACID | (Frequency) | CATEGORY | (Frequency) |
|---|---|---|---|---|---|
| | | GLYCINE | 0 | NONPOLAR | 24 |
| GCT | YES | ALANINE | 4 | (NPL) | |
| GCC | YES | | | | |
| GCA | YES | | | | |
| GCG | YES | | | | |

TABLE 63-continued

Mutagenic Cassette: N, A/C/T, N

| CODON | Represented | AMINO ACID | (Frequency) | CATEGORY | (Frequency) |
|---|---|---|---|---|---|
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| | | TRYPTOPHAN | 0 | | |
| CCT | YES | PROLINE | 4 | | |
| CCC | YES | | | | |
| CCA | YES | | | | |
| CCG | YES | | | | |
| TCT | YES | SERINE | 4 | POLAR NONIONIZABLE (POL) | 14 |
| TCC | YES | | | | |
| TCA | YES | | | | |
| TCG | YES | | | | |
| | | CYSTEINE | 0 | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| ACT | YES | THREONINE | 4 | | |
| ACC | YES | | | | |
| ACA | YES | | | | |
| ACG | YES | | | | |
| GAT | YES | ASPARTIC ACID | 2 | IONIZABLE: ACIDIC NEGATIVE CHARGE (NEG) | 4 |
| GAC | YES | | | | |
| GAA | YES | GLUTAMIC ACID | 2 | | |
| GAG | YES | | | | |
| AAA | YES | LYSINE | 2 | IONIZABLE: BASIC POSITIVE CHARGE (POS) | 4 |
| AAG | YES | | | | |
| | | ARGININE | 0 | | |
| CAT | YES | HISTIDINE | 2 | | |
| CAC | YES | | | | |
| TAA | YES | STOP CODON | 2 | STOP SIGNAL (STP) | 2 |
| TAG | YES | | | | |
| TOTAL | | 48 | 16 Amino Acids Are Represented | NPL:POL:NEG:POS:STP = 24:14:4:4:2 | |

TABLE 64

Mutagenic Cassette: N, A/G/T, N

| CODON | Represented | AMINO ACID | (Frequency) | CATEGORY | (Frequency) |
|---|---|---|---|---|---|
| GGT | YES | GLYCINE | 4 | NONPOLAR (NPL) | 21 |
| GGC | YES | | | | |
| GGA | YES | | | | |
| GGG | YES | | | | |
| | | ALANINE | 0 | | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |

TABLE 64-continued

Mutagenic Cassette: N, A/G/T, N

| CODON | Represented | AMINO ACID | (Frequency) | CATEGORY | (Frequency) |
|---|---|---|---|---|---|
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |
| TTT | YES | PHENYLALANINE | 2 | | |
| TTC | YES | | | | |
| TGG | YES | TRYPTOPHAN | 1 | | |
| | | PROLINE | 0 | | |
| AGT | YES | SERINE | 2 | POLAR | 10 |
| AGC | YES | | | NONIONIZABLE | |
| TGT | YES | CYSTEINE | 2 | (POL) | |
| TGC | YES | | | | |
| AAT | YES | ASPARAGINE | 2 | | |
| AAC | YES | | | | |
| CAA | YES | GLUTAMINE | 2 | | |
| CAG | YES | | | | |
| TAT | YES | TYROSINE | 2 | | |
| TAC | YES | | | | |
| | | THREONINE | 0 | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| AAA | YES | LYSINE | 2 | IONIZABLE: BASIC | 10 |
| AAG | YES | | | POSITIVE CHARGE | |
| CGT | YES | ARGININE | 6 | (POS) | |
| CGC | YES | | | | |
| CGA | YES | | | | |
| CGG | YES | | | | |
| AGA | YES | | | | |
| AGG | YES | | | | |
| CAT | YES | HISTIDINE | 2 | | |
| CAC | YES | | | | |
| TAA | YES | STOP CODON | 3 | STOP SIGNAL | 3 |
| TAG | YES | | | (STP) | |
| TGA | YES | | | | |
| TOTAL | 48 | 17 Amino Acids Are Represented | | NPL:POL:NEG:POS:STP = 21:10:4:10:3 | |

40

TABLE 65

Mutagenic Cassette: N, C/G/T, N

| CODON | Represented | AMINO ACID | (Frequency) | CATEGORY | (Frequency) |
|---|---|---|---|---|---|
| GGT | YES | GLYCINE | 4 | NONPOLAR | 29 |
| GGC | YES | | | (NPL) | |
| GGA | YES | | | | |
| GGG | YES | | | | |
| GCT | YES | ALANINE | 4 | | |
| GCC | YES | | | | |
| GCA | YES | | | | |
| GCG | YES | | | | |
| GTT | YES | VALINE | 4 | | |
| GTC | YES | | | | |
| GTA | YES | | | | |
| GTG | YES | | | | |
| TTA | YES | LEUCINE | 6 | | |
| TTG | YES | | | | |
| CTT | YES | | | | |
| CTC | YES | | | | |
| CTA | YES | | | | |
| CTG | YES | | | | |
| ATT | YES | ISOLEUCINE | 3 | | |
| ATC | YES | | | | |
| ATA | YES | | | | |
| ATG | YES | METHIONINE | 1 | | |

TABLE 65-continued

Mutagenic Cassette: N, C/G/T, N

| CODON | Represented | AMINO ACID | (Frequency) | CATEGORY | (Frequency) |
|---|---|---|---|---|---|
| TTT | YES | PHENYLALANINE | 2 | | |
| TTC | YES | | | | |
| TGG | YES | TRYPTOPHAN | 1 | | |
| CCT | YES | PROLINE | 4 | | |
| CCC | YES | | | | |
| CCA | YES | | | | |
| CCG | YES | | | | |
| TCT | YES | SERINE | 6 | POLAR | 12 |
| TCC | YES | | | NONIONIZABLE | |
| TCA | YES | | | (POL) | |
| TCG | YES | | | | |
| AGT | YES | | | | |
| AGC | YES | | | | |
| TGT | YES | CYSTEINE | 2 | | |
| TGC | YES | | | | |
| | | ASPARAGINE | 0 | | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 6 |
| CGT | YES | ARGININE | 6 | POSITIVE CHARGE (POS) | |
| CGC | YES | | | | |
| CGA | YES | | | | |
| CGG | YES | | | | |
| AGA | YES | | | | |
| AGG | YES | | | | |
| | | HISTIDINE | 0 | | |
| TGA | YES | STOP CODON | 1 | STOP SIGNAL (STP) | 1 |
| TOTAL | 48 | 13 Amino Acids Are Represented | | NPL: 29: POL: 12: NEG: 0: POS: 6: STP = 1 | |

TABLE 66

Mutagenic Cassette: C, C, N

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE (POS) | |
| | | HISTIDINE | 0 | | |

TABLE 66-continued

Mutagenic Cassette: C, C, N

| CODON | Represented | AMINO ACID | (Frequency) | CATEGORY | (Frequency) |
|---|---|---|---|---|---|
| | | STOP CODON | 0 | STOP SIGNAL (STP) | 0 |
| TOTAL | 4 | 1 Amino Acid Is Represented | | NPL:POL:NEG:POS:STP = 4:0:0:0:0 | |

TABLE 67

Mutagenic Cassette: G, G, N

| CODON | Represented | AMINO ACID | (Frequency) | CATEGORY | (Frequency) |
|---|---|---|---|---|---|
| GGT | YES | GLYCINE | 4 | NONPOLAR (NPL) | 4 |
| GGC | YES | | | | |
| GGA | YES | | | | |
| GGG | YES | | | | |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR NONIONIZABLE (POL) | 0 |
| | | CYSTEINE | 0 | | |
| | | ASPARAGINE | 0 | | |
| | | GLUTAMINE | 0 | | |
| | | TYROSINE | 0 | | |
| | | THREONINE | 0 | | |
| | | ASPARTIC ACID | 0 | IONIZABLE: ACIDIC NEGATIVE CHARGE (NEG) | 0 |
| | | GLUTAMIC ACID | 0 | | |
| | | LYSINE | 0 | IONIZABLE: BASIC POSITIVE CHARGE (POS) | 0 |
| | | ARGININE | 0 | | |
| | | HISTIDINE | 0 | | |
| | | STOP CODON | 0 | STOP SIGNAL (STP) | 0 |
| TOTAL 0 | 4 | 1 Amino Acid Is Represented | | NPL:POL:NEG:POS:STP = 4:0:0:0:0 | |

TABLE 68

Mutagenic Cassette: G, C, N

| CODON | Represented | AMINO ACID | (Frequency) | CATEGORY | (Frequency) |
|---|---|---|---|---|---|
| | | GLYCINE | 0 | NONPOLAR (NPL) | 4 |
| GCT | YES | ALANINE | 4 | | |
| GCC | YES | | | | |
| GCA | YES | | | | |
| GCG | YES | | | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR NONIONIZABLE (POL) | 0 |
| | | CYSTEINE | 0 | | |
| | | ASPARAGINE | 0 | | |
| | | GLUTAMINE | 0 | | |
| | | TYROSINE | 0 | | |
| | | THREONINE | 0 | | |

TABLE 68-continued

| | Mutagenic Cassette: G, C, N | | | | |
|---|---|---|---|---|---|
| CODON | Represented | AMINO ACID | (Frequency) | CATEGORY | (Frequency) |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 1 Amino Acid Is Represented | | NPL:POL:NEG:POS:STP = 4:0:0:0:0 | |

TABLE 69

| | Mutagenic Cassette: G, T, N | | | | |
|---|---|---|---|---|---|
| CODON | Represented | AMINO ACID | (Frequency) | CATEGORY | (Frequency) |
| | | GLYCINE | 0 | NONPOLAR | 4 |
| | | ALANINE | 0 | (NPL) | |
| GTT | YES | VALINE | 4 | | |
| GTC | YES | | | | |
| GTA | YES | | | | |
| GTG | YES | | | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | 4 | 1 Amino Acid Is Represented | | NPL:POL:NEG:POS:STP = 4:0:0:0:0 | |

TABLE 70

| | Mutagenic Cassette: C, G, N | | | | |
|---|---|---|---|---|---|
| CODON | Represented | AMINO ACID | (Frequency) | CATEGORY | (Frequency) |
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |

TABLE 70-continued

Mutagenic Cassette: C, G, N

| CODON | Represented | AMINO ACID | (Frequency) | CATEGORY | (Frequency) |
|---|---|---|---|---|---|
| | | GLUTAMINE | 0 | | |
| | | TYROSINE | 0 | | |
| | | THREONINE | 0 | | |
| | | ASPARTIC AACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 4 |
| CGT | YES | ARGININE | 4 | POSITIVE CHARGE | |
| CGC | YES | | | (POS) | |
| CGA | YES | | | | |
| CGG | YES | | | | |
| | | HISTIDINE | 0 | | |
| | | STOP CODON | 0 | STOP SIGNAL (STP) | 0 |
| TOTAL | | 4 | 1 Amino Acid Is Represented | NPL:POL:NEG:POS:STP = 0:0:0:4:0 | |

TABLE 71

Mutagenic Cassette: C, T, N

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| | | VALINE | 0 | | |
| CTT | YES | LEUCINE | 4 | | |
| CTC | YES | | | | |
| CTA | YES | | | | |
| CTG | YES | | | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 1 Amino Acid Is Represented | NPL:POL:NEG:POS:STP = 4:0:0:0:0 | |

TABLE 72

Mutagenic Cassette: T, C, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |

TABLE 72-continued

Mutagenic Cassette: T, C, N

| CODON | Represented | AMINO ACID | (Frequency) | CATEGORY | (Frequency) |
|---|---|---|---|---|---|
| | | PHENYLALANINE | 0 | | |
| | | TRYPTOPHAN | 0 | | |
| | | PROLINE | 0 | | |
| TCT | YES | SERINE | 4 | POLAR | 4 |
| TCC | YES | | | NONIONIZABLE | |
| TCA | YES | | | (POL) | |
| TCG | YES | | | | |
| | | CYSTEINE | 0 | | |
| | | ASPARAGINE | 0 | | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE | |
| | | | | (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL | 0 |
| | | | | (STP) | |
| TOTAL | | 4 | 1 Amino Acid Is Represented | NPL:POL:NEG:POS:STP = 0:4:0:0:0 | |

TABLE 73

Mutagenic Cassette: A, C, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 4 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| ACT | YES | THREONINE | 4 | | |
| ACC | YES | | | | |
| ACA | YES | | | | |
| ACG | YES | | | | |
| | | ASPARTIC ACID | 0 | IONIZABLE: ACIDIC | 0 |
| | | GLUTAMIC ACID | 0 | NEGATIVE CHARGE | |
| | | | | (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL | 0 |
| | | | | (STP) | |
| TOTAL | | 4 | 1 Amino Acid Is Represented | NPL:POL:NEG:POS:STP = 0:4:0:0:0 | |

TABLE 74

Mutagenic Cassette: G, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| GAT | YES | ASPARTIC ACID | 2 | IONIZABLE: ACIDIC | 4 |
| GAC | YES | | | NEGATIVE CHARGE | |
| GAA | YES | GLUTAMIC ACID | 2 | (NEG) | |
| GAG | YES | | | | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 2 Amino Acids Are Represented | NPL:POL:NEG:POS:STP = 0:0:4:0:0 | |

TABLE 75

Mutagenic Cassette: A, T, N

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| | | VALINE | 0 | | |
| | | LEUCINE | 0 | | |
| ATT | YES | ISOLEUCINE | 3 | | |
| ATC | YES | | | | |
| ATA | YES | | | | |
| ATG | YES | METHIONINE | 1 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 2 Amino Acids Are Represented | NPL:POL:NEG:POS:STP = 4:0:0:0:0 | |

TABLE 76

Mutagenic Cassette: C, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| | | ASPARAGINE | 0 | (POL) | |
| CAA | YES | GLUTAMINE | 2 | | |
| CAG | YES | | | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 2 |
| | | ARGININE | 0 | POSITIVE CHARGE | |
| CAT | YES | HISTIDINE | 2 | (POS) | |
| CAC | YES | | | | |
| | | STOP CODON | 0 | STOP SIGNAL (STP) | 0 |
| TOTAL | | 4 | 2 Amino Acids Are Represented | NPL: 0: POL: 2: NEG: 0: POS: 2: STP = 0 |

TABLE 77

Mutagenic Cassette: T, T, N

| CODON | Represented | AMINO ACID | (Frequency) | CATEGORY | (Frequency) |
|---|---|---|---|---|---|
| | | GLYCINE | 0 | NONPOLAR | 4 |
| | | ALANINE | 0 | (NPL) | |
| | | VALINE | 0 | | |
| TTA | YES | LEUCINE | 2 | | |
| TTG | YES | | | | |
| | | ISOLEUCINE | 0 | | |
| | | METHIONINE | 0 | | |
| TTT | YES | PHENYLALANINE | 2 | | |
| TTC | YES | | | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |
| TOTAL | | 4 | 2 Amino Acids Are Represented | NPL: 4: POL: 0: NEG: 0: POS: 0: STP = 0 |

TABLE 78

Mutagenic Cassette: A, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| AAT | YES | ASPARAGINE | 2 | (POL) | |
| AAC | YES | | | | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| AAA | YES | LYSINE | 2 | IONIZABLE: BASIC POSITIVE CHARGE | 2 |
| AAG | YES | | | | |
| | | ARGININE | 0 | (POS) | |
| | | HISTIDINE | 0 | | |
| | | STOP CODON | 0 | STOP SIGNAL (STP) | 0 |
| TOTAL | | 4 | 2 Amino Acids Are Represented | NPL: 0: POL: 2: NEG: 0: POS: 2: STP = 0 | |

TABLE 79

Mutagenic Cassette: T, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| | | ASPARAGINE | 0 | (POL) | |
| | | GLUTAMINE | 0 | | |
| TAT | YES | TYROSINE | 2 | | |
| TAC | YES | | | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| TAA | YES | STOP CODON | 2 | STOP SIGNAL | 2 |
| TAG | YES | | | (STP) | |
| TOTAL | | 4 | 1 Amino Acid Is Represented | NPL: 0: POL: 2: NEG: 0: POS: 0: STP = 2 | |

TABLE 80

Mutagenic Cassette: T, G, N

| CODON | Represented | AMINO ACID | (Frequency) | CATEGORY | (Frequency) |
|---|---|---|---|---|---|
| | | GLYCINE | 0 | NONPOLAR (NPL) | 1 |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| TGG | YES | TRYPTOPHAN | 1 | | |
| | | PROLINE | 0 | | |
| | | SERINE | 0 | POLAR NONIONIZABLE (POL) | 2 |
| TGT | YES | CYSTEINE | 2 | | |
| TGC | YES | | | | |
| | | TYROSINE | 0 | | |
| | | THREONINE | 0 | | |
| | | ASPARTIC ACID | 0 | IONIZABLE: ACIDIC NEGATIVE CHARGE (NEG) | 0 |
| | | GLUTAMIC ACID | 0 | | |
| | | LYSINE | 0 | IONIZABLE: BASIC POSITIVE CHARGE (POS) | 0 |
| | | ARGININE | 0 | | |
| | | HISTIDINE | 0 | | |
| TGA | YES | STOP CODON | 1 | STOP SIGNAL (STP) | 1 |
| TOTAL | | 4 | 2 Amino Acids Are Represented | NPL: 1: POL: 2: NEG: 0: POS: 0: STP = 1 | |

TABLE 81

Mutagenic Cassette: A, G, N

| CODON | Represented | AMINO ACID | (Frequency) | CATEGORY | (Frequency) |
|---|---|---|---|---|---|
| | | GLYCINE | 0 | NONPOLAR (NPL) | 0 |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| AGT | YES | SERINE | 2 | POLAR NONIONIZABLE (POL) | 2 |
| AGC | YES | | | | |
| | | CYSTEINE | 0 | | |
| | | ASPARAGINE | 0 | | |
| | | GLUTAMINE | 0 | | |
| | | TYROSINE | 0 | | |
| | | THREONINE | 0 | | |
| | | ASPARTIC ACID | 0 | IONIZABLE: ACIDIC NEGATIVE CHARGE (NEG) | 0 |
| | | GLUTAMIC ACID | 0 | | |
| | | LYSINE | 0 | IONIZABLE: BASIC POSITIVE CHARGE (POS) | 2 |
| AGA | YES | ARGININE | 2 | | |
| AGG | YES | | | | |
| | | HISTIDINE | 0 | | |
| | | STOP CODON | 0 | STOP SIGNAL (STP) | 0 |
| TOTAL | | 4 | 2 Amino Acids Are Represented | NPL: 0: POL: 2: NEG: 0: POS: 2: STP = 0 | |

TABLE 82

Mutagenic Cassette: G/C, G, N

| CODON | Represented | AMINO ACID | (Frequency) | CATEGORY | (Frequency) |
|---|---|---|---|---|---|
| GGT | YES | GLYCINE | 4 | NONPOLAR | 4 |
| GGC | YES | | | (NPL) | |
| GGA | YES | | | | |
| GGG | YES | | | | |
| | | ALANINE | 0 | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 4 |
| CGT | YES | ARGININE | 4 | POSITIVE CHARGE | |
| CGC | YES | | | (POS) | |
| CGA | YES | | | | |
| CGG | YES | | | | |
| | | HISTIDINE | 0 | | |
| | | STOP CODON | 0 | STOP SIGNAL (STP) | 0 |
| TOTAL | | 8 | 2 Amino Acids Are Represented | NPL: 4: POL: 0: NEG: 0: POS: 4: STP = 0 | |

TABLE 83

Mutagenic Cassette: G/C, C, N

| CODON | Represented | AMINO ACID | (Frequency) | CATEGORY | (Frequency) |
|---|---|---|---|---|---|
| | | GLYCINE | 0 | NONPOLAR | 8 |
| GCT | YES | ALANINE | 4 | (NPL) | |
| GCC | YES | | | | |
| GCA | YES | | | | |
| GCG | YES | | | | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| CCT | YES | PROLINE | 4 | | |
| CCC | YES | | | | |
| CCA | YES | | | | |
| CCG | YES | | | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE | |
| | | HISTIDINE | 0 | (POS) | |
| | | STOP CODON | 0 | STOP SIGNAL (STP) | 0 |

TABLE 83-continued

Mutagenic Cassette: G/C, C, N

| CODON | Represented | AMINO ACID | (Frequency) | CATEGORY | (Frequency) |
|---|---|---|---|---|---|
| TOTAL | | 8 | 2 Amino Acids Are Represented | NPL: 8: POL: 0: NEG: 0: POS: 0: STP = 0 | |

TABLE 84

Mutagenic Cassette: G/C, A, N

| CODON | Represented | AMINO ACID | (Frequency) | CATEGORY | (Frequency) |
|---|---|---|---|---|---|
| | | GLYCINE | 0 | NONPOLAR | 0 |
| | | ALANINE | 0 | (NPL) | |
| | | VALINE | 0 | | |
| | | LEUCINE | 0 | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 2 |
| | | CYSTEINE | 0 | NONIONIZABLE | |
| | | ASPARAGINE | 0 | (POL) | |
| CAA | YES | GLUTAMINE | 2 | | |
| CAG | YES | | | | |
| | | TYROSINE | 0 | | |
| | | THREONINE | 0 | | |
| GAT | YES | ASPARTIC ACID | 2 | IONIZABLE: ACIDIC | 4 |
| GAC | YES | | | NEGATIVE | |
| GAA | YES | GLUTAMIC ACID | 2 | CHARGE (NEG) | |
| GAG | YES | | | | |
| | | LYSINE | 0 | IONIZABLE: BASIC | 2 |
| | | ARGININE | 0 | POSITIVE CHARGE | |
| CAT | YES | HISTIDINE | 2 | (POS) | |
| CAC | YES | | | | |
| | | STOP CODON | 0 | STOP SIGNAL (STP) | 0 |
| TOTAL | | 8 | 4 Amino Acids Are Represented | NPL: 0: POL: 2: NEG: 4: POS: 2: STP = 0 | |

TABLE 85

Mutagenic Cassette: G/C, T, N

| CODON | Represented | AMINO ACID | (Frequency) | CATEGORY | (Frequency) |
|---|---|---|---|---|---|
| | | GLYCINE | 0 | NONPOLAR | 8 |
| | | ALANINE | 0 | (NPL) | |
| GTT | YES | VALINE | 4 | | |
| GTC | YES | | | | |
| GTA | YES | | | | |
| GTG | YES | | | | |
| CTT | YES | LEUCINE | 4 | | |
| CTC | YES | | | | |
| CTA | YES | | | | |
| CTG | YES | | | | |
| | | ISOLEUCINE | 0 | | |
| | | METHIONINE | 0 | | |
| | | PHENYLALANINE | 0 | | |
| | | TRYPTOPHAN | 0 | | |
| | | PROLINE | 0 | | |
| | | SERINE | 0 | POLAR | 0 |
| | | CYSTEINE | 0 | NONIONIZABLE | |
| | | ASPARAGINE | 0 | (POL) | |
| | | GLUTAMINE | 0 | | |

TABLE 85-continued

Mutagenic Cassette: G/C, T, N

| CODON | Represented | AMINO ACID | (Frequency) | CATEGORY | (Frequency) |
|---|---|---|---|---|---|
| | | TYROSINE | 0 | | |
| | | THREONINE | 0 | | |
| | | ASPARTIC ACID | 0 | IONIZABLE: ACIDIC | 0 |
| | | GLUTAMIC ACID | 0 | NEGATIVE CHARGE (NEG) | |
| | | LYSINE | 0 | IONIZABLE: BASIC | 0 |
| | | ARGININE | 0 | POSITIVE CHARGE (POS) | |
| | | HISTIDINE | 0 | | |
| | | STOP CODON | 0 | STOP SIGNAL (STP) | 0 |
| TOTAL | 8 | 2 Amino Acids Are Represented | | NPL: 8: POL: 0: NEG: 0: POS: 0: STP = 0 | |

2.11.2. Chimerization

2.11.2.1 "Shuffling"

Nucleic acid shuffling is a method for in vitro or in vivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

The advantage of the mutagenic shuffling of this invention over error-prone PCR alone for repeated selection can best be explained with an example from antibody engineering. Consider DNA shuffling as compared with error-prone PCR (not sexual PCR). The initial library of selected pooled sequences can consist of related sequences of diverse origin (i.e. antibodies from naive mRNA) or can be derived by any type of mutagenesis (including shuffling) of a single antibody gene. A collection of selected complementarity determining regions ("CDRs") is obtained after the first round of affinity selection. In the diagram the thick CDRs confer onto the antibody molecule increased affinity for the antigen. Shuffling allows the free combinatorial association of all of the CDR1s with all of the CDR2s with all of the CDR3s, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since cross-overs occur at regions of homology, recombination will primarily occur between members of the same sequence family. This discourages combinations of CDRs that are grossly incompatible (e.g., directed against different epitopes of the same antigen). It is contemplated that multiple families of sequences can be shuffled in the same reaction. Further, shuffling generally conserves the relative order, such that, for example, CDRI will not be found in the position of CDR2.

Rare shufflants will contain a large number of the best (eg. highest affinity) CDRs and these rare shufflants may be selected based on their superior affinity.

CDRs from a pool of 100 different selected antibody sequences can be permutated in up to 1006 different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence, generating a much smaller mutant cloud.

The template polynucleotide which may be used in the methods of this invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. No. 4,683,202 and U.S. Pat. No. 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often should be double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucletides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1: 100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure (36) and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art. The approach to be used for the assembly depends on the minimum degree of homology that should still yield crossovers. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. No. 4,683,195 and U.S. Pat. No. 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell. Preferred vectors include the pUC series and the pBR series of plasmids.

The resulting bacterial population will include a number of recombinant polynucleotides having random mutations. This mixed population may be tested to identify the desired recombinant polynucleotides. The method of selection will depend on the polynucleotide desired.

For example, if a polynucleotide which encodes a protein with increased binding efficiency to a ligand is desired, the proteins expressed by each of the portions of the polynucleotides in the population or library may be tested for their ability to bind to the ligand by methods known in the art (i.e.

panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. No. 4,683,202 and U.S. Pat. No. 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of hybrids by the present process. It is only necessary that a small population of hybrid sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into E. coli and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in,the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of hybrids does not increase. Utility can be readily determined by screening expressed polypeptides.

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting alternative sequences into genes may be useful for any therapeutically used protein, for example, interleukin I, antibodies, tPA and growth hormone. The approach may also be useful in any nucleic acid for example, promoters or introns or 31 untranslated region or 51 untranslated regions of genes to increase expression or alter specificity of expression of proteins. The approach may also be used to mutate ribozymes or aptamers.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

In vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of $E.\ coli$ (5, 000 kb) by PCR would require about 250 primers yielding 125 forty kb polynucleotides. This approach is not practical due to the unavailability of sufficient sequence data. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, this invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In vivo Shuffling

In an embodiment of in vivo shuffling, the mixed population of the specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, the specific nucleic acids sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a preferred embodiment, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination.

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of this invention, it is contemplated that during the first round a subset of the specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. If the sequences were originally single-stranded and have become double-stranded they can be denatured with heat, chemicals or enzymes prior to insertion into the host cell. The reaction conditions suitable for separating the strands of nucleic acid are well known in the art.

The steps of this process can be repeated indefinitely, being limited only by the number of possible hybrids which can be achieved. After a certain number of cycles, all possible hybrids will have been achieved and further cycles are redundant.

In an embodiment the same mutated template nucleic acid is repeatedly recombined and the resulting recombinants selected for the desired characteristic.

Therefore, the initial pool or population of mutated template nucleic acid is cloned into a vector capable of replicating in a bacteria such as E. coli. The particular vector is not essential, so long as it is capable of autonomous replication in E. coli. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the E. coli host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences.

The host cells are then clonally replicated and selected for the marker gene present on the vector. Only those cells having a plasmid will grow under the selection.

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

It has been shown that by this method nucleic acid sequences having enhanced desired properties can be selected.

In an alternate embodiment, the first generation of hybrids are retained in the cells and the parental mutated sequences are added again to the cells. Accordingly, the first cycle of Embodiment I is conducted as described above. However, after the daughter nucleic acid sequences are identified, the host cells containing these sequences are retained.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of this invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary or silent mutations.

2,11.2.3. Exonuclease-Mediated Reassembly

In a particular embodiment, this invention provides for a method for shuffling, assembling, reassembling, recombining, &/or concatenating at least two polynucleotides to form a progeny polynucleotide (e.g. a chimeric progeny polynucleotide that can be expressed to produce a polypeptide or a gene pathway). In a particular embodiment, a double stranded polynucleotide end (e.g. two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a nonpolynucleotide sequence) is subjected to a source of exonuclease activity. Serviceable sources of exonuclease activity may be an enzyme with 3' exonuclease activity, an enzyme with 5' exonuclease activity, an enzyme with both 3' exonuclease activity and 5' exonuclease activity, and any combination thereof. An exonuclease can be used to liberate nucleotides from one or both ends of a linear double stranded polynucleotide, and from one to all ends of a branched polynucleotide having more than two ends. The mechanism of action of this liberation is believed to be comprised of an enzymatically-catalyzed hydrolysis of terminal nucleotides, and can be allowed to proceed in a time-dependent fashion, allowing experimental control of the progression of the enzymatic process.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and/or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive reannealment between what were former partners before the denaturation step). The presence of the former hybridization partners in the reaction vessel, however, does not preclude, and may sometimes even favor, reannealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the instant invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). Additionally in contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

By way of further illustration, a specific exonuclease, namely exonuclease III is provided herein as an example of a 3' exonuclease; however, other exonucleases may also be used, including enzymes with 5' exonuclease activity and enzymes with 3' exonuclease activity, and including enzymes not yet discovered and enzymes not yet developed. It is particularly appreciated that enzymes can be discovered, optimized (e.g. engineered by directed evolution), or both discovered and optimized specifically for the instantly disclosed approach that have more optimal rates &/or more highly specific activities &/or greater lack of unwanted activities. In fact it is expected that the instant invention may encourage the discovery &/or development of such designer enzymes. In sum, this invention may be practiced with a variety of currently available exonuclease enzymes, as well enzymes not yet discovered and enzymes not yet developed.

The exonuclease action of exonuclease III requires a working double stranded polynucleotide end that is either blunt or has a 5' overhang, and the exonuclease action is comprised of enzymatically liberating 3' terminal nucleotides, leaving a single stranded 5' end that becomes longer and longer as the exonuclease action proceeds (see FIG. 1). Any 5' overhangs produced by this approach may be used to hybridize to another single stranded polynucleotide sequence (which may also be a single stranded polynucleotide or a terminal overhang of a partially double stranded polynucleotide) that shares enough homology to allow hybridization. The ability of these exonuclease III-generated single stranded sequences (e.g. in 5' overhangs) to hybridize to other single stranded sequences allows two or more polynucleotides to be shuffled, assembled, reassembled, &/or concatenated.

Furthermore, it is appreciated that one can protect the end of a double stranded polynucleotide or render it susceptible to a desired enzymatic action of a serviceable exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide (see FIG. 1). Alternatively, an exonuclease-mediated reaction can be terminated before proceeding to completion.

Thus this exonuclease-mediated approach is serviceable for shuffling, assembling &/or reassembling, recombining, and concatenating polynucleotide building blocks, which polynucleotide building blocks can be up to ten bases long or tens of bases long or hundreds of bases long or thousands of bases long or tens of thousands of bases long or hundreds of thousands of bases long or millions of bases long or even longer.

This exonuclease-mediated approach is based on the action of double stranded DNA specific exodeoxyribonuclease activity of E. coli exonuclease III. Substrates for exonuclease III may be generated by subjecting a double stranded polynucleotide to fragmentation. Fragmentation may be achieved by mechanical means (e.g., shearing, sonication, etc.), by enzymatic means (e.g. using restriction enzymes), and by any combination thereof. Fragments of a larger polynucleotide may also be generated by polymerase-mediated synthesis.

Exonuclease III is a 28K monomeric enzyme, product of the xthA gene of E. coli with four known activities: exodeoxyribonuclease (alternatively referred to as exonuclease herein), RNaseH, DNA-3'-phosphatase, and AP endonuclease. The exodeoxyribonuclease activity is specific for double stranded DNA. The mechanism of action is thought to involve enzymatic hydrolysis of DNA from a 3' end progressively towards a 5' direction, with formation of nucleoside 5'-phosphates and a residual single strand. The enzyme does not display efficient hydrolysis of single stranded DNA, single-stranded RNA, or double-stranded RNA; however it degrades RNA in an DNA-RNA hybrid releasing nucleoside 5'-phosphates. The enzyme also releases inorganic phosphate specifically from 3' phosphomonoester groups on DNA, but not from RNA or short oligonucleotides. Removal of these groups converts the terminus into a primer for DNA polymerase action.

Additional examples of enzymes with exonuclease activity include red-alpha and venom phosphodiesterases. Red alpha (reda) gene product (also referred to as lambda exonuclease) is of bacteriophage λ origin. The reda gene is transcribed from the leftward promoter and its product is involved (24 kD) in recombination. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

2.11.2.3. Non-Stochastic Ligation Reassembly

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

A particularly glaring difference is that the instant SLR method does not depend on the presence of a high level of homology between polynucleotides to be shuffled. In contrast, prior methods, particularly prior stochastic shuffling methods require that presence of a high level of homology, particularly at coupling sites, between polynucleotides to be shuffled. Accordingly these prior methods favor the regeneration of the original progenitor molecules, and are suboptimal for generating large numbers of novel progeny chimeras, particularly full-length progenies. The instant invention, on the other hand, can be used to non-stochastically generate libraries (or sets) of progeny molecules comprised of over $10^{100}$ different chimeras. Conceivably, SLR can even be used to generate libraries comprised of over $10^{1000}$ different progeny chimeras with (no upper limit in sight).

Thus, in one aspect, the present invention provides a method, which method is non-stochastic, of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). FIG. 4, Panel C illustrates an exemplary assembly process comprised of 2 sequential steps to achieve a designed (non-stochastic) overall assembly order for five nucleic acid building blocks. In a preferred embodiment of this invention, the annealed building pieces are treated with an enzyme, such as a ligase (e.g. T4 DNA ligase), achieve covalent bonding of the building pieces.

In a preferred embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, this invention provides for the chimerization of a family of related genes and their encoded family of related products. In a particular exemplification, the encoded products are enzymes. As a representative list of families of enzymes which may be mutagenized in accordance with the aspects of the present invention, there may be mentioned, the following enzymes and their functions:

1 Lipase/Esterase
  a. Enantioselective hydrolysis of esters (lipids)/thioesters
    1) Resolution of racemic mixtures
    2) Synthesis of optically active acids or alcohols from meso-diesters
  b. Selective syntheses
    1) Regiospecific hydrolysis of carbohydrate esters
    2) Selective hydrolysis of cyclic secondary alcohols
  c. Synthesis of optically active esters, lactones, acids, alcohols
    1) Transesterification of activated/nonactivated esters
    2) Interesterification
    3) Optically active lactones from hydroxyesters
    4) Regio- and enantioselective ring opening of anhydrides
  d. Detergents
  e. Fat/Oil conversion
  f. Cheese ripening 2 Protease
  a. Ester/amide synthesis
  b. Peptide synthesis
  c. Resolution of racemic mixtures of amino acid esters
  d. Synthesis of non-natural amino acids
  e. Detergents/protein hydrolysis
3 Glycosidase/Glycosyl transferase
  a. Sugar/polymer synthesis
  b. Cleavage of glycosidic linkages to form mono, di-and oligosaccharides
  c. Synthesis of complex oligosaccharides
  d. Glycoside synthesis using UDP-galactosyl transferase
  e. Transglycosylation of disaccharides, glycosyl fluorides, aryl galactosides
  f. Glycosyl transfer in oligosaccharide synthesis
  g. Diastereoselective cleavage of β-glucosylsulfoxides
  h. Asymmetric glycosylations
  i. Food processing
  j. Paper processing
4 Phosphatase/Kinase
  a. Synthesis/hydrolysis of phosphate esters
    1) Regio-, enantioselective phosphorylation
    2) Introduction of phosphate esters
    3) Synthesize phospholipid precursors
    4) Controlled polynucleotide synthesis
  b. Activate biological molecule
  c. Selective phosphate bond formation without protecting groups
5 Mono/Dioxygenase
  a. Direct oxyfunictionalization of unactivated organic substrates
  b. Hydroxylation of alkane, aromatics, steroids
  c. Epoxidation of alkenes
  d. Enantioselective sulphoxidation
  e. Regio- and stereoselective Bayer-Villiger oxidations
6 Haloperoxidase
  a. Oxidative addition of halide ion to nucleophilic sites
  b. Addition of hypohalous acids to olefinic bonds
  c. Ring cleavage of cyclopropanes
  d. Activated aromatic substrates converted to ortho and para derivatives
  e. 1.3 diketones converted to 2-halo-derivatives
  f. Heteroatom oxidation of sulfur and nitrogen containing substrates
  g. Oxidation of enol acetates, alkynes and activated aromatic rings
7 Lignin peroxidase/Diarylpropane peroxidase
  a. Oxidative cleavage of C—C bonds
  b. Oxidation of benzylic alcohols to aldehydes
  c. Hydroxylation of benzylic carbons
  d. Phenol dimerization
  e. Hydroxylation of double bonds to form diols
  f. Cleavage of lignin aldehydes
8 Epoxide hydrolase
  a. Synthesis of enantiomerically pure bioactive compounds
  b. Regio- and enantioselective hydrolysis of epoxide
  c. Aromatic and olefinic epoxidation by monooxygenases to form epoxides
  d. Resolution of racemic epoxides
  e. Hydrolysis of steroid epoxides
9 Nitrile hydratase/nitrilase
  a. Hydrolysis of aliphatic nitrites to carboxamides
  b. Hydrolysis of aromatic, heterocyclic, unsaturated aliphatic nitrites to corresponding acids
  c. Hydrolysis of acrylonitrile
  d. Production of aromatic and carboxamides, carboxylic acids (nicotinamide, picolinamide, isonicotinamide)
  e. Regioselective hydrolysis of acrylic dinitrile
  f. α-amino acids from α-hydroxynitriles
10 Transaminase
  a. Transfer of amino groups into oxo-acids
11 Amidase/Acylase
  a. Hydrolysis of amides, amidines, and other C-N bonds
  b. Non-natural amino acid resolution and synthesis These exemplifications, while illustrating certain specific aspects of the invention, do not portray the limitations or circumscribe the scope of the disclosed invention.

Thus according to one aspect of this invention, the sequences of a plurality of progenitor nucleic acid templates are aligned in order to select one or more demarcation points, which demarcation points can be located at an area of homology, and are comprised of one or more nucleotides, and which demarcation points are shared by at least two of the progenitor templates. The demarcation points can be used to delineate the boundaries of nucleic acid building blocks to be generated. Thus, the demarcation points identified and selected in the progenitor molecules serve as potential chimerization points in the assembly of the progeny molecules.

Preferably a serviceable demarcation point is an area of homology (comprised of at least one homologous nucleotide base) shared by at least two progenitor templates. More preferably a serviceable demarcation point is an area of homology that is shared by at least half of the progenitor templates. More preferably still a serviceable demarcation point is an area of homology that is shared by at least two thirds of the progenitor templates. Even more preferably a serviceable demarcation points is an area of homology that is shared by at least three fourths of the progenitor templates. Even more preferably still a serviceable demarcation points is an area of homology that is shared by at almost all of the progenitor templates. Even more preferably still a serviceable demarcation point is an area of homology that is shared by all of the progenitor templates.

The process of designing nucleic acid building blocks and of designing the mutually compatible ligatable ends of the nucleic acid building blocks to be assembled is illustrated in FIGS. 6 and 7. As shown, the alignment of a set of progenitor templates reveals several naturally occurring demarcation points, and the identification of demarcation points shared by these templates helps to non-stochastically determine the building blocks to be generated and used for the generation of the progeny chimeric molecules.

In a preferred embodiment, this invention provides that the ligation reassembly process is performed exhaustively in order to generate an exhaustive library. In other words, all possible ordered combinations of the nucleic acid building blocks are represented in the set of finalized chimeric nucleic acid molecules. At the same time, in a particularly preferred embodiment, the assembly order (i.e. the order of assembly of each building block in the 5' to 3' sequence of each finalized chimeric nucleic acid) in each combination is by design (or non-stochastic). Because of the non-stochastic nature of this invention, the possibility of unwanted side products is greatly reduced.

In another preferred embodiment, this invention provides that, the ligation reassembly process is performed systematically, for example in order to generate a systematically compartmentalized library, with compartments that can be screened systematically, e.g. one by one. In other words this invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly preferred embodiment of this invention, such a generated library is comprised of preferably greater than $10^3$ different progeny molecular species, more preferably greater than $10^5$ different progeny molecular species, more preferably still greater than $10^{10}$ different progeny molecular species, more preferably still greater than $10^{15}$ different progeny molecular species, more preferably still greater than $10^{20}$ different progeny molecular species, more preferably still greater than $10^{30}$ different progeny molecular species, more preferably still greater than $10^{40}$ different progeny molecular species, more preferably still greater than $10^{50}$ different progeny molecular species, more preferably still greater than $10^{60}$ different progeny molecular species, more preferably still greater than $10^{70}$ different progeny molecular species, more preferably still greater than $10^{80}$ different progeny molecular species, more preferably still greater than $10^{100}$ different progeny molecular species, more preferably still greater than $10^{110}$ different progeny molecular species, more preferably still greater than $10^{120}$ different progeny molecular species, more preferably still greater than $10^{130}$ different progeny molecular species, more preferably still greater than $10^{140}$ different progeny molecular species, more preferably still greater than $10^{150}$ different progeny molecular species, more preferably still greater than $10^{175}$ different progeny molecular species, more preferably still greater than $10^{200}$ different progeny molecular species, more preferably still greater than $10^{300}$ different progeny molecular species, more preferably still greater than $10^{400}$ different progeny molecular species, more preferably still greater than $10^{500}$ different progeny molecular species, and even more preferably still greater than $10^{1000}$ different progeny molecular species.

In one aspect, a set of finalized chimeric nucleic acid molecules, produced as described is comprised of a polynucleotide encoding a polypeptide. According to one preferred embodiment, this polynucleotide is a gene, which may be a man-made gene. According to another preferred embodiment, this polynucleotide is a gene pathway, which may be a man-made gene pathway. This invention provides that one or more man-made genes generated by this invention may be incorporated into a man-made gene pathway, such as pathway operable in a eukaryotic organism (including a plant).

It is appreciated that the power of this invention is exceptional, as there is much freedom of choice and control regarding the selection of demarcation points, the size and number of the nucleic acid building blocks, and the size and design of the couplings. It is appreciated, furthermore, that the requirement for intermolecular ahomology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This inventiop provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another exemplifaction, the synthetic nature of the step in which the building blocks are generated allows the design and introduction of nucleotides (e.g. one or more nucleotides, which may be, for example, codons or introns or regulatory sequences) that can later be optionally removed in an in vitro process (e.g. by mutageneis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, this invention provides that a nucleic acid building block can be used to introduce an intron. Thus, this invention provides that functional introns may be introduced into a man-made gene of this invention. This invention also provides that ftuctional introns may be introduced into a man-made gene pathway of this invention. Accordingly, this invention provides for the generation of a chimeric polynucleotide that is a man-made gene containing one (or more) artificially introduced intron(s).

Accordingly, this invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. This invention provides a process of producing man-made intron-containing polynucleotides to be introduced into host organisms for recombination and/or splicing.

The ability to achieve chimerizations, using couplings as described herein, in areas of little or no homology among the progenitor molecules, is particularly useful, and in fact critical, for the assembly of novel gene pathways. This invention thus provides for the generation of novel man-made gene pathways using synthetic ligation reassembly. In a particular aspect, this is achieved by the introduction of regulatory sequences, such as promoters, that are operable in an intended host, to confer operability to a novel gene pathway when it is introduced into the intended host. In a particular exemplification, this invention provides for the generation of novel man-made gene pathways that is operable in a plurality of intended hosts (e.g. in a microbial organism as well as in a plant cell). This can be achieve, for example, by the introduction of a plurality of regulatory sequences, comprised of a regulatory sequence that is operable in a first intended host and a regulatory sequence that is operable in a second intended host. A similar process can be performed to achieve operability of a gene pathway in a third intended host species, etc. The number of intended host species can be each integer from 1 to 10 or alternatively over 10. Alternatively, for example, operability of a gene pathway in a plurality of intended hosts can be achieved by the introduction of a regulatory sequence having intrinsic operability in a plurality of intended hosts.

Thus, according to a particular embodiment, this invention provides that a nucleic acid building block can be used to introduce a regulatory sequence, particularly a regulatory sequence for gene expression. Preferred regulatory sequences include, but are not limited to, those that are man-made, and those found in archeal, bacterial, eukaryotic (including mitochondrial), viral, and prionic or prion-like organisms. Preferred regulatory sequences include but are not limited to, promoters, operators, and activator binding sites. Thus, this invention provides that functional regulatory sequences may be introduced into a man-made gene of this invention. This invention also provides that ftmctional regulatory sequences may be introduced into a man-made gene pathway of this invention.

Accordingly, this invention provides for the generation of a chimeric polynucleotide that is a man-made gene containing one (or more) artificially introduced regulatory sequence(s). Accordingly, this invention also provides for the generation of a chimeric polynucleotide that is a man-made gene pathway containing one (or more) artificially introduced regulatory sequence(s). Preferably, an artificially introduced regulatory sequence(s) is operatively linked to one or more genes in the man-made polynucleotide, and are functional in one or more host cells.

Preferred bacterial promoters that are serviceable for this invention include lac, lacZ, T3, T7, gpt, lambda $P_R$, $P_L$ and trp. Serviceable eukaryotic promoters include CMV immediate early, HSV thymidine kinase, early and late SV40, LTRs from retrovirus, and mouse metallothionein-I. Particular plant regulatory sequences include promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamin synthase gene (Tingey et al., 1987), those for seed-specific expression, such as the cruciferin A promoter from *Brassica napus* (Ryan et al., 1989), those for tuber-specific expression, such as the class-I patatin promoter from potato (Rocha-Sasa et al., 1989; Wenzler et al., 1989) or those for fruit-specific expression, such as the polygalacturonase (PG) promoter from tomato (Bird et al., 1988).

Other regulatory sequences that are preferred for this invention include terminator sequences and polyadenylation signals and any such sequence functioning as such in plants, the choice of which is within the level of the skilled artisan. An example of such sequences is the 3' flanking region of the nopaline synthase (nos) gene of *Agrobacterium tumefaciens* (Bevan, 1984). The regulatory sequences may also include enhancer sequences, such as found in the 35S promoter of CaMV, and mRNA stabilizing sequences such as the leader sequence of Alfalfa Mosaic Cirus (AIMV) RNA4 (Brederode et al., 1980) or any other sequences functioning in a like manner.

A man-made genes produced using this invention can also serve as a substrate for recombination with another nucleic acid. Likewise, a man-made gene pathway produced using this invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by this invention, including a man-made gene or a man-made gene pathway. Recombination may be facilitated by or may occur at areas of homology that exist at the one (or more) artificially introduced intron(s) in the man-made gene.

The synthetic ligation reassembly method of this invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large depending on the choice of the experimenter. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100, 000 bp (including every integer value in between).

It is appreciated that current methods of polymerase-based amplification can be used to generate double-stranded nucleic acids of up to thousands of base pairs, if not tens of thousands of base pairs, in length with high fidelity. Chemical synthesis (e.g. phosphoramidite-based) can be used to generate nucleic acids of up to hundreds of nucleotides in length with high fidelity; however, these can be assembled, e.g. using overhangs or sticky ends, to form double-stranded nucleic acids of up to thousands of base pairs, if not tens of thousands of base pairs, in length if so desired.

A combination of methods (e.g. phosphoramidite-based chemical synthesis and PCR) can also be used according to this invention. Thus, nucleic acid building block made by different methods can also be used in combination to generate a progeny molecule of this invention.

The use of chemical synthesis to generate nucleic acid building blocks is particularly preferred in this invention & is advantageous for other reasons as well, including procedural safety and ease. No cloning or harvesting or actual handling of any biological samples is required. The design of the nucleic acid building blocks can be accomplished on paper. Accordingly, this invention teaches an advance in procedural safety in recombinant technologies.

Nonetheless, according to one preferred embodiment, a double-stranded nucleic acid building block according to this invention may also be generated by polymerase-based amplification of a polynucleotide template. In a non-limiting exemplification, as illustrated in FIG. 2, a first polymerase-based amplification reaction using a first set of primers, $F_2$ and $R_1$, is used to generate a blunt-ended product (labeled Reaction 1, Product 1), which is essentially identical to Product A. A second polymerase-based amplification reaction using a second set of primers, $F_1$ and $R_2$, is used to generate a blunt-ended product (labeled Reaction 2, Product 2), which is essentially identical to Product B. These two products are mixed and allowed to melt and anneal, generating potentially useful double-stranded nucleic acid building blocks with two overhangs. In the example of FIG. 2, the product with the 3' overhangs (Product C) is selected by nuclease-based degradation of the other 3 products using a 3' acting exonuclease, such as exonuclease III. It is appreciated that a 5' acting exonuclease (e.g. red alpha) may be also be used, for example to select Product D instead. It is also appreciated that other selection means can also be used, including hybridization-based means, and that these means can incorporate a further means, such as a magnetic bead-based means, to facilitate separation of the desired product.

Many other methods exist by which a double-stranded nucleic acid building block can be generated that is serviceable for this invention; and these are known in the art and can be readily performed by the skilled artisan.

According to particularly preferred embodiment, a double-stranded nucleic acid building block that is serviceable for this invention is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

Contained within an exemplary experimental design for achieving an ordered assembly according to this invention are:

1) The design of specific nucleic acid building blocks.
2) The design of specific ligatable ends on each nucleic acid building block.
3) The design of a particular order of assembly of the nucleic acid building blocks.

An overhang may be a 3' overhang or a 5' overhang. An overhang may also have a terminal phosphate group or alternatively may be devoid of a terminal phosphate group (having, e.g., a hydroxyl group instead). An overhang may be comprised of any number of nucleotides. Preferably an overhang is comprised of 0 nucleotides (as in a blunt end) to 10,000 nucleotides. Thus, a wide range of overhang sizes may be serviceable. Accordingly, the lower limit may be each integer from 1–200 and the upper limit may be each integer from 2–10,000. According to a particular exemplification, an overhang may consist of anywhere from 1 nucleotide to 200 nucleotides (including every integer value in between).

The final chimeric nucleic acid molecule may be generated by sequentially assembling 2 or more building blocks at a time until all the designated building blocks have been assembled. A working sample may optionally be subjected to a process for size selection or purification or other selection or enrichment process between the performance of two assembly steps. Alternatively, the final chimeric nucleic acid molecule may be generated by assembling all the designated building blocks at once in one step.

Utility

The in vivo recombination method of this invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

2.11.2.4. End-selection

This invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) &/or against (negative selection) each selectable polynucleotide. In a preferred aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g. using magnetic beads), of immunoreactivity, and of hybridization.

End-selection may be applied in combination with any method serviceable for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (&/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis &/or amplification method (see, e.g., Arnold, 1993; Caldwell and Joyce, 1992; Stemmer, 1994; following which method it is desirable to select for (including to screen for the presence of) desirable progeny molecules.

In addition, end-selection may be applied to a polynucleotide apart from any mutagenesis method. In a preferred embodiment, end-selection, as provided herein, can be used in order to facilitate a cloning step, such as a step of ligation to another polynucleotide (including ligation to a vector). This invention thus provides for end-selection as a serviceable means to facilitate library construction, selection &/or enrichment for desirable polynucleotides, and cloning in general.

In a particularly preferred embodiment, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection &/or screening, can be performed in an iterative fashion, with any combination of like or unlike selection &/or screening methods and serviceable mutagenesis methods, all of which can be performed in an iterative fashion and in any order, combination, and permutation.

It is also appreciated that, according to one embodiment of this invention, end-selection may also be used to select a polynucleotide is at least in part: circular (e.g. a plasmid or any other circular vector or any other polynucleotide that is partly circular), &/or branched, &/or modified or substituted with any chemical group or moiety. In accord with this embodiment, a polynucleotide may be a circular molecule comprised of an intermediate or central region, which region is flanked on a 5' side by a 5' flanking region (which, for the purpose of end-selection, serves in like manner to a 5' terminal region of a non-circular polynucleotide) and on a 3' side by a 3' terminal region (which, for the purpose of end-selection, serves in like manner to a 3' terminal region of a non-circular polynucleotide). As used in this non-limiting exemplification, there may be sequence overlap between any two regions or even among all three regions.

In one non-limiting aspect of this invention, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, serviceable polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

Relevant polynucleotide-acting enzymes thus also include any commercially available or non-commercially available polynucleotide endonucleases and their companion methylases including those catalogued at the website http://www.neb.com/rebase, and those mentioned in the following cited reference (Roberts and Macelis, 1996). Preferred polynucleotide endonucleases include—but are not limited to—type II restriction enzymes (including type IIS), and include enzymes that cleave both strands of a double stranded polynucleotide (e.g. Not I, which cleaves both strands at 5' . . . GC/GGCCGC . . . 3') and enzymes that cleave only one strand of a double stranded polynucleotide, i.e. enzymes that have polynucleotide-nicking activity, (e.g. N. BstNB I, which cleaves only one strand at 5' . . . GAGTCNNNN/N . . . 3'). Relevant polynucleotide-acting enzymes also include type III restriction enzymes.

It is appreciated that relevant polynucleotide-acting enzymes also include any enzymes that may be developed in the future, though currently unavailable, that are serviceable for generating a ligation compatible end, preferably a sticky end, in a polynucleotide.

In one preferred exemplification, a serviceable selection marker is a restriction site in a polynucleotide that allows a corresponding type II (or type IIS) restriction enzyme to cleave an end of the polynucleotide so as to provide a ligatable end (including a blunt end or alternatively a sticky end with at least a one base overhang) that is serviceable for a desirable ligation reaction without cleaving the polynucleotide internally in a manner that destroys a desired internal sequence in the polynucleotide. Thus it is provided that, among relevant restriction sites, those sites that do not occur internally (i.e. that do not occur apart from the termini) in a specific working polynucleotide are preferred when the use of a corresponding restriction enzyme(s) is not intended to cut the working polynucleotide internally. This allows one to perform restriction digestion reactions to completion or to near completion without incurring unwanted internal cleavage in a working polynucleotide.

According to a preferred aspect, it is thus preferable to use restriction sites that are not contained, or alternatively that are not expected to be contained, or alternatively that unlikely to be contained (e.g. when sequence information regarding a working polynucleotide is incomplete) internally in a polynucleotide to be subjected to end-selection. In accordance with this aspect, it is appreciated that restriction sites that occur relatively infrequently are usually preferred over those that occur more frequently. On the other hand it is also appreciated that there are occasions where internal cleavage of a polypeptide is desired, e.g. to achieve recombination or other mutagenic procedures along with end-selection.

In accord with this invention, it is also appreciated that methods (e.g. mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs. For example, it is appreciated that, while lambda DNA has 5 EcoR I sites, cleavage of the site nearest to the right terminus has been reported to occur 10 times faster than the sites in the middle of the molecule. Also, for example, it has been reported that, while Sac II has four sites on lambda DNA, the three clustered centrally in lambda are cleaved 50 times faster than the remaining site near the terminus (at nucleotide 40,386). Summarily, site preferences have been reported for various enzymes by many investigators (e.g., Thomas and Davis, 1975; Forsblum et al, 1976; Nath and Azzolina, 1981; Brown and Smith, 1977; Gingeras and Brooks, 1983; Kruger et al, 1988; Conrad and Topal, 1989; Oiler et al, 1991; Topal, 1991; and Pein, 1991; to name but a few). It is appreciated that any empirical observations as well as any mechanistic understandings of site preferences by any serviceable polynucleotide-acting enzymes, whether currently available or to be procured in the future, may be serviceable in end-selection according to this invention.

It is also appreciated that protection methods can be used to selectively protect specified restriction sites (e.g. internal sites) against unwanted digestion by enzymes that would otherwise cut a working polypeptide in response to the presence of those sites; and that such protection methods include modifications such as methylations and base substitutions (e.g. U instead of T) that inhibit an unwanted enzyme activity. It is appreciated that there are limited numbers of available restriction enzymes that are rare enough (e.g. having very long recognition sequences) to create large (e.g. megabase-long) restriction fragments, and that protection approaches (e.g. by methylation) are serviceable for increasing the rarity of enzyme cleavage sites. The use of M.Fnu II (mCGCG) to increase the apparent rarity of Not I approximately twofold is but one example among many (Qiang et al, 1990; Nelson et al, 1984; Maxam and Gilbert, 1980; Raleigh and Wilson, 1986).

According to a preferred aspect of this invention, it is provided that, in general, the use of rare restriction sites is preferred. It is appreciated that, in general, the frequency of occurrence of a restriction site is determined by the number of nucleotides contained therein, as well as by the ambiguity of the base requirements contained therein. Thus, in a non-limiting exemplification, it is appreciated that, in general, a restriction site composed of, for example, 8 specific nucleotides (e.g. the Not I site or GC/GGCCGC, with an estimated relative occurrence of 1 in $4^8$, i.e. 1 in 65,536, random 8-mers) is relatively more infrequent than one composed of, for example, 6 nucleotides (e.g. the Sma I site or CCC/GGG, having an estimated relative occurrence of 1 in $4^6$, i.e. I in 4,096, random 6-mers), which in turn is relatively more infrequent than one composed of, for example, 4 nucleotides (e.g. the Msp I site or C/CGG, having an estimated relative occurrence of 1 in $4^4$, i.e. in 256, random 4-mers). Moreover, in another non-limiting exemplification, it is appreciated that, in general, a restriction site having no ambiguous (but only specific) base requirements (e.g. the Fin I site or GTCCC, having an estimated relative occurrence of 1 in $4^5$, i.e. 1 in 1024, random 5-mers) is relatively more infrequent than one having an ambiguous W (where W=A or T) base requirement (e.g. the Ava II site or G/GWCC, having an estimated relative occurrence of 1 in 4×4×2×4×4—i.e. I in 512—random 5-mers), which in turn is relatively more infrequent than one having an ambiguous N (where N=A or C or G or T) base requirement (e.g. the Asu I site or G/GNCC, having an estimated relative occurrence of 1 in 4×4×4×4, i.e. 1 in 256 —random 5-mers). These relative occurrences are considered general estimates for actual polynucleotides, because it is appreciated that specific nucleotide bases (not to mention specific nucleotide sequences) occur with dissimilar frequencies in specific polynucleotides, in specific species of organisms, and in specific groupings of organisms. For example, it is appreciated that the % G+C contents of different species of organisms are often very different and wide ranging.

The use of relatively more infrequent restriction sites as a selection marker include—in a non-limiting fashion—preferably those sites composed at least a 4 nucleotide sequence, more preferably those composed at least a 5 nucleotide sequence, more preferably still those composed at least a 6 nucleotide sequence (e.g. the BamH I site or G/GATCC, the Bgl II site or A/GATCT, the Pst I site or CTGCA/G, and the Xba I site or T/CTAGA), more preferably still those composed at least a 7 nucleotide sequence, more preferably still those composed of an 8 nucleotide sequence nucleotide sequence (e.g. the Asc I site or GG/CGCGCC, the Not I site or GC/GGCCGC, the Pac I site or TTAAT/TAA, the Pme I site or GTTT/AAAC, the Srf I site or GCCC/GGGC, the Sse838 I site or CCTGCA/GG, and the Swa I site or ATTT/AAAT), more preferably still those composed of a 9 nucleotide sequence, and even more preferably still those composed of at least a 10 nucleotide sequence (e.g. the BspG I site or CG/CGCTGGAC). It is further appreciated that some restriction sites (e.g. for class IIS enzymes) are comprised of a portion of relatively high specificity (i.e. a portion containing a principal determinant of the frequency of occurrence of the restriction site) and a portion of relatively low specificity; and that a site of cleavage may or may not be contained within a portion of relatively low specificity. For example, in the Eco57 I site or CTGAAG(16/14), there is a portion of relatively high specificity (i.e. the CTGAAG portion) and a portion of relatively low specificity (i.e. the N 16 sequence) that contains a site of cleavage.

In another preferred embodiment of this invention, a serviceable end-selection marker is a terminal sequence that is recognized by a polynucleotide-acting enzyme that recognizes a specific polynucleotide sequence. In a preferred aspect of this invention, serviceable polynucleotide-acting enzymes also include other enzymes in addition to classic type II restriction enzymes. According to this preferred aspect of this invention, serviceable polynucleotide-acting enzymes also include gyrases, helicases, recombinases, relaxases, and any enzymes related thereto.

Among preferred examples are topoisomerases (which have been categorized by some as a subset of the gyrases) and any other enzymes that have polynucleotide-cleaving activity (including preferably polynucleotide-nicking activity) &/or polynucleotide-ligating activity. Among preferred topoisomerase enzymes are topoisomerase I enzymes, which is available from many commercial sources (Epicentre Technologies, Madison, Wis.; Invitrogen, Carlsbad, Calif.; Life Technologies, Gathesburg, Md.) and conceivably even more private sources. It is appreciated that similar enzymes may be developed in the future that are serviceable for end-selection as provided herein. A particularly preferred topoisomerase I enzyme is a topoisomerase I enzyme of vaccinia virus origin, that has a specific recognition sequence (e.g. 5' . . . AAGGG . . . 3') and has both polynucleotide-nicking activity and polynucleotide-ligating activity. Due to the specific nicking-activity of this enzyme (cleavage of one strand), internal recognition sites are not prone to polynucleotide destruction resulting from the nicking activity (but rather remain annealed) at a temperature that causes denaturation of a terminal site that has been nicked. Thus for use in end-selection, it is preferable that a nicking site for topoisomerase-based end-selection be no more than 100 nucleotides from a terminus, more preferably no more than 50 nucleotides from a terminus, more preferably still no more than 25 nucloetides from a terminus, even more preferably still no more than 20 nucleotides from a terminus, even more preferably still no more than 15 nucleotides from a terminus, even more preferably still no more than 10 nucleotides from a terminus, even more preferably still no more than 8 nucleotides from a terminus, even more preferably still no more than 6 nucleotides from a terminus, and even more preferably still no more than 4 nucleotides from a terminus.

In a particularly preferred exemplification that is non-limiting yet clearly illustrative, it is appreciated that when a nicking site for topoisomerase-based end-selection is 4 nucleotides from a terminus, nicking produces a single stranded oligo of 4 bases (in a terminal region) that can be denatured from its complementary strand in an end-selectable polynucleotide; this provides a sticky end (comprised of 4 bases) in a polynucleotide that is serviceable for an ensuing ligation reaction. To accomplish ligation to a cloning vector (preferably an expression vector), compatible sticky ends can be generated in a cloning vector by any means including by restriction enzyme-based means. The terminal nucleotides (comprised of 4 terminal bases in this specific example) in an end-selectable polynucleotide terminus are thus wisely chosen to provide compatibility with a sticky end generated in a cloning vector to which the polynucleotide is to be ligated.

On the other hand, internal nicking of an end-selectable polynucleotide, e.g. 500 bases from a terminus, produces a single stranded oligo of 500 bases that is not easily denatured from its complementary strand, but rather is serviceable for repair (e.g. by the same topoisomerase enzyme that produced the nick).

This invention thus provides a method—e.g. that is vaccinia topoisomerase-based &/or type II (or IIS) restriction endonuclease-based &/or type III restriction endonuclease-based &/or nicking enzyme-based (e.g. using N. BstNB I)—for producing a sticky end in a working polynucleotide, which end is ligation compatible, and which end can be comprised of at least a 1 base overhang. Preferably such a sticky end is comprised of at least a 2-base overhang, more preferably such a sticky end is comprised of at least a 3-base overhang, more preferably still such a sticky end is comprised of at least a 4-base overhang, even more preferably still such a sticky end is comprised of at least a 5-base overhang, even more preferably still such a sticky end is comprised of at least a 6-base overhang. Such a sticky end may also be comprised of at least a 7-base overhang, or at least an 8-base overhang, or at least a 9-base overhang, or at least a 10-base overhang, or at least 1 5-base overhang, or at least a 20-base overhang, or at least a 25-base overhang, or at least a 30-base overhang. These overhangs can be comprised of any bases, including A, C, G, or T.

It is appreciated that sticky end overhangs introduced using topoisomerase or a nicking enzyme (e.g. using N. BstNB I) can be designed to be unique in a ligation environment, so as to prevent unwanted fragment reassemblies, such as self-dimerizations and other unwanted concatamerizations.

According to one aspect of this invention, a plurality of sequences (which may but do not necessarily overlap) can be introduced into a terminal region of an end-selectable polynucleotide by the use of an oligo in a polymerase-based reaction. In a relevant, but by no means limiting example, such an oligo can be used to provide a preferred 5' terminal region that is serviceable for topoisomerase 1-based end-selection, which oligo is comprised of: a 1–10 base sequence that is convertible into a sticky end (preferably by a vaccinia topoisomerase I), a ribosome binding site (i.e. and "RBS", that is preferably serviceable for expression cloning), and optional linker sequence followed by an ATG start site and a template-specific sequence of 0–100 bases (to facilitate annealment to the template in the a polymerase-based reaction). Thus, according to this example, a serviceable oligo (which may be termed a forward primer) can have the sequence: 5'[terminal sequence=$(N)_{1-10}$][topoisomerase I site & RBS=AAGGGAGGAG][linker=$(N)_{1-100}$][start codon and template-specific sequence=ATG$(N)_{0-100}$]3'.

Analogously, in a relevant, but by no means limiting example, an oligo can be used to provide a preferred 3' terminal region that is serviceable for topoisomerase I-based end-selection, which oligo is comprised of: a 1–10 base sequence that is convertible into a sticky end (preferably by a vaccinia topoisomerase I), and optional linker sequence followed by a template-specific sequence of 0–100 bases (to facilitate annealment to the template in the a polymerase-based reaction). Thus, according to this example, a serviceable oligo (which may be termed a reverse primer) can have the sequence: 5'[terminal sequence=$(N)_{1-10}$][topoisomerase I site=AAGGG][linker=$(N)_{1-100}$][template-specific sequence=$(N)_{0-100}$]3'.

It is appreciated that, end-selection can be used to distinguish and separate parental template molecules (e.g. to be subjected to mutagenesis) from progeny molecules (e.g. generated by mutagenesis). For example, a first set of primers, lacking in a topoisomerase I recognition site, can be used to modify the terminal regions of the parental molecules (e.g. in polymerase-based amplification). A different second set of primers (e.g. having a topoisomerase I recognition site) can then be used to generate mutated progeny molecules (e.g. using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule as disclosed herein) from the amplified template molecules. The use of topoisomerase I-based end-selection can then facilitate, not only discernment, but selective topoisomerase I-based ligation of the desired progeny molecules.

Annealment of a second set of primers to thusly amplified parental molecules can be facilitated by including sequences in a first set of primers (i.e. primers used for amplifying a set parental molecules) that are similar to a toposiomerase I recognition site, yet different enough to prevent functional toposiomerase I enzyme recognition. For example, sequences that diverge from the AAGGG site by anywhere from I base to all 5 bases can be incorporated into a first set of primers (to be used for amplifying the parental templates prior to subjection to mutagenesis). In a specific, but non-limiting aspect, it is thus provided that a parental molecule can be amplified using the following exemplary—but by no means limiting—set of forward and reverse primers:

Forward Primer: 5' CTAGAAGAGAGGAGAAAACCATG(N)$_{10\text{-}100}$3', and

Reverse Primer: 5' GATCAAAGGCGCGCCTGCAGG(N)$_{10\text{-}100}$3'

According to this specific example of a first set of primers, (N)$_{10\text{-}100}$ represents preferably a 10 to 100 nucleotide-long template-specific sequence, more preferably a 10 to 50 nucleotide-long template-specific sequence, more preferably still a 10 to 30 nucleotide-long template-specific sequence, and even more preferably still a 15 to 25 nucleotide-long template-specific sequence.

According to a specific, but non-limiting aspect, it is thus provided that, after this amplification (using a disclosed first set of primers lacking in a true topoisomerase I recognition site), amplified parental molecules can then be subjected to mutagenesis using one or more sets of forward and reverse primers that do have a true topoisomerase I recognition site. In a specific, but non-limiting aspect, it is thus provided that a parental molecule can be used as templates for the generation of a mutagenized progeny molecule using the following exemplary—but by no means limiting—second set of forward and reverse primers:

Forward Primer: 5' CTAGAAGGGAGGAGAAAAC-CATG 3'

Reverse Primer: 5' GATCAAAGGCGCGCCTGCAGG 3' (contains Asc I recognition sequence)

It is appreciated that any number of different primers sets not specifically mentioned can be used as first, second, or subsequent sets of primers for end-selection consistent with this invention. Notice that type II restriction enzyme sites can be incorporated (e.g. an Asc I site in the above example). It is provided that, in addition to the other sequences mentioned, the experimentalist can incorporate one or more N,N,G/T triplets into a serviceable primer in order to subject a working polynucleotide to saturation mutagenesis. Summarily, use of a second and/or subsequent set of primers can achieve dual goals of introducing a topoisomerase I site and of generating mutations in a progeny polynucleotide.

Thus, according to one use provided, a serviceable end-selection marker is an enzyme recognition site that allows an enzyme to cleave (including nick) a polynucleotide at a specified site, to produce a ligation-compatible end upon denaturation of a generated single stranded oligo. Ligation of the produced polynucleotide end can then be accomplished by the same enzyme (e.g. in the case of vaccinia virus topoisomerase I), or alternatively with the use of a different enzyme. According to one aspect of this invention, any serviceable end-selection markers, whether like (e.g. two vaccinia virus topoisomerase I recognition sites) or unlike (e.g. a class II restriction enzyme recognition site and a vaccinia virus topoisomerase I recognition site) can be used in combination to select a polynucleotide. Each selectable polynucleotide can thus have one or more end-selection markers, and they can be like or unlike end-selection markers. In a particular aspect, a plurality of end-selection markers can be located on one end of a polynucleotide and can have overlapping sequences with each other.

It is important to emphasize that any number of enzymes, whether currently in existence or to be developed, can be serviceable in end-selection according to this invention. For example, in a particular aspect of this invention, a nicking enzyme (e.g. N. BstNB I, which cleaves only one strand at 5' . . . GAGTCNNNN/N . . . 3') can be used in conjunction with a source of polynucleotide-ligating activity in order to achieve end-selection. According to this embodiment, a recognition site for N. BstNB I—instead of a recognition site for topoisomerase I—should be incorporated into an end-selectable polynucleotide (whether end-selection is used for selection of a mutagenized progeny molecule or whether end-selection is used apart from any mutagenesis procedure).

It is appreciated that the instantly disclosed end-selection approach using topoisomerase-based nicking and ligation has several advantages over previously available selection methods. In sum, this approach allows one to achieve direction cloning (including expression cloning). Specifically, this approach can be used for the achievement of: direct ligation (i.e. without subjection to a classic restriction-purification-ligation reaction, that is susceptible to a multitude of potential problems from an initial restriction reaction to a ligation reaction dependent on the use of T4 DNA ligase); separation of progeny molecules from original template molecules (e.g. original template molecules lack topoisomerase I sites that not introduced until after mutagenesis), obviation of the need for size separation steps (e.g. by gel chromatography or by other electrophoretic means or by the use of size-exclusion membranes), preservation of internal sequences (even when topoisomerase I sites are present), obviation of concerns about unsuccessful ligation reactions (e.g. dependent on the use of T4 DNA ligase, particularly in the presence of unwanted residual restriction enzyme activity), and facilitated expression cloning (including obviation of frame shift concerns). Concerns about unwanted restriction enzyme-based cleavages—especially at internal restriction sites (or even at often unpredictable sites of unwanted star activity) in a working polynucleotide—that are potential sites of destruction of a working polynucleotide can also be obviated by the instantly disclosed end-selection approach using topoisomerase-based nicking and ligation.

2.11.3. Additional Screening Methods

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. one method of identifying peptides that possess a desired structure or ftmctional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold, 1990; Ellington and Szostak, 1990). A similar technique was used to identify DNA sequences which bind a predetermined human transcription factor (Thiesen and Bach, 1990; Beaudry and Joyce, 1992; PCT patent publications WO 92/05258 and WO 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publications WO 88/08453, WO 90/05785, WO 90/07003, WO 91/02076, WO 91/05058, and WO 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kemal, fixed, or the like. The present display methods include methods for in vitro and in vivo display of single-chain antibodies, such as nascent scFv on polysomes or scfv displayed on phage, which enable large-scale screening of scfv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A method of affinity enrichment allows a very large library of peptides and single-chain antibodies to be screened and the polynucleotide sequence encoding the desired peptide(s) or single-chain antibodies to be selected. The polynucleotide can then be isolated and shuffled to recombine combinatorially the amino acid sequence of the selected peptide(s) (or predetermined portions thereof) or single-chain antibodies (or just VHI, VLI or CDR portions thereof). Using these methods, one can identify a peptide or single-chain antibody as having a desired binding affinity for a molecule and can exploit the process of shuffling to converge rapidly to a desired high-affinity peptide or scfv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round (s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kemal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variabl e r egions which can be present in immunoglobulin chains. The naturally-occurring germ line immunoglobulin heavy chain locus is composed of separate tandem arrays of variable segment g e nes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated B cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al, 1989); Caton and Koprowski, 1990; Mullinax et al, 1990; Persson et al, 1991). Various embodiments of bacteriophage antibody display libraries and lambda phage expression libraries have been described (Kang et al, 1991; Clackson et al, 1991; McCafferty et al, 1990; Burton et al, 1991; Hoogenboom et al, 1991; Chang et al, 1991; Breitling et al, 1991; Marks et al, 1991, p. 581; Barbas et al, 1992; Hawkins and Winter, 1992; Marks et al, 1992, p. 779; Marks et al, 1992, p. 16007; and Lowman et al, 1991; Lerner et al, 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al, 1992, p. 779; Winter and Milstein, 1991; Clackson et al, 1991; Marks et al, 1991, p. 581; Chaudhary et al, 1990; Chiswell et al, 1992; McCafferty et al, 1990; and Huston et al, 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)3 or equivalent linker peptide(s). The linker bridges the C-terminus of the first V region and N-terminus of the second, ordered as either VH-linker-VL or VL-linker-VH' In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum) The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al, 1993), as has error-prone PCR and chemical mutagenesis (Deng et al, 1994). Riechmann (Riechmann et al, 1993) showed semi-rational design of an antibody scfv fragment using site-directed randomization by degenerate oligonucleotide PCR and subsequent phage display of the resultant scfv hybrids. Barbas (Barbas et al, 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDRI-3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al, 1992) only generated $5 \times 10^7$ transformants, which represents only a tiny fraction of the potential diversity of a library of thoroughly randomized CDRS.

Despite these substantial limitations, bacteriophage. display of scfv have already yielded a variety of useful antibodies and antibody fusion proteins. A bispecific single chain antibody has been shown to mediate efficient tumor cell lysis (Gruber et al, 1994). Intracellular expression of an anti-Rev scfv has been shown to inhibit HIV-1 virus replication in vitro (Duan et al, 1994), and intracellular expression of an anti-p2lrar, scfv has been shown to inhibit meiotic maturation of *Xenopus oocytes* (Biocca et al, 1993). Recombinant scfv which can be used to diagnose HIV infection have also been reported, demonstrating the diagnostic utility of scfv (Lilley et al, 1994). Fusion proteins wherein an scFv is linked to a second polypeptide, such as a toxin or fibrinolytic activator protein, have also been reported (Holvost et al, 1992; Nicholls et al, 1993).

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al, 1991); the pool (s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1 \times 10\ 6$ unique CDR sequences are included in the collection, although occasionally $1 \times 107$ to $1 \times 108$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1 \times 10$ m-, preferably with an affinity of about at least $5 \times 10^7$ M-1, more preferably with an affinity of at least $1 \times 10^8$ M-1 to $1 \times 10^9$ M-1 or more, sometimes up to $1 \times 10^{10}$ M-1 or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, Lselectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al, 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al, 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant' "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see Winnacker, 1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, and myeloma cell lines, but preferably transformed Bcells or hybridomas. Expression vectors for these cells can include expression control sequences, such as an origin of replication, a promoter, an enhancer (Queen et al, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 51 or 31 to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and micro-injection (see, generally, Sambrook et al, 1982 and 1989).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Two-Hybrid Based Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al, 1991). This approach identifies protein-protein interactions in vivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al, 1993; Yang et al, 1992; Luban et al, 1993; Hardy et al, 1992; Bartel et al, 1993; and Vojtek et al, 1993). However, variations of the two-hybrid method have been used to identify mutations of a known protein that affect its binding to a second known protein (Li and Fields, 1993; Lalo et al, 1993; Jackson et al, 1993; and Madura et al, 1993). Two-hybrid systems have also been used to identify interacting structural domains of two known proteins (Bardwell et al, 1993; Chakrabarty et al, 1992; Staudinger et al, 1993; and Milne and Weaver 1993) or domains responsible for oligomerization of a single protein (Iwabuchi et al, 1993; Bogerd et al, 1993). Variations of two-hybrid systems have been used to study the in vivo activity of a proteolytic enzyme (Dasmahapatra et al, 1992). Alternatively, an E. coli/BCCP interactive screening system (Germino et al, 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

In general, standard techniques of recombination DNA technology are described in various publications (e.g. Sambrook et al, 1989; Ausubel et al, 1987; and Berger and Kimmel, 1987; each of which is incorporated herein in its entirety by reference. Polynucleotide modifying enzymes were used according to the manufacturer's recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymease (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The present invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is a particularly preferred object of the invention to provide a process for producing hybrid polynucleotides which express a useful hybrid polypeptide by a series of steps comprising:

(a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;

(b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;

(c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a preferred aspect of the invention, the means for blocking or interrupting the amplification or synthesis process is by utilization of uv light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Generation of Random Size Polynucleotides Using U.V. Induced Photoproducts

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

EXAMPLE 2

Isolation of Random Size Polynucleotides

Polynucleotides of interest which are generated according to Example 1 are gel isolated on a 1.5% agarose gel. Polynucleotides in the 100–300 bp range are cut out of the gel and 3 volumes of 6 M NaI is added to the gel slice. The mixture is incubated at 50° C. for 10 minutes and 10 µl of glass milk (Bio 101) is added. The mixture is spun for 1 minute and the supernatant is decanted. The pellet is washed with 500 µl of Column Wash (Column Wash is 50% ethanol, 10mM Tris-HCl pH 7.5, 100 mM NaCl and 2.5 mM EDTA) and spin for 1 minute, after which the supernatant is decanted. The washing, spinning and decanting steps are then repeated. The glass milk pellet is resuspended in 20 µl of H$_2$O and spun for 1 minute. DNA remains in the aqueous phase.

EXAMPLE 3

Shuffling of Isolated Random Size 100–300bp Polynucleotides

The 100–300 bp polynucleotides obtained in Example 2 are recombined in an annealing mixture (0.2 mM each dNTP, 2.2 mM MgCl$_2$, 50 mM KCl, 10 mM Tris-HCl ph 8.8, 0.1% Triton X-100, 0.3 µ; Taq DNA polymerase, 50 µl total volume) without adding primers. A Robocycler by Stratagene was used for the annealing step with the following program: 95° C. for 30 seconds, 25–50 cycles of [95 ° C. for 30 seconds, 50–60 ° C. (preferably 58° C.) for 30 seconds, and 72° C. for 30 seconds] and 5 minutes at 72° C. Thus, the 100–300 bp polynucleotides combine to yield double-stranded polynucleotides having a longer sequence. After separating out the reassembled double-stranded polynucleotides and denaturing them to form single stranded polynucleotides, the cycling is optionally again repeated with some samples utilizing the single strands as template and primer DNA and other samples utilizing random primers in addition to the single strands.

EXAMPLE 4

Screening of Polypeptides From Shuffled Polynucleotides

The polynucleotides of Example 3 are separated and polypeptides are expressed therefrom. The original template DNA is utilized as a comparative control by obtaining comparative polypeptides therefrom. The polypeptides obtained from the shuffled polynucleotides of Example 3 are screened for the activity of the polypeptides obtained from the original template and compared with the activity levels of the control. The shuffled polynucleotides coding for interesting polypeptides discovered during screening are compared further for secondary desirable traits. Some shuffled polynucleotides corresponding to less interesting screened polypeptides are subjected to reshuffling.

EXAMPLE 5

Directed Evolution an Enzyme by Saturation Mutagenesis

Site-Saturation Mutagenesis: To accomplish site-saturation mutagenesis every residue (316) of a dehalogenase enzyme was converted into all 20 amino acids by site directed mutagenesis using 32-fold degenerate oligonucleotide primers, as follows:
1. A culture of the dehalogenase expression construct was grown and a preparation of the plasmid was made
2. Primers were made to randomize each codon—they have the common structure $X_{20}NN(G/T)X_{20}$
3. A reaction mix of 25 ul was prepared containing. ~50 ng of plasmid template, 125 ng of each primer, 1X native Pfu buffer, 200 uM each dNTP and 2.5 U native Pfu DNA polymerase
4. The reaction was cycled in a Robo96 Gradient Cycler as follows: Initial denaturation at 95° C. for 1 min 20 cycles of 95° C. for 45 sec, 53° C. for 1 min and 72° C for 11 min Final elongation step of 72° C. for 10 min
5. The reaction mix was digested with 10 U of DpnI at 37° C. for 1 hour to digest the methylated template DNA
6. Two ul of the reaction mix were used to transform 50 ul of XL1-Blue MRF' cells and the entire transformation mix was plated on a large LB-Amp-Met plate yielding 200–1000 colonies
7. Individual colonies were toothpicked into the wells of 96-well microtiter plates containing LB-Amp-IPTG and grown overnight
8. The clones on these plates were assayed the following day Screening: Approximately 200 clones of mutants for each position were grown in liquid media (384 well microtiter plates) and screened as follows:

1. Overnight cultures in 384-well plates were centrifuged and the media removed. To each well was added 0.06 mL 1 mM Tris/SO$_4^{2-}$ pH 7.8.
2. Made 2 assay plates from each parent growth plate consisting of 0.02 mL cell suspension.
3. One assay plate was placed at room temperature and the other at elevated temperature (initial screen used 55° C.) for a period of time (initially 30 minutes).
4. After the prescribed time 0.08 mL room temperature substrate (TCP saturated 1 mM Tris/SO$_4^{2-}$ pH 7.8 with 1.5 mM NaN$_3$ and 0.1 mM bromothymol blue) was added to each well.
5. Measurements at 620 nm were taken at various time points to generate a progress curve for each well.
6. Data were analyzed and the kinetics of the cells heated to those not heated were compared. Each plate contained 1–2 columns (24 wells) of unmutated 20F12 controls.
7. Wells that appeared to have improved stability were re-grown and tested under the same conditions.

Following this procedure nine single site mutations appeared to confer increased thermal stability on the enzyme. Sequence analysis was performed to determine of the exact amino acid changes at each position that were specifically responsible for the improvement. In sum, the improvement was conferred at 7 sites by one amino acid change alone, at an eighth site by each of two amino acid changes, and at a ninth site by each of three amino acid changes. Several mutants were then made each having a plurality of these nine beneficial site mutations in combination; of these two mutants proved superior to all the other mutants, including those with single point mutations.

EXAMPLE 6

Direct Expression Cloning Using End-selection

An esterase gene was amplified using 5' phosphorylated primers in a standard PCR reaction (10 ng template; PCR conditions: 3' 94 C; [1' 94 C; 1' 50 C; 1' 30" 68 C]×30; 10' 68 C.

Forward Primer=9511 TopF (CTAGAAGGGAGGAGAATTACATGAAGCGGCTTTTAGCCC)

Reverse Primer=9511 TopR (AGCTAAGGGTCAAGGCCGCACCCGAGG)

The resulting PCR product (ca. 1000 bp) was gel purified and quantified.

A vector for expression cloning, pASK3 (Institut fuer Bioanalytik, Goettingen, Germany), was cut with Xba I and Bgl II and dephosphorylated with CIP.

0.5 pmoles Vaccina Topoisomerase I (Invitrogen, Carlsbad, Calif.) was added to 60 ng (ca. 0.1 pmole) purified PCR product for 5' 37 C in buffer NEB I (New England Biolabs, Beverly, MA) in 5 µl total volume. The topogated PCR product was cloned into the vector pASK3 (5 µl, ca. 200 ng in NEB I) for 5' at room temperature. This mixture was dialyzed against H$_2$O for 30'. 2 µl were used for electroporation of DH10B cells (Gibco BRL, Gaithersburg, Md.).

Efficiency: Based on the actual clone numbers this method can produce 2×10$^6$ clones per µg vector. All tested recombinants showed esterase activity after induction with anhydrotetracycline.

EXAMPLE 7

Dehalogenase Thermal Stability

This invention provides that a desirable property to be generated by directed evolution is exemplified in a limiting fashion by an improved residual activity (e.g. an enzymatic activity, an immunoreactivity, an antibiotic acivity, etc.) of a molecule upon subjection to altered environment, including what may be considered a harsh enviroment, for a specified time. Such a harsh environment may comprise any combination of the following (iteratively or not, and in any order or permutation): an elevated temperature (including a temperature that may cause denaturation of a working enzyme), a decreased temperature, an elevated salinity, a decreased salinity, an elevated pH, a decreased pH, an elevated pressure, a decreassed pressure, and an change in exposure to a radiation source (including uv radiation, visible light, as well as the entire electromagnetic spectrum).

The following example shows an application of directed evolution to evolve the ability of an enzyme to regain &/or retain activity upon exposure to an elevated temperature. Every residue (316) of a dehalogenase enzyme was converted into all 20 amino acids by site directed mutagenesis using 32-fold degenerate oligonucleotide primers. These mutations were introduced into the already rate-improved variant Dhla 20F 12. Approximately 200 clones of each position were grown in liquid media (384 well microtiter plates) to be screened. The screening procedure was as follows:

1. Overnight cultures in 384-well plates were centrifuged and the media removed. To each well was added 0.06 mL 1 mM Tris/SO$_4^{2-}$ pH 7.8.
2. The robot made 2 assay plates from each parent growth plate consisting of 0.02 mL cell suspension.
3. One assay plate was placed at room temperature and the other at elevated temperature (initial screen used 55° C.) for a period of time (initially 30 minutes).
4. After the prescribed time 0.08 mL room temperature substrate (TCP saturated 1 mM Tris/SO$_4^{2-}$ pH 7.8 with 1.5 mM NaN$_3$ and 0.1 mM bromothymol blue) was added to each well. TCP=trichloropropane.
5. Measurements at 620 nm were taken at various time points to generate a progress curve for each well.
6. Data were analyzed and the kinetics of the cells heated to those not heated were compared. Each plate contained 1–2 columns (24 wells) of un-mutated 20F12 controls.
7. Wells that appeared to have improved stability were regrown and tested under the same conditions.

Following this procedure nine single site mutations appeared to confer increased thermal stability on Dhla-20F12. Sequence analysis showed that the following changes were beneficial:

D89G

F91S

T159L

G189Q, G189V

I220L

N238T

W251Y

P302A, P302L, P302S, P302K

P302R/S306R

Only two sites (189 and 302) had more than one substitution. The first 5 on the list were combined (using G189Q) into a single gene (this mutant is referred to as "Dhla5"). All changes but S306R were incorporated into another variant referred to as Dhla8.

Thermal stability was assessed by incubating the enzyme at the elevated temperature (55° C. and 80° C.) for some period of time and activity assay at 30° C. Initial rates were plotted vs. time at the higher temperature. The enzyme was in 50 mM Tris/SO$_4$ pH 7.8 for both the incubation and the assay. Product (Cl) was detected by a standard method using Fe(NO$_3$)$_3$ and HgSCN. Dhla 20F12 was used as the defacto wild type. The apparent half-life (T$_{1/2}$) was calculated by fitting the data to an exponential decay finction.

3. LITERATURE CITED

Unless otherwise indicated, all references cited herein (supra and infra) are incorporated by reference in their entirety.

Barret A J, et al., eds.: *Enzyme Nomenclature: Recommendations of the Nomenclature Committee of the International Union of Biochemistry and Molecular Biology*. San Diego: Academic Press, Inc., 1992.

Boyce COL, ed.: *Novo's Handbook of Practical Biotechnology*. 2$^{nd}$ ed. Bagsvaerd, Denmark, 1986.

Drauz K, Waldman H, eds.: *Enzyme Catalysis in Organic Synthesis: A Comprehensive Handbook*. Vol. 1. New York: VCH Publishers, 1995.

Drauz K, Waldman H, eds.: *Enzyme Catalysis in Organic Synthesis: A Comprehensive Handbook*. Vol. 2. New York: VCH Publishers, 1995.

Foster G D, Taylor S C, eds.: *Plant Virology Protocols: From Virus Isolation to Transgenic Resistance*. Methods in Molecular Biology, Vol. 81. New Jersey: Humana Press Inc., 1998.

Franks F, ed.: *Protein Biotechnology: Isolation, Characterization, and Stabilization*. New Jersey: Humana Press Inc., 1993.

Godfrey T, West S, eds.: *Industrial Enzymology*. 2$^{nd}$ ed. London: Macmillan Press Ltd, 1996.

Gottschalk G: *Bacterial Metabolism*. 2$^{nd}$ ed. New York: Springer-Verlag Inc., 1986.

Gresshoff P M, ed.: *Technology Transfer of Plant Biotechnology*. Current Topics in Plant Molecular Biology. Boca Raton: CRC Press, 1997.

Griffin H G, Griffin A M, eds.: *PCR Technology: Currrent Innovations*. Boca Raton: CRC Press, Inc., 1994.

Hansen G, Chilton M D: Lessons in gene transfer to plants by a gifted microbe. *Curr Top Microbiol Immunol* 240:21–57, 1999.

Hartmann H T, et al.: *Plant Propagation: Principles and Practices*. 6$^{th}$ ed. New Jersey: Prentice Hall, Inc., 1997.

Perun T J, Propst C L, eds.: *Computer-Aided Drug Design: Methods and Applications*. New York: Marcel Dekker, Inc., 1989.

Owen M R L, Pen J: *Transgenic Plants: A Production System for Industrial and Pharmaceutical Proteins*. Chichester: John Wiley & Sons, 1996.

Segel IH: *Enzyme Kinetics: Behavior and Analysis of Rapid Equilibrium and Steady-State Enzvme Systems*. New York: John Wiley & Sons, Inc., 1993.

White J S, White D C: *Source Book of Enzymes*. Boca Raton: CRC Press, 1997.

Wong C H, Whitesides G M: *Enzymes in Synthetic Organic Chemistrv*. Vol. 12. New York: Elsevier Science Publications, 1995.

WO 97/35966; Filed Mar. 20, 1997, Published Oct. 2, 1997. Minshull J, Stemmer W P: Mehtods and Compositions for Cellular and Metabolic Engineering.

WO 98/31837; Filed Jan. 16, 1998, Published Jul. 23, 1998. Delcardayre S B, Tobin M B, Stemmer W P, Minshull, J: Evolution of Whole Cells and Organisms by Recursive Sequence Recombination.

WO 98/37223; Filed Feb. 18 1998, Published Aug. 27, 1998. Pang S Z, Gonsalves D, Jan F J: DNA Construct to Confer Multiple Traits on Plants.

Alting-Mecs M A and Short J M: Polycos vectors: a system for packaging filamentous phage and phagemid vectors using lambda phage packaging extracts. *Gene* 137: 1,93–100, 1993.

Arkin A P and Youvan D C: An algorithm for protein engineering: simulations of recursive ensemble mutagenesis. *Proc Natl Acad Sci USA* 89(16):7811–7815, (Aug 15) 1992.

Arnold F H: Protein engineering for unusual environments. *Current Opinion in Biotechnology* 4(4):450–455, 1993.

Ausubel F M, et al Editors. *Current Protocols in Molecular Biology*, Vols. 1 and 2 and supplements. (a.k.a. "The Red Book") Greene Publishing Assoc., Brooklyn, N. Y., ©1987.

Ausubel F M, et al Editors. *Current Protocols in Molecular Biology*, Vols. 1 and 2 and supplements. (a.k.a. "The Red Book") Greene Publishing Assoc., Brooklyn, N. Y., ©1989.

Ausubel F M, et al Editors. *Short Protocols in Molecular Biology: A Compendium of Methods from Current Protocols in Molecular Biologv*. Greene Publishing Assoc., Brooklyn, N. Y., ©1989.

Ausubel F M, et al Editors. *Short Protocols in Molecular Biology: A Compendium of Methods from Current Protocols in Molecular Biology*, 2$^{nd}$ Edition. Greene Publishing Assoc., Brooklyn, N. Y., ©1992.

Barbas C F 3d, Bain J D, Hoekstra D M, Lemer R A: Semisynthetic combinatorial antibody libraries: a chemical solution to the diversity problem. *Proc Natl Acad Sci USA* 89(10):4457–4461, 1992.

Bardwell A J, Bardwell L, Johnson D K, Friedberg E C: Yeast DNA recombination and repair proteins Rad1 and Rad10 constitute a complex in vivo mediated by localized hydrophobic domains. *Mol Microbiol* 8(6):1177–1188, 1993.

Bartel P, Chien C T, Sternglanz R, Fields S: Elimination of false positives that arise in using the two-hybrid system. *Biotechniques* 14(6):920–924, 1993.

Beaudry A A and Joyce G F: Directed evolution of an RNA enzyme. *Science* 257(5070):635–641, 1992.

Berger and Kimmel, *Methods in Enzymology*, Volume 152, Guide to Molecular Cloning Techniques. Academic Press, Inc., San Diego, Calif., ©1 987. (Cumulative Subject Index: Volumes 135–139, 141–167, 1990, 272 pp.)

Bevan M: Binary Agrobacterium vectors for plant transformation. *Nucleic Acids Research* 12(22):8711–21, 1984.

Biocca S, Pierandrei-Amaldi P, Cattaneo A: Intracellular expression of anti-p21ras single chain Fv fragments inhibits meiotic maturation of xenopus oocytes. *Biochem Biophys Res Commun* 197(2):422–427, 1993.

Bird et al. *Plant Mol Biol* 11:651, 1988.

Bogerd H P, Fridell R A, Blair W S, Cullen B R: Genetic evidence that the Tat proteins of human immunodeficiency virus types 1 and 2 can multimerize in the eukaryotic cell nucleus. *J Virol* 67(8):5030–5034, 1993.

Brederode F T, Koper-Zawrthoff E C, Bol J F: Complete nucleotide sequence of alfalfa mosaic virus RNA 4. *Nucleic Acids Research* 8(10):2213–23, 1980.

Breitling F, Dubel S, Seehaus T, Klewinghaus I, Little M: A surface expression vector for antibody screening. *Gene* 104(2):147–153, 1991.

Brown N L, Smith M: Cleavage specificity of the restriction endonuclease isolated from Haemophilus gallinarum (Hga I). *Proc Natl Acad Sci USA* 74(8):3213–6, (August) 1977.

Burton D R, Barbas C F 3d, Persson M A, Koenig S, Chanock R M, Lerner R A: A large array of human monoclonal antibodies to type 1 human immunodeficiency virus from combinatorial libraries of asymptomatic seropositive individuals. *Proc Natl Acad Sci USA* 88(22):10134–7, Nov. 15, 1991.

Caldwell R C and Joyce G F: Randomization of genes by PCR mutagenesis. *PCR Methods Appl* 2(10):28–33, 1992.

Caton A J and Koprowski H: Influenze virus hemagglutinin-specific antibodies isolatedf froma combinatorial expression library are closely related to the immune response of the donor. *Proc Natl Acad Sci USA* 87(16):6450–6454, 1990.

Chakraborty T, Martin J F, Olson E N: Analysis of the oligomerization of myogenin and E2A products in vivo using a two-hybrid assay system. *J Biol Chem* 267(25): 17498–501, 1992.

Chang C N, Landolfi N F, Queen C: Expression of antibody Fab domains on bacteriophage surfaces. Potential use for antibody selection. *J Immunol* 147(10):3610–4, Nov. 15, 1991.

Chaudhary V K, Batra J K, Gallo M G, Willingham M C, FitzGerald D J, Pastan I: A rapid method of cloning functional variable-region antibody genes in *Escherichia coli* as single-chain immunotoxins. *Proc Natl Acad Sci USA* 87(3):1066–1070, 1990.

Chien C T, Bartel P L, Stemglanz R, Fields S: The two-hybrid system: a method to identify and clone genes for proteins that interact with a protein of interest. *Proc Natl Acad Sci USA* 88(21):9578–9582, 1991.

Chiswell D J, McCafferty J: Phage antibodies: will new 'coliclonal' antibodies replace monoclonal antibodies? *Trends Biotechnol* 10(3):80–84, 1992.

Chothia C and Lesk A M: Canonical structures for the hypervariable regions of immunoglobulins. *J Mol Biol* 196)4):901–917, 1987.

Chothia C, Lesk A M, Tramontano A, Levitt M, Smith-Gill S J, Air G, Sheriff S, Padlan E A, Davies D, Tulip W R, et al: Conformations of immunoglobulin hypervariable regions. *Nature* 342(6252):877–883, 1989.

Clackson T, Hoogenboom H R, Griffiths A D, Winter G: Making antibody fragments using phage display libraries. *Nature* 352(6336):624–628, 1991.

Conrad M, Topal M D: DNA and spermidine provide a switch mechanism to regulate the activity of restriction enzyme *Nae I. Proc Natl Acad Sci U S A* 86(24):9707–11, (December) 1989.

Coruzzi G, Broglie R, Edwards C, Chua N H: Tissue-specific and light-regulated expression of a pea nuclear gene encoding the small subunit of ribulose-1,5-bisphosphate carboxylase. *EMBO J* 3(8):1671–9, 1984.

Dasmahapatra B, DiDomenico B, Dwyer S, Ma J, Sadowski I, Schwartz J: A genetic system for studying the activity of a proteolytic enzyme. *Proc Natl Acad Sci USA* 89(9): 4159–4162, 1992.

Davis L G, Dibner M D, Battey J F. *Basic Methods in Molecular Biology*. Elsevier, New York, N. Y., ©1986.

Delegrave S and Youvan D.C. *Biotechnology Research* 11:1548–1552, 1993.

DeLong E F, Wu KY, Prezelin B B, Jovine R V: High abundance of Archaea in Antarctic marine picoplankton. *Nature* 371(6499):695–697, 1994.

Deng S J, MacKenzie C R, Sadowska J, Michniewicz J, Young N M, Bundle Dr, Narang S A: Selection of antibody single-chain variable fragments with improved carbohydrate binding by phage display. *J Biol Chem* 269(13):9533–9538, 1994.

Duan L, Bagasra O, Laughlin M A, Oakes J W, Pomerantz R J: Potent inhibition of human immunodeficiency virus type 1 replication by an intracellular anti-Rev single-chain antibody. *Proc Natl Acad Sci USA* 91(11):5075–5079, 1994.

Durfee T, Becherer K, Chen P L, Yeh S H, Yang Y, Kilburn A E, Lee W H, Elledge S J: The retinoblastoma protein associates with the protein phosphatase type 1 catalytic subunit. *Genes Dev* 7(4):555–569, 1993.

Ellington A D and Szostak J W: In vitro selection of RNA molecules that bind specific ligands. *Nature* 346(6287) :818–822, 1990.

Fields S and Song 0: A novel genetic system to detect protein-protein interactions. *Nature* 340(6230):245–246, 1989.

Firek S, Draper J, Owen M R, Gandecha A, Cockburn B, Whitelam G C: Secretion of a functional single-chain Fv protein in transgenic tobacco plants and cell suspension cultures. *Plant Mol Biol* 23(4):861–870, 1993.

Forsblom S, Rigler R, Ehrenberg M, Philipson L: Kinetic studies on the cleavage of adenovirus DNA by restriction endonuclease Eco RI. *Nucleic Acids Res* 3(12):3255–69, (December) 1976.

Germino F J, Wang Z X, Weissman S M: Screening for in vivo protein-protein interactions. *Proc Natl Acad Sci USA* 90(3):933–937, 1993.

Gingeras T R, Brooks J E: Cloned restriction/modification system from Pseudomonas aeruginosa. *Proc Natl Acad Sci USA* 80(2):402–6, 1983 (January). Gluzman Y: SV40-transformed simian cells support the replication of early SV40 mutants. *Cell* 23(1):175–182, 1981.

Gruber M, Schodin B A, Wilson E R, Kranz D M: Efficient tumor cell lysis mediated by a bispecific single chain antibody expressed in *Escherichia coli. J Immunol* 152 (11):5368–5374, 1994.

Guarente L: Strategies for the identification of interacting proteins. *Proc Natl Acad Sci USA* 90(5):1639–1641, 1993.

Guilley H, Dudley R K, Jonard G, Balazs E, Richards K E: Transcription of Cauliflower mosaic virus DNA: detection of promoter sequences, and characterization of transcripts. *Cell* 30(3):763–73, 1982.

Hardy C F, Sussel L, Shore D: A RAP1-interacting protein involved in transcriptional silencing and telomere length regulation. *Genes Dev* 6(5):801–814, 1992.

Hawkins R E and Winter G: Cell selection strategies for making antibodies from variable gene libraries: trapping the memory pool. *Eur J Immunol* 22(3):867–870, 1992.

Holvoet P, Laroche Y, Lijnen H R, Van Hoef B, Brouwers E, De Cock F, Lauwereys M, Gansemans Y, Collen D: Biochemical characterization of single-chain chimeric plasminogen activators consisting of a single-chain Fv fragment of a fibrin-specific antibody and single-chain urokinase. *Eur J Biochem* 210(3):945–952, 1992.

Honjo T, Alt F W, Rabbitts T H (eds): *Immunoglobulin genes*. Academic Press: San Diego, Calif., pp. 361–368, ©1989.

Hoogenboom H R, Griffiths A D, Johnson K S, Chiswell D J, Judson P, Winter G: Multi-subunit proteins on the surface of filamentous phage: methodologies for displaying antibody (Fab) heavy and light chains. *Nucleic Acids Res* 19(15):4133–4137, 1991.

Huse W D, Sastry L, Iverson S A, Kang A S, Alting-Mees M, Burton D R, Benkovic S J, Lerner R A: Generation of a large combinatorial library of the immunoglobulin repertoire in phage lambda. *Science* 246(4935):1275–1281, 1989.

Huston J S, Levinson D, Mudgett-Hunter M, Tai M S, Novotney J, Margolies M N, Ridge R J, Bruccoleri R E, Haber E, Crea R, et al: Protein engineering of antibody binding sites: recovery of specific activity in an anti-digoxin single-chain Fv analogue produced in *Escherichia coli*. *Proc Natl Acad Sci USA* 85(16):5879–5883, 1988.

Iwabuchi K, Li B, Bartel P, Fields S: Use of the two-hybrid system to identify the domain of p53 involved in oligomerization. *Oncogene* 8(6):1693–1696, 1993.

Jackson A L, Pahl P M, Harrison K, Rosamond J, Sclafani R A: Cell cycle regulation of the yeast Cdc7 protein kinase by association with the Dbf4 protein. *Mol Cell Biol* 13(5):2899–2908, 1993.

Johnson S and Bird R E: *Methods Enzymol* 203:88, 1991.

Kabat et al: Sequences of Proteins of Immunological Interest, 4th Ed. U.S. Department of Health and Human Services, Bethesda, Md.(1987)

Kang A S, Barbas C F, Janda K D, Benkovic S J, Lerner R A: Linkage of recognition and replication functions by assembling combinatorial antibody Fab libraries along phage surfaces. *Proc Natl Acad Sci USA* 88(10): 4363–4366, 1991.

Kettleborough C A, Ansell K H, Allen R W, Rosell-Vives E, Gussow D H, Bendig M M: Isolation of tumor cell-specific single-chain Fv from immunized mice using phage-antibody libraries and the re-construction of whole antibodies from these antibody fragments. *Eur J Immunol* 24(4):952–958, 1994.

Kruger D H, Barcak G J, Reuter M, Smith HO: EcoRII can be activated to cleave refractory DNA recognition sites. *Nucleic Acids Res* 16(9):3997–4008, (May 11) 1988.

Lalo D, Carles C, Sentenac A, Thuriaux P: Interactions between three common subunits of yeast RNA polymerases I and III. *Proc Natl Acad Sci USA* 90(12): 5524–5528, 1993.

Laskowski M Sr: Purification and properties of venom phosphodiesterase. *Methods Enzymol* 65(1):276–84, 1980.

Lefkovits I and Pernis B, Editors. *Immunological Methods*, Vols. I and II. Academic Press, New York, N. Y. Also Vol. III published in Orlando and Vol. IV published in San Diego. ©1979.

Ivan Lefkovits, Editor. Immunology methods manual: the comprehensive sourcebook of techniques. Academic Press, San Diego, ©1997.

Lerner R A, Kang A S, Bain J D, Burton D R, Barbas C F 3d: Antibodies without immunization. *Science* 258(5086) :1313–1314, 1992.

Leung, D. W., et al, Technique, 1:11–15, 1989.

Li B and Fields S: Identification of mutations in p53 that affect its binding to SV40 large T antigen by using the yeast two-hybrid system. *FASEB J* 7(10):957–963, 1993.

Lilley G G, Doelzal O, Hillyard C J, Bernard C, Hudson P J: Recombinant single-chain antibody peptide conjugates expressed in *Escherichia coli* for the rapid diagnosis of HIV. *J Immunol Methods* 171(2):211–226, 1994.

Lowman H B, Bass S H, Simpson N, Wells J A: Selecting high-affinity binding proteins by monovalent phage display. *Biochemistry* 30(45):10832–10838, 1991.

Luban J, Bossolt K L, Franke E K, Kalpana G V, Goff S P: Human immunodeficiency virus type 1 Gag protein binds to cyclophilins A and B. *Cell* 73(6):1067–1078, 1993.

Madura K, Dohmen R J, Varshavsky A: N-recognin/Ubc2 interactions in the N-end rule pathway. *J Biol Chem* 268(16):12046–54, Jun. 5, 1993.

Marks J D, Hoogenboom H R, Bonnert T P, McCafferty J, Griffiths A D, Winter G: By-passing immunization. Human antibodies from V-gene libraries displayed on phage. *J Mol Biol* 222(3):581–597, 1991.

Marks J D, Griffiths A d, Malmqvist M, Clackson T P, Bye J M, Winter G: By-passing immunization: building high affinity human antibodies by chain shuffling. *Biotechnology (N Y* 10(7):779–783, 1992.

Marks J D, Hoogenboom H R, Griffiths A D, Winter G: Molecular evolution of proteins on filamentous phage. Mimicking the strategy of the immune system. *J Biol Chem* 267(23):16007–16010, 1992.

Maxam A M, Gilbert W: Sequencing end-labeled DNA with base-specific chemical cleavages. *Methods Enzymol* 65(1): 499–560, 1980.

McCafferty J, Griffiths A D, Winter G, Chiswell D J: Phage antibodies: filamentous phage displaying antibody variable domains. *Nature* 348(6301):552–554, 1990.

Miller J H. *A Short Course in Bacterial Genetics: A Laboratory Manual and Handbook for Escherichia coli and Related Bacteria* (see inclusively p. 445). Cold Spring Harbor Laboratory Press, Plainview, N.Y., © 1992.

Milne G T and Weaver D T: Dominant negative alleles of RAD52 reveal a DNA repair/recombination complex including Rad51 and Rad52. *Genes Dev* 7(9): 1755–1765, 1993.

Mullinax R L, Gross E A, Amberg J R, Hay B N, Hogrefe H H, Kubtiz M M, Greener A, Alting-Mees M, Ardourel D, Short J M, et al: Identification of human antibody fragment clones specific for tetanus toxoid in a bacteriophage lambda immunoexpression library. *Proc natl Acad Sci USA* 87(20):8095–9099, 1990.

Nath K, Azzolina B A: in *Gene Amplification and Analysis* (ed. Chirikjian J G), vol. 1, p. 113, Elsevier North Holland, Inc., New York, N.Y., © 1981.

Needleman S B and Wunsch C D: A general method applicable to the search for similarities in the amino acid sequence of two proteins. *J Mol Biol* 48(3):443–453, 1970.

Nelson M, Christ C, Schildkraut I: Alteration of apparent restriction endonuclease recognition specificities by DNA methylases. *Nucleic Acids Res* 12(13):5165–73, Jul. 11, 1984.

Nicholls P J, Johnson V G, Andrew S M, Hoogenboom H R, Raus J C, Youle R J: Characterization of single-chain antibody (sFv)-toxin fusion proteins produced in vitro in rabbit reticulocyte lysate. *J Biol Chem* 268(7):5302–5308, 1993.

Oller A R, Vanden Broek W, Conrad M, Topal M D: Ability of DNA and spermidine to affect the activity of restriction endonucleases from several bacterial species. *Biochemistry* 30(9):2543–9, Mar. 5, 1991.

Owens R J and Young R J: The genetic engineering of monoclonal antibodies. *J Immunol Methods* 168(2): 149–165, 1994.

Pearson W R and Lipman D J: Improved tools for biological sequence comparison. *Proc NatlAcadSci USA* 85(8): 2444–2448, 1988.

Pein C D, Reuter M, Meisel A, Cech D, Kruger D H: Activation of restriction endonuclease EcoRII does not depend on the cleavage of stimulator DNA. *Nucleic Acids Re s* 19(19):5139–42, Oct. 11, 1991.

Persson M A, Caothien R H, Burton D R: Generation of diverse high-affinity human monoclonal antibodies by repertoire cloning. *Proc Natl Acad Sci USA* 88(6) :2432–2436, 1991.

Queen C, Foster J, Stauber C, Stafford J: Cell-type specific regulation of a kappa immunoglobulin gene by promoter and enhance elements. Immunol Rev 89:49–68, 1986.

Qiang B Q, McClelland M, Poddar S, Spokauskas A, Nelson M: The apparent specificity of NotI (5'-GCGGCCGC-3')

is enhanced by M.FnuDII or M.BepI methyltransferases (5'-mCGCG-3'): cutting bacterial chromosomes into a few large. pieces. *Gene* 88(1):101–5, Mar. 30, 1990.

Raleigh E A, Wilson G: *Escherichia coli* K-12 restricts DNA containing 5-methylcytosine. *Proc Natl Acad Sci USA* 83(23):9070–4, (December) 1986.

Reidhaar-Olson J F and Sauer R T: Combinatorial cassette mutagenesis as a probe of the informational content of protein sequences. *Science* 241(4861):53–57, 1988.

Riechmann L and Weill M: Phage display and selection of a site-directed randomized single-chain antibody Fv fragment for its affinity improvement. *Biochemistry* 32(34):8848–8855, 1993.

Roberts R J, Macelis D: REBASE—restriction enzymes and methylases. *Nucleic Acids Res* 24(1):223–35, Jan. 1, 1996.

Ryan A J, Royal C L, Hutchinson J, Shaw C H: Genomic sequence of a 12S seed storage protein from oilseed rape (Brassica napus c.v. jet neuf). *Nucl Acids Res* 17(9):3584, 1989.

Sambrook J, Fritsch E F, Maniatis T. *Molecular Cloning: A Laboratory Manual.* Cold Spring Harbor Laboratory Press, Cold Spring Harbor, N.Y., ©1982.

Sambrook J, Fritsch E F, Maniatis T. *Molecular Cloning; A Laboratory Manual.* Second Edition. Cold Spring Harbor Laboratory Press, Cold Spring Harbor, N.Y., © 1989.

Scopes R K. *Protein Purification: Principles and Practice.* Springer-Verlag, New York, N.Y., ©1982.

Silver S C and Hunt S W 3d: Techniques for cloning cDNAs encoding interactive transcriptional regulatory proteins. *Mol Biol Rep* 17(3):155–165, 1993.

Smith T F, Waterman M S. *Adv Appl Math* 2: 482-end of article, 1981.

Smith T F, Waterman M S: Overlapping genes and information theory. *J Theor Biol* 91(2):379–80, Jul. 21, 1981.

Smith T F, Waterman M S: Identification of common molecular subsequences. *J Mol Biol* 147(1):195–7, Mar. 25, 1981.

Smith T F, Waterman M S, Fitch W M: Comparative biosequence metrics. *J Mol Evol* 18(1):38–46, 1981.

Staudinger J, Perry M, Elledge S J, Olson E N: Interactions among vertebrate helix-loop-helix proteins in yeast using the two-hybrid system. *J Biol Chem* 268(7):4608–4611, 1993.

Stemmer W P, Morris S K, Wilson B S: Selection of an active single chain Fv antibody from a protein linker library prepared by enzymatic inverse PCR. *Biotechniques* 14(2):256–265, 1993.

Stemmer W P: DNA shuffling by random fragmentation and reassembly: in vitro recombination for molecular evolution. *Proc Natl Acad Sci USA* 91(22): 10747–10751, 1994.

Sun D, Hurley LH: Effect of the (+)-CC-1065-(N3-adenine) DNA adduct on in vitro DNA synthesis mediated by *Escherichia coli* DNA polymerase. *Biochemistry* 31:10, 2822–9, Mar. 17, 1992, Tague B W, Dickinson C D, Chrispeels M J: A short domain of the plant vacuolar protein phytohemagglutinin targets invertase to the yeast vacuole. *Plant Cell* 2(6):533–46, (June) 1990.

Takahashi N, Kobayashi I: Evidence for the double-strand break repair model of bacteriophage lambda recombination. *Proc Natl Acad Sci U S A* 87(7):2790–4, (Apilr) 1990.

Thiesen H J and Bach C: Target Detection Assay (TDA): a versatile procedure to determine DNA binding sites as demonstrated on SP1 protein. *Nucleic Acids Res* 18(11): 3203–3209, 1990.

Thomas M, Davis R W: Studies on the cleavage of bacteriophage lambda DNA with EcoRI Restriction endonuclease. *J Mol Biol* 91(3):315–28, Jan. 25, 1975.

Tingey S V, Walker E L, Corruzzi G M: Glutamine synthetase genes of pea encode distinct polypeptides which are differentially expressed in leaves, roots and nodules. *EMBO J* 6(1):1–9, 1987.

Topal M D, Thresher R J, Conrad M, Griffith J: Nael endonuclease binding to pBR322 DNA induces looping. *Biochemistry* 30(7):2006–10, Feb. 19, 1991.

Tramontano A, Chothia C, Lesk A M: Framework residue 71 is a major determinant of the position and conformation of the second hypervariable region in the VH domains of immunoglobulins. *J Mol Biol* 215(1): 175–182, 1990.

Tuerk C and Gold L: Systematic evolution of ligands by exponential enrichment: RNA ligands to bacteriophage T4 DNA polymerase. *Science* 249(4968):505–510, 1990.

van de Poll M L, Lafleur M V, van Gog F, Vrieling H, Meerman J H: N-acetylated and deacetylated 4'-fluoro-4-aminobiphenyl and 4-aminobiphenyl adducts differ in their ability to inhibit DNA replication of single-stranded M13 in vitro and of single-stranded phi X174 in *Escherichia coli. Carcinogenesis* 13(5):751–8, (May) 1992.

Vojtek A B, Hollenberg S M, Cooper J A: Mammalian Ras interacts directly with the serine/threonine kinase Raf. *Cell* 74(1):205–214, 1993.

Wenzler H, Mignery G, Fisher L, Park W: Sucrose-regulated expression of a chimeric potato tuber gene in leaves of transgenic tobacco plants. *Plant Mol Biol* 13(4):347–54, 1989.

Williams and Barclay, in *Immunoglobulin Genes, The Immunoglobulin Gene Superfamily*

Winnacker E L. *From Genes to Clones: Introduction to Gene Technology.* VCH Publishers, New York, N.Y., ©1987.

Winter G and Milstein C: Man-made antibodies. *Nature* 349(6307):293–299, 1991.

Yang X, Hubbard E J, Carlson M: A protein kinase substrate identified by the two-hybrid system. *Science* 257(5070): 680–2, Jul. 31, 1992.

U.S. Pat. No. 4,683,195; Filed Feb. 7, 1986, Issued Jul. 28.1987. Mullis K B, Erlich H A, Arnheim N, Horn G T, Saiki R K, Scharf S J: Process for Amplifying, Detecting, and/or Cloning Nucleic Acid Sequences.

U.S. Pat. No. 4,683,202; Filed Oct. 25, 1985, Issued Jul. 28, 1987. Mullis K B: Process for Amplifying Nucleic Acid Sequences.

U.S. Pat. No. 4,704,362; Filed Nov. 5, 1979, Issued Nov. 3, 1987. Itakura K, Riggs A D: Recombinant Cloning Vehicle Microbial Polypeptide Expression.

WO 88/08453; Filed Apr. 14, 1988, Published Nov. 3, 1988. Alakhov J B, Baranov V I, Ovodov S J, Ryabova L A, Spirin A S: Method of Obtaining Polypeptides in Cell-Free Translation System.

WO 90/05785; Filed Nov. 15, 1989, Published May 31, 1990. Schultz P: Method for Site-Specifically Incorporating Unnatural Amino Acids into Proteins.

WO 90/07003; Filed Jan. 27, 1989, Published Jun. 28, 1990. Baranov V I, Morozov I J, Spirin A S: Method for Preparative Expression of Genes in a Cell-free System of Conjugated Transcription/translation.

WO 91/02076; Filed Jun. 14, 1990, Published Feb. 21, 1991. Baranov V I, Ryabova L A, Yarchuk O B, Spirin A S: Method for Obtaining Polypeptides in a Cell-free System.

WO 91/05058; Filed Oct. 5, 1989, Published Apr. 18, 1991. Kawasaki G: Cell-free Synthesis and Isolation of Novel Genes and Polypeptides.

WO 91/17271; Filed May 1, 1990, Published Nov. 14, 1991. Dower W J, Cwirla S E: Recombinant Library Screening Methods.

WO 91/18980; Filed May 13, 1991, Published Dec. 12, 1991. Devlin J J: Compositions and Methods for Identifying Biologically Active Molecules.

WO 91/19818; Filed Jun. 20, 1990, Published Dec. 26, 1991. Dower W J, Cwirla S E, Barrett R W: Peptide Library and Screening Systems.

WO 92/02536; Filed Aug. 1, 1991, Published Feb. 20, 1992. Gold L, Tuerk C: Systematic Polypeptide Evolution by Reverse Translation.

WO 92/03918; Filed Aug. 28, 1991, Published Mar. 19, 1992. Lonberg N, Kay R M: Transgenic Non-human Animals Capable of Producing Heterologous Antibodies.

WO 92/03918; Filed Aug. 28, 1991, Published Mar. 19, 1992. Lonberg N, Kay R M: Transgenic Non-human Animals Capable of Producing Heterologous Antibodies.

WO 92/05258; Filed Sep. 17, 1991, Published Apr. 2, 1992. Fincher G B: *Gene Encoding Barley Enzyme.*

WO 92/14843; Filed Feb. 21, 1992, Published Sep. 3, 1992. Toole J J, Griffin L C, Bock L C, Latham J A, Muenchau D D, Krawczyk S: Aptamers Specific for Biomolecules and Method of Making.

WO 93/08278; Filed Oct. 15, 1992, Published Apr. 29, 1993. Schatz P J, Cull M G, Miller J F, Stemmer W P: Peptide Library and Screening Method.

WO 93/12227; Filed Dec 17, 1992, Published Jun. 24, 1993. Lonberg, N; Kay R M: Transgenic Non-human Animals Capable of Producing Heterologous Antibodies.

WO 93/12227; Filed Dec. 17, 1992, Published Jun. 24, 1993. Lonberg N, Kay R M: Transgenic Non-human Animals Capable of Producing Heterologous Antibodies.

WO 94/25585; Filed Apr. 25, 1994, Published Nov. 10, 1994. Lonberg, N, Kay R M: Transgenic Non-human Animals Capable of Producing Heterologous Antibodies.

WO 94/25585; Filed Apr. 25, 1994, Published Nov. 10, 1994. Lonberg N, Kay R M: Transgenic Non-human Animals Capable of Producing Heterologous Antibodies.

Arslan T, Abraham A T, Hecht S M: Structurally altered substrates for DNA topoisomerase I. Effects of inclusion of a single 3'-deoxynucleotide within the scissile strand. *Nucleosides Nucleotides* January–March; 1998 17(1–3): 515–30.

Aupeix K, Toulme J J: Binding of chemically-modified oligonucleotides to the double-stranded stem of an RNA hairpin. *Nucleosides Nucleotides* June–July; 1999 18(6–7): 1647–50.

Bazzanini R, Manfredini S, Durini E, Groschel B, Cinatl J, Balzarini J, De Clercq E, Imbach J L, Perigaud C, Gosselin G: Prodrugs of Ara-CMP and Ara-AMP with a S-acyl-2-thioethyl (SATE) biolabile phosphate protecting group: synthesis and biological evaluation. *Nucleosides Nucleotides* April–May; 1999 18(4–5):971–2.

Blackburn G M, Liu X, Rosler A, Brenner C: Two hydrolase resistant analogues of diadenosine 5',5'''-P1,P3-triphosphate for studies with Fhit, the human fragile histidine triad protein. *Nucleosides Nucleotides* January–March; 1998 17(1–3):301–8.

Bridson P K, Lin X, Melman N, Ji X D, Jacobson K A: Synthesis and adenosine receptor affinity of 7-beta-D-ribofuranosylxanthine. *Nucleosides Nucleotides* April; 1998 17(4):759–68.

Brodin P, Gottikh M, Auclair C, Mouscadet J F: Inhibition of HIV-1 integration by mono- & bi-functionalized triple helix forming oligonucleotides. *Nucleosides Nucleotides* June–July; 1999 18(6–7):1717–8.

Creighton T E: Proteins Structures and Molecular Principles. New York: W. H. Freeman and Co., 1984. De Clercq E: Carbocyclic adenosine analogues as S-adenosylhomocysteine hydrolase inhibitors and antiviral agents: recent advances. *Nucleosides Nucleotides* January–March; 1998 17(1–3):625–34.

de Zwart M, Link R, von Frijtag Drabbe Kunzel J K, Cristalli G, Jacobson K A, Townsend-Nicholson A, IJzerman A P: A functional screening of adenosine analogues at the adenosine A2B receptor: a search for potent agonists. *Nucleosides Nucleotides* June; 1998 17(6):969–85.

Egron D, Arzumanov A A, Dyatkina N B, Krayevsky A, Imbach J L, Aubertin A M, Gosselin G, Perigaud C: Synthesis, anti-HIV activity and stability studies of 3'-azido-2',3'-dideoxythymidine 5'-fluorophosphate. *Nucleosides Nucleotides April–May;* 1999 18(4–5):983–4

Gianolio D A, McLaughlin L W: Synthesis and triplex forming properties of pyrimidine derivative containing extended functionality. *Nucleosides Nucleotides* Aug; 1999 18(8):1751–69.

Gottikh M B, Volkov E M, Romanova E A, Oretskaya T S, Shabarova Z A: Synthesis of oligonucleotide-intercalator conjugates capable to inhibit HIV-1 DNA integration. *Nucleosides Nucleotides* June–July; 1999 18(6–7): 1645–6.

Hotoda H, Koizumi M, Ohmine T, Furukawa H, Nishigaki T, Abe K, Kosaka T, Tsutsumi S, Sone J, Kaneko M: Biologically active oligodeoxyribonucleotides. 10: anti-HIV-1 activity and stability of modified hexanucleotides containing glycerol-skeleton. *Nucleosides Nucleotides* January–March; 1998 17(1–3):243–52.

JP10113194; Filed 19971022, Published 19980506. Donnelly, J J ;Dwarki, V J ;Liu, M A ;Montgomery, D L ;Parker, S ;Shiver, J W ;Ulmer J B: Nucleic Acid Preparation.

Kang S H, Sinhababu A K, Cho M J: Synthesis and biological activity of bis(pivaloyloxymethyl) ester of 2'-azido-2'-deoxyuridine 5'-monophosphate. *Nucleosides Nucleotides* June; 1998 17(6): 1089–98.

Krayevsky A, Arzumanov A, Shirokova E, Dyatkina N, Victorova L, Jasko M, Alexandrova L: dNTP modified at triphosphate residues: substrate properties towards DNA polymerases and stability in human serum. *Nucleosides Nucleotides* January–March; 1998 17(1–3):681–93.

Krayevsky A A, Dyatkina N B, Semizarov D G, Victorova L S, Shirokova E A, Theil F, Von Janta Lipinski M J, Gosselin G, Imbach J L: Reasons and limits of substrate activity of modified L-dNTP in DNA biosynthesis. *Nucleosides Nucleotides* April–May; 1999 18(4–5): 863–4.

Kvasyuk E I, Mikhailopulo I A, Suhadolnik R J, Henderson E E, Muto N F, Iacono K T, Homon J, Pfleiderer W: Synthesis and biological activity of 2',5'-oligoadenylate trimers containing 5'-terminal 5'-amino-5'-deoxy- and 5'-amino-3',5'-dideoxyadenosine derivatives. *Nucleosides Nucleotides* June–July; 1999 18(6–7): 1483–4.

Liu J, Skradis A, Kolar C, Kolath J, Anderson J, Lawson T, Talmadge J, Gmeiner W H: Increased cytotoxicity and decreased in vivo toxicity of FdUMP[10] relative to 5-FU. *Nucleosides Nucleotides* August; 1999 18(8): 1789–802.

Lutz M J, Will D W, Breipohl G, Benner S A, Uhlmann E: Synthesis of a monocharged peptide nucleic acid (PNA) analog and its recognition as substrate by DNA polymerases. *Nucleosides Nucleotides* March; 1999 18(3): 393–401.

Monaco V, van de Wetering K I, Meeuwenoord N J, van den Elst H A, Stuivenberg H R, Visse R, van der Kaaden J C, Moolenaar G F, Verhoeven E E, Goosen N, van der Marel G A, van Boom J H: Synthesis and biological evaluation of modified DNA fragments for the study of nucleotide excision repair in *E. coli*. *Nucleosides Nucleotides* June–July; 1999 18(6–7):1339–41.

Morozova O V, Kolpashchikov D M, Ivanova T M, Godovikova T S: Synthesis of new photocross-linking 5-C-base-substituted UTP analogs and their application in highly selective affinity labelling of the tick-borne encephalitis virus RNA replicase proteins. *Nucleosides Nucleotides* June–July; 1999 18(6–7): 1513–4.

Nguyen-Ba N, Chan L, Quimpere M, Turcotte N, Lee N, Mitchell H, Bedard J: Design and SAR study of a novel class of nucleotide analogues as potent anti-HCMV agents. *Nucleosides Nucleotides* April–May; 1999 18(4–5):821–7.

Pandolfi D, Rauzi F, Capobianco M L: Evaluation of different types of end-capping modifications on the stability of oligonucleotides toward 3'- and 5'-exonucleases. *Nucleosides Nucleotides* 1999 Sep; 18(9):2051–69.

Pankiewicz K W, Lesiak-Watanabe K: Novel mycophenolic adenine bis(phosphonate)s as potent anticancer agents and inducers of cells differentiation. *Nucleosides Nucleotides* April–May; 1999 18(4–5):927–32.

Perrin D M, Garestier T, Helene C: Expanding the catalytic repertoire of nucleic acid catalysts: simultaneous incorporation of two modified deoxyribonucleoside triphosphates bearing ammonium and imidazolyl finctionalities. *Nucleosides Nucleotides* March; 1999 18(3):377–91.

Pfundheller H M, Koshkin A A, Olsen C E, Wengel J: Evaluation of oligonucleotides containing two novel 2'-O-methyl modified nucleotide monomers: a 3'-C-allyl and a 2'-O,3'-C-linked bicyclic derivative. *Nucleosides Nucleotides* September; 1999 18(9):2017–30.

Ramasamy K S, Stoisavljevic V: Synthesis and biophysical studies of modified oligonucleotides containing acyclic amino alcohol nucleoside analogs. *Nucleosides Nucleotides* Aug; 1999 18(8): 1845–61.

Schinazi R F, Lesnikowski Z J: Boron containing oligonucleotides. *Nucleosides Nucleotides* January–March; 1998 17(1–3):63 5–47.

Secrist J A 3rd, Parker W B, Allan P W, Bennett L L Jr, Waud W R, Truss J W, Fowler A T, Montgomery J A, Ealick S E, Wells A H, Gillespie G Y, Gadi V K, Sorscher E J: Gene therapy of cancer: activation of nucleoside prodrugs with *E. coli* purine nucleoside phosphorylase. *Nucleosides Nucleotides* April–May; 1999 18(4–5):745–57.

Shirokova E A, Shipitsin A V, Victorova L S, Dyatkina N B, Goryunova L E, Beabealashvilli R S, Hamilton C J, Roberts S M, Krayevsky A A: Modified nucleoside 5'-triphosphonates as a new type of antiviral agents. *Nucleosides Nucleotides* April–May; 1999 18(4–5): 1027–8.

Srivastava T K, Friedhoff P, Pingoud A, Katti S B: Application of oligonucleoside methylphosphonates in the studies on phosphodiester hydrolysis by Serratia endonuclease. *Nucleosides Nucleotides* September; 1999 18(9): 1945–60.

Stattel J M, Yanachkov I, Wright G E: Synthesis and biochemical study of N2-(p-n-butylphenyl)-2'-deoxyguanosine 5'-(alpha,beta-imido)triphosphate (BuPdGMPN HPP): a non-substrate inhibitor of B family DNA polymerases. *Nucleosides Nucleotides* August; 1998 17(8): 1505–13.

Terato H, Morita H, Ohyama Y, Ide H: Novel modification of 5-formyluracil by cysteine derivatives in aqueous solution. *Nucleosides Nucleotides* January–March; 1998 17(1–3):131–41.

Tomikawa A, Seno M, Sato-Kiyotaki K, Ohtsuki C, Hirai T, Yamaguchi T, Kawaguchi T, Yoshida S, Saneyoshi M: Synthetic nucleosides and nucleotides. 40. Selective inhibition of eukaryotic DNA polymerase alpha by 9-(beta-D-arabinofuranosyl)-2-(p-n-butylanilino) adenine 5'-triphosphate (BuAaraATP) and its 2'-up azido analog: synthesis and enzymatic evaluations. *Nucleosides Nucleotides* January–March; 1998 17(1–3):487–501.

U.S. Pat. No. 5,580,859; Filed 19940318, Issued 19961203. Felgner, P L. ;Wolff, J A. ;Rhodes, G H. ;Malone, R W. ;Carson, D A.: Delivery of exogenous DNA sequences in a mammal.

U.S. Pat. No. 5,589,466; Filed 19950126, Issued 19961231. Felgner, P L. ;Wolff, J A. ;Rhodes, G H. ;Malone, R W. ;Carson, D A.: Induction of a protective immune response in a mammal by injecting a DNA sequence.

U.S. Pat. No. 5,641,665; Filed 19941128, Issued 19970624. Hobart, P M. ;Margalith, M ;Parker, S E. ;Khatibi, S: Plasmids suitable for IL-2 expression.

U.S. Pat. No. 5,693,622; Filed 19950607, Issued 19971202. Wolff, J A. ;Duke, D J. ;Felgner, P L.: Expression of exogenous polynucleotide sequences cardiac muscle of a mammal.

U.S. Pat. No. 5,703,055; Filed 19940126, Issued 19971230. Felgner, P L. ;Wolff, J A ;Rhodes, G H. ;Malone, R W ;Carson, D A.: Generation of antibodies through lipid mediated DNA delivery.

U.S. Pat. No. 5,846,946; Filed 19960614, Issued 19981208. Huebner, R C. ;Norman, J A. ;Liang, X ;Carner, K R. ;Barbour, A G. ;Luke, C J.: Compositions and methods for administering Borrelia DNA.

U.S. Pat. No. 5,910,488; Filed 19951201, Issued 19990608. Nabel, G J. ;Nabel, E G. ;Lew, D ;Marquet, M: Plasmids suitable for gene therapy.

Victorova L S, Semizarov D G, Shirokova E A, Alexandrova L A, Arzumanov A A, Jasko M V, Krayevsky A A: Human DNA polymerases and retroviral reverse transcriptases: selectivity in respect to dNTPs modified at triphosphate residues. *Nucleosides Nucleotides* April–May; 1999 18(4–5):1031–2.

von Janta-Lipinski M, Gaertner K, Lehmann C, Scheer H, Schildt J, Matthes E: Protein and RNA of human telomerase as targets for modified oligonucleotides. *Nucleosides Nucleotides* June–July; 1999 18(6–7):1719–20

WO9011092; Filed 19900321, A1 Published 19901004. Felgner, P L. ;Wolff, J A;Rhodes, G H. ;Malone, R W ;Carson, D A.: Expression Of Exogenus Polynucleotide Sequences In A Vertebrate.

WO9314778; Filed 19930121, A1 Published 19930805. Rhodes, G H. ;Dwarki, V J.;Felgner, P L;Wang-Felgner, J;Manthorpe, M: ex vivo Gene Transfer.

WO9421797; Filed 19940314, A1 Published 19940929. Donnelly, J J. ;Dwarki, V J. ;Liu, M A. ;Montgomery, D L. ;Parker, S E. ;Shiver, J W. ;Ulmer, J B.: Nucleic Acid Pharmaceuticals.

WO9633736; Filed 19960426, A1 Published 19961031. Baruch D I; Pasloske B L; Howard, R J: Malaria Peptides and Vaccines.

WO9735992; Filed 19970317, A1 Published 19971002. Hobart, P M. ;Liang, X: Tetracycline Inducible/Repressible Systems.

WO9926663; Filed 19981120, A2 Published 19990603. Horton, H ;Parker, S;Manthorpe, M; Felgner, P: Treatment Of Cancer Using Cytokine-Expressing Polynucleotides And Compositions Therefor.

WO9941368; Filed 19990210, A2 Published 19990819. Punnonen J, Stemmer W P, Whalen R G; Howard, R: Optimization of Immunomodulatory Properties of Genetic Vaccines.

WO9941369; Filed 19990210, A2 Published 19990819. Punnonen J, Stemmer W P, Whalen R G; Howard, R: Genetic Vaccine Vector Engineering.

WO9941383; Filed 19990210, A1 Published 19990819. Punnonen J, Bass, S H, Whalen, R G, Howard, R, Stemmer, W P: Antigen Library Immunization.

WO9941402; Filed 19990210, A2 Published 19990819. Punnonen J, Stemmer, W P, Howard R, Patten P A: Targeting of Genetic Vaccine Vectors.

What is claimed is:

1. A method of providing an immunomodulatory polynucleotide that has an optimized modulatory effect on an immune response, or encodes a polypeptide that has an optimized modulatory effect on an immune response, the method comprising creating a library of non-stochastically generated progeny polynucleotides from a parental polynucleotide set, thereby providing an immunomodulatory polynucleotide.

2. The method of claim 1 wherein the library of non-stochastically generated progeny polynucleotides is optimized by directed evolution of the parental polynucleotides, such that polypeptides encoded by the optimized progeny polynucleotides are enhanced in their modulatory effect on an immune response.

3. The method of claim 2, wherein said progeny polynucleotide whose modulatory effect on an immune response is optimized by directed evolution is introduced into a genetic vaccine vector.

4. The method of claim 2, wherein said method of directed evolution is selected from the group consisting of codon site-saturation mutagenesis, amino acid site-saturation mutagenesis, gene site saturation mutagenesis, introduction of mutations by non-stochastic polynucleotide reassembly methods, synthetic ligation polynucleotide reassembly, gene reassembly, oligonucleotide-directed saturation mutagenesis, in vivo reassortment of polynucleotide sequences having partial homology, naturally occurring recombination processes which reduce sequence complexity, and any combination thereof.

5. The method of claim 4, wherein the method of directed evolution introduces at least at least one point mutation, addition, deletion, or chimerization, from one or more parental polynucleotides.

6. The method of claim 1, further comprising screening said library for progeny polynucleotides which encode polypeptides optimized for their immunomodulatory effect as compared to the parental polynucleotides.

7. The method of claim 1, wherein the optimized non-stochastically generated polynucleotide encodes a polypeptide that interacts with a cellular receptor.

8. The method of claim 7, wherein the cellular receptor is a macrophage scavenger receptor.

9. The method of claim 7, wherein the cellular receptor is selected from the group consisting of a cytokine receptor and a chemokine receptor.

10. The method of claim 9, wherein the chemokine receptor is CCR6.

11. The method of claim 7, wherein the polypeptide acts as an agonist or antagonist of the receptor.

12. The method of claim 1, wherein the library is screened by contacting replicable genetic packages, which express the encoded polypeptides of the optimized progeny polynucleotides as fusions with proteins displayed on the surface, with a plurality of cells that display the receptor.

13. The method of claim 12, further comprising identifying cells that exhibit a modulation of an immune response by the receptor.

14. The method of claim 12, wherein the replicable genetic package is selected from the group consisting of a bacteriophage, a cell, a spore, and a virus.

15. The method of claim 14, wherein the replicable genetic package is an M13 bacteriophage and the protein is encoded by geneIII or geneVIII.

16. The method of claim 1, further comprising introducing the optimized non-stochastically generated polynucleotide into a genetic vaccine vector and administering the vector to a subject.

17. The method of claim 16, wherein the peptide or polypeptide is an agonist or antagonist of the receptor.

18. The method of claim 1, wherein the optimized non-stochastically generated polynucleotide is inserted into an antigen-encoding nucleotide sequence of a genetic vaccine vector.

19. The method of claim 18, wherein the optimized non-stochastically generated polypeptide is introduced into a nucleotide sequence that encodes an HBsAg polypeptide.

20. The method of claim 1, wherein the optimized non-stochastically generated polynucleotide comprises a nucleotide sequence rich in unmethylated CpG.

21. The method of claim 1, wherein the optimized non-stochastically generated polynucleotide encodes a polypeptide that inhibits an allergic reaction.

22. The method of claim 21, wherein the polypeptide is selected from the group consisting of interferon-α, interferon-β, IL-10, IL-12, an antagonist of IL-4, an antagonist of IL-5, and an antagonist of IL-13.

23. The method of claim 1, wherein the optimized recombinant polynucleotide encodes an antagonist of IL-10.

24. The method of claim 23, wherein the antagonist of IL-10 is soluble or defective IL-10 receptor or IL-20/MDA-7.

25. The method of claim 1, wherein the optimized non-stochastically generated polynucleotide encodes a co-stimulator.

26. The method of claim 25, wherein the co-stimulator is B7-1 (CD80) or B7-2 (CD86).

27. The method of claim 26 wherein the screening step involves selecting variants with altered activity through CD28 or CTLA-4.

28. The method of claim 25, wherein the co-stimulator is CD1, CD40, CD154 (ligand for CD40) or CD150 (SLAM).

29. The method of claim 25, wherein the co-stimulator is a cytokine.

30. The method of claim 29, wherein the cytokine is selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, GM-CSF, G-CSF, TNF-α, IFN-α, IFN-γ, and IL-20 (MDA-7).

31. The method of 30, wherein the library of non-stochastically generated polynucleotides is screened by testing the ability of cytokines encoded by the non-stochastically generated polynucleotides to activate cells which contain a receptor for the cytokine.

32. The method of claim 31, wherein the cells contain a heterologous nucleic acid that encodes the receptor for the cytokine.

33. The method of 30, wherein the cytokine is interleukin-12 and screening is performed by growing mammalian cells which contain the genetic vaccine vector in a culture medium and detecting whether T cell proliferation or T cell differentiation is induced by contact with the culture medium.

34. The method of 30, wherein the cytokine is interferon-γ.

35. The method of claim 34, wherein the library is screened by contacting replicable genetic packages, which express the encoded polypeptides of the optimized progeny polynucleotides as fusions with proteins displayed on the surface, with a plurality of B cells that display the receptor.

36. The method of claim 35, further comprising identifying phage library members that are capable of inhibiting proliferation of the B cells.

37. The method of claim 30, wherein the immune response of interest is differentiation of T cells to $T_H1$ cells.

38. The method of claim 37, wherein said immune response of interest is screened by contacting a population of T cells with the cytokines encoded by the members of the library of recombinant polynucleotides and identifying library members that encode a cytokine that induces the T cells to produce IL-2 and interferon-γ.

39. The method of claim 29, wherein the cytokine encoded by the optimized non-stochastically generated polynucleotide exhibits reduced immunogenicity compared to a cytokine encoded by a non-optimized polynucleotide.

40. The method of claim 39, wherein the reduced immunogenicity is detected by introducing a cytokine encoded by the non-stochastically generated polynucleotide into a subject and determining whether an immune response is induced against the cytokine.

41. The method of claim 31, wherein the cell is tested for ability to costimulate an immune response.

42. The method of claim 1, wherein the optimized recombinant polynucleotide encodes a cytokine antagonist.

43. The method of claim 42, wherein the cytokine antagonist is selected from the group consisting of a soluble cytokine receptor, a transmembrane cytokine receptor having a defective signal sequence, IL-10R and IL-4R.

44. The method of claim 1, wherein the optimized non-stochastically generated polynucleotide encodes a polypeptide capable of inducing a predominantly $T_H1$ immune response.

45. The method of claim 1, wherein the optimized non-stochastically generated polynucleotide encodes a polypeptide capable of inducing a predominantly $T_H2$ immune response.

46. The method of claim 1, wherein said optimized modulatory effect on an immune response is a decrease in an unwanted modulatory effect on an immune response.

47. The method of claim 46, wherein said method generates a molecule having a decreased ability to elicit an immune response from a host recipient of said molecule.

48. The method of claim 47, wherein said recipient can be a human or an animal host.

49. The method of claim 48, wherein said method generates a molecule having decreased antigenicity with respect to at least one host recipient of said molecule.

50. The method of claim 49, wherein said recipient can be a human or an animal host.

51. The method of claim 1, wherein said optimized modulatory effect on an immune response is both a decrease in a first unwanted modulatory effect on an immune response and an increase in a second desirable modulatory effect on an immune response.

52. The method of claim 51, wherein the first and the second recipient hosts can be the same or different.

53. The method of claim 51, wherein each of the first and the second recipient hosts can be human or animal.

54. The method of claim 51, wherein said method generates a molecule having both a decreased ability to elicit a first immune response from a first host recipient of said molecule and an increased ability to elicit a second immune response from a second host recipient of said molecule.

55. The method of claim 54, wherein the first and the second recipient hosts can be the same or different.

56. The method of claim 54, wherein each of the first and the second recipient hosts can be a human or animal.

57. The method of claim 51, wherein said method generates a molecule having both a first decreased antigenicity with respect to at least one host recipient of said molecule and a second decreased antigenicity with respect to at least one host recipient of said molecule.

58. The method of claim 46, wherein said first and said second modulatory effect on an immune response are evolved for respectively a first and a second module on the same multimodule vaccine vector.

59. The method of claim 58, wherein said module is selected from the group of modules consisting of an antigen coding sequence, a polyadenylation sequence, a sequence coding for a co-stimulatory molecule, a sequence coding for an inducible repressor or transactivator, a eukaryotic origin of replication, a prokaryotic origin of replication, a sequence coding for a prokaryotic marker, an enhancer, a promoter, an operator, an intron, or derivative fragments or analogs thereof, and any combination thereof.

60. The method of claim 1, wherein the optimized modulatory effect on an immune response is comprised of an increase in the stability of the immunomodulatory (IM) polynucleotide or polypeptide encoded thereby.

61. The method of claim 60, wherein said method generates a molecule having an increased stability ex vivo.

62. The method of claim 60 wherein said method generates a molecule having increased stability in vivo, with respect to any means of biological elimination or degradation, upon administration to a host recipient.

63. The method of claim 1, wherein the immunomodulatory (IM) polynucleotide or polypeptide encoded thereby has an optimized modulatory effect on an immune response in an animal or human host recipient.

64. The method of claim 63, wherein said method generates an optimized genetic vaccine for any human and/or non-human recipients.

65. A method of providing an optimized non-stochastically generated polynucleotide that has a modulatory effect on an immune response said method comprising non-stochastically reassembling at least two parental template polynucleotides, each of which encodes a molecule that is involved in modulating an immune response, thereby providing a library of non-stochastically generated polynucleotides.

66. The method of claim 65, wherein the first and second parental templates differ from each other in two or more nucleotides.

67. The method of claim 65, further comprising screening the library to identify at least one optimized non-stochastically generated polynucleotide that exhibits through the encoded molecule an enhanced ability to modulate an immune response in comparison to a parental polynucleotide from which the library was created.

68. The method of claim 65, wherein an optimized non-stochastically generated polynucleotide is subjected to at least one further round of non-stochastic reassembly with at least one additional polynucleotide to produce additional working libraries of recombinant polynucleotides.

69. The method of claim 68, wherein said additional working libraries are screened to identify at least one further optimized non-stochastically generated polynucleotide which encodes a polypeptide that has been optimized for its immunomodulatory effect when compared to the parental polynucleotide from which the library was created.

70. A method of providing an optimized polynucleotide that encodes an accessory molecule that improves the transport or presentation of antigens by a cell, said method comprising creating a library of non-stochastically generated polynucleotides by subjecting to optimization by non-stochastic directed evolution a parental polynucleotide set in which is encoded all or part of the accessory molecule.

71. The method of claim 70, further comprising screening the library to identify an optimized non-stochastically generated progeny polynucleotide that encodes a recombinant molecule that confers upon a cell an increased or decreased ability to transport or present an antigen on a surface of the cell as compared to an accessory molecule encoded by template polynucleotides not subjected to the non-stochastic reassembly.

72. The method of claim 70, wherein said method of directed evolution is selected from the group consisting of codon site-saturation mutagenesis, amino acid site-saturation mutagenesis, gene site saturation mutagenesis, introduction of mutations by non-stochastic polynucleotide reassembly methods, synthetic ligation polynucleotide reassembly, gene reassembly, oligonucleotide-directed saturation mutagenesis, in vivo reassortment of polynucleotide sequences having partial homology, naturally occurring recombination processes which reduce sequence complexity, and any combination thereof.

73. The method of claim 70, wherein said method generates an optimized molecule for any human and/or non-human recipients.

74. The method of claim 70, further comprising forming a library of vectors by introducing the library of non-stochastically generated polynucleotides into a genetic vaccine vector that encodes an antigen.

75. The method of claim 74, wherein the library of vectors is introduced into mammalian cells.

76. The method of claim 75, wherein said cells that exhibit increased or decreased immunogenicity to the antigen are identified.

77. The method of claim 70, wherein the accessory molecule comprises a proteasome or a TAP polypeptide.

78. The method of claim 70, wherein the accessory molecule comprises a cytotoxic T-cell inducing sequence.

79. The method of claim 78, wherein the cytotoxic T-cell inducing sequence is obtained from a hepatitis B surface antigen.

80. The method of claim 70, wherein the accessory molecule comprises an immunogenic agonist sequence.

81. A method of providing an immunomodulatory polynucleotide that has an optimized expression in a recombinant expression host, said method comprising creating a library of non-stochastically generated progeny polynucleotides from a parental polynucleotide set, thereby providing an immunomodulatory polynucleotide.

82. The method of claim 81, wherein the library of non-stochastically generated polynucleotides is optimized by directed evolution.

83. The method of claim 82, wherein said method of directed evolution is selected from the group consisting of codon site-saturation mutagenesis, amino acid site-saturation mutagenesis, gene site saturation mutagenesis, introduction of mutations by non-stochastic polynucleotide reassembly methods, synthetic ligation polynucleotide reassembly, gene reassembly, oligonucleotide-directed saturation mutagenesis, in vivo reassortment of polynucleotide sequences having partial homology, naturally occurring recombination processes which reduce sequence complexity, and any combination thereof.

84. The method of claim 82, further comprising screening a library of non-stochastically generated progeny polynucleotides to identify an optimized non-stochastically generated progeny polynucleotide that has an optimized expression in a recombinant expression host as compared to the expression of parental polynucleotides.

85. The method of claim 82, wherein the recombinant expression host is a prokaryote.

86. The method of claim 82, wherein the recombinant expression host is a eukaryote.

87. The method of claim 86, wherein the recombinant expression host is a plant.

88. The method of claim 87, wherein the recombinant expression host is a monocot or dicot.

89. A method of producing a progeny polynucleotide set by subjecting a double-stranded circular parental polynucleotide molecule to mutagenesis, said method comprising synthesizing by means of a polymerase-catalyzed amplification reaction a first progeny polynucleotide strand comprised of said first primer and a second progeny polynucleotide strand comprised of said second primer, wherein the first progeny polynucleotide strand and the second progeny polynucleotide strand form a double-stranded mutagenized circular polynucleotide product, and wherein at least one of said primers contains a non-stochastic mutagenic cassette with respect to the parental polynucleotide molecule, thereby producing a progeny polynucleotide set.

90. The method of claim 89, wherein said non-stochastic mutagenic cassette contained in said at least one primer is degenerate in nature.

91. The method of claim 90, wherein a degenerate progeny polynucleotide set is produced.

92. A method of producing a set of progeny polypeptides, in which a non-stochastic range of single amino acid substitutions is represented at each amino acid position, from a template polypeptide set, said method comprising subjecting a codon-containing template polynucleotide to polymerase-based amplification using a degenerate oligonucleotide for each codon to be mutagenized.

93. The method of claim 92, wherein said method generates from at least one to twenty different amino acids at each amino acid site along a parental polypeptide template.

94. The method of claim 92, wherein said degenerate oligonucleotides is comprised of a first homologous sequence and a degenerate trinucleotide cassette.

95. The method of claim 92, wherein said degenerate oligonucleotide is comprised of a first homologous sequence, a degenerate trinucleotide cassette, and a second homologous sequence.

96. The method of claim 92, wherein said degenerate trinucleotide cassette is comprised of a first mononucleotide cassette selected from the group consisting of:

a degenerate A/C mononucleotide cassette, a degenerate A/G mononucleotide cassette, a degenerate A/T mononucleotide cassette, a degenerate C/G mononucleotide cassette, a degenerate C/T mononucleotide cassette,
a degenerate G/T mononucleotide cassette,
a degenerate C/G/T mononucleotide cassette,
a degenerate A/G/T mononucleotide cassette,
a degenerate A/C/T mononucleotide cassette,
a degenerate A/C/G mononucleotide cassette, and
a degenerate A/C/G/T mononucleotide cassette.

97. The method of claim 96, wherein said degenerate trinucleotide cassette is further comprises a second and a third mononucleotide cassette, each selected from the group consisting of:
a degenerate A/C mononucleotide cassette,
a degenerate A/G mononucleotide cassette,
a degenerate A/T mononucleotide cassette,
a degenerate C/G mononucleotide cassette,
a degenerate C/T mononucleotide cassette,
a degenerate G/T mononucleotide cassette,
a degenerate C/G/T mononucleotide cassette
a degenerate A/G/T mononucleotide cassette,
a degenerate A/C/T mononucleotide cassette,
a degenerate A/C/G mononucleotide cassette,
a degenerate A/C/G/T mononucleotide cassette,
a non-degenerate A mononucleotide cassette, and
a non-degenerate C mononucleotide cassette,
a non-degenerate G mononucleotide cassette,
and a non-degenerate T mononucleotide cassette.

98. The method of claim 92, where said degenerate trinucleotide cassette is selected from the group consisting of:
a degenerate N,N,N trinucleotide cassette,
a degenerate N,N,G/T trinucleotide cassette,
a degenerate N,N,G/C trinucleotide cassette,
a degenerate N,N,A/C/G trinucleotide cassette,
a degenerate N,N,A/G/T trinucleotide cassette, and
a degenerate N,N,C/G/T trinucleotide cassette.

99. The method of claim 92, wherein said degenerate oligonucleotide is comprised of a first homologous sequence and a plurality of trinucleotide cassettes.

100. The method of claim 99, wherein said method generates a progeny polypeptide having a plurality of concurrent single amino acid changes, at each amino acid site, with respect to a parental polvpeptide template.

101. The method of claim 9, wherein each of said degenerate trinucleotide cassettes is comprised of a first mononucleotide cassette selected from the group consisting of:
a degenerate A/C mononucleotide cassette,
a degenerate A/G mononucleotide cassette,
a degenerate A/T mononucleotide cassette,
a degenerate C/G mononucleotide cassette,
a degenerate C/T mononucleotide cassette,
a degenerate G/T mononucleotide cassette,
a degenerate C/G/T mononucleotide cassette,
a degenerate A/G/T mononucleotide cassette,
a degenerate A/C/T mononucleotide cassette,
a degenerate A/C/G mononucleotide cassette, and
a degenerate A/C/G/T mononucleotide cassette.

102. The method of claim 101, wherein each of said degenerate trinucleotide cassettes further comprises a second and third mononucleotide cassette, each selected from the group consisting of:
a degenerate A/C mononucleotide cassette,
a degenerate A/G mononucleotide cassette,
a degenerate A/T mononucleotide cassette,
a degenerate C/G mononucleotide cassette,
a degenerate C/T mononucleotide cassette,
a degenerate G/T mononucleotide cassette,
a degenerate C/G/T mononucleotide cassette
a degenerate A/G/T mononucleotide cassette,
a degenerate A/C/T mononucleotide cassette,
a degenerate A/C/G mononucleotide cassette,
a degenerate A/C/G/T mononucleotide cassette,
a non-degenerate A mononucleotide cassette,
a non-degenerate C mononucleotide cassette,
a non-degenerate G mononucleotide cassette, and
a non-degenerate T mononucleotide cassette.

103. The method of claim 99, where said degenerate trinucleotide cassette is selected from the group consisting of:
a degenerate N,N,N trinucleotide cassette,
a degenerate N,N,G/T trinucleotide cassette,
a degenerate N,N,G/C trinucleotide cassette,
a degenerate N,N,A/C/G trinucleotide cassette,
a degenerate N,N,A/G/T trinucleotide cassette, and
a degenerate N,N,C/G/T trinucleotide cassette.

104. The method of claim 92, wherein said degenerate oligonucleotide is comprised of a first homologous sequence, and a plurality of trinucleotide cassettes, and a second homologous sequence.

105. The method of claim 92, further comprising screening the progeny polypeptides to identify those that display a desirable change with respect to at least one molecular property as compared with its parental polypeptide.

* * * * *